US012709778B2

(12) United States Patent
Verosloff et al.

(10) Patent No.: US 12,709,778 B2
(45) Date of Patent: Aug. 18, 2026

(54) HIGH-PLEX GUIDE POOLING FOR NUCLEIC ACID DETECTION

(71) Applicant: Mammoth Biosciences, Inc., Brisbane, CA (US)

(72) Inventors: Matthew Verosloff, South San Francisco, CA (US); Clare Fasching, Redwood City, CA (US); Carley Gelenter Hendriks, Burlingame, CA (US); Xin Miao, Mountain View, CA (US); James Paul Broughton, South San Francisco, CA (US); Lucas Benjamin Harrington, San Francisco, CA (US); Janice Sha Chen, San Francisco, CA (US)

(73) Assignee: Mammoth Biosciences, Inc., Brisbane, CA (US)

( * ) Notice: Subject to any disclaimer, the term of this patent is extended or adjusted under 35 U.S.C. 154(b) by 538 days.

(21) Appl. No.: 17/938,640

(22) Filed: Oct. 6, 2022

(65) Prior Publication Data

US 2024/0084401 A1 Mar. 14, 2024

Related U.S. Application Data

(63) Continuation of application No. PCT/US2021/026719, filed on Apr. 9, 2021.

(60) Provisional application No. 63/008,500, filed on Apr. 10, 2020.

(51) Int. Cl.

| | |
|---|---|
| ***C12Q 1/689*** | (2018.01) |
| ***C12N 9/22*** | (2006.01) |
| ***C12Q 1/6806*** | (2018.01) |
| ***C12Q 1/6816*** | (2018.01) |
| ***C12Q 1/6844*** | (2018.01) |

(52) U.S. Cl.

CPC ............... *C12Q 1/689* (2013.01); *C12N 9/22* (2013.01); *C12Q 1/6806* (2013.01); *C12Q 1/6816* (2013.01); *C12Q 1/6844* (2013.01); *C12N 2310/20* (2017.05)

(58) Field of Classification Search

None

See application file for complete search history.

(56) References Cited

U.S. PATENT DOCUMENTS

| | | | |
|---|---|---|---|
| 11,453,907 B2 | 9/2022 | Zhang et al. | |
| 11,639,523 B2 | 5/2023 | Zhang et al. | |
| 2019/0367924 A1 | 12/2019 | Khalili et al. | |
| 2021/0292823 A1 | 9/2021 | Zhang et al. | |

FOREIGN PATENT DOCUMENTS

| | | | |
|---|---|---|---|
| WO | WO-2015122967 A1 * | 8/2015 | ......... C12N 15/1003 |
| WO | WO 2019/104058 A1 | 5/2019 | |
| WO | WO 2020/028729 A1 | 2/2020 | |
| WO | WO-2020124050 A1 * | 6/2020 | ............... C12N 9/22 |
| WO | WO 2020/186231 A2 | 9/2020 | |
| WO | WO 2021/163584 A1 | 8/2021 | |
| WO | WO 2022/132955 A2 | 6/2022 | |

OTHER PUBLICATIONS

Jacobi et al. Methods 121-122 (2017) 16-28.*

Kellner et al. Nat Protoc 14, 2986-3012 (2019).*

Liu et al., "Two Distant Catalytic Sites Are Responsible for C2c2 RNase Activities," *Cell*, 168(1-2):121-134 (2017).

Murugan et al., "The Revolution Continues: Newly Discovered Systems Expand the CRISPR-Cas Toolkit," *Mol. Cell*, 68(1):15-25 (2017).

Tambe et al., "RNA Binding and HEPN-Nuclease Activation Are Decoupled in CRISPR-Cas13a," *Cell Rep.*, 24(4):1025-1036 (2018).

Ackerman et al., "Massively multiplexed nucleic acid detection with Cas13," *Nature*, 582:277-282 (2020).

Broughton et al., "CRISPR-Cas12-based detection of SARS-CoV-2," *Nat. Biotechnol.*, pp. 1-8 (2020).

Chen et al., "CRISPR-Cas12a target binding unleashes indiscriminate single-stranded DNase activity," *Science*, 360:436-439 (2018).

Chen et al., "Supplementary Materials for CRISPR-Cas 12a target binding unleashes indiscriminate single-stranded DNase activity," *Science*, pp. 1-28 (2018).

Gootenberg et al., "Multiplexed and portable nucleic acid detection platform with Cas13, Cas12a, and Csm6," *Science*, 360:439-444 (2018).

Gootenberg et al., "Supplementary Materisla for Multiplexed and portable nucleic acid detection platform with Cas13, Cas12a, and Csm6," *Science*, pp. 1-85 (2018).

* cited by examiner

*Primary Examiner* — Oluwatosin A Ogunbiyi

(74) *Attorney, Agent, or Firm* — Greenberg Traurig, LLP

(57) ABSTRACT

Provided herein, in certain embodiments, are various methods, reagents, and devices for detection of multiple target nucleic acids in a sample, or multiple segments of a target nucleic acid in a sample, using a programmable nuclease. In certain embodiments, the present disclosure provides compositions of pools of guide nucleic acids, programmable nucleases, and detector nucleic acids and methods of using said compositions for detection of different segments of one target nucleic acid or different target nucleic acids in a sample.

19 Claims, 18 Drawing Sheets

Specification includes a Sequence Listing.

HIGH-PLEX GUIDE POOLING FOR NUCLEIC ACID DETECTION

CROSS-REFERENCE

This application claims the benefit of U.S. Provisional Patent Application No. 63/008,500 filed on Apr. 10, 2020, which is incorporated herein by reference in its entirety.

SEQUENCE LISTING

The instant application contains a Sequence Listing which has been submitted electronically in XML format and is hereby incorporated by reference in its entirety. Said XML copy, created on Nov. 10, 2022, is named 203477-731601_SL.xml and is 324,549 bytes in size.

BACKGROUND

Various communicable diseases can easily spread from an individual or environment to an individual. The detection of the ailments, especially at the early stages of infection, may provide guidance on treatment or intervention to reduce the progression or transmission of the ailment. Increased sensitivity of disease detection assays may provide earlier detection, leading to reduced transmission.

SUMMARY

In various aspects, the present disclosure provides a composition comprising a programmable nuclease and a pool of guide nucleic acids comprising greater than 20 distinct guide nucleic acid sequences, wherein at least one guide nucleic acid of the pool hybridizes to a segment of a target nucleic acid.

In some aspects, the pool of guide nucleic acids comprises at least 50 distinct guide nucleic acid sequences, at least 100 distinct guide nucleic acid sequences, at least 500 distinct guide nucleic acid sequences, or at least 1000 distinct guide nucleic acid sequences. In some aspects, the pool of guide nucleic acids comprises at least two guide nucleic acids that hybridize to a different segment of the target nucleic acid. In some aspects, a guide nucleic acid of the pool of guide nucleic acids has a sequence selected from a group of tiled guide nucleic acids that correspond to nucleic acids of the target nucleic acid.

In some aspects, a) the tiled guide nucleic acids are sequential along the target nucleic acid upon hybridization to the target nucleic acid; b) the tiled guide nucleic acids are non-sequential along the target nucleic acid upon hybridization to the target nucleic acid; c) the tiled guide nucleic acids are overlapping along the target nucleic acid upon hybridization to the target nucleic acid; or d) any combination thereof.

In some aspects, the target nucleic acid is from a pathogen. In some aspects, at least two guide nucleic acids of the pool of guide nucleic acids hybridize to segments of distinct target nucleic acids. In some aspects, at least two target nucleic acids of the distinct target nucleic acids are from different pathogens. In further aspects, the pathogen is a virus, a bacterium, a fungus, a protozoan, or a worm. In some aspects, a guide nucleic acid of the pool of guide nucleic acids hybridize to a segment from *Staphylococcus aureus*, methicillin resistant *Staphylococcus aureus, Candida albicans, Pseudomonas aeruginosa, Acinetobacter baumannii, Stenotrophomonas maltophilia, Clostridium difficile, Escherichia coli, Mycobacterium tuberculosis*, or *Legionella* sp.

In some aspects, at least two guide nucleic acids of the pool of guide nucleic acids differs from one another by at least one base. In some aspects, a total concentration of the pool of guide nucleic acids is about 400 nM, about 1000 nM (1 μM), or about 2000 nM (2 μM). In some aspects, each guide nucleic acid of the pool of guide nucleic acids comprises from 20 to 50 bases. In some aspects, each guide nucleic acid comprises from 30 to 50 bases.

In some aspects, the programmable nuclease is a Type V CRISPR-Cas enzyme. In further aspects, the programmable nuclease comprises three partial RuvC domains. In still further aspects, the programmable nuclease comprises a RuvC-I subdomain, a RuvC-II subdomain, and a RuvC-III subdomain. In some aspects, the programmable nuclease is a Cas12 enzyme. In further aspects, the Cas12 enzyme is Cas12a, Cas12b, Cas12c, CasY, or Cas12e. In still further aspects, the Cas 12 enzyme has at least 60% sequence identity to SEQ ID NO: 28.

In some aspects, the programmable nuclease is a Cas14 enzyme. In further aspects, the Cas14 enzyme is Cas14a, Cas14b, Cas14c, Cas14d, Cas14e, Cas14f, Cas14g, or Cas14h.

In other aspects, the programmable nuclease comprises at least two HEPN domains. In further aspects, the programmable nuclease is a Type VI Cas enzyme. In still further aspects, the programmable nuclease is a Cas13 enzyme. In still further aspects, the Cas13 enzyme is Cas13a, Cas13b, Cas13c, Cas13d, or Cas13e.

In some aspects, the target nucleic acid is DNA. In other aspects, the target nucleic acid is RNA. In some aspects, the composition further comprises the target nucleic acid. In some aspects, the target nucleic acid comprises distinct target nucleic acids.

In various aspects, the present disclosure provides a method of assaying for a segment of a target nucleic acid in a sample, the method comprising: contacting the sample to the composition of an embodiment disclosed herein; and assaying for a signal produced by cleavage of a detector nucleic acid.

In some aspects, the method further comprises reverse transcribing the target nucleic acid, amplifying the target nucleic acid, in vitro transcribing the target nucleic acid, or any combination thereof. In some aspects, the amplifying is isothermal amplification.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 2A shows a first set of multiplexed DETECTR reactions in which a guide RNA targeting a human β-globin gene (SEQ ID NO: 172) was present in 19-fold ("20plex"), 49-fold ("50plex"), or 99-fold ("100plex") higher concentration than a guide RNA targeting a human RNAase P gene (SEQ ID NO: 171). The pooled guide RNAs were used to detect the presence or absence of a double-stranded DNA target nucleic acid corresponding an amplified segment of the human RNase P gene (SEQ ID NO: 173, top row) or an amplified segment of the human β-globin gene (SEQ ID NO: 174, bottom row). Each multiplexed DETECTR reaction was performed in the presence of 0 pM, 10 pM, 100 pM, or 1000 pM of the target nucleic acid.

FIG. 2B shows a second set of multiplexed DETECTR reactions in which a guide RNA targeting a human RNAase P gene (SEQ ID NO: 171) was present in 19-fold ("20plex"), 49-fold ("50plex"), or 99-fold ("100plex") higher concentration than a guide RNA targeting a human β-globin gene (SEQ ID NO: 172). The pooled guide RNAs were used to detect the presence or absence of a double-stranded DNA target nucleic acid corresponding an amplified segment of the human RNase P gene (SEQ ID NO: 173, top row) or an amplified segment of the human β-globin gene (SEQ ID NO: 174, bottom row). Each multiplexed DETECTR reaction was performed in the presence of 0 pM, 10 pM, 100 pM, or 1000 pM of the target nucleic acid.

FIG. 9A shows raw fluorescence data for simulated 20-plex, 50-plex, 100-plex, and 200-plex DETECTR reactions with target nucleic acid corresponding to an amplified segment of the human RNase P gene (top, SEQ ID NO: 195) and with an amplified segment of the human β-globin gene (bottom, SEQ ID NO: 174) at concentrations of 1 nM, 100 pM, or 0 pM (left, middle, and right columns, respectively). Guide RNA targeting a human RNase P gene (SEQ ID NO: 171) was present in 19-fold ("20plex"), 49-fold ("50plex") 99-fold ("100plex"), or 199-fold ("200plex) higher concentration than a guide RNA sequence targeting a human RNase P gene (SEQ ID NO: 171).

FIG. 9B shows raw fluorescence data for simulated 20-plex, 50-plex, 100-plex, and 200-plex DETECTR reactions with target nucleic acid corresponding to an amplified segment of the human RNase P gene (top, SEQ ID NO: 195) and with an amplified segment of the human β-globin gene (bottom, SEQ ID NO: 174) at concentrations of 1 nM, 100 pM, or 0 pM (left, middle, and right columns, respectively).

Guide RNA targeting a human β-globin gene (SEQ ID NO: 172) was present in 19-fold ("20plex"), 49-fold ("50plex") 99-fold ("100plex"), or 199-fold ("200plex) higher concentration than a guide RNA sequence targeting a β-globin gene (SEQ ID NO: 171).

Figure 9A:
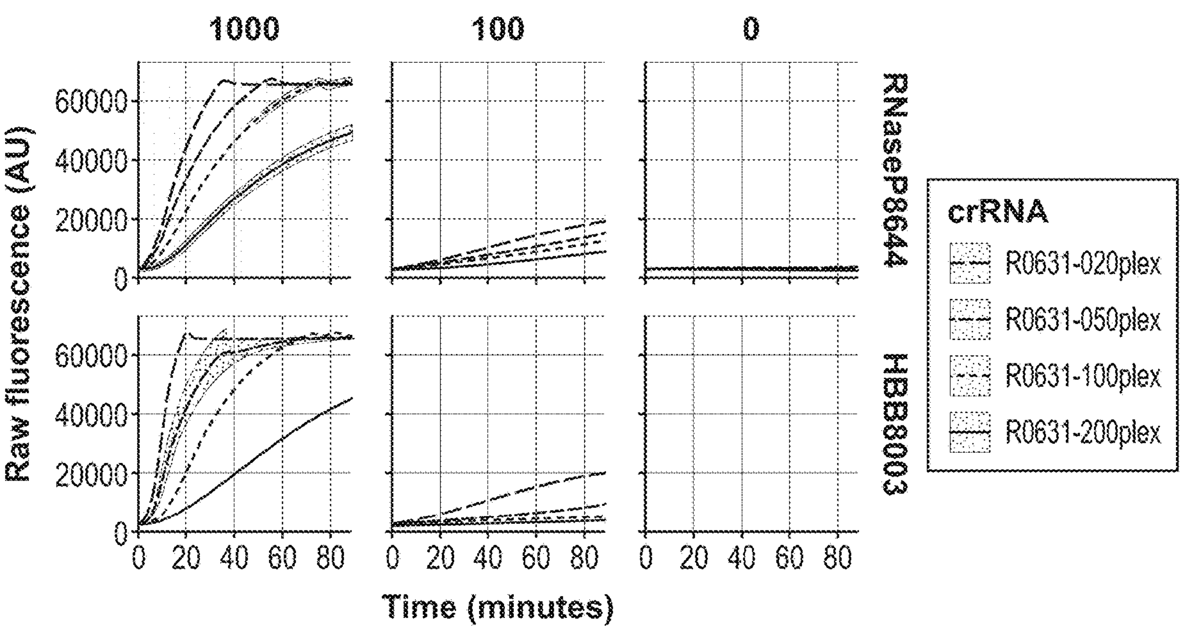
FIGS. 9A-9B show raw fluorescence over time of multiplexed DETECTR reactions using a Cas12 programmable nuclease (SEQ ID NO: 28). Each multiplexed DETECTR reaction was performed with two distinct guide RNA sequences. In each reaction, a first guide nucleic acid sequence was present at either 19-fold, 49-fold, 99-fold, or 199-fold higher concentration than the second guide nucleic acid sequence to simulate 20-plex, 50-plex, 100-plex, or 199-plex high-plex DETECTR reactions, respectively. An 8-nucleotide single-stranded DNA detector nucleic acid labeled at the 5' end with FAM and labeled at the 3' end with Iowa Black FQ with a sequence of SEQ ID NO: 9 was used in each reaction.
Figure 9B:
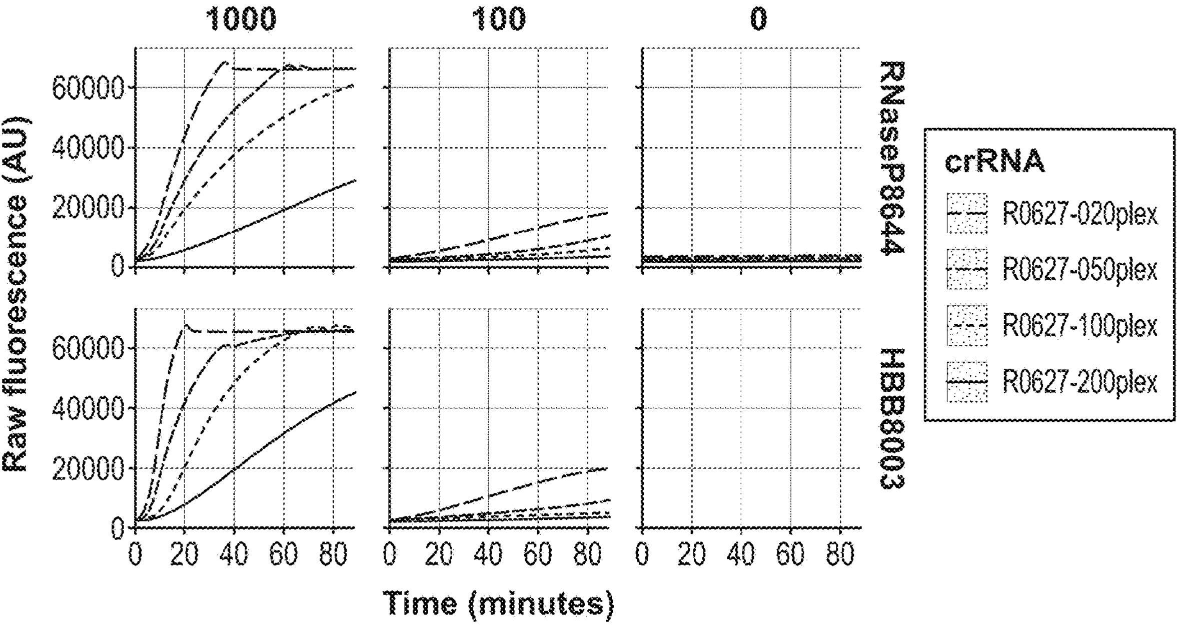
Figure 10:
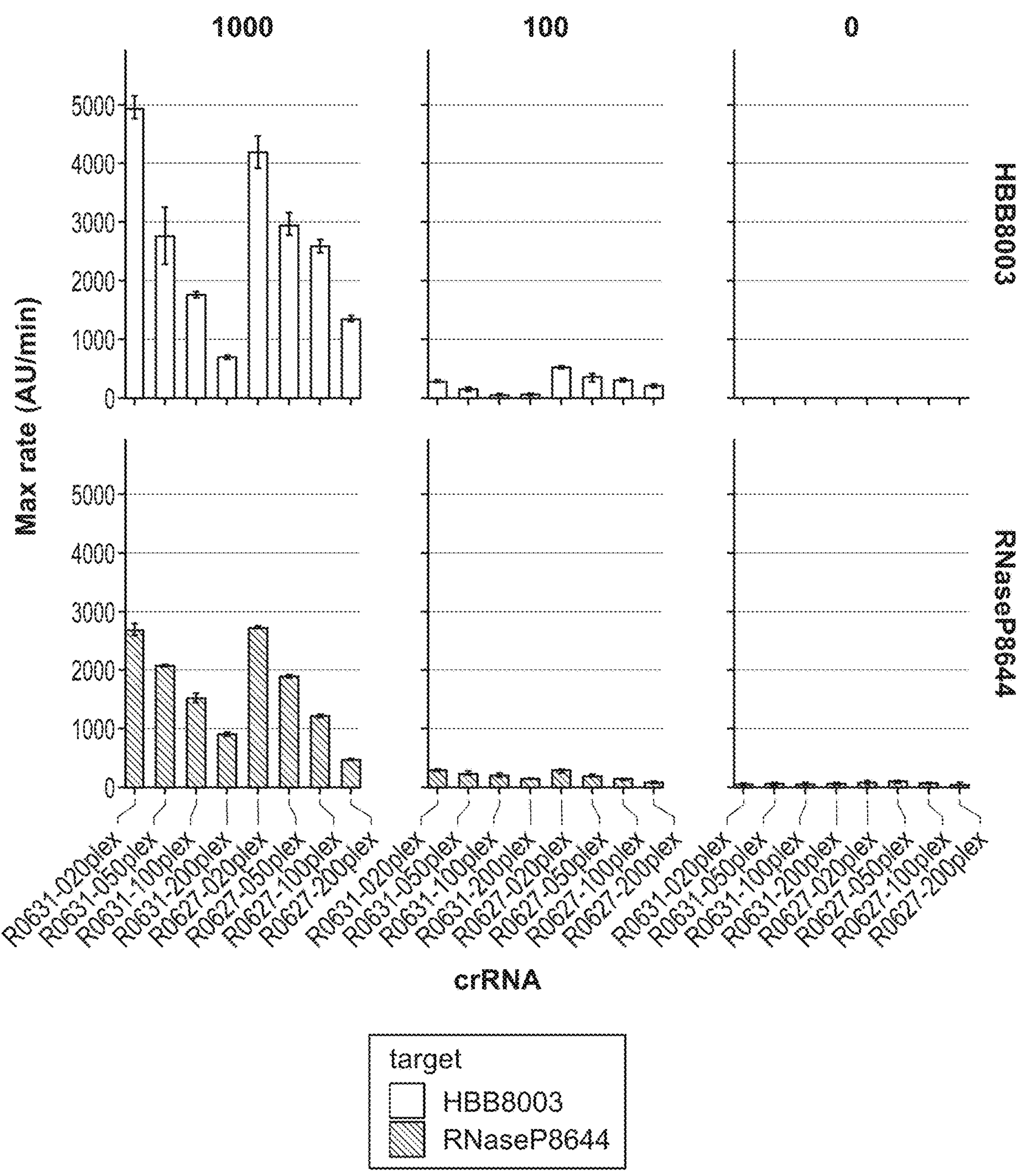

FIG. 10 shows the maximum fluorescence rate of the high-plex DETECTR reactions shown in FIG. 9. The left column corresponds to DETECTR reactions with 1000 pM (1 nM) target nucleic acid. The middle column corresponds to DETECTR reactions with 100 pM target nucleic acid. The right column corresponds to DETECTR reactions with 0 pM target nucleic acid. Bottom rows in each condition correspond to reactions using the human RNAase P gene (SEQ ID NO: 173) as the target nucleic acid, and top rows correspond to reactions the human β-globin gene (SEQ ID NO: 172) as the target nucleic acid.

Figure 11:
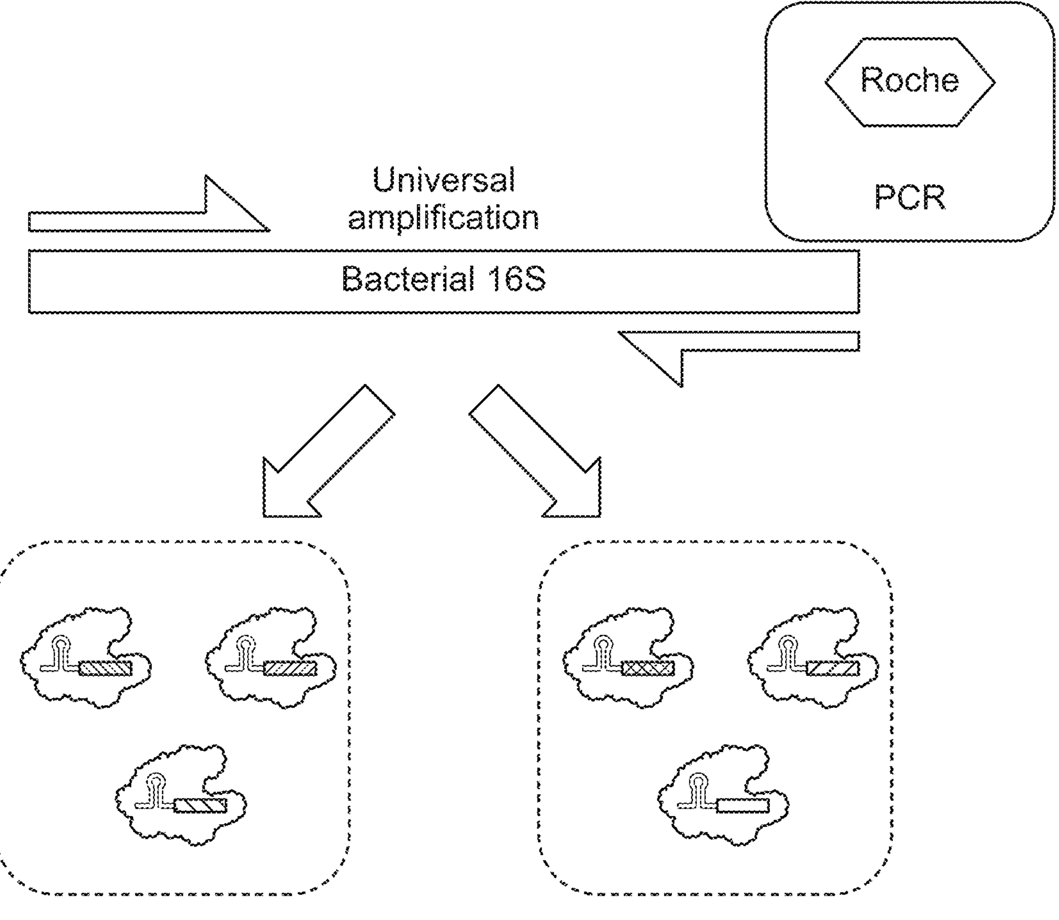

FIG. 11 depicts an assay procedure in which bacterial DNA encoding the 16S ribosomal subunit is amplified and then subject to interrogation by a high-plex DETECTR reaction.

Figure 12:
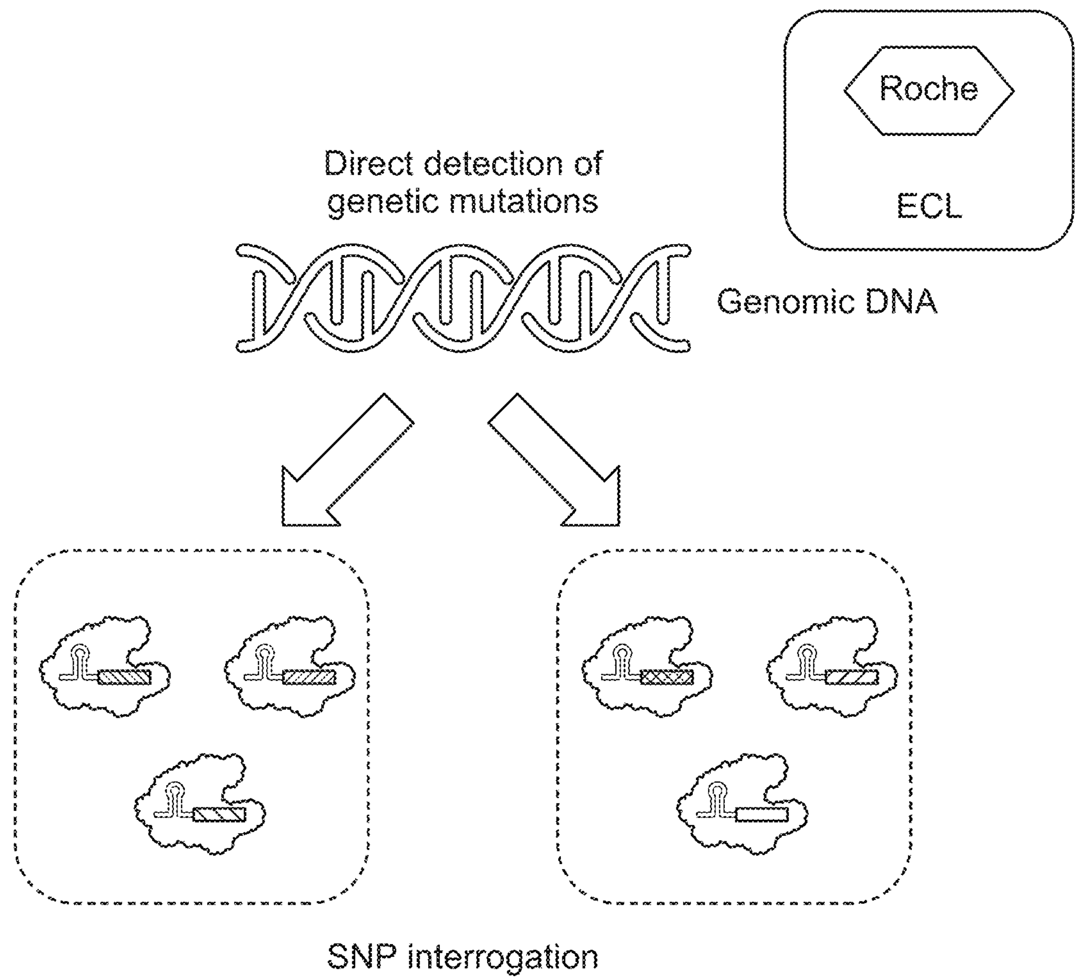

FIG. 12 depicts a high-plex DETECTR reaction designed to detect single nucleotide polymorphisms (SNP) in a DNA sample.

Figure 13:
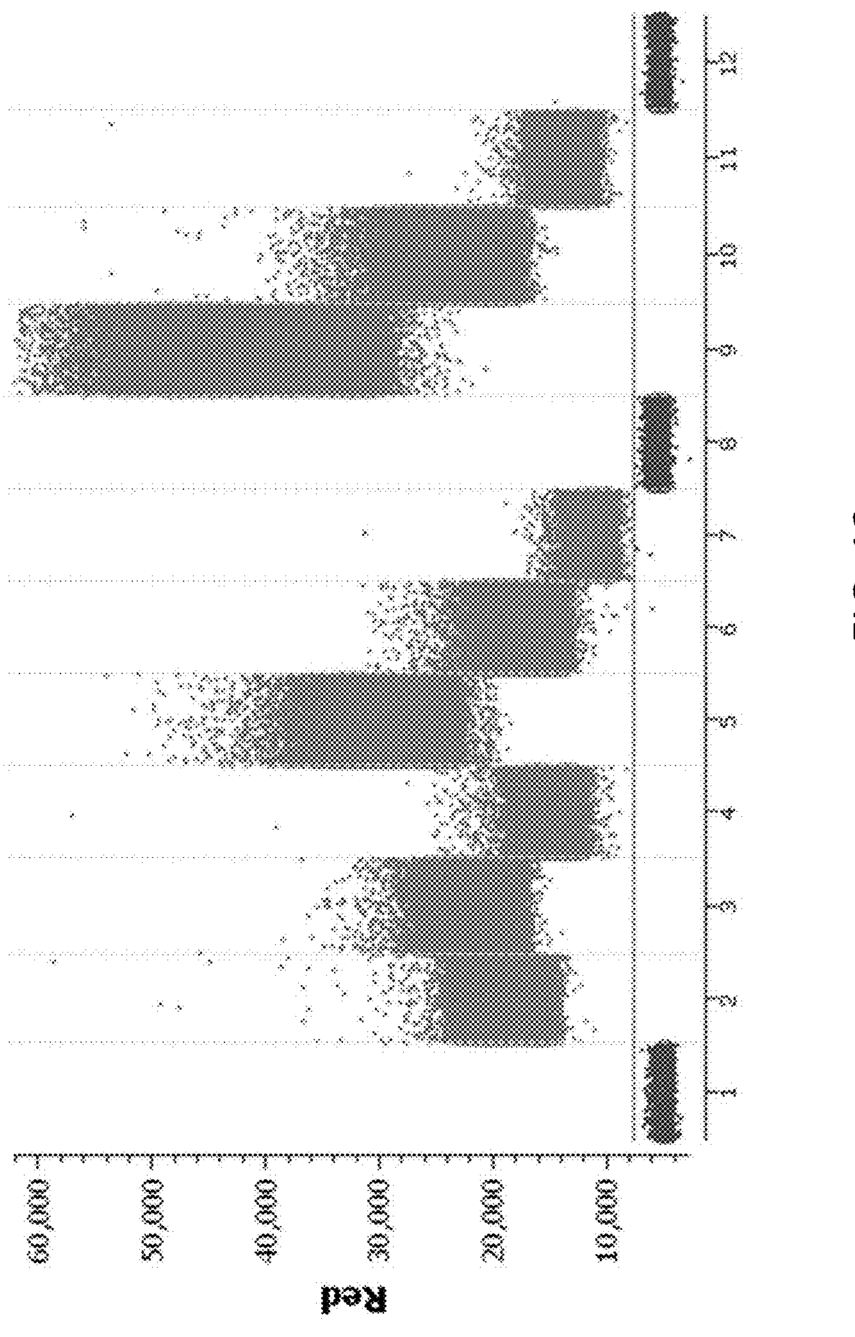

FIG. 13 depicts results of a DETECTR assay showing enhanced Cas12a-based detection of the GF184 target using a pooled-guide (pooled-gRNA) format compared to DETECTR Cas12a-based assay using an individual gRNA format.

Figure 14:
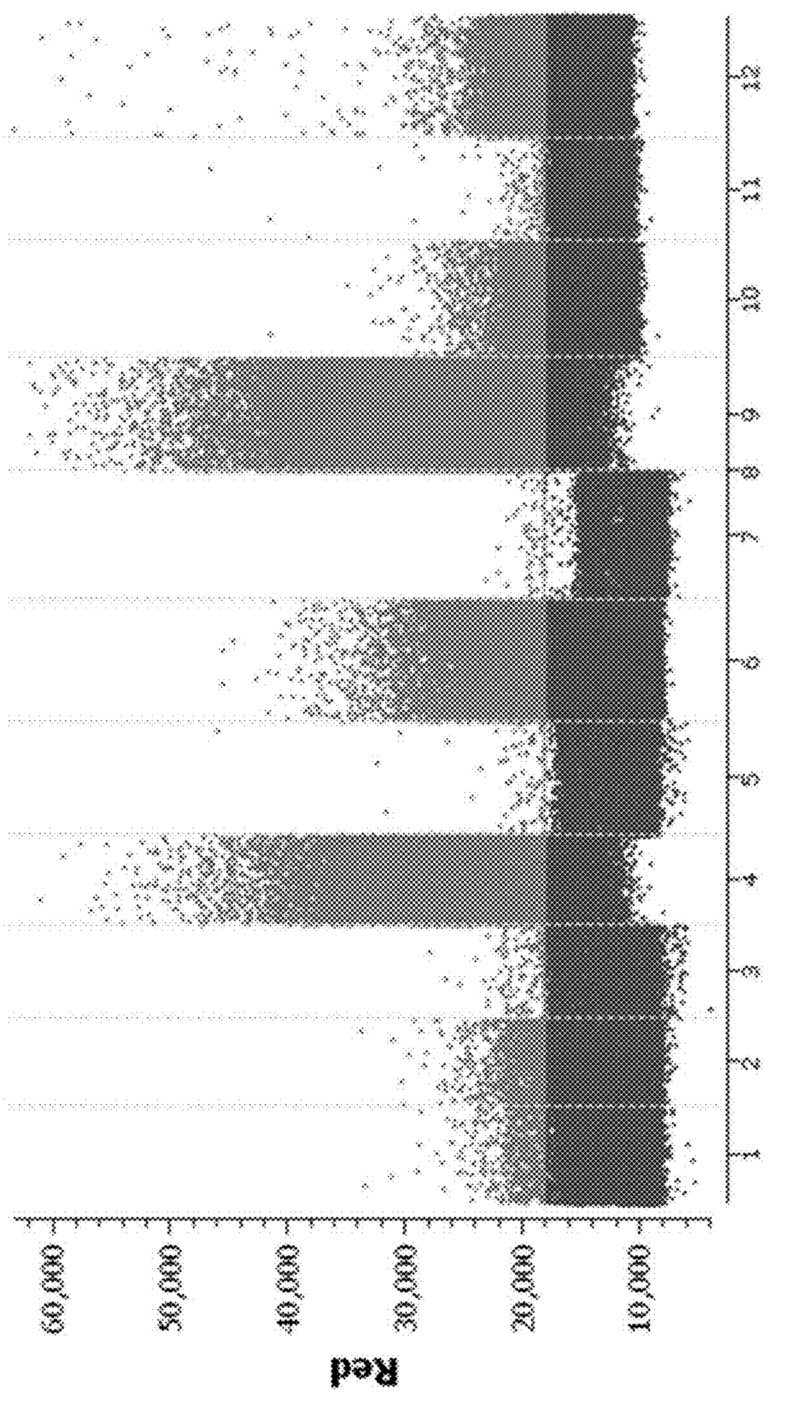

FIG. 14 depicts results of a DETECTR assay showing enhanced sensitivity of the Cas13a-based detection of the SC2 target using a pooled-guide format compared to the Cas13a-based assays using an individual guide format.

Figure 15:
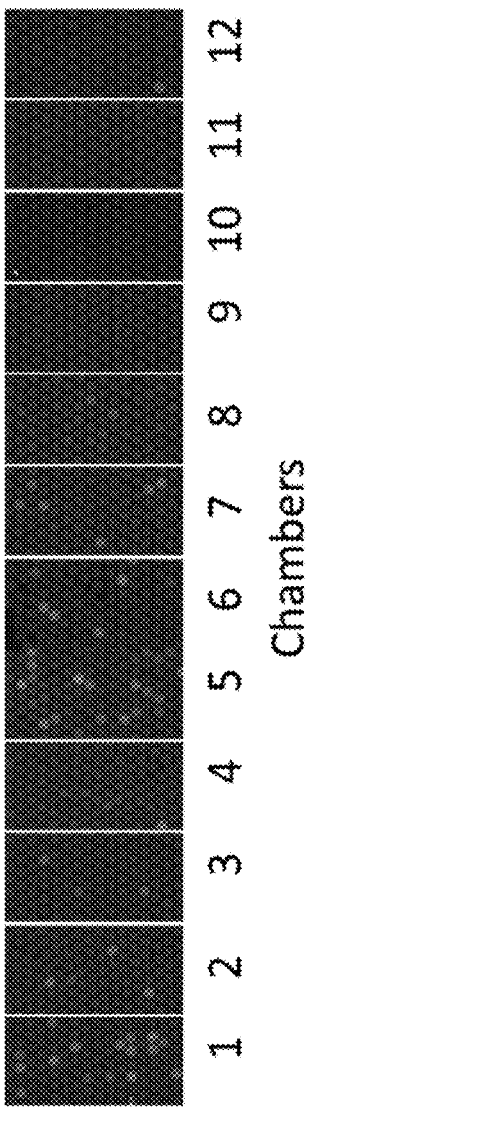

FIG. 15 shows that relative quantification performed by counting the number of positive droplets showed that the Cas13a-DETECTR assay samples containing the pooled guide RNAs generated more crystals containing the amplified products per starting copy of the target RNA than the Cas13a-DETECTR assay samples containing the guide RNAs in individual format.

Figure 16:
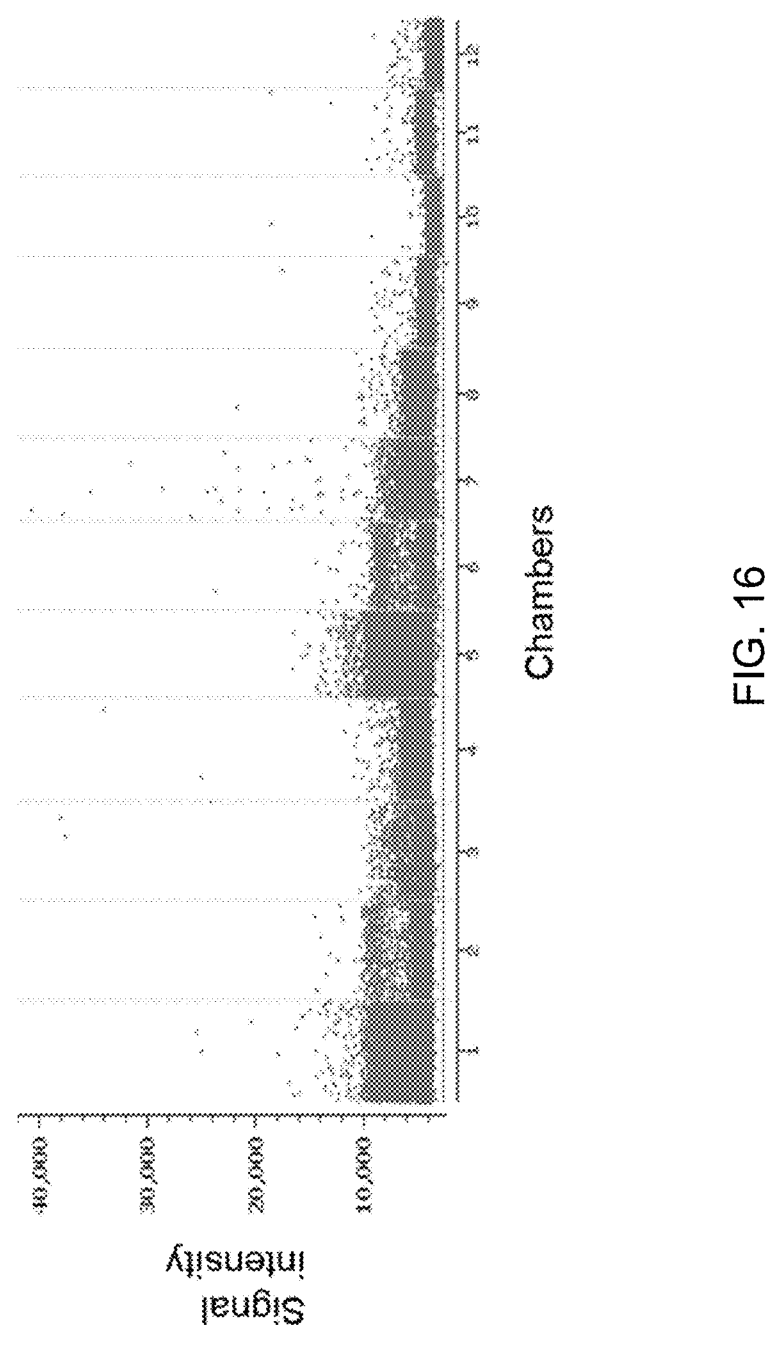

FIG. 16 shows that measurement of signal intensity following amplification showed that the Cas13a-DETECTR assay samples containing the pooled guide RNAs generated more signal intensity per starting copy of the target template RNA than the Cas13a-DETECTR assay samples containing the guide RNAs in individual format.

Figure 17:
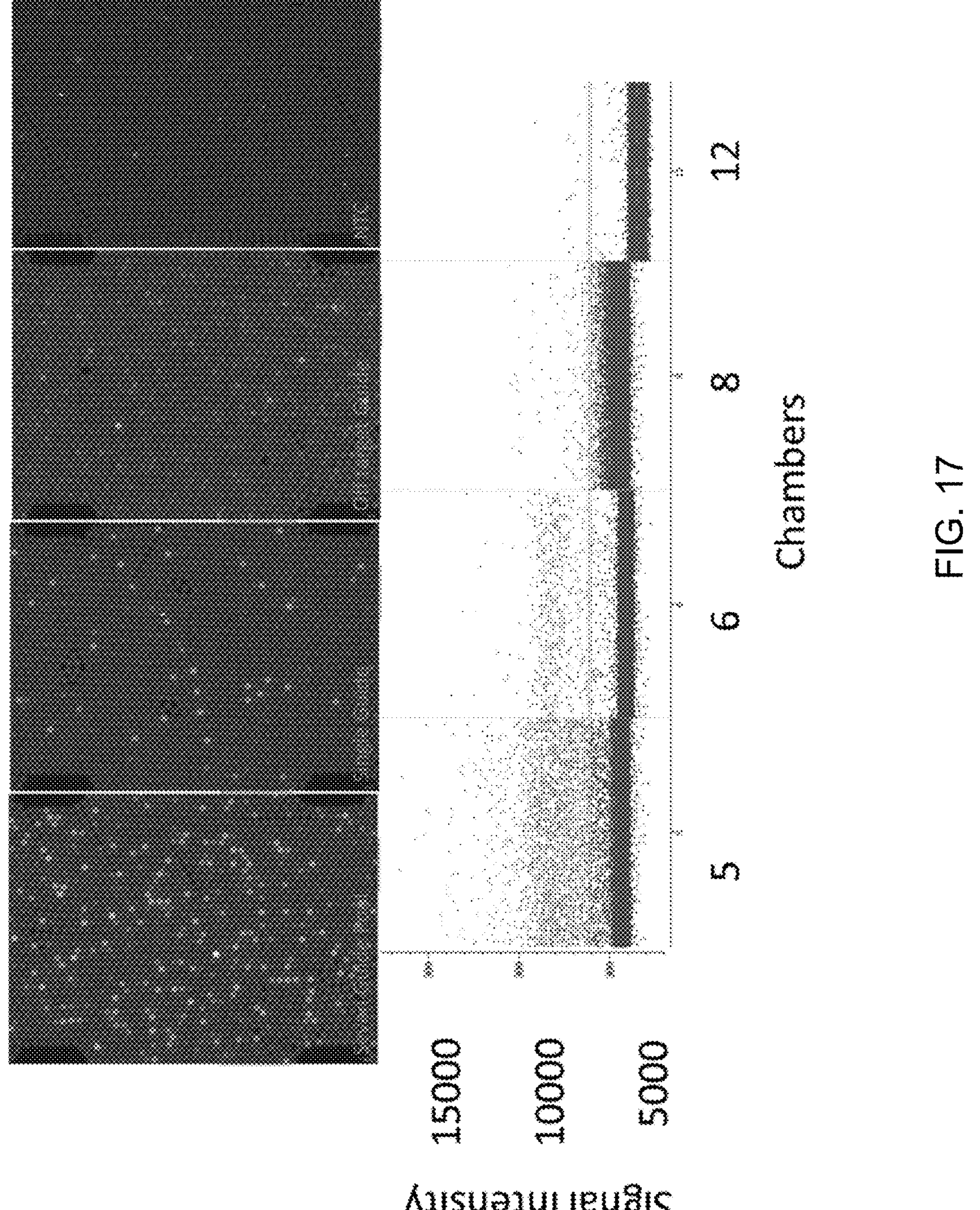

FIG. 17 shows that measurement of signal intensity following amplification showed that the Cas13a-DETECTR assay samples containing the pooled guide RNAs generated more signal intensity per starting copy of the target template RNA than the Cas13a-DETECTR assay samples containing the guide RNAs in individual format. FIG. 17 also shows that relative quantification performed by counting the number of positive droplets showed that the Cas13a-DETECTR assay samples containing the pooled guide RNAs generated more crystals containing the amplified products per starting copy of the target template RNA than the Cas13a-DETECTR assay samples containing the guide RNAs in individual format.

Figure 18:
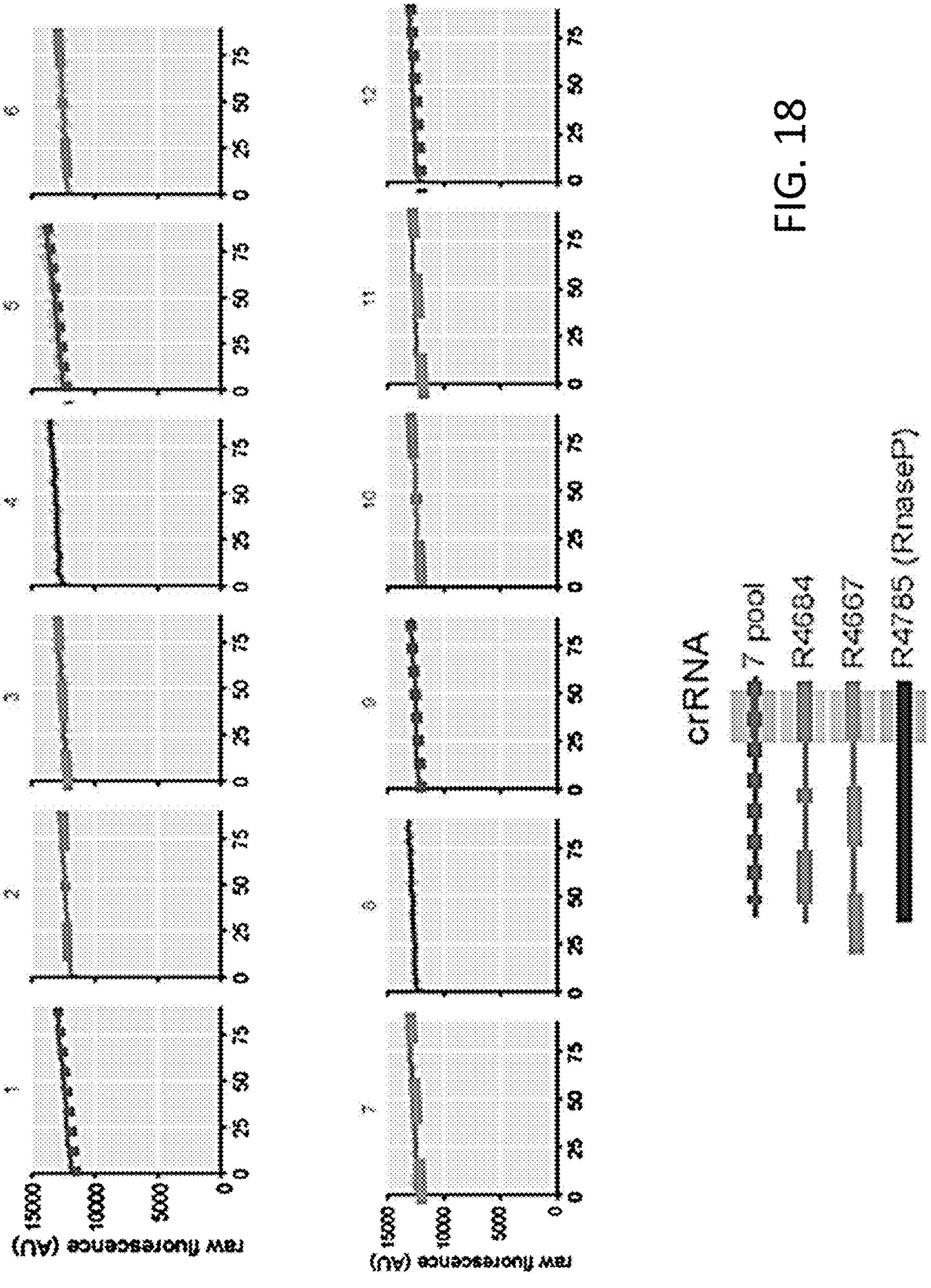

FIG. 18 shows that Cas13a DETECTR assay samples containing the pooled guides (R4637, R4638, R4667, R4676, R4684, R4689, R4691) did not exhibit higher target detection sensitivity per starting copy of the target than the Cas13a DETECTR samples containing the single guides R4684, R4667, or R4785 (RNAseP guide) in individual format.

DETAILED DESCRIPTION

Disclosed herein are non-naturally occurring compositions and systems comprising at least one of an engineered Cas protein and an engineered guide nucleic acid, which may simply be referred to herein as a Cas protein and a guide nucleic acid, respectively. In general, an engineered Cas protein and an engineered guide nucleic acid refer to a Cas protein and a guide nucleic acid, respectively, that are not found in nature. In some instances, systems and compositions comprise at least one non-naturally occurring component. For example, compositions and systems may comprise a guide nucleic acid, wherein the sequence of the guide nucleic acid is different or modified from that of a naturally-occurring guide nucleic acid. In some instances, compositions and systems comprise at least two components that do not naturally occur together. For example, compositions and systems may comprise a guide nucleic acid comprising a repeat region and a spacer region which do not naturally occur together. Also, by way of example, composition and systems may comprise a guide nucleic acid and a Cas protein that do not naturally occur together. Conversely, and for clarity, a Cas protein or guide nucleic acid that is "natural," "naturally-occurring," or "found in nature" includes Cas proteins and guide nucleic acids from cells or organisms that have not been genetically modified by a human or machine.

In some instances, the guide nucleic acid comprises a non-natural nucleobase sequence. In some instances, the non-natural sequence is a nucleobase sequence that is not found in nature. The non-natural sequence may comprise a portion of a naturally-occurring sequence, wherein the portion of the naturally-occurring sequence is not present in nature absent the remainder of the naturally-occurring sequence. In some instances, the guide nucleic acid comprises two naturally-occurring sequences arranged in an order or proximity that is not observed in nature. In some instances, compositions and systems comprise a ribonucleotide complex comprising a CRISPR/Cas effector protein and a guide nucleic acid that do not occur together in nature. Engineered guide nucleic acids may comprise a first sequence and a second sequence that do not occur naturally together. For example, an engineered guide nucleic acid may comprise a sequence of a naturally-occurring repeat region and a spacer region that is complementary to a naturally-occurring eukaryotic sequence. The engineered guide nucleic acid may comprise a sequence of a repeat region that occurs naturally in an organism and a spacer region that does not occur naturally in that organism. An engineered guide nucleic acid may comprise a first sequence that occurs in a first organism and a second sequence that occurs in a second organism, wherein the first organism and the second organism are different. The guide nucleic acid may comprise a third sequence disposed at a 3' or 5' end of the guide nucleic acid, or between the first and second sequences of the guide nucleic acid. For example, an engineered guide nucleic acid may comprise a naturally occurring crRNA and tracrRNA coupled by a linker sequence.

In some instances, compositions and systems described herein comprise an engineered Cas protein that is similar to a naturally occurring Cas protein. The engineered Cas protein may lack a portion of the naturally occurring Cas protein. The Cas protein may comprise a mutation relative to the naturally-occurring Cas protein, wherein the mutation is not found in nature. The Cas protein may also comprise at least one additional amino acid relative to the naturally-occurring Cas protein. For example, the Cas protein may comprise an addition of a nuclear localization signal relative to the natural occurring Cas protein. In certain embodiments, the nucleotide sequence encoding the Cas protein is codon optimized (e.g., for expression in a eukaryotic cell) relative to the naturally occurring sequence.

In some instances, compositions and systems provided herein comprise a multi-vector system encoding a Cas protein and a guide nucleic acid described herein, wherein the guide nucleic acid and the Cas protein are encoded by the same or different vectors. In some embodiments, the engineered guide and the engineered Cas protein are encoded by different vectors of the system.

The present disclosure provides various methods, reagents, and devices for high sensitivity detection of multiple target nucleic acids in a sample using a programmable nuclease. In particular, the various methods, reagents, and devices disclosed herein use programmable nucleases complexed with multiple guide nucleic acid sequences to detect multiple target nucleic acids in a sample. In some embodiments, the multiple target nucleic acids are associated with one or more diseases.

Figure 1:
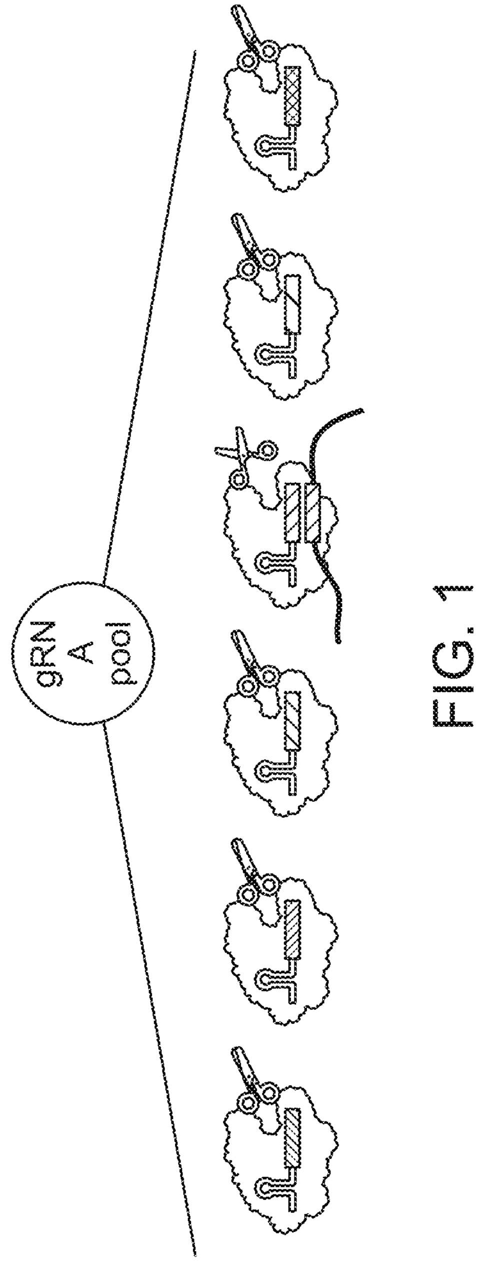
FIG. 1 depicts a pool of different guide nucleic acids complexed 1:1 with programmable nucleases.

The compositions disclosed herein include high-plex pools of guide nucleic acids (e.g., guide RNAs) comprising multiple distinct guide nucleic acid sequences (e.g., guide RNA sequences), wherein at least one guide nucleic acid of the pool hybridizes to a segment of a target nucleic acid, as is depicted in FIG. 1. For example, the pool of guide nucleic acids comprises greater than 20 distinct guide nucleic acid sequences, such as 21 distinct guide nucleic acid sequences (referred to as a 21-plex). In some instances, the pool of guide nucleic acids can comprise at least 30 distinct nucleic acid sequences (30-plex), at least 50 nucleic acid sequences (50-plex), at least 100 nucleic acid sequences (100-plex), at least 500 nucleic acid sequences (500-plex), or at least 1000 nucleic acid sequences (1000-plex). The pools of guide nucleic acids can include multiple copies of the same guide nucleic acid. For example, a 21-plex guide pool of the present disclosure can have 21 distinct guide nucleic acid sequences and can have multiple copies of each of the 21 distinct guide nucleic acid sequences. Said compositions of pools of guide nucleic acids can be used with other reagents disclosed herein (e.g., programmable nucleases, detector nucleic acids) to detect a target nucleic acid in any sample described herein, for example, using the DETECTR methods described herein.

In some embodiments, the methods, reagents, and devices of this disclosure may be used for high sensitivity detection of a single target population of nucleic acids in a biological sample by pooling programmable nucleases complexed with multiple guide nucleic acids directed toward multiple target sequences within the single target population to be detected. Therefore, the present disclosure provides pools of guide nucleic acids having at least two guide nucleic acid sequences that are different from one another, thereby targeting different sequences of a target nucleic acid from one another. Pooling guide nucleic acids that align to multiple segments of the same target population (e.g., the same target genome) may enhance the sensitivity of the DETECTR assay disclosed herein. In some embodiments, the pools of guide nucleic acids disclosed herein, thus, comprise at least one guide nucleic acid that hybridizes to a segment of a target nucleic acid. In some cases, each guide nucleic acid sequence of the pool of guide nucleic acids hybridizes to distinct segments of the same target nucleic acid. For example, the distinct guide nucleic acid sequences of the pools of guide nucleic acids disclosed herein can have a sequence from a group of tiled guide nucleic acids that correspond to nucleic acids of the target nucleic acid. The tiled guide nucleic acids can be sequential along the target nucleic acid upon hybridization to the target nucleic acid. The tiled guide nucleic acids can be non-sequential along the target nucleic acid upon hybridization to the target nucleic acid, the tiled guide nucleic acid can be overlapping along the target nucleic acid upon hybridization to the target nucleic acid, or any combination hereof.

In some embodiments, the methods, reagents, and devices of this disclosure may be used for high sensitivity detection of multiple target populations in a biological sample by pooling programmable nucleases complexed with multiple guide nucleic acid directed toward target sequences in multiple target populations to be detected. Pooling guide nucleic acids that align to multiple target sequences within different target populations (e.g., different target genomes) may increase the sensitivity of the DETECTR assays disclosed herein for diseases associated with multiple pathogenic species (e.g., tick-borne pathogens). A target population may be, for example, a chromosome, a plasmid, a bacterial genome, a viral genome, a fungal genome, or an amoeboid genome. In some embodiments, the multiple guide nucleic acid sequences may comprise at least 20 distinct guide nucleic acid sequences. A method utilizing multiple guide nucleic acid (e.g., at least 20 distinct guide nucleic acid sequences) may be referred to as a "high plex" detection method. A high-plex composition for detection of a target nucleic acid, as disclosed herein, may comprise at least 20, at least 50, at least 100, at least 250, at least 500, at least 1000, or more guide nucleic acid sequences. Each guide nucleic acid sequence may be directed to a distinct target nucleic acid. The distinct target nucleic acids may be within a single target population. The distinct target nucleic acids may be within multiple target populations (e.g., 2, 3, 4, 5, 10, 15, 20, 30, 50, or more target populations). The distinct target nucleic acids may be different variants or alleles of one or more target sequences. Thus, in some cases, each guide nucleic acid sequence of the pool of guide nucleic acids hybridizes to segments from distinct target nucleic acids. For example, in a 21-plex guide pool, at least two of the guide nucleic acid sequences of the 21-plex guide pool can bind to segments of two different target nucleic acids. As another example, in a 21-plex guide pool, each of the 21 guide nucleic acid sequences can bind to segments of 21 different target nucleic acids. These different target nucleic acids can be from different pathogens or different strains of the same pathogen.

The compositions of pools of guide nucleic acids, programmable nucleases, and methods of use thereof disclosed herein can be used as a companion diagnostic with any of the diseases disclosed herein (e.g., bacterial, viral, fungal, or amoebic diseases), or can be used in reagent kits, point-of-care diagnostics, or over-the-counter diagnostics. The methods may be used as a point of care diagnostic or as a lab test for detection of a target nucleic acid and, thereby, detection of a condition in a subject from which the sample was taken. The methods may be used in various sites or locations, such as in laboratories, in hospitals, in physician offices/laboratories (POLs), in clinics, at remotes sites, or at home. Sometimes, the present disclosure provides various methods, reagents, and devices for consumer genetic use or for over the counter use.

Also described herein are methods, reagents, and devices for detecting the presence of a target nucleic acid in a sample. The methods, reagents, and devices for detecting the presence of a target nucleic acid in a sample can be used in a rapid lab tests for detection of a target nucleic acid of interest (e.g., target nucleic acids from a target population). In particular, provided herein are methods, reagents, and devices wherein the rapid lab tests can be performed in a single system. The target nucleic acid may be a portion of a nucleic acid from a virus or a bacterium or other agents responsible for a disease in the sample. The target nucleic acid may be a portion of an RNA or DNA from any organism in the sample. In some embodiments, programmable nucleases disclosed herein are activated by RNA or DNA to initiate trans cleavage activity of a detector nucleic acid. A detector nucleic acid can be an RNA or DNA with a detection moiety that emits a detectable signal upon trans cleavage of the RNA or DNA by the programmable nuclease. A programmable nuclease as disclosed herein is, in some cases, binds to a target RNA to initiate trans cleavage of a detector nucleic acid, and this programmable nuclease can be referred to as an RNA-activated programmable RNA nuclease. In some instances, a programmable nuclease as disclosed herein binds to a target DNA to initiate trans cleavage of a detector nucleic acid, and this programmable nuclease can be referred to as a DNA-activated programmable RNA nuclease. In some cases, a programmable nuclease as described herein is capable of being activated by a target RNA or a target DNA. For example, a Cas13 enzyme, such as Cas13a, disclosed herein is activated by a target RNA nucleic acid or a target DNA nucleic acid to transcollaterally cleave RNA detector nucleic acid. In some embodiments, the Cas13 binds to a target ssDNA which initiates trans cleavage of RNA detector nucleic acid. The detection of the target nucleic acid in the sample may indicate the presence of the disease in the sample and may provide information for taking action to reduce the transmission of the disease to individuals in the disease-affected environment or near the disease-carrying individual. The detection of the target nucleic acid in the sample may indicate the presence of a disease mutation, such as a single nucleotide polymorphism (SNP) that provides antibiotic resistance to a disease-causing bacteria. The detection of the target nucleic acid is facilitated by a programmable nuclease. The programmable nuclease can become activated after binding of a guide nucleic acid with a target nucleic, in which the activated programmable nuclease can cleave the target nucleic acid and can have trans cleavage activity, which can also be referred to as "collateral" or "transcollateral" cleavage. Trans cleavage activity can be non-specific cleavage of nearby single-stranded nucleic acids by the activated programmable nuclease, such as trans cleavage of detector nucleic acids with a detection moiety. Once the detector nucleic acid is cleaved by the activated programmable nuclease, the detection moiety is released from the detector nucleic acid and generates a detectable signal that is immobilized to on a support medium. Often the detection moiety is at least one of a fluorophore, a dye, a polypeptide, or a nucleic acid. Sometimes the detection moiety binds to a capture molecule on the support medium to be immobilized. The detectable signal can be visualized on the support medium to assess the presence or level of the target nucleic acid associated with an ailment, such as a disease. The programmable nuclease can be a CRISPR-Cas (clustered regularly interspaced short palindromic repeats—CRISPR associated) nucleoprotein complex with trans cleavage activity, which can be activated by binding of a guide nucleic acid of the CRISPR-Cas nucleoprotein complex with a target nucleic acid. A reaction comprising production of a detectable signal upon cleavage of a detector nucleic acid by an activated programmable nuclease may be referred to herein as a DETECTR reaction. A DETECTR reaction comprising detection of a plurality of target nucleic acids using a pool of guide nucleic acids and may be referred to herein as a "multiplexed" or "high-plex" DETECTR reaction. A DETECTR reaction comprising detection of multiple target nucleic acids (e.g., at least 2 different segments of target nucleic acids) using multiple distinct guide nucleic acid sequences (e.g., greater than 20 guide nucleic acid sequences) may be referred to herein as a high-plex DETECTR reaction.

In one aspect, described herein is a method for detecting multiple target nucleic acids within a single target population. The method may comprising contacting programmable nucleases to a pool of guide nucleic acids comprising multiple guide nucleic acid sequences. The programmable nucleases are capable of being activated when complexed with a guide nucleic acid and a target sequence. Each guide nucleic acid of the pool of guide nucleic acids may be directed to a different segment within a single target nucleic acid to be detected (e.g., a target nucleic acid associated with a disease). The method may further comprising contacting the programmable nucleases complexed with the pool of guide nucleic acids to a biological sample and a detector nucleic acid, wherein the detector nucleic acid is capable of being cleaved by the activated programmable nuclease, thereby generating a detectable signal, to detect the presence or absence of the target nucleic acid in the biological sample.

In another aspect, described herein is a method for detecting multiple target nucleic acids within multiple target populations. The programmable nucleases are capable of being activated when complexed with a guide nucleic acid and a target sequence. The method may comprising contacting programmable nucleases to a pool of guide nucleic acids comprising multiple guide nucleic acid sequences. Each guide nucleic acid sequence of the pool of guide nucleic acids may be directed to a different target nucleic acids within a plurality of target nucleic acids to be detected (e.g., target nucleic acids associated with one or more diseases). The method may further comprising contacting the programmable nucleases complexed with the pool of guide nucleic acids to a biological sample and a detector nucleic acid, wherein the detector nucleic acid is capable of being cleaved by the activated programmable nuclease, thereby generating a detectable signal, to detect the presence or absence of one or more of the plurality of target nucleic acids in the biological sample.

In another aspect, described herein is a method for detecting multiple variations of a target nucleic acid within a single target population. The method may comprising contacting programmable nucleases to a plurality of guide nucleic acids. The programmable nucleases are capable of being activated when complexed with a guide nucleic acid and a target sequence. Each guide nucleic acid sequence of the pool of guide nucleic acids may be directed to a different variations (e.g., different alleles) of a target nucleic acid sequence within a single target nucleic acid to be detected (e.g., a target nucleic acid associated with a disease). The method may further comprising contacting the programmable nucleases complexed with the pool of guide nucleic acids to a biological sample and a detector nucleic acid, wherein the detector nucleic acid is capable of being cleaved by the activated programmable nuclease, thereby generating a detectable signal, to detect the presence or absence of the target nucleic acid in the biological sample.

Also described herein is a kit for detecting one or more target populations (e.g., one or more target populations associated with a disease). The kit may comprise a support medium; a pool of guide nucleic acid sequences targeted to different target nucleic acid sequences; a programmable nuclease capable of being activated when complexed with a guide nucleic acid and a target nucleic acid; and a single-stranded detector nucleic acid comprising a detection moiety, wherein the detector nucleic acid is capable of being cleaved by the activated nuclease, thereby generating a first detectable signal.

A biological sample from an individual or an environmental sample can be tested to determine whether the individual has a communicable disease. The biological sample can be tested to detect the presence or absence of at least one target nucleic acid from one or more target populations associated with the disease (e.g., a bacterial genome, a viral genome, a fungal genome, or an amoeboid genome). The at least one target nucleic acid from the one or more target populations associated with the disease that is detected can also indicate that one or more of the target populations is wild-type or comprises a mutation that confers resistance to treatment, such as antibiotic treatment. A sample from an individual or from an environment is applied to the reagents described herein. If the target nucleic acid is present in the sample, the target nucleic acid binds to the guide nucleic acid to activate the programmable nuclease. The activated programmable nuclease cleaves the detector nucleic acid and generates a detectable signal that can be visualized, for example on a support medium. If the target nucleic acid is absent in the sample or below the threshold of detection, the guide nucleic acid remains unbound, the programmable nuclease remains inactivated, and the detector nucleic acid remains uncleaved.

Such methods, reagents, and devices described herein may allow for detection of target nucleic acid, and in turn the disease associated with the target nucleic acids (e.g., a bacterial infection, a viral infection, a fungal infection, or an amoeboid infection), in remote regions or low resource settings without specialized equipment. Also, such methods, reagents, and devices described herein may allow for detection of target nucleic acid, and in turn the disease associated with the target nucleic acids, in healthcare clinics or doctor offices without specialized equipment. In some cases, this provides a point of care testing for users to quickly and easily test for a disease or infection with high sensitivity at home or in an office of a healthcare provider. Assays that deliver results in under an hour, for example, in 15 to 60 minutes, are particularly desirable for at home testing for many reasons. For example, antivirals can be most effective when administered within the first 48 hours after disease exposure. Thus, the methods disclosed herein, which are capable of delivering results in under an hour. may allow for the delivery of anti-viral therapy during the first 48 hours after infection. Additionally, the systems and assays provided herein, which are capable of delivering quick diagnoses and results, can help keep or send a patient at home, improve comprehensive disease surveillance, and prevent the spread of an infection. Assays that detect a target population (e.g., a target population associated with a disease) with high sensitivity may provide early and accurate detection of a disease. In some cases, early and accurate detection may improve antibiotic stewardship by enabling healthcare providers to selectively administer antibiotics based on the infecting target population. In other cases, this provides a test, which can be used in a lab to detect one or more nucleic acid populations or varieties of interest in a sample from a subject. In particular, provided herein are methods, reagents, and devices, wherein the high sensitivity lab tests can be performed in a single assay. In some cases, this may be valuable in detecting diseases in a developing country and as a global healthcare tool to detect the spread of a disease or efficacy of a treatment or provide early detection of a disease.

Some methods as described herein use an editing technique, such as a technique using an editing enzyme or a programmable nuclease and guide nucleic acid, to detect one or more target nucleic acid populations. An editing enzyme or a programmable nuclease in the editing technique can be activated by one or more target nucleic acids, after which the activated editing enzyme or activated programmable nuclease can cleave nearby single-stranded nucleic acids, such detector nucleic acids with a detection moiety. A target nucleic acid population (e.g., a target population from a chromosome, a plasmid, a bacterial genome, a viral genome, a fungal genome, or an amoeboid genome), can be amplified by isothermal amplification and then an editing technique can be used to detect the marker. In some instances, the editing technique can comprise an editing enzyme or programmable nuclease that, when activated, cleaves nearby RNA or DNA as the readout of the detection. The methods as described herein in some instances comprise obtaining a cell-free DNA sample, amplifying DNA from the sample, using an editing technique to cleave detector nucleic acids, and reading the output of the editing technique. In other instances, the method comprises obtaining a fluid sample from a patient, and without amplifying a nucleic acid of the fluid sample, using an editing technique to cleave detector nucleic acids, and detecting the nucleic acid. The method can also comprise using single-stranded detector DNA, cleaving the single-stranded detector DNA using an activated editing enzyme, wherein the editing enzyme cleaves at least 50% of a population of single-stranded detector DNA as measured by a change in color. A number of samples, guide nucleic acids, programmable nucleases or editing enzymes, support mediums, target nucleic acids, single-stranded detector nucleic acids, and reagents are consistent with the devices, systems, fluidic devices, kits, and methods disclosed herein.

Also disclosed herein are detector nucleic acids and methods detecting a target nucleic using the detector nucleic acids. Often, the detector nucleic acid is a protein-nucleic acid. For example, a method of assaying for one or more target nucleic acid populations in a sample comprises contacting the sample to a plurality of complexes comprising a guide nucleic acid, each guide nucleic acid sequence comprising a segment that is reverse complementary to a segment of a target nucleic acid sequence within a target nucleic acid population and programmable nucleases that exhibits sequence independent cleavage upon forming complexes comprising the segment of the guide nucleic acid binding to the segment of the target nucleic acid; and assaying for a signal indicating cleavage of at least some protein-nucleic acids of a population of protein-nucleic acids, wherein the signal indicates a presence of one or more of the target nucleic acid populations in the sample and wherein absence of the signal indicates an absence of the target nucleic acid population in the sample. Often, the protein-nucleic acid is an enzyme-nucleic acid or an enzyme substrate-nucleic acid. The nucleic acid can be DNA, RNA, or a DNA/RNA hybrid. The methods described herein use a programmable nuclease, such as a Cas enzyme, to detect one or more target nucleic acid populations. A method of assaying for one or more target nucleic acid populations in a sample, for example, comprises: a) contacting the sample to a plurality of complexes comprising a plurality of guide nucleic acids, each guide nucleic acid sequence comprising a segment that is reverse complementary to a segment of a nucleic acid target sequence within a target nucleic acid population, and programmable nucleases that exhibits sequence independent cleavage upon forming complexes comprising the segment of the guide nucleic acid binding to the segment of the target nucleic acid; b) contacting the complexes to a substrate; c) contacting the substrate to a reagent that differentially reacts with a cleaved substrate; and d) assaying for a signal indicating cleavage of the substrate, wherein the signal indicates a presence of one or more of the target nucleic acid populations in the sample and wherein absence of the signal indicates an absence of the target nucleic acid population in the sample. Often, the substrate is an enzyme-nucleic acid. Sometimes, the substrate is an enzyme substrate-nucleic acid.

Cleavage of the protein-nucleic acid produces a signal. For example, cleavage of the protein-nucleic acid produces a calorimetric signal, a potentiometric signal, an amperometric signal, an optical signal, or a piezo-electric signal. Various devices can be used to detect these different types signals, which indicate whether a target nucleic acid is present in the sample.

Sample

A number of samples are consistent with the methods, reagents, and devices disclosed herein. These samples are, for example, consistent with the high-plex detection methods disclosed herein, wherein the high-plex detection methods comprise contacting a sample to programmable nucleases complexed with a pool of guide nucleic acids (e.g., guide RNAs), and a detector nucleic acid. The pool of guide nucleic acids, can have any number of distinct guide nucleic acid sequences (e.g., guide RNA sequences), as disclosed herein. For example, the pool of guide nucleic acids can have at least 21 distinct guide nucleic acid sequences (corresponding to a 21-plex), at least 50 distinct guide nucleic acid sequences (corresponding to a 50-plex), at least 100 distinct guide nucleic acid sequences (corresponding to a 100-plex), at least 500 distinct guide nucleic acid sequences (corresponding to a 500-plex), or at least 1000 distinct guide nucleic acid sequences (corresponding to a 1000-plex). Said distinct guide nucleic acid sequences in the pool of guide nucleic acids can hybridize to different segments of a target nucleic acid that may be present in any sample disclosed as follows. Additionally, and or alternatively, said distinct guide nucleic acid sequences in the pool of guide nucleic acids can hybridize to different segments of distinct target nucleic acids (e.g., target nucleic acids from different pathogens or different strains from the same pathogen) that may be present in any sample disclosed as follows.

These samples can comprise a target nucleic acid for detection of an ailment, such as a disease, pathogen, or virus, such as influenza. A pathogen can be a virus, a bacterium, a fungus, a protozoan, or a worm. Generally, a sample from an individual or an animal or an environmental sample can be obtained to test for presence of a disease, or any mutation of interest. A biological sample from the individual may be blood, serum, plasma, saliva, urine, mucosal sample, peritoneal sample, cerebrospinal fluid, gastric secretions, nasal secretions, sputum, pharyngeal exudates, urethral or vaginal secretions, an exudate, an effusion, or tissue. A tissue sample may be dissociated or liquefied prior to application to detection system of the present disclosure. A sample from an environment may be from soil, air, or water. In some instances, the environmental sample is taken as a swab from a surface of interest or taken directly from the surface of interest. In some instances, the raw sample is applied to the detection system. In some instances, the sample is diluted with a buffer or a fluid or concentrated prior to application to the detection system or be applied neat to the detection system. Sometimes, the sample is contained in no more 20 μL. The sample, in some cases, is contained in no more than 1, 5, 10, 15, 20, 25, 30, 35, 40, 45, 50, 55, 60, 65, 70, 75, 80, 90, 100, 200, 300, 400, 500 μL, or any of value from 1 μL to 500 μL. Sometimes, the sample is contained in more than 500 μL.

In some instances, the sample is taken from single-cell eukaryotic organisms; a plant or a plant cell; an algal cell; a fungal cell; an animal cell, tissue, or organ; a cell, tissue, or organ from an invertebrate animal; a cell, tissue, fluid, or organ from a vertebrate animal such as fish, amphibian, reptile, bird, and mammal; a cell, tissue, fluid, or organ from a mammal such as a human, a non-human primate, an ungulate, a feline, a bovine, an ovine, and a caprine. In some instances, the sample is taken from nematodes, protozoans, helminths, or malarial parasites. In some cases, the sample comprises nucleic acids from a cell lysate from a eukaryotic cell, a mammalian cell, a human cell, a prokaryotic cell, or a plant cell. In some cases, the sample comprises nucleic acids expressed from a cell.

The sample used for disease testing may comprise at least one target sequence that can bind to a guide nucleic acid of the reagents described herein. The sample used for disease testing may comprise multiple target sequences, corresponding to multiple target nucleic acids. In some cases, the target sequence is a portion of a nucleic acid population. The multiple target sequences may be located within a single nucleic acid population. They multiple target sequences may be located within multiple target nucleic acid populations. A portion of a nucleic acid can be from a genomic locus, a transcribed mRNA, or a reverse transcribed cDNA. A portion of a nucleic acid can be from 5 to 100, 5 to 90, 5 to 80, 5 to 70, 5 to 60, 5 to 50, 5 to 40, 5 to 30, 5 to 25, 5 to 20, 5 to 15, or 5 to 10 nucleotides in length. A portion of a nucleic acid can be 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 60, 70, 80, 90, or 100 nucleotides in length. The target sequence can be reverse complementary to a guide nucleic acid. Each target sequences of the multiple target sequences can be reverse complementary to a distinct guide nucleic acid.

In some cases, the target sequence is a portion of a nucleic acid population from a virus or a bacterium or other agents responsible for a disease in the sample (e.g., a bacterial genome, a viral genome, a fungal genome, or an amoeboid genome). The target sequence, in some cases, is a portion of a nucleic acid population from a sexually transmitted infection or a contagious disease, in the sample. In some examples, in the target nucleic acid is a portion of a nucleic acid from a human immunodeficiency virus (HIV), a human papillomavirus (HPV), a *Chlamydia trachomatis* bacterium, a *Neisseria gonorrhoeae* bacterium, or a *Treponema pallidum* bacterium. The target sequence, in some cases, is a portion of a nucleic acid population from an upper respiratory tract infection, a lower respiratory tract infection, or a contagious disease, in the sample. The target sequence, in some cases, is a portion of a nucleic acid population from a hospital acquired infection, healthcare-associated infection (HAI), or a contagious disease, in the sample. The target sequence, in some cases, is an ssRNA. These target sequences may be from a disease, and the disease may include but is not limited to influenza virus, including influenza A virus (IAV) or influenza B virus (IBV), rhinovirus, cold viruses, a respiratory virus, an upper respiratory virus, a lower respiratory virus, or respiratory syncytial virus. In some examples the disease may be severe acute respiratory syndrome (SARS), a coronavirus, SARS-CoV, or SARS-CoV-2. In some examples, the disease is SARS-CoV-2 (also known as 2019 novel coronavirus, or 2019-nCoV). The coronavirus may be a variant of SARS-CoV-2, particularly the variant known as 20B/501Y.V1, VOC 202012/01, or B.1.1.7 lineage, or the variant known as: 20C/501Y.V2 or B.1.351 lineage. In some examples, the disease is IAV. In some examples, the disease is IBV. Pathogens include viruses, fungi, helminths, protozoa, and parasites. Pathogens include, e.g., *Mycobacterium tuberculosis, Streptococcus agalactiae*, methicillin-resistant *Staphylococcus aureus, Legionella pneumophila, Streptococcus pyogenes, Escherichia coli, Neisseria meningitidis, Pneumococcus, Hemophilus influenzae* B, influenza virus, respiratory syncytial virus (RSV), *M. pneumoniae, Streptococcus intermdius, Streptococcus pneumoniae*, and *Streptococcus pyogenes*. In some examples, the pathogen is a Group A *streptococcus* bacterium. In some examples, the pathogen is a *Neisseria gonorrhoeae* bacterium. In some examples, the pathogen is a *Mycoplasma genitalium* bacterium. In some examples, the pathogen is a *Trichomonas vaginalis* parasite. In some examples, the pathogen is a *Treponema pallidum* bacterium. In some examples, the pathogen is a bacterium or fungus causing a urinary tract infection. In some examples, the bacterium is a *Helicobacter pylori* bacterium. In some examples, the pathogen is a species of *candida*. In some examples, the pathogen is a bacterium causing bacterial vaginosis. In some examples, the pathogen is a *Clostridioides difficile* bacterium. In some examples, the pathogen is a norovirus. In some examples, the pathogen is a hepatitis B virus. In some examples, the pathogen is a virus, fungus, bacterium, parasite or other pathogen causing meningitis. In some examples, the pathogen is a herpes simplex virus. In some examples, the pathogen is a lentivirus. In some examples, the pathogen is a hepatitis C virus. In some examples, the pathogen is a zika virus. In some examples, the pathogen is a human immunodeficiency virus 1 or a human immunodeficiency virus 2. Pathogens may comprise multiple pathogenic species. For example, tick-borne pathogens may comprise one or more infections genera or species (e.g., one or more species of *Borrelia, Babesia*, or *Rickettsia*). In another example, pathogens may include healthcare-associated infections (HAI), which may comprise one or more genera or species. Pathogens may comprise multiple species of a genus (e.g., one or more species of *Borrelia*, one or more species of *Babesia*, or one or more species of *Rickettsia*). Often the target nucleic acid comprises a sequence from a virus or a bacterium or other agents responsible for a disease that can be found in the sample. Pathogenic viruses include but are not limited to influenza virus; RSV; an ssRNA virus, a respiratory virus, an upper respiratory virus, a lower respiratory virus, or a rhinovirus. Pathogens include, e.g., *Mycobacterium tuberculosis, Streptococcus agalactiae, Legionella pneumophila, Streptococcus pyogenes, Hemophilus influenzae* B influenza virus, respiratory syncytial virus (RSV), or *Mycobacterium tuberculosis*

The sample can be used for identifying a disease status. For example, a sample is any sample described herein, and is obtained from a subject for use in identifying a disease status of a subject. Sometimes, a method comprises obtaining a serum sample from a subject; and identifying a disease status of the subject.

In some instances, the target nucleic acid is a single-stranded nucleic acid. Alternatively or in combination, the target nucleic acid is a double stranded nucleic acid and is prepared into single-stranded nucleic acids before or upon contacting the reagents. The target nucleic acid may be a RNA, DNA, synthetic nucleic acids, or nucleic acids found in biological or environmental samples. The target nucleic acids include but are not limited to mRNA, rRNA, tRNA, non-coding RNA, long non-coding RNA, and microRNA (miRNA). In some cases, the target nucleic acid is mRNA. In some cases, the target nucleic acid is from a virus, a parasite, or a bacterium described herein. In some cases, the target nucleic acid is transcribed from a gene as described herein.

A number of target nucleic acids are consistent with the methods and compositions disclosed herein. Some methods described herein can detect a target nucleic acid present in the sample in various concentrations or amounts as a target nucleic acid. In some cases, the sample has at least 2 target nucleic acids. In some cases, the sample has at least 3, 5, 10, 20, 30, 40, 50, 100, 200, 300, 400, 500, 600, 700, 800, 900, 1000, 2000, 3000, 4000, 5000, 6000, 7000, 8000, 9000, or 10000 target nucleic acids. In some cases, the method detects target nucleic acid present at least at one copy per $10^1$ non-target nucleic acids, $10^2$ non-target nucleic acids, $10^3$ non-target nucleic acids, $10^4$ non-target nucleic acids, $10^5$ non-target nucleic acids, $10^6$ non-target nucleic acids, $10^7$ non-target nucleic acids, $10^8$ non-target nucleic acids, $10^9$ non-target nucleic acids, or $10^{10}$ non-target nucleic acids.

A number of target nucleic acids are consistent with the methods and compositions disclosed herein. Some methods described herein can detect two or more target nucleic acid sequences present in the sample in various concentrations or amounts. In some cases, the sample has at least 2 target nucleic acid sequences. In some cases, the sample has at least 3, 4, 5, 6, 7, 8, 9, 10, 20, 30, 40, or 50 target nucleic acid sequences. Some methods described herein can detect at least 20, at least 30, at least 40, at least 50, at least 60, at least 70, at least 80, at least 90, at least 100, at least 200, at least 300, at least 400, at least 500, at least 600, at least 700, at least 800, at least 900, at least 1000, or more target nucleic acid sequences. The target nucleic acid populations may be from one or more target nucleic acid sequences. For example, the target nucleic acid sequences may be from at least 1, at least 2, at least 3, at least 4, at least, 5, at least 6, at least 7, at least 8, at least 9, at least 10, at least 20, at least 30, at least 40, at least 50, at least 60, at least 70, at least 80, at least 90, at least 100, or more target nucleic acid populations. In some cases, the method detects target nucleic acids sequences that are present at least at one copy per $10^1$ non-target nucleic acids, $10^2$ non-target nucleic acids, $10^3$ non-target nucleic acids, $10^4$ non-target nucleic acids, $10^5$ non-target nucleic acids, $10^6$ non-target nucleic acids, $10^7$ non-target nucleic acids, $10^8$ non-target nucleic acids, $10^9$ non-target nucleic acids, or $10^{10}$ non-target nucleic acids. The target nucleic acid sequences can be present at different concentrations or amounts in the sample.

Any of the above disclosed samples are consistent with the systems, assays, and programmable nucleases disclosed herein and can be used as a companion diagnostic with any of the diseases disclosed herein (e.g., tick-bome pathogens or healthcare-associated infections), or can be used in reagent kits, point-of-care diagnostics, or over-the-counter diagnostics.

Reagents

A number of reagents are consistent with the methods, reagents, and devices disclosed herein. Reagents disclosed herein for detection of a target nucleic acid are compatible with the pools of guide nucleic acids (e.g., guide RNAs) disclosed herein (e.g., a 21-plex pool of guide nucleic acids, a 50-plex pool of guide nucleic acids, a 100-plex pool of guide nucleic acids, a 500-plex pool of guide nucleic acids, or a 1000-plex pool of guide nucleic acids). The pool of guide nucleic acids, can have any number of distinct guide nucleic acid sequences, as disclosed herein. For example, the pool of guide nucleic acids can have at least 21 distinct guide nucleic acid sequences (corresponding to a 21-plex), at least 50 distinct guide nucleic acid sequences (corresponding to a 50-plex), at least 100 distinct guide nucleic acid sequences (corresponding to a 100-plex), at least 500 distinct guide nucleic acid sequences (corresponding to a 500-plex), or at least 1000 distinct guide nucleic acid sequences (corresponding to a 1000-plex). Said distinct guide nucleic acid sequences in the pool of guide nucleic acids can hybridize to different segments of a target nucleic acid that may be detected using the reagents disclosed herein, as follows. Additionally, and or alternatively, said distinct guide nucleic acid sequences in the pool of guide nucleic acids can hybridize to different segments of distinct target nucleic acids (e.g., target nucleic acids from different pathogens or different strains from the same pathogen) that may be detected using the reagents disclosed herein, as follows.

These reagents are compatible with the samples, methods, and devices as described herein for detection of an ailment, such as a disease. The reagents described herein for detecting a disease comprise multiple guide nucleic acids, each guide nucleic acid targeting a target nucleic acid segment indicative of the disease. Each guide nucleic acid binds to the target nucleic acid comprising a segment of a nucleic acid sequence (e.g., a nucleic acid from a virus or a bacterium or other agents responsible for a disease) as described herein. Each guide nucleic acid can bind to the target nucleic acid comprising a portion of a nucleic acid (e.g., a target nucleic acid from a bacterium or other agents responsible for a disease) as described herein and further comprising a mutation, such as a single nucleotide polymorphism (SNP), that can confer resistance to a treatment, such as antibiotic treatment. Each guide nucleic acid binds to the target nucleic acid comprising a portion of a nucleic acid. Each guide nucleic acid is complementary to a target nucleic acid. Often the guide nucleic acid binds specifically to the target nucleic acid. The target nucleic acid may be a RNA, DNA, or synthetic nucleic acids.

Disclosed herein are methods of assaying for a plurality of target nucleic acids as described herein. For example, a method of assaying for a plurality of target nucleic acids in a sample comprises contacting the sample to a complex comprising a plurality of guide nucleic acid sequences, each guide nucleic acid sequence comprising a segment that is reverse complementary to a segment of the target nucleic acid, and programmable nucleases that exhibits sequence independent cleavage upon forming a complex comprising the segment of the guide nucleic acid binding to the segment of the target nucleic acid; and assaying for a signal indicating cleavage of at least some protein-nucleic acids of a population of protein-nucleic acids, wherein the signal indicates a presence of one or more target nucleic acid of the plurality of target nucleic acids in the sample and wherein absence of the signal indicates an absence of the target nucleic acids in the sample. As another example, a method of assaying for a target nucleic acid in a sample, for example, comprises: a) contacting the sample to a plurality of complexes, each complex comprising a guide nucleic acid comprising a segment that is reverse complementary to a segment of the target nucleic acid and a programmable nuclease that exhibits sequence independent cleavage upon forming a complex comprising the segment of the guide nucleic acid binding to the segment of the target nucleic acid; b) contacting the plurality of complexes to a substrate; c) contacting the substrate to a reagent that differentially reacts with a cleaved substrate; and d) assaying for a signal indicating cleavage of the substrate, wherein the signal indicates a presence of the target nucleic acid in the sample and wherein absence of the signal indicates an absence of the target nucleic acid in the sample. Often, the substrate is an enzyme-nucleic acid. Sometimes, the substrate is an enzyme substrate-nucleic acid.

A programmable nuclease can comprise a programmable nuclease capable of being activated when complexed with a guide nucleic acid and target nucleic acid. The programmable nuclease can become activated after binding of a guide nucleic acid with a target nucleic acid, in which the activated programmable nuclease can cleave the target nucleic acid and can have trans cleavage activity. Trans cleavage activity can be non-specific cleavage of nearby single-stranded nucleic acids by the activated programmable nuclease, such as trans cleavage of detector nucleic acids with a detection moiety. Once the detector nucleic acid is cleaved by the activated programmable nuclease, the detection moiety can be released from the detector nucleic acid and can generate a signal. A signal can be a calorimetric, potentiometric, amperometric, optical (e.g., fluorescent, colorometric, etc.), or piezo-electric signal. Often, the signal is present prior to detector nucleic acid cleavage and changes upon detector nucleic acid cleavage. Sometimes, the signal is absent prior to detector nucleic acid cleavage and is present upon detector nucleic acid cleavage. The detectable signal can be immobilized on a support medium for detection. The programmable nuclease can be a CRISPR-Cas (clustered regularly interspaced short palindromic repeats—CRISPR associated) nucleoprotein complex with trans cleavage activity, which can be activated by binding of a guide nucleic acid with a target nucleic acid. The CRISPR-Cas nucleoprotein complex can comprise a Cas enzyme complexed with a guide nucleic acid. The guide nucleic acid can be a guide RNA. The guide nucleic acid can comprise a CRISPR RNA (crRNA) and a trans-activating crRNA (tracrRNA). In some embodiments, the guide RNA comprises just the crRNA. The crRNA can complex with the tracrRNA to form the guide RNA. The crRNA can be made up of a repeat region and a spacer sequence. The entire spacer or a segment of the spacer of the crRNA can hybridize to a target nucleic acid.

The CRISPR-Cas nucleoprotein complex used to detect a modified target nucleic acids, wherein the CRISPR-Cas nucleoprotein complex can comprise CRISPR RNAs (crRNAs), trans-activating crRNAs (tracrRNAs), Cas enzymes, and detector nucleic acids.

A guide nucleic acid (e.g., guide RNA) can comprise a sequence that is reverse complementary to the sequence of a target nucleic acid. Said sequence that is reverse complementary to the sequence of the target nucleic acid in the guide nucleic acid can be a crRNA. Said sequence the is reverse complementary to the sequence of the target nucleic acid in the guide nucleic acid can be a or a portion of a crRNA. For example, either part or the entire sequence of the spacer region of the crRNA can be said sequence that is reverse complementary to the sequence of the target nucleic acid. Sometimes, a guide nucleic acid comprises a crRNA and tracrRNA. The guide nucleic acid can bind specifically to the target nucleic acid. In some cases, the guide nucleic acid is not naturally occurring and made by artificial combination of otherwise separate segments of sequence. Often, the artificial combination is performed by chemical synthesis, by genetic engineering techniques, or by the artificial manipulation of isolated segments of nucleic acids. The target nucleic acid can be designed and made to provide desired functions. In some cases, the targeting region of a guide nucleic acid is 20 nucleotides in length. The targeting region of the guide nucleic acid may have a length of at least 10, 11, 12, 13, 14, 15, 16, 17, 18, 19, 20, 21, 22, 23, 24, 25, 26, 27, 28, 29, or 30 nucleotides in length. In some instances, the targeting region of the guide nucleic acid is 10, 11, 12, 13, 14, 15, 16, 17, 18, 19, 20, 21, 22, 23, 24, 25, 26, 27, 28, 29, or 30 nucleotides in length. In some cases, the targeting region of a guide nucleic acid has a length from exactly or about 12 nucleotides (nt) to about 80 nt, from about 12 nt to about 50 nt, from about 12 nt to about 45 nt, from about 12 nt to about 40 nt, from about 12 nt to about 35 nt, from about 12 nt to about 30 nt, from about 12 nt to about 25 nt, from about 12 nt to about 20 nt, from about 12 nt to about 19 nt, from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. It is understood that the sequence of a polynucleotide need not be 100% complementary to that of its target nucleic acid to be specifically hybridizable or hybridizable or bind specifically. The guide nucleic acid can have a sequence comprising at least one uracil in a region from nucleic acid residue 5 to 20 that is reverse complementary to a modification variable region in the target nucleic acid. The guide nucleic acid, in some cases, has a sequence comprising at least one uracil in a region from nucleic acid residue 5 to 9, 10 to 14, or 15 to 20 that is reverse complementary to a modification variable region in the target nucleic acid. The guide nucleic acid can have a sequence comprising at least one uracil in a region from nucleic acid residue 5 to 20 that is reverse complementary to a methylation variable region in the target nucleic acid. The guide nucleic acid, in some cases, has a sequence comprising at least one uracil in a region from nucleic acid residue 5 to 9, 10 to 14, or 15 to 20 that is reverse complementary to a methylation variable region in the target nucleic acid.

The guide nucleic acid (e.g., guide RNA) can be selected from a group of guide nucleic acids that have been tiled against the nucleic acid sequence of a strain of an infection or genomic locus of interest. The guide nucleic acid can be selected from a group of guide nucleic acids that have been tiled against the nucleic acid sequence of a bacterial, viral, or fungal strain. Often, guide nucleic acids that are tiled against the nucleic acid of a strain of an infection or genomic locus of interest can be pooled for use in a method described herein. Often, these guide nucleic acids are pooled for detecting a target nucleic acid in a single assay. The pooling of guide nucleic acids that are tiled against a single target nucleic acid can enhance the detection of the target nucleic using the methods described herein. The pooling of guide nucleic acids that are tiled against a single target nucleic acid can ensure broad coverage of the target nucleic acid within a single reaction using the methods described herein. The tiling, for example, is sequential along the target nucleic acid. Sometimes, the tiling is overlapping along the target nucleic acid. In some instances, the tiling comprises gaps between the tiled guide nucleic acids along the target nucleic acid. In some instances the tiling of the guide nucleic acids is non-sequential. Often, a method for detecting a target nucleic acid comprises contacting a target nucleic acid to a pool of guide nucleic acids and a programmable nuclease, wherein a guide nucleic acid of the pool of guide nucleic acids has a sequence selected from a group of tiled guide nucleic acid that correspond to nucleic acids of a target nucleic acid; and assaying for a signal produce by cleavage of at least some detector nucleic acids of a population of detector nucleic acids. Pooling of guide nucleic acids can ensure broad spectrum identification, or broad coverage, of a target species within a single reaction. This can be particularly helpful in diseases or indications, like sepsis, that may be caused by multiple organisms.

A "plurality of guide nucleic acids" and a "pool of guide nucleic acids" can be used interchangeably herein. The pool of guide nucleic acids (e.g., guide RNAs) disclosed herein may comprise at least 20 distinct guide nucleic acid sequences, at least 30 distinct guide nucleic acid sequences, at least 40 distinct guide nucleic acid sequences, at least 50 distinct guide nucleic acid sequences, at least 60 distinct guide nucleic acid sequences, at least 70 distinct guide nucleic acid sequences, at least 80 distinct guide nucleic acid sequences, at least 90 distinct guide nucleic acid sequences, at least 100 distinct guide nucleic acid sequences, at least 200 distinct guide nucleic acid sequences, at least 300 distinct guide nucleic acid sequences, at least 400 distinct guide nucleic acid sequences, at least 500 distinct guide nucleic acid sequences, at least 600 distinct guide nucleic acid sequences, at least 700 distinct guide nucleic acid sequences, at least 800 distinct guide nucleic acid sequences, at least 900 distinct guide nucleic acid sequences, at least 1000 distinct guide nucleic acid sequences, or more distinct guide nucleic acid sequences. In each pool of guide nucleic acids, multiple copies of each of the guide nucleic acid sequences can be present. The plurality, or pool, of guide nucleic acids can have multiple copies of each distinct guide nucleic acid sequence. Each guide nucleic acid sequence in the pool of guide nucleic acids may be directed to a distinct segment target nucleic acid. The distinct target nucleic acids may be from a single target nucleic acid population. The distinct target nucleic acids may be from multiple target nucleic acid populations. The distinct target nucleic acids may be different variants of a target sequence from a single target nucleic acid population or multiple target nucleic acid populations. Each guide nucleic acid sequence of the pool of guide nucleic acid sequences may be complexed with a programmable nuclease.

Described herein are reagents comprising a programmable nuclease capable of being activated when complexed with the guide nucleic acid and the target nucleic acid segment. A programmable nuclease can be capable of being activated when complexed with a guide nucleic acid and the target sequence. The programmable nuclease can be activated upon binding of the guide nucleic acid to its target nucleic acid and degrades non-specifically nucleic acid in its environment. The programmable nuclease has trans cleavage activity once activated. A programmable nuclease can be a Cas enzyme. A guide nucleic acid and a Cas enzyme can form a CRISPR-Cas nucleoprotein complex.

Several programmable nucleases are consistent with the methods and devices of the present disclosure. For example, Cas enzymes are programmable nucleases used in the methods and systems disclosed herein. Cas enzymes can include any of the known Classes and Types of CRISPR-Cas enzymes. For example, programmable nucleases disclosed herein include Class 1 CRISPR-Cas enzymes, such as the Type I, Type IV, or Type III CRISPR-Cas enzymes. Programmable nucleases disclosed herein also include the Class 2 CRISPR-Cas enzymes, such as the Type II, Type V, and Type VI CRISPR-Cas enzymes. Preferable programmable nucleases included in the several devices disclosed herein (e.g., a microfluidic device such as a pneumatic valve device or a sliding valve device or a lateral flow assay) and methods of use thereof include a Type V or Type VI CRISPR-Cas enzyme.

In some embodiments, the Type V CRISPR-Cas enzyme is a programmable Cas12 nuclease. Type V CRISPR-Cas enzymes (e.g., Cas12 or Cas14) lack an HNH domain. A Cas12 nuclease of the present disclosure cleaves a nucleic acids via a single catalytic RuvC domain. The RuvC domain is within a nuclease, or "NUC" lobe of the protein, and the Cas12 nucleases further comprise a recognition, or "REC" lobe. The REC and NUC lobes are connected by a bridge helix and the Cas12 enzymes additionally include two domains for PAM recognition termed the PAM interacting (PI) domain and the wedge (WED) domain. (Murugan et al., Mol Cell. 2017 Oct. 5; 68(1): 15-25). A programmable Cas12 nuclease can be a Cas12a (also referred to as Cpf1) enzyme, a Cas12b enzyme, Cas12c enzyme, Cas12d enzyme, or a Cas12e enzyme. In some cases, a suitable Cas12 enzyme comprises an amino acid sequence having at least 80%, at least 85%, at least 90%, at least 95%, at least 98%, at least 99%, or 100%, amino acid sequence identity to any one of SEQ ID NO: 18-SEQ ID NO: 60.

TABLE 1

Cas12 Enzyme Sequences

| SEQ ID NO | Description | Sequence |
|---|---|---|
| SEQ ID NO: 18 | *Lachnospiraceae bacterium* ND2006 (LbCas12a) | MSKLEKFTNCYSLSKTLRFKAIPVGKTQEN<br>IDNKRLLVEDEKRAEDYKGVKKLLDRYYLS<br>FINDVLHSIKLKNLNNYISLFRKKTRTEKE<br>NKELENLEINLRKEIAKAFKGNEGYKSLFK<br>KDIIETILPEFLDDKDEIALVNSFNGFTTA<br>FTGFFDNRENMFSEEAKSTSIAFRCINENL<br>TRYISNMDIFEKVDAIFDKHEVQEIKEKIL<br>NSDYDVEDFFEGEFFNFVLTQEGIDVYNAI<br>IGGFVTESGEKIKGLNEYINLYNQKTKQKL<br>PKFKPLYKQVLSDRESLSFYGEGYTSDEEV<br>LEVFRNTLNKNSEIFSSIKKLEKLFKNFDE<br>YSSAGIFVKNGPAISTISKDIFGEWNVIRD<br>KWNAEYDDIHLKKKAVVTEKYEDDRRKSFK<br>KIGSFSLEQLQEYADADLSVVEKLKEIIIQ<br>KVDEIYKVYGSSEKLFDADFVLEKSLKKND<br>AVVAIMKDLLDSVKSFENYIKAFFGEGKET<br>NRDESFYGDFVLAYDILLKVDHIYDAIRNY<br>VTQKPYSKDKFKLYFQNPQFMGGWDKDKET<br>DYRATILRYGSKYYLAIMDKKYAKCLQKID<br>KDDVNGNYEKINYKLLPGPNKMLPKVFFSK<br>KWMAYYNPSEDIQKIYKNGTFKKGDMFNLN<br>DCHKLIDFFKDSISRYPKWSNAYDFNFSET<br>EKYKDIAGFYREVEEQGYKVSFESASKKEV<br>DKLVEEGKLYMFQIYNKDFSDKSHGTPNLH<br>TMYFKLLFDENNHGQIRLSGGAELFMRRAS<br>LKKEELVVHPANSPIANKNPDNPKKTTTLS<br>YDVYKDKRFSEDQYELHIPIAINKCPKNIF<br>KINTEVRVLLKHDDNPYVIGIDRGERNLLY<br>IVVVDGKGNIVEQYSLNEIINNFNGIRIKT<br>DYHSLLDKKEKERFEARQNWTSIENIKELK<br>AGYISQVVHKICELVEKYDAVIALEDLNSG<br>FKNSRVKVEKQVYQKFEKMLIDKLNYMVDK<br>KSNPCATGGALKGYQITNKFESFKSMSTQN<br>GFIFYIPAWLTSKIDPSTGFVNLLKTKYTS<br>IADSKKFISSFDRIMYVPEEDLFEFALDYK<br>NFSRTDADYIKKWKLYSYGNRIRIFRNPKK<br>NNVFDWEEVCLTSAYKELFNKYGINYQQGD<br>IRALLCEQSDKAFYSSFMALMSLMLQMRNS<br>ITGRTDVDFLISPVKNSDGIFYDSRNYEAQ |

TABLE 1-continued

Cas12 Enzyme Sequences

| SEQ ID NO | Description | Sequence |
|---|---|---|
| | | ENAILPKNADANGAYNIARKVLWAIGQFKK<br>AEDEKLDKVKIAISNKEWLEYAQTSVKH |
| SEQ ID NO: 19 | *Acidaminococcus* sp. BV316 (AsCas12a) | MTQFEGFTNLYQVSKTLRFELIPQGKTLKH<br>IQEQGFIEEDKARNDHYKELKPIIDRIYKT<br>YADQCLQLVQLDWENLSAAIDSYRKEKTEE<br>TRNALIEEQATYRNAIHDYFIGRTDNLTDA<br>INKRHAEIYKGLFKAELFNGKVLKQLGTVT<br>TTEHENALLRSFDKFTTYFSGFYENRKNVF<br>SAEDISTAIPHRIVQDNFPKFKENCHIFTR<br>LITAVPSLREHFENVKKAIGIFVSTSIEEV<br>FSFPFYNQLLTQTQIDLYNQLLGGISREAG<br>TEKIKGLNEVLNLAIQKNDETAHIIASLPH<br>RFIPLFKQILSDRNTLSFILEEFKSDEEVI<br>QSFCKYKTLLRNENVLETAEALFNELNSID<br>LTHIFISHKKLETISSALCDHWDTLRNALY<br>ERRISELTGKITKSAKEKVQRSLKHEDINL<br>QEIISAAGKELSEAFKQKTSEILSHAHAAL<br>DQPLPTTLKKQEEKEILKSQLDSLLGLYHL<br>LDWFAVDESNEVDPEFSARLTGIKLEMEPS<br>LSFYNKARNYATKKPYSVEKFKLNFQMPTL<br>ASGWDVNKEKNNGAILFVKNGLYYLGIMPK<br>QKGRYKALSFEPTEKTSEGFDKMYYDYFPD<br>AAKMIPKCSTQLKAVTAHFQTHTTPILLSN<br>NFIEPLEITKEIYDLNNPEKEPKKFQTAYA<br>KKTGDQKGYREALCKWIDFTRDFLSKYTKT<br>TSIDLSSLRPSSQYKDLGEYYAELNPLLYH<br>ISFQRIAEKEIMDAVETGKLYLFQIYNKDF<br>AKGHHGKPNLHTLYWTGLFSPENLAKTSIK<br>LNGQAELFYRPKSRMKRMAHRLGEKMLNKK<br>LKDQKTPIPDTLYQELYDYVNHRLSHDLSD<br>EARALLPNVITKEVSHEIIKDRRFTSDKFF<br>FHVPITLNYQAANSPSKFNQRVNAYLKEHP<br>ETPIIGIDRGERNLIYITVIDSTGKILEQR<br>SLNTIQQFDYQKKLDNREKERVAARQAWSV<br>VGTIKDLKQGYLSQVIHEIVDLMIHYQAVV<br>VLENLNFGFKSKRTGIAEKAVYQQFEKMLI<br>DKLNCLVLKDYPAEKVGGVLNPYQLTDQFT<br>SFAKMGTQSGFLFYVPAPYTSKIDPLTGFV<br>DPFVWKTIKNHESRKHFLEGFDFLHYDVKT<br>GDFILHFKMNRNLSFQRGLPGFMPAWDIVF<br>EKNETQFDAKGTPFIAGKRIVPVIENHRFT<br>GRYRDLYPANELIALLEEKGIVFRDGSNIL<br>PKLLENDDSHAIDTMVALIRSVLQMRNSNA<br>ATGEDYINSPVRDLNGVCFDSRFQNPEWPM<br>DADANGAYHIALKGQLLLNHLKESKDLKLQ<br>NGISNQDWLAYIQELRN |
| SEQ ID NO: 20 | *Francisella novicida* U112 (FnCas12a) | MSIYQEFVNKYSLSKTLRFELIPQGKTLEN<br>IKARGLILDDEKRAKDYKKAKQIIDKYHQF<br>FIEEILSSVCISEDLLQNYSDVYFKLKKSD<br>DDNLQKDFKSAKDTIKKQISEYIKDSEKFK<br>NLFNQNLIDAKKGQESDLILWLKQSKDNGI<br>ELFKANSDITDIDEALEIIKSFKGWTTYFK<br>GFHENRKNVYSSNDIPTSIIYRIVDDNLPK<br>FLENKAKYESLKDKAPEAINYEQIKKDLAE<br>ELTFDIDYKTSEVNQRVFSLDEVFEIANFN<br>NYLNQSGITKFNTIIGGKFVNGENTKRKGI<br>NEYINLYSQQINDKTLKKYKMSVLFKQILS<br>DTESKSFVIDKLEDDSDVVTTMQSFYEQIA<br>AFKTVEEKSIKETLSLLFDDLKAQKLDLSK<br>IYFKNDKSLTDLSQQVFDDYSVIGTAVLEY<br>ITQQIAPKNLDNPSKKEQELIAKKTEKAKY<br>LSLETIKLALEEFNKHRDIDKQCRFEEILA<br>NFAAIPMIFDEIAQNKDNLAQISIKYQNQG<br>KKDLLQASAEDDVKAIKDLLDQTNNLLHKL<br>KIFHISQSEDKANILDKDEHFYLVFEECYF<br>ELANIVPLYNKIRNYITQKPYSDEKFKLNF<br>ENSTLANGWDKNKEPDNTAILFIKDDKYYL<br>GVMNKKNNKIFDDKAIKENKGEGYKKIVYK<br>LLPGANKMLPKVFFSAKSIKFYNPSEDILR<br>IRNHSTHTKNGSPQKGYEKFEFNIEDCRKF<br>IDFYKQSISKHPEWKDFGFRFSDTQRYNSI<br>DEFYREVENQGYKLTFENISESYIDSVVNQ |

TABLE 1-continued

| Cas12 Enzyme Sequences | | |
|---|---|---|
| SEQ ID NO | Description | Sequence |
| | | GKLYLFQIYNKDFSAYSKGRPNLHTLYWKA<br>LFDERNLQDVVYKLNGEAELFYRKQSIPKK<br>ITHPAKEAIANKNKDNPKKESVFEYDLIKD<br>KRFTEDKFFFHCPITINFKSSGANKFNDEI<br>NLLLKEKANDVHILSIDRGERHLAYYTLVD<br>GKGNIIKQDTFNIIGNDRMKTNYHDKLAAI<br>EKDRDSARKDWKKINNIKEMKEGYLSQVVH<br>EIAKLVIEYNAIVVFEDLNFGFKRGRFKVE<br>KQVYQKLEKMLIEKLNYLVFKDNEFDKTGG<br>VLRAYQLTAPFETFKKMGKQTGIIYYVPAG<br>FTSKICPVTGFVNQLYPKYESVSKSQEFFS<br>KFDKICYNLDKGYFEFSFDYKNFGDKAAKG<br>KWTIASFGSRLINFRNSDKNHNWDTREVYP<br>TKELEKLLKDYSIEYGHGECIKAAICGESD<br>KKFFAKLTSVLNTILQMRNSKTGTELDYLI<br>SPVADVNGNFFDSRQAPKNMPQDADANGAY<br>HIGLKGLMLLGRIKNNQEGKKLNLVIKNEE<br>YFEFVQNRNN |
| 21 | *Porphyromonas macacae* (PmCas12a) | MKTQHFFEDFTSLYSLSKTIRFELKPIGKT<br>LENIKKNGLIRRDEQRLDDYEKLKKVIDEY<br>HEDFIANILSSFSFSEEILQSYIQNLSESE<br>ARAKIEKTMRDTLAKAFSEDERYKSIFKKE<br>LVKKDIPVWCPAYKSLCKKFDNFTTSLVPF<br>HENRKNLYTSNEITASIPYRIVHVNLPKFI<br>QNIEALCELQKKMGADLYLEMMENLRNVWP<br>SFVKTPDDLCNLKTYNHLMVQSSISEYNRF<br>VGGYSTEDGTKHQGINEWINIYRQRNKEMR<br>LPGLVFLHKQILAKVDSSSFISDTLENDDQ<br>VFCVLRQFRKLFWNTVSSKEDDAASLKDLF<br>CGLSGYDPEAIYVSDAHLATISKNIFDRWN<br>YISDAIRRKTEVLMPRKKESVERYAEKISK<br>QIKKRQSYSLAELDDLLAHYSEESLPAGFS<br>LLSYFTSLGGQKYLVSDGEVILYEEGSNIW<br>DEVLIAFRDLQVILDKDFTEKKLGKDEEAV<br>SVIKKALDSALRLRKFFDLLSGTGAEIRRD<br>SSFYALYTDRMDKLKGLLKMYDKVRNYLTK<br>KPYSIEKFKLHFDNPSLLSGWDKNKELNNL<br>SVIFRQNGYYYLGIMTPKGKNLFKTLPKLG<br>AEEMFYEKMEYKQIAEPMLMLPKVFFPKKT<br>KPAFAPDQSVVDIYNKKTFKTGQKGFNKKD<br>LYRLIDFYKEALTVHEWKLFNFSFSPTEQY<br>RNIGEFFDEVREQAYKVSMVNVPASYIDEA<br>VENGKLYLFQIYNKDFSPYSKGIPNLHTLY<br>WKALFSEQNQSRVYKLCGGGELFYRKASLH<br>MQDTTVHPKGISIHKKNLNKKGETSLFNYD<br>LVKDKRFTEDKFFFHVPISINYKNKKITNV<br>NQMVRDYIAQNDDLQIIGIDRGERNLLYIS<br>RIDTRGNLLEQFSLNVIESDKGDLRTDYQK<br>ILGDREQERLRRRQEWKSIESIKDLKDGYM<br>SQVVHKICNMVVEHKAIVVLENLNLSFMKG<br>RKKVEKSVYEKFERMLVDKLNYLVVDKKNL<br>SNEPGGLYAAYQLTNPLFSFEELHRYPQSG<br>ILFFVDPWNTSLTDPSTGFVNLLGRINYTN<br>VGDARKFFDRFNAIRYDGKGNILFDLDLSR<br>FDVRVETQRKLWTLTTFGSRIAKSKKSGKW<br>MVERIENLSLCFLELFEQFNIGYRVEKDLK<br>KAILSQDRKEFYVRLIYLFNLMMQIRNSDG<br>EEDYILSPALNEKNLQFDSRLIEAKDLPVD<br>ADANGAYNVARKGLMVVQRIKRGDHESIHR<br>IGRAQWLRYVQEGIVE |
| 22 | *Moraxella bovoculi* 237 (MbCas12a) | MLFQDFTHLYPLSKTVRFELKPIDRTLEHI<br>HAKNFLSQDETMADMHQKVKVILDDYHRDF<br>IADMMGEVKLTKLAEFYDVYLKFRKNPKDD<br>ELQKQLKDLQAVLRKEIVKPIGNGGKYKAG<br>YDRLFGAKLFKDGKELGDLAKFVIAQEGES<br>SPKLAHLAHFEKFSTYFTGFHDNRKNMYSD<br>EDKHTAIAYRLIHENLPRFIDNLQILTTIK<br>QKHSALYDQIINELTASGLDVSLASHLDGY<br>HKLLTQEGITAYNTLLGGISGEAGSPKIQG<br>INELINSHHNQHCHKSERIAKLRPLHKQIL<br>SDGMSVSFLPSKFADDSEMCQAVNEFYRHY<br>ADVFAKVQSLFDGFDDHQKDGIYVEHKNLN |

TABLE 1-continued

| Cas12 Enzyme Sequences | | |
|---|---|---|
| SEQ ID NO | Description | Sequence |
| | | ELSKQAFGDFALLGRVLDGYYVDVVNPEFN<br>ERFAKAKTDNAKAKLTKEKDKFIKGVHSLA<br>SLEQAIEHYTARHDDESVQAGKLGQYFKHG<br>LAGVDNPIQKIHNNHSTIKGFLERERPAGE<br>RALPKIKSGKNPEMTQLRQLKELLDNALNV<br>AHFAKLLTTKTTLDNQDGNFYGEFGVLYDE<br>LAKIPTLYNKVRDYLSQKPFSTEKYKLNFG<br>NPTLLNGWDLNKEKDNFGVILQKDGCYYLA<br>LLDKAHKKVFDNAPNTGKSIYQKMIYKYLE<br>VRKQFPKVFFSKEAIAINYHPSKELVEIKD<br>KGRQRSDDERLKLYRFILECLKIHPKYDKK<br>FEGAIGDIQLFKKDKKGREVPISEKDLFDK<br>INGIFSSKPKLEMEDFFIGEFKRYNPSQDL<br>VDQYNIYKKIDSNDNRKKENFYNNHPKFKK<br>DLVRYYYESMCKHEEWEESFEFSKKLQDIG<br>CYVDVNELFTEIETRRLNYKISFCNINADY<br>IDELVEQGQLYLFQIYNKDFSPKAHGKPNL<br>HTLYFKALFSEDNLADPIYKLNGEAQIFYR<br>KASLDMNETTIHRAGEVLENKNPDNPKKRQ<br>FVYDIIKDKRYTQDKFMLHVPITMNFGVQG<br>MTIKEFNKKVNQSIQQYDEVNVIGIDRGER<br>HLLYLTVINSKGEILEQCSLNDITTASANG<br>TQMTTPYHKILDKREIERLNARVGWGEIET<br>IKELKSGYLSHVVHQISQLMLKYNAIVVLE<br>DLNFGFKRGRFKVEKQIYQNFENALIKKLN<br>HLVLKDKADDEIGSYKNALQLTNNFTDLKS<br>IGKQTGFLFYVPAWNTSKIDPETGFVDLLK<br>PRYENIAQSQAFFGKFDKICYNADKDYFEF<br>HIDYAKFTDKAKNSRQIWTICSHGDKRYVY<br>DKTANQNKGAAKGINVNDELKSLFARHHIN<br>EKQPNLVMDICQNNDKEFHKSLMYLLKTLL<br>ALRYSNASSDEDFILSPVANDEGVFFNSAL<br>ADDTQPQNADANGAYHIALKGLWLLNELKN<br>SDDLNKVKLAIDNQTWLNFAQNR |
| 23 | *Moraxella bovoculi* AAX08_00205 (Mb2Cas12a) | MGIHGVPAALFQDFTHLYPLSKTVRFELKP<br>IGRTLEHIHAKNFLSQDETMADMYQKVKVI<br>LDDYHRDFIADMMGEVKLTKLAEFYDVYLK<br>FRKNPKDDGLQKQLKDLQAVLRKESVKPIG<br>SGGKYKTGYDRLFGAKLFKDGKELGDLAKF<br>VIAQEGESSPKLAHLAHFEKFSTYFTGFHD<br>NRKNMYSDEDKHTAIAYRLIHENLPRFIDN<br>LQILTTIKQKHSALYDQIINELTASGLDVS<br>LASHLDGYHKLLTQEGITAYNRIIGEVNGY<br>TNKHNQICHKSERIAKLRPLHKQILSDGMG<br>VSFLPSKFADDSEMCQAVNEFYRHYTDVFA<br>KVQSLFDGFDDHQKDGIYVEHKNLNELSKQ<br>AFGDFALLGRVLDGYYVDVVNPEFNERFAK<br>AKTDNAKAKLTKEKDKFIKGVHSLASLEQA<br>IEHHTARHDDESVQAGKLGQYFKHGLAGVD<br>NPIQKIHNNHSTIKGFLERERPAGERALPK<br>IKSGKNPEMTQLRQLKELLDNALNVAHFAK<br>LLTTKTTLDNQDGNFYGEFGVLYDELAKIP<br>TLYNKVRDYLSQKPFSTEKYKLNFGNPTLL<br>NGWDLNKEKDNFGVILQKDGCYYLALLDKA<br>HKKVFDNAPNTGKNVYQKMVYKLLPGPNKM<br>LPKVFFAKSNLDYYNPSAELLDKYAKGTHK<br>KGDNFNLKDCHALIDFFKAGINKHPEWQHF<br>GFKFSPTSSYRDLSDFYREVEPQGYQVKFV<br>DINADYIDELVEQGKLYLFQIYNKDFSPKA<br>HGKPNLHTLYFKALFSEDNLADPIYKLNGE<br>AQIFYRKASLDMNETTIHRAGEVLENKNPD<br>NPKKRQFVYDIIKDKRYTQDKFMLHVPITM<br>NFGVQGMTIKEFNKKVNQSIQQYDEVNVIG<br>IDRGERHLLYLTVINSKGEILEQRSLNDIT<br>TASANGTQVTTPYHKILDKREIERLNARVG<br>WGEIETIKELKSGYLSHVVHQINQLMLKYN<br>AIVVLEDLNFGFKRGRFKVEKQIYQNFENA<br>LIKKLNHLVLKDKADDEIGSYKNALQLTNN<br>FTDLKSIGKQTGFLFYVPAWNTSKIDPETG<br>FVDLLKPRYENIAQSQAFFGKFDKICYNTD<br>KGYFEFHIDYAKFTDKAKNSRQKWAICSHG<br>DKRYVYDKTANQNKGAAKGINVNDELKSLF<br>ARYHINDKQPNLVMDICQNNDKEFHKSLMC |

TABLE 1-continued

Cas12 Enzyme Sequences

| SEQ ID NO | Description | Sequence |
|---|---|---|
| | | LLKTLLALRYSNASSDEDFILSPVANDEGV<br>FFNSALADDTQPQNADANGAYHIALKGLWL<br>LNELKNSDDLNKVKLAIDNQTWLNFAQNR |
| SEQ ID NO: 24 | *Moraxella bovoculi* AAX11_00205 (Mb3Cas12a) | MGIHGVPAALFQDFTHLYPLSKTVRFELKP<br>IGKTLEHIHAKNFLNQDETMADMYQKVKAI<br>LDDYHRDFIADMMGEVKLTKLAEFYDVYLK<br>FRKNPKDDGLQKQLKDLQAVLRKEIVKPIG<br>NGGKYKAGYDRLFGAKLFKDGKELGDLAKF<br>VIAQEGESSPKLAHLAHFEKFSTYFTGFHD<br>NRKNMYSDEDKHTAIAYRLIHENLPRFIDN<br>LQILATIKQKHSALYDQIINELTASGLDVS<br>LASHLDGYHKLLTQEGITAYNTLLGGISGE<br>AGSRKIQGINELINSHHNQHCHKSERIAKL<br>RPLHKQILSDGMGVSFLPSKFADDSEVCQA<br>VNEFYRHYADVFAKVQSLFDGFDDYQKDGI<br>YVEYKNLNELSKQAFGDFALLGRVLDGYYV<br>DVVNPEFNERFAKAKTDNAKAKLTKEKDKF<br>IKGVHSLASLEQAIEHYTARHDDESVQAGK<br>LGQYFKHGLAGVDNPIQKIHNNHSTIKGFL<br>ERERPAGERALPKIKSDKSPEIRQLKELLD<br>NALNVAHFAKLLTTKTTLHNQDGNFYGEFG<br>ALYDELAKIATLYNKVRDYLSQKPFSTEKY<br>KLNFGNPTLLNGWDLNKEKDNFGVILQKDG<br>CYYLALLDKAHKKVFDNAPNTGKSVYQKMI<br>YKLLPGPNKMLPKVFFAKSNLDYYNPSAEL<br>LDKYAQGTHKKGDNFNLKDCHALIDFFKAG<br>INKHPEWQHFGFKFSPTSSYQDLSDFYREV<br>EPQGYQVKFVDINADYINELVEQGQLYLFQ<br>IYNKDFSPKAHGKPNLHTLYFKALFSEDNL<br>VNPIYKLNGEAEIFYRKASLDMNETTIHRA<br>GEVLENKNPDNPKKRQFVYDIIKDKRYTQD<br>KFMLHVPITMNFGVQGMTIKEFNKKVNQSI<br>QQYDEVNVIGIDRGERHLLYLTVINSKGEI<br>LEQRSLNDITTASANGTQMTTPYHKILDKR<br>EIERLNARVGWGEIETIKELKSGYLSHVVH<br>QISQLMLKYNAIVVLEDLNFGFKRGRFKVE<br>KQIYQNFENALIKKLNHLVLKDKADDEIGS<br>YKNALQLTNNFTDLKSIGKQTGFLFYVPAW<br>NTSKIDPETGFVDLLKPRYENIAQSQAFFG<br>KFDKICYNADRGYFEFHIDYAKFNDKAKNS<br>RQIWKICSHGDKRYVYDKTANQNKGATIGV<br>NVNDELKSLFTRYHINDKQPNLVMDICQNN<br>DKEFHKSLMYLLKTLLALRYSNASSDEDFI<br>LSPVANDEGVFFNSALADDTQPQNADANGA<br>YHIALKGLWLLNELKNSDDLNKVKLAIDNQ<br>TWLNFAQNR |
| SEQ ID NO: 25 | *Thiomicrospira* sp. XS5 (TsCas12a) | MGIHGVPAATKTFDSEFFNLYSLQKTVRFE<br>LKPVGETASFVEDFKNEGLKRVVSEDERRA<br>VDYQKVKEIIDDYHRDFIEESLNYFPEQVS<br>KDALEQAFHLYQKLKAAKVEEREKALKEWE<br>ALQKKLREKVVKCFSDSNKARFSRIDKKEL<br>IKEDLINWLVAQNREDDIPTVETFNNFTTY<br>FTGFHENRKNIYSKDDHATAISFRLIHENL<br>PKFFDNVISFNKLKEGFPELKFDKVKEDLE<br>VDYDLKHAFEIEYFVNFVTQAGIDQYNYLL<br>GGKTLEDGTKKQGMNEQINLFKQQQTRDKA<br>RQIPKLIPLFKQILSERTESQSFIPKQFES<br>DQELFDSLQKLHNNCQDKFTVLQQAILGLA<br>EADLKKVFIKTSDLNALSNTIFGNYSVFSD<br>ALNLYKESLKTKKAQEAFEKLPAHSIHDLI<br>QYLEQFNSSLDAEKQQSTDTVLNYFIKTDE<br>LYSRFIKSTSEAFTQVQPLFELEALSSKRR<br>PPESEDEGAKGQEGFEQIKRIKAYLDTLME<br>AVHFAKPLYLVKGRKMIEGLDKDQSFYEAF<br>EMAYQELESLIIPIYNKARSYLSRKPFKAD<br>KFKINFDNNTLLSGWDANKETANASILFKK<br>DGLYYLGIMPKGKTFLFDYFVSSEDSEKLK<br>QRRQKTAEEALAQDGESYFEKIRYKLLPGA<br>SKMLPKVFFSNKNIGFYNPSDDILRIRNTA<br>SHTKNGTPQKGHSKVEFNLNDCHKMIDFFK<br>SSIQKHPEWGSFGFTFSDTSDFEDMSAFYR<br>EVENQGYVISFDKIKETYIQSQVEQGNLYL |

TABLE 1-continued

Cas12 Enzyme Sequences

| SEQ ID NO | Description | Sequence |
|---|---|---|
| | | FQIYNKDFSPYSKGKPNLHTLYWKALFEEA<br>NLNNVVAKLNGEAEIFFRRHSIKASDKVVH<br>PANQAIDNKNPHTEKTQSTFEYDLVKDKRY<br>TQDKFFFHVPISLNFKAQGVSKFNDKVNGF<br>LKGNPDVNIIGIDRGERHLLYFTVVNQKGE<br>ILVQESLNTLMSDKGHVNDYQQKLDKKEQE<br>RDAARKSWTTVENIKELKEGYLSHVVHKLA<br>HLIIKYNAIVCLEDLNFGFKRGRFKVEKQV<br>YQKFEKALIDKLNYLVFKEKELGEVGHYLT<br>AYQLTAPFESFKKLGKQSGILFYVPADYTS<br>KIDPTTGFVNFLDLRYQSVEKAKQLLSDFN<br>AIRFNSVQNYFEFEIDYKKLTPKRKVGTQS<br>KWVICTYGDVRYQNRRNQKGHWETEEVNVT<br>EKLKALFASDSKTTTVIDYANDDNLIDVIL<br>EQDKASFFKELLWLLKLTMTLRHSKIKSED<br>DFILSPVKNEQGEFYDSRKAGEVWPKDADA<br>NGAYHIALKGLWNLQQINQWEKGKTLNLAI<br>KNQDWFSFIQEKPYQE |
| SEQ ID NO: 26 | *Butyrivibrio* sp. NC3005 (BsCas12a) | MGIHGVPAAYYQNLTKKYPVSKTIRNELIP<br>IGKTLENIRKNNILESDVKRKQDYEHVKGI<br>MDEYHKQLINEALDNYMLPSLNQAAEIYLK<br>KHVDVEDREEFKKTQDLLRREVTGRLKEHE<br>NYTKIGKKDILDLLEKLPSISEEDYNALES<br>FRNFYTYFTSYNKVRENLYSDEEKSSTVAY<br>RLINENLPKFLDNIKSYAFVKAAGVLADCI<br>EEEEQDALFMVETFNMTLTQEGIDMYNYQI<br>GKVNSAINLYNQKNHKVEEFKKIPKMKVLY<br>KQILSDREEVFIGEFKDDETLLSSIGAYGN<br>VLMTYLKSEKINIFFDALRESEGKNVYVKN<br>DLSKTTMSNIVFGSWSAFDELLNQEYDLAN<br>ENKKKDDKYFEKRQKELKKNKSYTLEQMSN<br>LSKEDISPIENYIERISEDIEKICIYNGEF<br>EKIVVNEHDSSRKLSKNIKAVKVIKDYLDS<br>IKELEHDIKLINGSGQELEKNLVVYVGQEE<br>ALEQLRPVDSLYNLTRNYLTKKPFSTEKVK<br>LNFNKSTLLNGWDKNKETDNLGILFFKDGK<br>YYLGIMNTTANKAFVNPPAAKTENVFKKVD<br>YKLLPGSNKMLPKVFFAKSNIGYYNPSTEL<br>YSNYKKGTHKKGPSFSIDDCHNLIDFFKES<br>IKKHEDWSKFGFEFSDTADYRDISEFYREV<br>EKQGYKLTFTDIDESYINDLIEKNELYLFQ<br>IYNKDFSEYSKGKLNLHTLYFMMLFDQRNL<br>DNVVYKLNGEAEVFYRPASIAENELVIHKA<br>GEGIKNKNPNRAKVKETSTFSYDIVKDKRY<br>SKYKFTLHIPITMNFGVDEVRRFNDVINNA<br>LRTDDNVNVIGIDRGERNLLYVVVINSEGK<br>ILEQISLNSIINKEYDIETNYHALLDERED<br>DRNKARKDWNTIENIKELKTGYLSQVVNVV<br>AKLVLKYNAIICLEDLNFGFKRGRQKVEKQ<br>VYQKFEKMLIEKLNYLVIDKSREQVSPEKM<br>GGALNALQLTSKFKSFAELGKQSGIIYYVP<br>AYLTSKIDPTTGFVNLFYIKYENIEKAKQF<br>FDGFDFIRFNKKDDMFEFSFDYKSFTQKAC<br>GIRSKWIVYTNGERIIKYPNPEKNNLFDEK<br>VINVTDEIKGLFKQYRIPYENGEDIKEIII<br>SKAEADFYKRLFRLLHQTLQMRNSTSDGTR<br>DYIISPVKNDRGEFFCSEFSEGTMPKDADA<br>NGAYNIARKGLWVLEQIRQKDEGEKVNLSM<br>TNAEWLKYAQLHLL |
| SEQ ID NO: 27 | AacCas12b | MAVKSIKVKLRLDDMPEIRAGLWKLHKEVN<br>AGVRYYTEWLSLLRQENLYRRSPNGDGEQE<br>CDKTAEECKAELLERLRARQVENGHRGPAG<br>SDDELLQLARQLYELLVPQAIGAKGDAQQI<br>ARKFLSPLADKDAVGGLGIAKAGNKPRWVR<br>MREAGEPGWEEEKEKAETRKSADRTADVLR<br>ALADFGLKPLMRVYTDSEMSSVEWKPLRKG<br>QAVRTWDRDMFQQAIERMMSWESWNQRVGQ<br>EYAKLVEQKNRFEQKNFVGQEHLVHLVNQL<br>QQDMKEASPGLESKEQTAHYVTGRALRGSD<br>KVFEKWGKLAPDAPFDLYDAEIKNVQRRNT<br>RRFGSHDLFAKLAEPEYQALWREDASFLTR<br>YAVYNSILRKLNHAKMFATFTLPDATAHPI |

TABLE 1-continued

Cas12 Enzyme Sequences

| SEQ ID NO | Description | Sequence |
|---|---|---|
| | | WTRFDKLGGNLHQYTFLFNEFGERRHAIRF<br>HKLLKVENGVAREVDDVTVPISMSEQLDNL<br>LPRDPNEPIALYFRDYGAEQHFTGEFGGAK<br>IQCRRDQLAHMHRRRGARDVYLNVSVRVQS<br>QSEARGERRPPYAAVFRLVGDNHRAFVHFD<br>KLSDYLAEHPDDGKLGSEGLLSGLRVMSVD<br>LGLRTSASISVFRVARKDELKPNSKGRVPF<br>FFPIKGNDNLVAVHERSQLLKLPGETESKD<br>LRAIREERQRTLRQLRTQLAYLRLLVRCGS<br>EDVGRRERSWAKLIEQPVDAANHMTPDWRE<br>AFENELQKLKSLHGICSDKEWMDAVYESVR<br>RVWRHMGKQVRDWRKDVRSGERPKIRGYAK<br>DVVGGNSIEQIEYLERQYKFLKSWSFFGKV<br>SGQVIRAEKGSRFAITLREHIDHAKEDRLK<br>KLADRIIMEALGYVYALDERGKGKWVAKYP<br>PCQLILLEELSEYQFNNDRPPSENNQLMQW<br>SHRGVFQELINQAQVHDLLVGTMYAAFSSR<br>FDARTGAPGIRCRRVPARCTQEHNPEPFPW<br>WLNKFVVEHTLDACPLRADDLIPTGEGEIF<br>VSPFSAEEGDFHQIHADLNAAQNLQQRLWS<br>DFDISQIRLRCDWGEVDGELVLIPRLTGKR<br>TADSYSNKVFYTNTGVTYYERERGKKRRKV<br>FAQEKLSEEEAELLVEADEAREKSVVLMRD<br>PSGIINRGNWTRQKEFWSMVNQRIEGYLVK<br>QIRSRVPLQDSACENTGDI |
| SEQ ID NO: 28 | Cas12 Variant | MKKIDNFVGCYPVSKTLRFKAIPIGKTQEN<br>IEKKRLVEEDEVRAKDYKAVKKLIDRYHRE<br>FIEGVLDNVKLDGLEEYYMLFNKSDREESD<br>NKKIEIMEERFRRVISKSFKNNEEYKKIFS<br>KKIIEEILPNYIKDEEEKELVKGFKGFYTA<br>FVGYAQNRENMYSDEKKSTAISYRIVNENM<br>PRFITNIKVFEKAKSILDVDKINEINEYIL<br>NNDYYVDDFFNIDFFNYVLNQKGIDIYNAI<br>IGGIVTGDGRKIQGLNECINLYNQENKKIR<br>LPQFKPLYKQILSESESMSFYIDEIESDDM<br>LIDMLKESLQIDSTINNAIDDLKVLFNNIF<br>DYDLSGIFINNGLPITTISNDVYGQWSTIS<br>DGWNERYDVLSNAKDKESEKYFEKRRKEYK<br>KVKSFSISDLQELGGKDLSICKKINEIISE<br>MIDDYKSKIEEIQYLFDIKELEKPLVTDLN<br>KIELIKNSLDGLKRIERYVIPFLGTGKEQN<br>RDEVFYGYFIKCIDAIKEIDGVYNKTRNYL<br>TKKPYSKDKFKLYFENPQLMGGWDRNKESD<br>YRSTLLRKNGKYYVAIIDKSSSNCMMNIEE<br>DENDNYEKINYKLLPGPNKMLPKVFFSKKN<br>REYFAPSKEIERIYSTGTFKKDTNFVKKDC<br>ENLITFYKDSLDRHEDWSKSFDFSFKESSA<br>YRDISEFYRDVEKQGYRVSFDLLSSNAVNT<br>LVEEGKLYLFQLYNKDFSEKSHGIPNLHTM<br>YFRSLFDDNNKGNIRLNGGAEMFMRRASLN<br>KQDVTVHKANQPIKNKNLLNPKKTTTLPYD<br>VYKDKRFTEDQYEVHIPITMNKVPNNPYKI<br>NHMVREQLVKDDNPYVIGIDRGERNLIYVV<br>VVDGQGHIVEQLSLNEIINENNGISIRTDY<br>HTLLDAKERERDESRKQWKQIENIKELKEG<br>YISQVVHKICELVEKYDAVIALEDLNSGFK<br>NSRVKVEKQVYQKFEKMLITKLNYMVDKKK<br>DYNKPGGVLNGYQLTTQFESFSKMGTQNGI<br>MFYIPAWLTSKMDPTTGFVDLLKPKYKNKA<br>DAQKFFSQFDSIRYDNQEDAFVFKVNYTKF<br>PRTDADYNKEWEIYTNGERIRVFRNPKKNN<br>EYDYETVNVSERMKELFDSYDLLYDKGELK<br>ETICEMEESKFFEELIKLFRLTLQMRNSIS<br>GRTDVDYLISPVKNSNGYFYNSNDYKKEGA<br>KYPKDADANGAYNIARKVLWAIEQFKMADE<br>DKLDKTKISIKNQEWLEYAQTHCE |
| SEQ ID NO: 29 | Cas12 Variant | MATLVSFTKQYQVQKTLRFELIPQGKTQAN<br>IDAKGFINDDLKRDENYMKVKGVIDELHKN<br>FIEQTLVNVDYDWRSLATAIKNYRKDRSDT<br>NKKNLEEYDEETQDAIACFDKFTTYFVGFH<br>ENRKNMYSTEAKSTSVAYRVVNENKTQEAA<br>RKEIIAWFEGKRGNSAFKNNQKSFYGKLFK |

TABLE 1-continued

Cas12 Enzyme Sequences

| SEQ ID NO | Description | Sequence |
|---|---|---|
| | | KELFSEILRSDDLFSKFLSNCEAFSVLEAV<br>CPNVLVEAEQELHLHKAFSDLKLSDVFKVE<br>AYNKYLSQTGIDYYNQIIGGISSAEGVRKI<br>RGVNEVVNNAIQQNDELKVALRNKQFTMVQ<br>LFKQILSDRSTLSFVSEQFTSDQEVITVVK<br>QFNDDIVNNKVLAVVKTLFENFNSYDLEKI<br>YINSKELASVSNALLKDWSKIRNAVLENKI<br>IELGANPPKTKISAVEKEVKNKDFSIAELA<br>SYNDKYLDKEGNDKEICSIANVVLEAVGAL<br>EIMLAESLPADLKTLENKNKVKGILDAYEN<br>LLHLLNYFKVSAVNDVDLAFYGAFEKVYVD<br>ISGVMPLYNKVRNYATKKPYSVEKFKLNFA<br>MPTLADGWDKNKERDNGSIILLKDGQYYLG<br>VMNPQNKPVIDNAVCNDAKGYQKMVYKMFP<br>EISKMVTKCSTQLNAVKAHFEDNTNDFVLD<br>DTDKFISDLTITKEIYDLNNVLYDGKKKFQ<br>IDYLRNTGDFAGYHKALETWIDFVKEFLSK<br>YRSTAIYDLTTLLPTNYYEKLDVFYSDVNN<br>LCYKIDYENISVEQVNEWVEEGNLYLFKIY<br>NKDFATGSTGKPNLHTMYWNAVFAEENLHD<br>VVVKLNGGAELFYRPKSNMPKVEHRVGEKL<br>VNRKNVNGEPIADSVHKEIYAYANGKISKS<br>ELSENAQEELPLAIIKDVKHNITKDKRYLS<br>DKYFFHVPITLNYKANGNPSAFNTKVQAFL<br>KNNPDVNIIGIDRGERNLLYVVVIDQQGNI<br>IDKKQVSYNKVNGYDYYEKLNQREKERIEA<br>RQSWGAVGKIKELKEGYLSLVVREIADMMV<br>KYNAIVVMENLNAGFKRVRGGIAEKAVYQK<br>FEKMLIDKLNYLVFKDVEAKEAGGVLNAYQ<br>LTDKFDSFEKMGNQSGFLFYVPAAYTSKID<br>PVTGFANVFSTKHITNTEAKKEFICSFNSL<br>RYDEAKDKFVLECDLNKFKIVANSHIKNWK<br>FIIGGKRIVYNSKNKTYMEKYPCEDLKATL<br>NASGIDFSSSEIINLLKNVPANREYGKLFD<br>ETYWAIMNTLQMRNSNALTGEDYIISAVAD<br>DNEKVFDSRTCGAELPKDADANGAYHIALK<br>GLYLLQRIDISEEGEKVDLSIKNEEWFKFV<br>QQKEYAR |
| SEQ ID NO: 30 | Cas12 Variant | MKEQFINRYPLSKTLRFSLIPVGETENNFN<br>KNLLLKKDKQRAENYEKVKCYIDRFHKEYI<br>ESVLSKARIEKVNEYANLYWKSNKDDSDIK<br>AMESLENDDETITKLNTDLYNIFGRNIEDI<br>FSVDYFEFVLTQSGIEIYNSMIGGYTCSDM<br>RKQISKQLTSTEIYKKRLFGKELICEDLPS<br>FLTDKDERETVECFRSFTTYFKGFNTNREN<br>MYSSDGKSTAIAYRCINDNLPRFLDNVKSF<br>QKVFDNLSKTKIQGLNECINLYNQQVAKNE<br>KSKKLPLMKPLYKQILSEKDSVSFIPEKFN<br>SDNEVLHAIDDYYTGHIGDFDLLTELLQSL<br>NTYNANGIFVKSGVAITDISNGAFNSWNVL<br>RSAWNEKYEALHPVTSKTKIDKYIEKQDKI<br>YKAIKSFSLFELQSLGNENGNEITDWYISS<br>INESNSKIKEAYLQAQKLLNSDYEKSYNKR<br>LYKNEKATELVKNLLDAIKEFQKLIKPLNG<br>TGKEENKDELFYGKFTSYYDSIADIDRLYD<br>KVRNYITQKPYSKDKIKLNFDNPQLLGGWD<br>KNKESDYRTVLLHKDGLYYLAVMDKSHSKA<br>FVDAPEITSDDKDYYEKMEYKLLPGPNKML<br>PKVFFASKNIDTFQPSDRILDIRKRESFKK<br>GATFNKAECHEFIDYFKDSIKKHDDWSQFG<br>FKFSPTESYNDISEFYREISDQGYSVRFNK<br>ISKNYIDGLVNNGYIYLFQIYNKDFSKYSK<br>GTPNLHTLYFKMLFDERNLSNVVYKLNGEA<br>EMFYREASIGDKEKITHYANQPIKNKNPDN<br>EKKESVFEYDIVKDKRFTKRQFSLHLPITI<br>NFKAHGQEFLNYDVRKAVKYKDDNYVIGID<br>RGERNLIYISVINSNGEIVEQMSLNEIISD<br>NGHKVDYQKLLDTKEKERDKARKNWTSVEN<br>IKELKEGYISQVVHKICELVIKYDAVIAME<br>DLNFGFKRGRFPVEKQVYQKFENMLISKLN<br>LLIDKKAEPTEDGGLLRAYQLTNKFDGVNK<br>AKQNGIIFYVPAWDTSKIDPATGFVNLLKP<br>KCNTSVPEAKKLFETIDDIKYNANTDMFEF |

TABLE 1-continued

Cas12 Enzyme Sequences

| SEQ ID NO | Description | Sequence |
|---|---|---|
| | | YIDYSKFPRCNSDFKKSWTVCTNSSRILTF RNKEKNNKWDNKQIVLTDEFKSLFNEFGID YKGNLKDSILSISNADFYRRLIKLLSLTLQ MRNSITGSTLPEDDYLISPVANKSGEFYDS RNYKGTNAALPCDADANGAYNIARKALWAI NVLKDTPDDMLNKAKLSITNAEWLEYTQK |
| SEQ ID NO: 31 | Cas12 Variant | MNNPRGAFGGFTNLYSLSKTLRFELKPYLE IPEGEKGKLFGDDKEYYKNCKTYTEYYLKK ANKEYYDNEKVKNTDLQLVNFLHDERIEDA YQVLKPLETERGKLRKAFTPIYEAEGKNLK NKAGKEKKDKDILKESGFKVLIEAPVFDTL HEEFITDSLESAEAKKIDFGNYYGLYEKQK SEQNKDEKKKIDKGILKYIKNNIDEFADKK LKNNEGKEITKKDIETALGAENIEGIFDGF FTYFSGFNQNRENYYSTEEKATAVASRIVD ENLSKFCDNILLYRKNENDYLKIFNFLKNK GKDLKLKNSKFGKENEPEFIPAYDMKNDEK SFSVADFVNCLSQGEIEKYNAKIANANYLI NLYNQNKDGNSSKLSMFKILYKQIGCGEKK DFIKTIKDNAELKQILEKACEAGKKYFIRG KSEDGGVSNIFDFTDYIQSHENYKGVYWSD KAINTISGKYFANWDTLKNKLGDAKVFNKN TGEDKADVKYKVPQAVMLSELFAVLDDNAG EDWREKGIFFKASLFEGDQNKSEIIKNANR PSQALLKMICDDMESLAKNFIDSGDKILKI SDRDYQKDENKQKIKNWLDNALWINQILKY FKVKANKIKGDSIDARIDSGLDMLVFSSDN PAEDYDMIRNYLTQKPQDEINKLKLNFENS SLAGGWDENKEKDNSCIILKDEQDKQYLAV MKYENTKVFEQKNSQLYIADNAAWKKMIYK LVPGASKTLPKVFFSKKWTANRPTPSDIVE IYQKGSFKKENVDFNDKKEKDESRKEKNRE KIIAELQKTCWMDIRYNIDGKIESAKYVNK EKLAKLIDFYKENLKKYPSEEESWDRLFAF GFSDTKSYKSIDQFYIEVDKQGYKLEFVTI NKARLDEYVRDGKIYLFEIRSRDNNLVNGE EKTSAKNLQTIYWNAAFGGDDNKPKLNGEA EIFYRPAIAENKLNKKKDKNGKEIIDGYRF SKEKFIFHCPITLNFCLKETKINDKLNAAL AKPENGQGVYFLGIDRGEKHLAYYSLVNQK GEILEQGTLNLPFLDKNGKSRSIKVEKKSF EKDSNGGIIKDKDGNDKIKIEFVECWNYND LLDARAGDRDYARKNWTTIGTIKELKDGYI SQVVRKIVDLSIYKNTETKEFREMPAFIVL EDLNIGFKRGRQKIEKQVYQKLELALAKKL NFLVDKKADIGEIGSVTKAIQLTPPVNNFG DMENRKQFGNMLYIRADYTSQTDPATGWRK SIYLKSGSESNVKEQIEKSFFDIRYESGDY CFEYRDRHGKMWQLYSSKNGVSLDRFHGER NNSKNVWESEKQPLNEMLDILFDEKRFDKS KSLYEQMFKGGVALTRLPKEINKKDKPAWE SLRFVIILIQQIRNTGKNGDDRNGDFIQSP VRDEKTGEHFDSRIYLDKEQKGEKADLPTS GDANGAYNIARKGIVVAEHIKRGFDKLYIS DEEWDTWLAGDEIWDKWLKENRESLTKTRK |
| SEQ ID NO: 32 | Cas12 Variant | MNGNRIIVYREFVGVTPVAKTLRNELRPIG HTQEHIIHNGLIQEDELRQEKSTELKNIMD DYYREYIDKSLSGVTDLDFTLLFELMNLVQ SSPSKDNKKDKAGKLETLALFNGFSTYFTD FFEKRKNVFTKEAVSTSIAYRIVHENSLTF LANMTSYKKISEKALDEIEVIEKNNQDKMG DWELNQIFNPDFYNMVLIALEKEQSKMREQ ICTHMQSDSNYKNIFNAKFLKEILPDFIKN YNQYDAKQSGIDFYNEICGVVNAHMNLYCQ QTKNNYNLFKMRKLHKQILAYTSTSFEVPK MFEDDMSVYNAVNAFIDETEKGNIIGKLKD IVNKYDELDEKRIYISKDFYETLSCFMSGN WNLITGCVENFYDENIHAKGKSKEEKVKKA VKEDKYKSINDVNDLVEKYIDEKERNEFKN SNAKQYIREISNIITDTETAHLEYDEHISL IESEEKADEMKKRLDMYMNMYHWAKAFIVD EVLDRDEMFYSDIDDIYNILENIVPLYNRV RNYVTQKPYNSKKIKLNFQSPTLANGWSQS KEFDNNAIILIRDNKYYLAIFNAKNKPDKK IIQGNSDKKNDNDYKKMVYNLLPGANKMLP KVFLSKKGIETFKPSDYIISGYNAHKHIKT SENFDISFCRDLIDYFKNSIEKHAEWRKYE FKFSATDSYNDISEFYREVEMQGYRIDWTY ISEADINKLDEEGKIYLFQIYNKDFAENST GKENLHTMYFKNIFSEENLKDIIIKLNGQA ELFYRRASVKNPVKHKKDSVLVNKTYKNQL DNGDVVRIPIPDDIYNEIYKMYNGYIKEND LSEAAKEYLDKVEVRTAQKDIVKDYRYTVD KYFIHTPITINYKVTARNNVNDMAVKYIAQ NDDIHVIGIDRGERNLIYISVIDSHGNIVK QKSYNILNNYDYKKKLVEKEKTREYARKNW KSIGNIKELKEGYISGVVHEIAMLMVEYNA IIAMEDLNYGFKRGRFKVERQVYQKFESML INKLNYFASKGKSVDEPGGLLKGYQLTYVP DNIKNLGKQCGVIFYVPAAFTSKIDPSTGF ISAFNFKSISTNASRKQFFMQFDEIRYCAE KDMFSFGFDYNNFDTYNITMSKTQWTVYTN GERLQSEFNNARRTGKTKSINLTETIKLLL EDNEINYADGHDVRIDMEKMDEDKNSEFFA QLLSLYKLTVQMRNSYTEAEEQEKGISYDK IISPVINDEGEFFDSDNYKESDDKECKMPK DADANGAYCIALKGLYEVLKIKSEWTEDGF DRNCLKLPHAEWLDFIQNKRYE |
| SEQ ID NO: 33 | Cas12 Variant | MKKIDSFVNYYPLSKTLRFSLIPVGKTEDN FNAKLLLEEDEKRAIEYEKVKRYIDRYHKH FIETVLANFHLDDVNEYAELYYKAGKDDKD LKYMEKLEGKMRKSISAAFTKDKKYKEIFG QEIIKNILPEFLENEDEKESVKMFQGFFTY FTGFNDNRKNMYTHEAQTTAISYRCINENL PKFLDNVQSFAKIKESISSDIMNKLDEVCM DLYGVYAQDMFCTDYFSFVLSQSGIDRYNN IIGGYVDDKGVKIQGINEYINLYNQQVDEK NKRLPLMKKLYKQILIEKESISFIPEKFES DNIVINAISDYYHNNVENLFDDFNKLFNEF SEYDDNGIFVTSGLAVTDISNAVFGSWNII SDSWNEEYKDSHPMKKTTNAEKYYEDMKKE YKKNLSFTIAELQRLGEAGCNDECKGDIKE YYKTTVAEKIENIKNAYEISKDLLASDYEK SNDKKLCKNDSAISLLKNLLDSIKDLEKTI KPLLGTGKEENKDDVFYGKFTNLYEMISEI DRLYDKVRNYVTQKPYSKDKIKLNFENPQH LGGWDKNKERDYRSVLLKKEDKYYLAIMDK SNNKAFIDFPDDGECYEKIEYKLLPGPNKM LPKVFFASSNIEYFAPSKKILEIRSRESFK KGDMFNLKDCHEFIDFFKESIKKHEDWSQF GFEFSPTEKYNDISEFYNEVKIQGYSLKYK NVSKKYIDELIECGQLYLFQIYNKDFSVYA KGNPNLHTMYFKMLFDERNLANVVYQLNGG AEMFYRKASIKDSEKIVHHANQPIKNKNAD NVKKESVFEYDIIKDKRFTKRQFSIHIPIT LNFKAKGQNFINNDVRMALKKADENYVIGI DRGERNLLYICVINSKGEIVEQKSLNEIIG DNGYRVDYHKLLDKKEAERDEARKSWGTIE NIKELKEGYLSQIVHEISKLVIKYDAVIAI EDLNSGFKKGRFKVEKQVYQKFENMLCTKL NYLVDKNADANECGGLLKAYQLTNKEDGAN RGRQNGIIFSVPAWLTSKIDPVTGFADLLR PKYKSVSEVEFISKIDNIRYNSKEDYFEF DIDYSKFPNSTASYKKKWTVCTYGERIINV RNKEKNNMWDNKTIVLTDEFKKLFADFGVD VSKNIKESVLAIDSKDFYYRFINLLANTLQ LRNSEVGNVDVDYLISPVKGVDGSFYDSRL VKEKTLPENADANGAYNIARKALWAIDVLK QTKDEELKNANLSIKNAEWLEYVQK |
| SEQ ID NO: 34 | Cas12 Variant | MRTMVTFEDFTKQYQVSKTLRFELIPQGKT LENMKRDGIISVDRQRNEDYQKAKGILDKL YKYILDFTMETVVIDWEALATATEEFRKSK DKKTYEKVQSKIRTALLEHVKKQKVGTEDL FKGMFSSKIITGEVLAAFPEIRLSDEENLI LEKFKDFTTYFTGFFENRKNVFTDEALSTS |

TABLE 1-continued

Cas12 Enzyme Sequences

| SEQ ID NO | Description | Sequence |
|---|---|---|
| | | FTYRLVNDNFIKFFDNCIVFKNVVNISPHM AKSLETCASDLGIFPGVSLEEVFSISFYNR LLTQTGIDQFNQLLGGISGKEGEHKQQGLN EIINLAMQQNLEVKEVLKNKAHRFTPLFKQ ILSDRSTMSFIPDAFADDDEVLSAVDAYRK YLSEKNIGDRAFQLISDMEAYSPELMRIGG KYVSVLSQLLFYSWSEIRDGVKAYKESLIT GKKTKKELENIDKEIKYGVTLQEIKEALPK KDIYEEVKKYAMSVVKDYHAGLAEPLPEKI ETDDERASIKHIMDSMLGLYRFLEYFSHDS IEDTDPVFGECLDTILDDMNETVPLYNKVR NFSTRKVYSTEKFKLNFNNSSLANGWDKNK EQANGAILLRKEGEYFLGIFNSKNKPKLVS DGGAGIGYEKMIYKQFPDFKKMLPKCTISL KDTKAHFQKSDEDFTLQTDKFEKSIVITKQ IYDLGTQTVNGKKKFQVDYPRLTGDMEGYR AALKEWIDFGKEFIQAYTSTAIYDTSLFRD SSDYPDLPSFYKDVDNICYKLTFEWIPDAV IDDCIDDGSLYLFKLHNKDFSSGSIGKPNL HTLYWKALFEEENLSDVVVKLNGQAELFYR PKSLTRPVVHEEGEVIINKTTSTGLPVPDD VYVELSKFVRNGKKGNLTDKAKNWLDKVTV RKMPHAITKDRRFTVDKFFFHVPITLNYKA DSSPYRFNDFVRQYIKDCSDVKIIGIDRGE RNLIYAVVIDGKGNIIEQRSFNTVGTYNYQ EKLEQKEKERQTARQDWATVTKIKDLKKGY LSAVVHELSKMIVKYKAIVALENLNVGFKR MRGGIAERSVYQQFEKALIDKLNYLVFKDE EQSGYGGVLNAYQLTDKFESFSKMGQQTGF LFYVPAAYTSKIDPLTGFINPFSWKHVKNR EDRRNFLNLFSKLYYDVNTHDFVLAYHHSN KDSKYTIKGNWEIADWDILIQENKEVFGKT GTPYCVGKRIVYMDDSTTGHNRMCAYYPHT ELKKLLSEYGIEYTSGQDLLKIIQEFDDDK LVKGLFYIIKAALQMRNSNSETGEDYISSP IEGRPGICFDSRAEADTLPYDADANGAFHI AMKGLLLTERIRNDDKLAISNEEWLNYIQE MRG |
| SEQ ID NO: 35 | Cas12 Variant | MNKDIRKNFTDFVGISEIQKTLRFILIPIG KTAQNIDKYNMFEDDEIRHEYYPILKEACD DFYRNHIDQQFENLELDWSKLDEALASEDR DLINETRATYNIFTDDEISTGSPYRLVNDN FTIFRINNSIYTKNKPFIEEDILEFEKKLK SKRQVLFNRLKNSVDIKGDSKKNKTLSLES SDKNLGKKKTKNTFQYNFNDLFKAKLIKAI LPLYIEYIYEGEKLENAKKALKMYNRFTSR LSNFWQARAKIIKDFESVDDYFTVNAFNKL CTQNGIDKYNSILGGFTTKEREKVKGLNEL FNLAQQSINKGKKGEYRKNIRLGKLTKLKK QILAISDSTSFLIEQIEDDQDLYNKIKDFF ELLLKEEIENENIFTQYANLQKLIEQADLS KIYINAKHLNKISHQVTGKWDSLNKGIALL LENININEESKEKSEVISNGQTKDISSEAY KRYLQIQSEEKDIERLRTQIYFSLEDLEKA LDLVLIDENMDRSDKSILSYVQSPDLNVNF ERDLTDLYSRIMKLEENNEKLLANHSAIDL IKEFLDLIMLRYSRWQILFCDSNYELDQTF YPIYDAVMEILSNIIRLYNLARNYLSRKPD RMKKKKINFNNPTLADGWSESKIPDNSSML FIKDGMYYLGIIKNRAAYSELLEAESLQSS EKKKSENSSYERMNYHFLPDAFRSIPKSSI AMKAVKEHFEINQKTADLLLDTDKFSKPLR ITKEIFDMQYVDLHKNKKKYQVDYLRDTGD KKGYRKALNTWLNFCKDFISKYKGRNLFDY SKIKDADHYETVNEFYNDVDKYSYHIFFTS VAETTVEKFISEGKLYLFQLYNKDFSPHST GKPNLHTIYWRALFSEENLTSKNIKLNGQA EIFFRPKQIETPFTHKKGSILVNRFDVNGN PIPINVYQEIKGFKNNVIKWDDLNKTTQEG LENDQYLYFESEFEIIKDRRYTEDQLFFHV PISFNWDIGSNPKINDLATQYIVNSNDIHI IGIDRGENHLIYYSVIDLQGAIVEQGSLNT ITEYTENKFLNNKTNNLRKIPYKDILQQRE |

TABLE 1-continued

Cas12 Enzyme Sequences

| SEQ ID NO | Description | Sequence |
|---|---|---|
| | | DERADARIKWHAIDKIKDLKDGYLGQIVHF LAKLIIKYNAIVILEDLNYGFKRGRFKVER QVYQKFEMALMKKLNVLVFKDYDIDEIGGP LKPWQLTRPIDSYERMGRQNGILFYVPAAY TSAVDPVTGFANLFYLNNVKNSEKFHFFSK FESIKYHSDQDMFSFAFDYNNFGTTTRIND LSKSKWQVFTNHERSVWNNKEKNYVTQNLT DLIKKLLRTYNIEFKNNQNVLDSILKIENN TDKENFARELFRLFRLTIQLRNTTVNENNT EITENELDYIISPVKDKNGNFFDSRDELKN LPDNGDANGAYNIARKGLLYIEQLQESIKT GKLPTLSISTLDWFNYIMK |
| SEQ ID NO: 36 | Cas12 Variant | MTPIFCNFVVYQIMLFNNNININVKTMNKK HLSDFTNLFPVSKTLRFRLEPQGKTMENIV KAQTIETDEERSHDYEKTKEYIDDYHRQFI DDTLDKFAPQFNLLFKKEMVKHLLPQFVDT DDKKRIVAKFNDFTTYFTGFFTNRENFKVE STGNNDSLQDYLDAYLSANDNRTKQTEEIQ TNLRKAIVSAFKMQMYSDEAKSTSIAYRIV NQNLIKFVENMLTFKSHILPILPQEQLATL YDDFKEYLNVASIAEMFELDHFSIVLTQRQ IEVYNSVIGGRKDENNKQIKPGLNQYINQH NQAVKDKSARLPLLKPLFNQILSEKAGVSF LPKQFKSASEVVKSLNEAYAELSPVLAAIQ DVVTNITDYDCNGIFIKNDLGLTDIAQRFY GNYDAVKRGLRNQYELETPMHNGQKAEKYE EQVAKHLKSIESVSLAQINQVVTDGGDICD YFKAFGATDDGDIQRENLLASINNAHTAIS PVLNKENANDNELRKNTMLIKDLLDAIKRL QWFAKPLLGAGDETNKDQVFYGKFEPLYNQ LDETISPLYDKVRSYLTKKPYSLDKFKINF EKSNLLGGWDPGADRKYQYNAVILRKDNDF YLGIMRDEATSKRKCIQVLDCNDEGLDENF EKVEYKQIKPSQNMPRCAFAKKECEENADI MELKRKKNAKSYNTNKDDKNALIRHYQRYL DRTYPEFGFVYKDADEYDTVKAFTDSMDSQ DYKLSFLQVSETGLNKLVDEGDLYLFKITN KDFSSYAKGRPNLHTIYWRMLFDPKNLANV VYKLEGKAEVFFRRKSLASTTTHKAKQAIK NKSRYNEAVKPQSTFDYDIIKDRRFTADKF EFHVPIKMNFKAAGWNSTRLTNEVREFIKS QGVRHIIGIDRGERHLLYLTMIDMDGNIVK QCSLNAPAQDNARASEVDYHQLLDSKEADR LAARRNWGTIENIKELKQGYLSQVVHLLAT MMVDNDAILVLENLNAGFMRGRQKVEKSVY QKFEKMLIDKLNYIVDKGQSPDKPTGALHA VQLTGLYSDFNKSNMKRANVRQCGFVFYIP AWNTSKIDPVTGFVNLFDTHLSSMGEIKAF FSKFDSIRYNQDKGWFEFKFDYSRFTTRAE GCRTQWTVCTYGERIWTHRSKNQNNQFVND TVNVTQQMLQLLQDCGIDPNGNLKEAIANI DSKKSLETLLHLFKLTVQMRNSVTGSEVDY MISPVADERGHFFDSRESDEHLPANADANG AFNIARKGLMVVRQIMATDDVSKIKFAVSN KDWLRFAQHIDD |
| SEQ ID NO: 37 | Cas12 Variant | MNKGGYVIMEKMTEKNRWENQFRITKTIKE EIIPTGYTKVNLQRVNMLKREMERNEDLKK MKEICDEYYRNMIDVSLRLEQVRTLGWESL IHKYRMLNKDEKEIKALEKEQEDLRKKISK GFGEKKAWTGEQFIKKILPQYLMDHYTGEE LEEKLRIVKKFKGCTMFLSTFFKNRENIFT DKPIHTAVGHRITSENAMLFAANINTYEKM ESNVTLEIERLQREFWRRGINISEIFTDAY YVNVLTQKQIEAYNKICGDINQHMNEYCQK QKLKFSEFRMRELKKQILAVVGEHFEIPEK IESTKEVYRELNEYYESLKELHGQFEELKS VQLKYSQIYVQKKGYDRISRYIGGQWDLIQ ECMKKDCASGMKGTKKNHDAKIEEEVAKVK YQSIEHIQKLVCTYEEDRGHKVTDYVDEFI VSVCDLLGADHIITRDGERIELPLQYEPGT DLLKNDTINQRRLSDIKTILDWHMDMLEWL KTFLVNDLVIKDEEFYMAIEELNERMQCVI |

TABLE 1-continued

Cas12 Enzyme Sequences

| SEQ ID NO | Description | Sequence |
| --- | --- | --- |
| | | SVYNRIRNYVTQKGYEPEKIRICFDKGTIL<br>TGWTTGDNYQYSGFLLMRNDKYYLGIINTN<br>EKSVRKILDGNEECKDENDYIRVGYHLIND<br>ASKQLPRIFVMPKAGKKSEILMKDEQCDYI<br>WDGYCHNKHNESKEFMRELIDYYKRSIMNY<br>DKWEGYCFKFSSTESYDNMQDFYKEVREQS<br>YNISFSYINENVLEQLDKDGKIYLFQVYNK<br>DFAAGSTGTPNLHTMYLQNLFSSQNLELKR<br>LRLGGNAELFYRPGTEKDVTHRKGSILVDR<br>TYVREEKDGIEVRDTVPEKEYLEIYRYLNG<br>KQKGDLSESAKQWLDKVHYREAPCDIIKDK<br>RYAQEKYFLHFSVEINPNAEGQTALNDNVR<br>RWLSEEEDIHVIGIDRGERNLIYVSLMDGK<br>GRIKDQKSYNIVNSGNKEPVDYLAKLKVRE<br>KERDEARRNWKAIGKIKDIKTGYLSYVVHE<br>IVEMAVREKAIIVMEDLNYGFKRGRFKVER<br>QVYQKFEEMLINKLNYVVDKQLSVDEPGGL<br>LRGYQLAFIPKDKKSSMRQNGIVFYVPAGY<br>TSKIDPTTGFVNIFKFPQFGKGDDDGNGKD<br>YDKIRAFFGKFDEIRYECDEKVTADNTREV<br>KERYRFDFDYSKFETHLVHMKKTKWTVYAE<br>GERIKRKKVGNYWTSEVISDIALRMSNTLN<br>IAGIEYKDGHNLVNEICALRGKQAGIILNE<br>LLEIVRLTVQLRNSTTEGDVDERDEIISPV<br>LNEKYGCFYHSTEYKQQNGDVLPKDADANG<br>AYCIGLKGIYEIRQIKNKWKEDMTKGEGKA<br>LNEGMRISHDQWFEFIQNMNKGE |
| SEQ ID NO: 38 | Cas12 Variant | MNELVKNRCKQTKTICQKLIPIGKTRETIE<br>KYNLMEIDRKIAANKELMNKLFSLIAGKHI<br>NDTLSKCTDLDFEPLLTSLSSLNNAKENDR<br>DNLREYYDSVFEEKKTLAEEISSRLTAVKF<br>AGKDFFTKNIPDFLETYEGDDKNEMSELVS<br>LVIENTVTAGYVKKLEKIDRSMEYRLVSGT<br>VVKRVLTDNADIYEKNIEKAKDFDYGVLNI<br>DEASQFTTLVAKDYANYLTADGIAIYNVGI<br>GKINLALNEYCQKNKEYSYNKLALLPLQKM<br>LYGEKLSLFEKLEDFTSDEELINSYNKFAK<br>TVNESGLAEIIKKAVPSYDEIVIKPNKISN<br>YSNSITGHWSLVNRIMKDYLENNGIKNADK<br>YMEKGLTLSEIGDALENKNIKHSDFISNLI<br>NDLGHTYTEIKENKESLKKDESVNALIIKK<br>ELDMLLSILQNLKVFDIDNEMFDTGFGIEV<br>SKAIEILGYGVPLYNKIRNYITKKPDPKKK<br>FMTKFGSATIGTGITTSVEGSKKATFLKDG<br>DAVFLLLYNTAGCKANNVSVSNLADLINSS<br>LEIENSGKCYQKMIYQTPGDIKKQIPRVFV<br>YKSEDDDLIKDFKAGLHKTDLSFLNGRLIP<br>YLKEAFATHETYKNYTFSYRNSYESYDEFC<br>EHMSEQAYILEWKWIDKKLIDDLVEDGSLL<br>MFRVWNRFMKKKEGKISKHAKIVNELFSDE<br>NASNAAIKLLSVFDIFYRDKQIDNPIVHKA<br>GTTLYNKRTKDGEVIVDYTTMVKNKEKRPN<br>VYTTTKKYDIIKDRRYTEEQFEIHLHVNIG<br>KEENKEKLETSKVINEKKNTLVVTRSNEHL<br>LYVVIFDENDNILLKKSLNTVKGMNFKSKL<br>EVVEIQKKENMQSWKTVGSNQALMEGYLSF<br>AIKEIADLVKEYDAILVLEQNSVGKNILNE<br>RVYTRFKEMLITNLSLDVDYENKDFYSYTE<br>LGGKVASWRDCVTNGICIQVPSAYKYKDPT<br>TSFSTISMYAKTTAEKSKKLKQIKSFKYNR<br>ERGLFELVIAKGVGLENNIVCDSFGSRSII<br>ENDISKEVSCTLKIEKYLIDAGIEYNDEKE<br>VLKDLDTAAKTDAVHKAVTLLLKCFNESPD<br>GRYYISPCGEHFTLCDAPEVLSAINYYIRS<br>RYIREQIVEGVKKMEYKKTILLAK |
| SEQ ID NO: 39 | Cas12 Variant | MNYKTGLEDFIGKESLSKTLRNALIPTEST<br>KIHMEEMGVIRDDELRAEKQQELKEIMDDY<br>YRTFIEEKLGQIQGIQWNSLFQKMEETMED<br>ISVRKDLDKIQNEKRKEICCYFTSDKRFKD<br>LFNAKLITDILPNFIKDNKEYTEEEKAEKE<br>QTRVLFQRFATAFTNYFNQRRNNFSEDNIS<br>TAISFRIVNENSEIHLQNMRAFQRIEQQYP |

TABLE 1-continued

Cas12 Enzyme Sequences

| SEQ ID NO | Description | Sequence |
| --- | --- | --- |
| | | EEVCGMEEEYKDMLQEWQMKHIYSVDFYDR<br>ELTQPGIEYYNGICGKINEHMNQFCQKNRI<br>NKNDFRMKKLHKQILCKKSSYYEIPFRFES<br>DQEVYDALNEFIKTMKKKEIIRRCVHLGQE<br>CDDYDLGKIYISSNKYEQISNALYGSWDTI<br>RKCIKEEYMDALPGKGEKKEEKAEAAAKKE<br>EYRSIADIDKIISLYGSEMDRTISAKKCIT<br>EICDMAGQISIDPLVCNSDIKLLQNKEKTT<br>EIKTILDSFLHVYQWGQTFIVSDIIEKDSY<br>FYSELEDVLEDFEGITTLYNHVRSYVTQKP<br>YSTVKFKLHFGSPTLANGWSQSKEYDNNAI<br>LLMRDQKFYLGIFNVRNKPDKQIIKGHEKE<br>EKGDYKKMIYNLLPGPSKMLPKVFITSRSG<br>QETYKPSKHILDGYNEKRHIKSSPKFDLGY<br>CWDLIDYYKECIHKHPDWKNYDFHFSDTKD<br>YEDISGFYREVEMQGYQIKWTYISADEIQK<br>LDEKGQIFLFQIYNKDFSVHSTGKDNLHTM<br>YLKNLFSEENLKDIVLKLNGEAELFFRKAS<br>IKTPIVHKKGSVLVNRSYTQTVGNKEIRVS<br>IPEEYYTEIYNYLNHIGKGKLSSEAQRYLD<br>EGKIKSFTATKDIVKNYRYCCDHYFLHLPI<br>TINFKAKSDVAVNERTLAYIAKKEDIHIIG<br>IDRGERNLLYISVVDVHGNIREQRSFNIVN<br>GYDYQQKLKDREKSRDAARKNWEEIEKIKE<br>LKEGYLSMVIHYIAQLVVKYNAVVAMEDLN<br>YGFKTGRFKVERQVYQKFETMLIEKLHYLV<br>FKDREVCEEGGVLRGYQLTYIPESLKKVGK<br>QCGFIFYVPAGYTSKIDPTTGFVNLFSFKN<br>LTNRESRQDFVGKFDEIRYDRDKKMFEFSF<br>DYNNYIKKGTILASTKWKVYTNGTRLKKIV<br>VNGKYTSQSMEVELTDAMEKMLQRAGIEYH<br>DGKDLKGQIVEKGIEAEIIDIFRLTVQMRN<br>SRSESEDREYDRLISPVLNDKGEFFDTATA<br>DKTLPQDADANGAYCIALKGLYEVKQIKEN<br>WKENEQFPRNKLVQDNKTWFDFMQKKRYL |
| SEQ ID NO: 40 | Cas12 Variant | MEDKQFLERYKEFIGLNSLSKTLRNSLIPV<br>GSTLKHIQEYGILEEDSLRAQKREELKGIM<br>DDYYRNYIEMHLRDVHDIDWNELFEALTEV<br>KKNQTDDAKKRLEKIQEKKRKEIYQYLSDD<br>AVFSEMFKEKMISGILPDFIRCNEGYSEEE<br>KEEKLKTVALFHRFTSSFNDFFLNRKNVFT<br>KEAIVTAIGYRVVHENAEIFLENMVAFQNI<br>QKSAESQISIIERKNEHYFMEWKLSHIFTA<br>DYYMMLMTQKAIEHYNEMCGVVNQQMREYC<br>QKEKKNWNLYRMKRLHKQILSNASTSFKIP<br>EKYENDAEVYESVNSFLQNVMEKTVMERIA<br>VLKNSTDNFDLSKIYITAPYYEKISNYLCG<br>SWNTITDCLTHYYEQQIAGKGARKDQKVKA<br>AVKADKWKSLSEIEQLLKEYARAEEVKRKP<br>EEYIAEIENIVSLKEAHLLEYHPEVNLIEN<br>EKYATEIKDVLDNYMELFHWMKWFYIEEAV<br>EKEVNFYGELDDLYEEIKDIVPLYNKVRNY<br>VTQKPYSDTKIKLNFGTPTLANGWSKSKEY<br>DYNAILLQKDGKYYMGIFNPIQKPEKEIIE<br>GHSQPLEGNEYKKMVYYYLPSANKMLPKVL<br>LSKKGMEIYQPSEYIINGYKERRHIKSEEK<br>FDLQFCHDLIDYFKSGIERNSDWKVFGFDF<br>SDTDTYQDISGFYREVEDQGYKIDWTYIKE<br>ADIDRLNEEGKLYLFQIYNKDFSEKSTGRE<br>NLHTMYLKNLFSEENVREQVLKLNGEAEIF<br>FRKSSVKKPIIHKKGTMLVNRTYMEEVNGN<br>SVRRNIPEKEYQEIYNYKNHRLKGELSTEA<br>KKYLEKAVCHETKKDIVKDYRYSVDKFFIH<br>LPITINYRASGKETLNSVAQRYIAHQNDMH<br>VIGIDRGERNLIYVSVINMQGEIKEQKSFN<br>IINEFNYKEKLKEREQSRGAARRNWKEIGQ<br>IKDLKEGYLSGVIHEIAKMMIKYHAIIAME<br>DLNYGFKRGRFKVERQVYQKFENMLIQKLN<br>YLVFKDRPADEDGGVLRGYQLAYIPDSVKK<br>MGRQCGMIFYVPAAFTSKIDPTTGFVDIFK<br>HKVYTTEQAKREFILSFDEICYDVERQLFR<br>FTFDYANFVTQNVTLARNNWTIYTNGTRAQ<br>KEFGNGRMRDKEDYNPKDKMVELLESEGIE |

TABLE 1-continued

Cas12 Enzyme Sequences

| SEQ ID NO | Description | Sequence |
|---|---|---|
| | | FKSGKNLLPALKKVSNAKVFEELQKIVRFT<br>VQLRNSKSEENDVDYDHVISPVLNEEGNFF<br>DSSKYKNKEEKKESLLPVDADANGAYCIAL<br>KGLYIMQAIQKNWSEEKALSPDVLRLNNND<br>WFDYIQNKRYR |
| SEQ ID NO: 41 | Cas12 Variant | MEKSLNDFIGLYSVSKTLRFELKPVSETLE<br>NIKKFHFLEEDKKKANDYKDVKKIIDNYHK<br>YFIDDVLKNASFNWKKLEEAIREYNKNKSD<br>DSALVAEAALKTFQKFTSYFTGFQENRKNV<br>YSAEAIPTAVPYRIVNDNFPKFLQNVQKKL<br>GDAILKLFTSDKRYKALTAATPKELFESIL<br>PDWFGEQCNQDLNKLIFKTIQEKCPQIIDE<br>VEKELSSYLGKEKLAGIFTLESFNKYLGQG<br>GKENQRGIDFYNQIIGGVVEKEGGINLRGV<br>NQFLNLYWQQHPDFTKEDRRIKMVPLYKQI<br>LSDRSSLSFKIESIENDEELKNALLECADK<br>LELKNDEKKSIFEEVCDLFSSVKNLDLSGI<br>YINRKDINSVSRILTGDWSWLQSRMNVYAE<br>EKFTTKAEKARWQKSLDDEGENKSKGFYSL<br>TDLNEVLEYSSENVAETDIRITDYFEHRCR<br>YYVDKETEMFVQGSELVALSLQEMCDDILK<br>KRKAMNTVLENLSSENKLREKTDDVAVIKE<br>YLDAVQELLHRIKPLKVNGVGDSTFYSVYD<br>SIYSALSEVISVYNKTRNYITKKAASPEKY<br>KLNFDNPTLADGWDLNKEQANTSVILRKDG<br>MFYLGIMNPKNKPKFAEKYDCGNESCYEKM<br>IYKQFDATKQIPKCSTQKKEVQKYFLSGAT<br>EPYILNDKKSFKSELIITKDIWFMNNHVWD<br>GEKFVPKRDNETRPKKFQIGYFKQTGDFDG<br>YKNALSNWISFCKNFLQSYLSATVYDYNFK<br>NSEEYEGLDEFYNYLNATCYKLNFINIPET<br>EINKMVSEGKLYLFQIYNKDFASGSTGMPN<br>MHTLYWKNLFSDENLKNVCLKLNGEAELFY<br>RPAGIKEPVIHKEGSYLVNRTTEDGESIPE<br>KIYFEIYKNANGKLEKLSDEAQNYISNHEV<br>VIKKAGHEIIKDRHYTEPKFLFHVPLTINF<br>KASGNSYSINENVRKFLKNNPDVNIIGLDR<br>GERHLIYLSLINQKGEIIKQFTFNEVERNK<br>NGRTIKVNYHEKLDQREKERDAARKSWQAI<br>GKIAELKEGYLSAVIHQLTKLMVEYNAVVV<br>MEDLNFGFKRGRFHVEKQVYQKFEHILIDK<br>SNYLVFKDRGLNEPGGVLNGYQIAGQFESF<br>QKLGKQSGMLFYVPAGYTSKIDPKTGFVSM<br>MNFKDLTNVHKKRDFFSKFDNIHYDEANGS<br>FVFTFDYKKFDGKAKEEMKLTKWSVYSRDK<br>RIVYFAKTKSYEDVLPTEKLQKIFESNGID<br>YKSGNNIQDSVMAIGADLKEGAKPSKEISD<br>FWDGLLSNFKLILQMRNSNARTGEDYIISP<br>VMADDGTFFDSREEFKKGEDAKLPLDADAN<br>GAYHIALKGLSLINKINLSKDEELKKFDMK<br>ISNADWFKFAQEKNYAK |
| SEQ ID NO: 42 | Cas12 Variant | MEEKKMSKIEKFIGKYKISKTLRFRAVPVG<br>KTQDNIEKKGILEKDKKRSEDYEKVKAYLD<br>SLHRDFIENTLKKVKLNELNEYACLFFSGT<br>KDDGDKKFFTSLNGYVNNRKNLYVSDAKPT<br>SIAYRCINENLPKFLRNVECYKKVVKMEKL<br>EEKMRKTISNEFCNDEMYKKIFSEKILSEN<br>NEEDVSDIVSSYKGQVIPKEQIEYMSNNLN<br>LSPYRIEDCFNIDFFEFCLSQGGIDLYNTF<br>IGGYSKKDGTKVQGINEIVNLYNQKNKKDK<br>EKYKLPQFTPLFKQILSDRDTKSFSIEKLE<br>NIYEVVELVKKSYSDEMFDDIETVFSNLNY<br>YDASGIYVKNGPAITHISMNLTKDWATIRN<br>NWNYEYDEKHSTKKNKNIEKYEDTRNTMYK<br>KIDSFTLEYISRLVGKDIDELVKYFENEVA<br>NFVMDIKKTYSKLTPLFDRCQKENFDISED<br>EVNDIKGYLDNVKLLESFMKSFTINGKENN<br>IDYVFYGKFTDDYDKLHEFDHIYNKVRNYI<br>TTSRKPYKLDKYKLYFDNPQLLGGWDINKE<br>KDYRTVMLTKDGKYYFAIIDKGEHPFDNIP<br>KDYFDNNGYYKKIIYRQIPNAAKYLSSKQI<br>VPQNPPEEVKRILDKKKADSKSLTEEEKNI |

TABLE 1-continued

Cas12 Enzyme Sequences

| SEQ ID NO | Description | Sequence |
|---|---|---|
| | | FIDYIKSDFLKNYKLLFDKNNNPYFNFAFR<br>ESSTYESLNEFFEDVERQAYSVRYENLPAD<br>YIDNLVNEGKIYLFEIYSKDFSEYSKGTNN<br>LHTMYFKALFDNDNLKNTVFKLSGNAELFI<br>RPASIKKDELVIHPKNQLLQNKNPLNPKKQ<br>SIFDYDLVKDKRFFENQYMLHISIEINKNE<br>RDAKKIKNINEMVRKELKDSDDNYIIGIDR<br>GERNLLYVCVINSAGKIVEQMSLNEIINEY<br>NGIKHTVDYQGLLDKCEKERNAQRQSWKSI<br>ENIKELKDGYISQVVHKLCQLVEKYDAIIA<br>MENLNGGFKRGRTKFEKQVYQKFENKLINK<br>MEYMADKKRKTTENGGILRGYQLTNGCINN<br>SYQNGFIFYVPAWLTSKIDPTTGFVDLLKP<br>KYTNVEEAHLWINKFNSITYDKKLDMFAFN<br>INYSQFPRADIDYRKIWTFYTNGYRIETFR<br>NSEKNNEFDWKEVHLTSVIKKLLEEYQINY<br>ISGKNIIDDLIQIKDKPFWNSFIKYIRLTL<br>QMRNSITGRTDVDYIISPVINNEGTFYDSR<br>KDLDEITLPQDADANGAYNIARKALWIIEK<br>LKESPDEELNKVKLAITQREWLEYAQINI |
| SEQ ID NO: 43 | Cas12 Variant | MIIHNCYIGGSFMKKIDSFTNCYSLSKTLR<br>FKLIPIGATQSNFDLNKMLDEDKKRAENYS<br>KAKSIIDKYHRFFIDKVLSSVTENKAFDSF<br>LEDVRAYAELYYRSNKDDSDKASMKTLESK<br>MRKFIALALQSDEGFKDLFGQNLIKKTLPE<br>FLESDTDKEIIAEFDGFSTYFTGFFNNRKN<br>MYSADDQPTAISYRCINDNLPKFLDNVRTF<br>KNSDVASILNDNLKILNEDFDGIYGTSAED<br>VFNVDYFPFVLSQKGIEAYNSILGGYTNSD<br>GSKIKGLNEYINLYNQKNENIHRIPKMKQL<br>FKQILSERESVSFIPEKFDSDDDVLSSIND<br>YYLERDGGKVLSIEKTVEKIEKLFSAVTDY<br>STDGIFVKNAAELTAVCSGAFGYWGTVQNA<br>WNNEYDALNGYKETEKYIDKRKKAYKSIES<br>FSLADIQKYADVSESSETNAEVTEWLRNEI<br>KEKCNLAVQGYESSKDLISKPYTESKKLFN<br>NDNAVELIKNALDSVKELENVLRLLLGTGK<br>EESKDENFYGEFLPCYERICEVDSLYDKVR<br>NYMTQKLYKTDKIKLNFQNPQFLGGWDRNK<br>EADYSAVLLRRNSLYYIAIMPSGYKRVFEK<br>IPAPKADETVYEKVIYKLLPGPNKMLPKVF<br>FSKKGIETFNPPKEILEKYELGTHKTGDGF<br>NLDDCHALIDYFKSALDVHSDWSNFGFRFS<br>DTSTYKNIADFYNEVKNQGYKITFCDVPQS<br>YINELVDEGKLYLFQLYNKDFSEHSKGTPN<br>LHTLYFKMLFDERNLENVVFKLNGEAEMFY<br>REASISKDDMIVHPKNQPIKNKNEQNSRKQ<br>STFEYDIVKDRRYTVDQFMLHIPITLNFTA<br>NGGTNINNEVRKALKDCDKNYVIGIDRGER<br>NLLYICVVDSEGRIIEQYSLNEIINEYNGN<br>TYSTDYHALLDKKEKERLESRKAWKTVENI<br>KELKEGYISQVVHKICELVEKYDAVIVMED<br>LNLGFKQGRSGKFEKSVYQKFEKMLIDKLN<br>YFADKKKSPEEIGSVLNAYQLTNAFESFEK<br>MGKQNGFIFYVPAYLTSKIDPTTGFADLLH<br>PSSKQSKESMRDFVGRFDSITENKTENYFE<br>FELDYNKFPRCNTDYRKKWTVCTYGSRIKT<br>FRNPEKNSEWDNKTVELTPAFMALFEKYSI<br>DVNGDIKAQIMSVDKKDFFVELIGLLRLTL<br>QMRNSETGKVDRDYLISPVKNSEGVFYNSD<br>DYKGIENASLPKDADANGAYNIARKGLWII<br>EQIKACENDAELNKIRLAISNAEWLEYAQK<br>K |
| SEQ ID NO: 44 | Cas12 Variant | MKEQFVNQYPISKTLRFSLIPIGKTEENFN<br>KNLLLKEDEKKAEEYQKVKGYIDRYHKFFI<br>ETALCNINFEGFEEYSLLYYKCSKDDNDLK<br>TMEDIEIKLRKQISKTMTSHKLYKDLFGEN<br>MIKTILPNFLDSDEEKNSLEMFRGFYTYFS<br>GFNTNRKNMYTEEAKSTSIAYRCINDNLPK<br>FLDNSKSFEKIKCALNKEELKAKNEEFYEI<br>FQIYATDIFNIDFFNFVLTQPGIDKYNGII<br>GGYTCSDGTKVQGLNEIINLYNQQIAKDDK |

TABLE 1-continued

| SEQ ID NO | Description | Sequence (Cas12 Enzyme Sequences) |
|---|---|---|
| | | SKRLPLLKMLYKQILSDRETVSFIPEKFSS DNEVLESINNYFSKNVSNAIKSLKELFQGF EAYNMNGIFISSGVAITDLSNAVFGDWNAI STAWEKAYFETNPPKKNKSQEKYEEELKAN YKKIKSFSLDEIQRLGSIAKSPDSIGSVAE YYKITVTEKIDNITELYDGSKELLNCNYSE SYDKKLIKNDTVIEKVKTLLDAVKSLEKLI KPLVGTGKEDKDELFYGTFLPLYTSLSAVD RLYDKVRNYATQKPYSKDKIKLNFNCSSFL SGWATDYSSNGGLIFEKDGLYYLGIVNKKF TTEEIDYLQQNADENPAQRIVYDFQKPDNK NTPRLFIRSKGTNYSPSVKEYNLPVEEIVE LYDKRYFTTEYRNKNPELYKASLVKLIDYF KLGFTRHESYRHYDFKWKKSEEYNDISEFY KDVEISCYSLKQEKINYNTLLNFVAENRIY LFQIYNKDFSKYSKGTPNLHTRYFKALFDE NNLSDVVFKLNGGSEMFFRKASIKDNEKVV HPANQPIDNKNPDNSKKQSTFDYELIKDKR FTKHQFSIHIPITMNFKARGRDFINNDIRK AIKSEYKPYVIGIDRGERNLIYISVINNNG EIVEQMSLNDIISDNGYKVDYQRLLDRKEK ERDNARKSWGTIENIKELKEGYISQVIHKI CELVIKYDAVIAMEDLNFGFKRGRFNVEKQ VYQKFENMLISKLNYLCDKKSEANSEGGLL KAYQLTNKFDGVNKGKQNGIIFYVPAWLTS KIDPVTGFVDLLHPKYISVEETHSLFEKLD DIRYNFEKDMFEFDIDYSKLPKCNADFKQK WTVCTNADRIMTFRNSEKNNEWDNKRILLS DEFKRLFEEFGIDYCHNLKNKILSISNKDF CYRFIKLFALTMQMRNSITGSTNPEDDYLI SPVRDENGVFYDSRNFIGSKAGLPIDADAN GAYNIARKGLWAINAIKSTADDMLDKVDLS ISNAKWLEYVQK |
| 45 | Cas12 Variant | MADLSQFTHKYQVPKTLRFELIPQGKTLEN LSAYGMVADDKQRSENYKKLKPVIDRIYKY FIEESLKNTNLDWNPLYEAIREYRKEKTTA TITNLKEQQDICRRAIASRFEGKVPDKGDK SVKDFNKKQSKLFKELFGKELFTDSVLEQL PGVSLSDEDKALLKSFDKFTTYFVGFYDNR KNVFSSDDISTGIPHRLVQENFPKFIDNCD DYKRLVLVAPELKEKLEKAAEATKIFEDVS LDEIFSIKFYNRLLQQNQIDQFNQLLGGIA GAPGTPKIQGLNETLNLSMQQDKTLEQKLK SVPHRFSPLYKQILSDRSSLSFIPESFSCD AEVLLAVQEYLDNLKTEHVIEDLKEVFNRL TTLDLKHIYVNSTKVTAFSQALFGDWNLCR EQLRVYKMSNGNEKITKKALGELESWLKNS DIAFTELQEALADEALPAKVNLKVQEAISG LNEQMAKSLPKELKIPEEKEELKALLDAIQ EVYHTLEWFIVSDDVETDTDFYVPLKETLQ IIQPIIPLYNKVRNFATQKPYSVEKFKLNF ANPTLADGWDENKEQQNCAVLFQKGNNYYL GILNPKNKPDFDNVDTEKQGNCYQKMVYKQ FPDFSKMMPKCTTQLKEVKQHFEGKDSDYI LNNKNFIKPLTITREVYDLNNVLYDGKKKF QIDYLRKTKDEDGYYTALHTWIDFAKKFVA SYKSTSIYDTSTILPPEKYEKLNEFYGALD NLFYQIKFENIPEEIIDTYVEDGKLFLFQI YNKDFAAGATGAPNLHTIYWKAVFDPENVK DVVVKLNGQAELFYRPKSNMDVIRHKVGEK LVNRTLKDGSILTDELHKELYLYANGSLKK GLSEDAKIILDKNLAVIYDVHHEIVKDRRF TTDKFFFHVPLTLNYKCDKNPVKFNAEVQE YLKENPDTYVIGIDRGERNLIYAVVIDPKG RIVEQKSFNVINGFDYHGKLDQREKERVKA RQAWTAVGKIKELKQGYLSLVVHEISKMMV RYQAVVVLENLNVGFKRVRSGIAEKAVYQQ FEKMLINKLNYLMFKDAGGTEPGSVLNAYQ LTDRFESFAKMGLQTGFLFYIPAAFTSKID PATGFVDPFRWGAIKTLADKREFLSGFESL KFDSTTGNFILHFDVSKNKNFQKKLEGFVP DWDIIIEANKMKTGKGATYIAGKRIEFVRD NNSQGHYEDYLPCNALAETLRQCDIPYEEG KDILPLILEKNDSKLLHSVFKVVRLTLQMR NSNAETGEDYISSPVEDVSGSCFDSRMENE KLPKDADANGAYHIALKGMLALERLRKDEK MAISNNDWLNYIQEKRA |
| 46 | Cas12 Variant | MTNFDNFTKKYVNSKTIRLEAIPVGKTLKN IEKMGFIAADRQRDEDYQKAKSVIDHIYKA FMDDCLKDLFLDWDPLYEAVVACWRERSPE GRQALQIMQADYRKKIADRFRNHELYGSLF TKKIFDGSVAQRLPDLEQSAEEKSLLSNFN KFTSYFRDFFDKRKRLFSDDEKHSAIAYRL INENFLKFVANCEAFRRMTERVPELREKLQ NTGSLQVYNGLALDEVFSADFYNQLIVQKQ IDLYNQLIGGIAGEPGTPNIQGLNATINLA LQGDSSLHEKLAGIPHRFNPLYKQILSDVS TLSFVPSAFQSDGEMLAAVRGFKVQLESGR VLQNVRRLFNGLETEADLSRVYVNNSKLAA FSSMFFGRWNLCSDALFAWKKGKQKKITNK KLTEIKKWLKNSDIAIAEIQEAFGEDFPRG KINEKIQAQADALHSQLALPIPENLKALCA KDGLKSMLDTVLGLYRMLQWFIVGDDNEKD SDFYFGLGKILGSLDPVLVLYNRVRNYITK KPYSLTKFRLNFDNSQLLNGWDENNLDTNC ASIFIKDGKYYLGISNKNNRPQFDTVATSG KSGYQRMVYKQFANWGRDLPHSTTQMKKVK KHFSASDADYVLDGDKFIRPLIITKEIFDL NNVKFNGKKKLQVDYLRNTGDREGYTHALH TWINFAKDFCACYKSTSIYDISCLRPTDQY DNLMDFYADLGNLSHRIVWQTIPEEAIDNY VEQGQLFLFQLYNKDFAPGADGKPNLHTLY WKAVFNPENLEDVVVKLNGKAELFYRPRSN MDVVRHKVGEKLVNRKLKNGLTLPSRLHEE IYRYVNGTLNKDLSADARSVLPLAVVRDVQ HEIIKDRRFTADKFFFHASLTFNFKSSDKP VGFNEDVREYLREHPDTYVVGVDRGERNLI YIVVIDPQGNIVEQRSFNMINGIDYWSLLD QKEKERVEAKQAWETVGKIKDLKCGYLSFL IHEITKIIIKYHAVVILENLSLGFKRVRTG IAEKAVYQQFERMLVTKLGYVVFKDRAGKA PGGVLNAYQLTDNTRTAENTGIQNGFLFYV PAAFTSRVDPATGFFDFYDWGKIKTATDKK NFIAGFNSVRYERSTGDFIVHVGAKNLAVR RVAEDVRTEWDIVIEANVRKMGIDGNSYIS GKRIRYRSGEQGHGQYENHLPCQELIRALQ QYGIQYETGKDILPAILQQDDAKLTDTVFD VFRLALQMRNTSAETGEDYFNSVVRDRSGR CFDTRRAEAMPKEADANDAYHIALKGLFV LEKLRKGESIGIKNTEWLRYVQQRHS |
| 47 | Cas12 Variant | MENYGGFTGLYPLQKTLKFELRPQGRTMEH LVSSNFFEEDRDRAEKYKIVKKVIDNYHKD FINECLSKRSFDWTPLMKTSEKYYASKEKN GKKKQDLDQKIIPTIENLSEKDRKELELEQ KRMRKEIVSVFKEDKRFKYLFSEKLFSILL KDEDYSKEKLTEKEILALKSFNKFSGYFIG LHKNRANFYSEGDESTAIAYRIVNENFPKF LSNLKKYREVCEKYPEIIQDAEQSLAGLNI KMDDIFPMENFNKVMTQDGIDLYNLAIGGK AQALGEKQKGLNEFLNEVNQSYKKGNDRIR MTPLFKQILSERTSYSYILDAFDDNSQLIT SINGFFTEVEKDKEGNTFDRAVGLIASYMK YDLSRVYIRKADLNKVSMEIFGSWERLGGL LRIFKSELYGDVNAEKTSKKVDKWLNSGEF SLSDVINAIAGSKSAETFDEYILKMRVARG EIDNALEKIKCINGNFSEDENSKMIIKAIL DSVQRLFHLFSSFQVRADFSQDGDFYAEYN EIYEKLFAIVPLYNRVRNYLTKNNLSMKKI KLNFKNPALANGWDLNKEYDNTAVIFLREG KYYLGIMNPSKKKNIKFEEGSGTGPFYKKM AYKLLPDPNKMLPKVFFAKKNINYYNPSDE IVKGYKAGKYKKGENFDIDFCHKLIDFFKE SIQKNEDWRAFNYLFSATESYKDISDFYSE VEDQGYRMYFLNVPVANIDEYVEKGDLFLF QIYNKDFASGAKGNKDMHTIYWNAAFSDEN |

TABLE 1-continued

Cas12 Enzyme Sequences

| SEQ ID NO | Description | Sequence |
|---|---|---|
| | | LRNVVVKLNGEAELFYRDKSIIEPICHKKG<br>EMLVNRTCFDKTPVPDKIHKELFDYHNGRA<br>KTLSIEAKGYLDRVGVFQASYEIIKDRRYS<br>ENKMYFHVPLKLNFKADGKKNLNKMVIEKF<br>LSDKDVHIIGIDRGERNLLYYSVIDRRGNI<br>IDQDSLNIIDGFDYQKKLGQREIERREARQ<br>SWNSIGKIKDLKEGYLSKAVHKVSKMVLEY<br>NAIVVLEDLNFGFKRGRFKVEKQVYQKFEK<br>MLIDKLNYLVFKEVLDSRDAGGVLNAYQLT<br>TQLESFNKLGKQSGILFYVPAAYTSKIDPT<br>TGFVSLFNTSRIESDSEKKDFLSGFDSIVY<br>SAKDGGIFAFKFDYRNRNFQREKTDHKNIW<br>TVYTNGDRIKYKGRMKGYEITSPTKRIKDV<br>LSSSGIRYDDGQELRDSIIQSGNKVLINEV<br>YNSFIDTLQMRNSDGEQDYIISPVKNRNGE<br>FFRTDPDRRELPVDADANGAYHIALRGELL<br>MQKIAEDFDPKSDKFTMPKMEHKDWFEFMQ<br>TRGD |
| SEQ ID NO: 48 | Cas12 Variant | MLHAFTNQYQLSKTLRFGATLKEDEKKCKS<br>HEELKGFVDISYENMKSSATIAESLNENEL<br>VKKCERCYSEIVKFHNAWEKIYYRTDQIAV<br>YKDFYRQLSRKARFDAGKQNSQLITLASLC<br>GMYQGAKLSRYITNYWKDNITRQKSFLKDF<br>SQQLHQYTRALEKSDKAHTKPNLINFNKTF<br>MVLANLVNEIVIPLSNGAISFPNISKLEDG<br>EESHLIEFALNDYSQLSELIGELKDAIATN<br>GGYTPFAKVTLNHYTAEQKPHVFKNDIDAK<br>IRELKLIGLVETLKGKSSEQIEEYFSNLDK<br>FSTYNDRNQSVIVRTQCFKYKPIPFLVKHQ<br>LAKYISEPNGWDEDAVAKVLDAVGAIRSPA<br>HDYANNQEGFDLNHYPIKVAFDYAWEQLAN<br>SLYTTVTFPQEMCEKYLNSIYGCEVSKEPV<br>FKFYADLLYIRKNLAVLEHKNNLPSNQEEF<br>ICKINNTFENIVLPYKISQFETYKKDILAW<br>INDGHDHKKYTDAKQQLGFIRGGLKGRIKA<br>EEVSQKDKYGKIKSYYENPYTKLTNEFKQI<br>SSTYGKTFAELRDKFKEKNEITKITHFGII<br>IEDKNRDRYLLASELKHEQINHVSTILNKL<br>DKSSEFITYQVKSLTSKTLIKLIKNHTTKK<br>GAISPYADFHTSKTGFNKNEIEKNWDNYKR<br>EQVLVEYVKDCLTDSTMAKNQNWAEFGWNF<br>EKCNSYEDIEHEIDQKSYLLQSDTISKQSI<br>ASLVEGGCLLLPIINQDITSKERKDKNQFS<br>KDWNHIFEGSKEFRLHPEFAVSYRTPIEGY<br>PVQKRYGRLQFVCAFNAHIVPQNGEFINLK<br>KQIENFNDEDVQKRNVTEFNKKVNHALSDK<br>EYVVIGIDRGLKQLATLCVLDKRGKILGDF<br>EIYKKEFVRAEKRSESHWEHTQAETRHILD<br>LSNLRVETTIEGKKVLVDQSLTLVKKNRDT<br>PDEEATEENKQKIKLKQLSYIRKLQHKMQT<br>NEQDVLDLINNEPSDEEFKKRIEGLISSFG<br>EGQKYADLPINTMREMISDLQGVIARGNNQ<br>TEKNKIIELDAADNLKQGIVANMIGIVNYI<br>FAKYSYKAYISLEDLSRAYGGAKSGYDGRY<br>LPSTSQDEDVDFKEQQNQMLAGLGTYQFFE<br>MQLLKKLQKIQSDNTVLRFVPAFRSADNYR<br>NILRLEETKYKSKPFGVVHFIDPKFTSKKC<br>PVCSKTNVYRDKDDILVCKECGFRSDSQLK<br>ERENNIHYIHNGDDNGAYHIALKSVENLIQ<br>MK |
| SEQ ID NO: 49 | Cas12 Variant | MKNGINLFKTKTTKTKGVDMEKYQITKTIR<br>FKLLPDNAHEIVEKVKSLKTSNVDELMDEV<br>KNVHLKGLELLFALKKYFYFDGNQCKSFKS<br>TLEIKARWLRLYTPDQYYLKKSSKNSYQLK<br>SLSYFKDVFNDWLFNWEESVSELAIIYEKY<br>KICQHQRDSRADIALLIKKLSMKEYFPFIS<br>DLIDCVNDKNSNKTFLMKLSEELSVLLEKC<br>NSRALPYQSNGIVVGKASLNYYTVSKSEKM<br>LQNEYEDVCQSLDKNYDITEMKVILYKEKL<br>DNLNFKDVTIANAYNLLKENKALQKRLFSE<br>YVSQGKVLSLIKTELPLFSNINDNDFEKYK<br>EWSNEIKKLADKKNTFCKKTQQDKIKDIQN |

TABLE 1-continued

Cas12 Enzyme Sequences

| SEQ ID NO | Description | Sequence |
|---|---|---|
| | | KISELKKKRGALFQYKFTSFQKHCDNYKKV<br>AVQYGKLKARKKAIEKDEIEANLLRYWSVI<br>LEQEDKHSLVLIPKNNAKDAKQYIETINTK<br>GGKYIIHHLDSLTLRALNKLCFNAVDIEKG<br>QMVRENTFYQGIKEEFERNKINCDNQGVLK<br>IQGLYSFKTEGGQINEKEAVEFFKEVLKSN<br>YAREVLNLPYDLESNIFQKEYTNLDQFRQD<br>LEKCCYALHSKIGKDDLDEFTRRFEAQVFD<br>ITSIDLKSKKEKTKTTGEMKKHTQLWLEFW<br>KGAIEQNFATRVNPELSIFWRAPKSSREKK<br>YGKGSDLYDPNKNNRYLYEQYTLALTITEN<br>AGSHFKDIAFKDTSKIKEAIKEFNMSLSQS<br>KYCFGIDRGNAELVSLCLIKNEKDFPFEKF<br>PVYRLRDLTYQGDFKDKHDQMRYGVAIKNI<br>SYFIDQEDLFEKNNLSAIDMTTAKLIKNKI<br>VLNGDVLTYLKLKEETAKHKLTQFFQGSSI<br>NKNSRVYFDEDENVFKITTNRNHNPEEIIY<br>FYRGEYGAIKNKNDLEDILNEYLCKMETGE<br>SEIVLLNRVNHLRDAISANIVGILSYLIDL<br>FPETIVALENLAKGTIDRHVSQSYENITRR<br>FEWALYRKLLNKQLAPPELKENILLREGDD<br>KIDQFGIIHFVEEKNTSKDCPNCRKTTQQT<br>NDNKFKEKKFVCKSCGFDTSKDRKGMDSLN<br>SPDTVAAYNVARKKFES |
| SEQ ID NO: 50 | Cas12 Variant | MAKETKEFKTFDDFTNLYEVQKTLRFELEA<br>VPETEIVLENRGIWYKRDKKRADEKPIVKF<br>YMDILHREFTDEALEKIKESGVLNLSGYFK<br>LFEELRRLQNHGANTKEEKKLKLEEIRAKK<br>REISNELSQIRRVFSVRGFDVVDSDWKKKY<br>TIEGKKIKNDKSKTYLILSENILNFLENRF<br>TSKEVERLRSIDKKHVEDYGNVVNSGGENI<br>FATFKGFFGYFDSLIKNRENFYETDGKAGR<br>VATRSVDENLNFFAENLHIFSTDLPKALKD<br>DLSDTQKAIFERSYYKNCLLQKDIKSYNLI<br>IGDINKEINKHRQQRDTKIKFLNTLFKQIL<br>SIEEKEQYKHIEINNDEDLIRAIRDFISLN<br>ESKISEGTKIFNQFIQRCLQKEDLGQIYLP<br>KDSVNTIAHRIFKPWDEIMALFDRKYFVSL<br>EEIKDLTESSVWKERVLEESKTKSLIFKDT<br>HIHTIISGQEIFSNFILILEKEYKNQFSGF<br>ISETRRGKAAFVGYDESLKNLRATIKWFEG<br>KNLKLSETEKVEWIKAIKDYADAALRIFQM<br>TKYLWLPVVGDEEDKDYLRIKAEIDQLTKD<br>NDFYNKINAFIDGYKPEPFIYRSSFQEYLT<br>RRPFSTDKFKINFENSRLLDGWDKDMIDDR<br>MGILLQRDGDYFLGILNKEDRHCLDNLVDV<br>KSEDKNSYALMQFKQLTGLYRQLPRMAFPK<br>KKQPVLEANAEIKKIKEDFDFLQKQKKERE<br>VNVNVVFDNKKLNLLINHYAEFLKENYKDE<br>KCYDFSLLNKEKVYESLSDFYADVDKITYS<br>LSFIQVSIDQLIKTGKILLFRLKNKDLLKG<br>SLGQNKNLHTYYFHALFERENLSQGRIRLG<br>AQAEIFFRPASIEKEKDKNRSNALKKSPKT<br>RYVKEILKNKRYSEDKVFLHLPIQLNADAY<br>DLPSINQNVFEFIKNRQEKVKIIGIDRGEK<br>NLAYYSVISQNSNGKIKIEEPPRDLNLGYL<br>EPLDELENKRQDERKAWQSISEIKSKRDGY<br>ISYAVSKIVELMLKYQAIIVLEDLSGKFKR<br>SRMKFEKAPYQQLELALIKKLNYLVKKNSK<br>SGKPGHYLSAYQLTEPVGSYKEMGKQTGII<br>FYTQAGYTSRTCPTCGWRKRVQGLYYKDRT<br>SAQRRFDPKTGVKIFYDSVNDRFVFQYHPV<br>YEQKELKEWDKEIYSDVTRIRWNNEEKKNN<br>EYRKGDITLKIKRLFRDRGIDLSRNINEQL<br>VNVGDASFWEELINLLRLITEIRNIDNENN<br>RDFIECPHCHFQSENGFHGVAWNGDANGAY<br>NIARKGLLITKAVCDPEKNVGDITWSDLKV<br>DMKDWDAATDEWAKKNPEK |
| SEQ ID NO: 51 | Cas12 Variant | MENEKIFSDLTNRYQVVKTLPFELKPVPRT<br>RVLLGLDNPNKGEIFSKDRERAENFTIIKK<br>YIDRLHSLFINESLKKADIDFSNFYKQYGK<br>NINTKNNKNIDDDNDINDDEKEDSENDNLK |

TABLE 1-continued

| SEQ ID NO | Description | Sequence |
|---|---|---|
| Cas12 Enzyme Sequences | | |
| | | KYRQEIANLFNKSKYKSWVNVGKDGDKISGMLFEKGLIDLLRTHFSDNLNEDIEIPELFSNKKIKDTRKLKEIINSFGKDGKDGQNFTTYFSVSFHNNRKNYYKSDGKMGRVSTRIVDENLERFCKNIYLYKEIIGKNEIKEIFSGNWDIYLQKKPNFSNDKTYKKLDEFKNDKYDWEMIFRDVNSYNKYFLQSDIEFYNYIRGKLNQDINEYNGKKRDSKEKINSQFENLRNQVHGEKKNYDDDFEIDEDNIIQFINEIFVRHNQNKMRFSEKLFSDFIDLLMVDNGDKLDKVYFSQKAVENAIARYYFVEETTNEGREPLLISLLLQNAGKDRKKLSNKPIKLGDIKFVLDQANNKPAEDIFKNRYVLSESNNDGIINANDKNHWANLLRLIKKDFYFHKDNLIKSQDKLALETKYNKGSDEGERQIETIKNFAESAKAILRMTKYFDLRKNGVIQNVIGGKDPIHEEVDKYFDGDVLSGEESCRISKYYDALRNFITKKAWSADKIILNFDCSEFLGGWDRSQEQKKRGIILRHRDGDEERYYLAVLGKNGKQYFENRTLFKGCESSDWQKIEYNVIQKPHMSLPKNLITPFFKKDKITNERFIDRSKKGAKALIEIDINPSDEFLNNYNLGKHTKENLDKSFLCDYFKYLMDAIAKYYKGEFNFNFPDVSNFDNTQPFYSFIEKNAYSIKYFGISSKEIEKLIADCYYKEDVYLFQIYCKDFEIDPKIGKAKYGNEFRTKAEIRKSKGEEAGNENLNTKYFKLLFDEKNLKNQNGIVYKLNGGAKMFYRPSSIKKDEKIDGKWRYKEDKYSLNITITCNFSSKKDDLSIDKDINKKIAEVNANSDFRIISIDRGEKNLAYCCVMDENANILDIKSLNRITRYDKNGKAIKEKNMFHEVKDGKLCYGEPVYDFYKDYQNLLDEREIKRLVNRRSWNVIEDIKNLKKGYVALLINYICKAVVIAINEGKYPIIVLESLDKGMLHNRVKIEKQIYRGVEEGLVRKLNYFVDKKTDNVLNAWQLLAKFETVGSSLDRKKQLGIIFYVDPGYTSITCPCCGFRQRKYIKAERAEENFKEIKIKFDGKRYSFAYDYRCIDDNGKEKSKEDIIYSNVKRLLRSGRNGRAVQIEDVTDELTNLFKKHNINIEQDINEQLAGKDNKFWKQLLWWFNAIEQIRNTQSLRRKFNTEENKLEILENNDCDFILCPHCYFDSNKDKFQNKIWNGDANGAFNIGRKGIIDIFEIKKHQRMLSDFMEQWGIDKLPKANGGNQAVIEIVKNDKKYNLCILNNKKIPYYCLRIGKEKIDSIADDRKCNQLPDLMVNWKKWDMWLDKWGK |
| SEQ ID NO: 52 | Cas12 Variant | MPEVKNVFQDFTNLYELSKTLRFELKPVPETEKILELNAAKTKKFPKDLYRAENFEIIKKYTDELHRTYIRETLNNVNIDYLKFLEIFRINGKKKNEMTDENEESDENNEKDDIQKIKKELRSKIGNLFNKWNNDKDNKFKDWVKIDVGKKEKEVSGDLFGKELITILKNYFKNKLDSKVNVPMLFFNEQEIKNGEAKKQRKLEAVFENFDKFTTYFTDSFYNNRKNYYKTEGRVGQVATRIIDENLPRFCSNLIAFNEVVSLYSTLLNNFDLGWKEYLNEKKINQTWVEKFELSNYDWKALFNDVNYYNQCLLQEGIDKYNYIIKKLNKDINEYTQNKYKSVEKGNNNNPDINFFQKLHKQIHGERDFKLIEIDIDENNIFTKILPEFILHSDMKLMTKIDEEVGVEEIVGAERIIKIFIKQELKDLEKIYLSRRAIETISAKWFHSWETLKDLILGYLNKDLLESKKRKKVPDFVDFNIIKIVLENNKDDYKDLFKRKYFEADKNEFVDWIDSSGGTKKLEFGGENWINFLNVFEYEFGTLLTEYKKNKNALLYLIDKKIDYDKNNEVGQTAAIKNFADSALGIFRMVSYFALRKKGVMVEPKNGKDEIFYAFVDRYLDGDDNDREEQNKIVQYYNTLRNFVTQKAWSIDKVRLCFDCGEFLKGWDKDKIHERLGIILRNNNKFYLGILNKNHKQIFIKIKSHDNNNFYYVIYDYKQLNNVYRQIPRLAFPSRSVKKGDAYMLRAIQERKKKFFLEDEEFIELQEIKNEYDKIGNDLSKEKLTKLIEYYKKVVISNYSSLYNVSNLNNKKFNSINEFNQYVENLMYSLIPTRISPDFI |

TABLE 1-continued

| SEQ ID NO | Description | Sequence |
|---|---|---|
| Cas12 Enzyme Sequences | | |
| | | KEKISKGELYLFQIYNKDFELDESIGKEKFGEDFAPVIMDGKNNLHTEYFKLLFNDSNLKNPNGVVFKLSGGAKMFYRPATENLPIKKDRDGNIIKNKKGENVIVGQRYKEDKYFLHLPIILNFVNKGKNYSINDMVNKAITNASDDQDKFRIIGLDRGEKHLVYYSVINERQEIIEIGSLNNISRKDNKGEIIEEKNWYHDKFGNIEKEPTKEYHKDYHNLLDQREIERLKSRQSWEKIENIKELKEGYISAVINKICNLVIKAIKENKIPIVALENLNSGMKRGRIKIDKQIYQKLELKLAKKLNFLVDKKEKNYLSAWQFTPKIETFSGDIEKKNQVGIIFYVDPAFTSATCPNCGFRKRIKMDPQNAKKKIKDMEITYENGIYKFDYPIENGENDVVYSDVERLKWDNEKKKVIKTKNVSDDFGKLFEDIKDKNNLKKELLSIGEENKEFWKEFSRCFNLLLRIRNSKLIKRKLNDDTGKVEIIADDDLADRDRDFIYCPQCHFHSEGGDVFGEFVKKKYLGKDNFEFNGDANGAYNIARKTIIAVNKIKDYQLGLNHFIEKYRISELPNNGKDKKNIFYNNNSYILSFFEVQDEKFRKVKVYGLKKDGDRQIIQKKEMWYRRYPDIFVNNKEWDKFVQNKS |
| SEQ ID NO: 53 | Cas12 Variant | MLFFMSTDITNKPREKGVFDNFTNLYEFSKTLTFGLIPLKWDDNKKMIVEDEDFSVLRKYGVIEEDKRIAESIKIAKFYLNILHRELIGKVLGSLKFEKKNLENYDRLLGEIEKNNKNENISEDKKKEIRKNFKKELSIAQDILLKKVGEVFESNGSGILSSKNCLDELTKRFTRQEVDKLRRENKDIGVEYPDVAYREKDGKEETKSFFAMDVGYLDDFHKNRKQLYSVKGKKNSLGRRILDNFEIFCKNKKLYEKYKNLDIDFSEIERNFNLTLEKVFDFDNYNERLTQEGLDEYAKILGGESNKQERTANIHGLNQIINLYIQKKQSEQKAEQKETGKKKIKFNKKDYPTFTCLQKQILSQVFRKEIIESDRDLIRELKFFVEESKEKVDKARGIIEFLLNHEENDIDLAMVYLPKSKINSFVYKVFKEPQDFLSVFQDGASNLDFVSFDKIKTHLENNKLTYKIFFKTLIKENHDFESFLILLQQEIDLLIDGGETVTLGGKKESITSLDEKKNRLKEKLGWFEGKVRENEKMKDEEEGEFCSTVLAYSQAVLNITKRAEIFWLNEKQDAKVGEDNKDMIFYKKFDEFADDGFAPFFYFDKFGNYLKRRSRNTTKEIKLHFGNDDLLEGWDMNKEPEYWSFILRDRNQYYLGIGKKDGEIFHKKLGNSVEAVKEAYELENEADFYEKIDYKQLNIDRFEGIAFPKKTKTEEAFRQVCKKRADEFLGGDTYEFKILLAIKKEYDDFKARRQKEKDWDSKFSKEKMSKLIEYYITCLGKRDDWKRFNLNFRQPKEYEDRSDFVRHIQRQAYWIDPRKVSKDYVDKKVAEGEMFLFKVHNKDFYDFERKSEDKKNHTANLFTQYLLELFSCENIKNIKSKDLIESIFELDGKAEIRFRPKTDDVKLKIYQKKGKDVTYADKRDGNKEKEVIQHRRFAKDALTLHLKIRLNFGKHVNLFDFNKLVNTELFAKVPVKILGMDRGENNLIYYCFLDEHGEIENGKCGSLNRVGEQIITLEDDKKVKEPVDYFQLLVDREGQRDWEQKNWQKMTRIKDLKKAYLGNVVSWISKEMLSGIKEGVVTIGVLEDLNSNFKRTRFFRERQVYQGFEKALVNKLGYLVDKKYDNYRNVYQFAPIVDSVEEMEKNKQIGTLVYVPASYTSKICPHPKCGWRERLYMKNSASKEKIVGLLKSDGIKISYDQKNDRFYFEYQWEQEHKSDGKKKKYSGVDKVFSNVSRMRWDVEQKKSIDFVDGTDGSITNKLKSLLKGKGIELDNINQQIVNQQKELGVEFFQSIIFYFNLIMQIRNYDKEKSGSEADYIQCPSCLFDSRKPEMNGKLSAITNGDANGAYNIARKGFMQLCRIRENPQEPMKLITNREWDEAVREWDIYSAAQKIPVLSEEN |

TABLE 1-continued

| Cas12 Enzyme Sequences | | |
|---|---|---|
| SEQ ID NO | Description | Sequence |
| SEQ ID NO: 54 | Cas12 Variant | MTIKKHKPFTNFECLTPVQKTLRFRLIPVGRTTEFVKCRNIIEADRKRSEMYPLLKELADRFYREFMTDQLSNLLFDWSPLVEALLLARNNTDPRENQRIASLVRDEQKKYRTLLLKRLSGQVDRNGTPLPKNTASVNKKYYDDLFWQARKNIFTDEDIATGFAYRIVHEIVPDYLFNRRVYEQHKLDFPEPLDLKARFVTETLPAYLEHLKNKPDGRISDELFDAYKDALDSYQKFTSRLTNFLETELKKKNLIANDESLDALFTIPAINRLLTQKGVDLHNAVIGGFFTDDHTKVQGFNELANLKNQTLKNVSDNSEIKPVGKMTRLKKHILSISESTSFLFEQIESDDDLLARIIEFNNTLSEPDIDGLSIADINDQLYNIMTGVDPSTILVHARNLNKLSHEASLSWNRLRDGLYQMATESPYREDERFKRYIDASEEERDLSKLKNDIYFSLQELQFALDQSIDLEEEATPTEDIFLPFEFPGMDLKSELTVLFRSIEQLISSETKLIGNPDAIATIKKYLDAIMARYSIWNLLSCEAVELQDDLFYPEYDRVMGSLSNIILLYNLARNYLSRKPSSKEKFRLNFDKPTLADGWSESKVPDNFSVLLRKDDLFYLGILKDRKAYRVLSYENCDETAKNIKGYYERMIYHFSPDAYRMIPKCSTARKDVKKHFGEQGETTGYTLYPGASNFVKPFTIPYEIYRLQTELVNDKKRYQADYLKQTEDEEGYRQAVTAWIDFCKSYLESYEGTSTFDYSHLLKSEDYEDVNQFYADVDRASYSIYFEKVSVDLIHTMVDRGDLYLFQLYNKDFSPHSTGKPNLHTMYWRALFSNDNLQNNTIKLNGQAELFYRPKQVEQPTVHLQGSYLLNRFDKHGDVIPAGLYCEIYNHINERHPEGYTLSEEATQGLLDGRFVYREAPFELVKDKRYTEDQLFLHVPLEFNWTASANVPFENLANEYIKKDSDLHIIGIDRGERNLLYYSVINLQGDIVKQGSLNTLIQQTTLKGETVERQIPYQSMLKQREDERAEARQNWQSIDRIKDLKEGYLSHVIYKLSRLIIKYHAIVVMENLNVGFKRGRFKVERQVYQKFEVALINKLNALSFKEYEPNELGGVMRPWQLARRVVSPEDTRSQNGIVFYVPASYTSIVDPVTGFANLFYLNRIRNKDLNSFYGHFQEIRYDHEFDRFIFRFNYADFGVFCRIKNVPSRTWNLVSGERKAFNPKRRMIEKRDTTDEIKKALEAHGIAYQNEQNLLPLLLENENLLARIHRSFRLVLQLRNSDSDRDDIVSPALDKENNTFDSGQQPYESSLPINADANGAYNIARKGLLLVDKVKNDKRAVLSNREWFEYLMAEE |
| SEQ ID NO: 55 | Cas12 Variant | MENKDYSLSRFTKQYQNSKTVRFALTPIGRTEEYIIQNQYIEAARRKNQAYKIVKPIIDEKFRSMIDDVLTHCEKQDWVTLDKLILQYQNNKCRENMDALAEQQEEIRKNISEEFTKSDEYKNFFGKEDSKKLFKIFLPEYLNQINASESDKEAVNEFQKFKTYFSNFLIVRADIFKADNKHNTIPYRIVNENFMIFAGNKRTFSNIIRLIPNALEEIAKDGMKKEEWSFYNIQNVDSWFEPDSFQMCMSQKGIQKYNFIIGLVNSYINLYTQQNPQATEVKRSRLKLRMLHKQILSDRVNPSWLPEQFKEGEEGEKQIYEAILALENDLIKNCFDKKYDLWIQSIDIQNPRIYIAASEMARVSSALHMGWNGLNDVRKTILLKSDKKQAKVEKILKQDVSLKDLSDTLNRYADIYKEEQIPSLYQYIEYGSELLQDCAITRKEYHDLLNGNSNTLSLNQNEKLIEGLKAYLDSYQAIVHFLNVFIVGDELDKDTDFYAELDGLVESLSEIVPLYNKVRNYITRKVYSLDKMRIMFERSDFLGGWGQSFDTKEALLFQKDNLYYIGIIEKKYTNMDVEYLHEGIKEGNRAIRFIYNFQKADNKNIPRTFIRSKGTNYAPAVRKYNLPIESIIDIYDVGKFKTNYKKINEKEYYESLEKLIDYFKDGILKNENYKKFHFNWKPSNEYENINEFYNDTNNACFLLEKEEINYDHLKEQANQGKIYLFQISSKDFNEGSKGTPNLQTMYWRELFSNQNCKDGVIKLCGGASIYMRDASIKQPVVHRKNAWLINKWYKVNGQNVVIPDNTYVKFTKIAQERMNEDELTPQERQLWNSGLIQKKKATHDIMKDRRFTKKQYMLHAPLTINYKQQDSPRYFNEKVRSFLKDNPDINIIGIDRGEKNLIYITIIDQKGNILKGMQKSFNQIEEKGKEGRTIDYYSKLESVEARHDAARKNWKQIGTIRELKEGYLSQVVHEITQLMIQYNAVIVMENLNMGFKKGRMKVEKSVYQKFEKMLIDKMNYLAFKRDMQGNAIDPYEVGGVMNGYQLTDRFTSFADMGSQNGFIFYVPAAYTSVIDPVTGFVNVFQKTEFKTNDFLHRFDSISWNDKEQSFVFTFDYQNFKCNGTCYQNKWSLYADVDRIETIIKNNQVDRIEPCNPNQKLIDFFDKKGIIYRDGHNIVDDLEKYDSKTISEIIHNFKLILQLRNSMRNPDTGEIIDYIASPVMHNEERFDSRKRNPELPQDADANGAYHIALKGLMFLQKINEYADSDGNMDNRKLKITNEEWFKYMQTRKEHTYF |
| SEQ ID NO: 56 | Cas12 Variant | MSNKTSSITTTNKLSYTGFHNNGKQSKTLMFELKPIGRTTEHLDRKGYLADDIDRAESYKTFKEIADNFHKNLIEESLATFTFSDTLKDYFDLWLSPVRTNEDTPKLRKMEAKLRKELSSALKQHPSFAATSSGKRLIDEALYPNASDKERQCLDRFKGRSSYLDSYTEVRSFIYTDLCKHNTIAYRVVNENLKIYLENILAYEKLMQTAVNGKLETVKEMFHDLYPTFSMDISIFFTSYGFDYCLSQNAITRYNILLGGWSDDNGIHHKGLNNYINEYNQTVPRNKRLPKLNKLQKMILSEENSMSFIIDKFENDVDLANAIRYWLKNCQFDALNLLIWTLDVHYNLDEIHFKNDNQGKNISDLSQALFKNHHVIRDAWDYDYDIVNAKAKSRQKPERYAEKRDKAFKKINSFSLSYLANILSQYDNQYANFVAQFKTRISVHIQNVQQMIADKTLDMRLDPLMLLKSISSDTKLVEDIKRVLDSLKDMQRMLTPLLGEGTEPNRDAMFYSDFEPLMNYVDTLTPLYNKVRNYITKKPYSTKKTSLYFGASNFGSGFDVTKLPVSHTIIMRDKGCYYLAVIDNNKLIDKLYDHNDNDGYEYMVYKQIPSPIKYFSLKNILPQDPPDDIRQLLEDRKNGAKWSHDDETRFIDYIVNEFLPTYPPIHDKNGNPYFSWKFKNPDEYESLNEFFDDVSKQAYQTSFRFVSRDFVDDAVENGDIFFFQIYNQDFSPASHGKPSPHTLWFRALFSDVNLETKDIRLKGNATAYFRPASIFYTDEKWRKGHHYEQLKNKFKFPIIKDKRYALDKFFFHITLEINCNATVEKYFNNRVNEEIRKADRYNILAINRGERNLLYAVVMDQDGTILEQKSFNIIKSELPNKTVKETDYWKKLHAREKERDTARKSWKSIECIKDLKKGYLSYVVKTITDMMFEYNAVLVMENLDIEMKRSRQKIEKNVYAQFQNAIIQKLSMYVNKDIDLHIARTAPGGTLNPYQLTYIPASRTKTPKQNGFVFFLNPWNITEIDPTTGFVDLFQTCFRTKNEYKDFFAKFKDIRYNEAQGWFEFDTDYTYFRDKEKAGKRTRWNICSYGTRLRRFRNPDKNYAEDAMTVYPTQMLKDLFDEYNIPYAPASAKSTSISIKDDIIQIDKLDFYKKLLYILKLIVQLRNTSPSSTEQEDDYIISPVINEDTNWFYDSRDYNEESLLPCNTDANGAYSLALKCNMVIDRIKNTIPGEPVDMYISNADWLDARQ |
| SEQ ID NO: 57 | Cas12 Variant | MNSKTSIFDFSNIFGRDITLRFKLTPVTINSKGEVKDANGADPYRPYLSADEELQEQYELLKTAIDAYHQMYIDKKLKHILCLPLTEKGKDGVEHDTALYEKDGKSTSVPYRCIDRNLPRFSKDYHLFEKILGDCSDVFDFEQLDKDKSKFVKSCLAYIKDYGEKDKKRQTADLRTFISRVFADDNISSLPPYKVKSDFITKTLRQWLEQPDTKVEKKEAILDLIEKNGSKLYANCQGLLEARQRFSEELKGIARLSGIRVESVREVFQPLLYLAYLNQEGIQYLNTIIGTKKEKGTSALGLNEYINQYNQKQGIKKKDGIPMLNKLNNQILFGDEVFIETLAEHKEAIPVIKKVVSSL |

TABLE 1-continued

| SEQ ID NO | Description | Sequence |
|---|---|---|
| | | GKLGAFDGECHENKLYQFLLSLSSYAGNIY<br>VNTKVVAQISSSLWGDYSILYDAVKHDKNG<br>RLIQKSVTLGELNEKIERLKLEDNRDAFEY<br>FRRSQVKDVVHGSSNVGVFEQLKNCYNDFV<br>EKKILKCSFFSEDQVLVIQRLFDSILSLQR<br>IFKVFCPSLYEVDSDGLFVAKFSDYWNVLR<br>GFDKDYDLLRNLFKRKPYSTDKIRVHFGLS<br>NLMDGFVDSWTDKKDKGTQYNGYILRQAHS<br>FVDENTSKELQEFQRYNYYLVISGNVRLFR<br>EKGNALVCEKKKEKLVASDEFSGFERFDYY<br>QSSINNFNREFKRLTGRDRKSFTDEILQNE<br>GKKELKSTYIENLIKVAKSMKRLTALQNLV<br>SDEKVRKYSENLDYETLSAEIGQILATGRE<br>RKYVPVSTNEMKNLLKSSKNNKGEEVRTFM<br>FRISNKDLSYAETMQKGERKSHGAENMHTM<br>YFRALLDTLQNTFDIGTGTVYFRKASDKRK<br>MKYDEKNPTHRKGDELAFKNPYNKGKKKSV<br>FGYDLIKDRRYTKDSYLFHLSITQNYQKKG<br>NAEDLNAMVRDYIRTQEDLRVIGIDRGERN<br>LLYATMIDGEGHILAQKSFNVIGYQGTTAS<br>GESFQVETDYHQLLNEKAEKMRSLQREWKE<br>MDKIQDMKDGYLSVVVHELAKMVVENNAII<br>VMEDLNMGFMESRQSQLANVYQKFEEKLRN<br>KLQFYVDKRKRNDEPSGLYHALQLAGTETK<br>DNQNGFIFYIPAWNTSKIDSVTGFVNLFNL<br>KYTNIKDAKAFFSTFEKIEKNVETGHYDFT<br>FSYSSMARKKMAKRMDGTRDSWTISTHGSR<br>IVREQKGNYWEYREIESLTSEFDALFEKYS<br>IDTRCRLKEAIDKCGEAEFFKELIRLMKWT<br>LQLRNYDDRGNDYIVSPVCYRGNEYYCSLD<br>YDNEEGMCISKIPCQMPKDADANGAFNIAR<br>KGLMLCERLKKGEKIGVIKGTEWLQYVQNM<br>SERYVGMV |
| SEQ ID NO: 58 | Cas12 Variant | MINTMEQPKKSIWDEFTNLYSLQKTLRFEL<br>KPQGKTKELVRTLFINPEEHHHKLISDDLE<br>LSKNYKKVKKLIDCMHRNIINNVLSKHQFT<br>GEELKKLDKNSNAEDNDTETDNADKKDPFA<br>KIRERLTKALNEESKIMFDNKLLNPKKGKN<br>KGECELKKWMDKAEDKYFELGNNEKIDKEA<br>VKADMERLEGFFTYFGGFNKNRENVYSSKK<br>IATAIPFRIIHDNFPIFKKNIENYKKITEK<br>HPELAKLLNEKGANEIFQLEHFNKCLTQDG<br>IDVYNNEKLGIIAKEQGKEQDKGINQLINE<br>YAQKKNKEIKENAKGGEKPKKIKIAVFDKL<br>KKQILSISKTKSFQFEVFEDTSDIINGINK<br>RYTFLTEAKEGMSIVDEIKKIIGSVGDEKY<br>SLDEIYLKEKFISTLSKKLFNYSRYIEVAL<br>EKWYDDRYDDKINKSGTDKRKFISAKQFSI<br>TSIQDAINYYLEKYEKDEELSKKYTGKNII<br>VDYFKNPTITIEHKQKEEVISEEKDLFKEL<br>EVRRNVIQHILNGDYKKDLKEEKQQDGDSE<br>KVKAFLDALLEFNYILNPFIIKDKNLRKEQ<br>EKDEEFYNEIKKLQESIFEAEILDLYNQTR<br>NYITKKPYKLDKFKLTFGSGYFLSGWSNDM<br>EEREGSILIKYNEDRSKNYYLIIMAKPLTD<br>DDKKQLFSDNGTHSKICIYEFQKMDMKNFP<br>RMFINSKGSNPAPAIEKYNLPIKTIWADYQ<br>KYKNLNQKGKDKFLEENPDFRHNLIGYFKI<br>CAEKHESLAPFKHQFSSIWKPTKEYENLAQ<br>FYKDTLEACYNLKFENVNFDNISQLVSSGK<br>LHLFKIHNKDFNPGSTGKKNLHTLYWEMLF<br>DEKNLQDVIFKLSGGAELFYREASILKNKI<br>IHKIGEKVLKKFFKLPDGKLEPVPAESIKN<br>LSAYFRKELPEHELTEIDRKYIDNYSIIGK<br>KDDKLGIMKDERFTVDKIQFHCPITINFKS<br>KNKNFINDDVLEYLHKRDDVHIIGLDRGER<br>HLIYLTMINKDGKIVDNMQFSLNELQRRYK<br>INGNEEIQKINYQKLLDTREVSRTEARRNW<br>QTIENIKNLKEGYLSLIVHQLAKLMIEKNA<br>IVVMENLNYGFKDSRARVEKQIYQKFESIL<br>IKKLQYLVMDKNNLYDSGGVLSAYQLTNQE<br>VPAYKYISKQNGFLFYVPPDYTSKIDPETG<br>FINLLDTRYYSRKNAVALLNKFDKIYYDRD |

TABLE 1-continued

Cas12 Enzyme Sequences

| SEQ ID NO | Description | Sequence |
|---|---|---|
| | | NKYFRFDFDYNSTDSNGNKNFDKLRVDISE<br>LTRTKWSVCSHPAKRSITVQINNKWVRQPI<br>NDVTDKLIKLFEDKQIGYESGKCLKDEILK<br>VEDAKFFEDLLRYLSVLLALRHTYTENGVE<br>YDLIISSVEKAPGSNEFFVSGKDNNLPANA<br>DANGAYNIARKGLWLLRKLDEIDNQELAIK<br>KFNELKHAKEIKKNGEESKEDKGDRKRKKK<br>WVSQWCPNKEWLAFAQSMQDVSEK |
| SEQ ID NO: 59 | Cas12 Variant | MNNGTNNFQNFIGISSLQKTLRNALIPTET<br>TQQFIVKNGIIKEDELRGENRQILKDIMDD<br>YYRGFISETLSSIDDIDWTSLFEKMEIQLK<br>NGDNKDTLIKEQTEYRKAIHKKFANDDRFK<br>NMFSAKLISDILPEFVIHNNNYSASEKEEK<br>TQVIKLFSRFATSFKDYFKNRANCFSADDI<br>SSSSCHRIVNDNAEIFFSNALVYRRIVKSL<br>SNDDINKISGDMKDSLKEMSLEEIYSYEKY<br>GEFITQEGISFYNDICGKVNSFMNLYCQKN<br>KENKNLYKLQKLHKQILCIADTSYEVPYKF<br>ESDEEVYQSVNGFLDNISSKHIVERLRKIG<br>DNYNGYNLDKIYIVSKFYESVSQKTYRDWE<br>TINTALEIHYNNILPGNGKSKADKVKKAVK<br>NDLQKSITEINELVSNYKLCSDDNIKAETY<br>IHEISHILNNFEAQELKYNPEIHLVESELK<br>ASELKNVLDVIMNAFHWCSVFMTEELVDKD<br>NNFYAELEEIYDEIYPVISLYNLVRNYVTQ<br>KPYSTKKIKLNFGIPTLADGWSKSKEYSNN<br>AIILMRDNLYYLGIFNAKNKPDKKIIEGNT<br>SENKGDYKKMIYNLLPGPNKMIPKVFLSSK<br>TGVETYKPSAYILEGYKQNKHIKSSKDFDI<br>TFCHDLIDYFKNCIAIHPEWKNFGFDFSDT<br>STYEDISGFYREVELQGYKIDWTYISEKDI<br>DLLQEKGQLYLFQIYNKDFSKKSTGNDNLH<br>TMYLKNLFSEENLKDIVLKLNGEAEIFFRK<br>SSIKNPIIHKKGSILVNRTYEAEEKDQFGN<br>IQIVRKNIPENIYQELYKYFNDKSDKELSD<br>EAAKLKNVVGHHEAATNIVKDYRYTYDKYF<br>LHMPITINFKANKTGFINDRILQYIAKEKD<br>LHVIGIDRGERNLIYVSVIDTCGNIVEQKS<br>FNIVNGYDYQIKLKQQEGARQIARKEWKEI<br>GKIKEIKEGYLSLVIHEISKMVIKYNAIIA<br>MEDLSYGFKKGRFKVERQVYQKFETMLINK<br>LNYLVFKDISITENGGLLKGYQLTYIPDKL<br>KNVGHQCGCIFYVPAAYTSKIDPTTGFVNI<br>FKFKDLTVDAKREFIKKFDSIRYDSEKNLF<br>CFTFDYNNFITQNTVMSKSSWSVYTYGVRI<br>KRRFVNGRFSNESDTIDITKDMEKTLEMTD<br>INWRDGHDLRQDIIDYEIVQHIFEIFRLTV<br>QMRNSLSELEDRDYDRLISPVLNENNIFYD<br>SAKAGDALPKDADANGAYCIALKGLYEIKQ<br>ITENWKEDGKFSRDKLKISNKDWFDFIQNK<br>RYL |
| SEQ ID NO: 60 | Cas12 Variant | MSNLNTFISPEFTGKIKMTKSLKVSMIPIG<br>ETEHWIAKHKVFEKDRELFDKNLKARPILD<br>EFIKYTVSRALPNLLFDFEAYYLVKKDRTK<br>ARAFEKELAKTVTDLILKEMDELKSASLID<br>SADFVKTTLKKFAGTHDIPGLSRIEAIESL<br>EAASKLTALNGKFNTSRIAIINTLIPKRII<br>ENFDIYLSNMEKIRNVYESGEFGFLFERYP<br>DTLLFMEPANYRTVCSPEAIEDYNRFISGY<br>GDSTESWIKGFNQELSEASNSSKSSNGGVR<br>RYSLIKPLHKQHLFETKKFFTFASISSDDD<br>VRELINSVKGSTEDACLNALAFFSSSDPKT<br>LFVKGSYLHTLSAFLYGSANSYILPERIKE<br>GEKARLTAEYDSVAKKTKAVTTRYNVAMNN<br>ISKKINEKIFSLADIDAYCCDISKRRSVRE<br>ILLGIMQEMYAAVYGENGKWSNIEAEAVLD<br>SKTKIWKAKNGAVAKAVNDYLTAILEIRKF<br>IRPFALRMEELEELGLDTSSALDAGEITNT<br>LFEAVRAQKLVHAYLTRNDADIALSTQVYF<br>GGTQKAAASWWNYETGDIQNRQIALAKKDG<br>MYYFIGTFDERGSYSIEPASPGEDYYEMLD<br>VKKGQDANKQIKKVLFSNKAIREHFADSSN |

TABLE 1-continued

| SEQ ID NO | Description | Sequence |
|---|---|---|
| | | DYVITTKVNSPITVRREIFDKYQAGEFKLTSQKIRKGDLVGEKEMTYYREYMDLLFQMAKGYTEYSRFNMDTLLPIEEYDTENDLLDDVNTNTIDYRWVRISAACIDDGVRNGDIFVFRAQTSSMYGKRENKKGYTGLFLELVSDENLLVTRGMSLNSAMSIYYRAKVHDAITVHKKGDVLVNKFTNARERIPENSYKAICAFYNSGKSIEELTIEDRDWLAKATTRICSGEIIKDRRYTKNQYSISISYNINRSVNNRKRVDLATIVDDTASAGRIISVTRGTKDLVYYTVIDDGGSVIEARSLNVINGINYAKMLAQISEERHDSNANFDIPKRVETIKEAYCAFAVHEIISAALKHNALIVVELISDAIKDKYSLLDNQVFLKFENVLKNCLMSVKVKGARGMEPGSISNPLQLCNADDKSFRNGILYQIPSSYINICPVTGYADIIDYYNIVSAGDIRNFFVRFENIVYNKEKARFEFSFDLKNIPIKLEKCPDRTKWTVLGRGEITTYDPLTKSNHYVFDAAQMLAETVSKEGLDPCANIVEHIDELSAATLKKMFNTFRNIAKGIVSECDEVPVSYYKSPVIDEADIKNKSLDNKSISEIKCYNLDEKARYYLALAKSSSDGENKNRYVSSTAIEWLNYIQEKRTHE |

Alternatively, the Type V CRISPR-Cas enzyme is a programmable Cas14 nuclease. A Cas14 enzyme of the present disclosure includes 3 partial RuvC domains (RuvC-I, RuvC-II, and RuvC-III, also referred to herein as subdomains) that are not contiguous with respect to the primary amino acid sequence of the Cas14 enzyme, but form a RuvC domain once the protein is produced and folds. A naturally occurring Cas14 enzyme functions as an endonuclease that catalyzes cleavage at a specific sequence in a target nucleic acid. A programmable Cas14 enzyme can be a Cas14a enzyme, a Cas14b enzyme, a Cas14c enzyme, a Cas14d enzyme, a Cas14e enzyme, a Cas14f enzyme, a Cas14g enzyme, a Cas14h enzyme, or a Cas14u enzyme. In some cases, a suitable Cas14 enzyme comprises an amino acid sequence having at least 80%, at least 85%, at least 90%, at least 95%, at least 98%, at least 99%, or 100%, amino acid sequence identity to any one of SEQ ID NO: 61-SEQ ID NO: 152.

TABLE 2

Cas14 Enzyme Sequences

| SEQ ID NO | Sequence |
|---|---|
| SEQ ID NO: 61 | MEVQKTVMKTLSLRILRPLYSQEIEKEIKEEKERRKQAGGTGELDGGFYKKLEKKHSEMFSFDRLNLLLNQLQREIAKVYNHAISELYIATIAQGNKSNKHYISSIVYNRAYGYFYNAYIALGICSKVEANFRSNELLTQQSALPTAKSDNFPIVLHKQKGAEGEDGGFRISTEGSDLIFEIPIPFYEYNGENRKEPYKWVKKGGQKPVLKLILSTFRRQRNKGWAKDEGTDAEIRKVTEGKYQVSQIEINRGKKLGEHQKWFANFSIEQPIYERKPNRSIVGGLDVGIRSPLVCAINNSFSRYSVDSNDVFKFSKQVFAFRRRLLSKNSLKRKGHGAAHKLEPITEMTEKNDKFRKKIIERWAKEVTNFFVKNQVGIVQIEDLSTMKDREDHFFNQYLRGFWPYYQMQTLIENKLKEYGIEVKRVQAKYTSQLCSNPNCRYWNNYFNFEYRKVNKFPKFKCEKCNLEISADYNAARNLSTPDIEKFVAKATKGINLPEK |
| SEQ ID | MEEAKTVSKTLSLRILRPLYSAEIEKEIKEEKERRKQGGKSGELDSGFYKKLEKKHTQMFGWDKLNLMLS |

TABLE 2-continued

Cas14 Enzyme Sequences

| SEQ ID NO | Sequence |
|---|---|
| NO: 62 | QLQRQIARVFNQSISELYIETVIQGKKSNKHYTSKIVYNRAYSVFYNAYLALGITSKVEANFRSTELLMQKSSLPTAKSDNFPILLHKQKGVEGEEGGFKISADGNDLIFEIPIPFYEYDSANKKEPFKWIKKGGQKPTIKLILSTFRRQRNKGWAKDEGTDAEIRKVIEGKYQVSHIEINRGKKLGDHQKWFVNFTIEQPIYERKLDKNIIGGIDVGIKSPLVCAVNNSFARYSVDSNDVLKFSKQAFAFRRRLLSKNSLKRSGHGSKNKLDPITRMTEKNDRFRKKIIERWAKEVTNFFIKNQVGTVQIEDLSTMKDRQDNFFNQYLRGFWPYYQMQNLIENKLKEYGIETKRIKARYTSQLCSNPSCRHWNSYFSFDHRKTNNFPKFKCEKCALEISADYNAARNISTPDIEKFVAKATKGINLPDKNENVILE |
| SEQ ID NO: 63 | MAKNTITKTLKLRIVRPYNSAEVEKIVADEKNNREKIALEKNKDKVKEACSKHLKVAAYCTTQVERNACLFCKARKLDDKFYQKLRGQFPDAVFWQEISEIFRQLQKQAAEIYNQSLIELYYEIFIKGKGIANASSVEHYLSDVCYTRAAELFKNAAIASGLRSKIKSNFRLKELKNMKSGLPTTKSDNFPIPLVKQKGGQYTGFEISNHNSDFIIKIPFGRWQVKKEIDKYRPWEKFDFEQVQKSPKPISLLLSTQRRKRNKGWSKDEGTEAEIKKVMNGDYQTSYIEVKRGSKIGEKSAWMLNLSIDVPKIDKGVDPSIIGGIDVGVKSPLVCAINNAFSRYSISDNDLFHFNKKMFARRRILLKKNRHKRAGHGAKNKLKPITILTEKSERFRKKLIERWACEIADFFIKNKVGTVQMENLESMKRKEDSYFNIRLRGFWPYAEMQNKIEFKLKQYGIEIRKVAPNNTSKTCSKCGHLNNYFNFEYRKKNKFPHFKCEKCNFKENADYNAALNISNPKLKSTKEEP |
| SEQ ID NO: 64 | MERQKVPQIRKIVRVVPLRILRPKYSDVIENALKKFKEKGDDTNTNDFWRAIRDRDTEFFRKELNFSEDEINQLERDTLFRVGLDNRVLFSYFDFLQEKLMKDYNKIISKLFINRQSKSSFENDLTDEEVEELIEKDVTPFYGAYIGKGIKSVIKSNLGGKFIKSVKIDRETKKVTKLTAINIGLMGLPVAKSDTFPIKIIKTNPDYITFQKSTKENLQKIEDYETGIEYGDLLVQITIPWFKNENKDFSLIKTKEAIEYYKLNGVGKKDLLNINLVLTTYHIRKKKSWQIDGSSQSLVREMANGELEEKWKSFFDTFIKKYGDEGKSALVKRRVNKKSRAKGEKGRELNLDERIKRLYDSIKAKSFPSEINLIPENYKWKLHFSIEIPPMVNDIDSNLYGGIDFGEQNIATLCVKNIEKDDYDFLTIYGNDLLKHAQASYARRRIMRVQDEYKARGHGKSRKTKAQEDYSERMQKLRQKITERLVKQISDFFLWRNKFHMAVCSLRYEDLNTLYKGESVKAKRMRQFINKQQLFNGIERKLKDYNSEIYVNSRYPHYTSRLCSKCGKLNLYFDFLKFRTKNIIIRKNPDGSEIKYMPFFICEFCGWKQAGDKNASANIADKDYQDKLNKEKEFCNIRKPKSKKEDIGEENEEERDYSRRFNRNSFIYNSLKKDNKLNQEKLFDEWKNQLKRKIDGRNKFEPKEYKDRFSYLFAYYQEIIKNESES |
| SEQ ID NO: 65 | MVPTELITKTLQLRVIRPLYFEEIEKELAELKEQKEKEFEETNSLLLESKKIDAKSLKKLKRKARSSAAVEFWKIAKEKYPDILTKPEMEFIFSEMQKMMARFYNKSMTNIFIEMNNDEKVNPLSLISKASTEANQVIKCSSISSGLNRKIAGSINKTKFKQVRDGLISLPTARTETFPISFYKSTANKDEIPISKINLPSEEEADLTITLPFPFFEIKKEKKGQKAYSYFNIIEKSGRSNNKIDLLLSTHRRQRRKGWKEEGGTSAEIRRLMEGEFDKEWEIYLGEAEKSEKAKNDLIKNMTRGKLSKDIKEQLEDIQVKYFSDNNVESWNDLSKEQKQELSKLRKKKVEELKDWKHVKEILKTRAKIGWVELKRGKRQRDRNKWFVNITITRPPFINKELDDTKFGGIDLGVKVPFVCAVHGSPARLIIKENEILQFNKMVSARNRQITKDSEQRKGRGKKNKFIKKEIFNERNELFRKKIIERWANQIVKFFEDQKCATVQIENLESFDRTSYK |
| SEQ ID NO: 66 | MKSDTKDKKIIIHQTKTLSLRIVKPQSIPMEEFTDLVRYHQMIIFPVYNNGAIDLYKKLFKAKIQKGNEARAIKYFMNKIVYAPIANTVKNSYIALGYSTKMQSSFSGKRLWDLRFGEATPPTIKADFPLPFYNQSGFKVSSENGEFIIGIPFGQYTKKTVSDIEKKTSFAWDKF |

TABLE 2-continued

Cas14 Enzyme Sequences

| SEQ ID NO | Sequence |
|---|---|
| | TLEDTTKKTLIELLLSTKTRKMNEGWKNNEGTEAEIKRVMDGTYQVTSLEILQRDDSWFVNFNIAYDSLKKQPDRDKIAGIHMGITRPLTAVIYNNKYRALSIYPNTVMHLTQKQLARIKEQRTNSKYATGGHGRNAKVTGTDTLSEAYRQRRKKIIEDWIASIVKFAINNEIGTIYLEDISNTNSFFAAREQKLIYLEDISNTNSFLSTYKYPISAISDTLQHKLEEKAIQVIRKKAYYVNQICSLCGHYNKGFTYQFRRKNKFPKMKCQGCLEATSTEFNAAANVANPDYEKLLIKHGLLQLKK |
| SEQ ID NO: 67 | MSTITRQVRLSPTPEQSRLLMAHCQQYISTVNVLVAAFDSEVLTGKVSTKDFRAALPSAVKNQALRDAQSVFKRSVELGCLPVLKKPHCQWNNQNWRVEGDQLILPICKDGKTQQERFRCAAVALEGKAGILRIKKKRGKWIADLTVTQEDAPESSGSAIMGVDLGIKVPAVAHIGGKGTRFFGNGRSQRSMRRRFYARRKTLQKAKKLRAVRKSKGKEARWMKTINHQLSRQIVNHAHALGVGTIKIEALQGIRKGTTRKSRGAAARKNNRMTNTWSFSQLTLFITYKAQRQGITVEQVDPAYTSQDCPACRARNGAQDRTYVCSECGWRGHRDTVGAINISRRAGLSGHRRGATGA |
| SEQ ID NO: 68 | MIAQKTIKIKLNPTKEQIIKLNSIIEEYIKVSNFTAKKIAEIQESFTDSGLTQGTCSECGKEKTYRKYHLLKKDNKLFCITCYKRKYSQFTLQKVEFQNKTGLRNVAKLPKTYYTNAIRFASDTFSGFDEIIKKKQNRLNSIQNRLNFWKELLYNPSNRNEIKIKVVKYAPKTDTREHPHYYSEAEIKGRIKRLEKQLKKFKMPKYPEFTSETISLQRELYSWKNPDELKISSITDKNESMNYYGKEYLKRYIDLINSQTPQILLEKENNSFYLCFPITKNIEMPKIDDTFEPVGIDWGITRNIAVVSILDSKTKKPKFVKFYSAGYILGKRKHYKSLRKHFGQKKRQDKINKLGTKEDRFIDSNIHKLAFLIVKEIRNHSNKPIILMENITDNREEAEKSMRQNILLHSVKSRLQNYIAYKALWNNIPTNLVKPEHTSQICNRCGHQDRENRPKGSKLFKCVKCNYMSNADFNASINIARKFYIGEYEP |
| SEQ ID NO: 69 | FYKDNEKMKSGVNSISMLKLSEQENITTGVKFKLKLDKETSEGLNDYFDEYGKAINFAIKVIQKELAEDRFAGKVRLDENKKPLLNEDGKKIWDFPNEFCSCGKQVNRYVNGKSLCQECYKNKFTEYGIRKRMYSAKGRKAEQDINIKNSTNKISKTHFNYAIREAFILDKSIKKQRKERFRRLREMKKKLQEFIEIRDGNKILCPKIEKQRVERYIHPSWINKEKKLEDFRGYSMSNVLGKIKILDRNIKREEKSLKEKGQINFKARRLMLDKSVKFLNDNKISFTISKNLPKEYELDLPEKEKRLNWLKEKIKIIKNQKPKYAYLLRKDDNFYLQYTLETEFNLKEDYSGIVGIDRGVSHIAVYTFVHNNGKNERPLFLNSSEILRLKNLQKERDRFLRRKHNKKRKKSNMRNIEKKIQLILHNYSKQIVDFAKNKNAFIVFEKLEKPKKNRSKMSKKSQYKLSQFTFKKLSDLVDYKAKREGIKVLYISPEYTSKECSHCGEKVNTQRPFNGNSSLFKCNKCGVELNADYNASINIAKKGLNILNSTN |
| SEQ ID NO: 70 | MEESIITGVKFKLRIDKETTKKLNEYFDEYGKAINFAVKIIQKELADDRFAGKAKLDQNKNPILDENGKKIYEFPDEFCSCGKQVNKYVNNKPFCQECYKIRFTENGIRKRMYSAKGRKAEHKINILNSTNKISKTHFNYAIREAFILDKSIKKQRKKRNERLRESKKRLQQFIDMRDGKREICPTIKGQKVDRFIHPSWITKDKKLEDFRGYTLSIINSKIKILDRNIKREEKSLKEKGQIIFKAKRLMLDKSIRFVGDRKVLFTISKTLPKEYELDLPSKEKRLNWLKEKIEIIKNQKPKYAYLLRKNIESEKKPNYEYYLQYTLEIKPELKDFYDGAIGIDRGINHIAVCTFISNDGKVTPPKFFSSGEILRLKNLQKERDRFLLRKHNKNRKKGNMRVIENKINLILHRYSKQIVDMAKKLNASIVFEELGRIGKSRTKMKKSQRYKLSLFIFKKLSDLVDYKSRREGIRVTYVPPEYTSKECSHCGEKVNTQRPFNGNYSLFKCNKCGIQLNSDYNASINIAKKGLKIPNST |

TABLE 2-continued

Cas14 Enzyme Sequences

| SEQ ID NO | Sequence |
|---|---|
| SEQ ID NO: 71 | LWTIVIGDFIEMPKQDLVTTGIKFKLDVDKETRKKLDDYFDEYGKAINFAVKIIQKNLKEDRFAGKIALGEDKKPLLDKDGKKIYNYPNESCSCGNQVRRYVNAKPFCVDCYKLKFTENGIRKRMYSARGRKADSDINIKNSTNKISKTHFNYAIREGFILDKSLKKQRSKRIKKLLELKRKLQEFIDIRQGQMVLCPKIKNQRVDKFIHPSWLKRDKKLEEFRGYSLSVVEGKIKIFNRNILREEDSLRQRGHVNFKANRIMLDKSVRFLDGGKVNFNLNKGLPKEYLLDLPKKENKLSWLNEKISLIKLQKPKYAYLLRREGSFFIQYTIENVPKTFSDYLGAIGIDRGISHIAVCTFVSKNGVNKAPVFFSSGEILKLKSLQKQRDLFLRGKHNKIRKKSNMRNIDNKINLILHKYSRNIVNLAKSEKAFIVFEKLEKIKKSRFKMSKSLQYKLSQFTFKKLSDLVEYKAKIEGIKVDYVPPEYTSKECSHCGEKVDTQRPFNGNSSLFKCNKCRVOLNADYNASINIAKKSLNISN |
| SEQ ID NO: 72 | MSKTTISVKLKIIDLSSEKKEFLDNYFNEYAKATTFCQLRIRRLLRNTHWLGKKEKSSKKWIFESGICDLCGENKELVNEDRNSGEPAKICKRCYNGRYGNQMIRKLFVSTKKREVQENMDIRRVAKLNNTHYHRIPEEAFDMIKAADTAEKRRKKNVEYDKKRQMEFIEMENDEKKRAARPKKPNERETRYVHISKLESPSKGYTLNGIKRKIDGMGKKIERAEKGLSRKKIFGYQGNRIKLDSNWVRFDLAESEITIPSLFKEMKLRITGPTNVHSKSGQIYFAEWFERINKQPNNYCYLIRKTSSNGKYEYYLQYTYEAEVEANKEYAGCLGVDIGCSKLAAAVYYDSKNKKAQKPIEIFTNPIKKIKMRREKLIKLLSRVKVRHRRRKLMQLSKTEPIIDYTCHKTARKIVEMANTAKAFISMENLETGIKQKQQARETKKQKFYRNMFLFRKLSKLIEYKALLKGIKIVYVKPDYTSQTCSSCGADKEKTERPSQAIFRCLNPTCRYYQRDINADFNAAVNIAKKALNNTEVVTTLL |
| SEQ ID NO: 73 | MARAKNQPYQKLTTTTGIKFKLDLSEEEGKRFDEYFSEYAKAVNFCAKVIYQLRKNLKFAGKKELAAKEWKFEISNCDFCNKQKEIYYKNIANGQKVCKGCHRTNFSDNAIRKKMIPVKGRKVESKFNIHNTTKKISGTHRHWAFEDAADIIESMDKQRKEKQKRLRREKRKLSYFFELFGDPAKRYELPKVGKQRVPRYLHKIIDKDSLTKKRGYSLSYIKNKIKISERNIERDEKSLRKASPIAFGARKIKMSKLDPKRAFDLENNVFKIPGKVIKGQYKFFGTNVANEHGKKFYKDRISKILAGKPKYFYLLRKKVAESDGNPIFEYYVQWSIDTETPAITSYDNILGIDAGITNLATTVLIPKNLSAEHCSHCGNNHVKPIFTKFFSGKELKAIKIKSRKQKYFLRGKHNKLVKIKRIRPIEQKVDGYCHVVSKQIVEMAKERNSCIALEKLEKPKKSKFRQRRREKYAVSMFVFKKLATFIKYKAAREGIEIIPVEPEGTSYTCSHCKNAQNNQRPYFKPNSKKSWTSMFKCGKCGIELNSDYNAAFNIAQKALNMTSA |
| SEQ ID NO: 74 | MDEKHFFCSYCNKELKISKNLINKISKGSIREDEAVSKAISIHNKKEHSLILGIKFKLFIENKLDKKKLNEYFDNYSKAVTFAARIFDKIRSPYKFIGLKDKNTKKWTFPKAKCVFCLEEKEVAYANEKDNSKICTECYLKEFGENGIRKKIYSTRGRKVEPKYNIFNSTKELSSTHYNYAIRDAFOLLDALKKQRQKKLKSIFNQKLRLKEFEDIFSDPQKRIELSLKPHQREKRYIHLSKSGQESINRGYTLRFVRGKIKSLTRNIEREEKSLRKKTPIHFKGNRLMIFPAGIKFDFASNKVKISISKNLPNEFNFSGTNVKNEHGKSFFKSRIELIKTQKPKYAYVLRKIKREYSKLRNYEIEKIRLENPNADLCDFYLQYTIETESRNNEEINGIIGIDRGITNLACLVLLKKGDKKPSGVKFYKGNKILGMKIAYRKHLYLLKGKRNKLRKQRQIRAIEPKINLILHQISKDIVKIAKEKNFAIALEQLEKPKKARFAQRKKEKYKLALFTFKNLSTLIEYKSKREGIPVIYVPPEKTSQMCSHCAINGDEHVDTQRPYKKPNAQKPSYSLFKCNKCGIELNADYNAAFNIAQKGLKTLMLNHSH |
| SEQ ID NO: | MLQTLLVKLDPSKEQYKMLYETMERFNEACNQIAETVFAIHSANKIEVQKTVYYPIREKFGLSAQLTILAIRKVCEAYKRDKSIKPEFRLDGALVYDQRVLSWKG |

TABLE 2-continued

Cas14 Enzyme Sequences

| SEQ ID NO | Sequence |
|---|---|
| 75 | LDKVSLVTLQGRQIIPIKFGDYQKARMDRIRGQADLILVKGVFYLCVVVEVSEESPYDPKGVLGVDLGIKNLAVDSDGEVHSGEQTTNTRERLDSLKARLQSKGTKSAKRHLKKLSGRMAKFSKDVNHCISKKLVAKAKGTLMSIALEDLQGIRDRVTVRKAQRRNLHTWNFGLLRMFVDYKAKIAGVPLVFVDPRNTSRTCPSCGHVAKANRPTRDEFRCVSCGFAGAADHIAAMNIAFRAEVSQPIVTRFFVQSQAPSFRVG |
| SEQ ID NO: 76 | MDEEPDSAEPNLAPISVKLKLVKLDGEKLAALNDYFNEYAKAVNFCELKMQKIRKNLVNIRGTYLKEKKAWINQTGECCICKKIDELRCEDKNPDINGKICKKCYNGRYGNQMIRKLFVSTNKRAVPKSLDIRKVARLHNTHYHRIPPEAADIIKAIETAERKRRNRILFDERRYNELKDALENEEKRVARPKKPKEREVRYVPISKKDTPSKGYTMNALVRKVSGMAKKIERAKRNLNKRKKIEYLGRRILLDKNWVRFDFDKSEISIPTMKEFFGEMRFEITGPSNVMSPNGREYFTKWFDRIKAQPDNYCYLLRKESEDETDFYLQYTWRPDAHPKKDYTGCLGIDIGGSKLASAVYFDADKNRAKQPIQIFSNPIGKWKTKRQKVIKVLSKAAVRHKTKKLESLRNIEPRIDVHCHRIARKIVGMALAANAFISMENLEGGIREKQKAKETKKQKFSRNMFVFRKLSKLIEYKALMEGVKVVYIVPDYTSQLCSSCGTNNTKRPKQAIFMCQNTECRYFGKNINADFNAAINIAKKALNRKDIVRELS |
| SEQ ID NO: 77 | MEKNNSEQTSITTGIKFKLKLDKETKEKLNNYFDEYGKAINFAVRIIQMQLNDDRLAGKYKRDEKGKPILGEDGKKILEIPNDFCSCGNQVNHYVNGVSFCQECYKKRFSENGIRKRMYSAKGRKAEQDINIKNSTNKISKTHFNYAIREAFNLDKSIKKQREKRFKKLKDMKRKLQEFLEIRDGKRVICPKIEKQKVERYIHPSWINKEKKLEEFRGYSLSIVNSKIKSFDRNIQREEKSLKEKGQINFKAQRLMLDKSVKFLKDNKVSFTISKELPKTFELDLPKKEKKLNWLNEKLEIIKNQKPKYAYLLRKENNIFLQYTLDSIPEIHSEYSGAVGIDRGVSHIAVYTFLDKDGKNERPFFLSSSGILRLKNLQKERDKFLRKKHNKIRKKGNMRNIEQKINLILHEYSKQIVNFAKDKNAFIVFELLEKPKKSRERMSKKIQYKLSQFTFKKLSDLVDYKAKREGIKVIYVEPAYTSKDCSHCGERVNTQRPFNGNFSLFKCNKCGIVLNSDYNASLNIARKGLNISAN |
| SEQ ID NO: 78 | MAEEKFFFCEKCNKDIKIPKNYINKQGAEEKARAKHEHRVHALILGIKFKIYPKKEDISKLNDYFDEYAKAVTFTAKIVDKLKAPFLFAGKRDKDTSKKKWVFPVDKCSFCKEKTEINYRTKQGKNICNSCYLTEFGEQGLLEKIYATKGRKVSSSFNLFNSTKKLTGTHNNYVVKESLQLLDALKKQRSKRLKKLSNTRRKLKQFEEMFEKEDKRFQLPLKEKQRELRFIHVSQKDRATEFKGYTMNKIKSKIKVLRRNIEREQRSLNRKSPVFFRGTRIRLSPSVQFDDKDNKIKLTLSKELPKEYSFSGLNVANEHGRKFFAEKLKLIKENKSKYAYLLRRQVNKNNKKPIYDYYLQYTVEFLPNIITNYNGILGIDRGINTLACIVLLENKKEKPSFVKFFSGKGILNLKNKRRKQLYFLKGVHNKYRKQQKIRPIEPRIDQILHDISKQIIDLAKEKRVAISLEQLEKPQKPKFRQSRKAKYKLSQFNFKTLSNYIDYKAKKEGIRVIYIAPEMTSQNCSRCAMKNDLHVNTQRPYKNTSSLFKCNKCGVELNADYNAAFNIAQKGLKILNS |
| SEQ ID NO: 79 | MISLKLKLLPDEEQKKLLDEMFWKWASICTRVGFGRADKEDLKPPKDAEGVWFSLTQLNQANTDINDLREAMKHQKHRLEYEKNRLEAQRDDTQDALKNPDRREISTKRKDLFRPKASVEKGFLKLKYHQERYWVRRLKEINKLIERKTKTLIKIEKGRIKFKATRITLHQGSFKIRFGDKPAFLIKALSGKNQIDAPFVVVPEQPICGSVVNSKKYLDEITTNFLAYSVNAMLFGLSRSEEMLLKAKRPEKIKKKEEKLAKKQSAFENKKKELQKLLGRELTQQEEAIIEETRNQFFQDFEVKITKQYSELLSKIANELKQKNDFLKVNKYPILLRKPLKKAKSKKINNLSPSEWKYYLQFGVKPLLKQKSRRKSRNVLGIDRGLKHLLAVTVLEPDKKTFVWNKLYPNPITGWKWRRRKLLRSLKRLKRRIKSQKHETIHENQTRKKLKSLQGRIDDLLHNISRKIVETAKEYDAVIVVEDLQSMRQHGRSKGNRLKTLNYALSLFDYANVMQLIKYKAGIEGIQIYDVKPAGTSQNCAYCLLAQRDSHEYKRSQENSKIGVCLNPNCQNHKKQIDADLNAARVIASCYALKINDSQPFGTRKRFKKRTTN |
| SEQ ID NO: 80 | METLSLKLKLNPSKEQLLVLDKMFWKWASICTRLGLKKAEMSDLEPPKDAEGVWFSKTQLNQANTDVNDLRKAMQHQGKRIEYELDKVENRRNEIQEMLEKPDRRDISPNRKDLFRPKAAVEKGYLKLKYHKLGYWSKELKTANKLIERKRKTLAKIDAGKMKFKPTRISLHTNSFRIKFGEEPKIALSTTSKHEKIELPLITSLQRPLKTSCAKKSKTYLDAAILNFLAYSTNAALFGLSRSEEMLLKAKKPEKIEKRDRKLATKRESFDKKLKTLEKLLERKLSEKEKSVFKRKQTEFFDKFCITLDETYVEALHRIAEELVSKNKYLEIKKYPVLLRKPESRLRSKKLKNLKPEDWTYYIQFGFQPLLDTPKPIKTKTVLGIDRGVRHLLAVSIFDPRTKTFTFNRLYSNPIVDWKWRRRKLLRSIKRLKRRLKSEKHVHLHENQFKAKLRSLEGRIEDHFHNLSKEIVDLAKENNSVIVVENLGGMRQHGRGRGKWLKALNYALSHFDYAKVMQLIKYKAELAGVFVYDVAPAGTSINCAYCLLNDKDASNYTRGKVINGKKNTKIGECKTCKKEFDADLNAARVIALCYEKRLNDPQPFGTRKQFKPKKP |
| SEQ ID NO: 81 | MKALKLQLIPTRKQYKILDEMFWKWASLANRVSQKGESKETLAPKKDIQKIQFNATQLNQIEKDIKDLRGAMKEQQKQKERLLLQIQERRSTISEMLNDDNNKERDPHRPLNFRPKGWRKFHTSKHWVGELSKILRQEDRVKKTIERIVAGKISFKPKRIGIWSSNYKINFFKRKISINPLNSKGFELTLMTEPTQDLIGKNGGKSVLNNKRYLDDSIKSLLMFALHSRFFGLNNTDTYLLGGKINPSLVKYYKKNQDMGEFGREIVEKFERKLKQEINEQQKKIIMSQIKEQYSNRDSAFNKDYLGLINEFSEVFNQRKSERAEYLLDSFEDKIKQIKQEIGESLNISDWDFLIDEAKKAYGYEEGFTEYVYSKRYLEILNKIVKAVLITDIYFDLRKYPILLRKPLDKIKKISNLKPDEWSYYIQFGYDSINPVQLMSTDKFLGIDRGLTHLLAYSVFDKEKKEFIINQLEPNPIMGWKWKLRKVKRSLQHLERRIRAQKMVKLPENQMKKKLKSIEPKIEVHYHNISRKIVNLAKDYNASIVVESLEGGGLKQHGRKKNARNRSLNYALSLFDYGKIASLIKYKADLEGVPMYEVLPAYTSQQCAKCVLEKGSFVDPEIIGYVEDIGIKGSLLDSLFEGTELSSIQVLKKIKNKIELSARDNHNKEINLILKYNFKGLVIVRGQDKEEIAEHPIKEINGKFAILDFVYKRGKEKVGKKGNQKVRYTGNKKVGYCSKHGQVDADLNASRVIALCKYLDINDPILFGEQRKSFK |
| SEQ ID NO: 82 | MVTRAIKLKLDPTKNQYKLLNEMFWKWASLANRFSQKGASKETLAPKDGTQKIQFNATQLNQIKKDVDDLRGAMEKQGKQKERLLIQIQERLLTISEILRDDSKKEKDPHRPQNFRPFGWRRFHTSAYWSSEASKLTRQVDRVRRTIERIKAGKINFKPKRIGLWSSTYKINFLKKKINISPLKSKSFELDLITEPQQKIIGKEGGKSVANSKKYLDDSIKSLLIFAIKSRLFGLNNKDKPLFENIITPNLVRYHKKGQEQENFKKEVIKKFENKLKKEISQKQKEIIFSQIERQYENRDATFSEDYLRAISEFSEIFNQRKKERAKELLNSFNEKIRQLKKEVNGNISEEDLKILEVEAEKAYNYENGFIEWEYSEQFLGVLEKIARAVLISDNYFDLKKYPILIRKPTNKSKKITNLKPEEWDYYIQFGYGLINSPMKIETKNFMGIDRGLTHLLAYSIFDRDSEKFTINQLELNPIKGWKWKLRKVKRSLQHLERRMRAQKGVKLPENQMKKRLKSIEPKIESYYHNLSRKIVNLAKANNASIVVESLEGGGLKQHGRKKNSRHRALNYALSLFDYGKIASLIKYKSDLEGVPMYEVLPAYTSQQCAKCVLKKGSFVEPEIIGYIEEIGFKENLLTLLFEDTGLSSVQVLKKSKNKMTLSARDKEGKMVDLVLKYNFKGLVISQEKKKEEIVEFPIKEIDGKFAVLDSAYKRGKERISKKGNQKLVYTGNKKVGYCSVHGQVDADLNASRVIALCKYLGINEPIVFGEQRKSFK |

TABLE 2-continued

Cas14 Enzyme Sequences

| SEQ ID NO | Sequence |
|---|---|
| SEQ ID NO: 83 | LDLITEPIQPHKSSSLRSKEFLEYQISDFLNFSLHSLFFGLASNEGPLVDFKIYDKIVIPKPEERFPKKESEEGKKLDSFDKRVEEYYSDKLEKKIERKLNTEEKNVIDREKTRIWGEVNKLEEIRSIIDEINEIKKQKHISEKSKLLGEKWKKVNNIQETLLSQEYVSLISNLSDELTNKKKELLAKKYSKFDDKIKKIKEDYGLEFDENTIKKEGEKAFLNPDKFSKYQFSSSYLKLIGEIARSLITYKGFLDLNKYPIIFRKPINKVKKIHNLEPDEWKYYIQFGYEQINNPKLETENILGIDRGLTHILAYSVFEPRSSKFILNKLEPNPIEGWKWKLRKLRRSIQNLERRWRAQDNVKLPENQMKKNLRSIEDKVENLYHNLSRKIVDLAKEKNACIVFEKLEGQGMKQHGRKKSDRLRGLNYKLSLFDYGKIAKLIKYKAEIEGIPIYRIDSAYTSQNCAKCVLESRRFAQPEEISCLDDFKEGDNLDKRILEGTGLVEAKIYKKLLKEKKEDFEIEEDIAMFDTKKVIKENKEKTVILDYVYTRRKEIIGTNHKKNIKGIAKYTGNTKIGYCMKHGQVDADLNASRTIALCKNFDINNPEIWK |
| SEQ ID NO: 84 | MSDESLVSSEDKLAIKIKIVPNAEQAKMLDEMFKKWSSICNRISRGKEDIETLRPDEGKELQFNSTQLNSATMDVSDLKKAMARQGERLEAEVSKLRGRYETIDASLRDPSRRHTNPQKPSSFYPSDWDISGRLTPRFHTARHYSTELRKLKAKEDKMLKTINKIKNGKIVFKPKRITLWPSSVNMAFKGSRLLLKPFANGFEMELPIVISPQKTADGKSQKASAEYMRNALLGLAGYSINQLLFGMNRSQKMLANAKKPEKVEKFLEQMKNKDANFDKKIKALEGKWLLDRKLKESEKSSIAVVRTKFFKSGKVELNEDYLKLLKHMANEILERDGFVNLNKYPILSRKPMKRYKQKNIDNLKPNMWKYYIQFGYEPIFERKASGKPKNIMGIDRGLTHLLAVAVFSPDQQKFLFNHLESNPIMHWKWKLRKIRRSIQHMERRIRAEKNKHIHEAQLKKRLGSIEEKTEQHYHIVSSKIINWAIEYEAAIVLESLSHMKQRGGKKSVRTRALNYALSLFDYEKVARLITYKARIRGIPVYDVLPGMTSKTCATCLLNGSQGAYVRGLETTKAAGKATKRKNMKIGKCMVCNSSENSMIDADLNAARVIAICKYKNLNDPQPAGSRKVFKRF |
| SEQ ID NO: 85 | MLALKLKIMPTEKQAEILDAMFWKWASICSRIAKMKKKVSVKENKKELSKKIPSNSDIWFSKTQLCQAEVDVGDHKKALKNFEKRQESLLDELKYKVKAINEVINDESKREIDPNNPSKFRIKDSTKKGNLNSPKFFTLKKWQKILQENEKRIKKKESTIEKLKRGNIFFNPTKISLHEEEYSINFGSSKLLLNCFYKYNKKSGINSDQLENKFNEFQNGLNIICSPLQPIRGSSKRSFEFIRNSIINFLMYSLYAKLFGIPRSVKALMKSNKDENKLKLEEKLKKKKSSFNKTVKEFEKMIGRKLSDNESKILNDESKKFFEIIKSNNKYIPSEEYLKLLKDISEEIYNSNIDFKPYKYSILIRKPLSKFKSKKLYNLKPTDYKYYLQLSYEPFSKQLIATKTILGIDRGLKHLLAVSVFDPSQNKFVYNKLIKNPVFKWKKRYHDLKRSIRNRERRIRALTGVHIHENQLIKKLKSMKNKINVLYHNVSKNIVDLAKKYESTIVLERLENLKQHGRSKGKRYKKLNYVLSNFDYKKIESLISYKAKKEGVPVSNINPKYTSKTCAKCLLEVNQLSELKNEYNRDSKNSKIGICNIHGQIDADLNAARVIALCYSKNLNEPHFK |
| SEQ ID NO: 86 | VINLFGYKFALYPNKTQEELLNKHLGECGWLYNKAIEQNEYYKADSNIEEAQKKFELLPDKNSDEAKVLRGNISKDNYVYRTLVKKKKSEINVQIRKAVVLRPAETIRNLAKVKKKGLSVGRLKFIPIREWDVLPFKQSDQIRLEENYLILEPYGRLKFKMHRPLLGKPKTFCIKRTATDRWTISFSTEYDDSNMRKNDGGQVGIDVGLKTHLRLSNENPDEDPRYPNPKIWKRYDRRLTILQRRISKSKKLGKNRTRLRLRLSRLWEKIRNSRADLIQNETYEILSENKLIAIEDLNVKGMQEKKDKKGRKGRTRAQEKGLHRSISDAAFSEFRRVLEYKAKRFGSEVKPVSAIDSSKECHNCGNKKGMPLESRIYECPKCGLKIDRDLNSAKVILARATGVRPGSNARADTKISATAGASVQTEGTVSEDFRQQMETSDQKPMQGEGSKEPPMNPEHKSSGRGSKHVNIGCKNKVGLYNEDENSRSTEKQIMDENRSTTEDMVEIGALHSPVLTT |
| SEQ ID NO: 87 | MIASIDYEAVSQALIVFEFKAKGKDSQYQAIDEAIRSYRFIRNSCLRYWMDNKKVGKYDLNKYCKVLAKQYPFANKLNSQARQSAAECSWSAISRFYDNCKRKVSGKKGFPKFKKHARSVEYKTSGWKLSENRKAITFTDKNGIGKLKLKGTYDLHFSQLEDMKRVRLVRRADGYYVQFCISVDVKVETEPTGKAIGLDVGIKYFLADSSGNTIENPQFYRKAEKKLNRANRRKSKKYIRGVKPQSKNYHKARCRYARKHLRVSRQRKEYCKRVAYCVIHSNDVVAYEDLNVKGMVKNRHLAKSISDVAWSTFRHWLEYFAIKYGKLTIPVAPHNTSQNCSNCDKKVPKSLSTRTHICHHCGYSEDRDVNAAKNILKKALSTVGQTGSLKLGEIEPLLVLEQSCTRKFDL |
| SEQ ID NO: 88 | LAEENTLHLTLAMSLPLNDLPENRTRSELWRRQWLPQKKLSLLLGVNQSVRKAAADCLRWFEPYQELLWWEPTDPDGKKLLDKEGRPIKRTAGHMRVLRKLEEIAPFRGYQLGSAVKNGLRHKVADLLLSYAKRKLDPQFTDKTSYPSIGDQFPIVWTGAFVCYEQSITGQLYLYLPLFPRGSHQEDITNNYDPDRGPALQVFGEKEIARLSRSTSGLLLPLQFDKWGEATFIRGENNPPTWKATHRRSDKKWLSEVLLREKDFQPKRVELLVRNGRIFVNVACEIPTKPLLEVENFMGVSFGLEHLVTVVVINRDGNVVHQRQEPARRYEKTYFARLERLRRRGGPFSQELETFHYRQVAQIVEEALRFKSVPAVEQVGNIPKGRYNPRLNLRLSYWPFGKLADLTSYKAVKEGLPKPYSVYSATAKMLCSTCGAANKEGDQPISLKGPTVYCGNCGTRHNTGFNTALNLARRAQELFVKGVVAR |
| SEQ ID NO: 89 | MSQSLLKWHDMAGRDKDASRSLQKSAVEGVLLHLTASHRVALEMLEKSVSQTVAVTMEAAQQRLVIVLEDDPTKATSRKRVISADLQFTREEFGSLPNWAQKLASTCPEIATKYADKHINSIRIAWGVAKESTNGDAVEQKLQWQIRLLDVTMFLQQLVLQLADKALLEQIPSSIRGGIGQEVAQQVTSHIQLLDSGTVLKAELPTISDRNSELARKQWEDAIQTVCTYALPFSRERARILDPGKYAAEDPRGDRLINIDPMWARVLKGPTVKSLPLLFVSGSSIRIVKLTLPRKHAAGHKHTFTATYLVLPVSREWINSLPGTVQEKVQWWKKPDVLATQELLVGKGALKKSANTLVIPISAGKKRFFNHILPALQRGFPLQWQRIVGRSYRRPATHRKWFAQLTIGYTNPSSLPEMALGIHFGMKDILWWALADKQGNILKDGSIPGNSILDFSLQEKGKIERQQKAGKNVAGKKYGKSLLNATYRVVNGVLEFSKGISAEHASQPIGLGLETIRFVDKASGSSPVNARHSNWNYGQLSGIFANKAGPAGFSVTEITLKKAQRDLSDAEQARVLAIEATKRFASRIKRLATKRKDDTLFV |
| SEQ ID NO: 90 | VEPVEKERFYYRTYTFRLDGQPRTQNLTTQSGWGLLTKAVLDNTKHYWEIVHHARIANQPIVFENPVIDEQGNPKLNKLGQPRFWKRPISDIVNQLRALFENQNPYQLGSSLIQGTYWDVAENLASWYALNKEYLAGTATWGEPSFPEPHPLTEINQWMPLTFSSGKVVRLLKNASGRYFIGLPILGENNPCYRMRTIEKLIPCDGKGRVTSGSLILFPLVGIYAQQHRRMTDICESIRTEKGKLAWAQVSIDYVREVDKRRRMRRTRKSQGWIQGPWQEVFILRLVLAHKAPKLYKPRCFAGISLGPKTLASCVILDQDERVVEKQQWSGSELLSLIHQGEERLRSLREQSKPTWNAAYRKQLKSLINTQVFTIVTFLRERGAAVRLESIARVRKSTPAPPVNFLLSHWAYRQITERLKDLAIRNGMPLTHSNGSYGVRFTCSQCGATNQGIKDPTKYKVDIESETFLCSICSHREIAAVNTATNLAKQLLDE |
| SEQ ID NO: 91 | MNDTETSETLTSHRTVCAHLHVVGETGSLPRLVEAALAELITLNGRATQALLSLAKNGLVLRRDKEENLIAAELTLPCRKNKYADVAAKAGEPILATRINNKGKLVTKKWYGEGNSYHIVRFTPETGMFTVRVFDRYAFDEELLHLHSEVVFGSDLPKGIKAKTDSLPANFLQAVFTSFLELPFQGFPDIVVKPAMKQAAEQLLSYVQLEAGENQQAEYPDTNERDPELRLVEWQKSLHELSVRTEPFEFVRARDIDYYAETDRRGNRFVNITPEWTKFAESPFARRLPLKIPPEFCILLRRKTEGHAKIPNRIYLGLQIFDGVTPDSTLGVLATAEDGKLFWWHDHLDE |

TABLE 2-continued

Cas14 Enzyme Sequences

| SEQ ID NO | Sequence |
| --- | --- |
| | FSNLEGKPEPKLKNKPQLLMVSLEYDREQRFEESV<br>GGDRKICLVTLKETRNFRRGWNGRILGIHFQHNPV<br>ITWALMDHDAEVLEKGFIEGNAFLGKALDKQALNE<br>YLQKGGKWVGDRSFGNKLKGITHTLASLIVRLARE<br>KDAWIALEEISWVQKQSADSVANHEIVEQPHHSLT<br>R |
| SEQ ID NO: 92 | MNDTETSETLTSHRTVCAHLHVVGETGSLPRLVEA<br>ALAELITLNGRATQALLSLAKNGLVLRRDKEENLI<br>AAELTLPCRKNKYADVAAKAGEPILATRINNKGKL<br>VTKKWYGEGNSYHIVRFTPETGMFTVRVFDRYAFD<br>EELLHLHSEVVFGSDLPKGIKAKTDSLPANFLQAV<br>FTSFLELPFQGFPDIVVKPAMKQAAEQLLSYVQLE<br>AGENQQAEYPDTNERDPELRLVEWQKSLHELSVRT<br>EPFEFVRARDIDYYAETDRRGNRFVNITPEWTKFA<br>ESPFARRLPLKIPPEFCILLRRKTEGHAKIPNRIY<br>LGLQIFDGVTPDSTLGVLATAEDGKLFWWHDHLDE<br>FSNLEGKPEPKLKNKPQLLMVSLEYDREQRFEESV<br>GGDRKICLVILKETRNFRRGRHGHTRTDRLPAGNT<br>LWRADFATSAEVAAPKWNGRILGIHFQHNPVITWA<br>LMDHDAEVLEKGFIEGNAFLGKALDKQALNEYLQK<br>GGKWVGDRSFGNKLKGITHTLASLIVRLAREKDAW<br>IALEEISWVQKQSADSVANRRFSMWNYSRLATLIE<br>WLGTDIATRDCGTAAPLAHKVSDYLTHFTCPECGA<br>CRKAGQKKEIADTVRAGDILTCRKCGFSGPIPDNF<br>IAEFVAKKALERMLKKKPV |
| SEQ ID NO: 93 | MAKRNFGEKSEALYRAVRFEVRPSKEELSILLAVS<br>EVLRMLFNSALAERQQVFTEFIASLYAELKSASVP<br>EEISEIRKKLREAYKEHSISLFDQINALTARRVED<br>EAFASVTRNWQEETLDALDGAYKSFLSLRRKGDYD<br>AHSPRSRDSGFFQKIPGRSGFKIGEGRIALSCGAG<br>RKLSFPIPDYQQGRLAETTKLKKFELYRDQPNLAK<br>SGRFWISVVYELPKPEATTCQSEQVAFVALGASSI<br>GVVSQRGEEVIALWRSDKHWVPKIEAVEERMKRRV<br>KGSRGWLRLLNSGKRRMHMISSRQHVQDEREIVDY<br>LVRNHGSHFVVTELVVRSKEGKLADSSKPERGGSL<br>GLNWAAQNTGSLSRLVRQLEEKVKEHGGSVRKHKL<br>TLTEAPPARGAENKLWMARKLRESFLKEV |
| SEQ ID NO: 94 | LAKNDEKELLYQSVKFEIYPDESKIRVLTRVSNIL<br>VLVWNSALGERRARFELYIAPLYEELKKFPRKSAE<br>SNALRQKIREGYKEHIPTFFDQLKKLLTPMRKEDP<br>ALLGSVPRAYQEETLNTLNGSFVSFMTLRRNNDMD<br>AKPPKGRAEDRFHEISGRSGFKIDGSEFVLSTKEQ<br>KLRFPIPNYQLEKLKEAKQIKKFTLYQSRDRRFWI<br>SIAYEIELPDQRPFNPEEVIYIAFGASSIGVISPE<br>GEKVIDFWRPDKHWKPKIKEVENRMRSCKKGSRAW<br>KKRAAARRKMYAMTQRQQKLNHREIVASLLRLGFH<br>FVVTEYTVRSKPGKLADGSNPKRGGAPQGFNWSAQ<br>NTGSFGEFILWLKQKVKEQGGTVQTFRLVLGQSER<br>PEKRGRDNKIEMVRLLREKYLESQTIVV |
| SEQ ID NO: 95 | MAKGKKKEGKPLYRAVRFEIFPTSDQITLFLRVSK<br>NLQQVWNEAWQERQSCYEQFFGSIYERIGQAKKRA<br>QEAGFSEVWENEAKKGLNKKLRQQEISMQLVSEKE<br>SLLQELSIAFQEHGVTLYDQINGLTARRIIGEFAL<br>IPRNWQEETLDSLDGSFKSFLALRKNGDPDAKPPR<br>QRVSENSFYKIPGRSGFKVSNGQIYLSFGKIGQTL<br>TSVIPEFQLKRLETAIKLKKFELCRDERDMAKPGR<br>FWISVAYEIPKPEKVPVVSKQITYLAIGASRLGVV<br>SPKGEFCLNLPRSDYHWKPQINALQERLEGVVKGS<br>RKWKKRMAACTRMFAKLGHQQKQHGQYEVVKKLLR<br>HGVHFVVTELKVRSKPGALADASKSDRKGSPTGPN<br>WSAQNTGNIARLIQKLTDKASEHGGTVIKRNPPLL<br>SLEERQLPDAQRKIFIAKKLREEFLADQK |
| SEQ ID NO: 96 | MAKREKKDDVVLRGTKMRIYPTDRQVTLMDMWRRR<br>CISLWNLLLNLETAAYGAKNTRSKLGWRSIWARVV<br>EENHAKALIVYQHGKCKKDGSFVLKRDGTVKHPPR<br>ERFPGDRKILLGLFDALRHTLDKGAKCKCNVNQPY<br>ALTRAWLDETGHGARTADIIAWLKDFKGECDCTAI<br>STAAKYCPAPPTAELLTKIKRAAPADDLPVDQAIL<br>LDLFGALRGGLKQKECDHTHARTVAYFEKHELAGR<br>AEDILAWLIAHGGTCDCKIVEEAANHCPGPRLFIW<br>EHELAMIMARLKAEPRTEWIGDLPSHAAQTVVKDL<br>VKALQTMLKERAKAAAGDESARKTGFPKFKKQAYA<br>AGSVYFPNTTMFFDVAAGRVQLPNGCGSMRCEIPR<br>QLVAELLERNLKPGLVIGAQLGLLGGRIWRQGDRW<br>YLSCQWERPQPTLLPKTGRTAGVKIAASIVFTTYD<br>NRGQTKEYPMPPADKKLTAVHLVAGKQNSRALEAQ<br>KEKEKKLKARKERLRLGKLEKGHDPNALKPLKRPR<br>VRRSKLFYKSAARLAACEAIERDRRDGFLHRVTNE<br>IVHKFDAVSVQKMSVAPMMRRQKQKEKQIESKKNE<br>AKKEDNGAAKKPRNLKPVRKLLRHVAMARGRQFLE<br>YKYNDLRGPGSVLIADRLEPEVQECSRCGTKNPQM<br>KDGRRLLRCIGVLPDGTDCDAVLPRNRNAARNAEK<br>RLRKHREAHNA |
| SEQ ID NO: 97 | MNEVLPIPAVGEDAADTIMRGSKMRIYPSVRQAAT<br>MDLWRRRCIQLWNLLLELEQAAYSGENRRTQIGWR<br>SIWATVVEDSHAEAVRVAREGKKRKDGTFRKAPSG<br>KEIPPLDPAMLAKIQRQMNGAVDVDPKTGEVTPAQ<br>PRLFMWEHELQKIMARLKQAPRTHWIDDLPSHAAQ<br>SVVKDLIKALQAMLRERKKRASGIGGRDTGFPKFK<br>KNRYAAGSVYFANTQLRFEAKRGKAGDPDAVRGEF<br>ARVKLPNGVGWMECRMPRHINAAHAYAQATLMGGR<br>IWRQGENWYLSCQWKMPKPAPLPRAGRTAAIKIAA<br>AIPITTVDNRGQTREYAMPPIDRERIAAHAAAGRA<br>QSRALEARKRRAKKREAYAKKRHAKKLERGIAAKP<br>PGRARIKLSPGFYAAAAKLAKLEAEDANAREAWLH<br>EITTQIVRNFDVIAVPRMEVAKLMKKPEPPEEKEE<br>QVKAPWQGKRRSLKAARVMMRRTAMALIQTTLKYK<br>AVDLRGPQAYEEIAPLDVTAAACSGCGVLKPEWKM<br>ARAKGREIMRCQEPLPGGKTCNTVLTYTRNSARVI<br>GRELAVRLAERQKA |
| SEQ ID NO: 98 | MTTQKTYNFCFYDQRFFELSKEAGEVYSRSLEEFW<br>KIYDETGVWLSKFDLQKHMRNKLERKLLHSDSFLG<br>AMQQVHANLASWKQAKKVVPDACPPRKPKFLQAIL<br>FKKSQIKYKNGFLRLTLGTEKEFLYLKWDINIPLP<br>IYGSVTYSKTRGWKINLCLETEVEQKNLSENKYLS<br>IDLGVKRVATIFDGENTITLSGKKFMGLMHYRNKL<br>NGKTQSRLSHKKKGSNNYKKIQRAKRKTTDRLLNI<br>QKEMLHKYSSFIVNYAIRNDIGNIIIGDNSSTHDS<br>PNMRGKTNQKISQNPEQKLKNYIKYKFESISGRVD<br>IVPEPYTSRKCPHCKNIKKSSPKGRTYKCKKCGFI<br>FDRDGVGAINIYNENVSFGQIISPGRIRSLTEPIG<br>MKFHNEIYFKSYVAA |
| SEQ ID NO: 99 | MSVRSFQARVECDKQTMEHLWRTHKVFNERLPEII<br>KILFKMKRGECGQNDKQKSLYKSISQSILEANAQN<br>ADYLLNSVSIKGWKPGTAKKYRNASFTWADDAAKL<br>SSQGIHVYDKKQVLGDLPGMMSQMVCRQSVEAISG<br>HIELTKKWEKEHNEWLKEKEKWESEDEHKKYLDLR<br>EKFEQFEQSIGGKITKRRGRWHLYLKWLSDNPDFA<br>AWRGNKAVINPLSEKAQIRINKAKPNKKNSVERDE<br>FFKANPEMKALDNLHGYYERNFVRRRKTKKNPDGF<br>DHKPTFTLPHPTIHPRWFVFNKPKTNPEGYRKLIL<br>PKKAGDLGSLEMRLLTGEKNKGNYPDDWISVKFKA<br>DPRLSLIRPVKGRRVVRKGKEQGQTKETDSYEFFD<br>KHLKKWRPAKLSGVKLIFPDKTPKAAYLYFTCDIP<br>DEPLTETAKKIQWLETGDVTKKGKKRKKKVLPHGL<br>VSCAVDLSMRRGTTGFATLCRYENGKIHILRSRNL<br>WVGYKEGKGCHPYRWTEGPDLGHIAKHKREIRILR<br>SKRGKPVKGEESHIDLQKHIDYMGEDRFKKAARTI<br>VNFALNTENAASKNGFYPRADVLLLENLEGLIPDA<br>EKERGINRALAGWNRRHLVERVIEMAKDAGFKRRV<br>FEIPPYGTSQVCSKCGALGRRYSIIRENNRREIRF<br>GYVEKLFACPNCGYCANADHNASVNLNRRFLIEDS<br>FKSYYDWKRLSEKKQKEEIETIESKLMDKLCAMHK<br>ISRGSISK |
| SEQ ID NO: 100 | MHLWRTHCVFNQRLPALLKRLFAMRRGEVGGNEAQ<br>RQVYQRVAQFVLARDAKDSVDLLNAVSLRKRSANS<br>AFKKKATISCNGQAREVTGEEVFAEAVALASKGVF<br>AYDKDDMRAGLPDSLFQPLTRDAVACMRSHEELVA<br>TWKKEYREWRDRKSEWEAEPEHALYLNLRPKFEEG |

TABLE 2-continued

Cas14 Enzyme Sequences

| SEQ ID NO | Sequence |
|---|---|
| | EAARGGRFRKRAERDHAYLDWLEANPQLAAWRRKAPPAVVPIDEAGKRRIARAKAWKQASVRAEEFWKRNPELHALHKIHVQYLREFVRPRRTRRNKRREGFKQRPTFTMPDPVRHPRWCLFNAPQTSPQGYRLLRLPQSRRTVGSVELRLLTGPSDGAGFPDAWVNVRFKADPRLAQLRPVKVPRTVTRGKNKGAKVEADGFRYYDDQLLIERDAQVSGVKLLFRDIRMAPFADKPIEDRLLSATPYLVFAVEIKDEARTERAKAIRFDETSELTKSGKKRKTLPAGLVSVAVDLDTRGVGFLTRAVIGVPEIQQTHHGVRLLQSRYVAVGQVEARASGEAEWSPGPDLAHIARHKREIRRLRQLRGKPVKGERSHVRLQAHIDRMGEDRFKKAARKIVNEALRGSNPAAGDPYTRADVLLYESLETLLPDAERERGINRALLRWNRAKLIEHLKRMCDDAGIRHFPVSPFGTSQVCSKCGALGRRYSLARENGRAVIRFGWVERLFACPNPECPGRRPDRPDRPFTCNSDHNASVNLHRVFALGDQAVAAFRALAPRDSPARTLAVKRVEDTLRPQLMRVHKLADAGVDSPF |
| SEQ ID NO: 101 | MATLVYRYGVRAHGSARQQDAVVSDPAMLEQLRLGHELRNALVGVQHRYEDGKRAVWSGFASVAAADHRVTTGETAVAELEKQARAEHSADRTAATRQGTAESLKAARAAVKQARADRKAAMAAVAEQAKPKIQALGDDRDAEIKDLYRRFCQDGVLLPRCGRCAGDLRSDGDCTDCGAAHEPRKLYWATYNAIREDHQTAVKLVEAKRKAGQPARLRFRRWTGDGTLTVQLQRMHGPACRCVTCAEKLTRRARKTDPQAPAVAADPAYPPTDPPRDPALLASGQGKWRNVLQLGTWIPPGEWSAMSRAERRRVGRSHIGWQLGGGRQLTLPVQLHRQMPADADVAMAQLTRVRVGGRHRMSVALTAKLPDPPQVQGLPPVALHLGWRQRPDGSLRVATWACPQPLDLPPAVADVVVSHGGRWGEVIMPARWLADAEVPPRLLGRRDKAMEPVLEALADWLEAHTEACTARMTPALVRRWRSQGRLAGLTNRWRGQPPTGSAEILTYLEAWRIQDKLLWERESHLRRRLAARRDDAWRRVASWLARHAGVLVVDDADIAELRRRDDPADTDPTMPASAAQAARARAALAAPGRLRHLATITATRDGLGVHTVASAGLTRLHRKCGHQAQPDPRYAASAVVTCPGCGNGYDQDYNAAMLMLDRQQQP |
| SEQ ID NO: 102 | MSRVELHRAYKFRLYPTPAQVAELAEWERQLRRLYNLAHSQRLAAMQRHVRPKSPGVLKSECLSCGAVAVAEIGTDGKAKKTVKHAVGCSVLECRSCGGSPDAEGRTAHTAACSFVDYYRQGREMTQLLEEDDQLARVVCSARQETLRDLEKAWQRWHKMPGFGKPHFKKRIDSCRIYFSTPKSWAVDLGYLSFTGVASSVGRIKIRQDRVWPGDAKFSSCHVVRDVDEWYAVFPLTFTKEIEKPKGGAVGINRGAVHAIADSTGRVVDSPKFYARSLGVIRHRARLLDRKVPFGRAVKPSPTKYHGLPKADIDAAAARVNASPGRLVYEARARGSIAAAEAHLAALVLPAPRQTSQLPSEGRNRERARRFLALAHQRVRRQREWFLHNESAHYAQSYTKIAIEDWSTKEMTSSEPRDAEEMKRVTRARNRSILDVGWYELGRQIAYKSEATGAEFAKVDPGLRETETHVPEAIVRERDVDVSGMLRGEAGISGTCSRCGGLLRASASGHADAECEVCLHVEVGDVNAAVNVLKRAMFPGAAPPSKEKAKVTIGIKGRKKKRAA |
| SEQ ID NO: 103 | MSRVELHRAYKFRLYPTPVQVAELSEWERQLRRLYNLGHEQRLLTLTRHLRPKSPGVLKGECLSCDSTQVQEVGADGRPKTTVRHAEQCPTLACRSCGALRDAEGRTAHTVACAFVDYYRQGREMTELLAADDQLARVVCSARQEVLRDLDKAWQRWRKMPGFGKPRFKKRRTDSCRIYFSTPKAWKLEGGHLSFTGAATTVGAIKMRQDRNWPASVQFSSCHVVRDVDEWYAVFPLTFVAEVARPKGGAVGINRGAVHAIADSTGRVVDSPRYYARALGVIRHRARLFDRKVPSGHAVKPSPTKYRGLSAIEVDRVARATGFTPGRVVTEALNRGGVAYAECALAAIAVLGHGPERPLTSDGRNREKARKFLALAHQRVRRQREWFLHNESAHYARTYSKIAIEDWSTKEMTASEPQGEETRRVTRSRNRSILDVGWYELGRQLAYKTEATGAEFAQVDPGLKETETNVPKAIADARDVDVSGMLRGEAGISGTCSKCGGLLRAPASGHADAECEICLNVEVGDVNAAVNVLKRAMFPGDAPPASGEKPKVSIGIKGRQKKKKAA |
| SEQ ID NO: 104 | MEAIATGMSPERRVELGILPGSVELKRAYKFRLYPMKVQQAELSEWERQLRRLYNLAHEQRLAALLRYRDWDFQKGACPSCRVAVPGVHTAACDHVDYFRQAREMTQLLEVDAQLSRVICCARQEVLRDLDKAWQRWRKKLGGRPRFKRRTDSCRIYLSTPKHWEIAGRYLRLSGLASSVGEIRIEQDRAFPEGALLSSCSIVRDVDEWYACLPLTFTQPIERAPHRSVGLNRGVVHALADSDGRVVDSPKFFERALATVQKRSRDLARKVSGSRNAHKARIKLAKAHQRVRRQRAAFLHQESAYYSKGFDLVALEDMSVRKMTATAGEAPEMGRGAQRDLNRGILDVGWYELARQIDYKRLAHGGELLRVDPGQTTPLACVTEEQPARGISSACAVCGIPLARPASGNARMRCTACGSSQVGDVNAAENVLTRALSSAPSGPKSPKASIKIKGRQKRLGTPANRAGEASGGDPPVRGPVEGGTLAYVVEPVSESQSDT |
| SEQ ID NO: 105 | MTVRTYKYRAYPTPEQAEALTSWLRFASQLYNAALEHRKNAWGRHDAHGRGFRFWDGDAAPRKKSDPPGRWVYRGGGGAHISKNDQGKLLTEFRREHAELLPPGMPALVQHEVLARLERSMAAFFQRATKGQKAGYPRWRSEHRYDSLTFGLTSPSKERFDPETGESLGRGKTVGAGTYHNGDLRLTGLGELRILEHRRIPMGAIPKSVIVRRSGKRWFVSIAMEMPSVEPAASGRPAVGLDMGVVTWGTAFTADTSAAAALVADLRRMATDPSDCRRLEELEREAAQLSEVLAHCRARGLDPARPRRCPKELTKLYRRSLHRLGELDRACARIRRRLQAAHDIAEPVPDEAGSAVLIEGSNAGMRHARRVARTQRRVARRTRAGHAHSNRRKKAVQAYARAKERERSARGDHRHKVSRALVRQFEEISVEALDIKQLTVAPEHNPDPQPDLPAHVQRRRNRGELDAAWGAFFAALDYKAADAGGRVARKPAPHTTQECARCGTLVPKPISLRVHRCPACGYTAPRTVNSARNVLQRPLEEPGRAGPSGANGRGVPHAVA |
| SEQ ID NO: 106 | MNCRYRYRIYPTPGQRQSLARLFGCVRVVWNDALFLCRQSEKLPKNSELQKLCITQAKKTEARGWLGQVSAIPLQQSVADLGVAFKNFFQSRSGKRKGKKVNPPRVKRRNNRQGARFTRGGFKVKTSKVYLARIGDIKIKWSRPLPSEPSSVTVIKDCAGQYFLSFVVEVKPEIKPPKNPSIGIDLGLKTFASCSNGEKIDSPDYSRLYRKLKRCQRRLAKRQRGSKRRERMRVKVAKLNAQIRDKRKDFLHKLSTKVVNENQVIALEDLNVGGMLKNRKLSRAISQAGWYEFRSLCEGKAEKHNRDFRVISRWEPTSQVCSECGYRWGKIDLSVRSIVCINCGVEHDRDDNASVNIEQAGLKVGVGHTHDSKRTGSACKTSNGAVCVEPSTHREYVQLTLFDW |
| SEQ ID NO: 107 | MKSRWTFRCYPTPEQEQHLARTFGCVRFVWNWALRARTDAFRAGERIGYPATDKALTLLKQQPETVWLNEVSSVCLQQALRDLQVAFSNFFDKRAAHPSFKRKEARQSANYTERGFSFDHERRILKLAKIGAIKVKWSRKAIPHPSSIRLIRTASGKYFVSLVVETQPAPMPETGESVGVDFGVARLATLSNGERISNPKHGAKWQRRLAFYQKRLARATKGSKRRMRIKRHVARIHEKIGNSRSDTLHKLSTDLVTRFDLICVEDLNLRGMVKNHSLARSLHDASIGSSAIRMIEEKAERYGKNVVKIDRWFPSSKTCSDCGHIVEQLPLNVREWTCPECGTTHDRDANAAANILAVGQTVSAHGGTVRRSRAKASERKSQRSANRQGVNRA |
| SEQ ID NO: 108 | KEPLNIGKTAKAVFKEIDPTSLNRAANYDASIELNCKECKFKPFKNVKRYEFNFYNNWYRCNPNSCLQSTYKAQVRKVEIGYEKLKNEILTQMQYYPWFGRLYQNFFHDERDKMTSLDEIQVIGVQNKVFFNTVEKAWREIIKKRFKDNKETMETIPELKHAAGHGKRKLSNKSLLRRRFAFVQKSFKFVDNSDVSYRSFSNNIACVLPSRIGVDLGGVISRNPKREYIPQEISFNAFWKQHEGLKKGRNIEIQSVQYKGETVKRIEADTGEDKAWGKNRQRRFTSLILKLVPKQGGKKVWKYPEKRNENGNYEYFPIPIEFILDSGETSIRFGGDEGEAGKQKHLVIPFNDSKATPLASQQTLLENSRFNAEVKSCIGLAIYANY |

TABLE 2-continued

Cas14 Enzyme Sequences

| SEQ ID NO | Sequence |
|---|---|
| | FYGYARNYVISSIYHKNSKNGQAITAIYLESIAHNYVKAIERQLQNLLLNLRDFSFMESHKKELKKYFGGDLEGTGGAQKRREKEEKIEKEIEQSYLPRLIRLSLTKMVTKQVEM |
| SEQ ID NO: 109 | ELIVNENKDPLNIGKTAKAVFKEIDPTSINRAANYDASIELACKECKFKPFNNTKRHDFSFYSNWHRCSPNSCLQSTYRAKIRKTEIGYEKLKNEILNQMQYYPWFGRLYQNFFNDQRDKMTSLDEIQVTGVQNKIFFNTVEKAWREIIKKRFRDNKETMRTIPDLKNKSGHGSRKLSNKSLLRRRFAFAQKSFKLVDNSDVSYRAFSNNVACVLPSKIGVDIGGIINKDLKREYIPQEITFNVFWKQHDGLKKGRNIEIHSVQYKGEIVKRIEADTGEDKAWGKNRQRRFTSLILKITPKQGGKKIWKFPEKKNASDYEYFPIPIEFILDNGDASIKFGGEEGEVGKQKHLLIPFNDSKATPLSSKQMLLETSRFNAEVKSTIGLALYANYFVSYARNYVIKSTYHKNSKKGQIVTEIYLESISQNFVRAIQRQLQSLMLNLKDWGFMQTHKKELKKYFGSDLEGSKGGQKRREKEEKIEKEIEASYLPRLIRLSLTKSVTKAEEM |
| SEQ ID NO: 110 | PEEKTSKLKPNSINLAANYDANEKFNCKECKFHPFKNKKRYEFNFYNNLHGCKSCTKSTNNPAVKRIEIGYQKLKFEIKNQMEAYPWFGRLRINFYSDEKRKMSELNEMQVTGVKNKIFFDAIECAWREILKKRFRESKETLITIPKLKNKAGHGARKHRNKKLLIRRRAFMKKNFHFLDNDSISYRSFANNIACVLPSKVGVDIGGIISPDVGKDIKPVDISLNLMWASKEGIKSGRKVEIYSTQYDGNMVKKIEAETGEDKSWGKNRKRRQTSLLLSIPKPSKQVQEFDFKEWPRYKDIEKKVQWRGFPIKIIFDSNHNSIEFGTYQGGKQKVLPIPFNDSKTTPLGSKMNKLEKLRFNSKIKSRLGSAIAANKFLEAARTYCVDSLYHEVSSANAIGKGKIFIEYYLEILSQNYIEAAQKQLQRFIESIEQWFVADPFQGRLKQYFKDDLKRAKCFLCANREVQTTCYAAVKLHKSCAEKVKDKNKELAIKERNNKEDAVIKEVEASNYPRVIRLKLTKTITNKAM |
| SEQ ID NO: 111 | SESENKIIEQYYAFLYSFRDKYEKPEFKNRGDIKRKLONKWEDFLKEQNLKNDKKLSNYIFSNRNFRRSYDREEENEEGIDEKKSKPKRINCFEKEKNLKDQYDKDAINASANKDGAQKWGCFECIFFPMYKIESGDPNKRIIINKTRFKLFDFYLNLKGCKSCLRSTYHPYRSNVYIESNYDKLKREIGNFLQQKNIFQRMRKAKVSEGKYLTNLDEYRLSCVAMHFKNRWLFFDSIQKVLRETIKQRLKQMRESYDEQAKTKRSKGHGRAKYEDQVRMIRRRAYSAQAHKLLDNGYITLFDYDDKEINKVCLTAINQEGFDIGGYLNSDIDNVMPPIEISFHLKWKYNEPILNIESPFSKAKISDYLRKIREDLNLERGKEGKARSKKNVRRKVLASKGEDGYKKIFTDFFSKWKEELEGNAMERVLSQSSGDIQWSKKKRIHYTTLVLNINLLDKKGVGNLKYYEIAEKTKILSFDKNENKFWPITIQVLLDGYEIGTEYDEIKQLNEKTSKQFTIYDPNTKIIKIPFTDSKAVPLGMLGINIATLKTVKKTERDIKVSKIFKGGLNSKIVSKIGKGIYAGYFPTVDKEILEEVEEDTLDNEFSSKSQRNIFLKSIIKNYDKMLKEQLFDFYSFLVRNDLGVRFLTDRELQNIEDESFNLEKRFFETDRDRIARWFDNTNTDDGKEKFKKLANEIVDSYKPRLIRLPVVRVIKRIQPVKQREM |
| SEQ ID NO: 112 | KYSTRDFSELNEIQVTACKQDEFFKVIQNAWREIIKKRFLENRENFIEKKIFKNKKGRGKRQESDKTIQRNRASVMKNFQLIENEKIILRAPSGHVACVFPVKVGLDIGGFKTDDLEKNIFPPRTITINVFWKNRDRQRKGRKLEVWGIKARTKLIEKVHKWDKLEEVKKKRLKSLEQKQEKSLDNWSEVNNDSFYKVQIDELQEKIDKSLKGRTMNKILDNKAKESKEAEGLYIEWEKDFEGEMLRRIEASTGGEEKWGKRRQRRHTSLLLDIKNNSRGSKEIINFYSYAKQGKKEKKIEFFPPPLTITLDAEEESPLNIKSIPIEDKNATSKYFSIPFTETRATPLSI |

TABLE 2-continued

Cas14 Enzyme Sequences

| SEQ ID NO | Sequence |
|---|---|
| | LGDRVQKFKTKNISGAIKRNLGSSISSCKIVQNAETSAKSILSLPNVKEDNNMEIFINTMSKNYFRAMMKQMESFIFEMEPKTLIDPYKEKAIKWFEVAASSRAKRKLKKLSKADIKKSELLLSNTEEFEKEKQEKLEALEKEIEEFYLPRIVRLQLTKTILETPVM |
| SEQ ID NO: 113 | KKLQLLGHKILLKEYDPNAVNAAANFETSTAELCGQCKMKPFKNKRRFQYTFGKNYHGCLSCIQNVYYAKKRIVQIAKEELKHQLTDSIASIPYKYTSLFSNTNSIDELYILKQERAAFFSNTNSIDELYITGIENNIAFKVISAIWDEIIKKRRQRYAESLTDTGTVKANRGHGGTAYKSNTRQEKIRALQKQTLHMVTNPYISLARYKNNYIVATLPRTIGMHIGAIKDRDPQKKLSDYAINFNVFWSDDRQLIELSTVQYTGDMVRKIEAETGENNKWGENMKRTKTSLLLEILTKKTTDELTFKDWAFSTKKEIDSVTKKTYQGFPIGIIFEGNESSVKFGSQNYFPLPFDAKITPPTAEGFRLDWLRKGSFSSQMKTSYGLAIYSNKVTNAIPAYVIKNMFYKIARAENGKQIKAKFLKKYLDIAGNNYVPFIIMQHYRVLDTFEEMPISQPKVIRLSLTKTQHIIIKKDKTDSKM |
| SEQ ID NO: 114 | NTSNLINLGKKAINISANYDANLEVGCKNCKFLSSNGNFPRQTNVKEGCHSCEKSTYEPSIYLVKIGERKAKYDVLDSLKKFTFQSLKYQSKKSMKSRNKKPKELKEFVIFANKNKAFDVIQKSYNHLILQIKKEINRMNSKKRKKNHKRRLFRDREKQLNKLRLIESSNLFLPRENKGNNHVFTYVAIHSVGRDIGVIGSYDEKLNFETELTYQLYFNDDKRLLYAYKPKQNKIIKIKEKLWNLRKEKEPLDLEYEKPLNKSITFSIKNDNLFKVSKDLMLRRAKFNIQGKEKLSKEERKINRDLIKIKGLVNSMSYGRFDELKKEKNIWSPHIYREVRQKEIKPCLIKNGDRIEIFEQLKKKMERLRRFREKRQKKISKDLIFAERIAYNFHTKSIKNTSNKINIDQEAKRGKASYMRKRIGYETFKNKYCEQCLSKGNVYRNVQKGCSCFENPFDWIKKGDENLLPKKNEDLRVKGAFRDEALEKQIVKIAFNIAKGYEDFYDNLGESTEKDLKLKFKVGTTINEQESLKL |
| SEQ ID NO: 115 | TSNPIKLGKKAINISANYDSNLQIGCKNCKFLSYNGNFPRQTNVKEGCHSCEKSTYEPPVYTVRIGERRSKYDVLDSLKKFIFLSLKYRQSKKMKTRSKGIRGLEEFVISANLKKAMDVIQKSYRHLILNIKNEIVRMNGKKRNKNHKRLLFRDREKQLNKLRLIEGSSFFKPPTVKGDNSIFTCVAIHNIGRDIGIAGDYFDKLEPKIELTYQLYYEYNPKKESEINKRLLYAYKPKQNKIIEIKEKLWNLRKEKSPLDLEYEKPLTKSITFLVKRDGVFRISKDLMLRKAKFIIQGKEKLSKEERKINRDLIKIKSNIISLTYGRFDELKKDKTIWSPHIFRDVKQGKITPCIERKGDRMDIFQQLRKKSERLRENRKKRQKKISKDLIFAERIAYNFHTKSIKNTSNLINIKHEAKRGKASYMRKRIGNETFRIKYCEQCFPKNNVYKNVQKGCSCFEDPFEYIKKGNEDLIPNKNQDLKAKGAFRDDALEKQIIKVAFNIAKGYEDFYENLKKTTEKDIRLKFKVGTIISEEM |
| SEQ ID NO: 116 | NNSINLSKKAINISANYDANLQVRCKNCKFLSSNGNFPRQTDVKEGCHSCEKSTYEPPVYDVKIGEIKAKYEVLDSLKKFTFQSLKYQLSKSMKFRSKKIKELKEFVIFAKESKALNVINRSYKHLILNIKNDINRMNSKKRIKNHKGRLFLDRQKQLSKLKLIEGSSFFVPAKNVGNKSVFTCVAIHSIGRDIGIAGLYDSFTKPVNEITYQIFFSGERRLLYAYKPKQLKILSIKENLWSLKNEKKPLDLLYEKPLGKNLNFNVKGGDLFRVSKDLMIRNAKFNVHGRQRLSDEERLINRNFIKIKGEVVSLSYGRFEELKKDRKLWSPHIFKDVRQNKIKPCLVMQGQRIDIFEQLKRKLELLKKIRKSRQKKLSKDLIFGERIAYNFHTKSIKNTSNKINIDSDAKRGRASYMRKRIGNETFKLKYCDVCFPKANVYRRVQNGCSCSENPYNYIKKGDKDLLPKKDEGLAIKGAFRDEKLNQIIKVAFNIAKGYEDFYDDLKKRTEKDVDLKFKIGTTVLDQKPMEIFDGIVITWL |

TABLE 2-continued

Cas14 Enzyme Sequences

| SEQ ID NO | Sequence |
|---|---|
| SEQ ID NO: 117 | LLTTVVETNNLAKKAINVAANFDANIDRQYYRCTPNLCRFIAQSPRETKEKDAGCSSCTQSTYDPKVYVIKIGKLLAKYEILKSLKRFLFMNRYFKQKKTERAQQKQKIGTELNEMSIFAKATNAMEVIKRATKHCTYDIIPETKSLQMLKRRRHRVKVRSLLKILKERRMKIKKIPNTFIEIPKQAKKNKSDYYVAAALKSCGIDVGLCGAYEKNAEVEAEYTYQLYYEYKGNSSTKRILYCYNNPQKNIREFWEAFYIQGSKSHVNTPGTIRLKMEKFLSPITIESEALDFRVWNSDLKIRNGQYGFIKKRSLGKEAREIKKGMGDIKRKIGNLTYGKSPSELKSIHVYRTERENPKKPRAARKKEDNFMEIFEMQRKKDYEVNKKRRKEATDAAKIMDFAEEPIRHYHTNNLKAVRRIDMNEQVERKKTSVFLKRIMQNGYRGNYCRKCIKAPEGSNRDENVLEKNEGCLDCIGSEFIWKKSSKEKKGLWHTNRLLRRIRLQCFTTAKAYENFYNDLFEKKESSLDIIKLKVSITTKSM |
| SEQ ID NO: 118 | ASTMNLAKQAINFAANYDSNLEIGCKGCKFMSTWSKKSNPKFYPRQNNQANKCHSCTYSTGEPEVPIIEIGERAAKYKIFTALKKFVFMSVAYKERRRQRFKSKKPKELKELAICSNREKAMEVIQKSVVHCYGDVKQEIPRIRKIKVLKNHKGRLFYKQKRSKIKIAKLEKGSFFKTFIPKVHNNGCHSCHEASLNKPILVTTALNTIGADIGLINDYSTIAPTETDISWQVYYEFIPNGDSEAVKKRLLYFYKPKGALIKSIRDKYFKKGHENAVNTGFFKYQGKIVKGPIKFVNNELDFARKPDLKSMKIKRAGFAIPSAKRLSKEDREINRESIKIKNKIYSLSYGRKKTLSDKDIIKHLYRPVRQKGVKPLEYRKAPDGFLEFFYSLKRKERRLRKQKEKRQKDMSEIIDAADEFAWHRHTGSIKKTTNHINFKSEVKRGKVPIMKKRIANDSFNTRHCGKCVKQGNAINKYYIEKQKNCFDCNSIEFKWEKAALEKKGAFKLNKRLQYIVKACFNVAKAYESFYEDFRKGEEESLDLKFKIGTTTTLKQYPQNKARAM |
| SEQ ID NO: 119 | HSHNLMLTKLGKQAINFAANYDANLEIGCKNCKFLSYSPKQANPKKYPRQTDVHEDGNIACHSCMQSTKEPPVYIVPIGERKSKYEILTSLNKFTFLALKYKEKKRQAFRAKKPKELQELAIAFNKEKAIKVIDKSIQHLILNIKPEIARIQRQKRLKNRKGKLLYLHKRYAIKMGLIKNGKYFKVGSPKKDGKKLLVLCALNTIGRDIGIIGNIEENNRSETEITYQLYFDCLDANPNELRIKEIEYNRLKSYERKIKRLVYAYKPKQTKILEIRSKFFSKGHENKVNTGSFNFENPLNKSISIKVKNSAFDFKIGAPFIMLRNGKFHIPTKKRLSKEEREINRTLSKIKGRVFRLTYGRNISEQGSKSLHIYRKERQHPKLSLEIRKQPDSFIDEFEKLRLKQNFISKLKKQRQKKLADLLQFADRIAYNYHTSSLEKTSNFINYKPEVKRGRTSYIKKRIGNEGFEKLYCETCIKSNDKENAYAVEKEELCFVCKAKPFTWKKTNKDKLGIFKYPSRIKDFIRAAFTVAKSYNDFYENLKKKDLKNEIFLKFKIGLILSHEKKNHISIAKSVAEDERISGKSIKNILNKSIKLEKNCYSCFFHKEDM |
| SEQ ID NO: 120 | SLERVIDKRNLAKKAINIAANFDANINKGFYRCETNQCMFIAQKPRKTNNTGCSSCLQSTYDPVIYVVKVGEMLAKYEILKSLKRFVFMNRSFKQKKTEKAKQKERIGGELNEMSIFANAALAMGVIKRAIRHCHVDIRPEINRLSELKKTKHRVAAKSLVKIVKQRKTKWKGIPNSFIQIPQKARNKDADFYVASALKSGGIDIGLCGTYDKKPHADPRWTYQLYFDTEDESEKRLLYCYNDPQAKIRDFWKTFYERGNPSMVNSPGTIEFRMEGFFEKMTPISIESKDFDFRVWNKDLLIRRGLYEIKKRKNLNRKAREIKKAMGSVKRVLANMTYGKSPTDKKSIPVYRVEREKPKKPRAVRKKEENELADKLENYRREDFLIRNRRKREATEIAKIIDAAEPPIRHYHTNHLRAVKRIDLSKPVARKNTSVFLKRIMQNGYRGNYCKKCIKGNIDPNKDECRLEDIKKCICCEGTQNIWAKKEKLYTGRINVLNKRIKQMKLECFNVAKAYENFYDNLAALKEGDLKVLKLKVSIPALNPEASDPEEDM |
| SEQ ID NO: 121 | NASINLGKRAINLSANYDSNLVIGCKNCKFLSFNGNFPRQTNVREGCHSCDKSTYAPEVYIVKIGERKAKYDVLDSLKKFTFQSLKYQIKKSMRERSKKPKELLEFVIFANKDKAFNVIQKSYEHLILNIKQEINRMNGKKRIKNHKKRLFKDREKQLNKLRLIGSSSLFFPRENKGDKDLFTYVAIHSVGRDIGVAGSYESHIEPISDLTYQLFINNEKRLLYAYKPKQNKIIELKENLWNLKKEKKPLDLEFTKPLEKSITFSVKNDKLFKVSKDLMLRQAKFNIQGKEKLSKEERQINRDFSKIKSNVISLSYGRFEELKKEKNIWSPHIYREVKQKEIKPCIVRKGDRIELFEQLKRKMDKLKKFRKERQKKISKDLNFAERIAYNFHTKSIKNTSNKINIDQEAKRGKASYMRKRIGNESFRKKYCEQCFSVGNVYHNVQNGCSCFDNPIELIKKGDEGLIPKGKEDRKYKGALRDDNLQMQIIRVAFNIAKGYEDFYNNLKEKTEKDLKLKFKIGTTISTQESNNKEM |
| SEQ ID NO: 122 | SNLIKLGKQAINFAANYDANLEVGCKNCKFLSSTNKYPRQTNVHLDNKMACRSCNQSTMEPAIYIVRIGEKKAKYDIYNSLTKFNFQSLKYKAKRSQRFKPKQPKELQELSIAVRKEKALDIIQKSIDHLIQDIRPEIPRIKQQKRYKNHVGKLFYLQKRRKNKLNLIGKGSFFKVFSPKEKKNELLVICALTNIGRDIGLIGNYNTIINPLFEVTYQLYYDYIPKKNNKNVQRRLLYAYKSKNEKILKLKEAFFKRGHENAVNLGSFSYEKPLEKSLTLKIKNDKDDFQVSPSLRIRTGRFFVPSKRNLSRQEREINRRLVKIKSKIKNMTYGKFETARDKQSVHIFRLERQKEKLPLQFRKDEKEFMEEFQKLKRRTNSLKKLRKSRQKKLADLLQLSEKVVYNNHTGTLKKTSNFLNFSSSVKRGKTAYIKELLGQEGFETLYCSNCINKGQKTRYNIETKEKCFSCKDVPFVWKKKSTDKDRKGAFLFPAKLKDVIKATFTVAKAYEDFYDNLKSIDEKKPYIKFKIGLILAHVRHEHKARAKEEAGQKNIYNKPIKIDKNCKECFFFKEEAM |
| SEQ ID NO: 123 | NTTRKKFRKRTGFPQSDNIKLAYCSAIVRAANLDADIQKKHNQCNPNLCVGIKSNEQSRKYEHSDRQALLCYACNQSTGAPKVDYIQIGEIGAKYKILQMVNAYDFLSLAYNLTKLRNGKSRGHQRMSQLDEVVIVADYEKATEVIKRSINHLLDDIRGQLSKLKKRTQNEHITEHKQSKIRRKLRKLSRLLKRRRWKWGTIPNPYLKNWVFTKKDPELVTVALLHKLGRDIGLVNRSKRRSKQKLLPKVGFQLYYKWESPSLNNIKKSKAKKLPKRLLIPYKNVKLFDNKQKLENAIKSLLESYQKTIKVEFDQFFQNRTEEIIAEEQQTLERGLLKQLEKKKNEFASQKKALKEEKKKIKEPRKAKLLMEESRSLGFLMANVSYALFNTTIEDLYKKSNVVSGCIPQEPVVVFPADIQNKGSLAKILFAPKDGFRIKFSGQHLTIRTAKFKIRGKEIKILTKTKREILKNIEKLRRVWYREQHYKLKLFGKEVSAKPRFLDKRKTSIERRDPNKLADQTDDRQAELRNKEYELRHKQHKMAERLDNIDTNAQNLQTLSFWVGEADKPPKLDEKDARGFGVRTCISAWKWFMEDLLKKQEEDPLLKLKLSIM |
| SEQ ID NO: 124 | PKKPKFQKRTGFPQPDNLRKEYCLAIVRAANLDADFEKKCTKCEGIKTNKKGNIVKGRTYNSADKDNLLCYACNISTGAPAVDYVFVGALEAKYKILQMVKAYDFHSLAYNLAKLWKGRGRGHQRMGGLNEVVIVSNNEKALDVIEKSLNHFHDEIRGELSRLKAKFQNEHLHVHKESKLRRKLRKISRLLKRRRWKWDVIPNSYLRNFTFTKTRPDFISVALLHRVGRDIGLVTKTKIPKPTDLLPQFGFQIYYTWDEPKLNKLKKSRLRSEPKRLLVPYKKIELYKNKSVLEEAIRHLAEVYTEDLTICFKDFFETQKRKFVSKEKESLKRELLKELTKLKKDFSERKTALKRDRKEIKEPKKAKLLMEESRSLGFLAANTSYALFNLIAADLYTKSKKACSTKLPRQLSTILPLEIKEHKSTTSLAIKPEEGFKIRFSNTHLSIRTPKFKMKGADIKALTKRKREILKNATKLEKSWYGLKHYKLKLYGKEVAAKPRFLDKRNPSIDRRDPKELMEQIENRRNEVKDLEYEIRKGQHQMAKRLDNVDTNAQNLQTKSFWVGEADKPPELDSMEAKKLGLRTCISAWKWFMKDLVLLQEKSPNLKLKLSLTEM |

TABLE 2-continued

Cas14 Enzyme Sequences

| SEQ ID NO | Sequence |
| --- | --- |
| SEQ ID NO: 125 | KFSKRQEGFLIPDNIDLYKCLAIVRSANLDADVQGHKSCYGVKKNGTYRVKQNGKKGVKEKGRKYVFDLIAFKGNIEKIPHEAIEEKDQGRVIVLGKFNYKLILNIEKNHNDRASLEIKNKIKKLVQISSLETGEFLSDLLSGKIGIDEVYGIIEPDVFSGKELVCKACQQSTYAPLVEYMPVGELDAKYKILSAIKGYDFLSLAYNLSRNRANKKRGHQKLGGGELSEVVISANYDKALNVIKRSINHYHVEIKPEISKLKKKMQNEPLKVMKQARIRRELHQLSRKVKRLKWKWGMIPNPELQNIIFEKKEKDFVSYALLHTLGRDIGLFKDTSMLQVPNISDYGFQIYYSWEDPKLNSIKKIKDLPKRLLIPYKRLDFYIDTILVAKVIKNLIELYRKSYVYETFGEEYGYAKKAEDILFDWDSINLSEGIEQKIQKIKDEFSDLLYEARESKRQNFVESFENILGLYDKNFASDRNSYQEKIQSMIIKKQQENIEQKLKREFKEVIERGFEGMDQNKKYYKVLSPNIKGGLLYTDTNNLGFFRSHLAFMLLSKISDDLYRKNNLVSKGGNKGILDQTPETMLTLEFGKSNLPNISIKRKFFNIKYNSSWIGIRKPKFSIKGAVIREITKKVRDEQRLIKSLEGVWHKSTHFKRWGKPRFNLPRHPDREKNNDDNLMESITSRREQIQLLLREKQKQQEKMAGRLDKIDKEIQNLQTANFQIKQIDKKPALTEKSEGKQSVRNALSAWKWFMEDLIKYQKRTPILQLKLAKM |
| SEQ ID NO: 126 | KFSKRQEGFVIPENIGLYKCLAIVRSANLDADVQGHVSCYGVKKNGTYVLKQNGKKSIREKGRKYASDLVAFKGDIEKIPFEVIEEKKKEQSIVLGKFNYKLVLDVMKGEKDRASLTMKNKSKKLVQVSSLGTDEFLLTLLNEKFGIEEIYGIIEPEVFSGKKLVCKACQQSTYAPLVEYMPVGELDSKYKILSAIKGYDFLSLAYNLARHRSNKKRGHQKLGGGELSEVVISANNAKALNVIKRSLNHYYSEIKPEISKLRKKMQNEPLKVGKQARMRRELHQLSRKVKRLKWKWGKIPNLELQNITFKESDRDFISYALLHTLGRDIGMFNKTEIKMPSNILGYGFQIYYDWEEPKLNTIKKSKNTPKRILIPYKKLDFYNDSILVARAIKELVGLFQESYEWEIFGNEYNYAKEAEVELIKLDEESINGNVEKKLQRIKENFSNLLEKAREKKRQNFIESFESIARLYDESFTADRNEYQREIQSFIIEKQKQSIEKKLKNEFKKIVEKKFNEQEQGKKHYRVLNPTIINEFLPKDKNNLGFLRSKIAFILLSKISDDLYKKSNAVSKGGEKGIIKQQPETILDLEFSKSKLPSINIKKKLFNIKYTSSWLGIRKPKFNIKGAKIREITRRVRDVQRTLKSAESSWYASTHFRRWGFPRFNQPRHPDKEKKSDDRLIESITLLREQIQILLREKQKGQKEMAGRLDDVDKKIQNLQTANFQIKQTGDKPALTEKSAGKQSFRNALSAWKWFMENLLKYQNKTPDLKLKIARTVM |
| SEQ ID NO: 127 | KWIEPNNIDFNKCLAITRSANLDADVQGHKMCYGIKTNGTYKAIGKINKKHNTGIIEKRRTYVYDLIVTKEKNEKIVKKTDFMAIDEEIEFDEKKEKLLKKYIKAEVLGTGELIRKDLNDGEKFDDLCSIEEPQAFRRSELVCKACNQSTYASDIRYIPIGEIEAKYKILKAIKGYDFLSLKYNLGRLRDSKKRGHQKMGQGELKEFVICANKEKALDVIKRSLNHYLNEVKDEISRLNKKMQNEPLKVNDQARWRRELNQISRRLKRLKWKWGEIPNPELKNLIFKSSRPEFVSYALIHTLGRDIGLINETELKPNNIQEYGFQIYYKWEDPELNHIKKVKNIPKRFIIPYKNLDLFGKYTILSRAIEGILKLYSSSFQYKSFKDPNLFAKEGEKKITNEDFELGYDEKIKKIKDDFKSYKKALLEKKKNTLEDSLNSILSVYEQSLLTEQINNVKKWKEGLLKSKESIHKQKKIENIEDIISRIEELKNVEGWIRTKERDIVNKEETNLKREIKKELKDSYYEEVRKDFSDLKKGEESEKKPFREEPKPIVIKDYIKFDVLPGENSALGFFLSHLSFNLFDSIQYELFEKSRLSSSKHPQIPETILDL |
| SEQ ID NO: 128 | FRKFVKRSGAPQPDNLNKYKCIAIVRAANLDADIMSNESSNCVMCKGIKMNKRKTAKGAAKTTELGRVYAGQSGNLLCTACTKSTMGPLVDYVPIGRIRAKYTILRAVKEYDFLSLAYNLARTRVSKKGGRQKMHSLSELVIAAEYEIAWNIIKSSVIHYHQETKEEISGLRKKLQAEHIHKNKEARIRREMHQISRRIKRLKWKWHMIPNSELHNFLFKQQDPSFVAVALLHTLGRDIGMINKPKGSAKREFIPEYGFQIYYKWMNPKLNDINKQKYRKMPKRSLIPYKNLNVFGDRELIENAMHKLLKLYDENLEVKGSKFFKTRVVAISSKESEKLKRDLLWKGELAKIKKDFNADKNKMQELFKEVKEPKKANALMKQSRNMGFLLQNISYGALGLLANRMYEASAKQSKGDATKQPSIVIPLEMEFGNAFPKLLLRSGKFAMNVSSPWLTIRKPKFVIKGNKIKNITKLMKDEKAKLKRLETSYHRATHFRPTLRGSIDWDSPYFSSPKQPNTHRRSPDRLSADITEYRGRLKSVEAELREGQRAMAKKLDSVDMTASNLQTSNFQLEKGEDPRLTEIDEKGRSIRNCISSWKKFMEDLMKAQEANPVIKIKIALKDESSVLSEDSM |
| SEQ ID NO: 129 | KFHPENLNKSYCLAIVRAANLDADIQGHINCIGIKSNKSDRNYENKLESLQNVELLCKACTKSTYKPNINSVPVGEKKAKYSILSEIKKYDFNSLVYNLKKYRKGKSRGHQKLNELRELVITSEYKKALDVINKSVNHYLVNIKNKMSKLKKILQNEHIHVGTLARIRRERNRISRKLDHYRKKWKFVPNKILKNYVFKNQSPDFVSVALLHKLGRDIGLITKTAILQKSFPEYSLQLYYKYDTPKLNYLKKSKFKSLPKRILISYKYPKFDINSNYIEESIDKLLKLYEESPIYKNNSKIIEFFKKSEDNLIKSENDSLKRGIMKEFEKVTKNFSSKKKKLKEELKLKNEDKNSKMLAKVSRPIGFLKAYLSYMLFNIISNRIFEFSRKSSGRIPQLPSCIINLGNQFENFKNELQDSNIGSKKNYKYFCNLLLKSSGFNISYEEEHLSIKTPNFFINGRKLKEITSEKKKIRKENEQLIKQWKKLTFFKPSNLNGKKTSDKIRFKSPNNPDIERKSEDNIVENIAKVKYKLEDLLSEQRKEFNKLAKKHDGVDVEAQCLQTKSFWIDSNSPIKKSLEKKNEKVSVKKKMKAIRSCISAWKWFMADLIEAQKETPMIKLKLALM |
| SEQ ID NO: 130 | TTLVPSHLAGIEVMDETTSRNEDMIQKETSRSNEDENYLGVKNKCGINVHKSGRGSSKHEPNMPPEKSGEGQMPKQDSTEMQQRFDESVTGETQVSAGATASIKTDARANSGPRVGTARALIVKASNLDRDIKLGCKPCEYIRSELPMGKKNGCNHCEKSSDIASVPKVESGFRKAKYELVRRFESFAADSISRHLGKEQARTRGKRGKKDKKEQMGKVNLDEIAILKNESLIEYTENQILDARSNRIKEWLRSLRLRLRTRNKGLKKSKSIRRQLITLRRDYRKWIKPNPYRPDEDPNENSLRLHTKLGVDIGVQGGDNKRMNSDDYETSFSITWRDTATRKICFTKPKGLLPRHMKFKLRGYPELILYNEELRIQDSQKFPLVDWERIPIFKLRGVSLGKKKVKALNRITEAPRLVVAKRIQVNIESKKKKVLTRYVYNDKSINGRLVKAEDSNKDPLLEFKKQAEEINSDAKYYENQEIAKNYLWGCEGLHKNLLEEQTKNPYLAFKYGFLNIV |
| SEQ ID NO: 131 | LDFKRTCSQELVLLPEIEGLKLSGTQGVTSLAKKLINKAANVDRDESYGCHHCIHTRTSLSKPVKKDCNSCNQSTNHPAVPITLKGYKIAFYELWHRFTSWAVDSISKALHRNKVMGKVNLDEYAVVDNSHIVCYAVRKCYEKRQRSVRLHKRAYRCRAKHYNKSQPKVGRIYKKSKRRNARNLKKEAKRYFQPNEITNGSSDALFYKIGVDLGIAKGTPETEVKVDVSICFQVYYGDARRVLRVRKMDELQSFHLDYTGKLKLKGIGNKDTFTIAKRNESLKWGSTKYEVSRAHKKFKPFGKKGSVKRKCNDYFRSIASWSCEAASQRAQSNLKNAFPYQKALVKCYKNLDYKGVKKNDMWYRLCSNRIFRYSRIAEDIAQYQSDKGKAKFEFVILAQSVAEYDISAIM |
| SEQ ID NO: 132 | VFLTDDKRKTALRKIRSAFRKTAEIALVRAQEADSLDRQAKKLTIETVSFGAPGAKNAFIGSLQGYNWNSHRANVPSSGSAKDVFRITELGLGIPQSAHEASIGKSFELVGNVVRYTANLLSKGYKKGAVNKGAKQQREIKGKEQLSFDLISNGPISGDKLINGQKDALAWWLIDKMGFHIGLAMEPLSSPNTYGITLQAFWKRHTAPRRYSRGVIRQWQLPFGRQLAPLIHNFFRKKGASIPIVLTNASKKLAGKGVLLEQTALVDPKKWWQVKEQVTGPLSNIWERSVPLVLYTATFTHKHGAAHKRPLTLKVIRISSGSVFLLPLSKVTPGKLVRAWMPDINILRDGRPDEAAYKGPDLIRARERSFPLAYTCVTQIADEWQKRALESNRDSITPLEAKLVTGSDLLQIHSTVQQAVEQGIGGRISSPIQELLAKDALQLVLQQLFMTVDLL |

TABLE 2-continued

| Cas14 Enzyme Sequences | |
|---|---|
| SEQ ID NO | Sequence |
| | RIQWQLKQEVADGNTSEKAVGWAIRISNIHKDAYK<br>TAIEPCTSALKQAWNPLSGFEERTFQLDASIVRKR<br>STAKTPDDELVIVLRQQAAEMTVAVTQSVSKELME<br>LAVRHSATLHLLVGEVASKQLSRSADKDRGAMDHW<br>KLLSQSM |
| SEQ ID NO: 133 | EDLLQKALNTATNVAAIERHSCISCLFTESEIDVK<br>YKTPDKIGQNTAGCQSCTFRVGYSGNSHTLPMGNR<br>IALDKLRETIQRYAWHSLLFNVPPAPTSKRVRAIS<br>ELRVAAGRERLFTVITFVQTNILSKLQKRYAANWT<br>PKSQERLSRLREEGQHILSLLESGSWQQKEVVRED<br>QDLIVCSALTKPGLSIGAFCRPKYLKPAKHALVLR<br>LIFVEQWPGQIWGQSKRTRRMRRRKDVERVYDISV<br>QAWALKGKETRISECIDTMRRHQQAYIGVLPFLIL<br>SGSTVRGKGDCPILKEITRMRYCPNNEGLIPLGIF<br>YRGSANKLLRVVKGSSFTLPMWQNIETLPHPEPFS<br>PEGWTATGALYEKNLAYWSALNEAVDWYTGQILSS<br>GLQYPNQNEFLARLQNVIDSIPRKWFRPQGLKNLK<br>PNGQEDIVPNEFVIPQNAIRAHHVIEWYHKTNDLV<br>AKTLLGWGSQTTLNQTRPQGDLRFTYTRYYFREKE<br>VPEV |
| SEQ ID NO: 134 | VPKKKLMRELAKKAVFEAIFNDPIPGSFGCKRCTL<br>IDGARVTDAIEKKQGAKRCAGCEPCTFHTLYDSVK<br>HALPAATGCDRTAIDTGLWEILTALRSYNWMSFRR<br>NAVSDASQKQVWSIEELAIWADKERALRVILSALT<br>HTIGKLKNGFSRDGVWKGGKQLYENLAQKDLAKGL<br>FANGEIFGKELVEADHDMLAWTIVPNHQFHIGLIR<br>GNWKPAAVEASTAFDARWLTNGAPLRDTRTHGHRG<br>RRFNRTEKLTVLCIKRDGGVSEEFRQERDYELSVM<br>LLQPKNKLKPEPKGELNSFEDLHDHWWFLKGDEAT<br>ALVGLTSDPTVGDFIQLGLYIRNPIKAHGETKRRL<br>LICFEPPIKLPLRRAFPSEAFKTWEPTINVFRNGR<br>RDTEAYYDIDRARVFEFPETRVSLEHLSKQWEVLR<br>LEPDRENTDPYEAQQNEGAELQVYSLLQEAAQKMA<br>PKVVIDPFGQFPLELFSTFVAQLFNAPLSDTKAKI<br>GKPLDSGFVVESHLHLLEEDFAYRDFVRVTFMGTE<br>PTFRVIHYSNGEGYWKKTVLKGKNNIRTALIPEGA<br>KAAVDAYKNKRCPLTLEAAILNEEKDRRLVLGNKA<br>LSLLAQTARGNLTILEALAAEVLRPLSGTEGVVHL<br>HACVTRHSTLTESTETDNM |
| SEQ ID NO: 135 | VEKLFSERLKRAMWLKNEAGRAPPAETLTLKHKRV<br>SGGHEKVKEELQRVLRSLSGTNQAAWNLGLSGGRE<br>PKSSDALKGEKSRVVLETVVFHSGHNRVLYDVIER<br>EDQVHQRSSIMHMRRKGSNLLRLWGRSGKVRRKMR<br>EEVAEIKPVWHKDSRWLAIVEEGRQSVVGISSAGL<br>AVFAVQESQCTTAEPKPLEYVVSIWFRGSKALNPQ<br>DRYLEFKKLKTTEALRGQQYDPIPFSLKRGAGCSL<br>AIRGEGIKFGSRGPIKQFFGSDRSRPSHADYDGKR<br>RLSLFSKYAGDLADLTEEQWNRTVSAFAEDEVRRA<br>TLANIQDFLSISHEKYAERLKKRIESIEEPVSASK<br>LEAYLSAIFETFVQQREALASNFLMRLVESVALLI<br>SLEEKSPRVEFRVARYLAESKEGFNRKAM |
| SEQ ID NO: 136 | VVITQSELYKERLLRVMEIKNDRGRKEPRESQGLV<br>LRFTQVTGGQEKVKQKLWLIFEGFSGTNQASWNFG<br>QPAGGRKPNSGDALKGPKSRVTYETVVFHFGLRLL<br>SAVIERHNLKQQRQTMAYMKRRAAARKKWARSGKK<br>CSRMRNEVEKIKPKWHKDPRWFDIVKEGEPSIVGI<br>SSAGFAIYIVEEPNFPRQDPLEIEYAISIWFRRDR<br>SQYLTFKKIQKAEKLKELQYNPIPFRLKQEKTSLV<br>FESGDIKFGSRGSIEHFRDEARGKPPKADMDNNRR<br>LTMFSVFSGNLTNLTEEQYARPVSGLLAPDEKRMP<br>TLLKKLQDFFTPIHEKYGERIKQRLANSEASKRPF<br>KKLEEYLPAIYLEFRARREGLASNWVLVLINSVRT<br>LVRIKSEDPYIEFKVSQYLLEKEDNKAL |
| SEQ ID NO: 137 | KQDALFEERLKKAIFIKRQADPLQREELSLLPPNR<br>KIVTGGHESAKDTLKQILRAINGTNQASWNPGTPS<br>GKRDSKSADALAGPKSRVKLETVVFHVGHRLLKKV<br>VEYQGHQKQQHGLKAFMRTCAAMRKKWKRSGKVVG<br>ELREQLANIQPKWHYDSRPLNLCFEGKPSVVGLRS<br>AGIALYTIQKSVVPVKEPKPIEYAVSIWFRGPKAM |

TABLE 2-continued

| Cas14 Enzyme Sequences | |
|---|---|
| SEQ ID NO | Sequence |
| | DREDRCLEFKKLKIATELRKLQFEPIVSTLTQGIK<br>GFSLYIQGNSVKFGSRGPIKYFSNESVRQRPPKAD<br>PDGNKRLALFSKFSGDLSDLTEEQWNRPILAFEGI<br>IRRATLGNIQDYLTVGHEQFAISLEQLLSEKESVL<br>QMSIEQQRLKKNLGKKAENEWVESFGAEQARKKAQ<br>GIREYISGFFQEYCSQREQWAENWVQQLNKSVRLF<br>LTIQDSTPFIEFRVARYLPKGEKKKGKAM |
| SEQ ID NO: 138 | ANHAERHKRLRKEANRAANRNRPLVADCDTGDPLV<br>GICRLLRRGDKMQPNKTGCRSCEQVEPELRDAILV<br>SGPGRLDNYKYELFQRGRAMAVHRLLKRVPKLNRP<br>KKAAGNDEKKAENKKSEIQKEKQKQRRMMPAVSMK<br>QVSVADFKHVIENTVRHLFGDRRDREIAECAALRA<br>ASKYFLKSRRVRPRKLPKLANPDHGKELKGLRLRE<br>KRAKLKKEKEKQAELARSNQKGAVLHVATLKKDAP<br>PMPYEKTQGRNDYTTFVISAAIKVGATRGTKPLLT<br>PQPREWQCSLYWRDGQRWIRGGLLGLQAGIVLGPK<br>LNRELLEAVLQRPIECRMSGCGNPLQVRGAAVDFF<br>MTTNPFYVSGAAYAQKKFKPFGTKRASEDGAAAKA<br>REKLMTQLAKVLDKVVTQAAHSPLDGIWETRPEAK<br>LRAMIMALEHEWIFLRPGPCHNAAEEVIKCDCTGG<br>HAILWALIDEARGALEHKEFYAVTRAHTHDCEKQK<br>LGGRLAGFLDLLIAQDVPLDDAPAARKIKTLLEAT<br>PPAPCYKAATSIATCDCEGKFDKLWAIIDATRAGH<br>GTEDLWARTLAYPQNVNCKCKAGKDLTHRLADFLG<br>LLIKRDGPFRERPPHKVTGDRKLVFSGDKKCKGHQ<br>YVILAKAHNEEVVRAWISRWGLKSRTNKAGYAATE<br>LNLLLNWLSICRRRWMDMLTVQRDTPYIRMKTGRL<br>VVDDKKERKAM |
| SEQ ID NO: 139 | AKQREALRVALERGIVRASNRTYTLVTNCTKGGPL<br>PEQCRMIERGKARAMKWEPKLVGCGSCAAATVDLP<br>AIEEYAQPGRLDVAKYKLTTQILAMATRRMMVRAA<br>KLSRRKGQWPAKVQEEKEEPPEPKKMLKAVEMRPV<br>AIVDFNRVIQTTIEHLWAERANADEAELKALKAAA<br>AYFGPSLKIRARGPPKAAIGRELKKAHRKKAYAER<br>KKARRKRAELARSQARGAAAHAAIRERDIPPMAYE<br>RTQGRNDVTTIPIAAAIKIAATRGARPLPAPKPMK<br>WQCSLYWNEGQRWIRGGMLTAQAYAHAANIHRPMR<br>CEMWGVGNPLKVRAFEGRVADPDGAKGRKAEFRLQ<br>TNAFYVSGAAYRNKKFKPFGTDRGGIGSARKKRER<br>LMAQLAKILDKVVSQAAHSPLDDIWHTRPAQKLRA<br>MIKQLEHEWMFLRPQAPTVEGTKPDVDVAGNMQRQ<br>IKALMAPDLPPIEKGSPAKRFTGDKRKKGERAVRV<br>AEAHSDEVVTAWISRWGIQTRRNEGSYAAQELELL<br>LNWLQICRRRWLDMTAAQRVSPYIRMKSGRMITDA<br>ADEGVAPIPLVENM |
| SEQ ID NO: 140 | KSISGRSIKHMACLKDMLKSEITEIEEKQKKESLR<br>KWDYYSKFSDEILFRRNLNVSANHDANACYGCNPC<br>AFLKEVYGFRIERRNNERIISYRRGLAGCKSCVQS<br>TGYPPIEFVRRKFGADKAMEIVREVLHRRNWGALA<br>RNIGREKEADPILGELNELLLVDARPYFGNKSAAN<br>ETNLAFNVITRAAKKFRDEGMYDIHKQLDIHSEEG<br>KVPKGRKSRLIRIERKHKAIHGLDPGETWRYPHCG<br>KGEKYGVWLNRSRLIHIKGNEYRCLTAFGTTGRRM<br>SLDVACSVLGHPLVKKKRKKGKKTVDGTELWQIKK<br>ATETLPEDPIDCTFYLYAAKPTKDPFILKVGSLKA<br>PRWKKLHKDFFEYSDTEKTQGQEKGKRVVRRGKVP<br>RILSLRPDAKFKVSIWDDPYNGKNKEGTLLRMELS<br>GLDGAKKPLILKRYGEPNTKPKNFVFWRPHITPHP<br>LTFTPKHDFGDPNKKTKRRRVFNREYYGHLNDLAK<br>MEPNAKFFEDREVSNKKNPKAKNIRIQAKESLPNI<br>VAKNGRWAAFDPNDSLWKLYLHWRGRRKTIKGGIS<br>QEFQEFKERLDLYKKHEDESEWKEKEKLWENHEKE<br>WKKTLEIHGSIAEVSQRCVMQSMMGPLDGLVQKKD<br>YVHIGQSSLKAADDAWTFSANRYKKATGPKWGKIS<br>VSNLLYDANQANAELISQSISKYLSKQKDNQGCEG<br>RKMKFLIKIIEPLRENFVKHTRWLHEMTQKDCEVR<br>AQFSRVSM |

TABLE 2-continued

| Cas14 Enzyme Sequences | |
|---|---|
| SEQ ID NO | Sequence |
| SEQ ID NO: 141 | FPSDVGADALKHVRMLQPRLTDEVRKVALTRAPSDRPALARFAAVAQDGLAFVRHLNVSANHDSNCTFPRDPRDPRRGPCEPNPCAFLREVWGFRIVARGNERALSYRRGLAGCKSCVQSTGFPSVPFHRIGADDCMRKLHEILKARNWRLLARNIGREREADPLLTELSEYLLVDARTYPDGAAPNSGRLAENVIKRAAKKFRDEGMRDIHAQLRVHSREGKVPKGRLQRLRRIERKHRAIHALDPGPSWEAEGSARAEVQGVAVYRSQLLRVGHHTQQIEPVGIVARTLFGVGRTDLDVAVSVLGAPLTKRKKGSKTLESTEDFRIAKARETRAEDKIEVAFVLYPTASLLRDEIPKDAFPAMRIDRFLLKVGSVQADREILLQDDYYRFGDAEVKAGKNKGRTVTRPVKVPRLQALRPDAKFRVNVWADPFGAGDSPGTLLRLEVSGVTRRSQPLRLLRYGQPSTQPANFLCWRPHRVPDPMTFTPRQKFGERRKNRRTRRPRVFERLYQVHIKHLAHLEPNRKWFEEARVSAQKWAKARAIRRKGAEDIPVVAPPAKRRWAALQPNAELWDLYAHDREARKRFRGGRAAEGEEFKPRLNLYLAHEPEAEWESKRDRWERYEKKWTAVLEEHSRMCAVADRTLPQFLSDPLGARMDDKDYAFVGKSALAVAEAFVEEGTVERAQGNCSITAKKKFASNASRKRLSVANLLDVSDKADRALVFQAVRQYVQRQAENGGVEGRRMAFLRKLLAPLRQNFVCHTRWLHM |
| SEQ ID NO: 142 | AARKKKRGKIGITVKAKEKSPPAAGPFMARKLVNVAANVDGVEVHLCVECEADAHGSASARLLGGCRSCTGSIGAEGRLMGSVDVDRERVIAEPVHTETERLGPDVKAFEAGTAESKYAIQRGLEYWGVDLISRNRARTVRKMEEADRPESSTMEKTSWDEIAIKTYSQAYHASENHLFWERQRRVRQHALALFRRARERNRGESPLQSTQRPAPLVLAALHAEAAAISGRARAEYVLRGPSANVRAAAADIDAKPLGHYKTPSPKVARGFPVKRDLLRARHRIVGLSRAYFKPSDVVRGTSDAIAHVAGRNIGVAGGKPKEIEKTFTLPFVAYWEDVDRVVHCSSFKADGPWVRDQRIKIRGVSSAVGTFSLYGLDVAWSKPTSFYIRCSDIRKKFHPKGFGPMKHWRQWAKELDRLTEQRASCVVRALQDDEELLQTMERGQRYYDVFSCAATHATRGEADPSGGCSRCELVSCGVAHKVTKKAKGDTGIEAVAVAGCSLCESKLVGPSKPRVHRQMAALRQSHALNYLRRLQREWEALEAVQAPTPYLRFKYARHLEVRSM |
| SEQ ID NO: 143 | AAKKKKQRGKIGISVKPKEGSAPPADGPFMARKLVNVAANVDGVEVNLCIECEADAHGSAPARLLGGCKSCTGSIGAEGRLMGSVDVDRADAIAKPVNTETEKLGPDVQAFEAGTAETKYALQRGLEYWGVDLISRNRSRTVRRTEEGQPESATMEKTSWDEIAIKSYTRAYHASENHLFWERQRRVRQHALALFKRAKERNRGDSTLPREPGHGLVAIAALACEAYAVGGRNLAETVVRGPTFGTARAVRDVEIASLGRYKTPSPKVAHGSPVKRDFLRARHRIVGLARAYYRPSDVVRGTSDAIAHVAGRNIGVAGGKPRAVEAVFTLPFVAYWEDVDRVVHCSSFQVSAPWNRDQRMKIAGVTTAAGTFSLHGGELKWAKPTSFYIRCSDTRRKFRPKGFGPMKRWRQWAKDLDRLVEQRASCVVRALQDDAALLETMERGQRYYDVFACAVTHATRGEADRLAGCSRCALTPCQEAHRVTTKPRGDAGVEQVQTSDCSLCEGKLVGPSKPRLHRTLTLLRQEHGLNYLRRLQREWESLEAVQVPTPYLRFKYARHLEVRSM |
| SEQ ID NO: 144 | TDSQSESVPEVVYALTGGEVPGRVPPDGGSAEGARNAPTGLRKQRGKIKISAKPSKPGSPASSLARTLVNEAANVDGVQSSGCATCRMRANGSAPRALPIGCVACASSIGRAPQEETVCALPTTQGPDVRLLEGGHALRKYDIQRALEYWGVDLIGRNLDRQAGRGMEPAEGATATMKRVSMDELAVLDFGKSYYASEQHLFAARQRRVRQHAKALKIRAKHANRSGSVKRALDRSRKQVTALAREFFKPSDVVRGDSDALAHVVGRNLGVSRHPAREIPQTFTLPLCAYWEDVDRVISCSSLLAGEPFARDQEIRIEGVSSALGSLRLYRGAIEWHKPTSLYIRCSDTRRKFRPRGGLKKRWRQWAKDLDRLVEQRACCIVRSLQADVELLQTMERAQRFYDVHDCAATHVGPVAVRCSPCAGKQFDWDRYRLLAALRQEHALNYLRRLQREWESLEAQQVKMPYLRFKYARKLEVSGPLIGLEVRREPSMGTAIAEM |

TABLE 2-continued

| Cas14 Enzyme Sequences | |
|---|---|
| SEQ ID NO | Sequence |
| SEQ ID NO: 145 | AGTAGRRHGSLGARRSINIAGVTDRHGRWGCESCVYTRDQAGNRARCAPCDQSTYAPDVQEVTIGQRQAKYTIFLTLQSFSWTNTMRNNKRAAAGRSKRTTGKRIGQLAEIKITGVGLAHAHNVIQRSLQHNITKMWRAEKGKSKRVARLKKAKQLTKRRAYFRRRMSRQSRGNGFFRTGKGGIHAVAPVKIGLDVGMIASGSSEPADEQTVTLDAIWKGRKKKIRLIGAKGELAVAACRFREQQTKGDKCIPLILQDGEVRWNQNNWQCHPKKLVPLCGLEVSRKFVSQADRLAQNKVASPLAARFDKTSVKGTLVESDFAAVLVNVTSIYQQCHAMLLRSQEPTPSLRVQRTITSM |
| SEQ ID NO: 146 | GVRFSPAQSQVFFRTVIPQSVEARFAINMAAIHDAAGAFGCSVCRFEDRTPRNAKAVHGCSPCTRSTNRPDVFVLPVGAIKAKYDVFMRLLGFNWTHLNRRQAKRVTVRDRIGQLDELAISMLTGKAKAVLKKSICHNVDKSFKAMRGSLKKLHRKASKTGKSQLRAKLSDLRERTNTTQEGSHVEGDSDVALNKIGLDVGLVGKPDYPSEESVEVVVCLYFVGKVLILDAQGRIRDMRAKQYDGFKIPIIQRGQLTVLSVKDLGKWSLVRQDYVLAGDLRFEPKISKDRKYAECVKRIALITLQASLGFKERIPYYVTKQVEIKNASHIAFVTEAIQNCAENFREMTEYLMKYQEKSPDLKVLLTQLM |
| SEQ ID NO: 147 | RAVVGKVFLEQARRALNLATNFGTNHRTGCNGCYVTPGKLSIPQDGEKNAAGCTSCLMKATASYVSYPKPLGEKVAKYSTLDALKGFPWYSLRLNLRPNYRGKPINGVQEVAPVSKFRLAEEVIQAVQRYHFTELEQSFPGGRRRLRELRAFYTKEYRRAPEQRQHVVNGDRNIVVVTVLHELGFSVGMFNEVELLPKTPIECAVNVFIRGNRVLLEVRKPQFDKERLLVESLWKKDSRRHTAKWTPPNNEGRIFTAEGWKDFQLPLLLGSTSRSLRAIEKEGFVQLAPGRDPDYNNTIDEQHSGRPFLPLYLYLQGTISQEYCVFAGTWVIPFQDGISPYSTKDTFQPDLKRKAYSLLLDAVKHRLGNKVASGLQYGRFPAIEELKRLVRMHGATRKIPRGEKDLLKKGDPDTPEWWLLEQYPEFWRLCDAAAKRVSQNVGLLLSLKKQPLWQRRWLESRTRNEPLDNLPLSMALTLHLTNEEAL |
| SEQ ID NO: 148 | AAVYSKFYIENHFKMGIPETLSRIRGPSIIQGFSVNENYINIAGVGDRDFIFGCKKCKYTRGKPSSKKINKCHPCKRSTYPEPVIDVRGSISEFKYKIYNKLKQEPNQSIKQNTKGRMNPSDHTSSNDGIIINGIDNRIAYNVIFSSYKHLMEKQINLLRDTTKRKARQIKKYNNSGKKKHSLRSQTKGNLKNRYHMLGMFKKGSLTITNEGDFITAVRKVGLDISLYKNESLNKQEVETELCLNIKWGRTKSYTVSGYIPLPINIDWKLYLFEKETGLTLRLFGNKYKIQSKKFLIAQLFKPKRPPCADPVVKKAQKWSALNAHVQQMAGLFSDSHLLKRELKNRMHKQLDFKSLWVGTEDYIKWFEELSRSYVEGAEKSLEFFRQDYFCFNYTKQTTM |
| SEQ ID NO: 149 | PQQQRDLMLMAANYDQDYGNGCGPCTVVASAAYRPDPQAQHGCKRHLRTLGASAVTHVGLGDRTATITALHRLRGPAALAARARAAQAASAPMTPDTDAPDDRRRLEAIDADDVVLVGAHRALWSAVRRWADDRRAALRRRLHSEREWLLKDQIRWAELYTLIEASGTPPQGRWRNTLGALRGQSRWRRVLAPTMRATCAETHAELWDALAELVPEMAKDRRGLLRPPVEADALWRAPMIVEGWRGGHSVVVDAVAPPLDLPQPCAWTAVRLSGDPRQRWGLHLAVPPLGQVQPPDPLKATLAVSMRHRGGVRVRTLQAMAVDADAPMQRHLQVPLTLQRGGGLQWGIHSRGVRRREARSMASWEGPPIWTGLQLVNRWKGQGSALLAPDRPPDTPPYAPDAAVAPAQPDTKRARRTLKEACTVCRCAPGHMRQLQVTLTGDGTWRRFRLRAPQGAKRKAEVLKVATQHDERIANYTAWYLKRPEHAAGCDTCDGDSRLDGACRGCRPLLVGDQCFRRYLDKIEADRDDGLAQIKPKAQEAVAAMAAKRDARAQKVAARAAKLSEATGQRTAATRDASHEARAQKELEAVATEGTTVRHDAAAVSAFGSWVARKGDEYRHQVGVLANRLEHGLRLQELMAPDSVVADQQRASGHARVGYRYVLTAM |

TABLE 2-continued

Cas14 Enzyme Sequences

| SEQ ID NO | Sequence |
|---|---|
| SEQ ID NO: 150 | AVAHPVGRGNAGSPGARGPEELPRQLVNRASNVTR PATYGCAPCRHVRLSIPKPVLTGCRACEQTTHPAP KRAVRGGADAAKYDLAAFFAGWAADLEGRNRRRQV HAPLDPQPDPNHEPAVTLQKIDLAEVSIEEFQRVL ARSVKHRHDGRASREREKARAYAQVAKKRRNSHAH GARTRRAVRRQTRAVRRAHRMGANSGEILVASGAE DPVPEAIDHAAQLRRRIRACARDLEGLRHLSRRYL KTLEKPCRRPRAPDLGRARCHALVESLQAAERELE ELRRCDSPDTAMRRLDAVLAAAASTDATFATGWTV VGMDLGVAPRGSAAPEVSPMEMAISVFWRKGSRRV IVSKPIAGMPIRRHELIRLEGLGTLRLDGNHYTGA GVTKGRGLSEGTEPDFREKSPSTLGFTLSDYRHES RWRPYGAKQGKTARQFFAAMSRELRALVEHQVLAP MGPPLLEAHERRFETLLKGQDNKSIHAGGGGRYVW RGPPDSKKRPAADGDWFRFGRGHADHRGWANKRHE LAANYLQSAFRLWSTLAEAQEPTPYARYKYTRVTM |
| SEQ ID NO: 151 | WDFLTLQVYERHTSPEVCVAGNSTKCASGTRKSDH THGVGVKLGAQEINVSANDDRDHEVGCNICVISRV SLDIKGWRYGCESCVQSTPEWRSIVRFDRNHKEAK GECLSRFEYWGAQSIARSLKRNKLMGGVNLDELAI VQNENVVKTSLKHLFDKRKDRIQANLKAVKVRMRE RRKSGRQRKALRRQCRKLKRYLRSYDPSDIKEGNS CSAFTKLGLDIGISPNKPPKIEPKVEVVFSLFYQG ACDKIVTVSSPESPLPRSWKIKIDGIRALYVKSTK VKFGGRTFRAGQRNNRRKVRPPNVKKGKRKGSRSQ FFNKFAVGLDAVSQQLPIASVQGLWGRAETKKAQT ICLKQLESNKPLKESQRCLFLADNWVVRVCGFLRA LSQRQGPTPYIRYRYRCNM |
| SEQ ID NO: 152 | ARNVGQRNASRQSKRESAKARSRRVTGGHASVTQG VALINAAANADRDHTTGCEPCTWERVNLPLQEVIH GCDSCTKSSPFWRDIKVVNKGYREAKEEIMRIASG ISADHLSRALSHNKVMGRLNLDEVCILDFRTVLDT SLKHLTDSRSNGIKEHIRAVHRKIRMRRKSGKTAR ALRKQYFALRRQWKAGHKPNSIREGNSLTALRAVG FDVGVSEGTEPMPAPQTEVVLSVFYKGSATRILRI SSPHPIAKRSWKVKIAGIKALKLIRREHDFSFGRE TYNASQRAEKRKFSPHAARKDFFNSFAVQLDRLAQ QLCVSSVENLWVTEPQQKLLTLAKDTAPYGIREGA RFADTRARLAWNWVFRVCGFTRALHQEQEPTPYCR FTWRSKM |

In some embodiments, the Type VI CRISPR-Cas enzyme is a programmable Cas13 nuclease. The general architecture of a Cas13 enzyme includes an N-terminal domain and two HEPN (higher eukaryotes and prokaryotes nucleotide-binding) domains separated by two helical domains (Liu et al., Cell 2017 Jan. 12; 168(1-2):121-134.e12). The HEPN domains each comprise aR-$X_4$—H motif Shared features across Cas13 enzymes include that upon binding of crRNA to a target nucleic acid, the enzyme undergoes a conformational change to bring together the HEPN domains and form a catalytically active RNase. (Tambe et al., Cell Rep. 2018 Jul. 24; 24(4): 1025-1036). Thus, two activatable HEPN domains are characteristic of a programmable Cas13 nuclease of the present disclosure. However, programmable Cas13 nucleases also consistent with the present disclosure include Cas13 nucleases comprising mutations in the HEPN domain that enhance the Cas13 enzymes cleavage efficiency or mutations that catalytically inactivate the HEPN domains. Programmable Cas13 nucleases consistent with the present disclosure also Cas13 nucleases comprising catalytic A programmable Cas13 nuclease can be a Cas13a enzyme (also referred to as "c2c2"), a Cas13b enzyme, a Cas13c enzyme, a Cas13d enzyme, or a Cas13e enzyme. Example C2c2 enzymes are set forth as SEQ ID NO: 153-SEQ ID NO: 160. In some cases, a subject C2c2 enzymes includes an amino acid sequence having 80% or more (e.g., 85% or more, 90% or more, 95% or more, 98% or more, 99% or more, 99.5% or more, or 100%) amino acid sequence identity with the amino acid sequence set forth in any one of SEQ ID NO: 153-SEQ ID NO: 160. In some cases, a suitable C2c2 polypeptide comprises an amino acid sequence having at least 80%, at least 85%, at least 90%, at least 95%, at least 98%, at least 99%, or 100%, amino acid sequence identity to the *Listeria seeligeri* C2c2 amino acid sequence set forth in SEQ ID NO: 153. In some cases, a suitable C2c2 polypeptide comprises an amino acid sequence having at least 80%, at least 85%, at least 90%, at least 95%, at least 98%, at least 99%, or 100%, amino acid sequence identity to the *Leptotrichia buccalis* C2c2 amino acid sequence set forth in SEQ ID NO: 154. In some cases, a suitable C2c2 polypeptide comprises an amino acid sequence having at least 80%, at least 85%, at least 90%, at least 95%, at least 98%, at least 99%, or 100%, amino acid sequence identity to the *Rhodobacter capsulatus* C2c2 amino acid sequence set forth in SEQ ID NO: 156. In some cases, a suitable C2c2 polypeptide comprises an amino acid sequence having at least 80%, at least 85%, at least 90%, at least 95%, at least 98%, at least 99%, or 100%, amino acid sequence identity to the *Carnobacterium gallinarum* C2c2 amino acid sequence set forth in SEQ ID NO: 157. In some cases, a suitable C2c2 polypeptide comprises an amino acid sequence having at least 80%, at least 85%, at least 90%, at least 95%, at least 98%, at least 99%, or 100%, amino acid sequence identity to the *Herbinix hemicellulosilytica* C2c2 amino acid sequence set forth in SEQ ID NO: 158. In some cases, the C2c2 enzyme includes an amino acid sequence having 80% or more amino acid sequence identity with the *Leptotrichia buccalis* (Lbu) C2c2 amino acid sequence set forth in SEQ ID NO: 154. In some cases, the C2c2 enzyme is a *Leptotrichia buccalis* (Lbu) C2c2 enzyme (e.g., see SEQ ID NO: 154). In some cases, the C2c2 enzyme includes the amino acid sequence set forth in any one of SEQ ID NO: 153, SEQ ID NO: 154 and SEQ ID NO: 156-SEQ ID NO: 160. In some cases, a C2c2 enzyme used in a method of the present disclosure is not a *Leptotrichia shahii* (Lsh) C2c2 enzyme. In some cases, a C2c2 enzyme used in a method of the present disclosure is not a C2c2 polypeptide having at least 80%, at least 85%, at least 90%, at least 95%, at least 98%, at least 99%, or 100%, amino acid sequence identity to the Lsh C2c2 polypeptide set forth in SEQ ID NO: 155. Other Cas13 enzyme sequences are set forth in SEQ ID NO: 153-SEQ ID NO: 170.

TABLE 3

Cas13 Enzyme Sequences

| SEQ ID NO | Description | Sequence |
|---|---|---|
| SEQ ID NO: 153 | *Listeria seeligeri* C2c2 amino acid sequence | MWISIKTLIHHLGVLFFCDYMYNRR EKKIIEVKTMRITKVEVDRKKVLIS RDKNGGKLVYENEMQDNTEQIMHHK KSSFYKSVVNKTICRPEQKQMKKLV HGLLQENSQEKIKVSDVTKLNISNF LNHRFKKSLYYFPENSPDKSEEYRI EINLSQLLEDSLKKQQGTFICWESF SKDMELYINWAENYISSKTKLIKKS IRNNRIQSTESRSGQLMDRYMKDIL NKNKPFDIQSVSEKYQLEKLTSALK ATFKEAKKNDKEINYKLKSTLQNHE RQIIEELKENSELNQFNIEIRKHLE TYFPIKKTNRKVGDIRNLEIGEIQK IVNHRLKNKIVQRILQEGKLASYEI |

TABLE 3-continued

Cas13 Enzyme Sequences

| SEQ ID NO | Description | Sequence |
|---|---|---|
| | | ESTVNSNSLQKIKIEEAFALKFINA<br>CLFASNNLRNMVYPVCKKDILMIGE<br>FKNSFKEIKHKKFIRQWSQFFSQEI<br>TVDDIELASWGLRGAIAPIRNEIIH<br>LKKHSWKKFFNNPTFKVKKSKIING<br>KTKDVTSEFLYKETLFKDYFYSELD<br>SVPELIINKMESSKILDYYSSDQLN<br>QVFTIPNFELSLLTSAVPFAPSFKR<br>VYLKGFDYQNQDEAQPDYNLKLNIY<br>NEKAFNSEAFQAQYSLFKMVYYQVF<br>LPQFTTNNDLFKSSVDFILTLNKER<br>KGYAKAFQDIRKMNKDEKPSEYMSY<br>IQSQLMLYQKKQEEKEKINHFEKFI<br>NQVFIKGFNSFIEKNRLTYICHPTK<br>NTVPENDNIEIPFHTDMDDSNIAFW<br>LMCKLLDAKQLSELRNEMIKFSCSL<br>QSTEEISTFTKAREVIGLALLNGEK<br>GCNDWKELFDDKEAWKKNMSLYVSE<br>ELLQSLPYTQEDGQTPVINRSIDLV<br>KKYGTETILEKLFSSSDDYKVSAKD<br>IAKLHEYDVTEKIAQQESLHKQWIE<br>KPGLARDSAWTKKYQNVINDISNYQ<br>WAKTKVELTQVRHLHQLTIDLLSRL<br>AGYMSIADRDFQFSSNYILERENSE<br>YRVTSWILLSENKNKNKYNDYELYN<br>LKNASIKVSSKNDPQLKVDLKQLRL<br>TLEYLELFDNRLKEKRNNISHFNYL<br>NGQLGNSILELFDDARDVLSYDRKL<br>KNAVSKSLKEILSSHGMEVTFKPLY<br>QTNHHLKIDKLQPKKIHHLGEKSTV<br>SSNQVSNEYCQLVRTLLTMK |
| SEQ ID NO: 154 | *Leptotrichia buccalis* (Lbu) C2c2 amino acid sequence | MKVTKVGGISHKKYTSEGRLVKSES<br>EENRTDERLSALLNMRLDMYIKNPS<br>STETKENQKRIGKLKKFFSNKMVYL<br>KDNTLSLKNGKKENIDREYSETDIL<br>ESDVRDKKNFAVLKKIYLNENVNSE<br>ELEVFRNDIKKKLNKINSLKYSFEK<br>NKANYQKINENNIEKVEGKSKRNII<br>YDYYRESAKRDAYVSNVKEAFDKLY<br>KEEDIAKLVLEIENLTKLEKYKIRE<br>FYHEIIGRKNDKENFAKIIYEEIQN<br>VNNMKELIEKVPDMSELKKSQVFYK<br>YYLDKEELNDKNIKYAFCHFVEIEM<br>SQLLKNYVYKRLSNISNDKIKRIFE<br>YQNLKKLIENKLLNKLDTYVRNCGK<br>YNYYLQDGEIATSDFIARNRQNEAF<br>LRNIIGVSSVAYFSLRNILETENEN<br>DITGRMRGKTVKNNKGEEKYVSGEV<br>DKIYNENKKNEVKENLKMFYSYDFN<br>MDNKNEIEDFFANIDEAISSIRHGI<br>VHFNLELEGKDIFAFKNIAPSEISK<br>KMFQNEINEKKLKLKIFRQLNSANV<br>FRYLEKYKILNYLKRTRFEFVNKNI<br>PFVPSFTKLYSRIDDLKNSLGIYWK<br>TPKTNDDNKTKEIIDAQIYLLKNIY<br>YGEFLNYFMSNNGNFFEISKEIIEL<br>NKNDKRNLKTGFYKLQKFEDIQEKI<br>PKEYLANIQSLYMINAGNQDEEEKD<br>TYIDFIQKIFLKGFMTYLANNGRLS<br>LIYIGSDEETNTSLAEKKQEFDKFL<br>KKYEQNNNIKIPYEINEFLREIKLG<br>NILKYTERLNMFYLILKLLNHKELT<br>NLKGSLEKYQSANKEEAFSDQLELI<br>NLLNLDNNRVTEDFELEADEIGKFL<br>DFNGNKVKDNKELKKFDTNKIYFDG<br>ENIIKHRAFYNIKKYGMLNLLEKIA<br>DKAGYKISIEELKKYSNKKNEIEKN<br>HKMQENLHRKYARPRKDEKFTDEDY<br>ESYKQAIENIEEYTHLKNKVEFNEL<br>NLLQGLLLRILHRLVGYTSIWERDL<br>RFRLKGEFPENQYIEEIFNFENKKN<br>VKYKGGQIVEKYIKFYKELHQNDEV<br>KINKYSSANIKVLKQEKKDLYIRNY<br>IAHFNYIPHAEISLLEVLENLRKLL<br>SYDRKLKNAVMKSVVDILKEYGFVA<br>TFKIGADKKIGIQTLESEKIVHLKN<br>LKKKKLMTDRNSEELCKLVKIMFEY<br>KMEEKKSEN |
| SEQ ID NO: 155 | *Leptotrichia shahii* (Lsh) C2c2 amino acid sequence | MGNLFGHKRWYEVRDKKDFKIKRKV<br>KVKRNYDGNKYILNINENNNKEKID<br>NNKFIRKYINYKKNDNILKEFTRKF<br>HAGNILFKLKGKEGIIRIENNDDFL<br>ETEEVVLYIEAYGKSEKLKALGITK<br>KKIIDEAIRQGITKDDKKIEIKRQE<br>NEEEIEIDIRDEYTNKTLNDCSIIL<br>RIIENDELETKKSIYEIFKNINMSL<br>YKIIEKIIENETEKVFENRYYEEHL<br>REKLLKDDKIDVILTNFMEIREKIK<br>SNLEILGFVKFYLNVGGDKKKSKNK<br>KMLVEKILNINVDLTVEDIADFVIK<br>ELEFWNITKRIEKVKKVNNEFLEKR<br>RNRTYIKSYVLLDKHEKFKIERENK<br>KDKIVKFFVENIKNNSIKEKIEKIL<br>AEFKIDELIKKLEKELKKGNCDTEI<br>FGIFKKHYKVNFDSKKFSKKSDEEK<br>ELYKIIYRYLKGRIEKILVNEQKVR<br>LKKMEKIEIEKILNESILSEKILKR<br>VKQYTLEHIMYLGKLRHNDIDMTTV<br>NTDDFSRLHAKEELDLELITFFAST<br>NMELNKIFSRENINNDENIDFFGGD<br>REKNYVLDKKILNSKIKIIRDLDFI<br>DNKNNITNNFIRKFTKIGTNERNRI<br>LHAISKERDLQGTQDDYNKVINIIQ<br>NLKISDEEVSKALNLDVVFKDKKNI<br>ITKINDIKISEENNNDIKYLPSFSK<br>VLPEILNLYRNNPKNEPFDTIETEK<br>IVLNALIYVNKELYKKLILEDDLEE<br>NESKNIFLQELKKTLGNIDEIDENI<br>IENYYKNAQISASKGNNKAIKKYQK<br>KVIECYIGYLRKNYEELFDFSDFKM<br>NIQEIKKQIKDINDNKTYERITVKT<br>SDKTIVINDDFEYIISIFALLNSNA<br>VINKIRNRFFATSVWLNTSEYQNII<br>DILDEIMQLNTLRNECITENWNLNL<br>EEFIQKMKEIEKDFDDFKIQTKKEI<br>FNNYYEDIKNNILTEFKDDINGCDV<br>LEKKLEKIVIFDDETKFEIDKKSNI<br>LQDEQRKLSNINKKDLKKKVDQYIK<br>DKDQEIKSKILCRIIFNSDFLKKYK<br>KEIDNLIEDMESENENKFQEIYYPK<br>ERKNELYIYKKNLFLNIGNPNFDKI<br>YGLISNDIKMADAKFLFNIDGKNIR<br>KNKISEIDAILKNLNDKLNGYSKEY<br>KEKYIKKLKENDDFFAKNIQNKNYK<br>SFEKDYNRVSEYKKIRDLVEFNYLN<br>KIESYLIDINWKLAIQMARFERDMH<br>YIVNGLRELGIIKLSGYNTGISRAY<br>PKRNGSDGFYTTTAYYKFFDEESYK<br>KFEKICYGFGIDLSENSEINKPENE<br>SIRNYISHFYIVRNPFADYSIAEQI<br>DRVSNLLSYSTRYNNSTYASVFEVF<br>KKDVNLDYDELKKKFKLIGNNDILE<br>RLMKPKKVSVLELESYNSDYIKNLI<br>IELLTKIENTNDTL |
| SEQ ID NO: 156 | *Rhodobacter capsulatus* C2c2 amino acid sequence | MQIGKVQGRTISEFGDPAGGLKRKI<br>STDGKNRKELPAHLSSDPKALIGQW<br>ISGIDKIYRKPDSRKSDGKAIHSPT<br>PSKMQFDARDDLGEAFWKLVSEAGL<br>AQDSDYDQFKRRLHPYGDKFQPADS<br>GAKLKFEADPPEPQAFHGRWYGAMS<br>KRGNDAKELAAALYEHLHVDEKRID<br>GQPKRNPKTDKFAPGLVVARALGIE<br>SSVLPRGMARLARNWGEEEIQTYFV<br>VDVAASVKEVAKAAVSAAQAFDPPR<br>QVSGRSLSPKVGFALAEHLERVTGS |

TABLE 3-continued

Cas13 Enzyme Sequences

| SEQ ID NO | Description | Sequence |
|---|---|---|
| | | KRCSFDPAAGPSVLALHDEVKKTYK RLCARGKNAARAFPADKTELLALMR HTHENRVRNQMVRMGRVSEYRGQQA GDLAQSHYWTSAGQTEIKESEIFVR LWVGAFALAGRSMKAWIDPMGKIVN TEKNDRDLTAAVNIRQVISNKEMVA EAMARRGIYFGETPELDRLGAEGNE GFVFALLRYLRGCRNQTFHLGARAG FLKEIRKELEKTRWGKAKEAEHVVL TDKTVAAIRAIIDNDAKALGARLLA DLSGAFVAHYASKEHFSTLYSEIVK AVKDAPEVSSGLPRLKLLLKRADGV RGYVHGLRDTRKHAFATKLPPPPAP RELDDPATKARYIALLRLYDGPFRA YASGITGTALAGPAARAKEAATALA QSVNVTKAYSDVMEGRSSRLRPPND GETLREYLSALTGETATEFRVQIGY ESDSENARKQAEFIENYRRDMLAFM FEDYIRAKGFDWILKIEPGATAMTR APVLPEPIDTRGQYEHWQAALYLVM HFVPASDVSNLLHQLRKWEALQGKY ELVQDGDATDQADARREALDLVKRF RDVLVLFLKTGEARFEGRAAPFDLK PFRALFANPATFDRLFMATPTTARP AEDDPEGDGASEPELRVARTLRGLR QIARYNHMAVLSDLFAKHKVRDEEV ARLAEIEDETQEKSQIVAAQELRTD LHDKVMKCHPKTISPEERQSYAAAI KTIEEHRFLVGRVYLGDHLRLHRLM MDVIGRLIDYAGAYERDTGTFLINA SKQLGAGADWAVTIAGAANTDARTQ TRKDLAHFNVLDRADGTPDLTALVN RAREMMAYDRKRKNAVPRSILDMLA RLGLTLKWQMKDHLLQDATITQAAI KHLDKVRLTVGGPAAVTEARFSQDY LQMVAAVFNGSVQNPKPRRRDDGDA WHKPPKPATAQSQPDQKPPNKAPSA GSRLPPPQVGEVYEGVVVKVIDTGS LGFLAVEGVAGNIGLHISRLRRIRE DAIIVGRRYRFRVEIYVPPKSNTSK LNAADLVRID |
| SEQ ID NO: 157 | *Carnobacterium gallinarum* C2c2 amino acid sequence | MRITKVKIKLDNKLYQVTMQKEEKY GTLKLNEESRKSTAEILRLKKASFN KSFHSKTINSQKENKNATIKKNGDY ISQIFEKLVGVDTNKNIRKPKMSLT DLKDLPKKDLALFIKRKFKNDDIVE IKNLDLISLFYNALQKVPGEHFTDE SWADFCQEMMPYREYKNKFIERKII LLANSIEQNKGFSINPETFSKRKRV LHQWAIEVQERGDFSILDEKLSKLA EIYNFKKMCKRVQDELNDLEKSMKK GKNPEKEKEAYKKQKNFKIKTIWKD YPYKTHIGLIEKIKENEELNQFNIE IGKYFEHYFPIKKERCTEDEPYYLN SETIATTVNYQLKNALISYLMQIGK YKQFGLENQVLDSKKLQEIGIYEGF QTKFMDACVFATSSLKNIIEPMRSG DILGKREFKEAIATSSFVNYHHFFP YFPFELKGMKDRESELIPFGEQTEA KQMQNIWALRGSVQQIRNEIFHSFD KNQKFNLPQLDKSNFEFDASENSTG KSQSYIETDYKFLFEAEKNQLEQFF IERIKSSGALEYYPLKSLEKLFAKK EMKFSLGSQVVAFAPSYKKLVKKGH SYQTATEGTANYLGLSYYNRYELKE ESFQAQYYLLKLIYQYVFLPNFSQG NSPAFRETVKAILRINKDEARKKMK KNKKFLRKYAFEQVREMEFKETPDQ YMSYLQSEMREEKVRKAEKNDKGFE KNITMNFEKLLMQIFVKGFDVFLTT FAGKELLLSSEEKVIKETEISLSKK INEREKTLKASIQVEHQLVATNSAI SYWLFCKLLDSRHLNELRNEMIKFK QSRIKFNHTQHAELIQNLLPIVELT ILSNDYDEKNDSQNVDVSAYFEDKS LYETAPYVQTDDRTRVSFRPILKLE KYHTKSLIEALLKDNPQFRVAATDI QEWMHKREEIGELVEKRKNLHTEWA EGQQTLGAEKREEYRDYCKKIDRFN WKANKVTLTYLSQLHYLITDLLGRM VGFSALFERDLVYFSRSFSELGGET YHISDYKNLSGVLRLNAEVKPIKIK NIKVIDNEENPYKGNEPEVKPFLDR LHAYLENVIGIKAVHGKIRNQTAHL SVLQLELSMIESMNNLRDLMAYDRK LKNAVTKSMIKILDKHGMILKLKID ENHKNFEIESLIPKEIIHLKDKAIK TNQVSEEYCQLVLALLTTNPGNQLN |
| SEQ ID NO: 158 | *Herbinix hemicellulosilytica* C2c2 amino acid sequence | MKLTRRRISGNSVDQKITAAFYRDM SQGLLYYDSEDNDCTDKVIESMDFE RSWRGRILKNGEDDKNPFYMFVKGL VGSNDKIVCEPIDVDSDPDNLDILI NKNLTGFGRNLKAPDSNDTLENLIR KIQAGIPEEEVLPELKKIKEMIQKD IVNRKEQLLKSIKNNRIPFSLEGSK LVPSTKKMKWLFKLIDVPNKTFNEK MLEKYWEIYDYDKLKANITNRLDKT DKKARSISRAVSEELREYHKNLRTN YNRFVSGDRPAAGLDNGGSAKYNPD KEEFLLFLKEVEQYFKKYFPVKSKH SNKSKDKSLVDKYKNYCSYKVVKKE VNRSIINQLVAGLIQQGKLLYYFYY NDTWQEDFLNSYGLSYIQVEEAFKK SVMTSLSWGINRLTSFFIDDSNTVK FDDITTKKAKEAIESNYFNKLRTCS RMQDHFKEKLAFFYPVYVKDKKDRP DDDIENLIVLVKNAIESVSYLRNRT FHFKESSLLELLKELDDKNSGQNKI DYSVAAEFIKRDIENLYDVFREQIR SLGIAEYYKADMISDCFKTCGLEFA LYSPKNSLMPAFKNVYKRGANLNKA YIRDKGPKETGDQGQNSYKALEEYR ELTWYIEVKNNDQSYNAYKNLLQLI YYHAFLPEVRENEALITDFINRTKE WNRKETEERLNTKNNKKHKNFDEND DITVNTYRYESIPDYQGESLDDYLK VLQRKQMARAKEVNEKEEGNNNYIQ FIRDVVVWAFGAYLENKLKNYKNEL QPPLSKENIGLNDTLKELFPEEKVK SPFNIKCRFSISTFIDNKGKSTDNT SAEAVKTDGKEDEKDKKNIKRKDLL CFYLFLRLLDENEICKLQHQFIKYR CSLKERRFPGNRTKLEKETELLAEL EELMELVRFTMPSIPEISAKAESGY DTMIKKYFKDFIEKKVFKNPKTSNL YYHSDSKTPVTRKYMALLMRSAPLH LYKDIFKGYYLITKKECLEYIKLSN IIKDYQNSLNELHEQLERIKLKSEK QNGKDSLYLDKKDFYKVKEYVENLE QVARYKHLQHKINFESLYRIFRIHV DIAARMVGYTQDWERDMHFLFKALV YNGVLEERRFEAIFNNNDDNNDGRI VKKIQNNLNNKNRELVSMLCWNKKL NKNEFGAIIWKRNPIAHLNHFTQTE QNSKSSLESLINSLRILLAYDRKRQ NAVTKTINDLLLNDYHIRIKWEGRV DEGQIYFNIKEKEDIENEPIIHLKH LHKKDCYIYKNSYMFDKQKEWICNG IKEEVYDKSILKCIGNLFKFDYEDK NKSSANPKHT |
| SEQ ID NO: 159 | *Paludibacter propionicigenes* C2c2 amino acid sequence | MRVSKVKVKDGGKDKMVLVHRKTTG AQLVYSGQPVSNETSNILPEKKRQS FDLSTLNKTIIKFDTAKKQKLNVDQ YKIVEKIFKYPKQELPKQIKAEEIL PFLNHKFQEPVKYWKNGKEESFNLT |

TABLE 3-continued

| SEQ ID NO | Description | Cas13 Enzyme Sequences<br>Sequence |
|---|---|---|
| | | LLIVEAVQAQDKRKLQPYYDWKTWY<br>IQTKSDLLKKSIENNRIDLTENLSK<br>RKKALLAWETEFTASGSIDLTHYHK<br>VYMTDVLCKMLQDVKPLTDDKGKIN<br>TNAYHRGLKKALQNHQPAIFGTREV<br>PNEANRADNQLSIYHLEVVKYLEHY<br>FPIKTSKRRNTADDIAHYLKAQTLK<br>TTIEKQLVNAIRANIIQQGKTNHHE<br>LKADTTSNDLIRIKTNEAFVLNLTG<br>TCAFAANNIRNMVDNEQTNDILGKG<br>DFIKSLLKDNTNSQLYSFFFGEGLS<br>TNKAEKETQLWGIRGAVQQIRNNVN<br>HYKKDALKTVFNISNFENPTITDPK<br>QQTNYADTIYKARFINELEKIPEAF<br>AQQLKTGGAVSYYTIENLKSLLTTF<br>QFSLCRSTIPFAPGFKKVFNGGINY<br>QNAKQDESFYELMLEQYLRKENFAE<br>ESYNARYFMLKLIYNNLFLPGFTTD<br>RKAFADSVGFVQMQNKKQAEKVNPR<br>KKEAYAFEAVRPMTAADSIADYMAY<br>VQSELMQEQNKKEEKVAEETRINFE<br>KFVLQVFIKGFDSFLRAKEFDFVQM<br>PQPQLTATASNQQKADKLNQLEASI<br>TADCKLTPQYAKADDATHIAFYVFC<br>KLLDAAHLSNLRNELIKFRESVNEF<br>KFHHLLEIIEICLLSADVVPTDYRD<br>LYSSEADCLARLRPFIEQGADITNW<br>SDLFVQSDKHSPVIHANIELSVKYG<br>TTKLLEQIINKDTQFKTTEANFTAW<br>NTAQKSIEQLIKQREDHHEQWVKAK<br>NADDKEKQERKREKSNFAQKFIEKH<br>GDDYLDICDYINTYNWLDNKMHFVH<br>LNRLHGLTIELLGRMAGFVALFDRD<br>FQFFDEQQIADEFKLHGFVNLHSID<br>KKLNEVPTKKIKEIYDIRNKIIQIN<br>GNKINESVRANLIQFISSKRNYYNN<br>AFLHVSNDEIKEKQMYDIRNHIAHF<br>NYLTKDAADFSLIDLINELRELLHY<br>DRKLKNAVSKAFIDLFDKHGMILKL<br>KLNADHKLKVESLEPKKIYHLGSSA<br>KDKPEYQYCTNQVMMAYCNMCRSLL<br>EMKK |
| SEQ ID NO: 160 | *Leptotrichia wadei* (Lwa) C2c2 amino acid sequence | MYMKITKIDGVSHYKKQDKGILKKK<br>WKDLDERKQREKIEARYNKQIESKI<br>YKEFFRLKNKKRIEKEEDQNIKSLY<br>FFIKELYLNEKNEEWELKNINLEIL<br>DDKERVIKGYKFKEDVYFFKEGYKE<br>YYLRILFNNLIEKVQNENREKVRKN<br>KEFLDLKEIFKKYKNRKIDLLLKSI<br>NNNKINLEYKKENVNEEIYGINPTN<br>DREMTFYELLKEIIEKKDEQKSILE<br>EKLDNFDITNFLENIEKIFNEETEI<br>NIIKGKVLNELREYIKEKEENNSDN<br>KLKQIYNLELKKYIENNFSYKKQKS<br>KSKNGKNDYLYLNFLKKIMFIEEVD<br>EKKEINKEKFKNKINSNFKNLFVQH<br>ILDYGKLLYYKENDEYIKNTGQLET<br>KDLEYIKTKETLIRKMAVLVSFAAN<br>SYYNLFGRVSGDILGTEVVKSSKTN<br>VIKVGSHIFKEKMLNYFFDFEIFDA<br>NKIVEILESISYSIYNVRNGVGHFN<br>KLILGKYKKKDINTNKRIEEDLNNN<br>EEIKGYFIKKRGEIERKVKEKFLSN<br>NLQYYYSKEKIENYFEVYEFEILKR<br>KIPFAPNFKRIIKKGEDLFNNKNNK<br>KYEYFKNFDKNSAEEKKEFLKTRNF<br>LLKELYYNNFYKEFLSKKEEFEKIV<br>LEVKEEKKSRGNINNKKSGVSFQSI<br>DDYDTKINISDYIASIHKKEMERVE<br>KYNEEKQKDTAKYIRDFVEEIFLTG<br>FINYLEKDKRLHFLKEEFSILCNNN<br>NNVVDFNININEEKIKEFLKENDSK<br>TLNLYLFFNMIDSKRISEFRNELVK |

TABLE 3-continued

| SEQ ID NO | Description | Cas13 Enzyme Sequences<br>Sequence |
|---|---|---|
| | | YKQFTKKRLDEEKEFLGIKIELYET<br>LIEFVILTREKLDTKKSEEIDAWLV<br>DKLYVKDSNEYKEYEEILKLFVDEK<br>ILSSKEAPYYATDNKTPILLSNFEK<br>TRKYGTQSFLSEIQSNYKYSKVEKE<br>NIEDYNKKEEIEQKKKSNIEKLQDL<br>KVELHKKWEQNKITEKEIEKYNNTT<br>RKINEYNYLKNKEELQNVYLLHEML<br>SDLLARNVAFFNKWERDFKFIVIAI<br>KQFLRENDKEKVNEFLNPPDNSKGK<br>KVYFSVSKYKNTVENIDGIHKNFMN<br>LIFLNNKFMNRKIDKMNCAIWVYFR<br>NYIAHFLHLHTKNEKISLISQMNLL<br>IKLFSYDKKVQNHILKSTKTLLEKY<br>NIQINFEISNDKNEVFKYKIKNRLY<br>SKKGKMLGKNNKFEILENEFLENVK<br>AMLEYSE |
| SEQ ID NO: 161 | *Bergeyella zoohelcum* Cas13b | MENKTSLGNNIYYNPFKPQDKSYFA<br>GYFNAAMENTDSVFRELGKRLKGKE<br>YTSENFFDAIFKENISLVEYERYVK<br>LLSDYFPMARLLDKKEVPIKERKEN<br>FKKNFKGIIKAVRDLRNFYTHKEHG<br>EVEITDEIFGVLDEMLKSTVLTVKK<br>KKVKTDKTKEILKKSIEKQLDILCQ<br>KKLEYLRDTARKIEEKRRNQRERGE<br>KELVAPFKYSDKRDDLIAAIYNDAF<br>DVYIDKKKDSLKESSKAKYNTKSDP<br>QQEEGDLKIPISKNGVVFLLSLFLT<br>KQEIHAFKSKIAGFKATVIDEATVS<br>EATVSHGKNSICFMATHEIFSHLAY<br>KKLKRKVRTAEINYGEAENAEQLSV<br>YAKETLMMQMLDELSKVPDVVYQNL<br>SEDVQKTFIEDWNEYLKENNGDVGT<br>MEEEQVIHPVIRKRYEDKFNYFAIR<br>FLDEFAQFPTLRFQVHLGNYLHDSR<br>PKENLISDRRIKEKITVFGRLSELE<br>HKKALFIKNTETNEDREHYWEIFPN<br>PNYDFPKENISVNDKDFPIAGSILD<br>REKQPVAGKIGIKVKLLNQQYVSEV<br>DKAVKAHQLKQRKASKPSIQNIIEE<br>IVPINESNPKEAIVFGGQPTAYLSM<br>NDIHSILYEFFDKWEKKKEKLEKKG<br>EKELRKEIGKELEKKIVGKIQAQIQ<br>QIIDKDTNAKILKPYQDGNSTAIDK<br>EKLIKDLKQEQNILQKLKDEQTVRE<br>KEYNDFIAYQDKNREINKVRDRNHK<br>QYLKDNLKRKYPEAPARKEVLYYRE<br>KGKVAVWLANDIKRFMPTDFKNEWK<br>GEQHSLLQKSLAYYEQCKEELKNLL<br>PEKVFQHLPFKLGGYFQQKYLYQFY<br>TCYLDKRLEYISGLVQQAENFKSEN<br>KVFKKVENECFKFLKKQNYTHKELD<br>ARVQSILGYPIFLERGFMDEKPTII<br>KGKTFKGNEALFADWFRYYKEYQNF<br>QTFYDTENYPLVELEKKQADRKRKT<br>KIYQQKKNDVFTLLMAKHIFKSVFK<br>QDSIDQFSLEDLYQSREERLGNQER<br>ARQTGERNTNYIWNKTVDLKLCDGK<br>ITVENVKLKNVGDFIKYEYDQRVQA<br>FLKYEENIEWQAFLIKESKEEENYP<br>YVVEREIEQYEKVRREELLKEVHLI<br>EEYILEKVKDKEILKKGDNQNFKYY<br>ILNGLLKQLKNEDVESYKVFNLNTE<br>PEDVNINQLKQEATDLEQKAFVLTY<br>IRNKFAHNQLPKKEFWDYCQEKYGK<br>IEKEKTYAEYFAEVFKKEKEALIK |
| SEQ ID NO: 162 | *Prevotella intermedia* Cas13b | MEDDKKTTDSIRYELKDKHFWAAFL<br>NLARHNVYITVNHINKILEEGEINR<br>DGYETTLKNTWNEIKDINKKDRLSK<br>LIIKHFPFLEAATYRLNPTDTTKQK<br>EEKQAEAQSLESLRKSFFVFIYKLR<br>DLRNHYSHYKHSKSLERPKFEEGLL |

TABLE 3-continued

| SEQ ID NO | Description | Sequence |
|---|---|---|
| | | EKMYNIFNASIRLVKEDYQYNKDIN<br>PDEDFKHLDRTEEEFNYYFTKDNEG<br>NITESGLLFFVSLFLEKKDAIWMQQ<br>KLRGFKDNRENKKKMTNEVFCRSRM<br>LLPKLRLQSTQTQDWILLDMLNELI<br>RCPKSLYERLREEDREKFRVPIEIA<br>DEDYDAEQEPFKNTLVRHQDRFPYF<br>ALRYFDYNEIFTNLRFQIDLGTYHF<br>SIYKKQIGDYKESHHLTHKLYGFER<br>IQEFTKQNRPDEWRKFVKTFNSFET<br>SKEPYIPETTPHYHLENQKIGIRFR<br>NDNDKIWPSLKTNSEKNEKSKYKLD<br>KSFQAEAFLSVHELLPMMFYYLLLK<br>TENTDNDNEIETKKKENKNDKQEKH<br>KIEEIIENKITEIYALYDTFANGEI<br>KSIDELEEYCKGKDIEIGHLPKQMI<br>AILKDEHKVMATEAERKQEEMLVDV<br>QKSLESLDNQINEEIENVERKNSSL<br>KSGKIASWLVNDMMRFQPVQKDNEG<br>KPLNNSKANSTEYQLLQRTLAFFGS<br>EHERLAPYFKQTKLIESSNPHPFLK<br>DTEWEKCNNILSFYRSYLEAKKNFL<br>ESLKPEDWEKNQYFLKLKEPKTKPK<br>TLVQGWKNGFNLPRGIFTEPIRKWF<br>MKHRENITVAELKRVGLVAKVIPLF<br>FSEEYKDSVQPFYNYHFNVGNINKP<br>DEKNFLNCEERRELLRKKKDEFKKM<br>TDKEKEENPSYLEFKSWNKFERELR<br>LVRNQDIVTWLLCMELFNKKKIKEL<br>NVEKIYLKNINTNTTKKEKNTEEKN<br>GEEKNIKEKNNILNRIMPMRLPIKV<br>YGRENFSKNKKKKIRRNTFFTVYIE<br>EKGTKLLKQGNFKALERDRRLGGLF<br>SFVKTPSKAESKSNTISKLRVEYEL<br>GEYQKARIEIIKDMLALEKTLIDKY<br>NSLDTDNFNKMLTDWLELKGEPDKA<br>SFQNDVDLLIAVRNAFSHNQYPMRN<br>RIAFANINPFSLSSANTSEEKGLGI<br>ANQLKDKTHKTIEKIIEIEKPIETK<br>E |
| SEQ ID NO: 163 | *Prevotella buccae* Cas13b | MQKQDKLFVDRKKNAIFAFPKYITI<br>MENKEKPEPIYYELTDKHFWAAFLN<br>LARHNVYTTINHINRRLEIAELKDD<br>GYMMGIKGSWNEQAKKLDKKVRLRD<br>LIMKHFPFLEAAAYEMTNSKSPNNK<br>EQREKEQSEALSLNNLKNVLFIFLE<br>KLQVLRNYYSHYKYSEESPKPIFET<br>SLLKNMYKVFDANVRLVKRDYMHHE<br>NIDMQRDFTHLNRKKQVGRTKNIID<br>SPNFHYHFADKEGNMTIAGLLFFVS<br>LFLDKKDAIWMQKKLKGFKDGRNLR<br>EQMTNEVFCRSRISLPKLKLENVQT<br>KDWMQLDMLNELVRCPKSLYERLRE<br>KDRESFKVPFDIFSDDYNAEEEPFK<br>NTLVRHQDRFPYFVLRYFDLNEIFE<br>QLRFQIDLGTYHFSIYNKRIGDEDE<br>VRHLTHHLYGFARIQDFAPQNQPEE<br>WRKLVKDLDHFETSQEPYISKTAPH<br>YHLENEKIGIKFCSAHNNLFPSLQT<br>DKTCNGRSKFNLGTQFTAEAFLSVH<br>ELLPMMFYYLLLTKDYSRKESADKV<br>EGIIRKEISNIYAIYDAFANNEINS<br>IADLTRRLQNTNILQGHLPKQMISI<br>LKGRQKDMGKEAERKIGEMIDDTQR<br>RLDLLCKQTNQKIRIGKRNAGLLKS<br>GKIADWLVNDMMRFQPVQKDQNNIP<br>INNSKANSTEYRMLQRALALFGSEN<br>FRLKAYFNQMNLVGNDNPHPFLAET<br>QWEHQTNILSFYRNYLEARKKYLKG<br>LKPQNWKQYQHFLILKVQKTNRNTL<br>VTGWKNSFNLPRGIFTQPIREWFEK<br>HNNSKRIYDQILSFDRVGFVAKAIP<br>LYFAEEYKDNVQPFYDYPFNIGNRL<br>KPKKRQFLDKKERVELWQKNKELFK<br>NYPSEKKKTDLAYLDFLSWKKFERE<br>LRLIKNQDIVTWLMFKELFNMATVE<br>GLKIGEIHLRDIDTNTANEESNNIL<br>NRIMPMKLPVKTYETDNKGNILKER<br>PLATFYIEETETKVLKQGNFKALVK<br>DRRLNGLFSFAETTDLNLEEHPISK<br>LSVDLELIKYQTTRISIFEMTLGLE<br>KKLIDKYSTLPTDSFRNMLERWLQC<br>KANRPELKNYVNSLIAVRNAFSHNQ<br>YPMYDATLFAEVKKFTLFPSVDTKK<br>IELNIAPQLLEIVGKAIKEIEKSEN<br>KN |
| SEQ ID NO: 164 | *Porphyromonas gingivalis* Cas13b | MNTVPASENKGQSRTVEDDPQYFGL<br>YLNLARENLIEVESHVRIKFGKKKL<br>NEESLKQSLLCDHLLSVDRWTKVYG<br>HSRRYLPFLHYFDPDSQIEKDHDSK<br>TGVDPDSAQRLIRELYSLLDFLRND<br>FSHNRLDGTTFEHLEVSPDISSFIT<br>GTYSLACGRAQSRFAVFFKPDDFVL<br>AKNRKEQLISVADGKECLTVSGFAF<br>FICLFLDREQASGMLSRIRGFKRTD<br>ENWARAVHETFCDLCIRHPHDRLES<br>SNTKEALLLDMLNELNRCPRILYDM<br>LPEEERAQFLPALDENSMNNLSENS<br>LDEESRLLWDGSSDWAEALTKRIRH<br>QDRFPYLMLRFIEEMDLLKGIRFRV<br>DLGEIELDSYSKKVGRNGEYDRTIT<br>DHALAFGKLSDFQNEEEVSRMISGE<br>ASYPVRFSLFAPRYAIYDNKIGYCH<br>TSDPVYPKSKTGEKRALSNPQSMGF<br>ISVHDLRKLLLMELLCEGSFSRMQS<br>DFLRKANRILDETAEGKLQFSALFP<br>EMRHRFIPPQNPKSKDRREKAETTL<br>EKYKQEIKGRKDKLNSQLLSAFDMD<br>QRQLPSRLLDEWMNIRPASHSVKLR<br>TYVKQLNEDCRLRLRKFRKDGDGKA<br>RAIPLVGEMATFLSQDIVRMIISEE<br>TKKLITSAYYNEMQRSLAQYAGEEN<br>RRQFRAIVAELRLLDPSSGHPFLSA<br>TMETAHRYTEGFYKCYLEKKREWLA<br>KIFYRPEQDENTKRRISVFFVPDGE<br>ARKLLPLLIRRRMKEQNDLQDWIRN<br>KQAHPIDLPSHLFDSKVMELLKVKD<br>GKKKWNEAFKDWWSTKYPDGMQPFY<br>GLRRELNIHGKSVSYIPSDGKKFAD<br>CYTHLMEKTVRDKKRELRTAGKPVP<br>PDLAADIKRSFHRAVNEREFMLRLV<br>QEDDRLMLMAINKMMTDREEDILPG<br>LKNIDSILDEENQFSLAVHAKVLEK<br>EGEGGDNSLSLVPATIEIKSKRKDW<br>SKYIRYRYDRRVPGLMSHFPEHKAT<br>LDEVKTLLGEYDRCRIKIFDWAFAL<br>EGAIMSDRDLKPYLHESSSREGKSG<br>EHSTLVKMLVEKKGCLTPDESQYLI<br>LIRNKAAHNQFPCAAEMPLIYRDVS<br>AKVGSIEGSSAKDLPEGSSLVDSLW<br>KKYEMIIRKILPILDPENRFFGKLL<br>NNMSQPINDL |
| SEQ ID NO: 165 | *Bacteroides pyogenes* Cas13b | MESIKNSQKSTGKTLQKDPPYFGLY<br>LNMALLNVRKVENHIRKWLGDVALL<br>PEKSGFHSLLTTDNLSSAKWTRFYY<br>KSRKFLPFLEMFDSDKKSYENRRET<br>AECLDTIDRQKISSLLKEVYGKLQD<br>IRNAFSHYHIDDQSVKHTALIISSE<br>MHRFIENAYSFALQKTRARFTGVFV<br>ETDFLQAEEKGDNKKFFAIGGNEGI<br>KLKDNALIFLICLFLDREEAFKFLS<br>RATGFKSTKEKGFLAVRETFCALCC<br>RQPHERLLSVNPREALLMDMLNELN<br>RCPDILFEMLDEKDQKSFLPLLGEE<br>EQAHILENSLNDELCEAIDDPFEMI |

TABLE 3-continued

Cas13 Enzyme Sequences

| SEQ ID NO | Description | Sequence |
|---|---|---|
| | | ASLSKRVRYKNRFPYLMLRYIEEKN<br>LLPFIRFRIDLGCLELASYPKKMGE<br>ENNYERSVTDHAMAFGRLTDFHNED<br>AVLQQITKGITDEVRFSLYAPRYAI<br>YNNKIGFVRTSGSDKISFPTLKKKG<br>GEGHCVAYTLQNTKSFGFISIYDLR<br>KILLLSFLDKDKAKNIVSGLLEQCE<br>KHWKDLSENLFDAIRTELQKEFPVP<br>LIRYTLPRSKGGKLVSSKLADKQEK<br>YESEFERRKEKLTEILSEKDFDLSQ<br>IPRRMIDEWLNVLPTSREKKLKGYV<br>ETLKLDCRERLRVFEKREKGEHPLP<br>PRIGEMATDLAKDIIRMVIDQGVKQ<br>RITSAYYSEIQRCLAQYAGDDNRRH<br>LDSIIRELRLKDTKNGHPFLGKVLR<br>PGLGHTEKLYQRYFEEKKEWLEATF<br>YPAASPKRVPRFVNPPTGKQKELPL<br>IIRNLMKERPEWRDWKQRKNSHPID<br>LPSQLFENEICRLLKDKIGKEPSGK<br>LKWNEMFKLYWDKEFPNGMQRFYRC<br>KRRVEVFDKVVEYEYSEEGGNYKKY<br>YEALIDEVVRQKISSSKEKSKLQVE<br>DLTLSVRRVFKRAINEKEYQLRLLC<br>EDDRLLFMAVRDLYDWKEAQLDLDK<br>IDNMLGEPVSVSQVIQLEGGQPDAV<br>IKAECKLKDVSKLMRYCYDGRVKGL<br>MPYFANHEATQEQVEMELRHYEDHR<br>RRVFNWVFALEKSVLKNEKLRRFYE<br>ESQGGCEHRRCIDALRKASLVSEEE<br>YEFLVHIRNKSAHNQFPDLEIGKLP<br>PNVTSGFCECIWSKYKAIICRIIPF<br>IDPERRFFGKLLEQK |
| SEQ ID NO: 166 | Cas13c | MTEKKSIIFKNKSSVEIVKKDIFSQ<br>TPDNMIRNYKITLKISEKNPRVVEA<br>EIEDLMNSTILKDGRRSARREKSMT<br>ERKLIEEKVAENYSLLANCPMEEVD<br>SIKIYKIKRFLTYRSNMLLYFASIN<br>SFLCEGIKGKDNETEEIWHLKDNDV<br>RKEKVKENFKNKLIQSTENYNSSLK<br>NQIEEKEKLLRKESKKGAFYRTIIK<br>KLQQERIKELSEKSLTEDCEKIIKL<br>YSELRHPLMHYDYQYFENLFENKEN<br>SELTKNLNLDIFKSLPLVRKMKLNN<br>KVNYLEDNDTLFVLQKTKKAKTLYQ<br>IYDALCEQKNGFNKFINDFFVSDGE<br>ENTVFKQIINEKFQSEMEFLEKRIS<br>ESEKKNEKLKKKFDSMKAHFHNINS<br>EDTKEAYFWDIHSSSNYKTKYNERK<br>NLVNEYTELLGSSKEKKLLREEITQ<br>INRKLLKLKQEMEEITKKNSLFRLE<br>YKMKIAFGFLFCEFDGNISKFKDEF<br>DASNQEKIIQYHKNGEKYLTYFLKE<br>EEKEKFNLEKMQKIIQKTEEEDWLL<br>PETKNNLFKFYLLTYLLLPYELKGD<br>FLGFVKKHYYDIKNVDFMDENQNNI<br>QVSQTVEKQEDYFYHKIRLFEKNTK<br>KYEIVKYSIVPNEKLKQYFEDLGID<br>IKYLTGSVESGEKWLGENLGIDIKY<br>LTVEQKSEVSEEKIKKFL |
| SEQ ID NO: 167 | Cas13c | MEKDKKGEKIDISQEMIEEDLRKIL<br>ILFSRLRHSMVHYDYEFYQALYSGK<br>DFVISDKNNLENRMISQLLDLNIFK<br>ELSKVKLIKDKAISNYLDKNTTIHV<br>LGQDIKAIRLLDIYRDICGSKNGFN<br>KFINTMITISGEEDREYKEKVIEHF<br>NKKMENLSTYLEKLEKQDNAKRNNK<br>RVYNLLKQKLIEQQKLKEWFGGPYV<br>YDIHSSKRYKELYIERKKLVDRHSK<br>LFEEGLDEKNKKELTKINDELSKLN<br>SEMKEMTKLNSKYRLQYKLQLAFGF<br>ILEEFDLNIDTFINNFDKDKDLIIS<br>NFMKKRDIYLNRVLDRGDNRLKNII |

TABLE 3-continued

Cas13 Enzyme Sequences

| SEQ ID NO | Description | Sequence |
|---|---|---|
| | | KEYKFRDTEDIFCNDRDNNLVKLYI<br>LMYILLPVEIRGDFLGFVKKNYYDM<br>KHVDFIDKKDKEDKDTFFHDLRLFE<br>KNIRKLEITDYSLSSGFLSKEHKVD<br>IEKKINDFINRNGAMKLPEDITIEE<br>FNKSLILPIMKNYQINFKLLNDIEI<br>SALFKIAKDRSITFKQAIDEIKNED<br>IKKNSKKNDKNNHKDKNINFTQLMK<br>RALHEKIPYKAGMYQIRNNISHIDM<br>EQLYIDPLNSYMNSNKNNITISEQI<br>EKIIDVCVTGGVTGKELNNNIINDY<br>YMKKEKLVFNLKLRKQNDIVSIESQ<br>EKNKREEFVFKKYGLDYKDGEINII<br>EVIQKVNSLQEELRNIKETSKEKLK<br>NKETLFRDISLINGTIRKNINFKIK<br>EMVLDIVRMDEIRHINIHIYYKGEN<br>YTRSNIIKFKYAIDGENKKYYLKQH<br>EINDINLELKDKFVTLICNMDKHPN<br>KNKQTINLESNYIQNVKFIIP |
| SEQ ID NO: 168 | Cas13c | MENKGNNKKIDFDENYNILVAQIKE<br>YFTKEIENYNNRIDNIIDKKELLKY<br>SEKKEESEKNKKLEELNKLKSQKLK<br>ILTDEEIKADVIKIIKIFSDLRHSL<br>MHYEYKYFENLFENKKNEELAELLN<br>LNLFKNLTLLRQMKIENKTNYLEGR<br>EEFNIIGKNIKAKEVLGHYNLLAEQ<br>KNGFNNFINSFFVQDGTENLEFKKL<br>IDEHFVNAKKRLERNIKKSKKLEKE<br>LEKMEQHYQRLNCAYVWDIHTSTTY<br>KKLYNKRKSLIEEYNKQINEIKDKE<br>VITAINVELLRIKKEMEEITKSNSL<br>FRLKYKMQIAYAFLEIEFGGNIAKF<br>KDEFDCSKMEEVQKYLKKGVKYLKY<br>YKDKEAQKNYEFPFEEIFENKDTHN<br>EEWLENTSENNLFKFYILTYLLLPM<br>EFKGDFLGVVKKHYYDIKNVDFTDE<br>SEKELSQVQLDKMIGDSFFHKIRLF<br>EKNTKRYEIIKYSILTSDEIKRYFR<br>LLELDVPYFEYEKGTDEIGIFNKNI<br>ILTIFKYYQIIFRLYNDLEIHGLFN<br>ISSDLDKILRDLKSYGNKNINFREF<br>LYVIKQNNNSSTEEEYRKIWENLEA<br>KYLRLHLLTPEKEEIKTKTKEELEK<br>LNEISNLRNGICHLNYKEIIEEILK<br>TEISEKNKEATLNEKIRKVINFIKE<br>NELDKVELGFNFINDFFMKKEQFMF<br>GQIKQVKEGNSDSITTERERKEKNN<br>KKLKETYELNCDNLSEFYETSNNLR<br>ERANSSSLLEDSAFLKKIGLYKVKN<br>NKVNSKVKDEEKRIENIKRKLLKDS<br>SDIMGMYKAEVVKKLKEKLILIFKH<br>DEEKRIYVTVYDTSKAVPENISKEI<br>LVKRNNSKEEYFFEDNNKKYVTEYY<br>TLEITETNELKVIPAKKLEGKEFKT<br>EKNKENKLMLNNHYCFNVKIIY |
| SEQ ID NO: 169 | Cas13c | MEEIKHKKNKSSIIRVIVSNYDMTG<br>IKEIKVLYQKQGGVDTFNLKTIINL<br>ESGNLEIISCKPKEREKYRYEFNCK<br>TEINTISITKKDKVLKKEIRKYSLE<br>LYFKNEKKDTVVAKVTDLLKAPDKI<br>EGERNHLRKLSSSTERKLLSKTLCK<br>NYSEISKTPIEEIDSIKIYKIKRFL<br>NYRSNFLIYFALINDFLCAGVKEDD<br>INEVWLIQDKEHTAFLENRIEKITD<br>YIFDKLSKDIENKKNQFEKRIKKYK<br>TSLEELKTETLEKNKTFYIDSIKTK<br>ITNLENKITELSLYNSKESLKEDLI<br>KIISIFTNLRHSLMHYDYKSFENLF<br>ENIENEELKNLLDLNLFKSIRMSDE<br>FKTKNRTNYLDGTESFTIVKKHQNL<br>KKLYTYYNNLCDKKNGFNTFINSFF<br>VTDGIENTDFKNLIILHFEKEMEEY |

TABLE 3-continued

| Cas13 Enzyme Sequences | | |
|---|---|---|
| SEQ ID NO | Description | Sequence |
| | | KKSIEYYKIKISNEKNKSKKEKLKE KIDLLQSELINMREHKNLLKQIYFF DIHNSIKYKELYSERKNLIEQYNLQ INGVKDVTAINHINTKLLSLKNKMD KITKQNSLYRLKYKLKIAYSFLMIE FDGDVSKFKNNFDPTNLEKRVEYLD KKEEYLNYTAPKNKFNFAKLEEELQ KIQSTSEMGADYLNVSPENNLFKFY ILTYIMLPVEFKGDFLGFVKNHYYN IKNVDFMDESLLDENEVDSNKLNEK IENLKDSSFFNKIRLFEKNIKKYEI VKYSVSTQENMKEYFKQLNLDIPYL DYKSTDEIGIFNKNMILPIFKYYQN VFKLCNDIEIHALLALANKKQQNLE YAIYCCSKKNSLNYNELLKTFNRKT YQNLSFIRNKIAHLNYKELFSDLFN NELDLNTKVRCLIEFSQNNKFDQID LGMNFINDYYMKKTRFIFNQRRLRD LNVPSKEKIIDGKRKQQNDSNNELL KKYGLSRTNIKDIFNKAWY |
| SEQ ID NO: 170 | Cas13c | MKVRYRKQAQLDTFIIKTEIVNNDI FIKSIIEKAREKYRYSFLFDGEEKY HFKNKSSVEIVKNDIFSQTPDNMIR NYKITLKISEKNPRVVEAEIEDLMN STILKDGRRSARREKSMTERKLIEE KVAENYSLLANCPIEEVDSIKIYKI KRFLTYRSNMLLYFASINSFLCEGI KGKDNETEEIWHLKDNDVRKEKVKE NFKNKLIQSTENYNSSLKNQIEEKE KLSSKEFKKGAFYRTIIKKLQQERI KELSEKSLTEDCEKIIKLYSELRHP LMHYDYQYFENLFENKENSELTKNL NLDIFKSLPLVRKMKLNNKVNYLED NDTLFVLQKTKKAKTLYQIYDALCE QKNGFNKFINDFFVSDGEENTVFKQ IINEKFQSEMEFLEKRISESEKKNE KLKKKLDSMKAHFRNINSEDTKEAY FWDIHSSRNYKTKYNERKNLVNEYT KLLGSSKEKKLLREEITKINRQLLK LKQEMEEITKKNSLFRLEYKMKIAF GFLFCEFDGNISKFKDEFDASNQEK IIQYHKNGEKYLTSFLKEEEKEKFN LEKMQKIIQKTEEEDWLLPETKNNL FKFYLLTYLLLPYELKGDFLGFVKK HYYDIKNVDFMDENQNNIQVSQTVE KQEDYFYHKIRLFEKNTKKYEIVKY SIVPNEKLKQYFEDLGIDIKYLTGS VESGEKWLGENLGIDIKYLTVEQKS EVSEEKNKKVSLKNNGMFNKTILLF VFKYYQIAFKLFNDIELYSLFFLRE KSEKPFEVFLEELKDKMIGKQLNFG QLLYVVYEVLVKNKDLDKILSKKID YRKDKSFSPEIAYLRNFLSHLNYSK FLDNFMKINTNKSDENKEVLIPSIK IQKMIQFIEKCNLQNQIDFDFNFVN DFYMRKEKMFFIQLKQIFPDINSTE KQKKSEKEEILRKRYHLINKKNEQI KDEHEAQSQLYEKILSLQKIFSCDK NNFYRRLKEEKLLFLEKQGKKKISM KEIKDKIASDISDLLGILKKEITRD IKDKLTEKFRYCEEKLLNISFYNHQ DKKKEEGIRVFLIRDKNSDNFKFES ILDDGSNKIFISKNGKEITIQCCDK VLETLMIEKNTLKISSNGKIISLIP HYSYSIDVKY |

The programmable nuclease can be Cas13 Sometimes the Cas13 can be Cas13a, Cas13b, Cas13c, Cas13d, or Cas13e. In some cases, the programmable nuclease can be Mad7 or Mad2. In some cases, the programmable nuclease can be Cas12. Sometimes the Cas12 can be Cas12a, Cas12b, Cas12c, Cas12d, or Cas12e. In some cases, the programmable nuclease can be Csm1, Cas9, C2c4, C2c8, C2c5, C2c10, C2c9, or CasZ. Sometimes, the Csm1 can also be also called smCms1, miCms1, obCms1, or suCms1. Sometimes Cas13a can also be also called C2c2. Sometimes CasZ can also be called Cas14a, Cas14b, Cas14c, Cas14d, Cas14e, Cas14f, Cas14g, or Cas14h. Sometimes, the programmable nuclease can be a Type V CRISPR-Cas enzyme. In some cases, the programmable nuclease can be a Type VI CRISPR-Cas enzyme. Sometimes the programmable nuclease can be a Type III CRISPR-Cas enzyme. In some cases, the programmable nuclease can be from at least one of *Leptotrichia shahii* (Lsh), *Listeria seeligeri* (Lse), *Leptotrichia buccalis* (Lbu), *Leptotrichia wadeu* (Lwa), *Rhodobacter capsulatus* (Rca), *Herbinix hemicellulosilytica* (Hhe), *Paludibacter propionicigenes* (Ppr), *Lachnospiraceae bacterium* (Lba), [*Eubacterium*] *rectale* (Ere), *Listeria newyorkensis* (Lny), *Clostridium aminophilum* (Cam), *Prevotella* sp. (Psm), *Capnocytophaga canimorsus* (Cca, *Lachnospiraceae bacterium* (Lba), *Bergeyella zoohelcum* (Bzo), *Prevotella intermedia* (Pin), *Prevotella buccae* (Pbu), *Alistipes* sp. (Asp), *Riemerella anatipestifer* (Ran), *Prevotella aurantiaca* (Pau), *Prevotella saccharolytica* (Psa), *Prevotella intermedia* (Pin2), *Capnocytophaga canimorsus* (Cca), *Porphyromonas gulae* (Pgu), *Prevotella* sp. (Psp), *Porphyromonas gingivalis* (Pig), *Prevotella intermedia* (Pin3), *Enterococcus italicus* (Ei), *Lactobacillus salivarius* (Ls), or *Thermus thermophilus* (Tt). Sometimes the Cas13 is at least one of LbuCas13a, LwaCas13a, LbaCas13a, HheCas13a, PprCas13a, EreCas13a, CamCas13a, or LshCas13a. The trans cleavage activity of the Cas enzyme can be activated when the crRNA is complexed with the target nucleic acid. The trans cleavage activity of the Cas enzyme can be activated when the guide nucleic acid comprising a tracrRNA and crRNA are complexed with the target nucleic acid. The target nucleic acid can be RNA or DNA.

In some embodiments, a programmable nuclease as disclosed herein is an RNA-activated programmable RNA nuclease. In some embodiments, a programmable nuclease as disclosed herein is a DNA-activated programmable RNA nuclease. In some embodiments, a programmable nuclease is capable of being activated by a target RNA to initiate trans cleavage of an RNA detector nucleic acid and is capable of being activated by a target DNA to initiate trans cleavage of an RNA detector nucleic acid, such as a Type VI CRISPR-Cas enzyme (e.g., Cas13). For example, Cas13a of the present disclosure can be activated by a target RNA to initiate trans cleavage activity of the Cas13a for the cleavage of an RNA detector nucleic acid and can be activated by a target DNA to initiate trans cleavage activity of the Cas13a for trans cleavage of an RNA detector nucleic acid. An RNA detector nucleic acid can be an RNA-based detector nucleic acid molecule. In some embodiments, the Cas13a recognizes and detects ssDNA to initiate transcleavage of RNA detector nucleic acids. Multiple Cas13a isolates can recognize, be activated by, and detect target DNA, including ssDNA, upon hybridization of a guide nucleic acid with the target DNA. For example, Lbu-Cas13a and Lwa-Cas13a can both be activated to transcollaterally cleave RNA detector nucleic acids by target DNA. Thus, Type VI CRISPR-Cas enzyme (e.g., Cas13, such as Cas13a) can be DNA-activated programmable RNA nucleases, and therefore, can be used to detect a target DNA using the methods as described herein. DNA-activated programmable RNA nuclease detection of ssDNA can be robust at multiple pH values. For example, target ssDNA detection by Cas13 can exhibit consistent cleavage across a wide range of pH conditions, such as from a pH of 6.8 to a pH of 8.2. In contrast, target RNA detection by Cas13 may exhibit high cleavage activity of pH values from 7.9 to 8.2. In some embodiments, a DNA-activated programmable RNA nuclease that also is capable of being an RNA-activated programmable RNA nuclease, can have DNA targeting preferences that are distinct from its RNA targeting preferences. For example, the optimal ssDNA targets for Cas13a have different properties than optimal RNA targets for Cas13a. As one example, gRNA performance on ssDNA may not necessarily correlate with the performance of the same gRNAs on RNA. As another example, gRNAs can perform at a high level regardless of target nucleotide identity at a 3' position on a target RNA sequence. In some embodiments, gRNAs can perform at a high level in the absence of a G at a 3' position on a target ssDNA sequence. Furthermore, target DNA detected by Cas13 disclosed herein can be directly from organisms, or can be indirectly generated by nucleic acid amplification methods, such as PCR and LAMP or any amplification method described herein. Key steps for the sensitive detection of a target DNA, such as a target ssDNA, by a DNA-activated programmable RNA nuclease, such as Cas13a, can include: (1) production or isolation of DNA to concentrations above about 0.1 nM per reaction for in vitro diagnostics, (2) selection of a target sequence with the appropriate sequence features to enable DNA detection as these features are distinct from those required for RNA detection, and (3) buffer composition that enhances DNA detection. The detection of a target DNA by a DNA-activated programmable RNA nuclease can be connected to a variety of readouts including fluorescence, lateral flow, electrochemistry, or any other readouts described herein. Multiplexing of programmable DNA nuclease, such as a Type V CRISPR-Cas enzyme, with a DNA-activated programmable RNA nuclease, such as a Type VI CRISPR-Cas enzyme, with a DNA detector nucleic acid and an RNA detector nucleic acid, can enable multiplexed detection of target ssDNAs or a combination of a target dsDNA and a target ssDNA, respectively. Multiplexing of different RNA-activated programmable RNA nucleases that have distinct RNA detector nucleic acid cleavage preferences can enable additional multiplexing. Methods for the generation of ssDNA for DNA-activated programmable RNA nuclease-based diagnostics can include (1) asymmetric PCR, (2) asymmetric isothermal amplification, such as RPA, LAMP, SDA, etc. (3) NEAR for the production of short ssDNA molecules, and (4) conversion of RNA targets into ssDNA by a reverse transcriptase followed by RNase H digestion. Thus, DNA-activated programmable RNA nuclease detection of target DNA is compatible with the various systems, kits, compositions, reagents, and methods disclosed herein. For example target ssDNA detection by Cas13a can be employed in a DETECTR assay disclosed herein (e.g., a multiplexed DETECTR reaction or a high-plex DETECTR reaction).

Described herein are reagents comprising a single-stranded detector nucleic acid comprising a detection moiety, wherein the detector nucleic acid is capable of being cleaved by the activated nuclease, thereby generating a first detectable signal. In some cases, the detector nucleic acid is a single-stranded nucleic acid comprising deoxyribonucleotides. In other cases, the detector nucleic acid is a single-stranded nucleic acid comprising ribonucleotides. The detector nucleic acid can be a single-stranded nucleic acid comprising at least one deoxyribonucleotide and at least one ribonucleotide. In some cases, the detector nucleic acid is a single-stranded nucleic acid comprising at least one ribonucleotide residue at an internal position that functions as a cleavage site. In some cases, the detector nucleic acid comprises at least 2, 3, 4, 5, 6, 7, 8, 9, or 10 ribonucleotide residues at an internal position. Sometimes the ribonucleotide residues are continuous. Alternatively, the ribonucleotide residues are interspersed in between non-ribonucleotide residues. In some cases, the detector nucleic acid has only ribonucleotide residues. In some cases, the detector nucleic acid has only deoxyribonucleotide residues. In some cases, the detector nucleic acid comprises nucleotides resistant to cleavage by the programmable nuclease described herein. In some cases, the detector nucleic acid comprises synthetic nucleotides. In some cases, the detector nucleic acid comprises at least one ribonucleotide residue and at least one non-ribonucleotide residue. In some cases, detector nucleic acid is 5-20, 5-15, 5-10, 7-20, 7-15, or 7-10 nucleotides in length. In some cases, the detector nucleic acid comprises at least one uracil ribonucleotide. In some cases, the detector nucleic acid comprises at least two uracil ribonucleotides. Sometimes the detector nucleic acid has only uracil ribonucleotides. In some cases, the detector nucleic acid comprises at least one adenine ribonucleotide. In some cases, the detector nucleic acid comprises at least two adenine ribonucleotide. In some cases, the detector nucleic acid has only adenine ribonucleotides. In some cases, the detector nucleic acid comprises at least one cytosine ribonucleotide. In some cases, the detector nucleic acid comprises at least two cytosine ribonucleotide. In some cases, the detector nucleic acid comprises at least one guanine ribonucleotide. In some cases, the detector nucleic acid comprises at least two guanine ribonucleotide. A detector nucleic acid can comprise only unmodified ribonucleotides, only unmodified deoxyribonucleotides, or a combination thereof. In some cases, the detector nucleic acid is from 5 to 12 nucleotides in length. In some cases, the detector nucleic acid is at least 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides in length. In some cases, the detector nucleic acid is 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides in length. For cleavage by a programmable nuclease comprising Cas13, a detector nucleic acid can be 5, 8, or 10 nucleotides in length. For cleavage by a programmable nuclease comprising Cas12, a detector nucleic acid can be 10 nucleotides in length.

The single-stranded detector nucleic acid comprises a detection moiety capable of generating a first detectable signal. Sometimes the detector nucleic acid comprises a protein capable of generating a signal. A signal can be a calorimetric, potentiometric, amperometric, optical (e.g., fluorescent, colorometric, etc.), or piezo-electric signal. In some cases, a detection moiety is on one side of the cleavage site. Optionally, a quenching moiety is on the other side of the cleavage site. Sometimes the quenching moiety is a fluorescence quenching moiety. In some cases, the quenching moiety is 5' to the cleavage site and the detection moiety is 3' to the cleavage site. In some cases, the detection moiety is 5' to the cleavage site and the quenching moiety is 3' to the cleavage site. Sometimes the quenching moiety is at the 5' terminus of the detector nucleic acid. Sometimes the detection moiety is at the 3' terminus of the detector nucleic acid. In some cases, the detection moiety is at the 5' terminus of the detector nucleic acid. In some cases, the quenching moiety is at the 3' terminus of the detector nucleic acid. In some cases, the single-stranded detector nucleic acid is at least one population of the single-stranded nucleic acid capable of generating a first detectable signal. In some cases, the single-stranded detector nucleic acid is a population of the single-stranded nucleic acid capable of generating a first detectable signal. Optionally, there is more than one population of single-stranded detector nucleic acid. In some cases, there are 2, 3, 4, 5, 6, 7, 8, 9, 10, 11, 12, 13, 14, 15, 20, 30, 40, 50, or greater than 50, or any number spanned by the range of this list of different populations of single-stranded detector nucleic acids capable of generating a detectable signal.

TABLE 4

Exemplary Single Stranded Detector Nucleic Acid

| 5' Detection Moiety* | Sequence (SEQ ID NO:) | 3' Quencher* |
|---|---|---|
| /56-FAM/ | rUrUrUrUrU (SEQ ID NO: 1) | /3IABkFQ/ |
| /5IRD700/ | rUrUrUrUrU (SEQ ID NO: 1) | /3IRQCIN/ |
| /5TYE665/ | rUrUrUrUrU (SEQ ID NO: 1) | /3IAbRQSp/ |
| /5Alex594N/ | rUrUrUrUrU (SEQ ID NO: 1) | /3IAbRQSp/ |
| /5ATTO633N/ | rUrUrUrUrU (SEQ ID NO: 1) | /3IAbRQSp/ |
| /56-FAM/ | rUrUrUrUrUrUrU(SEQ ID NO: 2) | /3IABkFQ/ |
| /5IRD700/ | rUrUrUrUrUrUrU(SEQ ID NO: 2) | /3IRQCIN/ |
| /5TYE665/ | rUrUrUrUrUrUrU(SEQ ID NO: 2) | /3IAbRQSp/ |
| /5Alex594N/ | rUrUrUrUrUrUrU(SEQ ID NO: 2) | /3IAbRQSp/ |
| /5ATTO633N/ | rUrUrUrUrUrUrU(SEQ ID NO: 2) | /3IAbRQSp/ |
| /56-FAM/ | rUrUrUrUrUrUrUrUrU(SEQ ID NO: 3) | /3IABkFQ/ |
| /5IRD700/ | rUrUrUrUrUrUrUrUrU(SEQ ID NO: 3) | /3IRQCIN/ |
| /5TYE665/ | rUrUrUrUrUrUrUrUrU(SEQ ID NO: 3) | /3IAbRQSp/ |
| /5Alex594N/ | rUrUrUrUrUrUrUrUrU(SEQ ID NO: 3) | /3IAbRQSp/ |
| /5ATTO633N/ | rUrUrUrUrUrUrUrUrU(SEQ ID NO: 3) | /3IAbRQSp/ |
| /56-FAM/ | TTTTrUrUTTTT(SEQ ID NO: 4) | /3IABkFQ/ |
| /5IRD700/ | TTTTrUrUTTTT(SEQ ID NO: 4) | /3IRQCIN/ |
| /5TYE665/ | TTTTrUrUTTTT(SEQ ID NO: 4) | /3IAbRQSp/ |
| /5Alex594N/ | TTTTrUrUTTTT(SEQ ID NO: 4) | /31AbRQSp/ |
| /5ATTO633N/ | TTTTrUrUTTTT(SEQ ID NO: 4) | /3IAbRQSp/ |
| /56-FAM/ | TTrUrUTT(SEQ ID NO: 5) | /3IABkFQ/ |
| /5IRD700/ | TTrUrUTT(SEQ ID NO: 5) | /3IRQCIN/ |
| /5TYE665/ | TTrUrUTT(SEQ ID NO: 5) | /3IAbRQSp/ |
| /5Alex594N/ | TTrUrUTT(SEQ ID NO: 5) | /3IAbRQSp/ |
| /5ATTO633N/ | TTrUrUTT(SEQ ID NO: 5) | /3IAbRQSp/ |
| /56-FAM/ | TArArUGC(SEQ ID NO: 6) | /3IABkFQ/ |
| /5IRD700/ | TArArUGC(SEQ ID NO: 6) | /3IRQCIN/ |
| /5TYE665/ | TArArUGC(SEQ ID NO: 6) | /3IAbRQSp/ |
| /5Alex594N/ | TArArUGC(SEQ ID NO: 6) | /3IAbRQSp/ |
| /5ATTO633N/ | TArArUGC(SEQ ID NO: 6) | /3IAbRQSp/ |
| /56-FAM/ | TArUrGGC(SEQ ID NO: 7) | /3IABkFQ/ |
| /5IRD700/ | TArUrGGC(SEQ ID NO: 7) | /3IRQCIN/ |

TABLE 4-continued

Exemplary Single Stranded Detector Nucleic Acid

| 5' Detection Moiety* | Sequence (SEQ ID NO:) | 3' Quencher* |
|---|---|---|
| /5TYE665/ | TArUrGGC(SEQ ID NO: 7) | /3IAbRQSp/ |
| /5Alex594N/ | TArUrGGC(SEQ ID NO: 7) | /3IAbRQSp/ |
| /5ATTO633N/ | TArUrGGC(SEQ ID NO: 7) | /3IAbRQSp/ |
| /56-FAM/ | rUrUrUrUrU(SEQ ID NO: 8) | /3IABkFQ/ |
| /5IRD700/ | rUrUrUrUrU(SEQ ID NO: 8) | /3IRQCIN/ |
| /5TYE665/ | rUrUrUrUrU(SEQ ID NO: 8) | /3IAbRQSp/ |
| /5Alex594N/ | rUrUrUrUrU(SEQ ID NO: 8) | /3IAbRQSp/ |
| /5ATTO633N/ | rUrUrUrUrU(SEQ ID NO: 8) | /3IAbRQSp/ |
| /56-FAM/ | TTATTATT (SEQ ID NO: 9) | /3IABkFQ/ |
| /56-FAM/ | TTATTATT (SEQ ID NO: 9) | /3IABkFQ/ |
| /5IRD700/ | TTATTATT (SEQ ID NO: 9) | /3IRQCIN/ |
| /5TYE665/ | TTATTATT (SEQ ID NO: 9) | /3IAbRQSp/ |
| /5Alex594N/ | TTATTATT (SEQ ID NO: 9) | /3IAbRQSp/ |
| /5ATTO633N/ | TTATTATT (SEQ ID NO: 9) | /3IAbRQSp/ |
| /56-FAM/ | TTTTTT (SEQ ID NO: 10) | /3IABkFQ/ |
| /56-FAM/ | TTTTTTTT (SEQ ID NO: 11) | /3IABkFQ/ |
| /56-FAM/ | TTTTTTTTTT (SEQ ID NO: 12) | /3IABkFQ/ |
| /56-FAM/ | TTTTTTTTTTTT (SEQ ID NO: 13) | /3IABkFQ/ |
| /56-FAM/ | TTTTTTTTTTTTTT (SEQ ID NO: 14) | /3IABkFQ/ |
| /56-FAM/ | AAAAAA (SEQ ID NO: 15) | /3IABkFQ/ |
| /56-FAM/ | CCCCCC (SEQ ID NO: 16) | /3IABkFQ/ |
| /56-FAM/ | GGGGGG (SEQ ID NO: 17) | /3IABkFQ/ |
| /56-FAM/ | TTATTATT (SEQ ID NO: 9) | /3IABkFQ/ |

/56-FAM/: 5' 6-Fluorescein (Integrated DNA Technologies)
/3IABkFQ/: 3' Iowa Black FQ (Integrated DNA Technologies)
/5IRD700/: 5' IRDye 700 (Integrated DNA Technologies)
/5TYE665/: 5' TYE 665 (Integrated DNA Technologies)
/5 Alex594N/: 5' Alexa Fluor 594 (NHS Ester) (Integrated DNA Technologies)
/5ATTO633N/: 5' ATTO TM 633 (NHS Ester) (Integrated DNA Technologies)
/3IRQCIN/: 3' IRDye QC-1 Quencher (Li-Cor)
/3IAbRQSp/: 3' Iowa Black RQ (Integrated DNA Technologies)
rU: uracil ribonucleotide
rG: guanine ribonucleotide
*This Table refers to the detection moiety and quencher moiety as their tradenames and their source is identified. However, alternatives, generics, or non-tradename moieties with similar function from other sources can also be used.

A detection moiety can be an infrared fluorophore. A detection moiety can be a fluorophore that emits fluorescence in the range of from 500 nm and 720 nm. A detection moiety can be a fluorophore that emits fluorescence in the range of from 500 nm and 720 nm. In some cases, the detection moiety emits fluorescence at a wavelength of 700 nm or higher. In other cases, the detection moiety emits fluorescence at about 660 nm or about 670 nm. In some cases, the detection moiety emits fluorescence at in the range of from 500 to 520, 500 to 540, 500 to 590, 590 to 600, 600 to 610, 610 to 620, 620 to 630, 630 to 640, 640 to 650, 650 to 660, 660 to 670, 670 to 680, 6890 to 690, 690 to 700, 700 to 710, 710 to 720, or 720 to 730 nm. A detection moiety can be a fluorophore that emits a fluorescence in the same range as 6-Fluorescein, IRDye 700, TYE 665, Alex Fluor, or ATTO TM 633 (NHS Ester). A detection moiety can be fluorescein amidite, 6-Fluorescein, IRDye 700, TYE 665, Alex Fluor 594, or ATTO TM 633 (NHS Ester). A detection moiety can be a fluorophore that emits a fluorescence in the same range as 6-Fluorescein (Integrated DNA Technologies), IRDye 700 (Integrated DNA Technologies), TYE 665 (Integrated DNA Technologies), Alex Fluor 594 (Integrated DNA Technologies), or ATTO TM 633 (NHS Ester) (Integrated DNA Technologies). A detection moiety can be fluorescein amidite, 6-Fluorescein (Integrated DNA Technologies), IRDye 700 (Integrated DNA Technologies), TYE 665 (Integrated DNA Technologies), Alex Fluor 594 (Integrated DNA Technologies), or ATTO TM 633 (NHS Ester)

(Integrated DNA Technologies). Any of the detection moieties described herein can be from any commercially available source, can be an alternative with a similar function, a generic, or a non-tradename of the detection moieties listed.

A detection moiety can be chosen for use based on the type of sample to be tested. For example, a detection moiety that is an infrared fluorophore is used with a urine sample. As another example, SEQ ID NO: 1 with a fluorophore that emits around 520 nm is used for testing in non-urine samples, and SEQ ID NO: 8 with a fluorophore that emits a fluorescence around 700 nm is used for testing in urine samples.

A quenching moiety can be chosen based on its ability to quench the detection moiety. A quenching moiety can be a non-fluorescent fluorescence quencher. A quenching moiety can quench a detection moiety that emits fluorescence in the range of from 500 nm and 720 nm. A quenching moiety can quench a detection moiety that emits fluorescence in the range of from 500 nm and 720 nm. In some cases, the quenching moiety quenches a detection moiety that emits fluorescence at a wavelength of 700 nm or higher. In other cases, the quenching moiety quenches a detection moiety that emits fluorescence at about 660 nm or about 670 nm. In some cases, the quenching moiety quenches a detection moiety emits fluorescence at in the range of from 500 to 520, 500 to 540, 500 to 590, 590 to 600, 600 to 610, 610 to 620, 620 to 630, 630 to 640, 640 to 650, 650 to 660, 660 to 670, 670 to 680, 6890 to 690, 690 to 700, 700 to 710, 710 to 720, or 720 to 730 nm. A quenching moiety can quench fluorescein amidite, 6-Fluorescein, IRDye 700, TYE 665, Alex Fluor 594, or ATTO TM 633 (NHS Ester). A quenching moiety can be Iowa Black RQ, Iowa Black FQ or IRDye QC-1 Quencher. A quenching moiety can quench fluorescein amidite, 6-Fluorescein (Integrated DNA Technologies), IRDye 700 (Integrated DNA Technologies), TYE 665 (Integrated DNA Technologies), Alex Fluor 594 (Integrated DNA Technologies), or ATTO TM 633 (NHS Ester) (Integrated DNA Technologies). A quenching moiety can be Iowa Black RQ (Integrated DNA Technologies), Iowa Black FQ (Integrated DNA Technologies) or IRDye QC-1 Quencher (Li-Cor). Any of the quenching moieties described herein can be from any commercially available source, can be an alternative with a similar function, a generic, or a non-tradename of the quenching moieties listed.

The generation of the detectable signal from the release of the detection moiety indicates that cleavage by the programmable nuclease has occurred and that the sample contains the target nucleic acid. In some cases, the detection moiety comprises a fluorescent dye. Sometimes the detection moiety comprises a fluorescence resonance energy transfer (FRET) pair. In some cases, the detection moiety comprises an infrared (IR) dye. In some cases, the detection moiety comprises an ultraviolet (UV) dye. Alternatively or in combination, the detection moiety comprises a polypeptide. Sometimes the detection moiety comprises a biotin. Sometimes the detection moiety comprises at least one of avidin or streptavidin. In some instances, the detection moiety comprises a polysaccharide, a polymer, or a nanoparticle. In some instances, the detection moiety comprises a gold nanoparticle or a latex nanoparticle.

A detection moiety can be any moiety capable of generating a calorimetric, potentiometric, amperometric, optical (e.g., fluorescent, colorimetric, etc.), or piezo-electric signal. A detector nucleic acid, sometimes, is protein-nucleic acid that is capable of generating a calorimetric, potentiometric, amperometric, optical (e.g., fluorescent, colorimetric, etc.), or piezo-electric signal upon cleavage of the nucleic acid. Often a calorimetric signal is heat produced after cleavage of the detector nucleic acids. Sometimes, a calorimetric signal is heat absorbed after cleavage of the detector nucleic acids. A potentiometric signal, for example, is electrical potential produced after cleavage of the detector nucleic acids. An amperometric signal can be movement of electrons produced after the cleavage of detector nucleic acid. Often, the signal is an optical signal, such as a colorimetric signal or a fluorescence signal. An optical signal is, for example, a light output produced after the cleavage of the detector nucleic acids. Sometimes, an optical signal is a change in light absorbance between before and after the cleavage of detector nucleic acids. Often, a piezo-electric signal is a change in mass between before and after the cleavage of the detector nucleic acid.

Often, the protein-nucleic acid is an enzyme-nucleic acid. The enzyme may be sterically hindered when present as in the enzyme-nucleic acid, but then functional upon cleavage from the nucleic acid. Often, the enzyme is an enzyme that produces a reaction with a substrate. An enzyme can be invertase. Often, the substrate of invertase is sucrose and DNS reagent.

Sometimes the protein-nucleic acid is a substrate-nucleic acid. Often the substrate is a substrate that produces a reaction with an enzyme.

A protein-nucleic acid may be attached to a solid support. The solid support, for example, is a surface. A surface can be an electrode. Sometimes the solid support is a bead. Often the bead is a magnetic bead. Upon cleavage, the protein is liberated from the solid and interacts with other mixtures. For example, the protein is an enzyme, and upon cleavage of the nucleic acid of the enzyme-nucleic acid, the enzyme flows through a chamber into a mixture comprising the substrate. When the enzyme meets the enzyme substrate, a reaction occurs, such as a colorimetric reaction, which is then detected. As another example, the protein is an enzyme substrate, and upon cleavage of the nucleic acid of the enzyme substrate-nucleic acid, the enzyme flows through a chamber into a mixture comprising the enzyme. When the enzyme substrate meets the enzyme, a reaction occurs, such as a calorimetric reaction, which is then detected.

In some embodiments, the detector nucleic acid comprises a nucleic acid conjugated to an affinity molecule and the affinity molecule conjugated to the fluorophore (e.g., nucleic acid—affinity molecule—fluorophore) or the nucleic acid conjugated to the fluorophore and the fluorophore conjugated to the affinity molecule (e.g., nucleic acid—fluorophore—affinity molecule). In some embodiments, a linker conjugates the nucleic acid to the affinity molecule. In some embodiments, a linker conjugates the affinity molecule to the fluorophore. In some embodiments, a linker conjugates the nucleic acid to the fluorophore. A linker can be any suitable linker known in the art. In some embodiments, the nucleic acid of the detector nucleic acid can be directly conjugated to the affinity molecule and the affinity molecule can be directly conjugated to the fluorophore or the nucleic acid can be directly conjugated to the fluorophore and the fluorophore can be directly conjugated to the affinity molecule. In this context, "directly conjugated" indicated that no intervening molecules, polypeptides, proteins, or other moieties are present between the two moieties directly conjugated to each other. For example, if a detector nucleic acid comprises a nucleic acid directly conjugated to an affinity molecule and an affinity molecule directly conjugated to a fluorophore—no intervening moiety is present between the nucleic acid and the affinity molecule and no intervening moiety is present between the affinity molecule and the fluorophore. The affinity molecule can be biotin, avidin, streptavidin, or any similar molecule.

In some cases, the detector nucleic acid comprises a substrate-nucleic acid. The substrate may be sequestered from its cognate enzyme when present as in the substrate-nucleic acid, but then is released from the nucleic acid upon cleavage, wherein the released substrate can contact the cognate enzyme to produce a detectable signal. Often, the substrate is sucrose and the cognate enzyme is invertase, and a DNS reagent can be used to monitor invertase activity.

A major advantage of the devices and methods disclosed herein is the design of excess detector nucleic acids to total nucleic acids in an unamplified or an amplified sample, not including the nucleic acid of the detector nucleic acid. Total nucleic acids can include the target nucleic acids and non-target nucleic acids, not including the nucleic acid of the detector nucleic acid. The non-target nucleic acids can be from the original sample, either lysed or unlysed. The non-target nucleic acids can also be byproducts of amplification. Thus, the non-target nucleic acids can include both non-target nucleic acids from the original sample, lysed or unlysed, and from an amplified sample. The presence of a large amount of non-target nucleic acids, an activated programmable nuclease may be inhibited in its ability to bind and cleave the detector nucleic acid sequences. This is because the activated programmable nucleases collaterally cleaves any nucleic acids. If total nucleic acids are in present in large amounts, they may outcompete detector nucleic acids for the programmable nucleases. The devices and methods disclosed herein are designed to have an excess of detector nucleic acid to total nucleic acids, such that the detectable signals from cleavage reactions (e.g., DETECTR reactions) are particularly superior. In some embodiments, the detector nucleic acid can be present in at least 1.5 fold, at least 2 fold, at least 3 fold, at least 4 fold, at least 5 fold, at least 6 fold, at least 7 fold, at least 8 fold, at least 9 fold, at least 10 fold, at least 11 fold, at least 12 fold, at least 13 fold, at least 14 fold, at least 15 fold, at least 16 fold, at least 17 fold, at least 18 fold, at least 19 fold, at least 20 fold, at least 30 fold, at least 40 fold, at least 50 fold, at least 60 fold, at least 70 fold, at least 80 fold, at least 90 fold, at least 100 fold, from 1.5 fold to 100 fold, from 2 fold to 10 fold, from 10 fold to 20 fold, from 20 fold to 30 fold, from 30 fold to 40 fold, from 40 fold to 50 fold, from 50 fold to 60 fold, from 60 fold to 70 fold, from 70 fold to 80 fold, from 80 fold to 90 fold, from 90 fold to 100 fold, from 1.5 fold to 10 fold, from 1.5 fold to 20 fold, from 10 fold to 40 fold, from 20 fold to 60 fold, or from 10 fold to 80 fold excess of total nucleic acids.

A second significant advantage of the devices and methods disclosed herein is the design of an excess volume comprising the guide nucleic acid (e.g., guide RNA), the programmable nuclease, and the detector nucleic acid, which contacts a smaller volume comprising the sample with the target nucleic acid of interest. The smaller volume comprising the sample can be unlysed sample, lysed sample, or lysed sample which has undergone any combination of reverse transcription, amplification, and in vitro transcription. The presence of various reagents in a crude, non-lysed sample, a lysed sample, or a lysed and amplified sample, such as buffer, magnesium sulfate, salts, the pH, a reducing agent, primers, dNTPs, NTPs, cellular lysates, non-target nucleic acids, primers, or other components, can inhibit the ability of the programmable nuclease to find and cleave the nucleic acid of the detector nucleic acid. This may be due to nucleic acids that are not the detector nucleic acid, which outcompete the nucleic acid of the detector nucleic acid, for the programmable nuclease. Alternatively, various reagents in the sample may simply inhibit the activity of the programmable nuclease. Thus, the devices and methods provided herein for contacting an excess volume comprising the guide nucleic acid (e.g., guide RNA), the programmable nuclease, and the detector nucleic acid to a smaller volume comprising the sample with the target nucleic acid of interest provides for superior detection of the target nucleic acid by ensuring that the programmable nuclease is able to find and cleaves the nucleic acid of the detector nucleic acid. In some embodiments, the volume comprising the guide nucleic acid, the programmable nuclease, and the detector nucleic acid (can be referred to as "a second volume") is 4-fold greater than a volume comprising the sample (can be referred to as "a first volume"). In some embodiments, the volume comprising the guide nucleic acid, the programmable nuclease, and the detector nucleic acid (can be referred to as "a second volume") is at least 1.5 fold, at least 2 fold, at least 3 fold, at least 4 fold, at least 5 fold, at least 6 fold, at least 7 fold, at least 8 fold, at least 9 fold, at least 10 fold, at least 11 fold, at least 12 fold, at least 13 fold, at least 14 fold, at least 15 fold, at least 16 fold, at least 17 fold, at least 18 fold, at least 19 fold, at least 20 fold, at least 30 fold, at least 40 fold, at least 50 fold, at least 60 fold, at least 70 fold, at least 80 fold, at least 90 fold, at least 100 fold, from 1.5 fold to 100 fold, from 2 fold to 10 fold, from 10 fold to 20 fold, from 20 fold to 30 fold, from 30 fold to 40 fold, from 40 fold to 50 fold, from 50 fold to 60 fold, from 60 fold to 70 fold, from 70 fold to 80 fold, from 80 fold to 90 fold, from 90 fold to 100 fold, from 1.5 fold to 10 fold, from 1.5 fold to 20 fold, from 10 fold to 40 fold, from 20 fold to 60 fold, or from 10 fold to 80 fold greater than a volume comprising the sample (can be referred to as "a first volume"). In some embodiments, the volume comprising the sample is at least 0.5 ul, at least 1 ul, at least at least 1 μL, at least 2 μL, at least 3 μL, at least 4 μL, at least 5 μL, at least 6 μL, at least 7 μL, at least 8 μL, at least 9 μL, at least 10 μL, at least 11 μL, at least 12 μL, at least 13 μL, at least 14 μL, at least 15 μL, at least 16 μL, at least 17 μL, at least 18 μL, at least 19 μL, at least 20 μL, at least 25 μL, at least 30 μL, at least 35 μL, at least 40 μL, at least 45 μL, at least 50 μL, at least 55 μL, at least 60 μL, at least 65 μL, at least 70 μL, at least 75 μL, at least 80 μL, at least 85 μL, at least 90 μL, at least 95 μL, at least 100 μL, from 0.5 μL to 5 ul μL, from 5 μL to 10 μL, from 10 μL to 15 μL, from 15 μL to 20 μL, from 20 μL to 25 μL, from 25 μL to 30 μL, from 30 μL to 35 μL, from 35 μL to 40 μL, from 40 μL to 45 μL, from 45 μL to 50 μL, from 10 μL to 20 μL, from 5 μL to 20 μL, from 1 μL to 40 μL, from 2 μL to 10 μL, or from 1 μL to 10 μL. In some embodiments, the volume comprising the programmable nuclease, the guide nucleic acid (e.g., guide RNA), and the detector nucleic acid is at least 10 μL, at least 11 μL, at least 12 μL, at least 13 μL, at least 14 μL, at least 15 μL, at least 16 μL, at least 17 μL, at least 18 μL, at least 19 μL, at least 20 μL, at least 21 μL, at least 22 μL, at least 23 μL, at least 24 μL, at least 25 μL, at least 26 μL, at least 27 μL, at least 28 μL, at least 29 μL, at least 30 μL, at least 40 μL, at least 50 μL, at least 60 μL, at least 70 μL, at least 80 μL, at least 90 μL, at least 100 μL, at least 150 μL, at least 200 μL, at least 250 μL, at least 300 μL, at least 350 μL, at least 400 μL, at least 450 μL, at least 500 μL, from 10 μL to 15 ul μL, from 15 μL to 20 μL, from 20 μL to 25 μL, from 25 μL to 30 μL, from 30 μL to 35 μL, from 35 μL to 40 μL, from 40 μL to 45 μL, from 45 μL to 50 μL, from 50 μL to 55 μL, from 55 μL to 60 μL, from 60 μL to 65 μL, from 65 μL to 70 μL, from 70 μL to 75 μL, from 75 μL to 80 μL, from 80 μL to 85 μL, from 85 μL to 90 μL, from 90 μL to 95 μL, from 95 μL to 100 μL, from 100 μL to 150 μL, from 150 μL to 200 μL, from 200 μL to 250 μL, from 250 μL to 300 μL, from 300 μL to 350 μL, from 350 μL to 400 μL, from 400 μL to 450 μL, from 450 μL to 500 μL, from 10 μL to 20 μL, from 10 μL to 30 μL, from 25 μL to 35 μL, from 10 μL to 40 μL, from 20 μL to 50 μL, from 18 μL to 28 μL, or from 17 μL to 22 μL.

A detector nucleic acid may be a hybrid nucleic acid detector nucleic acid. A hybrid nucleic acid detector nucleic acid comprises a nucleic acid with at least one deoxyribonucleotide and at least one ribonucleotide. In some embodiments, the nucleic acid of the hybrid nucleic acid detector nucleic acid can be of any length and can have any mixture of DNAs and RNAs. For example, in some cases, longer stretches of DNA can be interrupted by a few ribonucleotides. Alternatively, longer stretches of RNA can be interrupted by a few deoxyribonucleotides. Alternatively, every other base in the nucleic acid may alternate between ribonucleotides and deoxyribonucleotides. A major advantage of the hybrid nucleic acid detector nucleic acid is increased stability as compared to a pure RNA nucleic acid detector nucleic acid. For example, a hybrid nucleic acid detector nucleic acid can be more stable in solution, lyophilized, or vitrified as compared to a pure DNA or pure RNA detector nucleic acid.

The detector nucleic acid can be lyophilized or vitrified. The detector nucleic acid can be suspended in solution or immobilized on a surface. For example, the detector nucleic acid can be immobilized on the surface of a chamber in a device as disclosed herein. In some cases, the detector nucleic acid is immobilized on beads, such as magnetic beads, in a chamber of a device as disclosed herein where they are held in position by a magnet placed below the chamber.

Additionally, target nucleic acid can be amplified before binding to the crRNA of the CRISPR-Cas nucleoprotein complex. This amplification can be PCR amplification or isothermal amplification. This nucleic acid amplification of the sample can improve at least one of sensitivity, specificity, or accuracy of the detection the target RNA. The reagents for nucleic acid amplification can comprise a recombinase, a oligonucleotide primer, a single-stranded DNA binding (SSB) protein, and a polymerase. The nucleic acid amplification can be transcription mediated amplification (TMA). Nucleic acid amplification can be helicase dependent amplification (HDA) or circular helicase dependent amplification (cHDA). In additional cases, nucleic acid amplification is strand displacement amplification (SDA). The nucleic acid amplification can be recombinase polymerase amplification (RPA). The nucleic acid amplification can be at least one of loop mediated amplification (LAMP) or the exponential amplification reaction (EXPAR). Nucleic acid amplification is, in some cases, by rolling circle amplification (RCA), ligase chain reaction (LCR), simple method amplifying RNA targets (SMART), single primer isothermal amplification (SPIA), multiple displacement amplification (MDA), nucleic acid sequence based amplification (NASBA), hinge-initiated primer-dependent amplification of nucleic acids (HIP), nicking enzyme amplification reaction (NEAR), or improved multiple displacement amplification (IMDA). The nucleic acid amplification can be performed for no greater than 1, 2, 3, 4, 5, 6, 7, 8, 9, 10, 11, 12, 13, 14, 15, 16, 17, 18, 19, 20, 25, 30, 40, 50, or 60 minutes. Sometimes, the nucleic acid amplification reaction is performed at a temperature of around 20-45° C. The nucleic acid amplification reaction can be performed at a temperature no greater than 20° C., 25° C., 30° C., 35° C., 37° C., 40° C., 45° C. The nucleic acid amplification reaction can be performed at a temperature of at least 20° C., 25° C., 30° C., 35° C., 37° C., 40° C., or 45° C.

Disclosed herein are methods of assaying for a target nucleic acid as described herein wherein a signal is detected. For example, a method of assaying for a target nucleic acid in a sample comprises contacting the sample to a complex comprising a guide nucleic acid (e.g., guide RNA) comprising a segment that is reverse complementary to a segment of the target nucleic acid and a programmable nuclease that exhibits sequence independent cleavage upon forming a complex comprising the segment of the guide nucleic acid binding to the segment of the target nucleic acid; and assaying for a signal indicating cleavage of at least some protein-nucleic acids of a population of protein-nucleic acids, wherein the signal indicates a presence of the target nucleic acid in the sample and wherein absence of the signal indicates an absence of the target nucleic acid in the sample. As another example, a method of assaying for a target nucleic acid in a sample, for example, comprises: a) contacting the sample to a complex comprising a guide nucleic acid comprising a segment that is reverse complementary to a segment of the target nucleic acid and a programmable nuclease that exhibits sequence independent cleavage upon forming a complex comprising the segment of the guide nucleic acid binding to the segment of the target nucleic acid; b) contacting the complex to a substrate; c) contacting the substrate to a reagent that differentially reacts with a cleaved substrate; and d) assaying for a signal indicating cleavage of the substrate, wherein the signal indicates a presence of the target nucleic acid in the sample and wherein absence of the signal indicates an absence of the target nucleic acid in the sample. Often, the substrate is an enzyme-nucleic acid. Sometimes, the substrate is an enzyme substrate-nucleic acid.

A programmable nuclease can comprise a programmable nuclease capable of being activated when complexed with a guide nucleic acid (e.g., guide RNA) and target nucleic acid. The programmable nuclease can become activated after binding of a guide nucleic acid with a target nucleic acid, in which the activated programmable nuclease can cleave the target nucleic acid and can have trans cleavage activity. Trans cleavage activity can be non-specific cleavage of nearby nucleic acids by the activated programmable nuclease, such as trans cleavage of detector nucleic acids with a detection moiety. Once the detector nucleic acid is cleaved by the activated programmable nuclease, the detection moiety can be released from the detector nucleic acid and can generate a signal. The signal can be immobilized on a support medium for detection. The signal can be visualized to assess whether a target nucleic acid comprises a modification.

Often, the signal is a colorimetric signal or a signal visible by eye. In some instances, the signal is fluorescent, electrical, chemical, electrochemical, or magnetic. A signal can be a calorimetric, potentiometric, amperometric, optical (e.g., fluorescent, colorometric, etc.), or piezo-electric signal. In some cases, the detectable signal is a colorimetric signal or a signal visible by eye. In some instances, the detectable signal is fluorescent, electrical, chemical, electrochemical, or magnetic. In some cases, the first detection signal is generated by binding of the detection moiety to the capture molecule in the detection region, where the first detection signal indicates that the sample contained the target nucleic acid. Sometimes the system is capable of detecting more than one type of target nucleic acid, wherein the system comprises more than one type of guide nucleic acid (e.g., guide RNA) and more than one type of detector nucleic acid. In some cases, the detectable signal is generated directly by the cleavage event. Alternatively or in combination, the detectable signal is generated indirectly by the signal event. Sometimes the detectable signal is not a fluorescent signal. In some instances, the detectable signal is a colorimetric or color-based signal. In some cases, the detected target nucleic acid is identified based on its spatial location on the detection region of the support medium. In some cases, the second detectable signal is generated in a spatially distinct location than the first generated signal.

In some cases, the threshold of detection, for a subject method of detecting a single-stranded target nucleic acid in a sample, is less than or equal to 10 nM. The term "threshold of detection" is used herein to describe the minimal amount of target nucleic acid that must be present in a sample in order for detection to occur. For example, when a threshold of detection is 10 nM, then a signal can be detected when a target nucleic acid is present in the sample at a concentration of 10 nM or more. In some cases, the threshold of detection is less than or equal to 5 nM, 1 nM, 0.5 nM, 0.1 nM, 0.05 nM, 0.01 nM, 0.005 nM, 0.001 nM, 0.0005 nM, 0.0001 nM, 0.00005 nM, 0.00001 nM, 10 pM, 1 pM, 500 fM, 250 fM, 100 fM, 50 fM, 10 fM, 5 fM, 1 fM, 500 attomole (aM), 100 aM, 50 aM, 10 aM, or 1 aM. In some cases, the threshold of detection is in a range of from 1 aM to 1 nM, 1 aM to 500 pM, 1 aM to 200 pM, 1 aM to 100 pM, 1 aM to 10 pM, 1 aM to 1 pM, 1 aM to 500 fM, 1 aM to 100 fM, 1 aM to 1 fM, 1 aM to 500 aM, 1 aM to 100 aM, 1 aM to 50 aM, 1 aM to 10 aM, 10 aM to 1 nM, 10 aM to 500 pM, 10 aM to 200 pM, 10 aM to 100 pM, 10 aM to 10 pM, 10 aM to 1 pM, 10 aM to 500 fM, 10 aM to 100 fM, 10 aM to 1 fM, 10 aM to 500 aM, 10 aM to 100 aM, 10 aM to 50 aM, 100 aM to 1 nM, 100 aM to 500 pM, 100 aM to 200 pM, 100 aM to 100 pM, 100 aM to 10 pM, 100 aM to 1 pM, 100 aM to 500 fM, 100 aM to 100 fM, 100 aM to 1 fM, 100 aM to 500 aM, 500 aM to 1 nM, 500 aM to 500 pM, 500 aM to 200 pM, 500 aM to 100 pM, 500 aM to 10 pM, 500 aM to 1 pM, 500 aM to 500 fM, 500 aM to 100 fM, 500 aM to 1 fM, 1 fM to 1 nM, 1 fM to 500 pM, 1 fM to 200 pM, 1 fM to 100 pM, 1 fM to 10 pM, 1 fM to 1 pM, 10 fM to 1 nM, 10 fM to 500 pM, 10 fM to 200 pM, 10 fM to 100 pM, 10 fM to 10 pM, 10 fM to 1 pM, 500 fM to 1 nM, 500 fM to 500 pM, 500 fM to 200 pM, 500 fM to 100 pM, 500 fM to 10 pM, 500 fM to 1 pM, 800 fM to 1 nM, 800 fM to 500 pM, 800 fM to 200 pM, 800 fM to 100 pM, 800 fM to 10 pM, 800 fM to 1 pM, fom 1 pM to 1 nM, 1 pM to 500 pM, 1 pM to 200 pM, 1 pM to 100 pM, or 1 pM to 10 pM. In some cases, the threshold of detection in a range of from 800 fM to 100 pM, 1 pM to 10 pM, 10 fM to 500 fM, 10 fM to 50 fM, 50 fM to 100 fM, 100 fM to 250 fM, or 250 fM to 500 fM. In some cases, the minimum concentration at which a single-stranded target nucleic acid is detected in a sample is in a range of from 1 aM to 1 nM, 10 aM to 1 nM, 100 aM to 1 nM, 500 aM to 1 nM, 1 fM to 1 nM, 1 fM to 500 pM, 1 fM to 200 pM, 1 fM to 100 pM, 1 fM to 10 pM, 1 fM to 1 pM, 10 fM to 1 nM, 10 fM to 500 pM, 10 fM to 200 pM, 10 fM to 100 pM, 10 fM to 10 pM, 10 fM to 1 pM, 500 fM to 1 nM, 500 fM to 500 pM, 500 fM to 200 pM, 500 fM to 100 pM, 500 fM to 10 pM, 500 fM to 1 pM, 800 fM to 1 nM, 800 fM to 500 pM, 800 fM to 200 pM, 800 fM to 100 pM, 800 fM to 10 pM, 800 fM to 1 pM, 1 pM to 1 nM, 1 pM to 500 pM, from 1 pM to 200 pM, 1 pM to 100 pM, or 1 pM to 10 pM. In some cases, the minimum concentration at which a single-stranded target nucleic acid can be detected in a sample is in a range of from 1 aM to 100 pM. In some cases, the minimum concentration at which a single-stranded target nucleic acid can be detected in a sample is in a range of from 1 fM to 100 pM. In some cases, the minimum concentration at which a single-stranded target nucleic acid can be detected in a sample is in a range of from 10 fM to 100 pM. In some cases, the minimum concentration at which a single-stranded target nucleic acid can be detected in a sample is in a range of from 800 fM to 100 pM. In some cases, the minimum concentration at which a single-stranded target nucleic acid can be detected in a sample is in a range of from 1 pM to 10 pM. In some cases, the devices, systems, fluidic devices, kits, and methods described herein detect a target single-stranded nucleic acid in a sample comprising a plurality of nucleic acids such as a plurality of non-target nucleic acids, where the target single-stranded nucleic acid is present at a concentration as low as 1 aM, 10 aM, 100 aM, 500 aM, 1 fM, 10 fM, 500 fM, 800 fM, 1 pM, 10 pM, 100 pM, or 1 pM.

In some cases, the devices, systems, fluidic devices, kits, and methods described herein detect a target single-stranded nucleic acid in a sample where the sample is contacted with the reagents for a predetermined length of time sufficient for the trans cleavage to occur or cleavage reaction to reach completion. In some cases, the devices, systems, fluidic devices, kits, and methods described herein detect a target single-stranded nucleic acid in a sample where the sample is contacted with the reagents for no greater than 60 minutes. Sometimes the sample is contacted with the reagents for no greater than 120 minutes, 110 minutes, 100 minutes, 90 minutes, 80 minutes, 70 minutes, 60 minutes, 55 minutes, 50 minutes, 45 minutes, 40 minutes, 35 minutes, 30 minutes, 25 minutes, 20 minutes, 15 minutes, 10 minutes, 5 minutes, 4 minutes, 3 minutes, 2 minutes, or 1 minute. Sometimes the sample is contacted with the reagents for at least 120 minutes, 110 minutes, 100 minutes, 90 minutes, 80 minutes, 70 minutes, 60 minutes, 55 minutes, 50 minutes, 45 minutes, 40 minutes, 35 minutes, 30 minutes, 25 minutes, 20 minutes, 15 minutes, 10 minutes, or 5 minutes. In some cases, the devices, systems, fluidic devices, kits, and methods described herein can detect a target nucleic acid in a sample in less than 10 hours, less than 9 hours, less than 8 hours, less than 7 hours, less than 6 hours, less than 5 hours, less than 4 hours, less than 3 hours, less than 2 hours, less than 1 hour, less than 50 minutes, less than 45 minutes, less than 40 minutes, less than 35 minutes, less than 30 minutes, less than 25 minutes, less than 20 minutes, less than 15 minutes, less than 10 minutes, less than 9 minutes, less than 8 minutes, less than 7 minutes, less than 6 minutes, or less than 5 minutes.

When a guide nucleic acid (e.g., guide RNA) binds to a target nucleic acid, the programmable nuclease's trans cleavage activity can be initiated, and detector nucleic acids can be cleaved, resulting in the detection of fluorescence. Some methods as described herein can a method of assaying for a target nucleic acid in a sample comprises contacting the sample to a complex comprising a guide nucleic acid comprising a segment that is reverse complementary to a segment of the target nucleic acid and a programmable nuclease that exhibits sequence independent cleavage upon forming a complex comprising the segment of the guide nucleic acid binding to the segment of the target nucleic acid; and assaying for a signal indicating cleavage of at least some protein-nucleic acids of a population of protein-nucleic acids, wherein the signal indicates a presence of the target nucleic acid in the sample and wherein absence of the signal indicates an absence of the target nucleic acid in the sample. The cleaving of the detector nucleic acid using the programmable nuclease may cleave with an efficiency of 50% as measured by a change in a signal that is calorimetric, potentiometric, amperometric, optical (e.g., fluorescent, colorimetric, etc.), or piezo-electric, as non-limiting examples. Some methods as described herein can be a method of detecting a target nucleic acid in a sample comprising contacting the sample comprising the target nucleic acid with a guide nucleic acid targeting a target nucleic acid segment, a programmable nuclease capable of being activated when complexed with the guide nucleic acid and the target nucleic acid segment, a single-stranded detector nucleic acid comprising a detection moiety, wherein the detector nucleic acid is capable of being cleaved by the activated programmable nuclease, thereby generating a first detectable signal, cleaving the single-stranded detector nucleic acid using the programmable nuclease that cleaves as measured by a change in color, and measuring the first detectable signal on the support medium. The cleaving of the single-stranded detector nucleic acid using the programmable nuclease may cleave with an efficiency of 50% as measured by a change in color. In some cases, the cleavage efficiency is at least 40%, 50%, 60%, 70%, 80%, 90%, or 95% as measured by a change in color. The change in color may be a detectable colorimetric signal or a signal visible by eye. The change in color may be measured as a first detectable signal. The first detectable signal can be detectable within 5 minutes of contacting the sample comprising the target nucleic acid with a guide nucleic acid targeting a target nucleic acid segment, a programmable nuclease capable of being activated when complexed with the guide nucleic acid and the target nucleic acid segment, and a single-stranded detector nucleic acid comprising a detection moiety, wherein the detector nucleic acid is capable of being cleaved by the activated nuclease. The first detectable signal can be detectable within 1, 2, 3, 4, 5, 6, 7, 8, 9, 10, 11, 12, 13, 14, 15, 20, 25, 30, 35, 40, 45, 50, 55, 60, 70, 80, 90, 100, 110, or 120 minutes of contacting the sample.

In some cases, the methods, reagents, and devices described herein detect a plurality of target nucleic acids with a programmable nuclease and a single-stranded detector nucleic acid in a sample where the sample is contacted with the reagents for a predetermined length of time sufficient for trans cleavage of the detector nucleic acid. The reagents may comprise a pool of different guide nucleic acid sequences (e.g., guide RNA sequences) directed to different segments of target nucleic acids. Each guide nucleic acid may be capable of forming a complex comprising the guide nucleic acid, a programmable nuclease, and the target nucleic acid to which the guide nucleic acid is directed. In some embodiments, a programmable nuclease is a Cas12 programmable nuclease that detects a target nucleic acid and a detector nucleic acid (e.g., a single-stranded DNA or double-stranded DNA). In some embodiments, a programmable nuclease is a Cas14 programmable nuclease that detects a target nucleic acid and a single-stranded detector nucleic acid (e.g., single-stranded DNA). In some embodiments, a programmable nuclease is a Cas13 programmable nuclease that detects a target nucleic acid and a single-stranded detector nucleic acid (e.g., a single-stranded RNA). The target nucleic acid may be a single-stranded nucleic acid (e.g., a single-stranded DNA (ssDNA) or a single-stranded RNA), or the target nucleic acid may be a double-stranded nucleic acid (e.g., a double-stranded DNA (dsDNA) or a double-stranded RNA). The detector nucleic acid may be a single-stranded nucleic acid (e.g., a ssDNA or a single-stranded RNA), or the detector nucleic acid may be a double-stranded nucleic acid (e.g., a dsDNA or a double-stranded RNA).

In some cases, the methods, reagents, and devices described herein detect a target nucleic acid with a programmable nuclease and a single-stranded detector nucleic acid in a sample where the sample is contacted with the reagents for a predetermined length of time sufficient for trans cleavage of the single-stranded detector nucleic acid. For example, a programmable nuclease is LbuCas13a that detects a target nucleic acid and a single-stranded detector nucleic acid comprises two adjacent uracil nucleotides with a green detectable moiety that is detected upon cleavage. As another example, a programmable nuclease is LbaCas13a that detects a target nucleic acid and a single-stranded detector nucleic acid comprises two adjacent adenine nucleotides with a red detectable moiety that is detected upon cleavage. The target nucleic acid may be a single-stranded nucleic acid (e.g., a single-stranded DNA (ssDNA) or a single-stranded RNA), or the target nucleic acid may be a double-stranded nucleic acid (e.g., a double-stranded DNA (dsDNA) or a double-stranded RNA).

The reagents described herein can also include buffers, which are compatible with the devices, systems, fluidic devices, kits, and methods disclosed herein. These buffers are compatible with the other reagents, samples, and support mediums as described herein for detection of an ailment, such as a disease, including those caused by viruses such as influenza. The methods described herein can also include the use of buffers, which are compatible with the methods disclosed herein. For example, a buffer comprises 20 mM HEPES pH 6.8, 50 mM KCl, 5 mM $MgCl_2$, and 5% glycerol. In some instances the buffer comprises from 0 to 100, 0 to 75, 0 to 50, 0 to 25, 0 to 20, 0 to 10, 0 to 5, 5 to 10, 5 to 15, 5 to 20, 5 to 25, to 30, 5 to 40, 5 to 50, 5 to 75, 5 to 100, 10 to 20, 10 to 30, 10 to 40, 10 to 50, 15 to 20, 15 to 25, 15 to 30, 15 to 4, 15 to 50, 20 to 25, 20 to 30, 20 to 40, or 20 to 50 mM HEPES pH 6.8. The buffer can comprise to 0 to 500, 0 to 400, 0 to 300, 0 to 250, 0 to 200, 0 to 150, 0 to 100, 0 to 75, 0 to 50, 0 to 25, 0 to 20, 0 to 10, 0 to 5, 5 to 10, 5 to 15, 5 to 20, 5 to 25, to 30, 5 to 40, 5 to 50, 5 to 75, 5 to 100, 5 to 150, 5 to 200, 5 to 250, 5 to 300, 5 to 400, 5 to 500, 25 to 50, 25 to 75, 25 to 100, 50 to 100, 50 150, 50 to 200, 50 to 250, 50 to 300, 100 to 200, 100 to 250, 100 to 300, or 150 to 250 mM KCl. In other instances the buffer comprises 0 to 100, 0 to 75, 0 to 50, 0 to 25, 0 to 20, 0 to 10, 0 to 5, 5 to 10, 5 to 15, 5 to 20, 5 to 25, to 30, 5 to 40, 5 to 50, 5 to 75, 5 to 100, 10 to 20, 10 to 30, 10 to 40, 10 to 50, 15 to 20, 15 to 25, 15 to 30, 15 to 4, 15 to 50, 20 to 25, 20 to 30, 20 to 40, or 20 to 50 mM $MgCl_2$. The buffer can comprise 0 to 25, 0 to 20, 0 to 10, 0 to 5, 5 to 10, 5 to 15, 5 to 20, 5 to 25, 5 to 30% glycerol.

As another example, a buffer comprises 100 mM Imidazole pH 7.5; 250 mM KCl, 25 mM $MgCl_2$, 50 ug/mL BSA, 0.05% Igepal Ca-630, and 25% Glycerol. In some instances the buffer comprises 0 to 500, 0 to 400, 0 to 300, 0 to 250, 0 to 200, 0 to 150, 0 to 100, 0 to 75, 0 to 50, 0 to 25, 0 to 20, 0 to 10, 0 to 5, 5 to 10, 5 to 15, 5 to 20, 5 to 25, to 30, 5 to 40, 5 to 50, 5 to 75, 5 to 100, 5 to 150, 5 to 200, 5 to 250, 5 to 300, 5 to 400, 5 to 500, 25 to 50, 25 to 75, 25 to 100, 50 to 100, 50 150, 50 to 200, 50 to 250, 50 to 300, 100 to 200, 100 to 250, 100 to 300, or 150 to 250 mM Imidazole pH 7.5. The buffer can comprise to 0 to 500, 0 to 400, 0 to 300, 0 to 250, 0 to 200, 0 to 150, 0 to 100, 0 to 75, 0 to 50, 0 to 25, 0 to 20, 0 to 10, 0 to 5, 5 to 10, 5 to 15, 5 to 20, 5 to 25, to 30, 5 to 40, 5 to 50, 5 to 75, 5 to 100, 5 to 150, 5 to 200, 5 to 250, 5 to 300, 5 to 400, 5 to 500, 25 to 50, 25 to 75, 25 to 100, 50 to 100, 50 150, 50 to 200, 50 to 250, 50 to 300, 100 to 200, 100 to 250, 100 to 300, or 150 to 250 mM KCl. In other instances the buffer comprises 0 to 100, 0 to 75, 0 to 50, 0 to 25, 0 to 20, 0 to 10, 0 to 5, 5 to 10, 5 to 15, 5 to 20, 5 to 25, to 30, 5 to 40, 5 to 50, 5 to 75, 5 to 100, 10 to 20, 10 to 30, 10 to 40, 10 to 50, 15 to 20, 15 to 25, 15 to 30, 15 to 4, 15 to 50, 20 to 25, 20 to 30, 20 to 40, or 20 to 50 mM $MgCl_2$. The buffer, in some instances, comprises 0 to 100, 0 to 75, 0 to 50, 0 to 25, 0 to 20, 0 to 10, 0 to 5, 5 to 50, 5 to 75, 5 to 100, 10 to 20, 10 to 50, 10 to 75, 10 to 100, 25 to 50, 25 to 75 25 to 100, 50 to 75, or 50 to 100 ug/mL BSA. In some instances, the buffer comprises 0 to 1, 0 to 0.5, 0 to 0.25, 0 to 0.01, 0 to 0.05, 0 to 0.025, 0 to 0.01, 0.01 to 0.025, 0.01 to 0.05, 0.01 to 0.1, 0.01 to 0.25, 0.01, to 0.5, 0.01 to 1, 0.025 to 0.05, 0.025 to 0.1, 0.025, to 0.5, 0.025 to 1, 0.05 to 0.1, 0.05 to 0.25, 0.05 to 0.5, 0.05 to 0.75, 0.05 to 1, 0.1 to 0.25, 0.1 to 0.5, or 0.1 to 1% Igepal Ca-630. The buffer can comprise 0 to 25, 0 to 20, 0 to 10, 0 to 5, 5 to 10, 5 to 15, 5 to 20, 5 to 25, 5 to 30% glycerol.

A number of detection devices and methods are consistent with methods disclosed herein. For example, any device that can measure or detect a calorimetric, potentiometric, amperometric, optical (e.g., fluorescent, colorometric, etc.), or piezo-electric signal. Often a calorimetric signal is heat produced after cleavage of the detector nucleic acids. Sometimes, a calorimetric signal is heat absorbed after cleavage of the detector nucleic acids. A potentiometric signal, for example, is electrical potential produced after cleavage of the detector nucleic acids. An amperometric signal can be movement of electrons produced after the cleavage of detector nucleic acid. Often, the signal is an optical signal, such as a colorometric signal or a fluorescence signal. An optical signal is, for example, a light output produced after the cleavage of the detector nucleic acids. Sometimes, an optical signal is a change in light absorbance between before and after the cleavage of detector nucleic acids. Often, a piezo-electric signal is a change in mass between before and after the cleavage of the detector nucleic acid. Sometimes, the detector nucleic acid is protein-nucleic acid. Often, the protein-nucleic acid is an enzyme-nucleic acid.

The results from the detection region from a completed assay can be detected and analyzed in various ways, for example, by a glucometer. In some cases, the positive control spot and the detection spot in the detection region is visible by eye, and the results can be read by the user. In some cases, the positive control spot and the detection spot in the detection region is visualized by an imaging device or other device depending on the type of signal. Often, the imaging device is a digital camera, such a digital camera on a mobile device. The mobile device may have a software program or a mobile application that can capture an image of the support medium, identify the assay being performed, detect the detection region and the detection spot, provide image properties of the detection spot, analyze the image properties of the detection spot, and provide a result. Alternatively or in combination, the imaging device can capture fluorescence, ultraviolet (UV), infrared (IR), or visible wavelength signals. The imaging device may have an excitation source to provide the excitation energy and captures the emitted signals. In some cases, the excitation source can be a camera flash and optionally a filter. In some cases, the imaging device is used together with an imaging box that is placed over the support medium to create a dark room to improve imaging. The imaging box can be a cardboard box that the imaging device can fit into before imaging. In some instances, the imaging box has optical lenses, mirrors, filters, or other optical elements to aid in generating a more focused excitation signal or to capture a more focused emission signal. Often, the imaging box and the imaging device are small, handheld, and portable to facilitate the transport and use of the assay in remote or low resource settings.

The assay described herein can be visualized and analyzed by a mobile application (app) or a software program. Using the graphic user interface (GUI) of the app or program, an individual can take an image of the support medium, including the detection region, barcode, reference color scale, and fiduciary markers on the housing, using a camera on a mobile device. The program or app reads the barcode or identifiable label for the test type, locate the fiduciary marker to orient the sample, and read the detectable signals, compare against the reference color grid, and determine the presence or absence of the target nucleic acid, which indicates the presence of the gene, virus, or the agent responsible for the disease. The mobile application can present the results of the test to the individual. The mobile application can store the test results in the mobile application. The mobile application can communicate with a remote device and transfer the data of the test results. The test results can be viewable remotely from the remote device by another individual, including a healthcare professional. A remote user can access the results and use the information to recommend action for treatment, intervention, cleanup of an environment.

Disease Detection

Disclosed herein are methods of assaying for a plurality of target nucleic acid as described herein that can be used for disease detection. These methods are consistent for use with a pool of guide nucleic acids (e.g., guide RNAs), wherein at least two guide nucleic acid sequences of the pool of guide nucleic acids hybridizes to different segments of the same target nucleic acid or hybridizes to different segments of different target nucleic acids. method of assaying for a plurality of target nucleic acid (e.g., one or more target nucleic acid populations associated with a disease) in a sample comprises contacting the sample to a plurality of complexes comprising a guide nucleic acid comprising a segment that is reverse complementary to a segment of the target nucleic acid and a programmable nuclease that exhibits sequence independent cleavage upon forming a complex comprising the segment of the guide nucleic acid binding to the segment of a target nucleic acid of the plurality of target nucleic acids; and assaying for a signal indicating cleavage of at least some protein-nucleic acids of a population of protein-nucleic acids, wherein the signal indicates a presence of the target nucleic acid in the sample and wherein absence of the signal indicates an absence of the target nucleic acid in the sample. The plurality of complexes may comprise complexes with distinct guide nucleic acids directed to different target nucleic acids. The detection of the signal can indicate the presence of the target nucleic acid. Sometimes, a target nucleic acid of the plurality of target nucleic acids comprises a mutation. Often, the mutation is a single nucleotide mutation. As another example, a method of assaying for a target nucleic acid in a sample, for example, comprises: a) contacting the sample to a complex comprising a guide nucleic acid comprising a segment that is reverse complementary to a segment of the target nucleic acid and a programmable nuclease that exhibits sequence independent cleavage upon forming a complex comprising the segment of the guide nucleic acid binding to the segment of the target nucleic acid; b) contacting the complex to a substrate; c) contacting the substrate to a reagent that differentially reacts with a cleaved substrate; and d) assaying for a signal indicating cleavage of the substrate, wherein the signal indicates a presence of the target nucleic acid in the sample and wherein absence of the signal indicates an absence of the target nucleic acid in the sample. Often, the substrate is an enzyme-nucleic acid. Sometimes, the substrate is an enzyme substrate-nucleic acid.

Methods described herein can be used to identify multiple target nucleic acids from a bacteria, virus, or microbe, or any combination thereof. The multiple target nucleic acids may comprise sequence variations (e.g., mutations). The multiple target nucleic acids may be from a single target nucleic acid population associated with a disease (e.g., a single chromosome, plasmid, bacterial genome, viral genome, fungal genome, or amoeboid genome). The multiple target nucleic acids may be from multiple target nucleic acid populations (e.g., one or more of a chromosome, a plasmid, a bacterial genome, a viral genome, a fungal genome, or an amoeboid genome, or any combination thereof). The methods can be used to identify a mutation of a target nucleic acid that affects the expression of a gene. A mutation that affects the expression of gene can be a mutation of a target nucleic acid within the gene, a mutation of a target nucleic acid comprising RNA associated with the expression of a gene, or a target nucleic acid comprising a mutation of a nucleic acid associated with regulation of expression of a gene, such as an RNA or a promoter, enhancer, or repressor of the gene. Sometimes, a status of a target nucleic acid mutation is used to determine a pathogenicity of a bacteria, virus, or microbe or treatment resistance, such as resistance to antibiotic treatment. Often, a status of a mutation is used to diagnose or identify diseases associated with the mutation of target nucleic acids in the bacteria, virus, or microbe. Often, the mutation is a single nucleotide mutation.

Detection as a Research Tool, Point-of-Care, or Over-the-Counter

Disclosed herein are methods of assaying for a plurality of target nucleic acid (e.g., from a target population associated with a disease) as described herein that can be used as a research tool, and can be provided as reagent kits. For example, a method of assaying for a plurality of target nucleic acid in a sample comprises contacting the sample to a plurality of complexes comprising a guide nucleic acid (e.g., guide RNA) comprising a segment that is reverse complementary to a segment of a target nucleic acid of the plurality of target nucleic acids and a programmable nuclease that exhibits sequence independent cleavage upon forming a complex comprising the segment of the guide nucleic acid binding to the segment of the target nucleic acid; and assaying for a signal indicating cleavage of at least some protein-nucleic acids of a population of protein-nucleic acids, wherein the signal indicates a presence of the target nucleic acid in the sample and wherein absence of the signal indicates an absence of the target nucleic acid in the sample. The plurality of complexes may comprise complexes with distinct guide nucleic acids directed to different target nucleic acids. The detection of the signal can indicate the presence of the target nucleic acid. Sometimes, a target nucleic acid of the plurality of target nucleic acids comprises a mutation. Often, the mutation is a single nucleotide mutation. As another example, a method of assaying for a target nucleic acid in a sample, for example, comprises: a) contacting the sample to a complex comprising a guide nucleic acid comprising a segment that is reverse complementary to a segment of the target nucleic acid and a programmable nuclease that exhibits sequence independent cleavage upon forming a complex comprising the segment of the guide nucleic acid binding to the segment of the target nucleic acid; b) contacting the complex to a substrate; c) contacting the substrate to a reagent that differentially reacts with a cleaved substrate; and d) assaying for a signal indicating cleavage of the substrate, wherein the signal indicates a presence of the target nucleic acid in the sample and wherein absence of the signal indicates an absence of the target nucleic acid in the sample. Often, the substrate is an enzyme-nucleic acid. Sometimes, the substrate is an enzyme substrate-nucleic acid.

The methods as described herein can be used to identify multiple target nucleic acids. The multiple target nucleic acids may comprise sequence variations (e.g., mutations). The multiple target nucleic acids may be from a single target nucleic acid populations associated with a disease (e.g., a single chromosome, plasmid, bacterial genome, viral genome, fungal genome, or amoeboid genome). The multiple target nucleic acids may be from multiple target nucleic acid populations (e.g., one or more of a chromosome, a plasmid, a bacterial genome, a viral genome, a fungal genome, or an amoeboid genome, or any combination thereof). The methods can be used to identify mutation of a target nucleic acid that affects the expression of a gene. A mutation that affects the expression of gene can be a single nucleotide mutation of a target nucleic acid within the gene, a mutation of a target nucleic acid comprising RNA associated with the expression of a gene, or a target nucleic acid comprising a mutation of a nucleic acid associated with regulation of expression of a gene, such as an RNA or a promoter, enhancer, or repressor of the gene. Often, the mutation is a single nucleotide mutation.

The reagent kits or research tools can be used to detect any number of target nucleic acids, mutations, or other indications disclosed herein in a laboratory setting. Reagent kits can be provided as reagent packs for open box instrumentation.

In other embodiments, any of the systems, assay formats, guide nucleic acids (e.g., guide RNAs), detector nucleic acids, programmable nucleases, or other reagents can be used in a point-of-care (POC) test, which can be carried out at a decentralized location such as a hospital, POL, or clinic. These point-of-care tests can be used to diagnose any of the indications disclosed herein, such as influenza or streptococcal infections, or can be used to measure the presence or absence of a particular mutation in a target nucleic acid (e.g., EGFR). POC tests can be provided as small instruments with a consumable test card, wherein the test card is any of the assay formats (e.g., a lateral flow assay) disclosed herein.

In still other embodiments, any of the systems, assay formats, detector nucleic acids, programmable nucleases, or other reagents can be used in an over-the-counter (OTC), readerless format, which can be used at remote sites or at home to diagnose a range of indications, such as influenza. These indications can include influenza A, influenza B, streptococcal infections, or CT/NG infections. OTC products can include a consumable test card, wherein the test card is any of the assay formats (e.g., a lateral flow assay) disclosed herein. In an OTC product, the test card can be interpreted visually or using a mobile phone.

Multiplexing

The devices, systems, fluidic devices, kits, and methods described herein can be multiplexed in a number of ways. These methods of multiplexing are, for example, consistent with methods, reagents, and devices disclosed herein for detection of a target nucleic acid within the sample. A fluidic device may comprise multiple pumps, valves, reservoirs, and chambers for sample preparation, amplification of one or more than one sequences of target nucleic acids within the sample, mixing with a programmable nuclease, and detection of a detectable signal arising from cleavage of detector nucleic acids by the programmable nuclease within the fluidic system itself.

Methods consistent with the present disclosure include a multiplexing method of assaying for a target nucleic acid in a sample. A multiplexing method comprises contacting the sample to a complex comprising a guide nucleic acid (e.g., guide RNA) comprising a segment that is reverse complementary to a segment of the target nucleic acid and a programmable nuclease that exhibits sequence independent cleavage upon forming a complex comprising the segment of the guide nucleic acid binding to the segment of the target nucleic acid; and assaying for a signal indicating cleavage of at least some protein-nucleic acids of a population of protein-nucleic acids, wherein the signal indicates a presence of the target nucleic acid in the sample and wherein absence of the signal indicates an absence of the target nucleic acid in the sample. As another example, multiplexing method of assaying for a target nucleic acid in a sample, for example, comprises: a) contacting the sample to a complex comprising a guide nucleic acid comprising a segment that is reverse complementary to a segment of the target nucleic acid and a programmable nuclease that exhibits sequence independent cleavage upon forming a complex comprising the segment of the guide nucleic acid binding to the segment of the target nucleic acid; b) contacting the complex to a substrate; c) contacting the substrate to a reagent that differentially reacts with a cleaved substrate; and d) assaying for a signal indicating cleavage of the substrate, wherein the signal indicates a presence of the target nucleic acid in the sample and wherein absence of the signal indicates an absence of the target nucleic acid in the sample. Often, the substrate is an enzyme-nucleic acid. Sometimes, the substrate is an enzyme substrate-nucleic acid.

Multiplexing can be either spatial multiplexing wherein multiple different target nucleic acids are detected at the same time, but the reactions are spatially separated. Often, the multiple target nucleic acids are detected using the same programmable nuclease, but different guide nucleic acids (e.g., guide RNAs). The multiple target nucleic acids sometimes are detected using the different programmable nucleases. Sometimes, multiplexing can be single reaction multiplexing wherein multiple different target acids are detected in a single reaction volume. Often, a single population of programmable nucleases is used in single reaction multiplexing. Sometimes, at least two different programmable nucleases are used in single reaction multiplexing. For example, multiplexing can be enabled by immobilization of multiple categories of detector nucleic acids within a fluidic system, to enable detection of multiple target nucleic acids within a single sample. In another example, multiplexing can be enabled using a single category of detector nucleic acids in a single high-plex reaction (e.g., a reaction with a pool of guide nucleic acids (e.g., guide RNAs), wherein at least 21 guide nucleic acid sequences (e.g., guide RNA sequences) of the pool are distinct), to enable detection of the presence or absence of multiple target nucleic acids within a single sample. Multiplexing allows for detection of multiple target nucleic acids in one kit or system. In some cases, the multiple target nucleic acids comprise different target nucleic acids associated with a disease. In some cases, the multiple target nucleic acids comprise different target nucleic acids associated with a disease (e.g., a tick-borne pathogen, a healthcare-associated infection, sepsis, or a respiratory infection, such as an upper respiratory tract virus). The multiple target nucleic acids may be from the same target nucleic population associated with a single disease. The multiple target nucleic acids may be from multiple target nucleic acid populations associated with one or more diseases. Multiplexing for one disease increases at least one of sensitivity, specificity, or accuracy of the assay to detect the presence of the disease in the sample. In some cases, the multiple target nucleic acids comprise target nucleic acids directed to different viruses, bacteria, or pathogens responsible for more than one disease. In some cases, multiplexing allows for discrimination between multiple target nucleic acids, such as target nucleic acids that comprise different genotypes of the same bacteria or pathogen responsible for a disease, for example, for a wild-type genotype of a bacteria or pathogen and for genotype of a bacteria or pathogen comprising a mutation, such as a single nucleotide polymorphism (SNP) that can confer resistance to a treatment, such as antibiotic treatment. For example, multiplexing comprises method of assaying comprising a single assay for a microorganism species using a first programmable nuclease and an antibiotic resistance pattern in a microorganism using a second programmable nuclease. Sometimes, multiplexing allows for discrimination between multiple target nucleic acids of different influenza strains, for example, influenza A and influenza B. Often, multiplexing allows for discrimination between multiple target nucleic acids, such as target nucleic acids that comprise different genotypes, for example, for a wild-type genotype and for SNP genotype. Multiplexing for multiple viral infections provides the capability to test a panel of diseases from a single sample. For example, multiplexing for multiple diseases can be valuable in a broad panel testing of a new patient or in epidemiological surveys. Often multiplexing is used for identifying bacterial pathogens in sepsis or other diseases associated with multiple pathogens.

Multiplexing may comprise the detecting the presence or absence of any number of target nucleic acids. For example, multiplexing may comprise detecting the presence or absence of at least 20, at least 30, at least 40, at least 50, at least 60, at least 70, at least 80, at least 90, at least 100, at least 200, at least 300, at least 400, at least 500, at least 600, at least 700, at least 800, at least 900, at least 1000, or more target nucleic acids. The target nucleic acid populations may be from at least 1, at least 2, at least 3, at least 4, at least, 5, at least 6, at least 7, at least 8, at least 9, at least 10, at least 20, at least 30, at least 40, at least 50, at least 60, at least 70, at least 80, at least 90, at least 100, or more target nucleic acid populations. The target nucleic acids may be detected with at least 20, at least 30, at least 40, at least 50, at least 60, at least 70, at least 80, at least 90, at least 100, at least 200, at least 300, at least 400, at least 500, at least 600, at least 700, at least 800, at least 900, at least 1000, or more guide nucleic acids (e.g., guide RNAs). Each guide nucleic acid sequence in the plurality of guide nucleic acids may be directed to a distinct segment of a target nucleic acid or distinct segments of distinct target nucleic acids. The distinct target nucleic acids may be from a single target nucleic acid population. The distinct target nucleic acids may be from multiple target nucleic acid populations. The distinct target nucleic acids may be different variants of a target sequence from a single target nucleic acid population or multiple target nucleic acid populations. Each guide nucleic acid sequence of the pool of guide nucleic acids may be complexed with a programmable nuclease.

Furthermore, signals from multiplexing can be quantified. For example, a method of quantification for a disease panel comprises assaying for a plurality of unique target nucleic acids in a plurality of aliquots from a sample, assaying for a control nucleic acid control in a second aliquot of the sample, and quantifying a plurality of signals of the plurality of unique target nucleic acids by measuring signals produced by cleavage of detector nucleic acids compared to the signal produced in the second aliquot. Often the plurality of unique target nucleic acids are from a plurality of viruses in the sample. Sometimes the quantification of a signal of the plurality correlates with a concentration of a unique target nucleic acid of the plurality for the unique target nucleic acid of the plurality that produced the signal of the plurality. Sometimes the quantification comprises assaying for a plurality of unique target nucleic acids in a single sample and quantifying a single signal indicative of a total amount of the plurality of unique target nucleic acids.

The methods, reagents, and devices described herein can be multiplexed by various configurations of the reagents and the support medium. In some cases, the kit or system is designed to have multiple support mediums encased in a single housing. Sometimes, the multiple support mediums housed in a single housing share a single sample pad. The single sample pad may be connected to the support mediums in various designs such as a branching or a radial formation. Alternatively, each of the multiple support mediums has its own sample pad. In some cases, the kit or system is designed to have a single support medium encased in a housing, where the support medium comprises multiple detection spots for detecting multiple target nucleic acids. Sometimes, the reagents for multiplexed assays comprise multiple guide nucleic acids, multiple programmable nucleases, and multiple single stranded detector nucleic acids, where a combination of one of the guide nucleic acids, one of the programmable nucleases, and one of the single stranded detector nucleic acids detects one target nucleic acid and can provide a detection spot on the detection region. In some cases, the combination of a guide nucleic acid, a programmable nuclease, and a single stranded detector nucleic acid configured to detect one target nucleic acid is mixed with at least one other combination in a single reagent chamber. In some cases, the combination of a guide nucleic acid, a programmable nuclease, and a single stranded detector nucleic acid configured to detect one target nucleic acid is mixed with at least one other combination on a single support medium. When these combinations of reagents are contacted with the sample, the reaction for the multiple target nucleic acids occurs simultaneously in the same medium or reagent chamber. Sometimes, this reacted sample is applied to the multiplexed support medium described herein. In some cases, the methods, reagents, and devices described herein can be multiplexed in a configuration lacking a support medium.

In some cases, the combination of a guide nucleic acid, a programmable nuclease, and a single stranded detector nucleic acid configured to detect one target nucleic acid is provided in its own reagent chamber or its own support medium. In this case, multiple reagent chambers or support mediums are provided in the device, kit, or system, where one reagent chamber is designed to detect one target nucleic acid. In this case, multiple support mediums are used to detect the panel of viral infections, or other diseases of interest.

In some instances, the multiplexed methods, reagents, and devices detect at least 21 different target nucleic acids in a single reaction. In some instances, the multiplexed methods, reagents, and devices detect at least 30 different target nucleic acids in a single reaction. In some instances, the multiplexed methods, reagents, and devices detect at least 40 different target nucleic acids in a single reaction. In some instances, the multiplexed methods, reagents, and devices detect at least 50 different target nucleic acids in a single reaction. In some cases, the multiplexed methods, reagents, and devices detect at least 60, 70, 80, 90, or 100 different target nucleic acids in a single reaction. In some cases, the multiplexed methods, reagents, and devices detect at least 200, 300, 400, 500, 600, 700, 800, 900, or 1000 different target nucleic acids in a single reaction. In some instances, the multiplexed kits detect at least 20 different target nucleic acids in a single kit. In some instances, the multiplexed kits detect at least 30 different target nucleic acids in a single kit. In some instances, the multiplexed kits detect at least 40 different target nucleic acids in a single kit. In some instances, the multiplexed kits detect at least 50 different target nucleic acids in a single kit. In some instances, the multiplexed kits detect at least 60, 70, 80, 90, or 100 different target nucleic acids in a single kit. In some instances, the multiplexed kits detect at least 200, 300, 400, 500, 600, 700, 800, 900, or 1000 different target nucleic acids in a single kit.

Detection of a Target Nucleic Acid in a Fluidic Device

Disclosed herein are various fluidic devices for detection of a target nucleic acid of interest in a biological sample. The fluidic devices described in detail below can be used to monitor the reaction of target nucleic acids in samples with a programmable nuclease, thereby allowing for the detection of said target nucleic acid. All samples and reagents disclosed herein are compatible for use with a fluidic device disclosed below. Any programmable nuclease, such as any Cas nuclease described herein, are compatible for use with a fluidic device disclosed below. Support mediums and housing disclosed herein are also compatible for use in conjunction with the fluidic devices disclosed below. Multiplexing detection, as described throughout the present disclosure, can be carried out within the fluidic devices disclosed herein. Compositions and methods for detection and visualization disclosed herein are also compatible for use within the below described fluidic systems.

In the below described fluidic systems, any programmable nuclease (e.g., a Cas enzyme) reaction can be monitored. For example, any programmable nuclease disclosed herein can be used to cleave the detector nucleic acids to generate a detection signal. In some cases, the programmable nuclease is Cas13. Sometimes the Cas13 is Cas13a, Cas13b, Cas13c, Cas13d, or Cas13e. In some cases, the programmable nuclease is Mad7 or Mad2. In some cases, the programmable nuclease is Cas12. Sometimes the Cas12 is Cas12a, Cas12b, Cas12c, Cas12d, or Cas12e. In some cases, the programmable nuclease is Csm1, Cas9, C2c4, C2c8, C2c5, C2c10, C2c9, or CasZ. Sometimes, the Csm1 is also called smCms1, miCms1, obCms1, or suCms1. Sometimes Cas13a is also called C2c2. Sometimes CasZ is also called Cas14a, Cas14b, Cas14c, Cas14d, Cas14e, Cas14f, Cas14g, or Cas14h. Sometimes, the programmable nuclease is a Type V CRISPR-Cas enzyme. In some cases, the programmable nuclease is a Type VI CRISPR-Cas enzyme. Sometimes the programmable nuclease is a Type III CRISPR-Cas enzyme. In some cases, the programmable nuclease is from at least one of *Leptotrichia shahii* (Lsh), *Listeria seeligeri* (Lse), *Leptotrichia buccalis* (Lbu), *Leptotrichia wadeu* (Lwa),

*Rhodobacter capsulatus* (Rca), *Herbinix hemicellulosilytica* (Hhe), *Paludibacter propionicigenes* (Ppr), *Lachnospiraceae bacterium* (Lba), [*Eubacterium*] *rectale* (Ere), *Listeria newyorkensis* (Lny), *Clostridium aminophilum* (Cam), *Prevotella* sp. (Psm), *Capnocytophaga canimorsus* (Cca, *Lachnospiraceae bacterium* (Lba), *Bergeyella zoohelcum* (Bzo), *Prevotella intermedia* (Pin), *Prevotella buccae* (Pbu), *Alistipes* sp. (Asp), *Riemerella anatipestifer* (Ran), *Prevotella aurantiaca* (Pau), *Prevotella saccharolytica* (Psa), *Prevotella intermedia* (Pin2), *Capnocytophaga canimorsus* (Cca), *Porphyromonas gulae* (Pgu), *Prevotella* sp. (Psp), *Porphyromonas gingivalis* (Pig), *Prevotella intermedia* (Pin3), *Enterococcus italicus* (Ei), *Lactobacillus salivarius* (Ls), or *Thermus thermophilus* (Tt). Sometimes the Cas13 is at least one of LbuCas13a, LwaCas13a, LbaCas13a, HheCas13a, PprCas13a, EreCas13a, CamCas13a, or LshCas13a.

A workflow of a method for detecting a target nucleic acid in a sample within a fluidic device can include sample preparation, nucleic acid amplification, incubation with a programmable nuclease, and/or detection (readout). An exemplary workflow of a programmable nuclease reaction includes: Step 1—sample preparation; Step 2—nucleic acid amplification; Step 3—programmable nuclease incubation; and Step 4—detection (readout). Steps 1 and 2 are optional, and steps 3 and 4 can occur concurrently, if incubation and detection of programmable nuclease activity are within the same chamber. Sample preparation and amplification can be carried out within a fluidic device described herein or, alternatively, can be carried out prior to introduction into the fluidic device. As mentioned above, sample preparation of any nucleic acid amplification are optional, and can be excluded. In further cases, programmable nuclease reaction incubation and detection (readout) can be performed sequentially (one after another) or concurrently (at the same time). In some embodiments, sample preparation and/or amplification can be performed within a first fluidic device and then the sample can be transferred to a second fluidic device to carry out Steps 3 and 4 and, optionally, Step 2.

Workflows and systems compatible with the compositions and methods provided herein include one-pot reactions and two-pot reactions. In a one-pot reaction, amplification, reverse transcription, amplification and reverse transcription, or amplification and in vitro transcription, and detection can be carried out simultaneously in one chamber. In other words, in a one-pot reaction, any combination of reverse transcription, amplification, and in vitro transcription can be performed in the same reaction as detection. In a two-pot reaction, any combination of reverse transcription, amplification, and in vitro transcription can be performed in a first reaction, followed by detection in a second reaction. The one-pot or two-pot reactions can be carried out in any of the chambers of the devices disclosed herein.

A fluidic device for sample preparation can be referred to as a filtration device. In some embodiments, the filtration device for sample preparation resembles a syringe or, comprises, similar functional elements to a syringe. For example, a functional element of the filtration device for sample preparation includes a narrow tip for collection of liquid samples. Liquid samples can include blood, saliva, urine, or any other biological fluid. Liquid samples can also include liquid tissue homogenates. The tip, for collection of liquid samples, can be manufactured from glass, metal, plastic, or other biocompatible materials. The tip may be replaced with a glass capillary that may serve as a metering apparatus for the amount of biological sample added downstream to the fluidic device. For some samples, e.g., blood, the capillary may be the only fluidic device required for sample preparation. Another functional element of the filtration device for sample preparation may include a channel that can carry volumes from nL to mL, containing lysis buffers compatible with the programmable nuclease reaction downstream of this process. The channel may be manufactured from metal, plastic, or other biocompatible materials. The channel may be large enough to hold an entire fecal, buccal, or other biological sample collection swab. The filtration device may further contain a solution of reagents that will lyse the cells in each type of samples and release the nucleic acids so that they are accessible to the programmable nuclease. Active ingredients of the solution may be chaotropic agents, detergents, salts, and can be of high osmolality, ionic strength and pH. Chaotropic agents or chaotropes are substances that disrupt the three-dimensional structure in macromolecules such as proteins, DNA, or RNA. One example protocol comprises a 4 M guanidinium isothiocyanate, 25 mM sodium citrate·$2H_2O$, 0.5% (w/v) sodium lauryl sarcosinate, and 0.1 M β-mercaptoethanol), but numerous commercial buffers for different cellular targets may also be used. Alkaline buffers may also be used for cells with hard shells, particularly for environmental samples. Detergents such as sodium dodecyl sulphate (SDS) and cetyl trimethylammonium bromide (CTAB) may also be implemented to chemical lysis buffers. Cell lysis may also be performed by physical, mechanical, thermal or enzymatic means, in addition to chemically-induced cell lysis mentioned previously. The device may include more complex architecture depending on the type of sample, such as nanoscale barbs, nanowires, sonication capability in a separate chamber of the device, integrated laser, integrated heater, for example, a Peltier-type heater, or a thin-film planar heater, and/or microcapillary probes for electrical lysis. Any samples described herein can be used in this workflow. For example samples may include liquid samples collected from a subject being tested for a condition of interest. A fluidic, or filtration, device for sample preparation may be used for Step 1 of a workflow, as described above. A sample preparation fluidic device can process different types of biological sample: finger-prick blood, urine or swabs with fecal, cheek or other collection.

A fluidic device may be used to carry out any one of, or any combination of, Steps 2-4 (nucleic acid amplification, programmable nuclease reaction incubation, detection (readout)), as described above. Several variations of the fluidic device are consistent with the present disclosure. For example, fluidic devices can be compatible with a fluorescence or electrochemical readout that may be used in Step 2 to Step 4 of the workflow. Devices can perform three iterations of Steps 2 through 4 of the workflow. In one variation a this fluidic device, the programmable nuclease reaction, incubation, and detection (readout) steps are carried out, but not amplification. In another variation of said fluidic device, the device comprises a one-chamber reaction with amplification. In yet another variation of the fluidic device, the device comprises a two-chamber reaction with amplification.

In some embodiments, the fluidic device may be a pneumatic device. The pneumatic device may comprise one or more sample chambers connected to one or more detection chambers by one or more pneumatic valves. Optionally, the pneumatic device may further comprise one or more amplification chamber between the one or more sample chambers and the one or more detection chambers. The one or more amplification chambers may be connected to the one or more sample chambers and the one or more detection chambers by one or more pneumatic valves. A pneumatic valve may be made from PDMS, or any other suitable material. A pneumatic valve may comprise a channel perpendicular to a microfluidic channel connecting the chambers and allowing fluid to pass between chambers when the valve is open. In some embodiments, the channel deflects downward upon application of air pressure through the channel perpendicular to the microfluidic channel.

In some embodiments, the fluidic device may be a sliding valve device. The sliding valve device may comprise a sliding layer with one or more channels and a fixed layer with one or more sample chambers and one or more detection chambers. Optionally, the fixed layer may further comprise one or more amplification chambers. In some embodiments, the sliding layer is the upper layer and the fixed layer is the lower layer. In other embodiments, the sliding layer is the lower layer and the fixed layer is the upper layer. The sliding valve device may further comprise one or more of a side channel with an opening aligned with an opening in the sample chamber, a side channel with an opening aligned with an opening in the amplification chamber, or a side channel with an opening aligned with the opening in the detection chamber. In some embodiments the side channels are connected to a mixing chamber to allow transfer of fluid between the chambers. In some embodiments, the sliding valve device comprises a pneumatic pump for mixing, aspirating, and dispensing fluid in the device.

The chip (also referred to as fluidic device) may be manufactured from a variety of different materials. Exemplary materials that may be used include plastic polymers, such as poly-methacrylate (PMMA), cyclic olefin polymer (COP), cyclic olefin copolymer (COC), polyethylene (PE), high-density polyethylene (HDPE), polypropylene (PP); glass; and silicon. Features of the chip may be manufactured by various processes. For example, features may be (1) embossed using injection molding, (2) micro-milled or micro-engraved using computer numerical control (CNC) micromachining, or non-contact laser drilling (by means of a CO2 laser source); (3) additive manufacturing, and/or (4) photolithographic methods.

The design may include up to three (3) input ports operated by three (3) pumps. The pumps may be operated by external syringe pumps using low pressure or high pressure. The pumps may be passive, and/or active (pneumatic, piezoelectric, Braille pin, electroosmotic, acoustic, gas permeation, or other).

The ports may be connected to pneumatic pressure pumps, air or gas may be pumped into the microfluidic channels to control the injection of fluids into the fluidic device. At least three reservoirs may be connected to the device, each containing buffered solutions of: (1) sample, which may be a solution containing purified nucleic acids processed in a separate fluidic device, or neat sample (blood, saliva, urine, stool, and/or sputum); (2) amplification mastermix, which varies depending on the method used, wherein the method may include any of loop-mediated isothermal amplification (LAMP), strand displacement amplification (SDA), recombinase polymerase amplification (RPA), helicase dependent amplification (HDA), multiple displacement amplification (MDA), rolling circle amplification (RCA), and nucleic acid sequence-based amplification (NASBA), transcription mediated amplification (TMA), circular helicase dependent amplification (cHDA), exponential amplification reaction (EXPAR), ligase chain reaction (LCR), simple method amplifying RNA targets (SMART), single primer isothermal amplification (SPIA), hinge-initiated primer-dependent amplification of nucleic acids (HIP), nicking enzyme amplification reaction (NEAR), or improved multiple displacement amplification (IMDA); and (3) pre-complexed programmable nuclease mix, which includes one or more programmable nuclease and guide oligonucleotides. The method of nucleic acid amplification may also be polymerase chain reaction (PCR), which includes cycling of the incubation temperature at different levels, hence is not defined as isothermal. Often, the reagents for nucleic acid amplification comprise a recombinase, a oligonucleotide primer, a single-stranded DNA binding (SSB) protein, and a polymerase. Sometimes, nucleic acid amplification of the sample improves at least one of sensitivity, specificity, or accuracy of the assay in detecting the target nucleic acid. In some cases, the nucleic acid amplification is performed in a nucleic acid amplification region on the support medium. Alternatively or in combination, the nucleic acid amplification is performed in a reagent chamber, and the resulting sample is applied to the support medium. Sometimes, the nucleic acid amplification is isothermal nucleic acid amplification. Complex formation of a programmable nuclease with guides and detector nucleic acids may occur off the chip. An additional port for output of the final reaction products is depicted at the end of the fluidic path, and is operated by a similar pump, as the ones described for P1-P3. The reactions product can be, thus, collected for additional processing and/or characterization, e.g., sequencing.

The flow of liquid in this fluidic device may be controlled using up to four (4) microvalves. These valves can be electro-kinetic microvalves, pneumatic microvalves, vacuum microvalves, capillary microvalves, pinch microvalves, phase-change microvalves, burst microvalves.

The flow to and from the fluidic channel from each of P1-P4 is controlled by valves, labelled as V1-V4. The volume of liquids pumped into the ports can vary from nL to mL depending in the overall size of the device.

In some fluidic devices, no amplification is needed. After addition of sample and pre-complexed programmable nuclease mix in P1 and P2, respectively, the reagents may be mixed in the serpentine channel, S1, which then leads to chamber C1 where the mixture may be incubated at the required temperature and time. The readout can be done simultaneously in C1. Thermoregulation in C1 may be carried out using a thin-film planar heater manufactured, from e.g. Kapton, or other similar materials, and controlled by a proportional integral derivative (PID).

In some fluidic devices, after addition of sample, amplification mix, and pre-complexed programmable nuclease mix in P1, P2 and P3, respectively, the reagents can be mixed in the serpentine channel, S1, which then leads to chamber C1 where the mixture is incubated at the required temperature and time needed to efficient amplification, as per the conditions of the method used. The readout may be done simultaneously in C1. Thermoregulation may be achieved as previously described.

In some fluidic devices, amplification and programmable nuclease reactions occur in separate chambers. The pre-complexed programmable nuclease mix is pumped into the amplified mixture from C1 using pump P3. The liquid flow is controlled by valve V3, and directed into serpentine mixer S2, and subsequently in chamber C2 for incubation the required temperature, for example at 37° C. for 90 minutes.

During the detection step, the Cas-gRNA complex can bind to its matching nucleic acid target from the amplified sample and is activated into a non-specific nuclease, which cleaves a detector nucleic acid to generate a signal readout. In the absence of a matching nucleic acid target, the Cas-gRNA complex does not cleave the detector nucleic acid.

Real-time detection of the Cas reaction can be achieved by three methods: (1) fluorescence, (2) electrochemical detection, and (3) electrochemiluminescence. Detection of the signal can be achieved by multiple methods, which can detect a signal that is calorimetric, potentiometric, amperometric, optical (e.g., fluorescent, colorometric, etc.), or piezo-electric, as non-limiting examples.

Readout processes that can be used in conjunction with a fluidic device of the present disclosure includes (a) fluorescence readout and (b) electrochemical readout. The emitted fluorescence of cleaved detector nucleic acids may be monitored using a fluorimeter positioned directly above the detection and incubation chamber. The fluorimeter may be a commercially available instrument, the optical sensor of a mobile phone or smart phone, or a custom-made optical array comprising of fluorescence excitation means, e.g. CO2, other, laser and/or light emitting diodes (LEDs), and fluorescence detection means e.g. photodiode array, phototransistor, or others.

The fluorescence detection and excitation may be multiplexed, wherein, for example, fluorescence detection involves exciting and detecting more than one fluorophore in the incubation and detection chamber (C1 or C2). The fluorimeter itself may be multichannel, in which detecting and exciting light at different wavelengths, or more than one fluorimeter may be used in tandem, and their position above the incubation and detection chamber (C1 and C2) be modified by mechanical means, such as a motorized mechanism using micro or macro controllers and actuators (electric, electronic, and/or piezo-electric).

Two electrochemical detection variations are described herein, using integrated working, counter and reference electrodes in the incubation and detection chamber (C1 or C2):

Increase in Signal

The progress of the cleavage reaction catalyzed by the programmable nuclease may be detected using a streptavidin-biotin coupled reaction. The top surface of the detection and incubation chamber may be functionalized with nucleic acid molecules (ssRNA, ssDNA or ssRNA/DNA hybrid molecules) conjugated with a biotin moiety. The bottom surface of the detection and incubation chamber operates as an electrode, comprising of working, reference, and counter areas, manufactured (or screen-printed) from carbon, graphene, silver, gold, platinum, boron-doped diamond, copper, bismuth, titanium, antimony, chromium, nickel, tin, aluminum, molybdenum, lead, tantalum, tungsten, steel, carbon steel, cobalt, indium tin oxide (ITO), ruthenium oxide, palladium, silver-coated copper, carbon nano-tubes, or other metals. The bottom surface of the detection and incubation chamber may be coated with streptavidin molecules. In the absence of any biotin molecules, the current measured by a connected electrochemical analyzer (commercial, or custom-made) is low. When the pre-complexed programmable nuclease mix with amplified target flows in the detection and incubation chamber, and is activated at a higher temperature, for example at 37° C., cleavage of the single-stranded nucleic acid (ssNA) linker releases biotin molecules that can diffuse onto the streptavidin-coated bottom surface of the detection and incubation chamber. Because of the interaction of biotin and streptavidin molecules, an increase in the current is read by a coupled electrochemical analyzer.

Other types of signal amplification that use enrichment may also be used apart from biotin-streptavidin excitation. Non-limiting examples are: (1) glutathione, glutathione S-transferase, (2) maltose, maltose-binding protein, (3) chitin, chitin-binding protein.

Decrease in Signal

The progress of the programmable nuclease cleavage reaction may be monitored by recording the decrease in the current produced by a ferrocene (Fc), or other electroactive mediator moieties, conjugated to the individual nucleotides of nucleic acid molecules (ssRNA, ssDNA or ssRNA/DNA hybrid molecules) immobilized on the bottom surface of the detection and incubation chamber. In the absence of the amplified target, the programmable nuclease complex remains inactive, and a high current caused by the electroactive moieties is recorded. When the programmable nuclease complex with guides flows in the detection and incubation chamber and is activated by the matching nucleic acid target at 37° C., the programmable nuclease complex non-specifically degrades the immobilized Fc-conjugated nucleic acid molecules. This cleavage reaction decreases the number of electroactive molecules and, thus, leads to a decrease in recorded current.

The electrochemical detection may also be multiplexed. This is achieved by the addition of one or more working electrodes in the incubation and detection chamber (C1 or C2). The electrodes can be plain, or modified, as described above for the single electrochemical detection method.

Electrochemiluminescence in a Combined Optical and Electrochemical Readout Method The optical signal may be produced by luminescence of a compound, such as tri-propyl amine (TPA) generated as an oxidation product of an electroactive product, such as ruthenium bipyridine, [Ru (py)3]2+.

A number of different programmable nucleases may be multiplexed by: (1) separate fluidic paths (parallelization of channels), mixed with the same sample, for each of the nucleases, or (2) switching to digital (two-phase) microfluidics, where each individual droplet contains a separate reaction mix. The droplets could be generated from single or double emulsions of water and oil. The emulsions are compatible with programmable nuclease reaction, and optically inert.

In another example of a fluidic device consistent with the present disclosure, the device can be configured for coupled invertase/Cas reactions with colorimetric or electrochemical/glucometer readout. This diagram illustrates a fluidic device for miniaturizing a Cas reaction coupled with the enzyme invertase. Surface modification and readout processes are depicted in exploded view schemes at the bottom including (a) optical readout using DNS, or other compound and (b) electrochemical readout (electrochemical analyzer or glucometer). Described herein is the coupling of the Cas reaction with the enzyme invertase (EC 3.2.1.26), or sucrase or β-fructofuranosidase. This enzyme catalyzes the breakdown of sucrose to fructose and glucose.

The following methods may be used to couple the readout of the Cas reaction to invertase activity:

Colorimetry Using a Camera, Standalone, or an Integrated Mobile Phone Optical Sensor The amount of fructose and glucose is linked to a colorimetric reaction. Two examples are: (a) 3,5-Dinitrosalicylic acid (DNS), and (b) formazan dye thiazolyl blue. The color change can be monitored using a CCD camera, or the image sensor of a mobile phone. For this method, a variation of the device configured for coupled invertase/Cas reactions with colorimetric or electrochemical/glucometer readout can be used. The modification is the use of a camera, instead of a fluorimeter above C3.

Amperometry Using a Conventional Glucometer, or an Electrochemical Analyzer

In another example variation of a fluidic device, the device comprises the addition of one more incubation chamber C3. An additional step is added to the reaction scheme, which takes place in chamber C2. The top of the chamber surface is coated with single stranded nucleic acid that is conjugated to the enzyme invertase (Inv). The target-activated programmable nuclease complex cleaves the invertase enzyme from the oligo (ssRNA, ssDNA or ssRNA/DNA hybrid molecule), in C2, and invertase is then available to catalyze the hydrolysis of sucrose injected by pump P4, and controlled by valve V4. The mixture is mixed in serpentine mixer S3, and at chamber C3, the glucose produced may be detected colorimetrically, as previously described, electrochemically. The enzyme glucose oxidase is dried on the surface on C3, and catalyzes the oxidation of glucose to hydrogen peroxide and D-glucono-6-lactone.

A number of different devices are compatible with detection of target nucleic acids using the methods and compositions disclosed herein. In some embodiments, the device is any of the microfluidic devices disclosed herein. In other embodiments, the device is a lateral flow test strip connected to a reaction chamber. In further embodiments, the lateral flow strip may be connected to a sample preparation device.

In some embodiments, the fluidic device may be a pneumatic device. The pneumatic device may comprise one or more sample chambers connected to one or more detection chambers by one or more pneumatic valves. Optionally, the pneumatic device may further comprise one or more amplification chamber between the one or more sample chambers and the one or more detection chambers. The one or more amplification chambers may be connected to the one or more sample chambers and the one or more detection chambers by one or more pneumatic valves. A pneumatic valve may be made from PDMS, or any other suitable material. A pneumatic valve may comprise a channel perpendicular to a microfluidic channel connecting the chambers and allowing fluid to pass between chambers when the valve is open. In some embodiments, the channel deflects downward upon application of air pressure through the channel perpendicular to the microfluidic channel.

In some embodiments, the fluidic device may be a sliding valve device. The sliding valve device may comprise a sliding layer with one or more channels and a fixed layer with one or more sample chambers and one or more detection chambers. Optionally, the fixed layer may further comprise one or more amplification chambers. In some embodiments, the sliding layer is the upper layer and the fixed layer is the lower layer. In other embodiments, the sliding layer is the lower layer and the fixed layer is the upper layer. In some embodiments, the upper layer is made of a plastic polymer comprising poly-methacrylate (PMMA), cyclic olefin polymer (COP), cyclic olefin copolymer (COC), polyethylene (PE), high-density polyethylene (HDPE), polypropylene (PP); a glass; or a silicon. In some embodiments, the lower layer is made of a plastic polymer comprising poly-methacrylate (PMMA), cyclic olefin polymer (COP), cyclic olefin copolymer (COC), polyethylene (PE), high-density polyethylene (HDPE), polypropylene (PP); a glass; or a silicon. The sliding valve device may further comprise one or more of a side channel with an opening aligned with an opening in the sample chamber, a side channel with an opening aligned with an opening in the amplification chamber, or a side channel with an opening aligned with the opening in the detection chamber. In some embodiments the side channels are connected to a mixing chamber to allow transfer of fluid between the chambers. In some embodiments, the sliding valve device comprises a pneumatic pump for mixing, aspirating, and dispensing fluid in the device.

Pneumatic Valve Device

A microfluidic device particularly well suited for carrying out the DETECTR reactions described herein (e.g., multiplexed DETECTR reactions or high-plex DETECTR reactions) is one comprising a pneumatic valve, also referred to as a "quake valve". The pneumatic valve can be closed and opened by the flow of air from, for an example, an air manifold. The opening of the pneumatic valve can lead to a downward deflection of the channel comprising the pneumatic valve, which can subsequently deflect downwards and seal off a microfluidic channel beneath the channel comprising the pneumatic valve. This can lead to stoppage of fluid flow in the microfluidic channel. When the air manifold is turned off, the flow of air through the channel comprising the quake valve ceases and the microfluidic channel beneath the channel comprising the quake valve is "open", and fluid can flow through. In some embodiments, the channel comprising the pneumatic valve may be above or below the microfluidic channel carrying the fluid of interest. In some embodiments, the channel comprising the pneumatic valve can be parallel or perpendicular to the microfluidic channel carrying the fluid of interest. Pneumatic valves can be made of a two hard thermoplastic layers sandwiching a soft silicone layer.

One example layout is as follows. In some embodiments, the device comprises a sample chamber and a detection chamber, wherein the detection chamber is fluidically connected to the sample chamber by a pneumatic valve and wherein the detection chamber comprises any programmable nuclease of the present disclosure. Optionally, the device can also include an amplification chamber that is between the fluidic path from the sample chamber to the detection chamber, is connected to the sample chamber by a pneumatic valve, and is additionally connected to the detection chamber by a pneumatic valve. In some embodiments, the pneumatic valve is made of PDMS, or any other material for forming microfluidic valves. In some embodiments, the sample chamber has a port for inserting a sample. The sample can be inserted using a swab. The sample chamber can have a buffer for lysing the sample. The sample chamber can have a filter between the chamber and the fluidic channel to the amplification or detection chambers. The sample chamber may have an opening for insertion of a sample. A sample can be incubated in the sample chamber for from 30 seconds to 10 minutes. The air manifold may until this point be on, pushing air through the pneumatic valve and keeping the fluidic channel between the sample chamber and the amplification or detection chambers closed. At this stage, the air manifold can be turned off, such that no air is passing through the pneumatic valve, and allowing the microfluidic channel to open up and allow for fluid flow from the sample chamber to the next chamber (e.g., the amplification or detection chambers). In devices where there is an amplification chamber, the lysed sample flows from the sample chamber into the amplification chamber. Otherwise, the lysed sample flows from the sample chamber into the detection chamber. At this stage, the air manifold is turned back on, to push air through the pneumatic valve and seal the microfluidic channel. The amplification chamber holds various reagents for amplification and, optionally, reverse transcription of a target nucleic acid in the sample. These reagents may include forward and reverse primers, a deoxynucleotide triphosphate, a reverse transcriptase, a T7 promoter, a T7 polymerase, or any combination thereof. The sample is allowed to incubate in the amplification chamber for from 5 minutes to 40 minutes. The amplified and, optionally reverse transcribed, sample is moved into the detection chamber as described above: the air manifold is turned off, ceasing air flow through the pneumatic valve and opening the microfluidic channel. The detection chamber can include any programmable nuclease disclosed herein, a guide nucleic acid (e.g., a guide RNA) with a portion reverse complementary to a portion of the target nucleic acid, and any detector nucleic acid disclosed herein. In some embodiments, the detection chamber may comprise a plurality of guide RNAs. The plurality of guide RNAs may have the same sequence, or one or more of the plurality of guide RNAs may have different sequences. In some embodiments, the plurality of guide RNAs has a portion reverse complementary to a portion of a target nucleic acid different than a second RNA of the plurality of guide RNAs. The plurality of guide RNAs may comprise at least 5, at least 10, at least 15, at least 20, or at least 50 guide RNAs. Once the sample is moved into the detection chamber, the DETECTR reaction can be carried out for 1 minute to 20 minutes. Upon hybridization of the guide RNA to the target nucleic acid, the programmable nuclease is activated and begins to collaterally cleave the detector nucleic acid, which as described elsewhere in this disclosure has a nucleic acid and one or more molecules that enable detection of cleavage. The detection chamber can interface with a device for reading out for the signal. For example, in the case of a colorimetric or fluorescence signal generated upon cleavage, the detection chamber may be coupled to a spectrophotometer or fluorescence reader. In the case where an electrochemical signal is generated, the detection chamber may have one to 10 metal leads connected to a readout device (e.g., a glucometer). The top layer of a cartridge of a pneumatic valve device of the present disclosure can have dimensions of 2 inches by 1.5 inches. In a modification of a top layer of a cartridge of a pneumatic valve device of the present disclosure, the cartridge can be adapted for electrochemical detection. In this device, wiring (or "metal leads", which are co-molded, 3D-printed, or manually assembled in the disposable cartridge to form a three-electrode system can in the detection chambers Electrodes are termed as working, counter, and reference. Electrodes can also be screen printed on the cartridges. Metals used can be carbon, gold, platinum, or silver. A major advantage of the pneumatic valve device is that the pneumatic valves connecting the various chambers of the device prevent backflow from chamber to chamber, which reduces contamination. Prevention of backflow and preventing sample contamination is especially important for the applications described herein. Sample contamination can result in false positives or can generally confound the limit of detection for a target nucleic acid. As another example, the pneumatic valves disclosed herein are particularly advantageous for devices and methods for multiplex detection. In multiplexed assays, where two or more target nucleic acids are assayed for, it is particularly important that backflow and contamination is avoided. Backflow between chambers in a multiplexed assay can lead to cross-contamination of different guide nucleic acids or different programmable nuclease and can result in false results. Thus, the pneumatic valve device, which is designed to minimize or entirely avoid backflow, is particularly superior, in comparison to other device layouts, for carrying out the detection methods disclosed herein.

In one variation, a device consistent with the compositions and methods disclosed herein can have a layout comprising a quake valve pneumatic pump configured for a DETECTR assay. A pipette pump can aspirate and dispense samples. An air manifold can be connected to a pneumatic pump to open and close the normally closed valve. The pneumatic device can move fluid from one position to the next. The pneumatic design can have reduced channel cross talk compared to other device designs. A cartridge can be adapted for use in the pneumatic valve device. The normally closed valves can comprise an elastomeric seal on top of the channel to isolate each chamber from the rest of the system when the chamber is not in use. The pneumatic pump uses air to open and close the valve as needed to move fluid to the necessary chambers within the cartridge. A sample can be placed in the sample well while all valves are closed. The sample can be lysed in the sample well. The lysed sample can be moved from the sample chamber to a second chamber by opening the first quake valve, and the sample can be aspirated using the pipette pump. The sample can then be moved to the first amplification chamber by closing the first quake valve and opening a second quake valve where it is mixed with the amplification mixture. After the sample is mixed with the amplification mixture, it can be moved to a subsequent chamber by closing the second quake valve and opening a third quake valve. The sample can be moved to the DETECTR chamber by closing the third quake valve and opening a fourth quake valve. The sample can be moved through a different series of chambers by opening and closing a different series of quake valves. Actuation of individual valves in the desired chamber series prevents cross contamination between channels. In some embodiments the sliding valve device has a surface area of 5 cm by 5 cm, 5 by 6 cm, 6 by 7 cm, 7 by 8 cm, 8 by 9 cm, 9 by 10 cm, 10 by 11 cm, 11 by 12 cm, 6 by 9 cm, 7 by 10 cm, 8 by 11 cm, 9 by 12 cm, 10 by 13 cm, 11 by 14 cm, 12 by 11 cm, about 30 sq cm, about 35 sq cm, about 40 sq cm, about 45 sq cm, about 50 sq cm, about 55 sq cm, about 60 sq cm, about 65 sq cm, about 70 sq cm, about 75 sq cm, about 25 sq cm, about 20 sq cm, about 15 sq cm, about 10 sq cm, about 5 sq cm, from 1 to 100 sq cm, from 5 to 10 sq cm, from 10 to 15 sq cm, from 15 to 20 sq cm, from 20 to 25 sq cm, from 25 to 30 sq cm, from 30 to 35 sq cm, from 35 to 40 sq cm, from 40 to 45 sq cm, from 45 to 50 sq cm, from 5 to 90 sq cm, from 10 to 0 sq cm, from 15 to 5 sq cm, from 20 to 10 sq cm, or from 25 to 15 sq cm.

Sliding Valve Device

A microfluidic device particularly well suited for carrying out the DETECTR reactions described herein (e.g., multiplexed DETECTR reactions or high-plex DETECTR reactions) is a sliding valve device. The sliding valve device can have a sliding layer and a fixed layer. The sliding layer may be on top and the fixed layer may be on bottom. Alternatively, the sliding layer may be on bottom and the fixed layer may be on top. In some embodiments, the sliding valve has a channel. The channel can have an opening at one end that interacts with an opening in a chamber and the channel can also have an opening at the other end that interacts with an opening in a side channel. In some embodiments, the sliding layer has more than one opening. In some embodiments, the fixed layer comprises a sample chamber, an amplification chamber, and a detection chamber. The sample chamber, the amplification chamber, and the detection layer can all have an opening at the bottom of the chambers. For example, the sample chamber may have an opening for insertion of a sample. When the opening in a chamber is aligned with the opening in a channel, fluid can flow from the chamber into the channel. Further, when the opening in the channel is subsequently aligned with an opening in a side channel, fluid can flow from the channel into the side channel. The side channel can be further fluidically connected to a mixing chamber, or a port in which an instrument (e.g., a pipette pump) for mixing fluid is inserted. Alignment of openings can be enabled by physically moving or automatically actuating the sliding layer to slide along the length of the fixed layer. In some embodiment, the above described pneumatic valves can be added at any position to the sliding valve device in order to control the flow of fluid from one chamber into the next. The sliding valve device can also have multiple layers. For example, the sliding valve can have 2, 3, 4, 5, 6, 7, 8, 9, 10, or more layers.

In one layout of a device for a DETECTR assay, at top is a pneumatic pump, which interfaces with a cartridge. At middle, if observing from a top down view of the cartridge, is a layer with reservoirs. At bottom is a sliding valve containing the sample, which can flow into a a lysis chamber positioned to the left of the sample, following by amplification chambers to the right, and detection chambers further to the right. Offset pitches of the channels can allow for aspirating and dispensing into each well separately and helps to mitigate cross talk between the amplification chambers and corresponding chambers. In an initial closed position, the sample can be loaded into the sample well and lysed. The sliding valve can then be actuated by the instrument, and samples can be loaded into each of the channels using the pipette pump, which dispenses the appropriate volume into the channel. The sample can be delivered to the amplification chambers by actuating the sliding valve and mixed with the pipette pump. Samples from the amplification chamber can be aspirated into each channel and then dispensed and mixed into each DETECTR chamber by actuating the sliding valve and pipette pump. In some embodiments the sliding valve device can have a surface area of 5 cm by 8 cm, 5 by 6 cm, 6 by 7 cm, 7 by 8 cm, 8 by 9 cm, 9 by 10 cm, 10 by 11 cm, 11 by 12 cm, 6 by 9 cm, 7 by 10 cm, 8 by 11 cm, 9 by 12 cm, 10 by 13 cm, 11 by 14 cm, 12 by 11 cm, about 30 sq cm, about 35 sq cm, about 40 sq cm, about 45 sq cm, about 50 sq cm, about 55 sq cm, about 60 sq cm, about 65 sq cm, about 70 sq cm, about 75 sq cm, about 25 sq cm, about 20 sq cm, about 15 sq cm, about 10 sq cm, about 5 sq cm, from 1 to 100 sq cm, from 5 to 10 sq cm, from 10 to 15 sq cm, from 15 to 20 sq cm, from 20 to 25 sq cm, from 25 to 30 sq cm, from 30 to 35 sq cm, from 35 to 40 sq cm, from 40 to 45 sq cm, from 45 to 50 sq cm, from 5 to 90 sq cm, from 10 to 0 sq cm, from 15 to 5 sq cm, from 20 to 10 sq cm, or from 25 to 15 sq cm.

Lateral Flow Devices

In some embodiments, a device of the present disclosure comprises a chamber and a lateral flow strip. Lateral flow strips can be used in the DETECTR assay methods disclosed herein. Detector nucleic acids of the present disclosure can comprise a DNA linker linked to a biotin-dT bound to a FAM molecule. Milenia HybridDetect lateral flow strips can be used with the modified detector nucleic acids disclosed herein. This particular layout improves the test result by generating higher signal in the case of a positive result, while also minimizing false positives. In this assay layout, the detector nucleic acid comprises a biotin and a fluorophore attached at one of a nucleic acid. The nucleic acid can be conjugated directly to the biotin molecule and then the fluorophore or directly to the fluorophore and then to the biotin. Other affinity molecules, including those described herein can be used instead of biotin. Any of the fluorophores disclosed herein can also be used in the detector nucleic acid. The detector nucleic acid can be suspended in solution or immobilized on the surface of the Cas chamber. Alternatively, the detector nucleic acid can be immobilized on beads, such as magnetic beads, in the reaction chamber where they are held in position by a magnet placed below the chamber. When the detector nucleic acid is cleaved by an activated programmable nuclease, the cleaved biotin-fluorophore accumulates at the first line, which comprises a streptavidin (or another capture molecule). Gold nanoparticles, which are on the sample pad and flown onto the strip using a chase buffer, are coated with an anti-fluorophore antibody allowing binding and accumulation of the gold nanoparticle at the first line. The nanoparticles additionally accumulate at a second line which is coated with an antibody (e.g., anti-rabbit) against the antibody coated on the gold nanoparticles (e.g., rabbit, anti-FAM). In the case of a negative result, the detector nucleic acid is not cleaved and does not flow on the lateral flow strip. Thus, the nanoparticles only bind and accumulate at the second line Multiplexing on the lateral flow strip can be performed by having two detector nucleic acids (e.g., a biotin-FAM detector nucleic acid and a biotin-DIG detector nucleic acid). Anti-FAM and anti-DIG antibodies are coated onto the lateral flow strip at two different regions. Anti-biotin antibodies are coated on gold nanoparticles. Fluorophores are conjugated directly to the affinity molecules (e.g., biotin) by first generating a biotin-dNTP following from the nucleic acids of the detector nucleic acid and then conjugating the fluorophore. In some embodiments, the lateral flow strip comprises multiple layers.

In some embodiments, the above lateral flow strip can be additionally interfaced with a sample preparation device. Individual parts of sample preparation devices of the present disclosure can include the following: a single chamber sample extraction device comprising: (a) an insert holds the sample collection device and regulates the step between sample extraction and dispensing the sample into another reaction or detection device, (b) the single chamber contains extraction buffer. The dispensing chamber can be filled with material that further purifies the nucleic acid as it is dispensed: (a) the insert holds the sample collection device and regulates the "stages" of sample extraction and nucleic acid amplification. Each set of notches in a sample preparation device between the multiple chambers can be offset 90° from the preceding set, (b) the reaction module can contain multiple chambers separated by substrates that allow for independent reactions to occur. (e.g., i. a nucleic acid separation chamber, ii. a nucleic acid amplification chamber and iii. a DETECTR reaction chamber or dispensing chamber). Each chamber has notches that prevent the insert from progressing into the next chamber without a deliberate 90° turn. The first two chambers may be separated by material that removes inhibitors between the extraction and amplification reactions. Options for the reaction/dispensing chamber can include: (a) a single dispensing chamber may release only extracted sample or extraction/amplification or extraction/amplification/DETECTR reactions, (b) a duel dispensing chamber may release extraction/multiplex amplification products, and (c) a quadruple dispensing chamber would allow for multiplexing amplification and single DETECTR or four single amplification reactions. A sample work flow using a sample processing device can be as follows. The sample collection device is attached to the insert portion of the sample processing device. The insert is placed into the device chamber and pressed until the first stop (lower tabs on top portion meet upper tabs on bottom portion). This step allows the sample to come into contact with the nucleic acid extraction reagents. After the appropriate amount of time, the insert is turned 90° and depressed to the next set of notches. These actions transfer the sample into the amplification chamber. The sample collection device is no longer in contact with the sample or amplification products. After the appropriate incubation, the insert is rotated 90° and depressed to the next set of notches. These actions release the sample into the DETECTR (green reaction). The insert is again turned 90° and depressed to dispense the reaction.

General Features of Devices

In some embodiments, a device of the present disclosure can hold 2 or more amplification chambers. In some embodiments, a device of the present disclosure can hold 10 or more detection chambers. In some embodiments, a device of the present disclosure comprises a single chamber in which sample lysis, target nucleic acid amplification, reverse transcription, and detection are all carried out. In some cases, different buffers are present in the different chambers. In some embodiments, all the chambers of a device of the present disclosure have the same buffer. In some embodiments, the sample chamber comprises the lysis buffer and all of the materials in the amplification and detection chambers are lyophilized or vitrified. In some embodiments, the sample chamber includes any buffer for lysing a sample disclosed herein. The amplification chamber can include any buffer disclosed herein compatible with amplification and/or reverse transcription of target nucleic acids. The detection chamber can include any DETECTR or CRISPR buffer (e.g., an MBuffer) disclosed herein or otherwise capable of allowing DETECTR reactions to be carried out. In this case, once sample lysing has occurred, volume is moved from the sample chamber to the other chambers in an amount enough to rehydrate the materials in the other chambers. In some embodiments, the device further comprises a pipette pump at one end for aspirating, mixing, and dispensing liquids. In some embodiments, an automated instrument is used to control aspirating, mixing, and dispensing liquids. In some embodiments, no other instrument is needed for the fluids in the device to move from chamber to chamber or for sample mixing to occur. A device of the present disclosure may be made of any suitable thermoplastic, such as COC, polymer COP, teflon, or another thermoplastic material. Alternatively, the device may be made of glass. In some embodiments, the detection chamber may include beads, such as nanoparticles (e.g., a gold nanoparticle). In some embodiments, the detector nucleic acids are immobilized on the beads. In some embodiments, after cleavage from the bead, the liberated detector nucleic acids flow into a secondary detection chamber, where detection of a generated signal occurs by any one of the instruments disclosed herein. In some embodiments, the detection chamber is shallow, but has a large surface area that is optimized for optical detection. A device of the present disclosure may also be coupled to a thermoregulator. For example, the device may be on top of or adjacent to a planar heater that can heat the device up to high temperatures. Alternatively, a metal rod conducting heat is inserted inside the device and presses upon a soft polymer. The heat is transferred to the sample by dissipating through the polymer and into the sample. This allows for sample heating with direct contact between the metal rod and the sample. In some embodiments, in addition to or in place of a buffer for lysing a sample, the sample chamber may include an ultrasonicator for sample lysis. A swab carrying the sample may be inserted directly into the sample chamber. Commonly, a buccal swab may be used, which can carry blood, urine, or a saliva sample. A filter may be included in any of the chambers in the devices disclosed herein to filter the sample prior to carrying it to the next step of the method. Any of the devices disclosed herein can be couple to an additional sample preparation module for further manipulation of the sample before the various steps of the DETECTR reaction. In some embodiments the detector nucleic acid can be in solution in the detection chamber. In other embodiments, the detector nucleic acid can be immobilized directly on the surface of the detection chamber. The surface can be the top or the bottom of the chamber. In still other embodiments, the detector nucleic acid can be immobilized to the surface of a bead. In the case of a bead, after cleavage, the detectable signal may be washed into a subsequent chamber while the bead remains trapped—thus allowing for separation of the detectable signal from the bead. Alternatively, cleavage of the detector nucleic acid off of the surface of the bead is enough to generate a strong enough detectable signal to be measured. By sequestering or immobilizing the above described detector nucleic acids, the stability of the detector nucleic acids in the devices disclosed herein carrying out DETECTR reactions may be improved. Any of the above devices can be compatible for colorimetric, fluorescence, amperometric, potentiometric, or another electrochemical signal. In some embodiments, the colorimetric, fluorescence, amperometric, potentiometric, or another electrochemical sign may be detected using a measurement device connected to the detection chamber (e.g., a fluorescence measurement device, a spectrophotometer, or an oscilloscope).

In some embodiments, signals themselves can be amplified, for example via use of an enzyme such as horse radish peroxidase (HRP). In some embodiments, biotin and avidin reactions, which bind at a 4:1 ratio can be used to immobilize multiple enzymes or secondary signal molecules (e.g., 4 enzymes of secondary signal molecules, each on a biotin) to a single protein (e.g., avidin). In some embodiments, an electrochemical signal may be produced by an electrochemical molecule (e.g., biotin, ferrocene, digoxigenin, or invertase). In some embodiments, the above devices could be couple with an additional concentration step. For example, silica membranes may be used to capture nucleic acids off a column and directly apply the Cas reaction mixture on top of said filter. In some embodiments, the sample chamber of any one of the devices disclosed herein can hold from 20 ul to 1000 ul of volume. In some embodiments, the sample chamber holds from 20 to 500, from 40 to 400, from 30 to 300, from 20 to 200 or from 10 to 100 ul of volume. In preferred embodiments, the sample chamber holds 200 ul of volume. The amplification and detection chambers can hold a lower volume than the sample chamber. For example, the amplification and detection chambers may hold from 1 to 50, 10 to 40, 20 to 30, 10 to 40, 5 to 35, 40 to 50, or 1 to 30 ul of volume. Preferably, the amplification and detection chambers may hold about 200 ul of volume. In some embodiments, an exonuclease is present in the amplification chamber or may be added to the amplification chamber. The exonuclease can clean up single stranded nucleic acids that are not the target. In some embodiments, primers for the target nucleic acid can be phosophorothioated in order to prevent degradation of the target nucleic acid in the presence of the exonuclease. In some embodiments, any of the devices disclosed herein can have a pH balancing well for balancing the pH of a sample. In some embodiments, in each of the above devices, the detector nucleic acid is present in at least four-fold excess of total nucleic acids (target nucleic acids+non-target nucleic acids). Preferably the detector nucleic acid is present in at least 10-fold excess of total nucleic acids. In some embodiments, the detector nucleic acid is present in at least 4-fold, at least 5-fold at least 6-fold, at least 7-fold, at least 8-fold, at least 9-fold, at least 10-fold, at least 15-fold, at least 20-fold, at least 50-fold, at least 100-fold, from 1.5 to 100-fold, from 4 to 80-fold, from 4 to 10-fold, from 5 to 20-fold or from 4 to 15-fold excess of total nucleic acids. In some embodiments, any of the devices disclosed herein can carry out a DETECTR reaction (e.g., a multiplexed DETECTR reaction or a high-plex DETECTR reaction) with a limit of detection of at least 0.1 aM, at least 0.1 nM, at least 1 nM or from 0.1 aM to 1 nM. In some embodiments, the devices disclosed herein can carry out a DETECTR reaction with a positive predictive value of at least 75%, at least 80%, at least 85%, at least 90%, at least 92%, at least 95%, at least 97%, at least 99%, or 100%. In some embodiments, the devices disclosed herein can carry out a DETECTR reaction with a negative predictive value of at least 75%, at least 80%, at least 85%, at least 90%, at least 92%, at least 95%, at least 97%, at least 99%, or 100%. In some embodiments, spatial multiplexing in the above devices is carried out by having at least one, more than one, or every detection chamber in the device comprise a unique guide nucleic acid (e.g., guide RNA).

Kit

Disclosed herein are kits, reagents, methods, and systems for use to detect a target nucleic acid. In some embodiments, the kit comprises the reagents and a support medium. The reagent may be provided in a reagent chamber or on the support medium. Alternatively, the reagent may be placed into the reagent chamber or the support medium by the individual using the kit. Optionally, the kit further comprises a buffer and a dropper. The reagent chamber be a test well or container. The opening of the reagent chamber may be large enough to accommodate the support medium. The buffer may be provided in a dropper bottle for ease of dispensing. The dropper can be disposable and transfer a fixed volume. The dropper can be used to place a sample into the reagent chamber or on the support medium.

In some embodiments, a kit for detecting a plurality of target nucleic acids comprising a support medium; a plurality of guide nucleic acids (e.g., guide RNAs) targeting the plurality of target nucleic acids; a programmable nuclease capable of being activated when complexed with a guide nucleic acid from the plurality of guide nucleic acids and a target nucleic acid from the plurality of target nucleic acid populations; and a single-stranded detector nucleic acid comprising a detection moiety, wherein the detector nucleic acid is capable of being cleaved by the activated nuclease, thereby generating a first detectable signal.

In some embodiments, a kit for detecting a target nucleic acid comprising a PCR plate; a plurality of guide nucleic acids targeting a plurality of target nucleic acids; a programmable nuclease capable of being activated when complexed with a guide nucleic acid of the plurality of guide nucleic acids and a target nucleic acid of the plurality of target nucleic acids; and a single stranded detector nucleic acid comprising a detection moiety, wherein the detector nucleic acid is capable of being cleaved by the activated nuclease, thereby generating a first detectable signal. The wells of the PCR plate can be pre-aliquoted with one or more guide nucleic acids of the plurality of guide nucleic acids targeting one or more target nucleic acids of the plurality of target nucleic acids, a programmable nuclease capable of being activated when complexed with the guide nucleic acid and the target sequence, and at least one population of a single stranded detector nucleic acid comprising a detection moiety. In some embodiments, one or more wells of the PCR plate may be pre-aliquoted with the plurality of guide nucleic acids. In some embodiments, one or more wells of the PCR plate may be pre-aliquoted with a subset of the plurality of guide nucleic acids, wherein the subset comprises one or more guide nucleic acids of the plurality of guide nucleic acids. A user can thus add the biological sample of interest to a well of the pre-aliquoted PCR plate and measure for the detectable signal with a fluorescent light reader or a visible light reader.

In some instances, such kits may include a package, carrier, or container that is compartmentalized to receive one or more containers such as vials, tubes, and the like, each of the container(s) comprising one of the separate elements to be used in a method described herein. Suitable containers include, for example, test wells, bottles, vials, and test tubes. In one embodiment, the containers are formed from a variety of materials such as glass, plastic, or polymers.

The kit or systems described herein contain packaging materials. Examples of packaging materials include, but are not limited to, pouches, blister packs, bottles, tubes, bags, containers, bottles, and any packaging material suitable for intended mode of use.

A kit typically includes labels listing contents and/or instructions for use, and package inserts with instructions for use. A set of instructions will also typically be included. In one embodiment, a label is on or associated with the container. In some instances, a label is on a container when letters, numbers or other characters forming the label are attached, molded or etched into the container itself, a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

After packaging the formed product and wrapping or boxing to maintain a sterile barrier, the product may be terminally sterilized by heat sterilization, gas sterilization, gamma irradiation, or by electron beam sterilization. Alternatively, the product may be prepared and packaged by aseptic processing.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," "less than or equal to," or "at most" precedes the first numerical value in a series of two or more numerical values, the term "no more than," "less than" or "less than or equal to," or "at most" applies to each of the numerical values in that series of numerical values. For example, less than or equal to 3, 2, or 1 is equivalent to less than or equal to 3, less than or equal to 2, or less than or equal to 1.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

EXAMPLES

The following examples are illustrative and non-limiting to the scope of the devices, methods, reagents, systems, and kits described herein.

Example 1

DETECTR Reactions Simulating a 20-Plex Guide Pool, a 50-Plex Guide Pool, and a 100-Plex Guide Pool DETECTR Reactions This example describes DETECTR reactions simulating a 20-plex guide pool, a 50-plex guide pool, and a 100-plex guide pool DETECTR reactions using an LbCas12a programmable nuclease (SEQ ID NO: 18). To demonstrate the viability of high-plex guide pooling for use in high-plex DETECTR reactions, experiments using two guide nucleic acid sequences were performed. In each experiment two guide nucleic acid sequences were combined at different concentration ratios. The first guide nucleic acid was directed to a segment of a target nucleic acid and the second guide nucleic acid was a segment of an off-target nucleic acid. The lower concentration guide nucleic acid sequence was held constant at 20 nM in each reaction while the higher concentration guide nucleic acid sequence was varied at 380 nM, 980 nM, or 1980 nM in the simulated 20-plex, 50-plex, and 100-plex DETECTR reactions, respectively. The total guide nucleic acid concentration in the simulated 20-plex, 50-plex, and 100-plex DETECTR reactions was 400 nM, 1000 nM (1 μM), and 2000 nM (2 μM), respectively. The concentration of the LbCas12a in each reaction was proportional to the total guide nucleic acid concentration. The concentration of LbCas12a in the simulated 20-plex, 50-plex, and 100-plex DETECTR reactions was 400 nM, 1000 nM (1 μM), and 2000 nM (2 μM), respectively. The sequences of the guide nucleic acids and target nucleic acids used in this assay are provided in TABLE 5.

TABLE 5

Guide Nucleic Acid and Target Nucleic Acid Sequences

| SEQ ID NO: | Type | Sequence |
|---|---|---|
| SEQ ID NO: 171 | gRNA to human RNase P | UAAUUUCUACUAAGUGUAGAU CCAGAACACAUAGCGACAUG |
| SEQ ID NO: 172 | gRNA to human ß-globin | UAAUUUCUACUAAGUGUAGAU UAUUGGUCUCCUUAAACCUG |
| SEQ ID NO: 173 | Human RNase P target | CGTGGCCCCACTGATGAGCTT CCCTCCGCCCTATGGGAAAAA GTGGTCTCATACAGAACTTAT AAGATTCCCAAATCCAAAGAC ATTTCACGTTTATGGTGATTT CCCAGAACACATAGCGACATG CAAATA |
| SEQ ID NO: 174 | Human ß-globin target | CCTATCAGAAACCCAAGAGTC TTCTCTGTCTCCACATGCCCA GTTTCTATTGGTCTCCTTAAA CCTGTCTTGTAACCTTGATAC CAACCTGCCCAGGGCCTCACC ACCAACTTCATCCACGTTCAC |

For each reaction, guide nucleic acids were complexed 1:1 with the LbCas12a programmable nuclease at 4-fold the final concentration in Tris, pH 8.0 buffer (20 mM Tris HCl, pH 8.0, 100 mM NaCl, 5 mM $MgCl_2$, 1 mM DTT, 5% glycerol, 50 μg/mL Heparin). The concentration of each of the pooled guide nucleic acid and the programmable nuclease in the complexing reaction was 1.6 μM, 4 μM, and 8 μM for the simulated 20-plex, 50-plex, and 100-plex DETECTR reactions, respectively. Complexing reactions were incubated for 30 minutes at 37° C. to form complexes. Each complexing reaction was then combined in equal volumes with 400 nM single-stranded DNA detector nucleic acid (SEQ ID NO: 9 labeled at the 5' end with FAM and labeled at the 3' end with Iowa Black FQ) in Tris, pH 8.0 buffer with an additional 16% glycerol. The combined complexing reaction and detector nucleic acid were then combined in equal with a sample containing a target nucleic such that the final target nucleic acid concentration was 10 pM, 100 pM, or 1000 pM.

FIG. 2 shows raw fluorescence over time of multiplexed DETECTR reactions using an LbCas12a programmable nuclease (SEQ ID NO: 18). Each multiplexed DETECTR reaction was performed with two guide RNA sequences. In each reaction, a first guide nucleic acid sequence was present at either 19-fold, 49-fold, or 99-fold higher concentration than the second guide nucleic acid sequence to simulate 20-plex, 50-plex, or 100-plex high-plex DETECTR reactions, respectively. An 8-nucleotide single-stranded DNA detector nucleic acid labeled at the 5' end with FAM and labeled at the 3' end with Iowa Black FQ with a sequence of SEQ ID NO: 9 was used in each reaction.

Figure 2A:
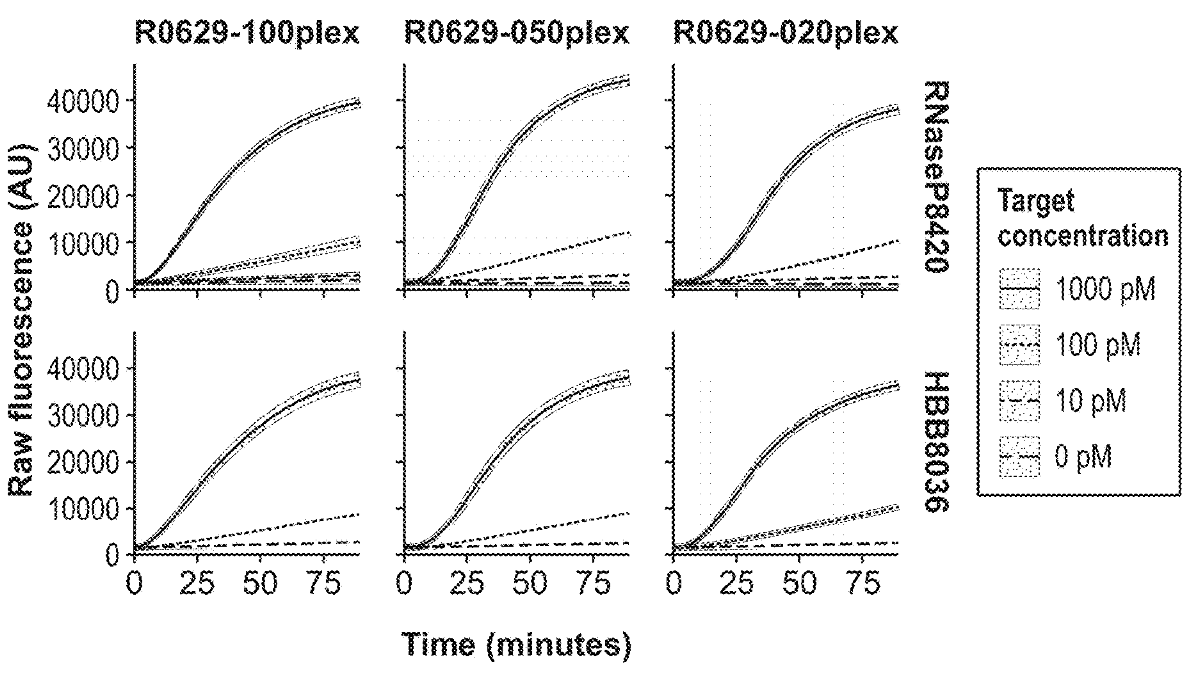
FIGS. 2A-2B show raw fluorescence over time of multiplexed DETECTR reactions using an LbCas12a programmable nuclease (SEQ ID NO: 18). Each multiplexed DETECTR reaction was performed with two distinct guide RNA sequences. In each reaction, a first guide nucleic acid sequence was present at either 19-fold, 49-fold, or 99-fold higher concentration than the second guide nucleic acid sequence to simulate 20-plex, 50-plex, or 100-plex high-plex DETECTR reactions, respectively. An 8-nucleotide single-stranded DNA detector nucleic acid labeled at the 5' end with FAM and labeled at the 3' end with Iowa Black FQ with a sequence of SEQ ID NO: 9 was used in each reaction.

FIG. 2A shows a first set of DETECTR reactions in which a guide RNA sequence targeting a human β-globin gene (SEQ ID NO: 172) was present in 19-fold ("20plex"), 49-fold ("50plex"), or 99-fold ("100plex") higher concentration than a guide RNA sequence targeting a human RNAase P gene (SEQ ID NO: 171). The pooled guide RNAs were used to detect the presence or absence of a double-stranded DNA target nucleic acid corresponding to an amplified segment of the human RNase P gene (SEQ ID NO: 173, top row) or an amplified segment of the human β-globin gene (SEQ ID NO: 174, bottom row). Each DETECTR reaction was performed in the presence of 0 pM, 10 pM, 100 pM, or 1000 pM of the target nucleic acid.

Figure 2B:
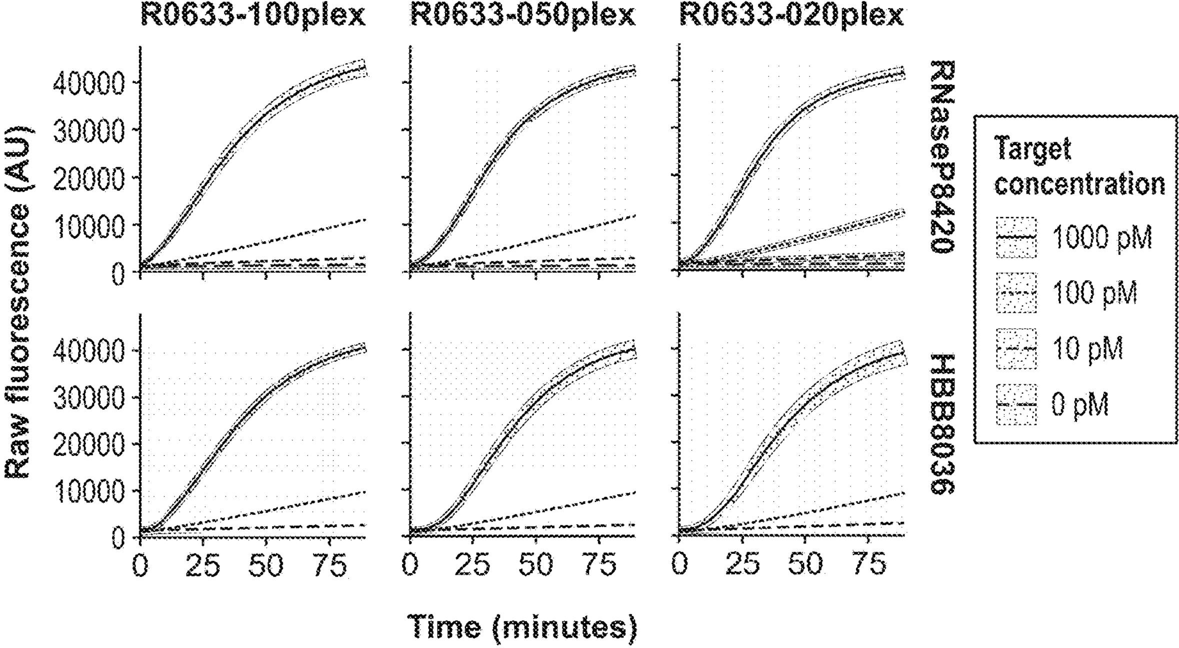
Figure 3:
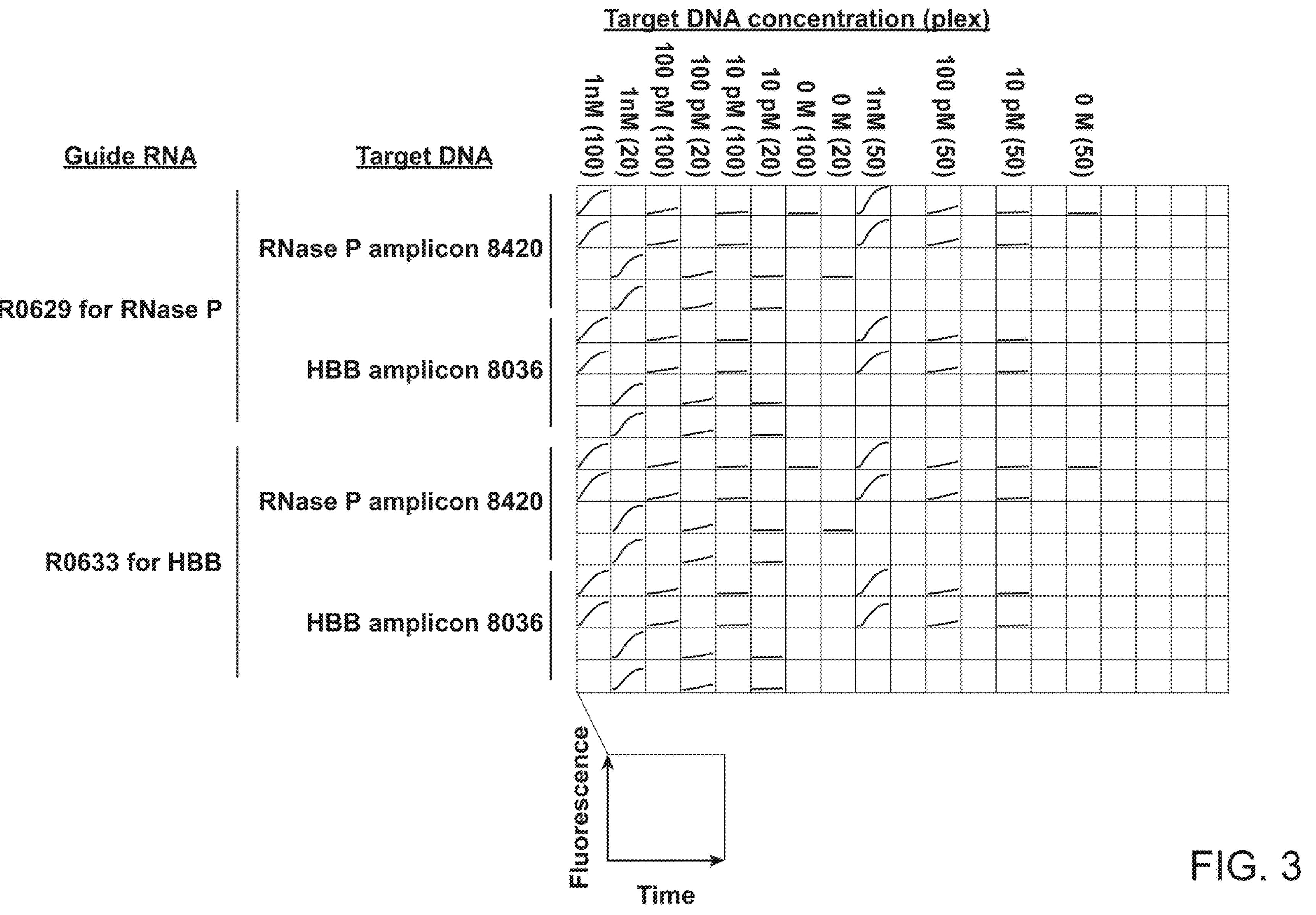
FIG. 3 shows the raw fluorescence over time data from FIG. 2. Each spectrum is the result of a separate DETECTR reaction, with time (spanning approximately 90 minutes) as the x-axis and raw fluorescence yield on the y-axis. All spectra are shown with the same scales. A blank spectrum indicates that a reaction was not run.

FIG. 2B shows a second set of multiplexed DETECTR reactions in which a guide RNA sequence targeting a human RNAase P gene (SEQ ID NO: 171) was present in 19-fold ("20plex"), 49-fold ("50plex"), or 99-fold ("100plex") higher concentration than a guide RNA sequence targeting a human β-globin gene (SEQ ID NO: 172). The pooled guide RNAs were used to detect the presence or absence of a double-stranded DNA target nucleic acid corresponding an amplified segment of the human RNase P gene (SEQ ID NO: 173, top row) or an amplified segment of the human β-globin gene (SEQ ID NO: 174, bottom row). Each multiplexed DETECTR reaction was performed in the presence of 0 pM, 10 pM, 100 pM, or 1000 pM of the target nucleic acid. The aggregate results from FIGS. 2A and 2B are shown in FIG. 3. The maximum rates of fluorescence detected in this assay are provided in TABLE 6.

TABLE 6

Maximum Rate of Fluorescence Detected in Multiplexed DETECTR Reactions

| | | Target Concentration | | |
|---|---|---|---|---|
| Target | Pool | 10 pM | 100 pM | 1000 pM |
| SEQ ID NO: 173 | SEQ ID NO: 171 20-Plex | 40 | 159 | 877 |
| | SEQ ID NO: 171 50-Plex | 40 | 187 | 1070 |
| | SEQ ID NO: 171 100-Plex | 40 | 145 | 824 |
| SEQ ID NO: 173 | SEQ ID NO: 172 20-Plex | 39 | 184 | 953 |
| | SEQ ID NO: 172 50-Plex | 46 | 170 | 910 |
| | SEQ ID NO: 172 100-Plex | 40 | 164 | 844 |
| SEQ ID NO: 174 | SEQ ID NO: 171 20-Plex | 37 | 164 | 775 |
| | SEQ ID NO: 171 50-Plex | 40 | 146 | 862 |
| | SEQ ID NO: 171 100-Plex | 38 | 138 | 734 |
| SEQ ID NO: 174 | SEQ ID NO: 172 20-Plex | 44 | 150 | 857 |
| | SEQ ID NO: 172 50-Plex | 35 | 145 | 879 |
| | SEQ ID NO: 172 100-Plex | 40 | 147 | 812 |

As shown in FIG. 2, FIG. 3 and TABLE 6, signals resulting from the lower concentration guide nucleic acid sequence complexing with a target nucleic acid are not affected by high concentrations of off-target guides nucleic acid sequences in the mixture. This assay demonstrates that up to 100 individual guide nucleic acid sequences may be pooled without adversely impacting the performance of the guide nucleic acid sequence directed to the target nucleic acid present in the sample.

Example 2

High-Plex DETECTR Reaction for Detection of *Borrelia* Species

This example describes a high-plex DETECTR reaction for detection of *Borrelia* species using an LbCas12a programmable nuclease (SEQ ID NO: 18) or a Cas12 variant programmable nuclease (SEQ ID NO: 28). Twenty guide nucleic acid sequences directed to 20 distinct target nucleic acids were pooled and used to detect samples containing varying amounts of amplified *Borrelia* DNA (isolated from *Borrelia burgdorferi* strain B3, obtained from American Type Culture Collection). Nineteen of the 20 guide nucleic acid sequences (corresponding to SEQ ID NO: 175-SEQ ID NO: 193 in Table 7) were directed toward the 16S ribosomal RNA gene of *Borrelia burgdorferi, Borrelia miyamotoi*, or both. The remaining guide nucleic acid sequence was directed toward the RNase P RNA component H1 gene.

TABLE 7

| SEQ ID NO | Guide | 5' to 3' sequence |
|---|---|---|
| SEQ ID NO: 175 | R0643 | UAAUUUCUACUAAGUGUAGAUAAGCUUCGCUUGU AGAUGAG |
| SEQ ID NO: 176 | R0644 | UAAUUUCUACUAAGUGUAGAUACUUGCAUGCUUA AGACGCA |
| SEQ ID NO: 177 | R0645 | UAAUUUCUACUAAGUGUAGAUAUCCUGGCUUAGA ACUAACG |
| SEQ ID NO: 178 | R0646 | UAAUUUCUACUAAGUGUAGAUAUUCGAUGAUACG CGAGGAA |
| SEQ ID NO: 179 | R0647 | UAAUUUCUACUAAGUGUAGAUCAACAUAGGUCCAC AGUUGA |
| SEQ ID NO: 180 | R0648 | UAAUUUCUACUAAGUGUAGAUCAACAUAGUUCCAC AGUUGA |
| SEQ ID NO: 181 | R0649 | UAAUUUCUACUAAGUGUAGAUCAGCAUAGUUCCAC AGUUGA |
| SEQ ID NO: 182 | R0650 | UAAUUUCUACUAAGUGUAGAUCAGCGUACACUACC AGGGUA |
| SEQ ID NO: 183 | R0651 | UAAUUUCUACUAAGUGUAGAUCCCUACCAACUAGC UAAUAA |

TABLE 7-continued

| SEQ ID NO | Guide | 5' to 3' sequence |
|---|---|---|
| SEQ ID NO: 184 | R0652 | UAAUUUCUACUAAGUGUAGAUCUACAAAGCUUAU UCCUCAU |
| SEQ ID NO: 185 | R0653 | UAAUUUCUACUAAGUGUAGAUGGGUCUAUAUACA GGUGCUG |
| SEQ ID NO: 186 | R0654 | UAAUUUCUACUAAGUGUAGAUGGGUCUGUAUACA GGUGCUG |
| SEQ ID NO: 187 | R0655 | UAAUUUCUACUAAGUGUAGAUGUGACUCAGCGUC AGUCUUG |
| SEQ ID NO: 188 | R0656 | UAAUUUCUACUAAGUGUAGAUGUUAACACCAAGU GUGCAUC |
| SEQ ID NO: 189 | R0657 | UAAUUUCUACUAAGUGUAGAUUAGGAAAUGACAA AGCGAUG |
| SEQ ID NO: 190 | R0658 | UAAUUUCUACUAAGUGUAGAUUCAUUUCCUACAA AGCUUAU |
| SEQ ID NO: 191 | R0659 | UAAUUUCUACUAAGUGUAGAUUGCAUAGACUUAU AUAUCCG |
| SEQ ID NO: 192 | R0660 | UAAUUUCUACUAAGUGUAGAUAGGUAUGUUUAGU GAGGGGG |
| SEQ ID NO: 193 | R0661 | UAAUUUCUACUAAGUGUAGAUGUGAGGGGGGUGA AGUCGUA |

For the Cas112 variant reactions, each of the 20 guide nucleic acid sequences were complexed individually at high concentration (1.6 μM) with 1.6 μM of the Cas112 variant programmable nuclease (SEQ ID NO: 28) in HEPES, pH 7.5 buffer (20 mM HEPES, pH 7.5, 2 mM potassium acetate, 5 mM magnesium acetate, 100 glycerol, and 0.00016% Triton X-100). The complexing reactions were incubated at 37° C. for 30 minutes. Complexing reactions for each of the 20 guide nucleic acid sequences were combined in equal volumes. The pooled complexed guide nucleic acid sequences were combined with a mixture containing a single-stranded DNA detector nucleic acid in 3×HEPES, pH 7.5 buffer.

For the LbCas12a reactions, each of the 20 guide nucleic acid sequences were complexed individually at high concentration (3.2 μM) with 3.2 μM of LbCas12a programmable nuclease (SEQ ID NO: 18) in Tris, pH 8.0 buffer (20 mM Tris HCl, pH 8.0, 100 mM NaCl, 5 mM $MgCl_2$, 1 mM DTT, 5% glycerol, 50 μg/mL Heparin). The complexing reactions were incubated at 37° C. for 30 minutes. Complexing reactions for each of the 20 guide nucleic acid sequences were combined in equal volumes. The pooled complexed guide nucleic acid sequences were combined with a mixture containing a single-stranded DNA detector nucleic acid in 3× Tris, pH 8.0 buffer.

Separately, *Borrelia* culture diluted into negative matrix at different dilution factors was PCR amplified to amplify the 16S rRNA gene. Guide nucleic acid pools complexed with either the Cas12 variant or LbCas12a were combined with the diluted and PCR-amplified *Borrelia* samples.

Figure 4:
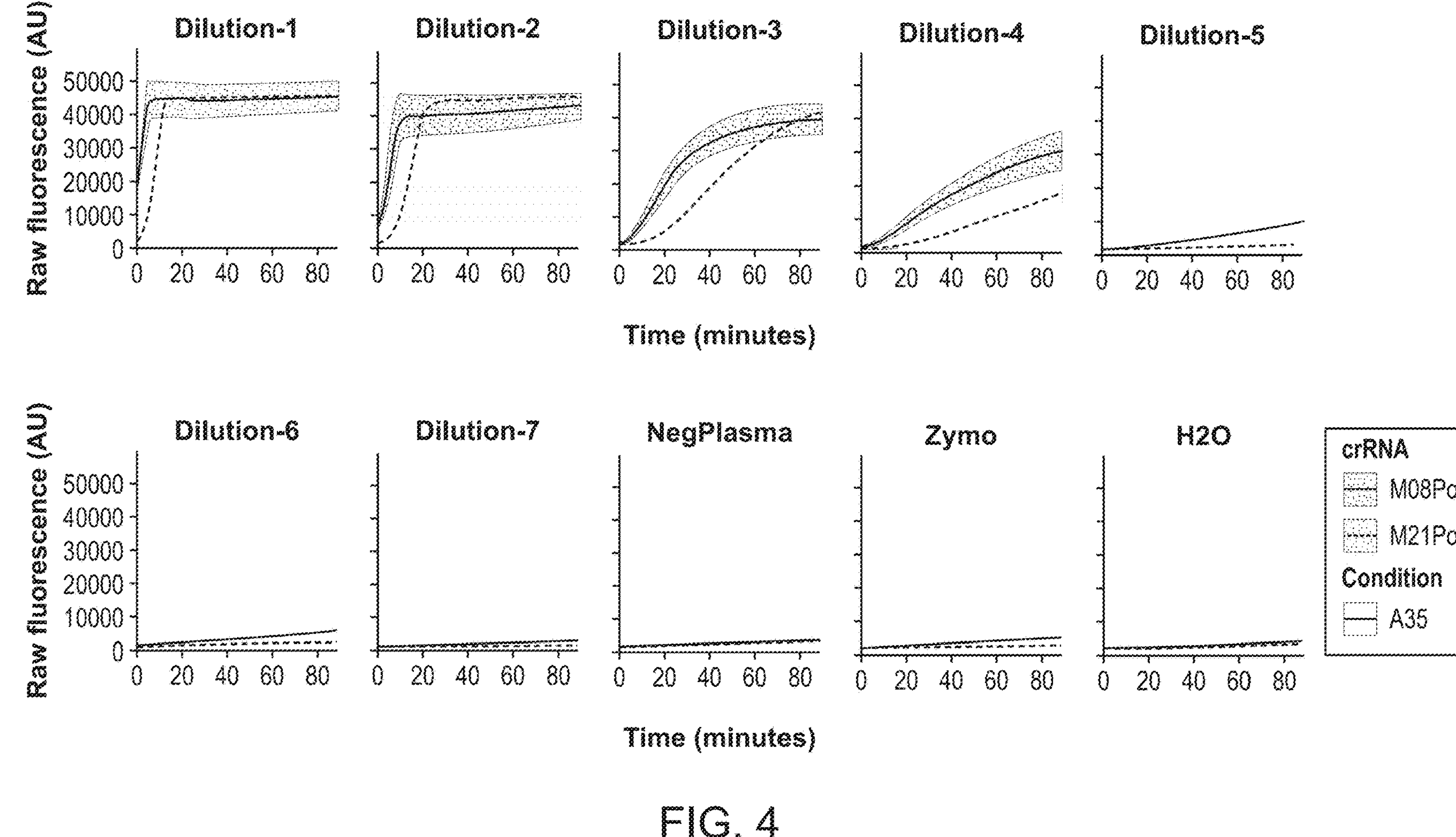
FIG. 4 shows raw fluorescence over time of high-plex DETECTR reactions using an LbCas12a programmable nuclease (SEQ ID NO: 18, dashed lines) and a Cas12 variant programmable nuclease (SEQ ID NO: 28, solid lines). A guide RNA pool of 20 distinct guide nucleic acid sequences was used to detect the presence or absence of target nucleic acids in *Borrelia* culture diluted 10-fold ("Dilution-1"), $10^2$-fold ("Dilution-2"), $10^3$-fold ("Dilution-3"), $10^4$-fold ("Dilution-4"), $10^5$-fold ("Dilution-5"), $10^6$-fold ("Dilution-6"), or $10^7$-fold ("Dilution-7") in a negative matrix and PCR-amplified. Diluted *Borrelia* cultures were PCR-amplified prior to detection to amplify the 16S gene. Negative plasma ("NegPlasma"), Zymo standard with *Pseudomonas aeruginosa, Escherichia coli, Salmonella enterica, Lactobacillus subtilis, Saccharomyces cerevisiae*, and *Cryptococcus neoformans* ("Zymo"), and water ("H2O') were tested as negative controls.

FIG. 4 shows raw fluorescence over time of high-plex DETECTR reactions using an LbCas12a programmable nuclease (SEQ ID NO: 18, dashed lines) and a Cas12 variant programmable nuclease (SEQ ID NO: 28, solid lines). A guide RNA pool of 20 distinct guide nucleic acid sequences was used to detect the presence or absence of target nucleic acids in *Borrelia* culture diluted 10-fold ("Dilution-1"), $10^2$-fold ("Dilution-2"), $10^3$-fold ("Dilution-3"), $10^4$-fold ("Dilution-4"), $10^5$-fold ("Dilution-5"), $10^6$-fold ("Dilution-6"), or $10^7$-fold ("Dilution-7") in a negative matrix and PCR-amplified. Diluted *Borrelia* cultures were PCR-amplified prior to detection to amplify the 16S gene. Negative plasma ("NegPlasma"), Zymo standard with *Pseudomonas aeruginosa, Escherichia coli, Salmonella enterica, Lactobacillus subtilis, Saccharomyces cerevisiae*, and *Cryptococcus neoformans* ("Zymo"), and water ("H2O') were tested as negative controls.

Figure 5:
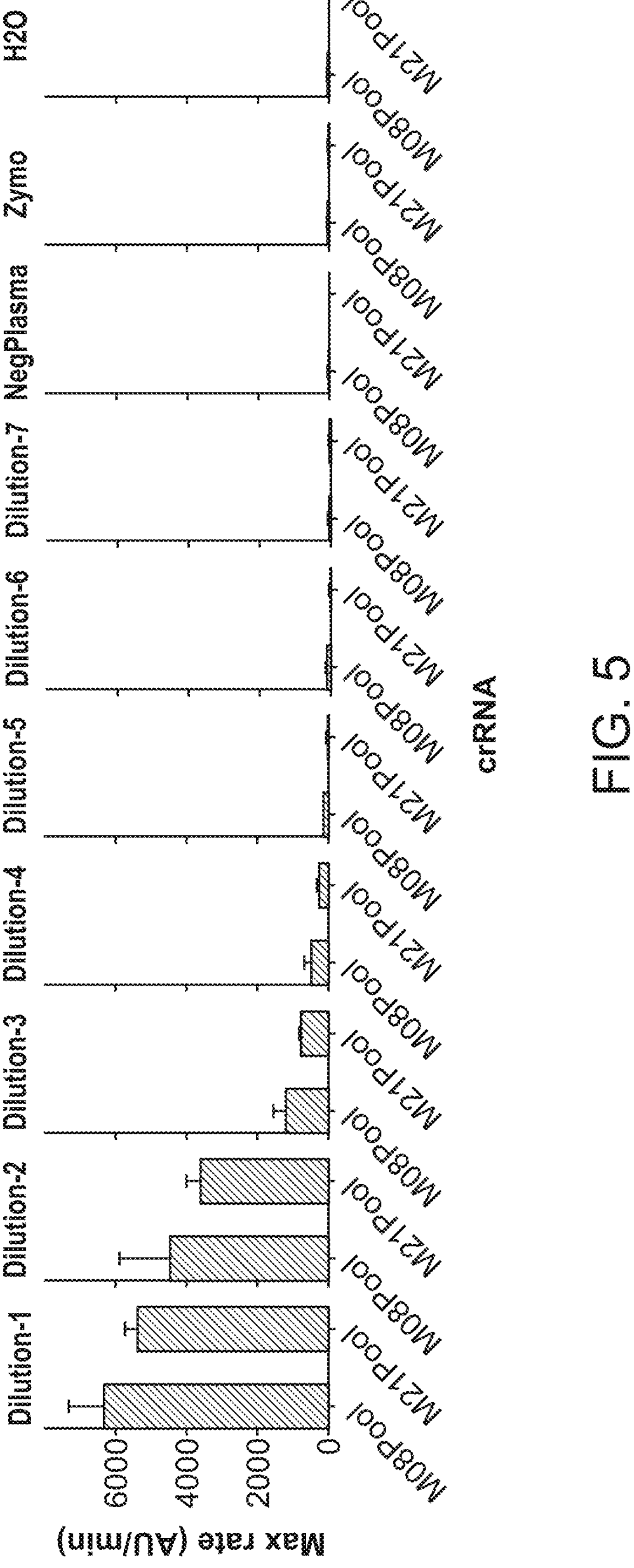
FIG. 5 shows the maximum fluorescence rates of the high-plex DETECTR reactions shown in FIG. 4. Left columns in each condition correspond to reactions using the Cas12 variant programmable nuclease (SEQ ID NO: 28), and right columns correspond to reactions using the LbCas12a programmable nuclease (SEQ ID NO: 18).

FIG. 5 shows the maximum fluorescence rate of the high-plex DETECTR reactions shown in FIG. 4. Left columns in each condition correspond to reactions using the Cas12 variant programmable nuclease (SEQ ID NO: 28), and right columns correspond to reactions using the LbCas12a programmable nuclease (SEQ ID NO: 18).

Figure 6:
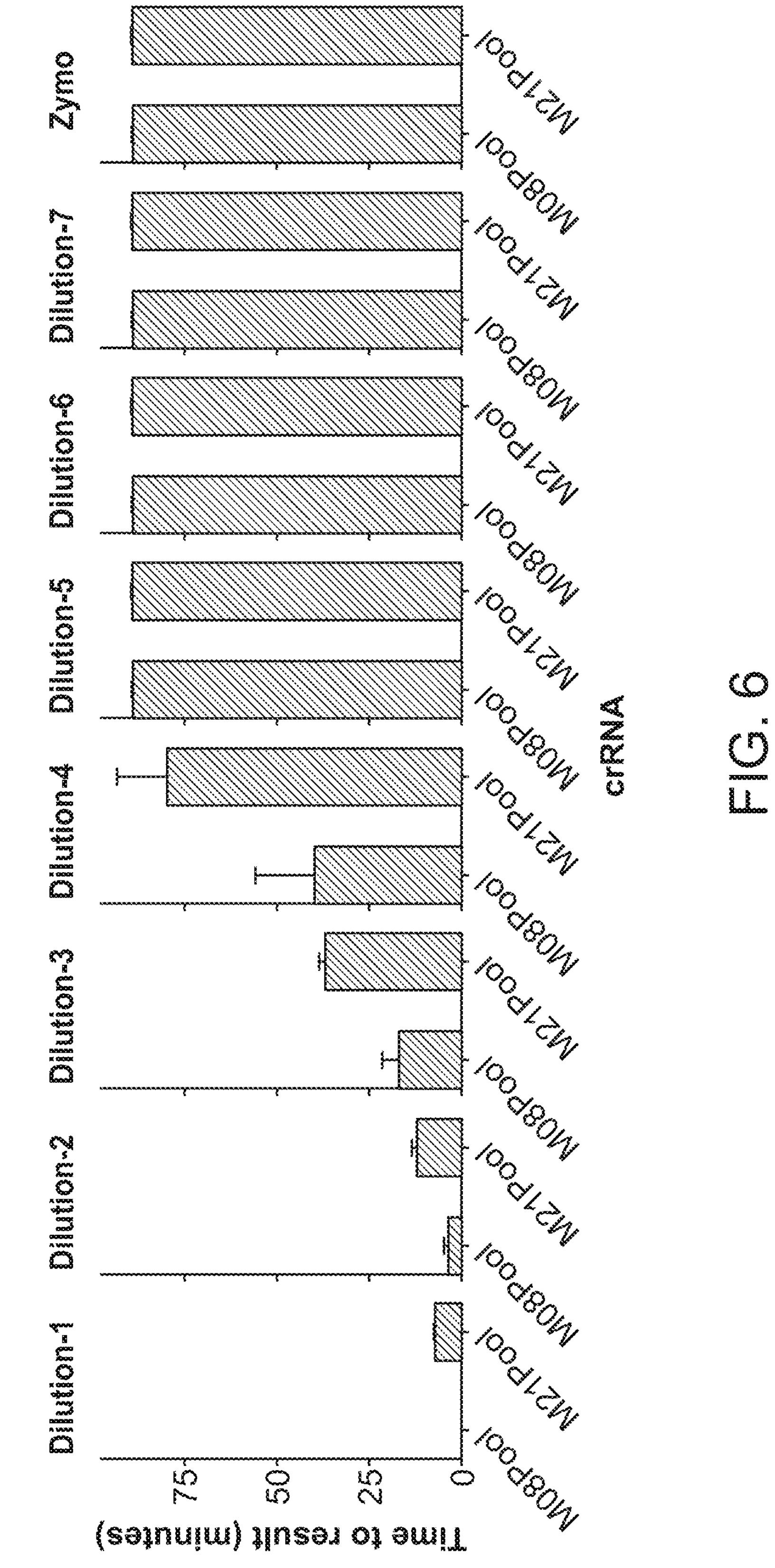
FIG. 6 shows the time to result of the high-plex DETECTR reactions shown in FIG. 4 and FIG. 5. Left columns in each condition correspond to reactions using the Cas12 variant programmable nuclease (SEQ ID NO: 28), and right columns correspond to reactions using the LbCas12a programmable nuclease (SEQ ID NO: 18). A low time to result is indicative of a positive DETECTR reaction.

FIG. 6 shows the time to result of the high-plex DETECTR reactions shown in FIG. 4 and FIG. 5. Left columns in each condition correspond to reactions using the Cas12 variant programmable nuclease (SEQ ID NO: 28), and right columns correspond to reactions using the LbCas12a programmable nuclease (SEQ ID NO: 18). A low time to result is indicative of a positive DETECTR reaction.

As illustrated by FIG. 4-FIG. 6, the Cas12 variant (SEQ ID NO: 28) shows higher sensitivity for the target nucleic acids in a high-plex guide pooling assay than LbCas12a (SEQ ID NO: 18). Additionally, the Cas12 variant shows higher sensitivity and a faster time to result than LbCas12a. This assay demonstrates that high-plex DETECTR reactions (for example the 20-plex DETECTR reaction shown here) may be used to detect the presence of multiple species of target nucleic acids associated with a disease.

Example 3

High-Plex DETECTR Reaction for Detection of Healthcare-Associated Infections Using a Cas12 Programmable Nuclease This example describes a high-plex DETECTR reaction for detection of health-care associated infections. One thousand guide nucleic acids sequences directed to target nucleic acids corresponding to distinct segments within each of *Staphylococcus aureus*, methicillin resistant *Staphylococcus aureus, Candida albicans, Pseudomonas aeruginosa, Acinetobacter baumannii, Stenotrophomonas maltophilia, Clostridium difficile, Escherichia coli, Mycobacterium tuberculosis*, and *Legionella* sp. are pooled and complexed at a 1:1 ratio with a Cas12 programmable nuclease. The complexed guide nucleic acids and Cas12 programmable nucleases are then combined with a detector nucleic acid and a biological sample from a patient suspected of having a healthcare-associated infection. If the biological sample is positive for a hospital-associated infection, one or more of the guide nucleic acids and Cas12 programmable nucleases binds a target nucleic acid in the sample, activating the Cas12 programmable nuclease, and initiating transcollateral cleavage of the detector nucleic acid. The cleaved detector nucleic acid produces a detectable signal.

Example 4

High-Plex DETECTR Reaction for Detection of Healthcare-Associated Infections Using a Cas13 Programmable Nuclease This example describes a high-plex DETECTR reaction for detection of health-care associated infections using a Cas13 programmable nuclease. One thousand guide nucleic acid sequences directed to target nucleic acids corresponding to distinct regions within each of *Staphylococcus aureus*, methicillin resistant *Staphylococcus aureus, Candida albicans, Pseudomonas aeruginosa, Acinetobacter baumannii, Stenotrophomonas maltophilia, Clostridium difficile, Escherichia coli, Mycobacterium tuberculosis*, and *Legionella* sp. are pooled and complexed at a 1:1 ratio with a Cas13 programmable nuclease. The complexed guide nucleic acids and Cas13 programmable nucleases are then combined with a detector nucleic acid and a biological sample from a patient suspected of having a healthcare-associated infection. If the biological sample is positive for a hospital-associated infection, one or more of the guide nucleic acids and Cas13 programmable nucleases binds a target nucleic acid in the sample, activating the Cas13 programmable nuclease, and initiating transcollateral cleavage of the detector nucleic acid. The cleaved detector nucleic acid produces a detectable signal. Optionally, target RNA in the sample are reverse transcribed, amplified, and in vitro transcribed prior to contacting the sample with the pool of guide nucleic acids complexed with the Cas13 programmable nuclease, and the detector nucleic acid.

Example 5

High-Plex DETECTR Reaction for Detection of Healthcare-Associated Infections Using a Cas14 Programmable Nuclease This example describes a high-plex DETECTR reaction for detection of health-care associated infections using a Cas14 programmable nuclease. One thousand guide nucleic acid sequences directed to target nucleic acids corresponding to distinct segments within each of *Staphylococcus aureus*, methicillin resistant *Staphylococcus aureus, Candida albicans, Pseudomonas aeruginosa, Acinetobacter baumannii, Stenotrophomonas maltophilia, Clostridium difficile, Escherichia coli, Mycobacterium tuberculosis*, and *Legionella* sp. are pooled and complexed at a 1:1 ratio with a Cas14 programmable nuclease. The complexed guide nucleic acids and Cas14 programmable nucleases are then combined with a detector nucleic acid and a biological sample from a patient suspected of having a healthcare-associated infection. If the biological sample is positive for a hospital-associated infection, one or more of the guide nucleic acids and Cas14 programmable nucleases binds a target nucleic acid in the sample, activating the Cas14 programmable nuclease, and initiating transcollateral cleavage of the detector nucleic acid. The cleaved detector nucleic acid produces a detectable signal.

Example 6

DETECTR Reactions Simulating a 20-Plex Guide Pool, a 50-Plex Guide Pool, and a 100-Plex Guide Pool DETECTR Reactions This example describes a set of DETECTR reactions for a single plex (single sequence of a guide nucleic acid) assay and simulated 500-plex and simulated 1000-plex guide pool assays using a Cas12 programmable nuclease (SEQ ID NO: 18). Reaction components included a first guide nucleic acid directed to a segment of a target nucleic acid comprising a human RNase P gene (SEQ ID NO: 172). The multiplex reactions further comprised three guide nucleic acids directed toward segments of off-target nucleic acids. The guide nucleic acid directed toward human RNase P was held constant at 20 μM in each reaction while the aggregate concentrations of off-target guide nucleic acid sequences were provided at 9.8 μM and 19.8 μM for the simulated 500-plex and 1000-plex DETECTR reactions, respectively. The concentration of SEQ ID NO: 18 in each reaction was proportional to the total guide nucleic acid concentration, at 20 nM, 10 μM and 20 μM for the single plex, 500-plex and 1000-plex DETECTR reactions, respectively.

Guide nucleic acids were complexed 1:1 with SEQ ID NO: 18 at 37° C. for 30 minutes to form complexes, yielding a first sample comprising 4 μM complex with RNase P gene guide nucleic acid and a second sample comprising 40 μM complex with off-target guide nucleic. The two samples were mixed with an 8-nucleotide single-stranded DNA detector nucleic acid labeled at the 5' end with FAM and labeled at the 3' end with Iowa Black FQ with a sequence of SEQ ID NO: 9, and then combined at volume ratios of 1:49 and 1:99 ratios (RNase P gene to off-target guide nucleic acid) to simulate 500-plex and 1000-plex DETECTR reactions, respectively. A further portion of the RNase P gene guide nucleic acid complex left unmixed with the off-target guide nucleic pool was used for the single plex DETECTR reactions. The resulting mixtures were combined with sample containing target nucleic acid to achieve final target nucleic acid concentrations of 1000 pM (1 nM), 100 pM, 10 pM or 0 pM.

Figure 7:
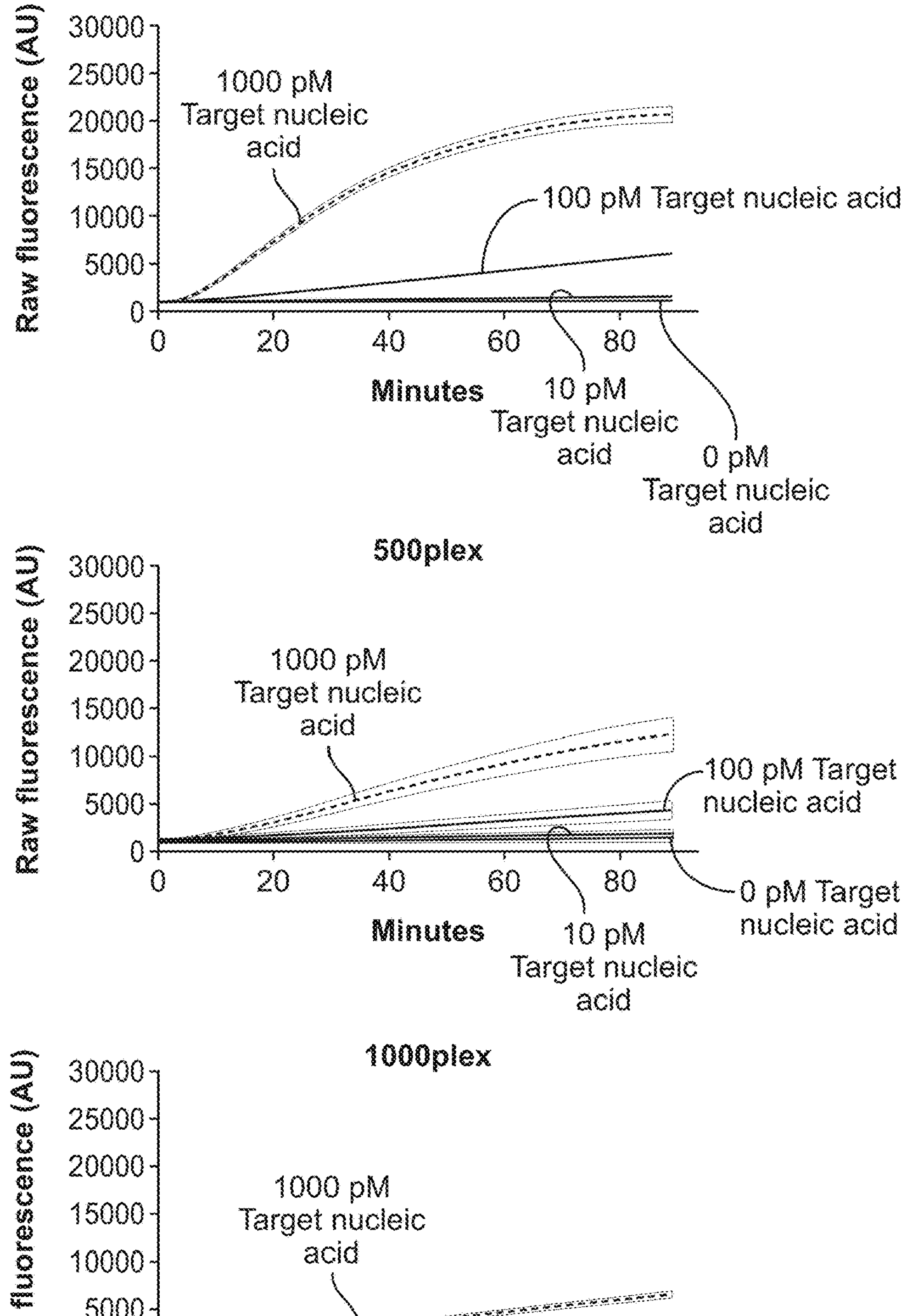
FIG. 7 shows raw fluorescence over time of multiplexed DETECTR reactions using a Cas12 programmable nuclease (SEQ ID NO: 18). The multiplexed DETECTR reactions were performed with four distinct guide RNA sequences, a first guide nucleic acid directed to a segment of a target nucleic acid comprising a human RNase P gene (SEQ ID NO: 172), and three off target guide sequences. The pool of off-target guide nucleic acid sequences were present at either 499-fold or 999-fold the first guide nucleic acid sequence to simulate 500-plex and 1000-plex DETECTR reactions, respectively. Additionally, single plex assays were also performed with no off-target guide nucleic acids present. An 8-nucleotide single-stranded DNA detector nucleic acid labeled at the 5' end with FAM and labeled at the 3' end with Iowa Black FQ with a sequence of SEQ ID NO: 9 was used in each reaction.

FIG. 7 shows raw fluorescence data for the single plex, 500-plex, and 1000-plex samples with 1000 pM (1 nM), 100 pM, 10 pM or 0 pM target nucleic acid present.

Figure 8:
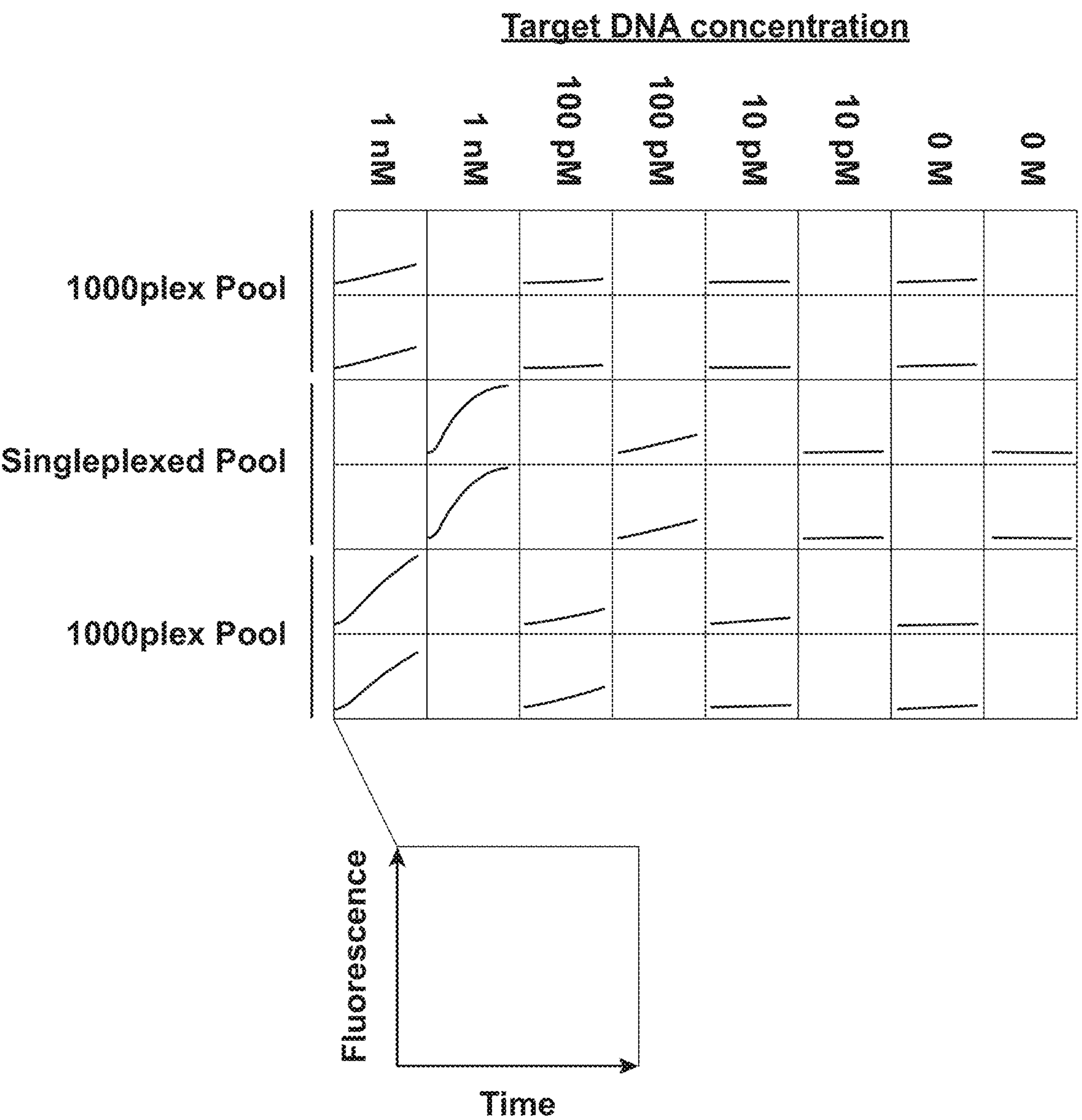
FIG. 8 shows the raw fluorescence over time data from FIG. 7. Each spectrum is the result of a separate DETECTR reaction, with time (spanning approximately 90 minutes) as the x-axis and raw fluorescence yield on the y-axis. All spectra are shown with the same scales. A blank spectrum indicates that a reaction was not run.

FIG. 8 Shows raw fluorescence data for the single plex and simulated 500-plex and 1000-plex reactions. In assays with 100 pM or 1000 pM (1 nM) target nucleic acid present, the maximum rate of fluorescence signal increase was inversely correlated with simulated plex, such that the single plex reactions had the highest maximum rates of fluorescence signal increase and the simulated 1000-plex reactions had the lowest maximum rates of fluorescence signal increase. The maximum rates of fluorescence signal increase detected in this assay are provided in TABLE 8.

TABLE 8

| Maximum Rate of Fluorescence Detected in DETECTR Reactions | | | | |
|---|---|---|---|---|
| | Target Nucleic Acid Concentration | | | |
| Plex | 0 pM | 10 pM | 100 pM | 1000 pM |
| Human RNase P Gene Single Plex | 34 | 23 | 89 | 467 |
| Human RNase P Gene 500-plex | 21 | 32 | 60 | 194 |
| Human RNase P Gene 1000-plex | 30 | 43 | 29 | 93 |

Example 7

DETECTR Reactions Simulating a 20-Plex Guide Pool, a 50-Plex Guide Pool, and a 100-Plex Guide Pool DETECTR Reactions This example describes a set of DETECTR reactions simulating a 20-plex guide pool, a 50-plex guide pool, a 100-plex and a 200-plex guide pool. Experiments were performed using a programmable nuclease of SEQ ID NO: 28, and two guide nucleic acids to mimic high-plex DETECTR reactions. The first guide nucleic acid was directed to a segment of a target nucleic acid and the second guide nucleic acid was directed toward a segment of an off-target nucleic acid. The lower concentration guide nucleic acid sequence was held constant at 10 nM in each reaction while the higher concentration guide nucleic acid sequence was varied at 190 nM, 490 nM, 990 nM or 1990 nM in the simulated 20-plex, 50-plex, 100-plex and 200-plex DETECTR reactions, respectively. The total guide nucleic acid concentrations in the simulated 20-plex, 50-plex, 100-plex and 200-plex DETECTR reactions were 200 nM, 500 nM, 1000 nM (1 μM) and 2000 nM (2 μM), respectively. The concentration of SEQ ID NO: 28 in each reaction was proportional to the total guide nucleic acid concentration, at 200 nM, 500 nM, 1000 nM (1 μM) and 2000 nM (2 μM) for the 20-plex, 50-plex, 100-plex and 200-plex DETECTR reactions, respectively. An 8-nucleotide single-stranded DNA detector nucleic acid labeled at the 5' end with FAM and labeled at the 3' end with Iowa Black FQ with a sequence of SEQ ID NO: 9 was used in each reaction The sequences of the guide nucleic acids and target nucleic acids used in this assay are provided in TABLE 9.

TABLE 9

| Guide Nucleic Acid and Target Nucleic Acid Sequences | | |
|---|---|---|
| SEQ ID NO: | Type | Sequence |
| SEQ ID NO: 194 | gRNA to human RNase P 8644 | UAAUUUCUACUAAGUGUAGAUGAUUUGGGAAUCUUAUAAGU |
| SEQ ID NO: 172 | gRNA to human ß-globin | UAAUUUCUACUAAGUGUAGAUUAUUGGUCUCCUUAAACCUG |
| SEQ ID NO: 195 | Human RNase P 8644 target | ATGGGAAAAAGTGGTCTCATACAGAACTTATAAGATTCCCAAATCCAAAGACATTTCACGTTTATGGTGATTTCCCAGAACACATAGCGACATGCAAATATTGCAGGGCGCCACTCCCCTGTCCCTCACAG |
| SEQ ID NO: 174 | Human ß-globin target | CCTATCAGAAACCCAAGAGTCTTCTCTGTCTCCACATGCCCAGTTTCTATTGGTCTCCTTAAACCTGTCTTGTAACCTTGATACCAACCTGCCCAGGGCCTCACCACCAACTTCATCCACGTTCAC |

Guide nucleic acids were complexed 1:1 with SEQ ID NO: 28 at 4-fold the final concentration in HEPES, pH 7.5 buffer (100 mM HEPES, 10 mM potassium Acetate, 25 mM magnesium acetate, 5% glycerol, 0.0008% Triton X-100) and incubated for 30 minutes at 37° C. to form complexes with concentrations of 400 nM, 1000 nM (1 μM), 2000 nM (2 μM) and 4000 nM (4 μM) for the simulated 20-plex, 50-plex, 100-plex and 200-plex DETECTR reactions, respectively. The complexing reactions were then combined in equal volumes with 200 nM single-stranded DNA detector nucleic acid (SEQ ID NO: 9 labeled at the 5' end with FAM and labeled at the 3' end with Iowa Black FQ) in Tris, pH 8.0 buffer with an additional 16% glycerol. The resulting mixtures were then combined with equal volumes of sample containing target nucleic acid to achieve final target nucleic acid concentrations of 1000 pM (1 nM), 100 pM, or 0 pM.

FIG. 9A shows raw fluorescence data for simulated 20-plex, 50-plex, 100-plex, and 200-plex DETECTR reactions with target nucleic acid corresponding to an amplified segment of the human RNase P gene (top, SEQ ID NO: 173) and with an amplified segment of the human ß-globin gene (bottom, SEQ ID NO: 174) at concentrations of 1 nM, 100 pM, or 0 pM (left, middle, and right columns, respectively). Guide RNA targeting a human RNase P gene (SEQ ID NO: 171) was present in 19-fold ("20plex"), 49-fold ("50plex") 99-fold ("100plex"), or 199-fold ("200plex) higher concentration than a guide RNA sequence targeting a human RNase P gene (SEQ ID NO: 171).

FIG. 9B shows raw fluorescence data for simulated 20-plex, 50-plex, 100-plex, and 200-plex DETECTR reactions with target nucleic acid corresponding to an amplified segment of the human RNase P gene (top, SEQ ID NO: 173) and with an amplified segment of the human ß-globin gene (bottom, SEQ ID NO: 174) at concentrations of 1 nM, 100 pM, or 0 pM (left, middle, and right columns, respectively). Guide RNA targeting a human ß-globin gene (SEQ ID NO: 172) was present in 19-fold ("20plex"), 49-fold ("50plex") 99-fold ("100plex"), or 199-fold ("200plex) higher concentration than a guide RNA sequence targeting a ß-globin gene (SEQ ID NO: 171).

FIG. 10 provides the maximum rates of fluorescence from the above assays. Low fluorescence signal was detected in assays with 0 pM target nucleic acid present. In assays with 100 pM or 1 nM target nucleic acid present, the maximum rate of fluorescence signal was inversely correlated with simulated plex, such that the simulated 20-plex reactions had the highest maximum rate of fluorescence and the simulated 200-plex reactions had the lowest maximum rate of fluorescence.

Example 8

DETECTR Reaction Enabling Bacterial Community Profiling at the Species-Level This example describes a multi-plex DETECTR reaction for profiling a bacterial population. DNA extraction is performed on a community of bacteria using techniques standard to the field. PCR amplification is performed using a set of universal primers targeting DNA encoding the 16S ribosomal subunit. In parallel, a set of guide nucleic acids targeting loci encoding 16S ribosomal subunits from species of interest are pooled and complexed at a 1:1 ratio with a programmable nuclease e.g., a Cas12 programmable nuclease. The complexed guide nucleic acids and programmable nuclease are then combined with a pool of detector nucleic acids and the PCR product (FIG. 11). If the biological sample is positive for a species of interest, one or more of the guide nucleic acids and programmable nucleases binds a target nucleic acid in the sample, activating the Cas14 programmable nuclease, and initiating transcollateral cleavage of the detector nucleic acid. The cleaved detector nucleic acid produces a detectable signal. In some cases, the rate of fluorescence increase upon initiation of the DETECTR reaction correlates with the number of target species present. In some cases, the rate of fluorescence increase upon initiation of the DETECTR reaction is proportional to the number of target species present.

Example 9

Assaying for SNPs in a Bacterial Population with a Single DETECTR Reaction

This example describes a multi-plex DETECTR reaction for determining the presence of an SNP in a bacterial population. A set of guide nucleic acids targeting potential SNPs of interest from a bacteria of interest are pooled and complexed at a 1:1 ratio with a programmable nuclease, e.g., a Cas12 programmable nuclease. DNA is extracted and amplified from a bacterial population suspected of harboring an SNP. The amplicons are then mixed with the complexed guide nucleic acids and programmable nuclease (FIG. 12). After an optional incubation period, a pool of detector nucleic acids is added to the mixture. If the biological sample is positive for an SNP targeted by a guide nucleic acid, a guide nucleic acid and Cas14 programmable nucleases binds a target nucleic acid in the sample, activating the Cas14 programmable nuclease, and initiating transcollateral cleavage of the detector nucleic acid. The cleaved detector nucleic acid produces a detectable signal, indicating that an SNP is present in the bacterial population.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

Example 10

Guide Pooling for Enhanced Target Detection Signal in DETECTR Assays

Guide RNAs that were designed to bind to a different region within a single target molecule were pooled as a strategy for enhancing the target detection signal from DETECTR assays. For examples, in this strategy, each DETECTR™ reaction contained a pool of CRISPR-Cas RNP complexes each of which targeted a different region within a single molecule. As discussed in the paragraphs below, this strategy resulted in increased sensitivity to target detection by using increased number of complexes/single target such that the signal is strong enough to detect within a Poisson distribution (sub-one copy/droplet) and provide a quantitative evaluation of target numbers within a sample.

To test the effect of guide pooling on target detection using the Cas12a nuclease, first, a Cas12a complexing mix was prepared wherein the R1965 (off-target guide), R1767, R3164, R3178 guides were present in either a pooled-gRNA format (a pool of two or more of the three guides selected from R1767, R3164, or R3178) or in a single-gRNA format (wherein R1767, R3164, R3178 were present individually) and the mix was incubated for 20 minutes at 37° C. A 2-fold dilution series for the template RNA (GF184) was created from a starting dilution concentration (wherein 5.4 μl of GF184 at 0.1 ng/μL was added to 44.6 μl of nuclease-free water). DETECTR master mixes which included the Cas12 complex, Reporter substrate, Fluorescein, Buffer, and diluted template (GF184 or off-target template GF577) were then assembled as shown in Table 10. The DETECTR mixes were then loaded into a Stilla Sapphire chip and placed into the Naica Geode. Crystals were created from thousands of droplets from each samples. No amplification step was performed The signal from the Sapphire chips was measured in the Red channel. The results of the DETECTR assay showed enhanced Cas12a-based detection of the GF184 target using a pooled-guide format compared to DETECTR Cas12a-based assay using an individual guide format. For example, the DETECTR assays showed an enhanced signal from chamber 5 containing a pool of two guides R1767 and R3178, compared to the signal from chamber 2 or chamber 4 which contained the R1767 and R3178 in individual guide format respectively (FIG. 13). Similarly, the DETECTR assays showed an enhanced signal from chamber 9 containing a pool of three guides (R1767, R3164, and R3178), compared to the signal from chamber 5 which contained a pool of two guides (R1767 and R3178) and compared to the signal from chamber 2, chamber 3, or chamber 4 which contained the R1767, R3164, and R3178 in individual guide format respectively (FIG. 13).

TABLE 10

| Chamber | Condition | Copies/ Chamber | # Droplets | copies/ droplet |
|---|---|---|---|---|
| 1 | Off Target Guide (1965) | $2.5 \times 10^7$ | 29336 | 852 |
| 2 | Single R1767 | $2.5 \times 10^7$ | 26838 | 931 |
| 3 | Single R3164 | $2.5 \times 10^7$ | 29590 | 845 |
| 4 | Single R3178 | $2.5 \times 10^7$ | 27769 | 900 |
| 5 | 2 × pool (R1767, R3178) | $2.5 \times 10^7$ | 27929 | 895 |
| 6 | 2 × pool (R1767, R3178) | $1.25 \times 10^7$ | 28787 | 434 |
| 7 | 2 × pool (R1767, R3178) | $6.125 \times 10^6$ | 27503 | 223 |
| 8 | 2 × pool (R1767, R3178) | 0 | 28814 | 0 |
| 9 | 3 × Pool (R1767, R3164, R3178) | $2.5 \times 10^7$ | 27881 | 897 |

TABLE 10-continued

| Chamber | Condition | Copies/ Chamber | # Droplets | copies/ droplet |
|---|---|---|---|---|
| 10 | 3 × Pool (R1767, R3164, R3178) | 1.25 × $10^7$ | 29523 | 423 |
| 11 | 3 × Pool (R1767, R3164, R3178) | 6.125 × $10^6$ | 28957 | 211 |
| 12 | 3 × Pool (R1767, R3164, R3178) | 0 | 29087 | 0 |

Enhanced sensitivity to target detection with guide-pooling was observed in the case of Cas13a nuclease also. In these assays, a Cas13a complexing mix was prepared wherein the R002(off-target guide), R4517, R4519, R4530 guides were present in either a pooled-gRNA format (a pool of two or more of the three guides R4517, R4519, and R4530) or single-gRNA format (wherein R4517, R4519, and R4530 were present individually) and the mix was incubated for 20 minutes at 37 C. DETECTR master mixes which included the Cas13a complex, FAM-U5 Reporter substrate, Buffer, and diluted template SC2 RNA (or off-target template 5S-87) was then assembled as shown in Table 11. The DETECTR mixes were then loaded into a Stilla Sapphire chip and placed into the Naica Geode. Crystals were created from thousands of droplets from each samples and incubated at 37 C. No amplification step was performed. The signal from the Sapphire chips was measured in the Red channel. The results of the DETECTR assay showed enhanced Cas13a-based detection of the SC2 target RNA using a pooled-guide format compared to a Cas13a-based detection of the SC2 target RNA using a single-guide format. For example, the DETECTR assays showed an enhanced signal from chamber 8, containing the template at a concentration of $1 \times 10^6$ copies, and a pool of the three guides R4517, R4519, and R4530, compared to the signal from chamber 2, chamber 4, or chamber 6 which contained the template at a concentration of $1 \times 10^6$ copies, and the guides R4517, R4519, and R4530 in individual guide format respectively (FIG. 14). Similarly, the DETECTR assays showed an enhanced signal from chamber 9 which contained the template at a concentration of $1 \times 10^5$ copies and a pool of three guides (R1767, R3164, and R3178), compared to the signal from chamber 2, chamber 6, or chamber 4, which contained the template at a concentration of $1 \times 10^6$ copies, and which contained the R1767, R3164, and R3178 in individual guide format respectively (FIG. 14).

TABLE 11

| Chamber | Condition | Copies/ Chamber | # Droplets | copies/ droplet |
|---|---|---|---|---|
| 1 | Off Target Guide (R002) | 1 × $10^6$ | 19960 | 50 |
| 2 | Single R4517 | 1 × $10^6$ | 18102 | 55 |
| 3 | Single R4517 | 0 | 19146 | 0 |
| 4 | Single R4519 | 1 × $10^6$ | 18289 | 55 |
| 5 | Single R4519 | 0 | 23324 | 0 |
| 6 | Single R4530 | 1 × $10^6$ | 25402 | 39 |
| 7 | Single R4530 | 0 | 26285 | 0 |
| 8 | 3 pool | 1 × $10^6$ | saturated | ~40 |
| 9 | 3 pool | 1 × $10^5$ | 23209 | 4.3 |
| 10 | 3 pool | 1 × $10^4$ | 24064 | 0.41 |
| 11 | 3 pool | 0 | 21137 | 0 |
| 12 | 3 pool | 1 × $10^6$ | 24885 | 40 |

Next, the sensitivity of a target detection in Cas13a digital droplet DETECTR assays containing guide RNA in either a pooled-guide format versus a single guide format was assayed. DETECTR reaction master-mixes was prepared for each gRNA (R4637, R4638, R4667, R4676, R4684, R4689, R4691, or R4785 (RNaseP)) and included, in addition to the gRNA, the Cas13a nuclease, and the reporter substrate. After complexing, 2 μL of each RNP was combined in either a pooled-gRNA format (a pool of the seven gRNAs, i.e., R4637, R4638, R4676, R4689, R4691, R4667, and R4684) or remained in the single-gRNA format (wherein R4667, R4684, and R4785 (RNAse P were present individually). The template RNAs (Twist SC2, ATCC SC2, and 5s-87 off-target) were diluted to obtain a series of template concentrations. DETECTR reactions directed to the detection of the template RNAs (Twist SC2, ATCC SC2, and 5s-87 off-target template RNAs) were assembled by combining the Cas13a-gRNA RNPs with the diluted template RNA from the previous step as shown in Table 12. The assembled DETECTR reactions were loaded into chambers on a Stilla Sapphire Chip. The Chips were placed into the Naica Geode and crystals were generated using the droplet generation program. The chips were incubated and the crystals generated were imaged to reveal droplets that contain detected targets.

The sensitivity of target detection by the DETECTR assays containing the pooled guides (R4637, R4638, R4667, R4676, R4684, R4689, R4691) was compared with the sensitivity of target detection by the DETECTR assays containing the single guides R4684, R4667, R4785 (RNAseP guide) in individual format. Relative quantification performed by counting the number of these positive droplets showed that the samples containing the pooled guide RNAs generated more crystals containing the amplified products per copy of starting target RNA than the samples containing the guide RNAs in individual format (FIG. 15). For example, the number of droplets from chamber 1 is higher than the number of droplets in chamber 2 and 3; and the number of droplets from chamber 5 is higher than the number of droplets in chambers 6 and 7 (FIG. 15 and FIG. 17). Measurement of the target detection signal intensity from the chips also confirmed that the sensitivity of target detection per copy of starting target RNA by the DETECTR assays containing the pooled guides (R4637, R4638, R4667, R4676, R4684, R4689, R4691) was higher than the sensitivity of target detection by the DETECTR assays containing the single guides R4684, R4667, R4785 (RNAseP guide) in individual format (FIG. 16). For example, signal intensity from chamber 1 (containing the seven-guide pool and the Twist SC2 template RNA is higher than the signal intensity in chamber 2 and 3 (containing the R4684, and the R4667 gRNAs in individual format respectively in the presence of the Twist SC2 RNA); and the signal intensity from chamber 5 (containing the seven-guide pool and the ATCC SC2 template RNA) is higher than the signal intensity in chambers 6 and 7 (containing the R4684, and the R4667 gRNAs in individual format respectively, in the presence of the ATCC SC2 RNA) (FIG. 16). Similarly, the signal intensity from chamber 5 (containing the seven-guide pool and the ATCC SC2 template RNA) is higher than the signal intensity in chamber 6 (containing the gRNA R4684 in individual format and the ATCC SC2 RNA), the signal intensity from chamber 8 (containing the control RNaseP gRNA in individual format with the ATCC SC2 template RNA) and the signal intensity from chamber 12 (containing the seven pooled gRNAs with no template RNA) (FIG. 16). Similarly, the relative quantification of the number of droplets containing amplified target (per copy of starting target RNA) observed in chamber 5 (containing the seven-guide pool and the ATCC SC2 template RNA) is higher than the number of droplets observed in chamber 6 (containing the gRNA R4684 in individual format and the ATCC SC2 RNA), the number of droplets observed in chamber 8 (containing the control RNaseP gRNA in individual format with the ATCC SC2 template RNA) and the number of droplets observed in chamber 12 (containing the seven pooled gRNAs with no template RNA) (FIG. 17) The sensitivity of target detection by the assays containing the pooled guides (R4637, R4638, R4667, R4676, R4684, R4689, R4691) was compared with the sensitivity of target detection by the assays containing the single guides R4684, R4667, R4785 (RNAseP guide) in individual format, when the assays were conducted in a benchtop assay format (FIG. 18). Results from the bench top assay showed that the samples containing the pooled guides (R4637, R4638, R4667, R4676, R4684, R4689, R4691) was not higher than the sensitivity of target detection by the in the samples containing the single guides R4684, R4667, or R4785 (RNAseP guide) in individual format (FIG. 18).

TABLE 12

| Chamber | Guide | Template |
|---|---|---|
| 1 | 7 pool | 5000 copies Twist SC2 |
| 2 | R4684 | 5000 copies Twist SC2 |
| 3 | R4667 | 5000 copies Twist SC2 |
| 4 | R4785(RNaseP) | 5000 copies Twist SC2 |
| 5 | 7 pool | 5000 copies ATCC SC2 |
| 6 | R4684 | 5000 copies ATCC SC2 |
| 7 | R4667 | 5000 copies ATCC SC2 |
| 8 | R4785(RNaseP) | 5000 copies ATCC SC2 |
| 9 | 7 pool | 5000 copies 5s-87 |
| 10 | R4684 | 5000 copies 5s-87 |
| 11 | R4667 | 5000 copies 5s-87 |
| 12 | 7 pool | NTC |

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition comprising a programmable nuclease, a detector nucleic acid, and a pool of guide nucleic acids comprising greater than 20 distinct guide nucleic acid sequences, wherein:

(i) at least one guide nucleic acid of the pool hybridizes to a segment of a target nucleic acid;

(ii) the detector nucleic acid comprises a detection moiety that produces a detectable signal responsive to cleavage by the programmable nuclease upon formation of a complex comprising the programmable nuclease, the at least one guide nucleic acid, and the segment of the target nucleic acid; and (iii) a total concentration of the pool of guide nucleic acids is about 400 nM to about 2000 nM (2 μM).

2. The composition of claim 1, wherein the pool of guide nucleic acids comprises at least 50 distinct guide nucleic acid sequences, at least 100 distinct guide nucleic acid sequences, at least 500 distinct guide nucleic acid sequences, or at least 1000 distinct guide nucleic acid sequences.

3. The composition of claim 1, wherein the pool of guide nucleic acids comprises at least two guide nucleic acids that hybridize to a different segment of the target nucleic acid.

4. The composition of claim 1, wherein a guide nucleic acid of the pool of guide nucleic acids has a sequence selected from a group of tiled guide nucleic acids that correspond to nucleic acids of the target nucleic acid.

5. The composition of claim 4, wherein:

a) the tiled guide nucleic acids are sequential along the target nucleic acid upon hybridization to the target nucleic acid;

b) the tiled guide nucleic acids are non-sequential along the target nucleic acid upon hybridization to the target nucleic acid;

c) the tiled guide nucleic acids are overlapping along the target nucleic acid upon hybridization to the target nucleic acid; or d) any combination thereof.

6. The composition of claim 1, wherein the target nucleic acid is from a pathogen.

7. The composition of claim 1, wherein at least two guide nucleic acids of the pool of guide nucleic acids hybridize to segments of distinct target nucleic acids.

8. The composition of claim 7, wherein at least two target nucleic acids of the distinct target nucleic acids are from different pathogens.

9. The composition of claim 6, wherein the pathogen is a virus, a bacterium, a fungus, a protozoan, or a worm.

10. The composition of claim 1, wherein at least two guide nucleic acids of the pool of guide nucleic acids differs from one another by at least one base.

11. The composition of claim 1, wherein the total concentration of the pool of guide nucleic acids is about 400 nM, about 1000 nM (1 μM), or about 2000 nM (2 μM).

12. The composition of claim 1, wherein each guide nucleic acid of the pool of guide nucleic acids comprises from 20 to 50 bases.

13. The composition of claim 1, wherein the programmable nuclease is a Type V CRISPR-Cas enzyme or a Type VI CRISPR-Cas enzyme.

14. The composition of claim 1, wherein the target nucleic acid is DNA or RNA.

15. The composition of claim 1, wherein the composition further comprises the target nucleic acid.

16. The composition of claim 15, wherein the target nucleic acid comprises distinct target nucleic acids.

17. A method of assaying for a segment of a target nucleic acid in a sample, the method comprising:

contacting the sample to the composition of claim 1; and assaying for the detectable signal.

18. The method of claim 17, further comprising reverse transcribing the target nucleic acid, amplifying the target nucleic acid, in vitro transcribing the target nucleic acid, or any combination thereof.

19. The method of claim 18, wherein the amplifying is isothermal amplification.

* * * * *

SEQUENCE LISTING

```
Sequence total quantity: 195
SEQ ID NO: 1            moltype =   length =
SEQUENCE: 1
000

SEQ ID NO: 2            moltype =   length =
SEQUENCE: 2
000

SEQ ID NO: 3            moltype = RNA  length = 10
FEATURE                 Location/Qualifiers
source                  1..10
                        mol_type = other RNA
                        organism = synthetic construct
                        note = Description of Artificial Sequence: Synthetic
                         oligonucleotide
SEQUENCE: 3
tttttttttt                                                        10

SEQ ID NO: 4            moltype = DNA  length = 10
FEATURE                 Location/Qualifiers
source                  1..10
                        mol_type = other DNA
                        organism = synthetic construct
                        note = Description of Artificial Sequence: Synthetic
                         oligonucleotide
                        note = Description of Combined DNA/RNA Molecule: Synthetic
                         oligonucleotide
misc_feature            1..4
                        note = DNA
misc_feature            5..6
                        note = RNA
misc_feature            7..10
                        note = DNA
SEQUENCE: 4
tttttttttt                                                        10

SEQ ID NO: 5            moltype =   length =
SEQUENCE: 5
000
```

```
SEQ ID NO: 6            moltype =   length =
SEQUENCE: 6
000

SEQ ID NO: 7            moltype =   length =
SEQUENCE: 7
000

SEQ ID NO: 8            moltype =   length =
SEQUENCE: 8
000

SEQ ID NO: 9            moltype =   length =
SEQUENCE: 9
000

SEQ ID NO: 10           moltype =   length =
SEQUENCE: 10
000

SEQ ID NO: 11           moltype =   length =
SEQUENCE: 11
000

SEQ ID NO: 12           moltype = DNA  length = 10
FEATURE                 Location/Qualifiers
source                  1..10
                        mol_type = other DNA
                        organism = synthetic construct
                        note = Description of Artificial Sequence: Synthetic
                         oligonucleotide
SEQUENCE: 12
tttttttttt                                                       10

SEQ ID NO: 13           moltype = DNA  length = 12
FEATURE                 Location/Qualifiers
source                  1..12
                        mol_type = other DNA
                        organism = synthetic construct
                        note = Description of Artificial Sequence: Synthetic
                         oligonucleotide
SEQUENCE: 13
tttttttttt tt                                                    12

SEQ ID NO: 14           moltype = DNA  length = 14
FEATURE                 Location/Qualifiers
source                  1..14
                        mol_type = other DNA
                        organism = synthetic construct
                        note = Description of Artificial Sequence: Synthetic
                         oligonucleotide
SEQUENCE: 14
tttttttttt tttt                                                  14

SEQ ID NO: 15           moltype =   length =
SEQUENCE: 15
000

SEQ ID NO: 16           moltype =   length =
SEQUENCE: 16
000

SEQ ID NO: 17           moltype =   length =
SEQUENCE: 17
000

SEQ ID NO: 18           moltype = AA  length = 1228
FEATURE                 Location/Qualifiers
source                  1..1228
                        mol_type = protein
                        organism = unidentified
                        note = Description of Unknown: Lachnospiraceae bacterium
                         sequence
SEQUENCE: 18
MSKLEKFTNC YSLSKTLRFK AIPVGKTQEN IDNKRLLVED EKRAEDYKGV KKLLDRYYLS  60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
```

```
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQNPQF MGGWDKDKET  540
DYRATILRYG SKYYLAIMDK KYAKCLQKID KDDVNGNYEK INYKLLPGPN KMLPKVFFSK  600
KWMAYYNPSE DIQKIYKNGT FKKGDMFNLN DCHKLIDFFK DSISRYPKWS NAYDFNFSET  660
EKYKDIAGFY REVEEQGYKV SFESASKKEV DKLVEEGKLY MFQIYNKDFS DKSHGTPNLH  720
TMYFKLLFDE NNHGQIRLSG GAELFMRRAS LKKEELVVHP ANSPIANKNP DNPKKTTTLS  780
YDVYKDKRFS EDQYELHIPI AINKCPKNIF KINTEVRVLL KHDDNPYVIG IDRGERNLLY  840
IVVVDGKGNI VEQYSLNEII NNFNGIRIKT DYHSLLDKKE KERFEARQNW TSIENIKELK  900
AGYISQVVHK ICELVEKYDA VIALEDLNSG FKNSRVKVEK QVYQKFEKML IDKLNYMVDK  960
KSNPCATGGA LKGYQITNKF ESFKSMSTQN GFIFYIPAWL TSKIDPSTGF VNLLKTKYTS  1020
IADSKKFISS FDRIMYVPEE DLFEFALDYK NFSRTDADYI KKWKLYSYGN RIRIFRNPKK  1080
NNVFDWEEVC LTSAYKELFN KYGINYQQGD IRALLCEQSD KAFYSSFMAL MSLMLQMRNS  1140
ITGRTDVDFL ISPVKNSDGI FYDSRNYEAQ ENAILPKNAD ANGAYNIARK VLWAIGQFKK  1200
AEDEKLDKVK IAISNKEWLE YAQTSVKH                                  1228

SEQ ID NO: 19          moltype = AA  length = 1307
FEATURE                Location/Qualifiers
source                 1..1307
                       mol_type = protein
                       organism = Acidaminococcus sp.
SEQUENCE: 19
MTQFEGFTNL YQVSKTLRFE LIPQGKTLKH IQEQGFIEED KARNDHYKEL KPIIDRIYKT  60
YADQCLQLVQ LDWENLSAAI DSYRKEKTEE TRNALIEEQA TYRNAIHDYF IGRTDNLTDA  120
INKRHAEIYK GLFKAELFNG KVLKQLGTVT TTEHENALLR SFDKFTTYFS GFYENRKNVF  180
SAEDISTAIP HRIVQDNFPK FKENCHIFTR LITAVPSLRE HFENVKKAIG IFVSTSIEEV  240
FSFPFYNQLL TQTQIDLYNQ LLGGISREAG TEKIKGLNEV LNLAIQKNDE TAHIIASLPH  300
RFIPLFKQIL SDRNTLSFIL EEFKSDEEVI QSFCKYKTLL RNENVLETAE ALFNELNSID  360
LTHIFISHKK LETISSALCD HWDTLRNALY ERRISELTGK ITKSAKEKVQ RSLKHEDINL  420
QEIISAAGKE LSEAFKQKTS EILSHAHAAL DQPLPTTLKK QEEKEILKSQ LDSLLGLYHL  480
LDWFAVDESN EVDPEFSARL TGIKLEMEPS LSFYNKARNY ATKKPYSVEK FKLNFQMPTL  540
ASGWDVNKEK NNGAILFVKN GLYYLGIMPK QKGRYKALSF EPTEKTSEGF DKMYYDYFPD  600
AAKMIPKCST QLKAVTAHFQ THTTPILLSN NFIEPLEITK EIYDLNNPEK EPKKFQTAYA  660
KKTGDQKGYR EALCKWIDFT RDFLSKYTKT TSIDLSSLRP SSQYKDLGEY YAELNPLLYH  720
ISFQRIAEKE IMDAVETGKL YLFQIYNKDF AKGHHGKPNL HTLYWTGLFS PENLAKTSIK  780
LNGQAELFYR PKSRMKRMAH RLGEKMLNKK LKDQKTPIPD TLYQELYDYV NHRLSHDLSD  840
EARALLPNVI TKEVSHEIIK DRRFTSDKFF FHVPITLNYQ AANSPSKFNQ RVNAYLKEHP  900
ETPIIGIDRG ERNLIYITVI DSTGKILEQR SLNTIQQFDY QKKLDNREKE RVAARQAWSV  960
VGTIKDLKQG YLSQVIHEIV DLMIHYQAVV VLENLNFGFK SKRTGIAEKA VYQQFEKMLI  1020
DKLNCLVLKD YPAEKVGGVL NPYQLTDQFT SFAKMGTQSG FLFYVPAPYT SKIDPLTGFV  1080
DPFVWKTIKN HESRKHFLEG FDFLHYDVKT GDFILHFKMN RNLSFQRGLP GFMPAWDIVF  1140
EKNETQFDAK GTPFIAGKRI VPVIENHRFT GRYRDLYPAN ELIALLEEKG IVFRDGSNIL  1200
PKLLENDDSH AIDTMVALIR SVLQMRNSNA ATGEDYINSP VRDLNGVCFD SRFQNPEWPM  1260
DADANGAYHI ALKGQLLLNH LKESKDLKLQ NGISNQDWLA YIQELRN             1307

SEQ ID NO: 20          moltype = AA  length = 1300
FEATURE                Location/Qualifiers
source                 1..1300
                       mol_type = protein
                       organism = Francisella tularensis
SEQUENCE: 20
MSIYQEFVNK YSLSKTLRFE LIPQGKTLEN IKARGLILDD EKRAKDYKKA KQIIDKYHQF  60
FIEEILSSVC ISEDLLQNYS DVYFKLKKSD DDNLQKDFKS AKDTIKKQIS EYIKDSEKFK  120
NLFNQNLIDA KKGQESDLIL WLKQSKDNGI ELFKANSDIT DIDEALEIIK SFKGWTTYFK  180
GFHENRKNVY SSNDIPTSII YRIVDDNLPK FLENKAKYES LKDKAPEAIN YEQIKKDLAE  240
ELTFDIDYKT SEVNQRVFSL DEVFEIANFN NYLNQSGITK FNTIIGGKFV NGENTKRKGI  300
NEYINLYSQQ INDKTLKKYK MSVLFKQILS DTESKSFVID KLEDDSDVVT TMQSFYEQIA  360
AFKTVEEKSI KETLSLLFDD LKAQKLDLSK IYFKNDKSLT DLSQQVFDDY SVIGTAVLEY  420
ITQQIAPKNL DNPSKKEQEL IAKKTEKAKY LSLETIKLAL EEFNKHRDID KQCRFEEILA  480
NFAAIPMIFD EIAQNKDNLA QISIKYQNQG KKDLLQASAE DDVKAIKDLL DQTNNLLHKL  540
KIFHISQSED KANILDKDEH FYLVFEECYF ELANIVPLYN KIRNYITQKP YSDEKFKLNF  600
ENSTLANGWD KNKEPDNTAI LFIKDDKYYL GVMNKKNNKI FDDKAIKENK GEGYKKIVYK  660
LLPGANKMLP KVFFSAKSIK FYNPSEDILR IRNHSTHTKN GSPQKGYEKF EFNIEDCRKF  720
IDFYKQSISK HPEWKDFGFR FSDTQRYNSI DEFYREVENQ GYKLTFENIS ESYIDSVVNQ  780
GKLYLFQIYN KDFSAYSKGR PNLHTLYWKA LFDERNLQDV VYKLNGEAEL FYRKQSIPKK  840
ITHPAKEAIA NKNKDNPKKE SVFEYDLIKD KRFTEDKFFF HCPITINFKS SGANKFNDEI  900
NLLLKEKAND VHILSIDRGE RHLAYYTLVD GKGNIIKQDT FNIIGNDRMK TNYHDKLAAI  960
EKDRDSARKD WKKINNIKEM KEGYLSQVVH EIAKLVIEYN AIVVFEDLNF GFKRGRFKVE  1020
KQVYQKLEKM LIEKLNYLVF KDNEFDKTGG VLRAYQLTAP FETFKKMGKQ TGIIYYVPAG  1080
FTSKICPVTG FVNQLYPKYE SVSKSQEFFS KFDKICYNLD KGYFEFSFDY KNFGDKAAKG  1140
KWTIASFGSR LINFRNSDKN HNWDTREVYP TKELEKLLKD YSIEYGHGEC IKAAICGESD  1200
KKFFAKLTSV LNTILQMRNS KTGTELDYLI SPVADVNGNF FDSRQAPKNM PQDADANGAY  1260
HIGLKGLMLL GRIKNNQEGK KLNLVIKNEE YFEFVQNRNN                     1300

SEQ ID NO: 21          moltype = AA  length = 1246
FEATURE                Location/Qualifiers
source                 1..1246
```

```
                        mol_type = protein
                        organism = Porphyromonas macacae
SEQUENCE: 21
MKTQHFFEDF TSLYSLSKTI RFELKPIGKT LENIKKNGLI RRDEQRLDDY EKLKKVIDEY  60
HEDFIANILS SFSFSEEILQ SYIQNLSESE ARAKIEKTMR DTLAKAFSED ERYKSIFKKE  120
LVKKDIPVWC PAYKSLCKKF DNFTTSLVPF HENRKNLYTS NEITASIPYR IVHVNLPKFI  180
QNIEALCELQ KKMGADLYLE MMENLRNVWP SFVKTPDDLC NLKTYNHLMV QSSISEYNRF  240
VGGYSTEDGT KHQGINEWIN IYRQRNKEMR LPGLVFLHKQ ILAKVDSSSF ISDTLENDDQ  300
VFCVLRQFRK LFWNTVSSKE DDAASLKDLF CGLSGYDPEA IYVSDAHLAT ISKNIFDRWN  360
YISDAIRRKT EVLMPRKKES VERYAEKISK QIKKRQSYSL AELDDLLAHY SEESLPAGFS  420
LLSYFTSLGG QKYLVSDGEV ILYEEGSNIW DEVLIAFRDL QVILDKDFTE KKLGKDEEAV  480
SVIKKALDSA LRLRKFFDLL SGTGAEIRRD SSFYALYTDR MDKLKGLLKM YDKVRNYLTK  540
KPYSIEKFKL HFDNPSLLSG WDKNKELNNL SVIFRQNGYY YLGIMTPKGK NLFKTLPKLG  600
AEEMFYEKME YKQIAEPMLM LPKVFFPKKT KPAFAPDQSV VDIYNKKTFK TGQKGFNKKD  660
LYRLIDFYKE ALTVHEWKLF NFSFSPTEQY RNIGEFFDEV REQAYKVSMV NVPASYIDEA  720
VENGKLYLFQ IYNKDFSPYS KGIPNLHTLY WKALFSEQNQ SRVYKLCGGG ELFYRKASLH  780
MQDTTVHPKG ISIHKKNLNK KGETSLFNYD LVKDKRFTED KFFFHVPISI NYKNKKITNV  840
NQMVRDYIAQ NDDLQIIGID RGERNLLYIS RIDTRGNLLE QFSLNVIESD KGDLRTDYQK  900
ILGDREQERL RRRQEWKSIE SIKDLKDGYM SQVVHKICNM VVEHKAIVVL ENLNLSFMKG  960
RKKVEKSVYE KFERMLVDKL NYLVVDKKNL SNEPGGLYAA YQLTNPLFSF EELHRYPQSG  1020
ILFFVDPWNT SLTDPSTGFV NLLGRINYTN VGDARKFFDR FNAIRYDGKG NILFDLDLSR  1080
FDVRVETQRK LWTLTTFGSR IAKSKKSGKW MVERIENLSL CFLELFEQFN IGYRVEKDLK  1140
KAILSQDRKE FYVRLIYLFN LMMQIRNSDG EEDYILSPAL NEKNLQFDSR LIEAKDLPVD  1200
ADANGAYNVA RKGLMVVQRI KRGDHESIHR IGRAQWLRYV QEGIVE                1246

SEQ ID NO: 22           moltype = AA  length = 1373
FEATURE                 Location/Qualifiers
source                  1..1373
                        mol_type = protein
                        organism = Moraxella bovoculi
SEQUENCE: 22
MLFQDFTHLY PLSKTVRFEL KPIDRTLEHI HAKNFLSQDE TMADMHQKVK VILDDYHRDF  60
IADMMGEVKL TKLAEFYDVY LKFRKNPKDD ELQKQLKDLQ AVLRKEIVKP IGNGGKYKAG  120
YDRLFGAKLF KDGKELGDLA KFVIAQEGES SPKLAHLAHF EKFSTYFTGF HDNRKNMYSD  180
EDKHTAIAYR LIHENLPRFI DNLQILTTIK QKHSALYDQI INELTASGLD VSLASHLDGY  240
HKLLTQEGIT AYNTLLGGIS GEAGSPKIQG INELINSHHN QHCHKSERIA KLRPLHKQIL  300
SDGMSVSFLP SKFADDSEMC QAVNEFYRHY ADVFAKVQSL FDGFDDHQKD GIYVEHKNLN  360
ELSKQAFGDF ALLGRVLDGY YVDVVNPEFN ERFAKAKTDN AKAKLTKEKD KFIKGVHSLA  420
SLEQAIEHYT ARHDDESVQA GKLGQYFKHG LAGVDNPIQK IHNNHSTIKG FLERERPAGE  480
RALPKIKSGK NPEMTQLRQL KELLDNALNV AHFAKLLTTK TTLDNQDGNF YGEFGVLYDE  540
LAKIPTLYNK VRDYLSQKPF STEKYKLNFG NPTLLNGWDL NKEKDNFGVI LQKDGCYYLA  600
LLDKAHKKVF DNAPNTGKSI YQKMIYKYLE VRKQFPKVFF SKEAIAINYH PSKELVEIKD  660
KGRQRSDDER LKLYRFILEC LKIHPKYDKK FEGAIGDIQL FKKDKKGREV PISEKDLFDK  720
INGIFSSKPK LEMEDFFIGE FKRYNPSQDL VDQYNIYKKI DSNDNRKKEN FYNNHPKFKK  780
DLVRYYYESM CKHEEWEESF EFSKKLQDIG CYVDVNELFT EIETRRLNYK ISFCNINADY  840
IDELVEQGQL YLFQIYNKDF SPKAHGKPNL HTLYFKALFS EDNLADPIYK LNGEAQIFYR  900
KASLDMNETT IHRAGEVLEN KNPDNPKKRQ FVYDIIKDKR YTQDKFMLHV PITMNFGVQG  960
MTIKEFNKKV NQSIQQYDEV NVIGIDRGER HLLYLTVINS KGEILEQCSL NDITTASANG  1020
TQMTTPYHKI LDKREIERLN ARVGWGEIET IKELKSGYLS HVVHQISQLM LKYNAIVVLE  1080
DLNFGFKRGR FKVEKQIYQN FENALIKKLN HLVLKDKADD EIGSYKNALQ LTNNFTDLKS  1140
IGKQTGFLFY VPAWNTSKID PETGFVDLLK PRYENIAQSQ AFFGKFDKIC YNADKDYFEF  1200
HIDYAKFTDK AKNSRQIWTI CSHGDKRYVY DKTANQNKGA AKGINVNDEL KSLFARHHIN  1260
EKQPNLVMDI CQNNDKEFHK SLMYLLKTLL ALRYSNASSD EDFILSPVAN DEGVFFNSAL  1320
ADDTQPQNAD ANGAYHIALK GLWLLNELKN SDDLNKVKLA IDNQTWLNFA QNR         1373

SEQ ID NO: 23           moltype = AA  length = 1259
FEATURE                 Location/Qualifiers
source                  1..1259
                        mol_type = protein
                        organism = Moraxella bovoculi
SEQUENCE: 23
MGIHGVPAAL FQDFTHLYPL SKTVRFELKP IGRTLEHIHA KNFLSQDETM ADMYQKVKVI  60
LDDYHRDFIA DMMGEVKLTK LAEFYDVYLK FRKNPKDDGL QKQLKDLQAV LRKESVKPIG  120
SGGKYKTGYD RLFGAKLFKD GKELGDLAKF VIAQEGESSP KLAHLAHFEK FSTYFTGFHD  180
NRKNMYSDED KHTAIAYRLI HENLPRFIDN LQILTTIKQK HSALYDQIIN ELTASGLDVS  240
LASHLDGYHK LLTQEGITAY NRIIGEVNGY TNKHNQICHK SERIAKLRPL HKQILSDGMG  300
VSFLPSKFAD DSEMCQAVNE FYRHYTDVFA KVQSLFDGFD DHQKDGIYVE HKNLNELSKQ  360
AFGDFALLGR VLDGYYVDVV NPEFNERFAK AKTDNAKAKL TKEKDKFIKG VHSLASLEQA  420
IEHHTARHDD ESVQAGKLGQ YFKHGLAGVD NPIQKIHNNH STIKGFLERE RPAGERALPK  480
IKSGKNPEMT QLRQLKELLD NALNVAHFAK LLTTKTTLDN QDGNFYGEFG VLYDELAKIP  540
TLYNKVRDYL SQKPFSTEKY KLNFGNPTLL NGWDLNKEKD NFGVILQKDG CYYLALLDKA  600
HKKVFDNAPN TGKNVYQKMV YKLLPGPNKM LPKVFFAKSN LDYYNPSAEL LDKYAKGTHK  660
KGDNFNLKDC HALIDFFKAG INKHPEWQHF GFKFSPTSSY RDLSDFYREV EPQGYQVKFV  720
DINADYIDEL VEQGKLYLFQ IYNKDFSPKA HGKPNLHTLY FKALFSEDNL ADPIYKLNGE  780
AQIFYRKASL DMNETTIHRA GEVLENKNPD NPKKRQFVYD IIKDKRYTQD KFMLHVPITM  840
NFGVQGMTIK EFNKKVNQSI QQYDEVNVIG IDRGERHLLY LTVINSKGEI LEQRSLNDIT  900
TASANGTQVT TPYHKILDKR EIERLNARVG WGEIETIKEL KSGYLSHVVH QINQLMLKYN  960
AIVVLEDLNF GFKRGRFKVE KQIYQNFENA LIKKLNHLVL KDKADDEIGS YKNALQLTNN  1020
FTDLKSIGKQ TGFLFYVPAW NTSKIDPETG FVDLLKPRYE NIAQSQAFFG KFDKICYNTD  1080
```

```
KGYFEFHIDY AKFTDKAKNS RQKWAICSHG DKRYVYDKTA NQNKGAAKGI NVNDELKSLF  1140
ARYHINDKQP NLVMDICQNN DKEFHKSLMC LLKTLLALRY SNASSDEDFI LSPVANDEGV  1200
FFNSALADDT QPQNADANGA YHIALKGLWL LNELKNSDDL NKVKLAIDNQ TWLNFAQNR   1259

SEQ ID NO: 24          moltype = AA  length = 1269
FEATURE                Location/Qualifiers
source                 1..1269
                       mol_type = protein
                       organism = Moraxella bovoculi
SEQUENCE: 24
MGIHGVPAAL FQDFTHLYPL SKTVRFELKP IGKTLEHIHA KNFLNQDETM ADMYQKVKAI  60
LDDYHRDFIA DMMGEVKLTK LAEFYDVYLK FRKNPKDDGL QKQLKDLQAV LRKEIVKPIG  120
NGGKYKAGYD RLFGAKLFKD GKELGDLAKF VIAQEGESSP KLAHLAHFEK FSTYFTGFHD  180
NRKNMYSDED KHTAIAYRLI HENLPRFIDN LQILATIKQK HSALYDQIIN ELTASGLDVS  240
LASHLDGYHK LLTQEGITAY NTLLGGISGE AGSRKIQGIN ELINSHHNQH CHKSERIAKL  300
RPLHKQILSD GMGVSFLPSK FADDSEVCQA VNEFYRHYAD VFAKVQSLFD GFDDYQKDGI  360
YVEYKNLNEL SKQAFGDFAL LGRVLDGYYV DVVNPEFNER FAKAKTDNAK AKLTKEKDKF  420
IKGVHSLASL EQAIEHYTAR HDDESVQAGK LGQYFKHGLA GVDNPIQKIH NNHSTIKGFL  480
ERERPAGERA LPKIKSDKSP EIRQLKELLD NALNVAHFAK LLTTKTTLHN QDGNFYGEFG  540
ALYDELAKIA TLYNKVRDYL SQKPFSTEKY KLNFGNPTLL NGWDLNKEKD NFGVILQKDG  600
CYYLALLDKA HKKVFDNAPN TGKSVYQKMI YKLLPGPNKM LPKVFFAKSN LDYYNPSAEL  660
LDKYAQGTHK KGDNFNLKDC HALIDFFKAG INKHPEWQHF GFKFSPTSSY QDLSDFYREV  720
EPQGYQVKFV DINADYINEL VEQGQLYLFQ IYNKDFSPKA HGKPNLHTLY FKALFSEDNL  780
VNPIYKLNGE AEIFYRKASL DMNETTIHRA GEVLENKNPD NPKKRQFVYD IIKDKRYTQD  840
KFMLHVPITM NFGVQGMTIK EFNKKVNQSI QQYDEVNVIG IDRGERHLLY LTVINSKGEI  900
LEQRSLNDIT TASANGTQMT TPYHKILDKR EIERLNARVG WGEIETIKEL KSGYLSHVVH  960
QISQLMLKYN AIVVLEDLNF GFKRGRFKVE KQIYQNFENA LIKKLNHLVL KDKADDEIGS  1020
YKNALQLTNN FTDLKSIGKQ TGFLFYVPAW NTSKIDPETG FVDLLKPRYE NIAQSQAFFG  1080
KFDKICYNAD RGYFEFHIDY AKFNDKAKNS RQIWKICSHG DKRYVYDKTA NQNKGATIGV  1140
NVNDELKSLF TRYHINDKQP NLVMDICQNN DKEFHKSLMY LLKTLLALRY SNASSDEDFI  1200
LSPVANDEGV FFNSALADDT QPQNADANGA YHIALKGLWL LNELKNSDDL NKVKLAIDNQ  1260
TWLNFAQNR                                                         1269

SEQ ID NO: 25          moltype = AA  length = 1306
FEATURE                Location/Qualifiers
source                 1..1306
                       mol_type = protein
                       organism = Thiomicrospira sp.
SEQUENCE: 25
MGIHGVPAAT KTFDSEFFNL YSLQKTVRFE LKPVGETASF VEDFKNEGLK RVVSEDERRA  60
VDYQKVKEII DDYHRDFIEE SLNYFPEQVS KDALEQAFHL YQKLKAAKVE EREKALKEWE  120
ALQKKLREKV VKCFSDSNKA RFSRIDKKEL IKEDLINWLV AQNREDDIPT VETFNNFTTY  180
FTGFHENRKN IYSKDDHATA ISFRLIHENL PKFFDNVISF NKLKEGFPEL KFDKVKEDLE  240
VDYDLKHAFE IEYFVNFVTQ AGIDQYNYLL GGKTLEDGTK KQGMNEQINL FKQQQTRDKA  300
RQIPKLIPLF KQILSERTES QSFIPKQFES DQELFDSLQK LHNNCQDKFT VLQQAILGLA  360
EADLKKVFIK TSDLNALSNT IFGNYSVFSD ALNLYKESLK TKKAQEAFEK LPAHSIHDLI  420
QYLEQFNSSL DAEKQQSTDT VLNYFIKTDE LYSRFIKSTS EAFTQVQPLF ELEALSSKRR  480
PPESEDEGAK GQEGFEQIKR IKAYLDTLME AVHFAKPLYL VKGRKMIEGL DKDQSFYEAF  540
EMAYQELESL IIPIYNKARS YLSRKPFKAD KFKINFDNNT LLSGWDANKE TANASILFKK  600
DGLYYLGIMP KGKTFLFDYF VSSEDSEKLK QRRQKTAEEA LAQDGESYFE KIRYKLLPGA  660
SKMLPKVFFS NKNIGFYNPS DDILRIRNTA SHTKNGTPQK GHSKVEFNLN DCHKMIDFFK  720
SSIQKHPEWG SFGFTFSDTS DFEDMSAFYR EVENQGYVIS FDKIKETYIQ SQVEQGNLYL  780
FQIYNKDFSP YSKGKPNLHT LYWKALFEEA NLNNVVAKLN GEAEIFFRRH SIKASDKVVH  840
PANQAIDNKN PHTEKTQSTF EYDLVKDKRY TQDKFFFHVP ISLNFKAQGV SKFNDKVNGF  900
LKGNPDVNII GIDRGERHLL YFTVVNQKGE ILVQESLNTL MSDKGHVNDY QQKLDKKEQE  960
RDAARKSWTT VENIKELKEG YLSHVVHKLA HLIIKYNAIV CLEDLNFGFK RGRFKVEKQV  1020
YQKFEKALID KLNYLVFKEK ELGEVGHYLT AYQLTAPFES FKKLGKQSGI LFYVPADYTS  1080
KIDPTTGFVN FLDLRYQSVE KAKQLLSDFN AIRFNSVQNY FEFEIDYKKL TPKRKVGTQS  1140
KWVICTYGDV RYQNRRNQKG HWETEEVNVT EKLKALFASD SKTTTVIDYA NDDNLIDVIL  1200
EQDKASFFKE LLWLLKLTMT LRHSKIKSED DFILSPVKNE QGEFYDSRKA GEVWPKDADA  1260
NGAYHIALKG LWNLQQINQW EKGKTLNLAI KNQDWFSFIQ EKPYQE                1306

SEQ ID NO: 26          moltype = AA  length = 1214
FEATURE                Location/Qualifiers
source                 1..1214
                       mol_type = protein
                       organism = Butyrivibrio sp.
SEQUENCE: 26
MGIHGVPAAY YQNLTKKYPV SKTIRNELIP IGKTLENIRK NNILESDVKR KQDYEHVKGI  60
MDEYHKQLIN EALDNYMLPS LNQAAEIYLK KHVDVEDREE FKKTQDLLRR EVTGRLKEHE  120
NYTKIGKKDI LDLLEKLPSI SEEDYNALES FRNFYTYFTS YNKVRENLYS DEEKSSTVAY  180
RLINENLPKF LDNIKSYAFV KAAGVLADCI EEEEQDALFM VETFNMTLTQ EGIDMYNYQI  240
GKVNSAINLY NQKNHKVEEF KKIPKMKVLY KQILSDREEV FIGEFKDDET LLSSIGAYGN  300
VLMTYLKSEK INIFFDALRE SEGKNVYVKN DLSKTTMSNI VFGSWSAFDE LLNQEYDLAN  360
ENKKKDDKYF EKRQKELKKN KSYTLEQMSN LSKEDISPIE NYIERISEDI EKICIYNGEF  420
EKIVVNEHDS SRKLSKNIKA VKVIKDYLDS IKELEHDIKL INGSGQELEK NLVVYVGQEE  480
ALEQLRPVDS LYNLTRNYLT KKPFSTEKVK LNFNKSTLLN GWDKNKETDN LGILFFKDGK  540
YYLGIMNTTA NKAFVNPPAA KTENVFKKVD YKLLPGSNKM LPKVFFAKSN IGYYNPSTEL  600
YSNYKKGTHK KGPSFSIDDC HNLIDFFKES IKKHEDWSKF GFEFSDTADY RDISEFYREV  660
```

```
EKQGYKLTFT DIDESYINDL IEKNELYLFQ IYNKDFSEYS KGKLNLHTLY FMMLFDQRNL  720
DNVVYKLNGE AEVFYRPASI AENELVIHKA GEGIKNKNPN RAKVKETSTF SYDIVKDKRY  780
SKYKFTLHIP ITMNFGVDEV RRFNDVINNA LRTDDNVNVI GIDRGERNLL YVVVINSEGK  840
ILEQISLNSI INKEYDIETN YHALLDERED DRNKARKDWN TIENIKELKT GYLSQVVNVV  900
AKLVLKYNAI ICLEDLNFGF KRGRQKVEKQ VYQKFEKMLI EKLNYLVIDK SREQVSPEKM  960
GGALNALQLT SKFKSFAELG KQSGIIYYVP AYLTSKIDPT TGFVNLFYIK YENIEKAKQF  1020
FDGFDFIRFN KKDDMFEFSF DYKSFTQKAC GIRSKWIVYT NGERIIKYPN PEKNNLFDEK  1080
VINVTDEIKG LFKQYRIPYE NGEDIKEIII SKAEADFYKR LFRLLHQTLQ MRNSTSDGTR  1140
DYIISPVKND RGEFFCSEFS EGTMPKDADA NGAYNIARKG LWVLEQIRQK DEGEKVNLSM  1200
TNAEWLKYAQ LHLL                                                   1214

SEQ ID NO: 27          moltype = AA  length = 1129
FEATURE                Location/Qualifiers
source                 1..1129
                       mol_type = protein
                       organism = Alicyclobacillus acidoterrestris
SEQUENCE: 27
MAVKSIKVKL RLDDMPEIRA GLWKLHKEVN AGVRYYTEWL SLLRQENLYR RSPNGDGEQE  60
CDKTAEECKA ELLERLRARQ VENGHRGPAG SDDELLQLAR QLYELLVPQA IGAKGDAQQI  120
ARKFLSPLAD KDAVGGLGIA KAGNKPRWVR MREAGEPGWE EEKEKAETRK SADRTADVLR  180
ALADFGLKPL MRVYTDSEMS SVEWKPLRKG QAVRTWDRDM FQQAIERMMS WESWNQRVGQ  240
EYAKLVEQKN RFEQKNFVGQ EHLVHLVNQL QQDMKEASPG LESKEQTAHY VTGRALRGSD  300
KVFEKWGKLA PDAPFDLYDA EIKNVQRRNT RRFGSHDLFA KLAEPEYQAL WREDASFLTR  360
YAVYNSILRK LNHAKMFATF TLPDATAHPI WTRFDKLGGN LHQYTFLFNE FGERRHAIRF  420
HKLLKVENGV AREVDDVTVP ISMSEQLDNL LPRDPNEPIA LYFRDYGAEQ HFTGEFGGAK  480
IQCRRDQLAH MHRRRGARDV YLNVSVRVQS QSEARGERRP PYAAVFRLVG DNHRAFVHFD  540
KLSDYLAEHP DDGKLGSEGL LSGLRVMSVD LGLRTSASIS VFRVARKDEL KPNSKGRVPF  600
FFPIKGNDNL VAVHERSQLL KLPGETESKD LRAIREERQR TLRQLRTQLA YLRLLVRCGS  660
EDVGRRERSW AKLIEQPVDA ANHMTPDWRE AFENELQKLK SLHGICSDKE WMDAVYESVR  720
RVWRHMGKQV RDWRKDVRSG ERPKIRGYAK DVVGGNSIEQ IEYLERQYKF LKSWSFFGKV  780
SGQVIRAEKG SRFAITLREH IDHAKEDRLK KLADRIIMEA LGYVYALDER GKGKWVAKYP  840
PCQLILLEEL SEYQFNNDRP PSENNQLMQW SHRGVFQELI NQAQVHDLLV GTMYAAFSSR  900
FDARTGAPGI RCRRVPARCT QEHNPEPFPW WLNKFVVEHT LDACPLRADD LIPTGEGEIF  960
VSPFSAEEGD FHQIHADLNA AQNLQQRLWS DFDISQIRLR CDWGEVDGEL VLIPRLTGKR  1020
TADSYSNKVF YTNTGVTYYE RERGKKRRKV FAQEKLSEEE AELLVEADEA REKSVVLMRD  1080
PSGIINRGNW TRQKEFWSMV NQRIEGYLVK QIRSRVPLQD SACENTGDI             1129

SEQ ID NO: 28          moltype = AA  length = 1224
FEATURE                Location/Qualifiers
source                 1..1224
                       mol_type = protein
                       organism = synthetic construct
                       note = Description of Artificial Sequence: Synthetic
                        polypeptide
SEQUENCE: 28
MKKIDNFVGC YPVSKTLRFK AIPIGKTQEN IEKKRLVEED EVRAKDYKAV KKLIDRYHRE  60
FIEGVLDNVK LDGLEEYYML FNKSDREESD NKKIEIMEER FRRVISKSFK NNEEYKKIFS  120
KKIIEEILPN YIKDEEEKEL VKGFKGFYTA FVGYAQNREN MYSDEKKSTA ISYRIVNENM  180
PRFITNIKVF EKAKSILDVD KINEINEYIL NNDYYVDDFF NIDFFNYVLN QKGIDIYNAI  240
IGGIVTGDGR KIQGLNECIN LYNQENKKIR LPQFKPLYKQ ILSESESMSF YIDEIESDDM  300
LIDMLKESLQ IDSTINNAID DLKVLFNNIF DYDLSGIFIN NGLPITTISN DVYGQWSTIS  360
DGWNERYDVL SNAKDKESEK YFEKRRKEYK KVKSFSISDL QELGGKDLSI CKKINEIISE  420
MIDDYKSKIE EIQYLFDIKE LEKPLVTDLN KIELIKNSLD GLKRIERYVI PFLGTGKEQN  480
RDEVFYGYFI KCIDAIKEID GVYNKTRNYL TKKPYSKDKF KLYFENPQLM GGWDRNKESD  540
YRSTLLRKNG KYYVAIIDKS SSNCMMNIEE DENDNYEKIN YKLLPGPNKM LPKVFFSKKN  600
REYFAPSKEI ERIYSTGTFK KDTNFVKKDC ENLITFYKDS LDRHEDWSKS FDFSFKESSA  660
YRDISEFYRD VEKQGYRVSF DLLSSNAVNT LVEEGKLYLF QLYNKDFSEK SHGIPNLHTM  720
YFRSLFDDNN KGNIRLNGGA EMFMRRASLN KQDVTVHKAN QPIKNKNLLN PKKTTTLPYD  780
VYKDKRFTED QYEVHIPITM NKVPNNPYKI NHMVREQLVK DDNPYVIGID RGERNLIYVV  840
VVDGQGHIVE QLSLNEIINE NNGISIRTDY HTLLDAKERE RDESRKQWKQ IENIKELKEG  900
YISQVVHKIC ELVEKYDAVI ALEDLNSGFK NSRVKVEKQV YQKFEKMLIT KLNYMVDKKK  960
DYNKPGGVLN GYQLTTQFES FSKMGTQNGI MFYIPAWLTS KMDPTTGFVD LLKPKYKNKA  1020
DAQKFFSQFD SIRYDNQEDA FVFKVNYTKF PRTDADYNKE WEIYTNGERI RVFRNPKKNN  1080
EYDYETVNVS ERMKELFDSY DLLYDKGELK ETICEMEESK FFEELIKLFR LTLQMRNSIS  1140
GRTDVDYLIS PVKNSNGYFY NSNDYKKEGA KYPKDADANG AYNIARKVLW AIEQFKMADE  1200
DKLDKTKISI KNQEWLEYAQ THCE                                        1224

SEQ ID NO: 29          moltype = AA  length = 1297
FEATURE                Location/Qualifiers
source                 1..1297
                       mol_type = protein
                       organism = synthetic construct
                       note = Description of Artificial Sequence: Synthetic
                        polypeptide
SEQUENCE: 29
MATLVSFTKQ YQVQKTLRFE LIPQGKTQAN IDAKGFINDD LKRDENYMKV KGVIDELHKN  60
FIEQTLVNVD YDWRSLATAI KNYRKDRSDT NKKNLEKTQE AARKEIIAWF EGKRGNSAFK  120
NNQKSFYGKL FKKELFSEIL RSDDLEYDEE TQDAIACFDK FTTYFVGFHE NRKNMYSTEA  180
KSTSVAYRVV NENFSKFLSN CEAFSVLEAV CPNVLVEAEQ ELHLHKAFSD LKLSDVFKVE  240
```

```
AYNKYLSQTG IDYYNQIIGG ISSAEGVRKI RGVNEVVNNA IQQNDELKVA LRNKQFTMVQ  300
LFKQILSDRS TLSFVSEQFT SDQEVITVVK QFNDDIVNNK VLAVVKTLFE NFNSYDLEKI  360
YINSKELASV SNALLKDWSK IRNAVLENKI IELGANPPKT KISAVEKEVK NKDFSIAELA  420
SYNDKYLDKE GNDKEICSIA NVVLEAVGAL EIMLAESLPA DLKTLENKNK VKGILDAYEN  480
LLHLLNYFKV SAVNDVDLAF YGAFEKVYVD ISGVMPLYNK VRNYATKKPY SVEKFKLNFA  540
MPTLADGWDK NKERDNGSII LLKDGQYYLG VMNPQNKPVI DNAVCNDAKG YQKMVYKMFP  600
EISKMVTKCS TQLNAVKAHF EDNTNDFVLD DTDKFISDLT ITKEIYDLNN VLYDGKKKFQ  660
IDYLRNTGDF AGYHKALETW IDFVKEFLSK YRSTAIYDLT TLLPTNYYEK LDVFYSDVNN  720
LCYKIDYENI SVEQVNEWVE EGNLYLFKIY NKDFATGSTG KPNLHTMYWN AVFAEENLHD  780
VVVKLNGGAE LFYRPKSNMP KVEHRVGEKL VNRKNVNGEP IADSVHKEIY AYANGKISKS  840
ELSENAQEEL PLAIIKDVKH NITKDKRYLS DKYFFHVPIT LNYKANGNPS AFNTKVQAFL  900
KNNPDVNIIG IDRGERNLLY VVVIDQQGNI IDKKQVSYNK VNGYDYYEKL NQREKERIEA  960
RQSWGAVGKI KELKEGYLSL VVREIADMMV KYNAIVVMEN LNAGFKRVRG GIAEKAVYQK  1020
FEKMLIDKLN YLVFKDVEAK EAGGVLNAYQ LTDKFDSFEK MGNQSGFLFY VPAAYTSKID  1080
PVTGFANVFS TKHITNTEAK KEFICSFNSL RYDEAKDKFV LECDLNKFKI VANSHIKNWK  1140
FIIGGKRIVY NSKNKTYMEK YPCEDLKATL NASGIDFSSS EIINLLKNVP ANREYGKLFD  1200
ETYWAIMNTL QMRNSNALTG EDYIISAVAD DNEKVFDSRT CGAELPKDAD ANGAYHIALK  1260
GLYLLQRIDI SEEGEKVDLS IKNEEWFKFV QQKEYAR                           1297

SEQ ID NO: 30          moltype = AA  length = 1229
FEATURE                Location/Qualifiers
source                 1..1229
                       mol_type = protein
                       organism = synthetic construct
                       note = Description of Artificial Sequence: Synthetic
                        polypeptide
SEQUENCE: 30
MKEQFINRYP LSKTLRFSLI PVGETENNFN KNLLLKKDKQ RAENYEKVKC YIDRFHKEYI  60
ESVLSKARIE KVNEYANLYW KSNKDDSDIK AMESLENDMR KQISKQLTST EIYKKRLFGK  120
ELICEDLPSF LTDKDERETV ECFRSFTTYF KGFNTNRENM YSSDGKSTAI AYRCINDNLP  180
RFLDNVKSFQ KVFDNLSDET ITKLNTDLYN IFGRNIEDIF SVDYFEFVLT QSGIEIYNSM  240
IGGYTCSDKT KIQGLNECIN LYNQQVAKNE KSKKLPLMKP LYKQILSEKD SVSFIPEKFN  300
SDNEVLHAID DYYTGHIGDF DLLTELLQSL NTYNANGIFV KSGVAITDIS NGAFNSWNVL  360
RSAWNEKYEA LHPVTSKTKI DKYIEKQDKI YKAIKSFSLF ELQSLGNENG NEITDWYISS  420
INESNSKIKE AYLQAQKLLN SDYEKSYNKR LYKNEKATEL VKNLLDAIKE FQKLIKPLNG  480
TGKEENKDEL FYGKFTSYYD SIADIDRLYD KVRNYITQKP YSKDKIKLNF DNPQLLGGWD  540
KNKESDYRTV LLHKDGLYYL AVMDKSHSKA FVDAPEITSD DKDYYEKMEY KLLPGPNKML  600
PKVFFASKNI DTFQPSDRIL DIRKRESFKK GATFNKAECH EFIDYFKDSI KKHDDWSQFG  660
FKFSPTESYN DISEFYREIS DQGYSVRFNK ISKNYIDGLV NNGYIYLFQI YNKDFSKYSK  720
GTPNLHTLYF KMLFDERNLS NVVYKLNGEA EMFYREASIG DKEKITHYAN QPIKNKNPDN  780
EKKESVFEYD IVKDKRFTKR QFSLHLPITI NFKAHGQEFL NYDVRKAVKY KDDNYVIGID  840
RGERNLIYIS VINSNGEIVE QMSLNEIISD NGHKVDYQKL LDTKEKERDK ARKNWTSVEN  900
IKELKEGYIS QVVHKICELV IKYDAVIAME DLNFGFKRGR FPVEKQVYQK FENMLISKLN  960
LLIDKKAEPT EDGGLLRAYQ LTNKFDGVNK AKQNGIIFYV PAWDTSKIDP ATGFVNLLKP  1020
KCNTSVPEAK KLFETIDDIK YNANTDMFEF YIDYSKFPRC NSDFKKSWTV CTNSSRILTF  1080
RNKEKNNKWD NKQIVLTDEF KSLFNEFGID YKGNLKDSIL SISNADFYRR LIKLLSLTLQ  1140
MRNSITGSTL PEDDYLISPV ANKSGEFYDS RNYKGTNAAL PCDADANGAY NIARKALWAI  1200
NVLKDTPDDM LNKAKLSITN AEWLEYTQK                                   1229

SEQ ID NO: 31          moltype = AA  length = 1470
FEATURE                Location/Qualifiers
source                 1..1470
                       mol_type = protein
                       organism = synthetic construct
                       note = Description of Artificial Sequence: Synthetic
                        polypeptide
SEQUENCE: 31
MNNPRGAFGG FTNLYSLSKT LRFELKPYLE IPEGEKGKLF GDDKEYYKNC KTYTEYYLKK  60
ANKEYYDNEK VKNTDLQLVN FLHDERIEDA YQVLKPVFDT LHEEFITDSL ESAEAKKIDF  120
GNYYGLYEKQ KSEQNKDEKK KIDKPLETER GKLRKAFTPI YEAEGKNLKN KAGKEKKDKD  180
ILKESGFKVL IEAGILKYIK NNIDEFADKK LKNNEGKEIT KKDIETALGA ENIEGIFDGF  240
FTYFSGFNQN RENYYSTEEK ATAVASRIVD ENLSKFCDNI LLYRKNENDY LKIFNFLKNK  300
GKDLKLKNSK FGKENEPEFI PAYDMKNDEK SFSVADFVNC LSQGEIEKYN AKIANANYLI  360
NLYNQNKDGN SSKLSMFKIL YKQIGCGEKK DFIKTIKDNA ELKQILEKAC EAGKKYFIRG  420
KSEDGGVSNI FDFTDYIQSH ENYKGVYWSD KAINTISGKY FANWDTLKNK LGDAKVFNKN  480
TGEDKADVKY KVPQAVMLSE LFAVLDDNAG EDWREKGIFF KASLFEGDQN KSEIIKNANR  540
PSQALLKMIC DDMESLAKNF IDSGDKILKI SDRDYQKDEN KQKIKNWLDN ALWINQILKY  600
FKVKANKIKG DSIDARIDSG LDMLVFSSDN PAEDYDMIRN YLTQKPQDEI NKLKLNFENS  660
SLAGGWDENK EKDNSCIILK DEQDKQYLAV MKYENTKVFE QKNSQLYIAD NAAWKKMIYK  720
LVPGASKTLP KVFFSKKWTA NRPTPSDIVE IYQKGSFKKE NVDFNDKKEK DESRKEKNRE  780
KIIAELQKTC WMDIRYNIDG KIESAKYVNK EKLAKLIDFY KENLKKYPSE EESWDRLFAF  840
GFSDTKSYKS IDQFYIEVDK QGYKLEFVTI NKARLDEYVR DGKIYLFEIR SRDNNLVNGE  900
EKTSAKNLQT IYWNAAFGGD DNKPKLNGEA EIFYRPAIAE NKLNKKKDKN GKEIIDGYRF  960
SKEKFIFHCP ITLNFCLKET KINDKLNAAL AKPENGQGVY FLGIDRGEKH LAYYSLVNQK  1020
GEILEQGTLN LPFLDKNGKS RSIKVEKKSF EKDSNGGIIK DKDGNDKIKI EFVECWNYND  1080
LLDARAGDRD YARKNWTTIG TIKELKDGYI SQVVRKIVDL SIYKNTETKE FREMPAFIVL  1140
EDLNIGFKRG RQKIEKQVYQ KLELALAKKL NFLVDKKADI GEIGSVTKAI QLTPPVNNFG  1200
DMENRKQFGN MLYIRADYTS QTDPATGWRK SIYLKSGSES NVKEQIEKSF FDIRYESGDY  1260
CFEYRDRHGK MWQLYSSKNG VSLDRFHGER NNSKNVWESE KQPLNEMLDI LFDEKRFDKS  1320
```

```
KSLYEQMFKG GVALTRLPKE INKKDKPAWE SLRFVIILIQ QIRNTGKNGD DRNGDFIQSP  1380
VRDEKTGEHF DSRIYLDKEQ KGEKADLPTS GDANGAYNIA RKGIVVAEHI KRGFDKLYIS  1440
DEEWDTWLAG DEIWDKWLKE NRESLTKTRK                                   1470

SEQ ID NO: 32          moltype = AA  length = 1282
FEATURE                Location/Qualifiers
source                 1..1282
                       mol_type = protein
                       organism = synthetic construct
                       note = Description of Artificial Sequence: Synthetic
                        polypeptide
SEQUENCE: 32
MNGNRIIVYR EFVGVTPVAK TLRNELRPIG HTQEHIIHNG LIQEDELRQE KSTELKNIMD  60
DYYREYIDKS LSGVTDLDFT LLFELMNLVQ SSPSKDNKKA LEKEQSKMRE QICTHMQSDS  120
NYKNIFNAKF LKEILPDFIK NYNQYDAKDK AGKLETLALF NGFSTYFTDF FEKRKNVFTK  180
EAVSTSIAYR IVHENSLTFL ANMTSYKKIS EKALDEIEVI EKNNQDKMGD WELNQIFNPD  240
FYNMVLIQSG IDFYNEICGV VNAHMNLYCQ QTKNNYNLFK MRKLHKQILA YTSTSFEVPK  300
MFEDDMSVYN AVNAFIDETE KGNIIGKLKD IVNKYDELDE KRIYISKDFY ETLSCFMSGN  360
WNLITGCVEN FYDENIHAKG KSKEEKVKKA VKEDKYKSIN DVNDLVEKYI DEKERNEFKN  420
SNAKQYIREI SNIITDTETA HLEYDEHISL IESEEKADEM KKRLDMYMNM YHWAKAFIVD  480
EVLDRDEMFY SDIDDIYNIL ENIVPLYNRV RNYVTQKPYN SKKIKLNFQS PTLANGWSQS  540
KEFDNNAIIL IRDNKYYLAI FNAKNKPDKK IIQGNSDKKN DNDYKKMVYN LLPGANKMLP  600
KVFLSKKGIE TFKPSDYIIS GYNAHKHIKT SENFDISFCR DLIDYFKNSI EKHAEWRKYE  660
FKFSATDSYN DISEFYREVE MQGYRIDWTY ISEADINKLD EEGKIYLFQI YNKDFAENST  720
GKENLHTMYF KNIFSEENLK DIIIKLNGQA ELFYRRASVK NPVKHKKDSV LVNKTYKNQL  780
DNGDVVRIPI PDDIYNEIYK MYNGYIKEND LSEAAKEYLD KVEVRTAQKD IVKDYRYTVD  840
KYFIHTPITI NYKVTARNNV NDMAVKYIAQ NDDIHVIGID RGERNLIYIS VIDSHGNIVK  900
QKSYNILNNY DYKKKLVEKE KTREYARKNW KSIGNIKELK EGYISGVVHE IAMLMVEYNA  960
IIAMEDLNYG FKRGRFKVER QVYQKFESML INKLNYFASK GKSVDEPGGL LKGYQLTYVP  1020
DNIKNLGKQC GVIFYVPAAF TSKIDPSTGF ISAFNFKSIS TNASRKQFFM QFDEIRYCAE  1080
KDMFSFGFDY NNFDTYNITM SKTQWTVYTN GERLQSEFNN ARRTGKTKSI NLTETIKLLL  1140
EDNEINYADG HDVRIDMEKM DEDKNSEFFA QLLSLYKLTV QMRNSYTEAE EQEKGISYDK  1200
IISPVINDEG EFFDSDNYKE SDDKECKMPK DADANGAYCI ALKGLYEVLK IKSEWTEDGF  1260
DRNCLKLPHA EWLDFIQNKR YE                                           1282

SEQ ID NO: 33          moltype = AA  length = 1225
FEATURE                Location/Qualifiers
source                 1..1225
                       mol_type = protein
                       organism = synthetic construct
                       note = Description of Artificial Sequence: Synthetic
                        polypeptide
SEQUENCE: 33
MKKIDSFVNY YPLSKTLRFS LIPVGKTEDN FNAKLLLEED EKRAIEYEKV KRYIDRYHKH  60
FIETVLANFH LDDVNEYAEL YYKAGKDDKD LKYMEKLEGK MRKSISAAFT KDKKYKEIFG  120
QEIIKNILPE FLENEDEKES VKMFQGFFTY FTGFNDNRKN MYTHEAQTTA ISYRCINENL  180
PKFLDNVQSF AKIKESISSD IMNKLDEVCM DLYGVYAQDM FCTDYFSFVL SQSGIDRYNN  240
IIGGYVDDKG VKIQGINEYI NLYNQQVDEK NKRLPLMKKL YKQILIEKES ISFIPEKFES  300
DNIVINAISD YYHNNVENLF DDFNKLFNEF SEYDDNGIFV TSGLAVTDIS NAVFGSWNII  360
SDSWNEEYKD SHPMKKTTNA EKYYEDMKKE YKKNLSFTIA ELQRLGEAGC NDECKGDIKE  420
YYKTTVAEKI ENIKNAYEIS KDLLASDYEK SNDKKLCKND SAISLLKNLL DSIKDLEKTI  480
KPLLGTGKEE NKDDVFYGKF TNLYEMISEI DRLYDKVRNY VTQKPYSKDK IKLNFENPQH  540
LGGWDKNKER DYRSVLLKKE DKYYLAIMDK SNNKAFIDFP DDGECYEKIE YKLLPGPNKM  600
LPKVFFASSN IEYFAPSKKI LEIRSRESFK KGDMFNLKDC HEFIDFFKES IKKHEDWSQF  660
GFEFSPTEKY NDISEFYNEV KIQGYSLKYK NVSKKYIDEL IECGQLYLFQ IYNKDFSVYA  720
KGNPNLHTMY FKMLFDERNL ANVVYQLNGG AEMFYRKASI KDSEKIVHHA NQPIKNKNAD  780
NVKKESVFEY DIIKDKRFTK RQFSIHIPIT LNFKAKGQNF INNDVRMALK KADENYVIGI  840
DRGERNLLYI CVINSKGEIV EQKSLNEIIG DNGYRVDYHK LLDKKEAERD EARKSWGTIE  900
NIKELKEGYL SQIVHEISKL VIKYDAVIAI EDLNSGFKKG RFKVEKQVYQ KFENMLCTKL  960
NYLVDKNADA NECGGLLKAY QLTNKEDGAN RGRQNGIIFS VPAWLTSKID PVTGFADLLR  1020
PKYKSVSESV EFISKIDNIR YNSKEDYFEF DIDYSKFPNS TASYKKKWTV CTYGERIINV  1080
RNKEKNNMWD NKTIVLTDEF KKLFADFGVD VSKNIKESVL AIDSKDFYYR FINLLANTLQ  1140
LRNSEVGNVD VDYLISPVKG VDGSFYDSRL VKEKTLPENA DANGAYNIAR KALWAIDVLK  1200
QTKDEELKNA NLSIKNAEWL EYVQK                                        1225

SEQ ID NO: 34          moltype = AA  length = 1293
FEATURE                Location/Qualifiers
source                 1..1293
                       mol_type = protein
                       organism = synthetic construct
                       note = Description of Artificial Sequence: Synthetic
                        polypeptide
SEQUENCE: 34
MRTMVTFEDF TKQYQVSKTL RFELIPQGKT LENMKRDGII SVDRQRNEDY QKAKGILDKL  60
YKYILDFTME TVVIDWEALA TATEEFRKSK DKKTYEKVQS KIRTALLEHV KKQKVGTEDL  120
FKGMFSSKII TGEVLAAFPE IRLSDEENLI LEKFKDFTTY FTGFFENRKN VFTDEALSTS  180
FTYRLVNDNF IKFFDNCIVF KNVVNISPHM AKSLETCASD LGIFPGVSLE EVFSISFYNR  240
LLTQTGIDQF NQLLGGISGK EGEHKQQGLN EIINLAMQQN LEVKEVLKNK AHRFTPLFKQ  300
ILSDRSTMSF IPDAFADDDE VLSAVDAYRK YLSEKNIGDR AFQLISDMEA YSPELMRIGG  360
```

```
KYVSVLSQLL FYSWSEIRDG VKAYKESLIT GKKTKKELEN IDKEIKYGVT LQEIKEALPK  420
KDIYEEVKKY AMSVVKDYHA GLAEPLPEKI ETDDERASIK HIMDSMLGLY RFLEYFSHDS  480
IEDTDPVFGE CLDTILDDMN ETVPLYNKVR NFSTRKVYST EKFKLNFNNS SLANGWDKNK  540
EQANGAILLR KEGEYFLGIF NSKNKPKLVS DGGAGIGYEK MIYKQFPDFK KMLPKCTISL  600
KDTKAHFQKS DEDFTLQTDK FEKSIVITKQ IYDLGTQTVN GKKKFQVDYP RLTGDMEGYR  660
AALKEWIDFG KEFIQAYTST AIYDTSLFRD SSDYPDLPSF YKDVDNICYK LTFEWIPDAV  720
IDDCIDDGSL YLFKLHNKDF SSGSIGKPNL HTLYWKALFE EENLSDVVVK LNGQAELFYR  780
PKSLTRPVVH EEGEVIINKT TSTGLPVPDD VYVELSKFVR NGKKGNLTDK AKNWLDKVTV  840
RKMPHAITKD RRFTVDKFFF HVPITLNYKA DSSPYRFNDF VRQYIKDCSD VKIIGIDRGE  900
RNLIYAVVID GKGNIIEQRS FNTVGTYNYQ EKLEQKEKER QTARQDWATV TKIKDLKKGY  960
LSAVVHELSK MIVKYKAIVA LENLNVGFKR MRGGIAERSV YQQFEKALID KLNYLVFKDE  1020
EQSGYGGVLN AYQLTDKFES FSKMGQQTGF LFYVPAAYTS KIDPLTGFIN PFSWKHVKNR  1080
EDRRNFLNLF SKLYYDVNTH DFVLAYHHSN KDSKYTIKGN WEIADWDILI QENKEVFGKT  1140
GTPYCVGKRI VYMDDSTTGH NRMCAYYPHT ELKKLLSEYG IEYTSGQDLL KIIQEFDDDK  1200
LVKGLFYIIK AALQMRNSNS ETGEDYISSP IEGRPGICFD SRAEADTLPY DADANGAFHI  1260
AMKGLLLTER IRNDDKLAIS NEEWLNYIQE MRG                               1293

SEQ ID NO: 35           moltype = AA  length = 1399
FEATURE                 Location/Qualifiers
source                  1..1399
                        mol_type = protein
                        organism = synthetic construct
                        note = Description of Artificial Sequence: Synthetic
                         polypeptide
SEQUENCE: 35
MNKDIRKNFT DFVGISEIQK TLRFILIPIG KTAQNIDKYN MFEDDEIRHE YYPILKEACD  60
DFYRNHIDQQ FENLELDWSK LDEALASEDR DLINETRATY RQVLFNRLKN SVDIKGDSKK  120
NKTLSLESSD KNLGKKKTKN TFQYNFNDLF KAKLIKAILP LYIEYIYEGE KLENAKKALK  180
MYNRFTSRLS NFWQARANIF TDDEISTGSP YRLVNDNFTI FRINNSIYTK NKPFIEEDIL  240
EFEKKLKSKK IIKDFESVDD YFTVNAFNKL CTQNGIDKYN SILGGFTTKE REKVKGLNEL  300
FNLAQQSINK GKKGEYRKNI RLGKLTKLKK QILAISDSTS FLIEQIEDDQ DLYNKIKDFF  360
ELLLKEEIEN ENIFTQYANL QKLIEQADLS KIYINAKHLN KISHQVTGKW DSLNKGIALL  420
LENININEES KEKSEVISNG QTKDISSEAY KRYLQIQSEE KDIERLRTQI YFSLEDLEKA  480
LDLVLIDENM DRSDKSILSY VQSPDLNVNF ERDLTDLYSR IMKLEENNEK LLANHSAIDL  540
IKEFLDLIML RYSRWQILFC DSNYELDQTF YPIYDAVMEI LSNIIRLYNL ARNYLSRKPD  600
RMKKKKINFN NPTLADGWSE SKIPDNSSML FIKDGMYYLG IIKNRAAYSE LLEAESLQSS  660
EKKKSENSSY ERMNYHFLPD AFRSIPKSSI AMKAVKEHFE INQKTADLLL DTDKFSKPLR  720
ITKEIFDMQY VDLHKNKKKY QVDYLRDTGD KKGYRKALNT WLNFCKDFIS KYKGRNLFDY  780
SKIKDADHYE TVNEFYNDVD KYSYHIFFTS VAETTVEKFI SEGKLYLFQL YNKDFSPHST  840
GKPNLHTIYW RALFSEENLT SKNIKLNGQA EIFFRPKQIE TPFTHKKGSI LVNRFDVNGN  900
PIPINVYQEI KGFKNNVIKW DDLNKTTQEG LENDQYLYFE SEFEIIKDRR YTEDQLFFHV  960
PISFNWDIGS NPKINDLATQ YIVNSNDIHI IGIDRGENHL IYYSVIDLQG AIVEQGSLNT  1020
ITEYTENKFL NNKTNNLRKI PYKDILQQRE DERADARIKW HAIDKIKDLK DGYLGQIVHF  1080
LAKLIIKYNA IVILEDLNYG FKRGRFKVER QVYQKFEMAL MKKLNVLVFK DYDIDEIGGP  1140
LKPWQLTRPI DSYERMGRQN GILFYVPAAY TSAVDPVTGF ANLFYLNNVK NSEKFHFFSK  1200
FESIKYHSDQ DMFSFAFDYN NFGTTTRIND LSKSKWQVFT NHERSVWNNK EKNYVTQNLT  1260
DLIKKLLRTY NIEFKNNQNV LDSILKIENN TDKENFAREL FRLFRLTIQL RNTTVNENNT  1320
EITENELDYI ISPVKDKNGN FFDSRDELKN LPDNGDANGA YNIARKGLLY IEQLQESIKT  1380
GKLPTLSIST LDWFNYIMK                                               1399

SEQ ID NO: 36           moltype = AA  length = 1272
FEATURE                 Location/Qualifiers
source                  1..1272
                        mol_type = protein
                        organism = synthetic construct
                        note = Description of Artificial Sequence: Synthetic
                         polypeptide
SEQUENCE: 36
MTPIFCNFVV YQIMLFNNNI NINVKTMNKK HLSDFTNLFP VSKTLRFRLE PQGKTMENIV  60
KAQTIETDEE RSHDYEKTKE YIDDYHRQFI DDTLDKFAFK VESTGNNDSL QDYLDAYLSA  120
NDNRTKQTEE IQTNLRKAIV SAFKMQPQFN LLFKKEMVKH LLPQFVDTDD KKRIVAKFND  180
FTTYFTGFFT NRENMYSDEA KSTSIAYRIV NQNLIKFVEN MLTFKSHILP ILPQEQLATL  240
YDDFKEYLNV ASIAEMFELD HFSIVLTQRQ IEVYNSVIGG RKDENNKQIK PGLNQYINQH  300
NQAVKDKSAR LPLLKPLFNQ ILSEKAGVSF LPKQFKSASE VVKSLNEAYA ELSPVLAAIQ  360
DVVTNITDYD CNGIFIKNDL GLTDIAQRFY GNYDAVKRGL RNQYELETPM HNGQKAEKYE  420
EQVAKHLKSI ESVSLAQINQ VVTDGGDICD YFKAFGATDD GDIQRENLLA SINNAHTAIS  480
PVLNKENAND NELRKNTMLI KDLLDAIKRL QWFAKPLLGA GDETNKDQVF YGKFEPLYNQ  540
LDETISPLYD KVRSYLTKKP YSLDKFKINF EKSNLLGGWD PGADRKYQYN AVILRKDNDF  600
YLGIMRDEAT SKRKCIQVLD CNDEGLDENF EKVEYKQIKP SQNMPRCAFA KKECEENADI  660
MELKRKKNAK SYNTNKDDKN ALIRHYQRYL DRTYPEFGFV YKDADEYDTV KAFTDSMDSQ  720
DYKLSFLQVS ETGLNKLVDE GDLYLFKITN KDFSSYAKGR PNLHTIYWRM LFDPKNLANV  780
VYKLEGKAEV FFRRKSLAST TTHKAKQAIK NKSRYNEAVK PQSTFDYDII KDRRFTADKF  840
EFHVPIKMNF KAAGWNSTRL TNEVREFIKS QGVRHIIGID RGERHLLYLT MIDMDGNIVK  900
QCSLNAPAQD NARASEVDYH QLLDSKEADR LAARRNWGTI ENIKELKQGY LSQVVHLLAT  960
MMVDNDAILV LENLNAGFMR GRQKVEKSVY QKFEKMLIDK LNYIVDKGQS PDKPTGALHA  1020
VQLTGLYSDF NKSNMKRANV RQCGFVFYIP AWNTSKIDPV TGFVNLFDTH LSSMGEIKAF  1080
FSKFDSIRYN QDKGWFEFKF DYSRFTTRAE GCRTQWTVCT YGERIWTHRS KNQNNQFVND  1140
TVNVTQQMLQ LLQDCGIDPN GNLKEAIANI DSKKSLETLL HLFKLTVQMR NSVTGSEVDY  1200
MISPVADERG HFFDSRESDE HLPANADANG AFNIARKGLM VVRQIMATDD VSKIKFAVSN  1260
```

```
KDWLRFAQHI DD                                                1272

SEQ ID NO: 37          moltype = AA  length = 1313
FEATURE                Location/Qualifiers
source                 1..1313
                       mol_type = protein
                       organism = synthetic construct
                       note = Description of Artificial Sequence: Synthetic
                        polypeptide
SEQUENCE: 37
MNKGGYVIME KMTEKNRWEN QFRITKTIKE EIIPTGYTKV NLQRVNMLKR EMERNEDLKK  60
MKEICDEYYR NMIDVSLRLE QVRTLGWESL IHKYRMLNKD EKEIKALEKE QEDLRKKISK  120
GFGEKKAWTG EQFIKKILPQ YLMDHYTGEE LEEKLRIVKK FKGCTMFLST FFKNRENIFT  180
DKPIHTAVGH RITSENAMLF AANINTYEKM ESNVTLEIER LQREFWRRGI NISEIFTDAY  240
YVNVLTQKQI EAYNKICGDI NQHMNEYCQK QKLKFSEFRM RELKKQILAV VGEHFEIPEK  300
IESTKEVYRE LNEYYESLKE LHGQFEELKS VQLKYSQIYV QKKGYDRISR YIGGQWDLIQ  360
ECMKKDCASG MKGTKKNHDA KIEEEVAKVK YQSIEHIQKL VCTYEEDRGH KVTDYVDEFI  420
VSVCDLLGAD HIITRDGERI ELPLQYEPGT DLLKNDTINQ RRLSDIKTIL DWHMDMLEWL  480
KTFLVNDLVI KDEEFYMAIE ELNERMQCVI SVYNRIRNYV TQKGYEPEKI RICFDKGTIL  540
TGWTTGDNYQ YSGFLLMRND KYYLGIINTN EKSVRKILDG NEECKDENDY IRVGYHLIND  600
ASKQLPRIFV MPKAGKKSEI LMKDEQCDYI WDGYCHNKHN ESKEFMRELI DYYKRSIMNY  660
DKWEGYCFKF SSTESYDNMQ DFYKEVREQS YNISFSYINE NVLEQLDKDG KIYLFQVYNK  720
DFAAGSTGTP NLHTMYLQNL FSSQNLELKR LRLGGNAELF YRPGTEKDVT HRKGSILVDR  780
TYVREEKDGI EVRDTVPEKE YLEIYRYLNG KQKGDLSESA KQWLDKVHYR EAPCDIIKDK  840
RYAQEKYFLH FSVEINPNAE GQTALNDNVR RWLSEEEDIH VIGIDRGERN LIYVSLMDGK  900
GRIKDQKSYN IVNSGNKEPV DYLAKLKVRE KERDEARRNW KAIGKIKDIK TGYLSYVVHE  960
IVEMAVREKA IIVMEDLNYG FKRGRFKVER QVYQKFEEML INKLNYVVDK QLSVDEPGGL  1020
LRGYQLAFIP KDKKSSMRQN GIVFYVPAGY TSKIDPTTGF VNIFKFPQFG KGDDDGNGKD  1080
YDKIRAFFGK FDEIRYECDE KVTADNTREV KERYRFDFDY SKFETHLVHM KKTKWTVYAE  1140
GERIKRKKVG NYWTSEVISD IALRMSNTLN IAGIEYKDGH NLVNEICALR GKQAGIILNE  1200
LLEIVRLTVQ LRNSTTEGDV DERDEIISPV LNEKYGCFYH STEYKQQNGD VLPKDADANG  1260
AYCIGLKGIY EIRQIKNKWK EDMTKGEGKA LNEGMRISHD QWFEFIQNMN KGE         1313

SEQ ID NO: 38          moltype = AA  length = 1134
FEATURE                Location/Qualifiers
source                 1..1134
                       mol_type = protein
                       organism = synthetic construct
                       note = Description of Artificial Sequence: Synthetic
                        polypeptide
SEQUENCE: 38
MNELVKNRCK QTKTICQKLI PIGKTRETIE KYNLMEIDRK IAANKELMNK LFSLIAGKHI  60
NDTLSKCTDL DFEPLLTSLS SLNNAKENDR DNLREYYDSV FEEKKTLAEE ISSRLTAVKF  120
AGKDFFTKNI PDFLETYEGD DKNEMSELVS LVIENTVTAG YVKKLEKIDR SMEYRLVSGT  180
VVKRVLTDNA DIYEKNIEKA KDFDYGVLNI DEASQFTTLV AKDYANYLTA DGIAIYNVGI  240
GKINLALNEY CQKNKEYSYN KLALLPLQKM LYGEKLSLFE KLEDFTSDEE LINSYNKFAK  300
TVNESGLAEI IKKAVPSYDE IVIKPNKISN YSNSITGHWS LVNRIMKDYL ENNGIKNADK  360
YMEKGLTLSE IGDALENKNI KHSDFISNLI NDLGHTYTEI KENKESLKKD ESVNALIIKK  420
ELDMLLSILQ NLKVFDIDNE MFDTGFGIEV SKAIEILGYG VPLYNKIRNY ITKKPDPKKK  480
FMTKFGSATI GTGITTSVEG SKKATFLKDG DAVFLLLYNT AGCKANNVSV SNLADLINSS  540
LEIENSGKCY QKMIYQTPGD IKKQIPRVFV YKSEDDDLIK DFKAGLHKTD LSFLNGRLIP  600
YLKEAFATHE TYKNYTFSYR NSYESYDEFC EHMSEQAYIL EWKWIDKKLI DDLVEDGSLL  660
MFRVWNRFMK KKEGKISKHA KIVNELFSDE NASNAAIKLL SVFDIFYRDK QIDNPIVHKA  720
GTTLYNKRTK DGEVIVDYTT MVKNKEKRPN VYTTTKKYDI IKDRRYTEEQ FEIHLHVNIG  780
KEENKEKLET SKVINEKKNT LVVTRSNEHL LYVVIFDEND NILLKKSLNT VKGMNFKSKL  840
EVVEIQKKEN MQSWKTVGSN QALMEGYLSF AIKEIADLVK EYDAILVLEQ NSVGKNILNE  900
RVYTRFKEML ITNLSLDVDY ENKDFYSYTE LGGKVASWRD CVTNGICIQV PSAYKYKDPT  960
TSFSTISMYA KTTAEKSKKL KQIKSFKYNR ERGLFELVIA KGVGLENNIV CDSFGSRSII  1020
ENDISKEVSC TLKIEKYLID AGIEYNDEKE VLKDLDTAAK TDAVHKAVTL LLKCFNESPD  1080
GRYYISPCGE HFTLCDAPEV LSAINYYIRS RYIREQIVEG VKKMEYKKTI LLAK         1134

SEQ ID NO: 39          moltype = AA  length = 1259
FEATURE                Location/Qualifiers
source                 1..1259
                       mol_type = protein
                       organism = synthetic construct
                       note = Description of Artificial Sequence: Synthetic
                        polypeptide
SEQUENCE: 39
MNYKTGLEDF IGKESLSKTL RNALIPTEST KIHMEEMGVI RDDELRAEKQ QELKEIMDDY  60
YRTFIEEKLG QIQGIQWNSL FQKMEETMED ISVRKDLDKI QNEKRKEICC YFTSDKRFKD  120
LFNAKLITDI LPNFIKDNKE YTEEEKAEKE QTRVLFQRFA TAFTNYFNQR RNNFSEDNIS  180
TAISFRIVNE NSEIHLQNMR AFQRIEQQYP EEVCGMEEEY KDMLQEWQMK HIYSVDFYDR  240
ELTQPGIEYY NGICGKINEH MNQFCQKNRI NKNDFRMKKL HKQILCKKSS YYEIPFRFES  300
DQEVYDALNE FIKTMKKKEI IRRCVHLGQE CDDYDLGKIY ISSNKYEQIS NALYGSWDTI  360
RKCIKEEYMD ALPGKGEKKE EKAEAAAKKE EYRSIADIDK IISLYGSEMD RTISAKKCIT  420
EICDMAGQIS IDPLVCNSDI KLLQNKEKTT EIKTILDSFL HVYQWGQTFI VSDIIEKDSY  480
FYSELEDVLE DFEGITTLYN HVRSYVTQKP YSTVKFKLHF GSPTLANGWS QSKEYDNNAI  540
LLMRDQKFYL GIFNVRNKPD KQIIKGHEKE EKGDYKKMIY NLLPGPSKML PKVFITSRSG  600
```

```
QETYKPSKHI LDGYNEKRHI KSSPKFDLGY CWDLIDYYKE CIHKHPDWKN YDFHFSDTKD  660
YEDISGFYRE VEMQGYQIKW TYISADEIQK LDEKGQIFLF QIYNKDFSVH STGKDNLHTM  720
YLKNLFSEEN LKDIVLKLNG EAELFFRKAS IKTPIVHKKG SVLVNRSYTQ TVGNKEIRVS  780
IPEEYYTEIY NYLNHIGKGK LSSEAQRYLD EGKIKSFTAT KDIVKNYRYC CDHYFLHLPI  840
TINFKAKSDV AVNERTLAYI AKKEDIHIIG IDRGERNLLY ISVVDVHGNI REQRSFNIVN  900
GYDYQQKLKD REKSRDAARK NWEEIEKIKE LKEGYLSMVI HYIAQLVVKY NAVVAMEDLN  960
YGFKTGRFKV ERQVYQKFET MLIEKLHYLV FKDREVCEEG GVLRGYQLTY IPESLKKVGK  1020
QCGFIFYVPA GYTSKIDPTT GFVNLFSFKN LTNRESRQDF VGKFDEIRYD RDKKMFEFSF  1080
DYNNYIKKGT ILASTKWKVY TNGTRLKKIV VNGKYTSQSM EVELTDAMEK MLQRAGIEYH  1140
DGKDLKGQIV EKGIEAEIID IFRLTVQMRN SRSESEDREY DRLISPVLND KGEFFDTATA  1200
DKTLPQDADA NGAYCIALKG LYEVKQIKEN WKENEQFPRN KLVQDNKTWF DFMQKKRYL   1259

SEQ ID NO: 40          moltype = AA  length = 1271
FEATURE                Location/Qualifiers
source                 1..1271
                       mol_type = protein
                       organism = synthetic construct
                       note = Description of Artificial Sequence: Synthetic
                        polypeptide
SEQUENCE: 40
MEDKQFLERY KEFIGLNSLS KTLRNSLIPV GSTLKHIQEY GILEEDSLRA QKREELKGIM  60
DDYYRNYIEM HLRDVHDIDW NELFEALTEV KKNQTDDAKK RLEKIQEKKR KEIYQYLSDD  120
AVFSEMFKEK MISGILPDFI RCNEGYSEEE KEEKLKTVAL FHRFTSSFND FFLNRKNVFT  180
KEAIVTAIGY RVVHENAEIF LENMVAFQNI QKSAESQISI IERKNEHYFM EWKLSHIFTA  240
DYYMMLMTQK AIEHYNEMCG VVNQQMREYC QKEKKNWNLY RMKRLHKQIL SNASTSFKIP  300
EKYENDAEVY ESVNSFLQNV MEKTVMERIA VLKNSTDNFD LSKIYITAPY YEKISNYLCG  360
SWNTITDCLT HYYEQQIAGK GARKDQKVKA AVKADKWKSL SEIEQLLKEY ARAEEVKRKP  420
EEYIAEIENI VSLKEAHLLE YHPEVNLIEN EKYATEIKDV LDNYMELFHW MKWFYIEEAV  480
EKEVNFYGEL DDLYEEIKDI VPLYNKVRNY VTQKPYSDTK IKLNFGTPTL ANGWSKSKEY  540
DYNAILLQKD GKYYMGIFNP IQKPEKEIIE GHSQPLEGNE YKKMVYYYLP SANKMLPKVL  600
LSKKGMEIYQ PSEYIINGYK ERRHIKSEEK FDLQFCHDLI DYFKSGIERN SDWKVFGFDF  660
SDTDTYQDIS GFYREVEDQG YKIDWTYIKE ADIDRLNEEG KLYLFQIYNK DFSEKSTGRE  720
NLHTMYLKNL FSEENVREQV LKLNGEAEIF FRKSSVKKPI IHKKGTMLVN RTYMEEVNGN  780
SVRRNIPEKE YQEIYNYKNH RLKGELSTEA KKYLEKAVCH ETKKDIVKDY RYSVDKFFIH  840
LPITINYRAS GKETLNSVAQ RYIAHQNDMH VIGIDRGERN LIYVSVINMQ GEIKEQKSFN  900
IINEFNYKEK LKEREQSRGA ARRNWKEIGQ IKDLKEGYLS GVIHEIAKMM IKYHAIIAME  960
DLNYGFKRGR FKVERQVYQK FENMLIQKLN YLVFKDRPAD EDGGVLRGYQ LAYIPDSVKK  1020
MGRQCGMIFY VPAAFTSKID PTTGFVDIFK HKVYTTEQAK REFILSFDEI CYDVERQLFR  1080
FTFDYANFVT QNVTLARNNW TIYTNGTRAQ KEFGNGRMRD KEDYNPKDKM VELLESEGIE  1140
FKSGKNLLPA LKKVSNAKVF EELQKIVRFT VQLRNSKSEE NDVDYDHVIS PVLNEEGNFF  1200
DSSKYKNKEE KKESLLPVDA DANGAYCIAL KGLYIMQAIQ KNWSEEKALS PDVLRLNNND  1260
WFDYIQNKRY R                                                      1271

SEQ ID NO: 41          moltype = AA  length = 1367
FEATURE                Location/Qualifiers
source                 1..1367
                       mol_type = protein
                       organism = synthetic construct
                       note = Description of Artificial Sequence: Synthetic
                        polypeptide
SEQUENCE: 41
MEKSLNDFIG LYSVSKTLRF ELKPVSETLE NIKKFHFLEE DKKKANDYKD VKKIIDNYHK  60
YFIDDVLKNA SFNWKKLEEA IREYNKNKSD DSALVAEQKK LGDAILKLFT SDKRYKALTA  120
ATPKELFESI LPDWFGEQCN QDLNKAALKT FQKFTSYFTG FQENRKNVYS AEAIPTAVPY  180
RIVNDNFPKF LQNVLIFKTI QEKCPQIIDE VEKELSSYLG KEKLAGIFTL ESFNKYLGQG  240
GKENQRGIDF YNQIIGGVVE KEGGINLRGV NQFLNLYWQQ HPDFTKEDRR IKMVPLYKQI  300
LSDRSSLSFK IESIENDEEL KNALLECADK LELKNDEKKS IFEEVCDLFS SVKNLDLSGI  360
YINRKDINSV SRILTGDWSW LQSRMNVYAE EKFTTKAEKA RWQKSLDDEG ENKSKGFYSL  420
TDLNEVLEYS SENVAETDIR ITDYFEHRCR YYVDKETEMF VQGSELVALS LQEMCDDILK  480
KRKAMNTVLE NLSSENKLRE KTDDVAVIKE YLDAVQELLH RIKPLKVNGV GDSTFYSVYD  540
SIYSALSEVI SVYNKTRNYI TKKAASPEKY KLNFDNPTLA DGWDLNKEQA NTSVILRKDG  600
MFYLGIMNPK NKPKFAEKYD CGNESCYEKM IYKQFDATKQ IPKCSTQKKE VQKYFLSGAT  660
EPYILNDKKS FKSELIITKD IWFMNNHVWD GEKFVPKRDN ETRPKKFQIG YFKQTGDFDG  720
YKNALSNWIS FCKNFLQSYL SATVYDYNFK NSEEYEGLDE FYNYLNATCY KLNFINIPET  780
EINKMVSEGK LYLFQIYNKD FASGSTGMPN MHTLYWKNLF SDENLKNVCL KLNGEAELFY  840
RPAGIKEPVI HKEGSYLVNR TTEDGESIPE KIYFEIYKNA NGKLEKLSDE AQNYISNHEV  900
VIKKAGHEII KDRHYTEPKF LFHVPLTINF KASGNSYSIN ENVRKFLKNN PDVNIIGLDR  960
GERHLIYLSL INQKGEIIKQ FTFNEVERNK NGRTIKVNYH EKLDQREKER DAARKSWQAI  1020
GKIAELKEGY LSAVIHQLTK LMVEYNAVVV MEDLNFGFKR GRFHVEKQVY QKFEHILIDK  1080
SNYLVFKDRG LNEPGGVLNG YQIAGQFESF QKLGKQSGML FYVPAGYTSK IDPKTGFVSM  1140
MNFKDLTNVH KKRDFFSKFD NIHYDEANGS FVFTFDYKKF DGKAKEEMKL TKWSVYSRDK  1200
RIVYFAKTKS YEDVLPTEKL QKIFESNGID YKSGNNIQDS VMAIGADLKE GAKPSKEISD  1260
FWDGLLSNFK LILQMRNSNA RTGEDYIISP VMADDGTFFD SREEFKKGED AKLPLDADAN  1320
GAYHIALKGL SLINKINLSK DEELKKFDMK ISNADWFKFA QEKNYAK               1367

SEQ ID NO: 42          moltype = AA  length = 1229
FEATURE                Location/Qualifiers
source                 1..1229
                       mol_type = protein
```

```
                        organism = synthetic construct
                        note = Description of Artificial Sequence: Synthetic
                         polypeptide
SEQUENCE: 42
MEEKKMSKIE KFIGKYKISK TLRFRAVPVG KTQDNIEKKG ILEKDKKRSE DYEKVKAYLD  60
SLHRDFIENT LKKVKLNELN EYACLFFSGT KDDGDKKKME KLEEKMRKTI SNEFCNDEMY  120
KKIFSEKILS ENNEEDVSDI VSSYKGFFTS LNGYVNNRKN LYVSDAKPTS IAYRCINENL  180
PKFLRNVECY KKVVQVIPKE QIEYMSNNLN LSPYRIEDCF NIDFFEFCLS QGGIDLYNTF  240
IGGYSKKDGT KVQGINEIVN LYNQKNKKDK EKYKLPQFTP LFKQILSDRD TKSFSIEKLE  300
NIYEVVELVK KSYSDEMFDD IETVFSNLNY YDASGIYVKN GPAITHISMN LTKDWATIRN  360
NWNYEYDEKH STKKNKNIEK YEDTRNTMYK KIDSFTLEYI SRLVGKDIDE LVKYFENEVA  420
NFVMDIKKTY SKLTPLFDRC QKENFDISED EVNDIKGYLD NVKLLESFMK SFTINGKENN  480
IDYVFYGKFT DDYDKLHEFD HIYNKVRNYI TTSRKPYKLD KYKLYFDNPQ LLGGWDINKE  540
KDYRTVMLTK DGKYYFAIID KGEHPFDNIP KDYFDNNGYY KKIIYRQIPN AAKYLSSKQI  600
VPQNPPEEVK RILDKKKADS KSLTEEEKNI FIDYIKSDFL KNYKLLFDKN NNPYFNFAFR  660
ESSTYESLNE FFEDVERQAY SVRYENLPAD YIDNLVNEGK IYLFEIYSKD FSEYSKGTNN  720
LHTMYFKALF DNDNLKNTVF KLSGNAELFI RPASIKKDEL VIHPKNQLLQ NKNPLNPKKQ  780
SIFDYDLVKD KRFFENQYML HISIEINKNE RDAKKIKNIN EMVRKELKDS DDNYIIGIDR  840
GERNLLYVCV INSAGKIVEQ MSLNEIINEY NGIKHTVDYQ GLLDKCEKER NAQRQSWKSI  900
ENIKELKDGY ISQVVHKLCQ LVEKYDAIIA MENLNGGFKR GRTKFEKQVY QKFENKLINK  960
MEYMADKKRK TTENGGILRG YQLTNGCINN SYQNGFIFYV PAWLTSKIDP TTGFVDLLKP  1020
KYTNVEEAHL WINKFNSITY DKKLDMFAFN INYSQFPRAD IDYRKIWTFY TNGYRIETFR  1080
NSEKNNEFDW KEVHLTSVIK KLLEEYQINY ISGKNIIDDL IQIKDKPFWN SFIKYIRLTL  1140
QMRNSITGRT DVDYIISPVI NNEGTFYDSR KDLDEITLPQ DADANGAYNI ARKALWIIEK  1200
LKESPDEELN KVKLAITQRE WLEYAQINI                                  1229

SEQ ID NO: 43           moltype = AA  length = 1261
FEATURE                 Location/Qualifiers
source                  1..1261
                        mol_type = protein
                        organism = synthetic construct
                        note = Description of Artificial Sequence: Synthetic
                         polypeptide
SEQUENCE: 43
MIIHNCYIGG SFMKKIDSFT NCYSLSKTLR FKLIPIGATQ SNFDLNKMLD EDKKRAENYS  60
KAKSIIDKYH RFFIDKVLSS VTENKAFDSF LEDVRAYAEL YYRSNKDDSD KASMKTLESK  120
MRKFIALALQ SDEGFKDLFG QNLIKKTLPE FLESDTDKEI IAEFDGFSTY FTGFFNNRKN  180
MYSADDQPTA ISYRCINDNL PKFLDNVRTF KNSDVASILN DNLKILNEDF DGIYGTSAED  240
VFNVDYFPFV LSQKGIEAYN SILGGYTNSD GSKIKGLNEY INLYNQKNEN IHRIPKMKQL  300
FKQILSERES VSFIPEKFDS DDDVLSSIND YYLERDGGKV LSIEKTVEKI EKLFSAVTDY  360
STDGIFVKNA AELTAVCSGA FGYWGTVQNA WNNEYDALNG YKETEKYIDK RKKAYKSIES  420
FSLADIQKYA DVSESSETNA EVTEWLRNEI KEKCNLAVQG YESSKDLISK PYTESKKLFN  480
NDNAVELIKN ALDSVKELEN VLRLLLGTGK EESKDENFYG EFLPCYERIC EVDSLYDKVR  540
NYMTQKLYKT DKIKLNFQNP QFLGGWDRNK EADYSAVLLR RNSLYYIAIM PSGYKRVFEK  600
IPAPKADETV YEKVIYKLLP GPNKMLPKVF FSKKGIETFN PPKEILEKYE LGTHKTGDGF  660
NLDDCHALID YFKSALDVHS DWSNFGFRFS DTSTYKNIAD FYNEVKNQGY KITFCDVPQS  720
YINELVDEGK LYLFQLYNKD FSEHSKGTPN LHTLYFKMLF DERNLENVVF KLNGEAEMFY  780
REASISKDDM IVHPKNQPIK NKNEQNSRKQ STFEYDIVKD RRYTVDQFML HIPITLNFTA  840
NGGTNINNEV RKALKDCDKN YVIGIDRGER NLLYICVVDS EGRIIEQYSL NEIINEYNGN  900
TYSTDYHALL DKKEKERLES RKAWKTVENI KELKEGYISQ VVHKICELVE KYDAVIVMED  960
LNLGFKQGRS GKFEKSVYQK FEKMLIDKLN YFADKKKSPE EIGSVLNAYQ LTNAFESFEK  1020
MGKQNGFIFY VPAYLTSKID PTTGFADLLH PSSKQSKESM RDFVGRFDSI TFNKTENYFE  1080
FELDYNKFPR CNTDYRKKWT VCTYGSRIKT FRNPEKNSEW DNKTVELTPA FMALFEKYSI  1140
DVNGDIKAQI MSVDKKDFFV ELIGLLRLTL QMRNSETGKV DRDYLISPVK NSEGVFYNSD  1200
DYKGIENASL PKDADANGAY NIARKGLWII EQIKACENDA ELNKIRLAIS NAEWLEYAQK  1260
K                                                                1261

SEQ ID NO: 44           moltype = AA  length = 1242
FEATURE                 Location/Qualifiers
source                  1..1242
                        mol_type = protein
                        organism = synthetic construct
                        note = Description of Artificial Sequence: Synthetic
                         polypeptide
SEQUENCE: 44
MKEQFVNQYP ISKTLRFSLI PIGKTEENFN KNLLLKEDEK KAEEYQKVKG YIDRYHKFFI  60
ETALCNINFE GFEEYSLLYY KCSKDDNDLK TMEDIEIKLR KQISKTMTSH KLYKDLFGEN  120
MIKTILPNFL DSDEEKNSLE MFRGFYTYFS GFNTNRKNMY TEEAKSTSIA YRCINDNLPK  180
FLDNSKSFEK IKCALNKEEL KAKNEEFYEI FQIYATDIFN IDFFNFVLTQ PGIDKYNGII  240
GGYTCSDGTK VQGLNEIINL YNQQIAKDDK SKRLPLLKML YKQILSDRET VSFIPEKFSS  300
DNEVLESINN YFSKNVSNAI KSLKELFQGF EAYNMNGIFI SSGVAITDLS NAVFGDWNAI  360
STAWEKAYFE TNPPKKNKSQ EKYEEELKAN YKKIKSFSLD EIQRLGSIAK SPDSIGSVAE  420
YYKITVTEKI DNITELYDGS KELLNCNYSE SYDKKLIKND TVIEKVKTLL DAVKSLEKLI  480
KPLVGTGKED KDELFYGTFL PLYTSLSAVD RLYDKVRNYA TQKPYSKDKI KLNFNCSSFL  540
SGWATDYSSN GGLIFEKDGL YYLGIVNKKF TTEEIDYLQQ NADENPAQRI VYDFQKPDNK  600
NTPRLFIRSK GTNYSPSVKE YNLPVEEIVE LYDKRYFTTE YRNKNPELYK ASLVKLIDYF  660
KLGFTRHESY RHYDFKWKKS EEYNDISEFY KDVEISCYSL KQEKINYNTL LNFVAENRIY  720
LFQIYNKDFS KYSKGTPNLH TRYFKALFDE NNLSDVVFKL NGGSEMFFRK ASIKDNEKVV  780
HPANQPIDNK NPDNSKKQST FDYELIKDKR FTKHQFSIHI PITMNFKARG RDFINNDIRK  840
```

```
AIKSEYKPYV IGIDRGERNL IYISVINNNG EIVEQMSLND IISDNGYKVD YQRLLDRKEK  900
ERDNARKSWG TIENIKELKE GYISQVIHKI CELVIKYDAV IAMEDLNFGF KRGRFNVEKQ  960
VYQKFENMLI SKLNYLCDKK SEANSEGGLL KAYQLTNKFD GVNKGKQNGI IFYVPAWLTS  1020
KIDPVTGFVD LLHPKYISVE ETHSLFEKLD DIRYNFEKDM FEFDIDYSKL PKCNADFKQK  1080
WTVCTNADRI MTFRNSEKNN EWDNKRILLS DEFKRLFEEF GIDYCHNLKN KILSISNKDF  1140
CYRFIKLFAL TMQMRNSITG STNPEDDYLI SPVRDENGVF YDSRNFIGSK AGLPIDADAN  1200
GAYNIARKGL WAINAIKSTA DDMLDKVDLS ISNAKWLEYV QK                    1242

SEQ ID NO: 45          moltype = AA  length = 1307
FEATURE                Location/Qualifiers
source                 1..1307
                       mol_type = protein
                       organism = synthetic construct
                       note = Description of Artificial Sequence: Synthetic
                        polypeptide
SEQUENCE: 45
MADLSQFTHK YQVPKTLRFE LIPQGKTLEN LSAYGMVADD KQRSENYKKL KPVIDRIYKY  60
FIEESLKNTN LDWNPLYEAI REYRKEKTTA TITNLKEQQD ICRRAIASRF EGKVPDKGDK  120
SVKDFNKKQS KLFKELFGKE LFTDSVLEQL PGVSLSDEDK ALLKSFDKFT TYFVGFYDNR  180
KNVFSSDDIS TGIPHRLVQE NFPKFIDNCD DYKRLVLVAP ELKEKLEKAA EATKIFEDVS  240
LDEIFSIKFY NRLLQQNQID QFNQLLGGIA GAPGTPKIQG LNETLNLSMQ QDKTLEQKLK  300
SVPHRFSPLY KQILSDRSSL SFIPESFSCD AEVLLAVQEY LDNLKTEHVI EDLKEVFNRL  360
TTLDLKHIYV NSTKVTAFSQ ALFGDWNLCR EQLRVYKMSN GNEKITKKAL GELESWLKNS  420
DIAFTELQEA LADEALPAKV NLKVQEAISG LNEQMAKSLP KELKIPEEKE ELKALLDAIQ  480
EVYHTLEWFI VSDDVETDTD FYVPLKETLQ IIQPIIPLYN KVRNFATQKP YSVEKFKLNF  540
ANPTLADGWD ENKEQQNCAV LFQKGNNYYL GILNPKNKPD FDNVDTEKQG NCYQKMVYKQ  600
FPDFSKMMPK CTTQLKEVKQ HFEGKDSDYI LNNKNFIKPL TITREVYDLN NVLYDGKKKF  660
QIDYLRKTKD EDGYYTALHT WIDFAKKFVA SYKSTSIYDT STILPPEKYE KLNEFYGALD  720
NLFYQIKFEN IPEEIIDTYV EDGKLFLFQI YNKDFAAGAT GAPNLHTIYW KAVFDPENVK  780
DVVVKLNGQA ELFYRPKSNM DVIRHKVGEK LVNRTLKDGS ILTDELHKEL YLYANGSLKK  840
GLSEDAKIIL DKNLAVIYDV HHEIVKDRRF TTDKFFFHVP LTLNYKCDKN PVKFNAEVQE  900
YLKENPDTYV IGIDRGERNL IYAVVIDPKG RIVEQKSFNV INGFDYHGKL DQREKERVKA  960
RQAWTAVGKI KELKQGYLSL VVHEISKMMV RYQAVVVLEN LNVGFKRVRS GIAEKAVYQQ  1020
FEKMLINKLN YLMFKDAGGT EPGSVLNAYQ LTDRFESFAK MGLQTGFLFY IPAAFTSKID  1080
PATGFVDPFR WGAIKTLADK REFLSGFESL KFDSTTGNFI LHFDVSKNKN FQKKLEGFVP  1140
DWDIIIEANK MKTGKGATYI AGKRIEFVRD NNSQGHYEDY LPCNALAETL RQCDIPYEEG  1200
KDILPLILEK NDSKLLHSVF KVVRLTLQMR NSNAETGEDY ISSPVEDVSG SCFDSRMENE  1260
KLPKDADANG AYHIALKGML ALERLRKDEK MAISNNDWLN YIQEKRA               1307

SEQ ID NO: 46          moltype = AA  length = 1286
FEATURE                Location/Qualifiers
source                 1..1286
                       mol_type = protein
                       organism = synthetic construct
                       note = Description of Artificial Sequence: Synthetic
                        polypeptide
SEQUENCE: 46
MTNFDNFTKK YVNSKTIRLE AIPVGKTLKN IEKMGFIAAD RQRDEDYQKA KSVIDHIYKA  60
FMDDCLKDLF LDWDPLYEAV VACWRERSPE GRQALQIMQA DYRKKIADRF RNHELYGSLF  120
TKKIFDGSVA QRLPDLEQSA EEKSLLSNFN KFTSYFRDFF DKRKRLFSDD EKHSAIAYRL  180
INENFLKFVA NCEAFRRMTE RVPELREKLQ NTGSLQVYNG LALDEVFSAD FYNQLIVQKQ  240
IDLYNQLIGG IAGEPGTPNI QGLNATINLA LQGDSSLHEK LAGIPHRFNP LYKQILSDVS  300
TLSFVPSAFQ SDGEMLAAVR GFKVQLESGR VLQNVRRLFN GLETEADLSR VYVNNSKLAA  360
FSSMFFGRWN LCSDALFAWK KGKQKKITNK KLTEIKKWLK NSDIAIAEIQ EAFGEDFPRG  420
KINEKIQAQA DALHSQLALP IPENLKALCA KDGLKSMLDT VLGLYRMLQW FIVGDDNEKD  480
SDFYFGLGKI LGSLDPVLVL YNRVRNYITK KPYSLTKFRL NFDNSQLLNG WDENNLDTNC  540
ASIFIKDGKY YLGISNKNNR PQFDTVATSG KSGYQRMVYK QFANWGRDLP HSTTQMKKVK  600
KHFSASDADY VLDGDKFIRP LIITKEIFDL NNVKFNGKKK LQVDYLRNTG DREGYTHALH  660
TWINFAKDFC ACYKSTSIYD ISCLRPTDQY DNLMDFYADL GNLSHRIVWQ TIPEEAIDNY  720
VEQGQLFLFQ LYNKDFAPGA DGKPNLHTLY WKAVFNPENL EDVVVKLNGK AELFYRPRSN  780
MDVVRHKVGE KLVNRKLKNG LTLPSRLHEE IYRYVNGTLN KDLSADARSV LPLAVVRDVQ  840
HEIIKDRRFT ADKFFFHASL TFNFKSSDKP VGFNEDVREY LREHPDTYVV GVDRGERNLI  900
YIVVIDPQGN IVEQRSFNMI NGIDYWSLLD QKEKERVEAK QAWETVGKIK DLKCGYLSFL  960
IHEITKIIIK YHAVVILENL SLGFKRVRTG IAEKAVYQQF ERMLVTKLGY VVFKDRAGKA  1020
PGGVLNAYQL TDNTRTAENT GIQNGFLFYV PAAFTSRVDP ATGFFDFYDW GKIKTATDKK  1080
NFIAGFNSVR YERSTGDFIV HVGAKNLAVR RVAEDVRTEW DIVIEANVRK MGIDGNSYIS  1140
GKRIRYRSGE QGHGQYENHL PCQELIRALQ QYGIQYETGK DILPAILQQD DAKLTDTVFD  1200
VFRLALQMRN TSAETGEDYF NSVVRDRSGR CFDTRRAEAA MPKEADANDA YHIALKGLFV  1260
LEKLRKGESI GIKNTEWLRY VQQRHS                                      1286

SEQ ID NO: 47          moltype = AA  length = 1264
FEATURE                Location/Qualifiers
source                 1..1264
                       mol_type = protein
                       organism = synthetic construct
                       note = Description of Artificial Sequence: Synthetic
                        polypeptide
SEQUENCE: 47
MENYGGFTGL YPLQKTLKFE LRPQGRTMEH LVSSNFFEED RDRAEKYKIV KKVIDNYHKD  60
```

-continued

```
FINECLSKRS FDWTPLMKTS EKYYASKEKN GKKKQDLDQK IIPTIENLSE KDRKELELEQ  120
KRMRKEIVSV FKEDKRFKYL FSEKLFSILL KDEDYSKEKL TEKEILALKS FNKFSGYFIG  180
LHKNRANFYS EGDESTAIAY RIVNENFPKF LSNLKKYREV CEKYPEIIQD AEQSLAGLNI  240
KMDDIFPMEN FNKVMTQDGI DLYNLAIGGK AQALGEKQKG LNEFLNEVNQ SYKKGNDRIR  300
MTPLFKQILS ERTSYSYILD AFDDNSQLIT SINGFFTEVE KDKEGNTFDR AVGLIASYMK  360
YDLSRVYIRK ADLNKVSMEI FGSWERLGGL LRIFKSELYG DVNAEKTSKK VDKWLNSGEF  420
SLSDVINAIA GSKSAETFDE YILKMRVARG EIDNALEKIK CINGNFSEDE NSKMIIKAIL  480
DSVQRLFHLF SSFQVRADFS QDGDFYAEYN EIYEKLFAIV PLYNRVRNYL TKNNLSMKKI  540
KLNFKNPALA NGWDLNKEYD NTAVIFLREG KYYLGIMNPS KKKNIKFEEG SGTGPFYKKM  600
AYKLLPDPNK MLPKVFFAKK NINYYNPSDE IVKGYKAGKY KKGENFDIDF CHKLIDFFKE  660
SIQKNEDWRA FNYLFSATES YKDISDFYSE VEDQGYRMYF LNVPVANIDE YVEKGDLFLF  720
QIYNKDFASG AKGNKDMHTI YWNAAFSDEN LRNVVVKLNG EAELFYRDKS IIEPICHKKG  780
EMLVNRTCFD KTPVPDKIHK ELFDYHNGRA KTLSIEAKGY LDRVGVFQAS YEIIKDRRYS  840
ENKMYFHVPL KLNFKADGKK NLNKMVIEKF LSDKDVHIIG IDRGERNLLY YSVIDRRGNI  900
IDQDSLNIID GFDYQKKLGQ REIERREARQ SWNSIGKIKD LKEGYLSKAV HKVSKMVLEY  960
NAIVVLEDLN FGFKRGRFKV EKQVYQKFEK MLIDKLNYLV FKEVLDSRDA GGVLNAYQLT  1020
TQLESFNKLG KQSGILFYVP AAYTSKIDPT TGFVSLFNTS RIESDSEKKD FLSGFDSIVY  1080
SAKDGGIFAF KFDYRNRNFQ REKTDHKNIW TVYTNGDRIK YKGRMKGYEI TSPTKRIKDV  1140
LSSSGIRYDD GQELRDSIIQ SGNKVLINEV YNSFIDTLQM RNSDGEQDYI ISPVKNRNGE  1200
FFRTDPDRRE LPVDADANGA YHIALRGELL MQKIAEDFDP KSDKFTMPKM EHKDWFEFMQ  1260
TRGD                                                              1264

SEQ ID NO: 48          moltype = AA  length = 1232
FEATURE                Location/Qualifiers
source                 1..1232
                       mol_type = protein
                       organism = synthetic construct
                       note = Description of Artificial Sequence: Synthetic
                        polypeptide
SEQUENCE: 48
MLHAFTNQYQ LSKTLRFGAT LKEDEKKCKS HEELKGFVDI SYENMKSSAT IAESLNENEL  60
VKKCERCYSE IVKFHNAWEK IYYRTDQIAV YKDFYRQLSR KARFDAGKQN SQLITLASLC  120
GMYQGAKLSR YITNYWKDNI TRQKSFLKDF SQQLHQYTRA LEKSDKAHTK PNLINFNKTF  180
MVLANLVNEI VIPLSNGAIS FPNISKLEDG EESHLIEFAL NDYSQLSELI GELKDAIATN  240
GGYTPFAKVT LNHYTAEQKP HVFKNDIDAK IRELKLIGLV ETLKGKSSEQ IEEYFSNLDK  300
FSTYNDRNQS VIVRTQCFKY KPIPFLVKHQ LAKYISEPNG WDEDAVAKVL DAVGAIRSPA  360
HDYANNQEGF DLNHYPIKVA FDYAWEQLAN SLYTTVTFPQ EMCEKYLNSI YGCEVSKEPV  420
FKFYADLLYI RKNLAVLEHK NNLPSNQEEF ICKINNTFEN IVLPYKISQF ETYKKDILAW  480
INDGHDHKKY TDAKQQLGFI RGGLKGRIKA EEVSQKDKYG KIKSYYENPY TKLTNEFKQI  540
SSTYGKTFAE LRDKFKEKNE ITKITHFGII IEDKNRDRYL LASELKHEQI NHVSTILNKL  600
DKSSEFITYQ VKSLTSKTLI KLIKNHTTKK GAISPYADFH TSKTGFNKNE IEKNWDNYKR  660
EQVLVEYVKD CLTDSTMAKN QNWAEFGWNF EKCNSYEDIE HEIDQKSYLL QSDTISKQSI  720
ASLVEGGCLL LPIINQDITS KERKDKNQFS KDWNHIFEGS KEFRLHPEFA VSYRTPIEGY  780
PVQKRYGRLQ FVCAFNAHIV PQNGEFINLK KQIENFNDED VQKRNVTEFN KKVNHALSDK  840
EYVVIGIDRG LKQLATLCVL DKRGKILGDF EIYKKEFVRA EKRSESHWEH TQAETRHILD  900
LSNLRVETTI EGKKVLVDQS LTLVKKNRDT PDEEATEENK QKIKLKQLSY IRKLQHKMQT  960
NEQDVLDLIN NEPSDEEFKK RIEGLISSFG EGQKYADLPI NTMREMISDL QGVIARGNNQ  1020
TEKNKIIELD AADNLKQGIV ANMIGIVNYI FAKYSYKAYI SLEDLSRAYG GAKSGYDGRY  1080
LPSTSQDEDV DFKEQQNQML AGLGTYQFFE MQLLKKLQKI QSDNTVLRFV PAFRSADNYR  1140
NILRLEETKY KSKPFGVVHF IDPKFTSKKC PVCSKTNVYR DKDDILVCKE CGFRSDSQLK  1200
ERENNIHYIH NGDDNGAYHI ALKSVENLIQ MK                               1232

SEQ ID NO: 49          moltype = AA  length = 1067
FEATURE                Location/Qualifiers
source                 1..1067
                       mol_type = protein
                       organism = synthetic construct
                       note = Description of Artificial Sequence: Synthetic
                        polypeptide
SEQUENCE: 49
MKNGINLFKT KTTKTKGVDM EKYQITKTIR FKLLPDNAHE IVEKVKSLKT SNVDELMDEV  60
KNVHLKGLEL LFALKKYFYF DGNQCKSFKS TLEIKARWLR LYTPDQYYLK KSSKNSYQLK  120
SLSYFKDVFN DWLFNWEESV SELAIIYEKY KICQHQRDSR ADIALLIKKL SMKEYFPFIS  180
DLIDCVNDKN SNKTFLMKLS EELSVLLEKC NSRALPYQSN GIVVGKASLN YYTVSKSEKM  240
LQNEYEDVCQ SLDKNYDITE MKVILYKEKL DNLNFKDVTI ANAYNLLKEN KALQKRLFSE  300
YVSQGKVLSL IKTELPLFSN INDNDFEKYK EWSNEIKKLA DKKNTFCKKT QQDKIKDIQN  360
KISELKKKRG ALFQYKFTSF QKHCDNYKKV AVQYGKLKAR KKAIEKDEIE ANLLRYWSVI  420
LEQEDKHSLV LIPKNNAKDA KQYIETINTK GGKYIIHHLD SLTLRALNKL CFNAVDIEKG  480
QMVRENTFYQ GIKEEFERNK INCDNQGVLK IQGLYSFKTE GGQINEKEAV EFFKEVLKSN  540
YAREVLNLPY DLESNIFQKE YTNLDQFRQD LEKCCYALHS KIGKDDLDEF TRRFEAQVFD  600
ITSIDLKSKK EKTKTTGEMK KHTQLWLEFW KGAIEQNFAT RVNPELSIFW RAPKSSREKK  660
YGKGSDLYDP NKNNRYLYEQ YTLALTITEN AGSHFKDIAF KDTSKIKEAI KEFNMSLSQS  720
KYCFGIDRGN AELVSLCLIK NEKDFPFEKF PVYRLRDLTY QGDFKDKHDQ MRYGVAIKNI  780
SYFIDQEDLF EKNNLSAIDM TTAKLIKNKI VLNGDVLTYL KLKEETAKHK LTQFFQGSSI  840
NKNSRVYFDE DENVFKITTN RNHNPEEIIY FYRGEYGAIK NKNDLEDILN EYLCKMETGE  900
SEIVLLNRVN HLRDAISANI VGILSYLIDL FPETIVALEN LAKGTIDRHV SQSYENITRR  960
FEWALYRKLL NKQLAPPELK ENILLREGDD KIDQFGIIHF VEEKNTSKDC PNCRKTTQQT  1020
NDNKFKEKKF VCKSCGFDTS KDRKGMDSLN SPDTVAAYNV ARKKFES                1067
```

```
SEQ ID NO: 50          moltype = AA  length = 1309
FEATURE                Location/Qualifiers
source                 1..1309
                       mol_type = protein
                       organism = synthetic construct
                       note = Description of Artificial Sequence: Synthetic
                        polypeptide
SEQUENCE: 50
MAKETKEFKT FDDFTNLYEV QKTLRFELEA VPETEIVLEN RGIWYKRDKK RADEKPIVKF  60
YMDILHREFT DEALEKIKES GVLNLSGYFK LFEELRRLQN HGANTKEEKK LKLEEIRAKK  120
REISNELSQI RRVFSVRGFD VVDSDWKKKY TIEGKKIKND KSKTYLILSE NILNFLENRF  180
TSKEVERLRS IDKKHVEDYG NVVNSGGENI FATFKGFFGY FDSLIKNREN FYETDGKAGR  240
VATRSVDENL NFFAENLHIF STDLPKALKD DLSDTQKAIF ERSYYKNCLL QKDIKSYNLI  300
IGDINKEINK HRQQRDTKIK FLNTLFKQIL SIEEKEQYKH IEINNDEDLI RAIRDFISLN  360
ESKISEGTKI FNQFIQRCLQ KEDLGQIYLP KDSVNTIAHR IFKPWDEIMA LFDRKYFVSL  420
EEIKDLTESS VWKERVLEES KTKSLIFKDT HIHTIISGQE IFSNFILILE KEYKNQFSGF  480
ISETRRGKAA FVGYDESLKN LRATIKWFEG KNLKLSETEK VEWIKAIKDY ADAALRIFQM  540
TKYLWLPVVG DEEDKDYLRI KAEIDQLTKD NDFYNKINAF IDGYKPEPFI YRSSFQEYLT  600
RRPFSTDKFK INFENSRLLD GWDKDMIDDR MGILLQRDGD YFLGILNKED RHCLDNLVDV  660
KSEDKNSYAL MQFKQLTGLY RQLPRMAFPK KKQPVLEANA EIKKIKEDFD FLQKQKKERE  720
VNVNVVFDNK KLNLLINHYA EFLKENYKDE KCYDFSLLNK EKVYESLSDF YADVDKITYS  780
LSFIQVSIDQ LIKTGKILLF RLKNKDLLKG SLGQNKNLHT YYFHALFERE NLSQGRIRLG  840
AQAEIFFRPA SIEKEKDKNR SNALKKSPKT RYVKEILKNK RYSEDKVFLH LPIQLNADAY  900
DLPSINQNVF EFIKNRQEKV KIIGIDRGEK NLAYYSVISQ NSNGKIKIEE PPRDLNLGYL  960
EPLDELENKR QDERKAWQSI SEIKSKRDGY ISYAVSKIVE LMLKYQAIIV LEDLSGKFKR  1020
SRMKFEKAPY QQLELALIKK LNYLVKKNSK SGKPGHYLSA YQLTEPVGSY KEMGKQTGII  1080
FYTQAGYTSR TCPTCGWRKR VQGLYYKDRT SAQRRFDPKT GVKIFYDSVN DRFVFQYHPV  1140
YEQKELKEWD KEIYSDVTRI RWNNEEKKNN EYRKGDITLK IKRLFRDRGI DLSRNINEQL  1200
VNVGDASFWE ELINLLRLIT EIRNIDNENN RDFIECPHCH FQSENGFHGV AWNGDANGAY  1260
NIARKGLLIT KAVCDPEKNV GDITWSDLKV DMKDWDAATD EWAKKNPEK             1309

SEQ ID NO: 51          moltype = AA  length = 1456
FEATURE                Location/Qualifiers
source                 1..1456
                       mol_type = protein
                       organism = synthetic construct
                       note = Description of Artificial Sequence: Synthetic
                        polypeptide
SEQUENCE: 51
MENEKIFSDL TNRYQVVKTL PFELKPVPRT RVLLGLDNPN KGEIFSKDRE RAENFTIIKK  60
YIDRLHSLFI NESLKKADID FSNFYKQYGK NINTKNNKNI DDDNDINDDE KEDSENDNLK  120
KYRQEIANLF NKSKYKSWVN VGKDGDKISG MLFEKGLIDL LRTHFSDNLN EDIEIPELFS  180
NKKIKDTRKL KEIINSFGKD GKDGQNFTTY FSVSFHNNRK NYYKSDGKMG RVSTRIVDEN  240
LERFCKNIYL YKEIIGKNEI KEIFSGNWDI YLQKKPNFSN DKTYKKLDEF KNDKYDWEMI  300
FRDVNSYNKY FLQSDIEFYN YIRGKLNQDI NEYNGKKRDS KEKINSQFEN LRNQVHGEKK  360
NYDDDFEIDE DNIIQFINEI FVRHNQNKMR FSEKLFSDFI DLLMVDNGDK LDKVYFSQKA  420
VENAIARYYF VEETTNEGRE PLLISLLLQN AGKDRKKLSN KPIKLGDIKF VLDQANNKPA  480
EDIFKNRYVL SESNNDGIIN ANDKNHWANL LRLIKKDFYF HKDNLIKSQD KLALETKYNK  540
GSDEGERQIE TIKNFAESAK AILRMTKYFD LRKNGVIQNV IGGKDPIHEE VDKYFDGDVL  600
SGEESCRISK YYDALRNFIT KKAWSADKII LNFDCSEFLG GWDRSQEQKK RGIILRHRDG  660
DEERYYLAVL GKNGKQYFEN RTLFKGCESS DWQKIEYNVI QKPHMSLPKN LITPFFKKDK  720
ITNERFIDRS KKGAKALIEI DINPSDEFLN NYNLGKHTKE NLDKSFLCDY FKYLMDAIAK  780
YYKGEFNFNF PDVSNFDNTQ PFYSFIEKNA YSIKYFGISS KEIEKLIADC YYKEDVYLFQ  840
IYCKDFEIDP KIGKAKYGNE FRTKAEIRKS KGEEAGNENL NTKYFKLLFD EKNLKNQNGI  900
VYKLNGGAKM FYRPSSIKKD EKIDGKWRYK EDKYSLNITI TCNFSSKKDD LSIDKDINKK  960
IAEVNANSDF RIISIDRGEK NLAYCCVMDE NANILDIKSL NRITRYDKNG KAIKEKNMFH  1020
EVKDGKLCYG EPVYDFYKDY QNLLDEREIK RLVNRRSWNV IEDIKNLKKG YVALLINYIC  1080
KAVVIAINEG KYPIIVLESL DKGMLHNRVK IEKQIYRGVE EGLVRKLNYF VDKKTDNVLN  1140
AWQLLAKFET VGSSLDRKKQ LGIIFYVDPG YTSITCPCCG FRQRKYIKAE RAEENFKEIK  1200
IKFDGKRYSF AYDYRCIDDN GKEKSKEDII YSNVKRLLRS GRNGRAVQIE DVTDELTNLF  1260
KKHNINIEQD INEQLAGKDN KFWKQLLWWF NAIEQIRNTQ SLRRKFNTEE NKLEILENND  1320
CDFILCPHCY FDSNKDKFQN KIWNGDANGA FNIGRKGIID IFEIKKHQRM LSDFMEQWGI  1380
DKLPKANGGN QAVIEIVKND KKYNLCILNN KKIPYYCLRI GKEKIDSIAD DRKCNQLPDL  1440
MVNWKKWDMW LDKWGK                                                 1456

SEQ ID NO: 52          moltype = AA  length = 1486
FEATURE                Location/Qualifiers
source                 1..1486
                       mol_type = protein
                       organism = synthetic construct
                       note = Description of Artificial Sequence: Synthetic
                        polypeptide
SEQUENCE: 52
MPEVKNVFQD FTNLYELSKT LRFELKPVPE TEKILELNAA KTKKFPKDLY RAENFEIIKK  60
YTDELHRTYI RETLNNVNID YLKFLEIFRI NGKKKNEMTD ENEESDENNE KDDIQKIKKE  120
LRSKIGNLFN KWNNDKDNKF KDWVKIDVGK KEKEVSGDLF GKELITILKN YFKNKLDSKV  180
NVPMLFFNEQ EIKNGEAKKQ RKLEAVFENF DKFTTYFTDS FYNNRKNYYK TEGRVGQVAT  240
RIIDENLPRF CSNLIAFNEV VSLYSTLLNN FDLGWKEYLN EKKINQTWVE KFELSNYDWK  300
ALFNDVNYYN QCLLQEGIDK YNYIIKKLNK DINEYTQNKY KSVEKGNNNN PDINFFQKLH  360
```

```
KQIHGERDFK LIEIDIDENN IFTKILPEFI LHSDMKLMTK IDEEVGVEEI VGAERIIKIF  420
IKQELKDLEK IYLSRRAIET ISAKWFHSWE TLKDLILGYL NKDLLESKKR KKVPDFVDFN  480
IIKIVLENNK DDYKDLFKRK YFEADKNEFV DWIDSSGGTK KLEFGGENWI NFLNVFEYEF  540
GTLLTEYKKN KNALLYLIDK KIDYDKNNEV GQTAAIKNFA DSALGIFRMV SYFALRKKGV  600
MVEPKNGKDE IFYAFVDRYL DGDDNDREEQ NKIVQYYNTL RNFVTQKAWS IDKVRLCFDC  660
GEFLKGWDKD KIHERLGIIL RNNNKFYLGI LNKNHKQIFI KIKSHDNNNF YYVIYDYKQL  720
NNVYRQIPRL AFPSRSVKKG DAYMLRAIQE RKKKFFLEDE EFIELQEIKN EYDKIGNDLS  780
KEKLTKLIEY YKKVVISNYS SLYNVSNLNN KKFNSINEFN QYVENLMYSL IPTRISPDFI  840
KEKISKGELY LFQIYNKDFE LDESIGKEKF GEDFAPVIMD GKNNLHTEYF KLLFNDSNLK  900
NPNGVVFKLS GGAKMFYRPA TENLPIKKDR DGNIIKNKKG ENVIVGQRYK EDKYFLHLPI  960
ILNFVNKGKN YSINDMVNKA ITNASDDQDK FRIIGLDRGE KHLVYYSVIN ERQEIIEIGS  1020
LNNISRKDNK GEIIEEKNWY HDKFGNIEKE PTKEYHKDYH NLLDQREIER LKSRQSWEKI  1080
ENIKELKEGY ISAVINKICN LVIKAIKENK IPIVALENLN SGMKRGRIKI DKQIYQKLEL  1140
KLAKKLNFLV DKKEKNYLSA WQFTPKIETF SGDIEKKNQV GIIFYVDPAF TSATCPNCGF  1200
RKRIKMDPQN AKKKIKDMEI TYENGIYKFD YPIENGENDV VYSDVERLKW DNEKKKVIKT  1260
KNVSDDFGKL FEDIKDKNNL KKELLSIGEE NKEFWKEFSR CFNLLLRIRN SKLIKRKLND  1320
DTGKVEIIAD DDLADRDRDF IYCPQCHFHS EGGDVFGEFV KKKYLGKDNF EFNGDANGAY  1380
NIARKTIIAV NKIKDYQLGL NHFIEKYRIS ELPNNGKDKK NIFYNNNSYI LSFFEVQDEK  1440
FRKVKVYGLK KDGDRQIIQK KEMWYRRYPD IFVNNKEWDK FVQNKS                1486

SEQ ID NO: 53           moltype = AA  length = 1403
FEATURE                 Location/Qualifiers
source                  1..1403
                        mol_type = protein
                        organism = synthetic construct
                        note = Description of Artificial Sequence: Synthetic
                         polypeptide
SEQUENCE: 53
MLFFMSTDIT NKPREKGVFD NFTNLYEFSK TLTFGLIPLK WDDNKKMIVE DEDFSVLRKY  60
GVIEEDKRIA ESIKIAKFYL NILHRELIGK VLGSLKFEKK NLENYDRLLG EIEKNNKNEN  120
ISEDKKKEIR KNFKKELSIA QDILLKKVGE VFESNGSGIL SSKNCLDELT KRFTRQEVDK  180
LRRENKDIGV EYPDVAYREK DGKEETKSFF AMDVGYLDDF HKNRKQLYSV KGKKNSLGRR  240
ILDNFEIFCK NKKLYEKYKN LDIDFSEIER NFNLTLEKVF DFDNYNERLT QEGLDEYAKI  300
LGGESNKQER TANIHGLNQI INLYIQKKQS EQKAEQKETG KKKIKFNKKD YPTFTCLQKQ  360
ILSQVFRKEI IESDRDLIR ELKFFVEESK EKVDKARGII EFLLNHEEND IDLAMVYLPK  420
SKINSFVYKV FKEPQDFLSV FQDGASNLDF VSFDKIKTHL ENNKLTYKIF FKTLIKENHD  480
FESFLILLQQ EIDLLIDGGE TVTLGGKKES ITSLDEKKNR LKEKLGWFEG KVRENEKMKD  540
EEEGEFCSTV LAYSQAVLNI TKRAEIFWLN EKQDAKVGED NKDMIFYKKF DEFADDGFAP  600
FFYFDKFGNY LKRRSRNTTK EIKLHFGNDD LLEGWDMNKE PEYWSFILRD RNQYYLGIGK  660
KDGEIFHKKL GNSVEAVKEA YELENEADFY EKIDYKQLNI DRFEGIAFPK KTKTEEAFRQ  720
VCKKRADEFL GGDTYEFKIL LAIKKEYDDF KARRQKEKDW DSKFSKEKMS KLIEYYITCL  780
GKRDDWKRFN LNFRQPKEYE DRSDFVRHIQ RQAYWIDPRK VSKDYVDKKV AEGEMFLFKV  840
HNKDFYDFER KSEDKKNHTA NLFTQYLLEL FSCENIKNIK SKDLIESIFE LDGKAEIRFR  900
PKTDDVKLKI YQKKGKDVTY ADKRDGNKEK EVIQHRRFAK DALTLHLKIR LNFGKHVNLF  960
DFNKLVNTEL FAKVPVKILG MDRGENNLIY YCFLDEHGEI ENGKCGSLNR VGEQIITLED  1020
DKKVKEPVDY FQLLVDREGQ RDWEQKNWQK MTRIKDLKKA YLGNVVSWIS KEMLSGIKEG  1080
VVTIGVLEDL NSNFKRTRFF RERQVYQGFE KALVNKLGYL VDKKYDNYRN VYQFAPIVDS  1140
VEEMEKNKQI GTLVYVPASY TSKICPHPKC GWRERLYMKN SASKEKIVGL LKSDGIKISY  1200
DQKNDRFYFE YQWEQEHKSD GKKKKYSGVD KVFSNVSRMR WDVEQKKSID FVDGTDGSIT  1260
NKLKSLLKGK GIELDNINQQ IVNQQKELGV EFFQSIIFYF NLIMQIRNYD KEKSGSEADY  1320
IQCPSCLFDS RKPEMNGKLS AITNGDANGA YNIARKGFMQ LCRIRENPQE PMKLITNREW  1380
DEAVREWDIY SAAQKIPVLS EEN                                         1403

SEQ ID NO: 54           moltype = AA  length = 1356
FEATURE                 Location/Qualifiers
source                  1..1356
                        mol_type = protein
                        organism = synthetic construct
                        note = Description of Artificial Sequence: Synthetic
                         polypeptide
SEQUENCE: 54
MTIKKHKPFT NFECLTPVQK TLRFRLIPVG RTTEFVKCRN IIEADRKRSE MYPLLKELAD  60
RFYREFMTDQ LSNLLFDWSP LVEALLARN NTDPRENQRI ASLVRDEQKK YRTLLLKRLS  120
GQVDRNGTPL PKNTASVNKK YYDDLFKARF VTETLPAYLE HLKNKPDGRI SDELFDAYKD  180
ALDSYQKFTS RLTNFWQARK NIFTDEDIAT GFAYRIVHEI VPDYLFNRRV YEQHKLDFPE  240
PLDLLETELK KKNLIANDES LDALFTIPAI NRLLTQKGVD LHNAVIGGFF TDDHTKVQGF  300
NELANLKNQT LKNVSDNSEI KPVGKMTRLK KHILSISEST SFLFEQIESD DLLARIIEF  360
NNTLSEPDID GLSIADINDQ LYNIMTGVDP STILVHARNL NKLSHEASLS WNRLRDGLYQ  420
MATESPYRED ERFKRYIDAS EEERDLSKLK NDIYFSLQEL QFALDQSIDL EEEATPTEDI  480
FLPFEFPGMD LKSELTVLFR SIEQLISSET KLIGNPDAIA TIKKYLDAIM ARYSIWNLLS  540
CEAVELQDDL FYPEYDRVMG SLSNIILLYN LARNYLSRKP SSKEKFRLNF DKPTLADGWS  600
ESKVPDNFSV LLRKDDLFYL GILKDRKAYR VLSYENCDET AKNIKGYYER MIYHFSPDAY  660
RMIPKCSTAR KDVKKHFGEQ GETTGYTLYP GASNFVKPFT IPYEIYRLQT ELVNDKKRYQ  720
ADYLKQTEDE EGYRQAVTAW IDFCKSYLES YEGTSTFDYS HLLKSEDYED VNQFYADVDR  780
ASYSIYFEKV SVDLIHTMVD RGDLYLFQLY NKDFSPHSTG KPNLHTMYWR ALFSNDNLQN  840
NTIKLNGQAE LFYRPKQVEQ PTVHLQGSYL LNRFDKHGDV IPAGLYCEIY NHINERHPEG  900
YTLSEEATQG LLDGRFVYRE APFELVKDKR YTEDQLFLHV PLEFNWTASA NVPFENLANE  960
YIKKDSDLHI IGIDRGERNL LYYSVINLQG DIVKQGSLNT LIQQTTLKGE TVERQIPYQS  1020
MLKQREDERA EARQNWQSID RIKDLKEGYL SHVIYKLSRL IIKYHAIVVM ENLNVGFKRG  1080
```

```
RFKVERQVYQ KFEVALINKL NALSFKEYEP NELGGVMRPW QLARRVVSPE DTRSQNGIVF  1140
YVPASYTSIV DPVTGFANLF YLNRIRNKDL NSFYGHFQEI RYDHEFDRFI FRFNYADFGV  1200
FCRIKNVPSR TWNLVSGERK AFNPKRRMIE KRDTTDEIKK ALEAHGIAYQ NEQNLLPLLL  1260
ENENLLARIH RSFRLVLQLR NSDSDRDDIV SPALDKENNT FDSGQQPYES SLPINADANG  1320
AYNIARKGLL LVDKVKNDKR AVLSNREWFE YLMAEE                            1356

SEQ ID NO: 55          moltype = AA  length = 1296
FEATURE                Location/Qualifiers
source                 1..1296
                       mol_type = protein
                       organism = synthetic construct
                       note = Description of Artificial Sequence: Synthetic
                        polypeptide
SEQUENCE: 55
MENKDYSLSR FTKQYQNSKT VRFALTPIGR TEEYIIQNQY IEAARRKNQA YKIVKPIIDE  60
KFRSMIDDVL THCEKQDWVT LDKLILQYQN NKCRENMDAL AEQQEEIRKN ISEEFTKSDE  120
YKNFFGKEDS KKLFKIFLPE YLNQINASES DKEAVNEFQK FKTYFSNFLI VRADIFKADN  180
KHNTIPYRIV NENFMIFAGN KRTFSNIIRL IPNALEEIAK DGMKKEEWSF YNIQNVDSWF  240
EPDSFQMCMS QKGIQKYNFI IGLVNSYINL YTQQNPQATE VKRSRLKLRM LHKQILSDRV  300
NPSWLPEQFK EGEEGEKQIY EAILALENDL IKNCFDKKYD LWIQSIDIQN PRIYIAASEM  360
ARVSSALHMG WNGLNDVRKT ILLKSDKKQA KVEKILKQDV SLKDLSDTLN RYADIYKEEQ  420
IPSLYQYIEY GSELLQDCAI TRKEYHDLLN GNSNTLSLNQ NEKLIEGLKA YLDSYQAIVH  480
FLNVFIVGDE LDKDTDFYAE LDGLVESLSE IVPLYNKVRN YITRKVYSLD KMRIMFERSD  540
FLGGWGQSFD TKEALLFQKD NLYYIGIIEK KYTNMDVEYL HEGIKEGNRA IRFIYNFQKA  600
DNKNIPRTFI RSKGTNYAPA VRKYNLPIES IIDIYDVGKF KTNYKKINEK EYYESLEKLI  660
DYFKDGILKN ENYKKFHFNW KPSNEYENIN EFYNDTNNAC FLLEKEEINY DHLKEQANQG  720
KIYLFQISSK DFNEGSKGTP NLQTMYWREL FSNQNCKDGV IKLCGGASIY MRDASIKQPV  780
VHRKNAWLIN KWYKVNGQNV VIPDNTYVKF TKIAQERMNE DELTPQERQL WNSGLIQKKK  840
ATHDIMKDRR FTKKQYMLHA PLTINYKQQD SPRYFNEKVR SFLKDNPDIN IIGIDRGEKN  900
LIYITIIDQK GNILKGMQKS FNQIEEKGKE GRTIDYYSKL ESVEARHDAA RKNWKQIGTI  960
RELKEGYLSQ VVHEITQLMI QYNAVIVMEN LNMGFKKGRM KVEKSVYQKF EKMLIDKMNY  1020
LAFKRDMQGN AIDPYEVGGV MNGYQLTDRF TSFADMGSQN GFIFYVPAAY TSVIDPVTGF  1080
VNVFQKTEFK TNDFLHRFDS ISWNDKEQSF VFTFDYQNFK CNGTCYQNKW SLYADVDRIE  1140
TIIKNNQVDR IEPCNPNQKL IDFFDKKGII YRDGHNIVDD LEKYDSKTIS EIIHNFKLIL  1200
QLRNSMRNPD TGEIIDYIAS PVMHNEERFD SRKRNPELPQ DADANGAYHI ALKGLMFLQK  1260
INEYADSDGN MDNRKLKITN EEWFKYMQTR KEHTYF                            1296

SEQ ID NO: 56          moltype = AA  length = 1250
FEATURE                Location/Qualifiers
source                 1..1250
                       mol_type = protein
                       organism = synthetic construct
                       note = Description of Artificial Sequence: Synthetic
                        polypeptide
SEQUENCE: 56
MSNKTSSITT TNKLSYTGFH NNGKQSKTLM FELKPIGRTT EHLDRKGYLA DDIDRAESYK  60
TFKEIADNFH KNLIEESLAT FTFSDTLKDY FDLWLSPVRT NEDTPKLRKM EAKLRKELSS  120
ALKQHPSFAA TSSGKRLIDE ALYPNASDKE RQCLDRFKGR SSYLDSYTEV RSFIYTDLCK  180
HNTIAYRVVN ENLKIYLENI LAYEKLMQTA VNGKLETVKE MFHDLYPTFS MDISIFFTSY  240
GFDYCLSQNA ITRYNILLGG WSDDNGIHHK GLNNYINEYN QTVPRNKRLP KLNKLQKMIL  300
SEENSMSFII DKFENDVDLA NAIRYWLKNC QFDALNLLIW TLDVHYNLDE IHFKNDNQGK  360
NISDLSQALF KNHHVIRDAW DYDYDIVNAK AKSRQKPERY AEKRDKAFKK INSFSLSYLA  420
NILSQYDNQY ANFVAQFKTR ISVHIQNVQQ MIADKTLDMR LDPLMLLKSI SSDTKLVEDI  480
KRVLDSLKDM QRMLTPLLGE GTEPNRDAMF YSDFEPLMNY VDTLTPLYNK VRNYITKKPY  540
STKKTSLYFG ASNFGSGFDV TKLPVSHTII MRDKGCYYLA VIDNNKLIDK LYDHNDNDGY  600
EYMVYKQIPS PIKYFSLKNI LPQDPPDDIR QLLEDRKNGA KWSHDDETRF IDYIVNEFLP  660
TYPPIHDKNG NPYFSWKFKN PDEYESLNEF FDDVSKQAYQ TSFRFVSRDF VDDAVENGDI  720
FFFQIYNQDF SPASHGKPSP HTLWFRALFS DVNLETKDIR LKGNATAYFR PASIFYTDEK  780
WRKGHHYEQL KNKFKPIIK DKRYALDKFF FHITLEINCN ATVEKYFNNR VNEEIRKADR  840
YNILAINRGE RNLLYAVVMD QDGTILEQKS FNIIKSELPN KTVKETDYWK KLHAREKERD  900
TARKSWKSIE CIKDLKKGYL SYVVKTITDM MFEYNAVLVM ENLDIEMKRS RQKIEKNVYA  960
QFQNAIIQKL SMYVNKDIDL HIARTAPGGT LNPYQLTYIP ASRTKTPKQN GFVFFLNPWN  1020
ITEIDPTTGF VDLFQTCFRT KNEYKDFFAK FKDIRYNEAQ GWFEFDTDYT YFRDKEKAGK  1080
RTRWNICSYG TRLRRFRNPD KNYAEDAMTV YPTQMLKDLF DEYNIPYAPA SAKSTSISIK  1140
DDIIQIDKLD FYKKLLYILK LIVQLRNTSP SSTEQEDDYI ISPVINEDTN WFYDSRDYNE  1200
ESLLPCNTDA NGAYSLALKC NMVIDRIKNT IPGEPVDMYI SNADWLDARQ             1250

SEQ ID NO: 57          moltype = AA  length = 1328
FEATURE                Location/Qualifiers
source                 1..1328
                       mol_type = protein
                       organism = synthetic construct
                       note = Description of Artificial Sequence: Synthetic
                        polypeptide
SEQUENCE: 57
MNSKTSIFDF SNIFGRDITL RFKLTPVTIN SKGEVKDANG ADPYRPYLSA DEELQEQYEL  60
LKTAIDAYHQ MYIDKKLKHI LCLPLTEKGK DGVEHDTAKS KFVKSCLAYI KDYGEKDKKR  120
QTADLRTFIS RVFADDNISS LPPYKVKSDF ITKTLRQWLE QPDTKVEKKE AILDLIEKNG  180
SKLYANCQGL LEARQRLYEK DGKSTSVPYR CIDRNLPRFS KDYHLFEKIL GDCSDVFDFE  240
```

```
QLDKDFSEEL KGIARLSGIR VESVREVFQP LLYLAYLNQE GIQYLNTIIG TKKEKGTSAL  300
GLNEYINQYN QKQGIKKKKD GIPMLNKLNN QILFGDEVFI ETLAEHKEAI PVIKKVVSSL  360
GKLGAFDGEC HENKLYQFLL SLSSYAGNIY VNTKVVAQIS SSLWGDYSIL YDAVKHDKNG  420
RLIQKSVTLG ELNEKIERLK LEDNRDAFEY FRRSQVKDVV HGSSNVGVFE QLKNCYNDFV  480
EKKILKCSFF SEDQVLVIQR LFDSILSLQR IFKVFCPSLY EVDSDGLFVA KFSDYWNVLR  540
GFDKDYDLLR NLFKRKPYST DKIRVHFGLS NLMDGFVDSW TDKKDKGTQY NGYILRQAHS  600
FVDENTSKEL QEFQRYNYYL VISGNVRLFR EKGNALVCEK KKEKLVASDE FSGFERFDYY  660
QSSINNFNRE FKRLTGRDRK SFTDEILQNE GKKELKSTYI ENLIKVAKSM KRLTALQNLV  720
SDEKVRKYSE NLDYETLSAE IGQILATGRE RKYVPVSTNE MKNLLKSSKN NKGEEVRTFM  780
FRISNKDLSY AETMQKGERK SHGAENMHTM YFRALLDTLQ NTFDIGTGTV YFRKASDKRK  840
MKYDEKNPTH RKGDELAFKN PYNKGKKKSV FGYDLIKDRR YTKDSYLFHL SITQNYQKKG  900
NAEDLNAMVR DYIRTQEDLR VIGIDRGERN LLYATMIDGE GHILAQKSFN VIGYQGTTAS  960
GESFQVETDY HQLLNEKAEK MRSLQREWKE MDKIQDMKDG YLSVVVHELA KMVVENNAII  1020
VMEDLNMGFM ESRQSQLANV YQKFEEKLRN KLQFYVDKRK RNDEPSGLYH ALQLAGTETK  1080
DNQNGFIFYI PAWNTSKIDS VTGFVNLFNL KYTNIKDAKA FFSTFEKIEK NVETGHYDFT  1140
FSYSSMARKK MAKRMDGTRD SWTISTHGSR IVREQKGNYW EYREIESLTS EFDALFEKYS  1200
IDTRCRLKEA IDKCGEAEFF KELIRLMKWT LQLRNYDDRG NDYIVSPVCY RGNEYYCSLD  1260
YDNEEGMCIS KIPCQMPKDA DANGAFNIAR KGLMLCERLK KGEKIGVIKG TEWLQYVQNM  1320
SERYVGMV                                                          1328

SEQ ID NO: 58          moltype = AA  length = 1434
FEATURE                Location/Qualifiers
source                 1..1434
                       mol_type = protein
                       organism = synthetic construct
                       note = Description of Artificial Sequence: Synthetic
                        polypeptide
SEQUENCE: 58
MINTMEQPKK SIWDEFTNLY SLQKTLRFEL KPQGKTKELV RTLFINPEEH HHKLISDDLE  60
LSKNYKKVKK LIDCMHRNII NNVLSKHQFT GEELKKLDKN SNAEDNDTET DNADKKDPFA  120
KIRERLTKAL NEESKIMFDN KLLNPKKGKN KGECELKKWM DKAEDKYFEL GNNEKIDKEA  180
VKADMERLEG FFTYFGGFNK NRENVYSSKK IATAIPFRII HDNFPIFKKN IENYKKITEK  240
HPELAKLLNE KGANEIFQLE HFNKCLTQDG IDVYNNEKLG IIAKEQGKEQ DKGINQLINE  300
YAQKKNKEIK ENAKGGEKPK KIKIAVFDKL KKQILSISKT KSFQFEVFED TSDIINGINK  360
RYTFLTEAKE GMSIVDEIKK IIGSVGDEKY SLDEIYLKEK FISTLSKKLF NYSRYIEVAL  420
EKWYDDRYDD KINKSGTDKR KFISAKQFSI TSIQDAINYY LEKYEKDEEL SKKYTGKNII  480
VDYFKNPTIT IEHKQKEEVI SEEKDLFKEL EVRRNVIQHI LNGDYKKDLK EEKQQDGDSE  540
KVKAFLDALL EFNYILNPFI IKDKNLRKEQ EKDEEFYNEI KKLQESIFEA EILDLYNQTR  600
NYITKKPYKL DKFKLTFGSG YFLSGWSNDM EEREGSILIK YNEDRSKNYY LIIMAKPLTD  660
DDKKQLFSDN GTHSKICIYE FQKMDMKNFP RMFINSKGSN PAPAIEKYNL PIKTIWADYQ  720
KYKNLNQKGK DKFLEENPDF RHNLIGYFKI CAEKHESLAP FKHQFSSIWK PTKEYENLAQ  780
FYKDTLEACY NLKFENVNFD NISQLVSSGK LHLFKIHNKD FNPGSTGKKN LHTLYWEMLF  840
DEKNLQDVIF KLSGGAELFY REASILKNKI IHKIGEKVLK KFFKLPDGKL EPVPAESIKN  900
LSAYFRKELP EHELTEIDRK YIDNYSIIGK KDDKLGIMKD ERFTVDKIQF HCPITINFKS  960
KNKNFINDDV LEYLHKRDDV HIIGLDRGER HLIYLTMINK DGKIVDNMQF SLNELQRRYK  1020
INGNEEIQKI NYQKLLDTRE VSRTEARRNW QTIENIKNLK EGYLSLIVHQ LAKLMIEKNA  1080
IVVMENLNYG FKDSRARVEK QIYQKFESIL IKKLQYLVMD KNNLYDSGGV LSAYQLTNQE  1140
VPAYKYISKQ NGFLFYVPPD YTSKIDPETG FINLLDTRYY SRKNAVALLN KFDKIYYDRD  1200
NKYFRFDFDY NSTDSNGNKN FDKLRVDISE LTRTKWSVCS HPAKRSITVQ INNKWVRQPI  1260
NDVTDKLIKL FEDKQIGYES GKCLKDEILK VEDAKFFEDL LRYLSVLLAL RHTYTENGVE  1320
YDLIISSVEK APGSNEFFVS GKDNNLPANA DANGAYNIAR KGLWLLRKLD EIDNQELAIK  1380
KFNELKHAKE IKKNGEESKE DKGDRKRKKK WVSQWCPNKE WLAFAQSMQD VSEK        1434

SEQ ID NO: 59          moltype = AA  length = 1263
FEATURE                Location/Qualifiers
source                 1..1263
                       mol_type = protein
                       organism = synthetic construct
                       note = Description of Artificial Sequence: Synthetic
                        polypeptide
SEQUENCE: 59
MNNGTNNFQN FIGISSLQKT LRNALIPTET TQQFIVKNGI IKEDELRGEN RQILKDIMDD  60
YYRGFISETL SSIDDIDWTS LFEKMEIQLK NGDNKDTLIK EQTEYRKAIH KKFANDDRFK  120
NMFSAKLISD ILPEFVIHNN NYSASEKEEK TQVIKLFSRF ATSFKDYFKN RANCFSADDI  180
SSSSCHRIVN DNAEIFFSNA LVYRRIVKSL SNDDINKISG DMKDSLKEMS LEEIYSYEKY  240
GEFITQEGIS FYNDICGKVN SFMNLYCQKN KENKNLYKLQ KLHKQILCIA DTSYEVPYKF  300
ESDEEVYQSV NGFLDNISSK HIVERLRKIG DNYNGYNLDK IYIVSKFYES VSQKTYRDWE  360
TINTALEIHY NNILPGNGKS KADKVKKAVK NDLQKSITEI NELVSNYKLC SDDNIKAETY  420
IHEISHILNN FEAQELKYNP EIHLVESELK ASELKNVLDV IMNAFHWCSV FMTEELVDKD  480
NNFYAELEEI YDEIYPVISL YNLVRNYVTQ KPYSTKKIKL NFGIPTLADG WSKSKEYSNN  540
AIILMRDNLY YLGIFNAKNK PDKKIIEGNT SENKGDYKKM IYNLLPGPNK MIPKVFLSSK  600
TGVETYKPSA YILEGYKQNK HIKSSKDFDI TFCHDLIDYF KNCIAIHPEW KNFGFDFSDT  660
STYEDISGFY REVELQGYKI DWTYISEKDI DLLQEKGQLY LFQIYNKDFS KKSTGNDNLH  720
TMYLKNLFSE ENLKDIVLKL NGEAEIFFRK SSIKNPIIHK KGSILVNRTY EAEEKDQFGN  780
IQIVRKNIPE NIYQELYKYF NDKSDKELSD EAAKLKNVVG HHEAATNIVK DYRYTYDKYF  840
LHMPITINFK ANKTGFINDR ILQYIAKEKD LHVIGIDRGE RNLIYVSVID TCGNIVEQKS  900
FNIVNGYDYQ IKLKQQEGAR QIARKEWKEI GKIKEIKEGY LSLVIHEISK MVIKYNAIIA  960
MEDLSYGFKK GRFKVERQVY QKFETMLINK LNYLVFKDIS ITENGGLLKG YQLTYIPDKL  1020
KNVGHQCGCI FYVPAAYTSK IDPTTGFVNI FKFKDLTVDA KREFIKKFDS IRYDSEKNLF  1080
```

```
CFTFDYNNFI TQNTVMSKSS WSVYTYGVRI KRRFVNGRFS NESDTIDITK DMEKTLEMTD  1140
INWRDGHDLR QDIIDYEIVQ HIFEIFRLTV QMRNSLSELE DRDYDRLISP VLNENNIFYD  1200
SAKAGDALPK DADANGAYCI ALKGLYEIKQ ITENWKEDGK FSRDKLKISN KDWFDFIQNK  1260
RYL                                                                1263

SEQ ID NO: 60           moltype = AA  length = 1283
FEATURE                 Location/Qualifiers
source                  1..1283
                        mol_type = protein
                        organism = synthetic construct
                        note = Description of Artificial Sequence: Synthetic
                         polypeptide
SEQUENCE: 60
MSNLNTFISP EFTGKIKMTK SLKVSMIPIG ETEHWIAKHK VFEKDRELFD KNLKARPILD  60
EFIKYTVSRA LPNLLFDFEA YYLVKKDRTK ARAFEKELAK TVTDLILKEM DELKSASLID  120
SADFVKTTLK KFAGTHDIPG LSRIEAIESL EAASKLTALN GKFNTSRIAI INTLIPKRII  180
ENFDIYLSNM EKIRNVYESG EFGFLFERYP DTLLFMEPAN YRTVCSPEAI EDYNRFISGY  240
GDSTESWIKG FNQELSEASN SSKSSNGGVR RYSLIKPLHK QHLFETKKFF TFASISSDDD  300
VRELINSVKG STEDACLNAL AFFSSSDPKT LFVKGSYLHT LSAFLYGSAN SYILPERIKE  360
GEKARLTAEY DSVAKKTKAV TTRYNVAMNN ISKKINEKIF SLADIDAYCC DISKRRSVRE  420
ILLGIMQEMY AAVYGENGKW SNIEAEAVLD SKTKIWKAKN GAVAKAVNDY LTAILEIRKF  480
IRPFALRMEE LEELGLDTSS ALDAGEITNT LFEAVRAQKL VHAYLTRNDA DIALSTQVYF  540
GGTQKAAASW WNYETGDIQN RQIALAKKDG MYYFIGTFDE RGSYSIEPAS PGEDYYEMLD  600
VKKGQDANKQ IKKVLFSNKA IREHFADSSN DYVITTKVNS PITVRREIFD KYQAGEFKLT  660
SQKIRKGDLV GEKEMTYYRE YMDLLFQMAK GYTEYSRFNM DTLLPIEEYD TENDLLDDVN  720
TNTIDYRWVR ISAACIDDGV RNGDIFVFRA QTSSMYGKRE NKKGYTGLFL ELVSDENLLV  780
TRGMSLNSAM SIYYRAKVHD AITVHKKGDV LVNKFTNARE RIPENSYKAI CAFYNSGKSI  840
EELTIEDRDW LAKATTRICS GEIIKDRRYT KNQYSISISY NINRSVNNRK RVDLATIVDD  900
TASAGRIISV TRGTKDLVYY TVIDDGGSVI EARSLNVING INYAKMLAQI SEERHDSNAN  960
FDIPKRVETI KEAYCAFAVH EIISAALKHN ALIVVELISD AIKDKYSLLD NQVFLKFENV  1020
LKNCLMSVKV KGARGMEPGS ISNPLQLCNA DDKSFRNGIL YQIPSSYINI CPVTGYADII  1080
DYYNIVSAGD IRNFFVRFEN IVYNKEKARF EFSFDLKNIP IKLEKCPDRT KWTVLGRGEI  1140
TTYDPLTKSN HYVFDAAQML AETVSKEGLD PCANIVEHID ELSAATLKKM FNTFRNIAKG  1200
IVSECDEVPV SYYKSPVIDE ADIKNKSLDN KSISEIKCYN LDEKARYYLA LAKSSSDGEN  1260
KNRYVSSTAI EWLNYIQEKR THE                                          1283

SEQ ID NO: 61           moltype = AA  length = 500
FEATURE                 Location/Qualifiers
source                  1..500
                        mol_type = protein
                        organism = synthetic construct
                        note = Description of Artificial Sequence: Synthetic
                         polypeptide
SEQUENCE: 61
MEVQKTVMKT LSLRILRPLY SQEIEKEIKE EKERRKQAGG TGELDGGFYK KLEKKHSEMF  60
SFDRLNLLLN QLQREIAKVY NHAISELYIA TIAQGNKSNK HYISSIVYNR AYGYFYNAYI  120
ALGICSKVEA NFRSNELLTQ QSALPTAKSD NFPIVLHKQK GAEGEDGGFR ISTEGSDLIF  180
EIPIPFYEYN GENRKEPYKW VKKGGQKPVL KLILSTFRRQ RNKGWAKDEG TDAEIRKVTE  240
GKYQVSQIEI NRGKKLGEHQ KWFANFSIEQ PIYERKPNRS IVGGLDVGIR SPLVCAINNS  300
FSRYSVDSND VFKFSKQVFA FRRRLLSKNS LKRKGHGAAH KLEPITEMTE KNDKFRKKII  360
ERWAKEVTNF FVKNQVGIVQ IEDLSTMKDR EDHFFNQYLR GFWPYYQMQT LIENKLKEYG  420
IEVKRVQAKY TSQLCSNPNC RYWNNYFNFE YRKVNKFPKF KCEKCNLEIS ADYNAARNLS  480
TPDIEKFVAK ATKGINLPEK                                              500

SEQ ID NO: 62           moltype = AA  length = 507
FEATURE                 Location/Qualifiers
source                  1..507
                        mol_type = protein
                        organism = synthetic construct
                        note = Description of Artificial Sequence: Synthetic
                         polypeptide
SEQUENCE: 62
MEEAKTVSKT LSLRILRPLY SAEIEKEIKE EKERRKQGGK SGELDSGFYK KLEKKHTQMF  60
GWDKLNLMLS QLQRQIARVF NQSISELYIE TVIQGKKSNK HYTSKIVYNR AYSVFYNAYL  120
ALGITSKVEA NFRSTELLMQ KSSLPTAKSD NFPILLHKQK GVEGEEGGFK ISADGNDLIF  180
EIPIPFYEYD SANKKEPFKW IKKGGQKPTI KLILSTFRRQ RNKGWAKDEG TDAEIRKVIE  240
GKYQVSHIEI NRGKKLGDHQ KWFVNFTIEQ PIYERKLDKN IIGGIDVGIK SPLVCAVNNS  300
FARYSVDSND VLKFSKQAFA FRRRLLSKNS LKRSGHGSKN KLDPITRMTE KNDRFRKKII  360
ERWAKEVTNF FIKNQVGTVQ IEDLSTMKDR QDNFFNQYLR GFWPYYQMQN LIENKLKEYG  420
IETKRIKARY TSQLCSNPSC RHWNSYFSFD HRKTNNFPKF KCEKCALEIS ADYNAARNIS  480
TPDIEKFVAK ATKGINLPDK NENVILE                                      507

SEQ ID NO: 63           moltype = AA  length = 529
FEATURE                 Location/Qualifiers
source                  1..529
                        mol_type = protein
                        organism = synthetic construct
                        note = Description of Artificial Sequence: Synthetic
                         polypeptide
```

```
SEQUENCE: 63
MAKNTITKTL KLRIVRPYNS AEVEKIVADE KNNREKIALE KNKDKVKEAC SKHLKVAAYC  60
TTQVERNACL FCKARKLDDK FYQKLRGQFP DAVFWQEISE IFRQLQKQAA EIYNQSLIEL  120
YYEIFIKGKG IANASSVEHY LSDVCYTRAA ELFKNAAIAS GLRSKIKSNF RLKELKNMKS  180
GLPTTKSDNF PIPLVKQKGG QYTGFEISNH NSDFIIKIPF GRWQVKKEID KYRPWEKFDF  240
EQVQKSPKPI SLLLSTQRRK RNKGWSKDEG TEAEIKKVMN GDYQTSYIEV KRGSKIGEKS  300
AWMLNLSIDV PKIDKGVDPS IIGGIDVGVK SPLVCAINNA FSRYSISDND LFHFNKKMFA  360
RRRILLKKNR HKRAGHGAKN KLKPITILTE KSERFRKKLI ERWACEIADF FIKNKVGTVQ  420
MENLESMKRK EDSYFNIRLR GFWPYAEMQN KIEFKLKQYG IEIRKVAPNN TSKTCSKCGH  480
LNNYFNFEYR KKNKFPHFKC EKCNFKENAD YNAALNISNP KLKSTKEEP             529

SEQ ID NO: 64          moltype = AA  length = 726
FEATURE                Location/Qualifiers
source                 1..726
                       mol_type = protein
                       organism = synthetic construct
                       note = Description of Artificial Sequence: Synthetic
                        polypeptide
SEQUENCE: 64
MERQKVPQIR KIVRVVPLRI LRPKYSDVIE NALKKFKEKG DDTNTNDFWR AIRDRDTEFF  60
RKELNFSEDE INQLERDTLF RVGLDNRVLF SYFDFLQEKL MKDYNKIISK LFINRQSKSS  120
FENDLTDEEV EELIEKDVTP FYGAYIGKGI KSVIKSNLGG KFIKSVKIDR ETKKVTKLTA  180
INIGLMGLPV AKSDTFPIKI IKTNPDYITF QKSTKENLQK IEDYETGIEY GDLLVQITIP  240
WFKNENKDFS LIKTKEAIEY YKLNGVGKKD LLNINLVLTT YHIRKKKSWQ IDGSSQSLVR  300
EMANGELEEK WKSFFDTFIK KYGDEGKSAL VKRRVNKKSR AKGEKGRELN LDERIKRLYD  360
SIKAKSFPSE INLIPENYKW KLHFSIEIPP MVNDIDSNLY GGIDFGEQNI ATLCVKNIEK  420
DDYDFLTIYG NDLLKHAQAS YARRRIMRVQ DEYKARGHGK SRKTKAQEDY SERMQKLRQK  480
ITERLVKQIS DFFLWRNKFH MAVCSLRYED LNTLYKGESV KAKRMRQFIN KQQLFNGIER  540
KLKDYNSEIY VNSRYPHYTS RLCSKCGKLN LYFDFLKFRT KNIIIRKNPD GSEIKYMPFF  600
ICEFCGWKQA GDKNASANIA DKDYQDKLNK EKEFCNIRKP KSKKEDIGEE NEEERDYSRR  660
FNRNSFIYNS LKKDNKLNQE KLFDEWKNQL KRKIDGRNKF EPKEYKDRFS YLFAYYQEII  720
KNESES                                                            726

SEQ ID NO: 65          moltype = AA  length = 517
FEATURE                Location/Qualifiers
source                 1..517
                       mol_type = protein
                       organism = synthetic construct
                       note = Description of Artificial Sequence: Synthetic
                        polypeptide
SEQUENCE: 65
MVPTELITKT LQLRVIRPLY FEEIEKELAE LKEQKEKEFE ETNSLLLESK KIDAKSLKKL  60
KRKARSSAAV EFWKIAKEKY PDILTKPEME FIFSEMQKMM ARFYNKSMTN IFIEMNNDEK  120
VNPLSLISKA STEANQVIKC SSISSGLNRK IAGSINKTKF KQVRDGLISL PTARTETFPI  180
SFYKSTANKD EIPISKINLP SEEEADLTIT LPFPFFEIKK EKKGQKAYSY FNIIEKSGRS  240
NNKIDLLLST HRRQRRKGWK EEGGTSAEIR RLMEGEFDKE WEIYLGEAEK SEKAKNDLIK  300
NMTRGKLSKD IKEQLEDIQV KYFSDNNVES WNDLSKEQKQ ELSKLRKKKV EELKDWKHVK  360
EILKTRAKIG WVELKRGKRQ RDRNKWFVNI TITRPPFINK ELDDTKFGGI DLGVKVPFVC  420
AVHGSPARLI IKENEILQFN KMVSARNRQI TKDSEQRKGR GKKNKFIKKE IFNERNELFR  480
KKIIERWANQ IVKFFEDQKC ATVQIENLES FDRTSYK                          517

SEQ ID NO: 66          moltype = AA  length = 481
FEATURE                Location/Qualifiers
source                 1..481
                       mol_type = protein
                       organism = synthetic construct
                       note = Description of Artificial Sequence: Synthetic
                        polypeptide
SEQUENCE: 66
MKSDTKDKKI IIHQTKTLSL RIVKPQSIPM EEFTDLVRYH QMIIFPVYNN GAIDLYKKLF  60
KAKIQKGNEA RAIKYFMNKI VYAPIANTVK NSYIALGYST KMQSSFSGKR LWDLRFGEAT  120
PPTIKADFPL PFYNQSGFKV SSENGEFIIG IPFGQYTKKT VSDIEKKTSF AWDKFTLEDT  180
TKKTLIELLL STKTRKMNEG WKNNEGTEAE IKRVMDGTYQ VTSLEILQRD DSWFVNFNIA  240
YDSLKKQPDR DKIAGIHMGI TRPLTAVIYN NKYRALSIYP NTVMHLTQKQ LARIKEQRTN  300
SKYATGGHGR NAKVTGTDTL SEAYRQRRKK IIEDWIASIV KFAINNEIGT IYLEDISNTN  360
SFFAAREQKL IYLEDISNTN SFLSTYKYPI SAISDTLQHK LEEKAIQVIR KKAYYVNQIC  420
SLCGHYNKGF TYQFRRKNKF PKMKCQGCLE ATSTEFNAAA NVANPDYEKL LIKHGLLQLK  480
K                                                                 481

SEQ ID NO: 67          moltype = AA  length = 358
FEATURE                Location/Qualifiers
source                 1..358
                       mol_type = protein
                       organism = synthetic construct
                       note = Description of Artificial Sequence: Synthetic
                        polypeptide
SEQUENCE: 67
MSTITRQVRL SPTPEQSRLL MAHCQQYIST VNVLVAAFDS EVLTGKVSTK DFRAALPSAV  60
KNQALRDAQS VFKRSVELGC LPVLKKPHCQ WNNQNWRVEG DQLILPICKD GKTQQERFRC  120
```

```
AAVALEGKAG ILRIKKKRGK WIADLTVTQE DAPESSGSAI MGVDLGIKVP AVAHIGGKGT  180
RFFGNGRSQR SMRRRFYARR KTLQKAKKLR AVRKSKGKEA RWMKTINHQL SRQIVNHAHA  240
LGVGTIKIEA LQGIRKGTTR KSRGAAARKN NRMTNTWSFS QLTLFITYKA QRQGITVEQV  300
DPAYTSQDCP ACRARNGAQD RTYVCSECGW RGHRDTVGAI NISRRAGLSG HRRGATGA    358

SEQ ID NO: 68          moltype = AA  length = 507
FEATURE                Location/Qualifiers
source                 1..507
                       mol_type = protein
                       organism = synthetic construct
                       note = Description of Artificial Sequence: Synthetic
                        polypeptide
SEQUENCE: 68
MIAQKTIKIK LNPTKEQIIK LNSIIEEYIK VSNFTAKKIA EIQESFTDSG LTQGTCSECG  60
KEKTYRKYHL LKKDNKLFCI TCYKRKYSQF TLQKVEFQNK TGLRNVAKLP KTYYTNAIRF  120
ASDTFSGFDE IIKKKQNRLN SIQNRLNFWK ELLYNPSNRN EIKIKVVKYA PKTDTREHPH  180
YYSEAEIKGR IKRLEKQLKK FKMPKYPEFT SETISLQREL YSWKNPDELK ISSITDKNES  240
MNYYGKEYLK RYIDLINSQT PQILLEKENN SFYLCFPITK NIEMPKIDDT FEPVGIDWGI  300
TRNIAVVSIL DSKTKKPKFV KFYSAGYILG KRKHYKSLRK HFGQKKRQDK INKLGTKEDR  360
FIDSNIHKLA FLIVKEIRNH SNKPIILMEN ITDNREEAEK SMRQNILLHS VKSRLQNYIA  420
YKALWNNIPT NLVKPEHTSQ ICNRCGHQDR ENRPKGSKLF KCVKCNYMSN ADFNASINIA  480
RKFYIGEYEP FYKDNEKMKS GVNSISM                                     507

SEQ ID NO: 69          moltype = AA  length = 534
FEATURE                Location/Qualifiers
source                 1..534
                       mol_type = protein
                       organism = synthetic construct
                       note = Description of Artificial Sequence: Synthetic
                        polypeptide
SEQUENCE: 69
LKLSEQENIT TGVKFKLKLD KETSEGLNDY FDEYGKAINF AIKVIQKELA EDRFAGKVRL  60
DENKKPLLNE DGKKIWDFPN EFCSCGKQVN RYVNGKSLCQ ECYKNKFTEY GIRKRMYSAK  120
GRKAEQDINI KNSTNKISKT HFNYAIREAF ILDKSIKKQR KERFRRLREM KKKLQEFIEI  180
RDGNKILCPK IEKQRVERYI HPSWINKEKK LEDFRGYSMS NVLGKIKILD RNIKREEKSL  240
KEKGQINFKA RRLMLDKSVK FLNDNKISFT ISKNLPKEYE LDLPEKEKRL NWLKEKIKII  300
KNQKPKYAYL LRKDDNFYLQ YTLETEFNLK EDYSGIVGID RGVSHIAVYT FVHNNGKNER  360
PLFLNSSEIL RLKNLQKERD RFLRRKHNKK RKKSNMRNIE KKIQLILHNY SKQIVDFAKN  420
KNAFIVFEKL EKPKKNRSKM SKKSQYKLSQ FTFKKLSDLV DYKAKREGIK VLYISPEYTS  480
KECSHCGEKV NTQRPFNGNS SLFKCNKCGV ELNADYNASI NIAKKGLNIL NSTN        534

SEQ ID NO: 70          moltype = AA  length = 537
FEATURE                Location/Qualifiers
source                 1..537
                       mol_type = protein
                       organism = synthetic construct
                       note = Description of Artificial Sequence: Synthetic
                        polypeptide
SEQUENCE: 70
MEESIITGVK FKLRIDKETT KKLNEYFDEY GKAINFAVKI IQKELADDRF AGKAKLDQNK  60
NPILDENGKK IYEFPDEFCS CGKQVNKYVN NKPFCQECYK IRFTENGIRK RMYSAKGRKA  120
EHKINILNST NKISKTHFNY AIREAFILDK SIKKQRKKRN ERLRESKKRL QQFIDMRDGK  180
REICPTIKGQ KVDRFIHPSW ITKDKKLEDF RGYTLSIINS KIKILDRNIK REEKSLKEKG  240
QIIFKAKRLM LDKSIRFVGD RKVLFTISKT LPKEYELDLP SKEKRLNWLK EKIEIIKNQK  300
PKYAYLLRKN IESEKKPNYE YYLQYTLEIK PELKDFYDGA IGIDRGINHI AVCTFISNDG  360
KVTPPKFFSS GEILRLKNLQ KERDRFLLRK HNKNRKKGNM RVIENKINLI LHRYSKQIVD  420
MAKKLNASIV FEELGRIGKS RTKMKKSQRY KLSLFIFKKL SDLVDYKSRR EGIRVTYVPP  480
EYTSKECSHC GEKVNTQRPF NGNYSLFKCN KCGIQLNSDY NASINIAKKG LKIPNST     537

SEQ ID NO: 71          moltype = AA  length = 540
FEATURE                Location/Qualifiers
source                 1..540
                       mol_type = protein
                       organism = synthetic construct
                       note = Description of Artificial Sequence: Synthetic
                        polypeptide
SEQUENCE: 71
LWTIVIGDFI EMPKQDLVTT GIKFKLDVDK ETRKKLDDYF DEYGKAINFA VKIIQKNLKE  60
DRFAGKIALG EDKKPLLDKD GKKIYNYPNE SCSCGNQVRR YVNAKPFCVD CYKLKFTENG  120
IRKRMYSARG RKADSDINIK NSTNKISKTH FNYAIREGFI LDKSLKKQRS KRIKKLLELK  180
RKLQEFIDIR QGQMVLCPKI KNQRVDKFIH PSWLKRDKKL EEFRGYSLSV VEGKIKIFNR  240
NILREEDSLR QRGHVNFKAN RIMLDKSVRF LDGGKVNFNL NKGLPKEYLL DLPKKENKLS  300
WLNEKISLIK LQKPKYAYLL RREGSFFIQY TIENVPKTFS DYLGAIGIDR GISHIAVCTF  360
VSKNGVNKAP VFFSSGEILK LKSLQKQRDL FLRGKHNKIR KKSNMRNIDN KINLILHKYS  420
RNIVNLAKSE KAFIVFEKLE KIKKSRFKMS KSLQYKLSQF TFKKLSDLVE YKAKIEGIKV  480
DYVPPEYTSK ECSHCGEKVD TQRPFNGNSS LFKCNKCRVQ LNADYNASIN IAKKSLNISN  540

SEQ ID NO: 72          moltype = AA  length = 542
FEATURE                Location/Qualifiers
```

```
source                  1..542
                        mol_type = protein
                        organism = synthetic construct
                        note = Description of Artificial Sequence: Synthetic
                         polypeptide
SEQUENCE: 72
MSKTTISVKL KIIDLSSEKK EFLDNYFNEY AKATTFCQLR IRRLLRNTHW LGKKEKSSKK  60
WIFESGICDL CGENKELVNE DRNSGEPAKI CKRCYNGRYG NQMIRKLFVS TKKREVQENM  120
DIRRVAKLNN THYHRIPEEA FDMIKAADTA EKRRKKNVEY DKKRQMEFIE MFNDEKKRAA  180
RPKKPNERET RYVHISKLES PSKGYTLNGI KRKIDGMGKK IERAEKGLSR KKIFGYQGNR  240
IKLDSNWVRF DLAESEITIP SLFKEMKLRI TGPTNVHSKS GQIYFAEWFE RINKQPNNYC  300
YLIRKTSSNG KYEYYLQYTY EAEVEANKEY AGCLGVDIGC SKLAAAVYYD SKNKKAQKPI  360
EIFTNPIKKI KMRREKLIKL LSRVKVRHRR RKLMQLSKTE PIIDYTCHKT ARKIVEMANT  420
AKAFISMENL ETGIKQKQQA RETKKQKFYR NMFLFRKLSK LIEYKALLKG IKIVYVKPDY  480
TSQTCSSCGA DKEKTERPSQ AIFRCLNPTC RYYQRDINAD FNAAVNIAKK ALNNTEVVTT  540
LL                                                                 542

SEQ ID NO: 73           moltype = AA  length = 564
FEATURE                 Location/Qualifiers
source                  1..564
                        mol_type = protein
                        organism = synthetic construct
                        note = Description of Artificial Sequence: Synthetic
                         polypeptide
SEQUENCE: 73
MARAKNQPYQ KLTTTTGIKF KLDLSEEEGK RFDEYFSEYA KAVNFCAKVI YQLRKNLKFA  60
GKKELAAKEW KFEISNCDFC NKQKEIYYKN IANGQKVCKG CHRTNFSDNA IRKKMIPVKG  120
RKVESKFNIH NTTKKISGTH RHWAFEDAAD IIESMDKQRK EKQKRLRREK RKLSYFFELF  180
GDPAKRYELP KVGKQRVPRY LHKIIDKDSL TKKRGYSLSY IKNKIKISER NIERDEKSLR  240
KASPIAFGAR KIKMSKLDPK RAFDLENNVF KIPGKVIKGQ YKFFGTNVAN EHGKKFYKDR  300
ISKILAGKPK YFYLLRKKVA ESDGNPIFEY YVQWSIDTET PAITSYDNIL GIDAGITNLA  360
TTVLIPKNLS AEHCSHCGNN HVKPIFTKFF SGKELKAIKI KSRKQKYFLR GKHNKLVKIK  420
RIRPIEQKVD GYCHVVSKQI VEMAKERNSC IALEKLEKPK KSKFRQRRRE KYAVSMFVFK  480
KLATFIKYKA AREGIEIIPV EPEGTSYTCS HCKNAQNNQR PYFKPNSKKS WTSMFKCGKC  540
GIELNSDYNA AFNIAQKALN MTSA                                         564

SEQ ID NO: 74           moltype = AA  length = 610
FEATURE                 Location/Qualifiers
source                  1..610
                        mol_type = protein
                        organism = synthetic construct
                        note = Description of Artificial Sequence: Synthetic
                         polypeptide
SEQUENCE: 74
MDEKHFFCSY CNKELKISKN LINKISKGSI REDEAVSKAI SIHNKKEHSL ILGIKFKLFI  60
ENKLDKKKLN EYFDNYSKAV TFAARIFDKI RSPYKFIGLK DKNTKKWTFP KAKCVFCLEE  120
KEVAYANEKD NSKICTECYL KEFGENGIRK KIYSTRGRKV EPKYNIFNST KELSSTHYNY  180
AIRDAFQLLD ALKKQRQKKL KSIFNQKLRL KEFEDIFSDP QKRIELSLKP HQREKRYIHL  240
SKSGQESINR GYTLRFVRGK IKSLTRNIER EEKSLRKKTP IHFKGNRLMI FPAGIKFDFA  300
SNKVKISISK NLPNEFNFSG TNVKNEHGKS FFKSRIELIK TQKPKYAYVL RKIKREYSKL  360
RNYEIEKIRL ENPNADLCDF YLQYTIETES RNNEEINGII GIDRGITNLA CLVLLKKGDK  420
KPSGVKFYKG NKILGMKIAY RKHLYLLKGK RNKLRKQRQI RAIEPKINLI LHQISKDIVK  480
IAKEKNFAIA LEQLEKPKKA RFAQRKKEKY KLALFTFKNL STLIEYKSKR EGIPVIYVPP  540
EKTSQMCSHC AINGDEHVDT QRPYKKPNAQ KPSYSLFKCN KCGIELNADY NAAFNIAQKG  600
LKTLMLNHSH                                                         610

SEQ ID NO: 75           moltype = AA  length = 369
FEATURE                 Location/Qualifiers
source                  1..369
                        mol_type = protein
                        organism = synthetic construct
                        note = Description of Artificial Sequence: Synthetic
                         polypeptide
SEQUENCE: 75
MLQTLLVKLD PSKEQYKMLY ETMERFNEAC NQIAETVFAI HSANKIEVQK TVYYPIREKF  60
GLSAQLTILA IRKVCEAYKR DKSIKPEFRL DGALVYDQRV LSWKGLDKVS LVTLQGRQII  120
PIKFGDYQKA RMDRIRGQAD LILVKGVFYL CVVVEVSEES PYDPKGVLGV DLGIKNLAVD  180
SDGEVHSGEQ TTNTRERLDS LKARLQSKGT KSAKRHLKKL SGRMAKFSKD VNHCISKKLV  240
AKAKGTLMSI ALEDLQGIRD RVTVRKAQRR NLHTWNFGLL RMFVDYKAKI AGVPLVFVDP  300
RNTSRTCPSC GHVAKANRPT RDEFRCVSCG FAGAADHIAA MNIAFRAEVS QPIVTRFFVQ  360
SQAPSFRVG                                                          369

SEQ ID NO: 76           moltype = AA  length = 552
FEATURE                 Location/Qualifiers
source                  1..552
                        mol_type = protein
                        organism = synthetic construct
                        note = Description of Artificial Sequence: Synthetic
                         polypeptide
```

```
SEQUENCE: 76
MDEEPDSAEP NLAPISVKLK LVKLDGEKLA ALNDYFNEYA KAVNFCELKM QKIRKNLVNI  60
RGTYLKEKKA WINQTGECCI CKKIDELRCE DKNPDINGKI CKKCYNGRYG NQMIRKLFVS  120
TNKRAVPKSL DIRKVARLHN THYHRIPPEA ADIIKAIETA ERKRRNRILF DERRYNELKD  180
ALENEEKRVA RPKKPKEREV RYVPISKKDT PSKGYTMNAL VRKVSGMAKK IERAKRNLNK  240
RKKIEYLGRR ILLDKNWVRF DFDKSEISIP TMKEFFGEMR FEITGPSNVM SPNGREYFTK  300
WFDRIKAQPD NYCYLLRKES EDETDFYLQY TWRPDAHPKK DYTGCLGIDI GGSKLASAVY  360
FDADKNRAKQ PIQIFSNPIG KWKTKRQKVI KVLSKAAVRH KTKKLESLRN IEPRIDVHCH  420
RIARKIVGMA LAANAFISME NLEGGIREKQ KAKETKKQKF SRNMFVFRKL SKLIEYKALM  480
EGVKVVYIVP DYTSQLCSSC GTNNTKRPKQ AIFMCQNTEC RYFGKNINAD FNAAINIAKK  540
ALNRKDIVRE LS                                                    552

SEQ ID NO: 77          moltype = AA  length = 534
FEATURE                Location/Qualifiers
source                 1..534
                       mol_type = protein
                       organism = synthetic construct
                       note = Description of Artificial Sequence: Synthetic
                        polypeptide
SEQUENCE: 77
MEKNNSEQTS ITTGIKFKLK LDKETKEKLN NYFDEYGKAI NFAVRIIQMQ LNDDRLAGKY  60
KRDEKGKPIL GEDGKKILEI PNDFCSCGNQ VNHYVNGVSF CQECYKKRFS ENGIRKRMYS  120
AKGRKAEQDI NIKNSTNKIS KTHFNYAIRE AFNLDKSIKK QREKRFKKLK DMKRKLQEFL  180
EIRDGKRVIC PKIEKQKVER YIHPSWINKE KKLEEFRGYS LSIVNSKIKS FDRNIQREEK  240
SLKEKGQINF KAQRLMLDKS VKFLKDNKVS FTISKELPKT FELDLPKKEK KLNWLNEKLE  300
IIKNQKPKYA YLLRKENNIF LQYTLDSIPE IHSEYSGAVG IDRGVSHIAV YTFLDKDGKN  360
ERPFFLSSSG ILRLKNLQKE RDKFLRKKHN KIRKKGNMRN IEQKINLILH EYSKQIVNFA  420
KDKNAFIVFE LLEKPKKSRE RMSKKIQYKL SQFTFKKLSD LVDYKAKREG IKVIYVEPAY  480
TSKDCSHCGE RVNTQRPFNG NFSLFKCNKC GIVLNSDYNA SLNIARKGLN ISAN        534

SEQ ID NO: 78          moltype = AA  length = 577
FEATURE                Location/Qualifiers
source                 1..577
                       mol_type = protein
                       organism = synthetic construct
                       note = Description of Artificial Sequence: Synthetic
                        polypeptide
SEQUENCE: 78
MAEEKFFFCE KCNKDIKIPK NYINKQGAEE KARAKHEHRV HALILGIKFK IYPKKEDISK  60
LNDYFDEYAK AVTFTAKIVD KLKAPFLFAG KRDKDTSKKK WVFPVDKCSF CKEKTEINYR  120
TKQGKNICNS CYLTEFGEQG LLEKIYATKG RKVSSSFNLF NSTKKLTGTH NNYVVKESLQ  180
LLDALKKQRS KRLKKLSNTR RKLKQFEEMF EKEDKRFQLP LKEKQRELRF IHVSQKDRAT  240
EFKGYTMNKI KSKIKVLRRN IEREQRSLNR KSPVFFRGTR IRLSPSVQFD DKDNKIKLTL  300
SKELPKEYSF SGLNVANEHG RKFFAEKLKL IKENKSKYAY LLRRQVNKNN KKPIYDYYLQ  360
YTVEFLPNII TNYNGILGID RGINTLACIV LLENKKEKPS FVKFFSGKGI LNLKNKRRKQ  420
LYFLKGVHNK YRKQQKIRPI EPRIDQILHD ISKQIIDLAK EKRVAISLEQ LEKPQKPKFR  480
QSRKAKYKLS QFNFKTLSNY IDYKAKKEGI RVIYIAPEMT SQNCSRCAMK NDLHVNTQRP  540
YKNTSSLFKC NKCGVELNAD YNAAFNIAQK GLKILNS                           577

SEQ ID NO: 79          moltype = AA  length = 613
FEATURE                Location/Qualifiers
source                 1..613
                       mol_type = protein
                       organism = synthetic construct
                       note = Description of Artificial Sequence: Synthetic
                        polypeptide
SEQUENCE: 79
MISLKLKLLP DEEQKKLLDE MFWKWASICT RVGFGRADKE DLKPPKDAEG VWFSLTQLNQ  60
ANTDINDLRE AMKHQKHRLE YEKNRLEAQR DDTQDALKNP DRREISTKRK DLFRPKASVE  120
KGFLKLKYHQ ERYWVRRLKE INKLIERKTK TLIKIEKGRI KFKATRITLH QGSFKIRFGD  180
KPAFLIKALS GKNQIDAPFV VVPEQPICGS VVNSKKYLDE ITTNFLAYSV NAMLFGLSRS  240
EEMLLKAKRP EKIKKKEEKL AKKQSAFENK KKELQKLLGR ELTQQEEAII EETRNQFFQD  300
FEVKITKQYS ELLSKIANEL KQKNDFLKVN KYPILLRKPL KKAKSKKINN LSPSEWKYYL  360
QFGVKPLLKQ KSRRKSRNVL GIDRGLKHLL AVTVLEPDKK TFVWNKLYPN PITGWKWRRR  420
KLLRSLKRLK RRIKSQKHET IHENQTRKKL KSLQGRIDDL LHNISRKIVE TAKEYDAVIV  480
VEDLQSMRQH GRSKGNRLKT LNYALSLFDY ANVMQLIKYK AGIEGIQIYD VKPAGTSQNC  540
AYCLLAQRDS HEYKRSQENS KIGVCLNPNC QNHKKQIDAD LNAARVIASC YALKINDSQP  600
FGTRKRFKKR TTN                                                     613

SEQ ID NO: 80          moltype = AA  length = 615
FEATURE                Location/Qualifiers
source                 1..615
                       mol_type = protein
                       organism = synthetic construct
                       note = Description of Artificial Sequence: Synthetic
                        polypeptide
SEQUENCE: 80
METLSLKLKL NPSKEQLLVL DKMFWKWASI CTRLGLKKAE MSDLEPPKDA EGVWFSKTQL  60
NQANTDVNDL RKAMQHQGKR IEYELDKVEN RRNEIQEMLE KPDRRDISPN RKDLFRPKAA  120
```

```
VEKGYLKLKY HKLGYWSKEL KTANKLIERK RKTLAKIDAG KMKFKPTRIS LHTNSFRIKF  180
GEEPKIALST TSKHEKIELP LITSLQRPLK TSCAKKSKTY LDAAILNFLA YSTNAALFGL  240
SRSEEMLLKA KKPEKIEKRD RKLATKRESF DKKLKTLEKL LERKLSEKEK SVFKRKQTEF  300
FDKFCITLDE TYVEALHRIA EELVSKNKYL EIKKYPVLLR KPESRLRSKK LKNLKPEDWT  360
YYIQFGFQPL LDTPKPIKTK TVLGIDRGVR HLLAVSIFDP RTKTFTFNRL YSNPIVDWKW  420
RRRKLLRSIK RLKRRLKSEK HVHLHENQFK AKLRSLEGRI EDHFHNLSKE IVDLAKENNS  480
VIVVENLGGM RQHGRGRGKW LKALNYALSH FDYAKVMQLI KYKAELAGVF VYDVAPAGTS  540
INCAYCLLND KDASNYTRGK VINGKKNTKI GECKTCKKEF DADLNAARVI ALCYEKRLND  600
PQPFGTRKQF KPKKP                                                  615

SEQ ID NO: 81           moltype = AA  length = 775
FEATURE                 Location/Qualifiers
source                  1..775
                        mol_type = protein
                        organism = synthetic construct
                        note = Description of Artificial Sequence: Synthetic
                         polypeptide
SEQUENCE: 81
MKALKLQLIP TRKQYKILDE MFWKWASLAN RVSQKGESKE TLAPKKDIQK IQFNATQLNQ  60
IEKDIKDLRG AMKEQQKQKE RLLLQIQERR STISEMLNDD NNKERDPHRP LNFRPKGWRK  120
FHTSKHWVGE LSKILRQEDR VKKTIERIVA GKISFKPKRI GIWSSNYKIN FFKRKISINP  180
LNSKGFELTL MTEPTQDLIG KNGGKSVLNN KRYLDDSIKS LLMFALHSRF FGLNNTDTYL  240
LGGKINPSLV KYYKKNQDMG EFGREIVEKF ERKLKQEINE QQKKIIMSQI KEQYSNRDSA  300
FNKDYLGLIN EFSEVFNQRK SERAEYLLDS FEDKIKQIKQ EIGESLNISD WDFLIDEAKK  360
AYGYEEGFTE YVYSKRYLEI LNKIVKAVLI TDIYFDLRKY PILLRKPLDK IKKISNLKPD  420
EWSYYIQFGY DSINPVQLMS TDKFLGIDRG LTHLLAYSVF DKEKKEFIIN QLEPNPIMGW  480
KWKLRKVKRS LQHLERRIRA QKMVKLPENQ MKKKLKSIEP KIEVHYHNIS RKIVNLAKDY  540
NASIVVESLE GGGLKQHGRK KNARNRSLNY ALSLFDYGKI ASLIKYKADL EGVPMYEVLP  600
AYTSQQCAKC VLEKGSFVDP EIIGYVEDIG IKGSLLDSLF EGTELSSIQV LKKIKNKIEL  660
SARDNHNKEI NLILKYNFKG LVIVRGQDKE EIAEHPIKEI NGKFAILDFV YKRGKEKVGK  720
KGNQKVRYTG NKKVGYCSKH GQVDADLNAS RVIALCKYLD INDPILFGEQ RKSFK       775

SEQ ID NO: 82           moltype = AA  length = 777
FEATURE                 Location/Qualifiers
source                  1..777
                        mol_type = protein
                        organism = synthetic construct
                        note = Description of Artificial Sequence: Synthetic
                         polypeptide
SEQUENCE: 82
MVTRAIKLKL DPTKNQYKLL NEMFWKWASL ANRFSQKGAS KETLAPKDGT QKIQFNATQL  60
NQIKKDVDDL RGAMEKQGKQ KERLLIQIQE RLLTISEILR DDSKKEKDPH RPQNFRPFGW  120
RRFHTSAYWS SEASKLTRQV DRVRRTIERI KAGKINFKPK RIGLWSSTYK INFLKKKINI  180
SPLKSKSFEL DLITEPQQKI IGKEGGKSVA NSKKYLDDSI KSLLIFAIKS RLFGLNNKDK  240
PLFENIITPN LVRYHKKGQE QENFKKEVIK KFENKLKKEI SQKQKEIIFS QIERQYENRD  300
ATFSEDYLRA ISEFSEIFNQ RKKERAKELL NSFNEKIRQL KKEVNGNISE EDLKILEVEA  360
EKAYNYENGF IEWEYSEQFL GVLEKIARAV LISDNYFDLK KYPILIRKPT NKSKKITNLK  420
PEEWDYYIQF GYGLINSPMK IETKNFMGID RGLTHLLAYS IFDRDSEKFT INQLELNPIK  480
GWKWKLRKVK RSLQHLERRM RAQKGVKLPE NQMKKRLKSI EPKIESYYHN LSRKIVNLAK  540
ANNASIVVES LEGGGLKQHG RKKNSRHRAL NYALSLFDYG KIASLIKYKS DLEGVPMYEV  600
LPAYTSQQCA KCVLKKGSFV EPEIIGYIEE IGFKENLLTL LFEDTGLSSV QVLKKSKNKM  660
TLSARDKEGK MVDLVLKYNF KGLVISQEKK KEEIVEFPIK EIDGKFAVLD SAYKRGKERI  720
SKKGNQKLVY TGNKKVGYCS VHGQVDADLN ASRVIALCKY LGINEPIVFG EQRKSFK     777

SEQ ID NO: 83           moltype = AA  length = 610
FEATURE                 Location/Qualifiers
source                  1..610
                        mol_type = protein
                        organism = synthetic construct
                        note = Description of Artificial Sequence: Synthetic
                         polypeptide
SEQUENCE: 83
LDLITEPIQP HKSSSLRSKE FLEYQISDFL NFSLHSLFFG LASNEGPLVD FKIYDKIVIP  60
KPEERFPKKE SEEGKKLDSF DKRVEEYYSD KLEKKIERKL NTEEKNVIDR EKTRIWGEVN  120
KLEEIRSIID EINEIKKQKH ISEKSKLLGE KWKKVNNIQE TLLSQEYVSL ISNLSDELTN  180
KKKELLAKKY SKFDDKIKKI KEDYGLEFDE NTIKKEGEKA FLNPDKFSKY QFSSSYLKLI  240
GEIARSLITY KGFLDLNKYP IIFRKPINKV KKIHNLEPDE WKYYIQFGYE QINNPKLETE  300
NILGIDRGLT HILAYSVFEP RSSKFILNKL EPNPIEGWKW KLRKLRRSIQ NLERRWRAQD  360
NVKLPENQMK KNLRSIEDKV ENLYHNLSRK IVDLAKEKNA CIVFEKLEGQ GMKQHGRKKS  420
DRLRGLNYKL SLFDYGKIAK LIKYKAEIEG IPIYRIDSAY TSQNCAKCVL ESRRFAQPEE  480
ISCLDDFKEG DNLDKRILEG TGLVEAKIYK KLLKEKKEDF EIEEDIAMFD TKKVIKENKE  540
KTVILDYVYT RRKEIIGTNH KKNIKGIAKY TGNTKIGYCM KHGQVDADLN ASRTIALCKN  600
FDINNPEIWK                                                        610

SEQ ID NO: 84           moltype = AA  length = 632
FEATURE                 Location/Qualifiers
source                  1..632
                        mol_type = protein
                        organism = synthetic construct
```

```
                        note = Description of Artificial Sequence: Synthetic
                         polypeptide
SEQUENCE: 84
MSDESLVSSE DKLAIKIKIV PNAEQAKMLD EMFKKWSSIC NRISRGKEDI ETLRPDEGKE  60
LQFNSTQLNS ATMDVSDLKK AMARQGERLE AEVSKLRGRY ETIDASLRDP SRRHTNPQKP  120
SSFYPSDWDI SGRLTPRFHT ARHYSTELRK LKAKEDKMLK TINKIKNGKI VFKPKRITLW  180
PSSVNMAFKG SRLLLKPFAN GFEMELPIVI SPQKTADGKS QKASAEYMRN ALLGLAGYSI  240
NQLLFGMNRS QKMLANAKKP EKVEKFLEQM KNKDANFDKK IKALEGKWLL DRKLKESEKS  300
SIAVVRTKFF KSGKVELNED YLKLLKHMAN EILERDGFVN LNKYPILSRK PMKRYKQKNI  360
DNLKPNMWKY YIQFGYEPIF ERKASGKPKN IMGIDRGLTH LLAVAVFSPD QQKFLFNHLE  420
SNPIMHWKWK LRKIRRSIQH MERRIRAEKN KHIHEAQLKK RLGSIEEKTE QHYHIVSSKI  480
INWAIEYEAA IVLESLSHMK QRGGKKSVRT RALNYALSLF DYEKVARLIT YKARIRGIPV  540
YDVLPGMTSK TCATCLLNGS QGAYVRGLET TKAAGKATKR KNMKIGKCMV CNSSENSMID  600
ADLNAARVIA ICKYKNLNDP QPAGSRKVFK RF                               632

SEQ ID NO: 85           moltype = AA  length = 625
FEATURE                 Location/Qualifiers
source                  1..625
                        mol_type = protein
                        organism = synthetic construct
                        note = Description of Artificial Sequence: Synthetic
                         polypeptide
SEQUENCE: 85
MLALKLKIMP TEKQAEILDA MFWKWASICS RIAKMKKKVS VKENKKELSK KIPSNSDIWF  60
SKTQLCQAEV DVGDHKKALK NFEKRQESLL DELKYKVKAI NEVINDESKR EIDPNNPSKF  120
RIKDSTKKGN LNSPKFFTLK KWQKILQENE KRIKKKESTI EKLKRGNIFF NPTKISLHEE  180
EYSINFGSSK LLLNCFYKYN KKSGINSDQL ENKFNEFQNG LNIICSPLQP IRGSSKRSFE  240
FIRNSIINFL MYSLYAKLFG IPRSVKALMK SNKDENKLKL EEKLKKKSS FNKTVKEFEK  300
MIGRKLSDNE SKILNDESKK FFEIIKSNNK YIPSEEYLKL LKDISEEIYN SNIDFKPYKY  360
SILIRKPLSK FKSKKLYNLK PTDYKYYLQL SYEPFSKQLI ATKTILGIDR GLKHLLAVSV  420
FDPSQNKFVY NKLIKNPVFK WKKRYHDLKR SIRNRERRIR ALTGVHIHEN QLIKKLKSMK  480
NKINVLYHNV SKNIVDLAKK YESTIVLERL ENLKQHGRSK GKRYKKLNYV LSNFDYKKIE  540
SLISYKAKKE GVPVSNINPK YTSKTCAKCL LEVNQLSELK NEYNRDSKNS KIGICNIHGQ  600
IDADLNAARV IALCYSKNLN EPHFK                                       625

SEQ ID NO: 86           moltype = AA  length = 517
FEATURE                 Location/Qualifiers
source                  1..517
                        mol_type = protein
                        organism = synthetic construct
                        note = Description of Artificial Sequence: Synthetic
                         polypeptide
SEQUENCE: 86
VINLFGYKFA LYPNKTQEEL LNKHLGECGW LYNKAIEQNE YYKADSNIEE AQKKFELLPD  60
KNSDEAKVLR GNISKDNYVY RTLVKKKKSE INVQIRKAVV LRPAETIRNL AKVKKKGLSV  120
GRLKFIPIRE WDVLPFKQSD QIRLEENYLI LEPYGRLKFK MHRPLLGKPK TFCIKRTATD  180
RWTISFSTEY DDSNMRKNDG GQVGIDVGLK THLRLSNENP DEDPRYPNPK IWKRYDRRLT  240
ILQRRISKSK KLGKNRTRLR LRLSRLWEKI RNSRADLIQN ETYEILSENK LIAIEDLNVK  300
GMQEKKDKKG RKGRTRAQEK GLHRSISDAA FSEFRRVLEY KAKRFGSEVK PVSAIDSSKE  360
CHNCGNKKGM PLESRIYECP KCGLKIDRDL NSAKVILARA TGVRPGSNAR ADTKISATAG  420
ASVQTEGTVS EDFRQQMETS DQKPMQGEGS KEPPMNPEHK SSGRGSKHVN IGCKNKVGLY  480
NEDENSRSTE KQIMDENRST TEDMVEIGAL HSPVLTT                          517

SEQ ID NO: 87           moltype = AA  length = 410
FEATURE                 Location/Qualifiers
source                  1..410
                        mol_type = protein
                        organism = synthetic construct
                        note = Description of Artificial Sequence: Synthetic
                         polypeptide
SEQUENCE: 87
MIASIDYEAV SQALIVFEFK AKGKDSQYQA IDEAIRSYRF IRNSCLRYWM DNKKVGKYDL  60
NKYCKVLAKQ YPFANKLNSQ ARQSAAECSW SAISRFYDNC KRKVSGKKGF PKFKKHARSV  120
EYKTSGWKLS ENRKAITFTD KNGIGKLKLK GTYDLHFSQL EDMKRVRLVR RADGYYVQFC  180
ISVDVKVETE PTGKAIGLDV GIKYFLADSS GNTIENPQFY RKAEKKLNRA NRRKSKKYIR  240
GVKPQSKNYH KARCRYARKH LRVSRQRKEY CKRVAYCVIH SNDVVAYEDL NVKGMVKNRH  300
LAKSISDVAW STFRHWLEYF AIKYGKLTIP VAPHNTSQNC SNCDKKVPKS LSTRTHICHH  360
CGYSEDRDVN AAKNILKKAL STVGQTGSLK LGEIEPLLVL EQSCTRKFDL            410

SEQ ID NO: 88           moltype = AA  length = 486
FEATURE                 Location/Qualifiers
source                  1..486
                        mol_type = protein
                        organism = synthetic construct
                        note = Description of Artificial Sequence: Synthetic
                         polypeptide
SEQUENCE: 88
LAEENTLHLT LAMSLPLNDL PENRTRSELW RRQWLPQKKL SLLLGVNQSV RKAAADCLRW  60
FEPYQELLWW EPTDPDGKKL LDKEGRPIKR TAGHMRVLRK LEEIAPFRGY QLGSAVKNGL  120
```

```
RHKVADLLLS YAKRKLDPQF TDKTSYPSIG DQFPIVWTGA FVCYEQSITG QLYLYLPLFP  180
RGSHQEDITN NYDPDRGPAL QVFGEKEIAR LSRSTSGLLL PLQFDKWGEA TFIRGENNPP  240
TWKATHRRSD KKWLSEVLLR EKDFQPKRVE LLVRNGRIFV NVACEIPTKP LLEVENFMGV  300
SFGLEHLVTV VVINRDGNVV HQRQEPARRY EKTYFARLER LRRRGGPFSQ ELETFHYRQV  360
AQIVEEALRF KSVPAVEQVG NIPKGRYNPR LNLRLSYWPF GKLADLTSYK AVKEGLPKPY  420
SVYSATAKML CSTCGAANKE GDQPISLKGP TVYCGNCGTR HNTGFNTALN LARRAQELFV  480
KGVVAR                                                             486

SEQ ID NO: 89           moltype = AA  length = 602
FEATURE                 Location/Qualifiers
source                  1..602
                        mol_type = protein
                        organism = synthetic construct
                        note = Description of Artificial Sequence: Synthetic
                         polypeptide
SEQUENCE: 89
MSQSLLKWHD MAGRDKDASR SLQKSAVEGV LLHLTASHRV ALEMLEKSVS QTVAVTMEAA  60
QQRLVIVLED DPTKATSRKR VISADLQFTR EEFGSLPNWA QKLASTCPEI ATKYADKHIN  120
SIRIAWGVAK ESTNGDAVEQ KLQWQIRLLD VTMFLQQLVL QLADKALLEQ IPSSIRGGIG  180
QEVAQQVTSH IQLLDSGTVL KAELPTISDR NSELARKQWE DAIQTVCTYA LPFSRERARI  240
LDPGKYAAED PRGDRLINID PMWARVLKGP TVKSLPLLFV SGSSIRIVKL TLPRKHAAGH  300
KHTFTATYLV LPVSREWINS LPGTVQEKVQ WWKKPDVLAT QELLVGKGAL KKSANTLVIP  360
ISAGKKRFFN HILPALQRGF PLQWQRIVGR SYRRPATHRK WFAQLTIGYT NPSSLPEMAL  420
GIHFGMKDIL WWALADKQGN ILKDGSIPGN SILDFSLQEK GKIERQQKAG KNVAGKKYGK  480
SLLNATYRVV NGVLEFSKGI SAEHASQPIG LGLETIRFVD KASGSSPVNA RHSNWNYGQL  540
SGIFANKAGP AGFSVTEITL KKAQRDLSDA EQARVLAIEA TKRFASRIKR LATKRKDDTL  600
FV                                                                 602

SEQ ID NO: 90           moltype = AA  length = 494
FEATURE                 Location/Qualifiers
source                  1..494
                        mol_type = protein
                        organism = synthetic construct
                        note = Description of Artificial Sequence: Synthetic
                         polypeptide
SEQUENCE: 90
VEPVEKERFY YRTYTFRLDG QPRTQNLTTQ SGWGLLTKAV LDNTKHYWEI VHHARIANQP  60
IVFENPVIDE QGNPKLNKLG QPRFWKRPIS DIVNQLRALF ENQNPYQLGS SLIQGTYWDV  120
AENLASWYAL NKEYLAGTAT WGEPSFPEPH PLTEINQWMP LTFSSGKVVR LLKNASGRYF  180
IGLPILGENN PCYRMRTIEK LIPCDGKGRV TSGSLILFPL VGIYAQQHRR MTDICESIRT  240
EKGKLAWAQV SIDYVREVDK RRRMRRTRKS QGWIQGPWQE VFILRLVLAH KAPKLYKPRC  300
FAGISLGPKT LASCVILDQD ERVVEKQQWS GSELLSLIHQ GEERLRSLRE QSKPTWNAAY  360
RKQLKSLINT QVFTIVTFLR ERGAAVRLES IARVRKSTPA PPVNFLLSHW AYRQITERLK  420
DLAIRNGMPL THSNGSYGVR FTCSQCGATN QGIKDPTKYK VDIESETFLC SICSHREIAA  480
VNTATNLAKQ LLDE                                                    494

SEQ ID NO: 91           moltype = AA  length = 526
FEATURE                 Location/Qualifiers
source                  1..526
                        mol_type = protein
                        organism = synthetic construct
                        note = Description of Artificial Sequence: Synthetic
                         polypeptide
SEQUENCE: 91
MNDTETSETL TSHRTVCAHL HVVGETGSLP RLVEAALAEL ITLNGRATQA LLSLAKNGLV  60
LRRDKEENLI AAELTLPCRK NKYADVAAKA GEPILATRIN NKGKLVTKKW YGEGNSYHIV  120
RFTPETGMFT VRVFDRYAFD EELLHLHSEV VFGSDLPKGI KAKTDSLPAN FLQAVFTSFL  180
ELPFQGFPDI VVKPAMKQAA EQLLSYVQLE AGENQQAEYP DTNERDPELR LVEWQKSLHE  240
LSVRTEPFEF VRARDIDYYA ETDRRGNRFV NITPEWTKFA ESPFARRLPL KIPPEFCILL  300
RRKTEGHAKI PNRIYLGLQI FDGVTPDSTL GVLATAEDGK LFWWHDHLDE FSNLEGKPEP  360
KLKNKPQLLM VSLEYDREQR FEESVGGDRK ICLVTLKETR NFRRGWNGRI LGIHFQHNPV  420
ITWALMDHDA EVLEKGFIEG NAFLGKALDK QALNEYLQKG GKWVGDRSFG NKLKGITHTL  480
ASLIVRLARE KDAWIALEEI SWVQKQSADS VANHEIVEQP HHSLTR                 526

SEQ ID NO: 92           moltype = AA  length = 649
FEATURE                 Location/Qualifiers
source                  1..649
                        mol_type = protein
                        organism = synthetic construct
                        note = Description of Artificial Sequence: Synthetic
                         polypeptide
SEQUENCE: 92
MNDTETSETL TSHRTVCAHL HVVGETGSLP RLVEAALAEL ITLNGRATQA LLSLAKNGLV  60
LRRDKEENLI AAELTLPCRK NKYADVAAKA GEPILATRIN NKGKLVTKKW YGEGNSYHIV  120
RFTPETGMFT VRVFDRYAFD EELLHLHSEV VFGSDLPKGI KAKTDSLPAN FLQAVFTSFL  180
ELPFQGFPDI VVKPAMKQAA EQLLSYVQLE AGENQQAEYP DTNERDPELR LVEWQKSLHE  240
LSVRTEPFEF VRARDIDYYA ETDRRGNRFV NITPEWTKFA ESPFARRLPL KIPPEFCILL  300
RRKTEGHAKI PNRIYLGLQI FDGVTPDSTL GVLATAEDGK LFWWHDHLDE FSNLEGKPEP  360
KLKNKPQLLM VSLEYDREQR FEESVGGDRK ICLVTLKETR NFRRGRHGHT RTDRLPAGNT  420
```

```
LWRADFATSA EVAAPKWNGR ILGIHFQHNP VITWALMDHD AEVLEKGFIE GNAFLGKALD  480
KQALNEYLQK GGKWVGDRSF GNKLKGITHT LASLIVRLAR EKDAWIALEE ISWVQKQSAD  540
SVANRRFSMW NYSRLATLIE WLGTDIATRD CGTAAPLAHK VSDYLTHFTC PECGACRKAG  600
QKKEIADTVR AGDILTCRKC GFSGPIPDNF IAEFVAKKAL ERMLKKKPV             649

SEQ ID NO: 93          moltype = AA  length = 414
FEATURE                Location/Qualifiers
source                 1..414
                       mol_type = protein
                       organism = synthetic construct
                       note = Description of Artificial Sequence: Synthetic
                        polypeptide
SEQUENCE: 93
MAKRNFGEKS EALYRAVRFE VRPSKEELSI LLAVSEVLRM LFNSALAERQ QVFTEFIASL  60
YAELKSASVP EEISEIRKKL REAYKEHSIS LFDQINALTA RRVEDEAFAS VTRNWQEETL  120
DALDGAYKSF LSLRRKGDYD AHSPRSRDSG FFQKIPGRSG FKIGEGRIAL SCGAGRKLSF  180
PIPDYQQGRL AETTKLKKFE LYRDQPNLAK SGRFWISVVY ELPKPEATTC QSEQVAFVAL  240
GASSIGVVSQ RGEEVIALWR SDKHWVPKIE AVEERMKRRV KGSRGWLRLL NSGKRRMHMI  300
SSRQHVQDER EIVDYLVRNH GSHFVVTELV VRSKEGKLAD SSKPERGGSL GLNWAAQNTG  360
SLSRLVRQLE EKVKEHGGSV RKHKLTLTEA PPARGAENKL WMARKLRESF LKEV        414

SEQ ID NO: 94          moltype = AA  length = 413
FEATURE                Location/Qualifiers
source                 1..413
                       mol_type = protein
                       organism = synthetic construct
                       note = Description of Artificial Sequence: Synthetic
                        polypeptide
SEQUENCE: 94
LAKNDEKELL YQSVKFEIYP DESKIRVLTR VSNILVLVWN SALGERRARF ELYIAPLYEE  60
LKKFPRKSAE SNALRQKIRE GYKEHIPTFF DQLKKLLTPM RKEDPALLGS VPRAYQEETL  120
NTLNGSFVSF MTLRRNNDMD AKPPKGRAED RFHEISGRSG FKIDGSEFVL STKEQKLRFP  180
IPNYQLEKLK EAKQIKKFTL YQSRDRRFWI SIAYEIELPD QRPFNPEEVI YIAFGASSIG  240
VISPEGEKVI DFWRPDKHWK PKIKEVENRM RSCKKGSRAW KKRAAARRKM YAMTQRQQKL  300
NHREIVASLL RLGFHFVVTE YTVRSKPGKL ADGSNPKRGG APQGFNWSAQ NTGSFGEFIL  360
WLKQKVKEQG GTVQTFRLVL GQSERPEKRG RDNKIEMVRL LREKYLESQT IVV         413

SEQ ID NO: 95          moltype = AA  length = 449
FEATURE                Location/Qualifiers
source                 1..449
                       mol_type = protein
                       organism = synthetic construct
                       note = Description of Artificial Sequence: Synthetic
                        polypeptide
SEQUENCE: 95
MAKGKKKEGK PLYRAVRFEI FPTSDQITLF LRVSKNLQQV WNEAWQERQS CYEQFFGSIY  60
ERIGQAKKRA QEAGFSEVWE NEAKKGLNKK LRQQEISMQL VSEKESLLQE LSIAFQEHGV  120
TLYDQINGLT ARRIIGEFAL IPRNWQEETL DSLDGSFKSF LALRKNGDPD AKPPRQRVSE  180
NSFYKIPGRS GFKVSNGQIY LSFGKIGQTL TSVIPEFQLK RLETAIKLKK FELCRDERDM  240
AKPGRFWISV AYEIPKPEKV PVVSKQITYL AIGASRLGVV SPKGEFCLNL PRSDYHWKPQ  300
INALQERLEG VVKGSRKWKK RMAACTRMFA KLGHQQKQHG QYEVVKKLLR HGVHFVVTEL  360
KVRSKPGALA DASKSDRKGS PTGPNWSAQN TGNIARLIQK LTDKASEHGG TVIKRNPPLL  420
SLEERQLPDA QRKIFIAKKL REEFLADQK                                   449

SEQ ID NO: 96          moltype = AA  length = 711
FEATURE                Location/Qualifiers
source                 1..711
                       mol_type = protein
                       organism = synthetic construct
                       note = Description of Artificial Sequence: Synthetic
                        polypeptide
SEQUENCE: 96
MAKREKKDDV VLRGTKMRIY PTDRQVTLMD MWRRRCISLW NLLLNLETAA YGAKNTRSKL  60
GWRSIWARVV EENHAKALIV YQHGKCKKDG SFVLKRDGTV KHPPRERFPG DRKILLGLFD  120
ALRHTLDKGA KCKCNVNQPY ALTRAWLDET GHGARTADII AWLKDFKGEC DCTAISTAAK  180
YCPAPPTAEL LTKIKRAAPA DDLPVDQAIL LDLFGALRGG LKQKECDHTH ARTVAYFEKH  240
ELAGRAEDIL AWLIAHGGTC DCKIVEEAAN HCPGPRLFIW EHELAMIMAR LKAEPRTEWI  300
GDLPSHAAQT VVKDLVKALQ TMLKERAKAA AGDESARKTG FPKFKKQAYA AGSVYFPNTT  360
MFFDVAAGRV QLPNGCGSMR CEIPRQLVAE LLERNLKPGL VIGAQLGLLG GRIWRQGDRW  420
YLSCQWERPQ PTLLPKTGRT AGVKIAASIV FTTYDNRGQT KEYPMPPADK KLTAVHLVAG  480
KQNSRALEAQ KEKEKKLKAR KERLRLGKLE KGHDPNALKP LKRPRVRRSK LFYKSAARLA  540
ACEAIERDRR DGFLHRVTNE IVHKFDAVSV QKMSVAPMMR RQKQKEKQIE SKKNEAKKED  600
NGAAKKPRNL KPVRKLLRHV AMARGRQFLE YKYNDLRGPG SVLIADRLEP EVQECSRCGT  660
KNPQMKDGRR LLRCIGVLPD GTDCDAVLPR NRNAARNAEK RLRKHREAHN A           711

SEQ ID NO: 97          moltype = AA  length = 574
FEATURE                Location/Qualifiers
source                 1..574
                       mol_type = protein
```

```
                        organism = synthetic construct
                        note = Description of Artificial Sequence: Synthetic
                         polypeptide
SEQUENCE: 97
MNEVLPIPAV GEDAADTIMR GSKMRIYPSV RQAATMDLWR RRCIQLWNLL LELEQAAYSG  60
ENRRTQIGWR SIWATVVEDS HAEAVRVARE GKKRKDGTFR KAPSGKEIPP LDPAMLAKIQ  120
RQMNGAVDVD PKTGEVTPAQ PRLFMWEHEL QKIMARLKQA PRTHWIDDLP SHAAQSVVKD  180
LIKALQAMLR ERKKRASGIG GRDTGFPKFK KNRYAAGSVY FANTQLRFEA KRGKAGDPDA  240
VRGEFARVKL PNGVGWMECR MPRHINAAHA YAQATLMGGR IWRQGENWYL SCQWKMPKPA  300
PLPRAGRTAA IKIAAAIPIT TVDNRGQTRE YAMPPIDRER IAAHAAAGRA QSRALEARKR  360
RAKKREAYAK KRHAKKLERG IAAKPPGRAR IKLSPGFYAA AAKLAKLEAE DANAREAWLH  420
EITTQIVRNF DVIAVPRMEV AKLMKKPEPP EEKEEQVKAP WQGKRRSLKA ARVMMRRTAM  480
ALIQTTLKYK AVDLRGPQAY EEIAPLDVTA AACSGCGVLK PEWKMARAKG REIMRCQEPL  540
PGGKTCNTVL TYTRNSARVI GRELAVRLAE RQKA                            574

SEQ ID NO: 98           moltype = AA  length = 400
FEATURE                 Location/Qualifiers
source                  1..400
                        mol_type = protein
                        organism = synthetic construct
                        note = Description of Artificial Sequence: Synthetic
                         polypeptide
SEQUENCE: 98
MTTQKTYNFC FYDQRFFELS KEAGEVYSRS LEEFWKIYDE TGVWLSKFDL QKHMRNKLER  60
KLLHSDSFLG AMQQVHANLA SWKQAKKVVP DACPPRKPKF LQAILFKKSQ IKYKNGFLRL  120
TLGTEKEFLY LKWDINIPLP IYGSVTYSKT RGWKINLCLE TEVEQKNLSE NKYLSIDLGV  180
KRVATIFDGE NTITLSGKKF MGLMHYRNKL NGKTQSRLSH KKKGSNNYKK IQRAKRKTTD  240
RLLNIQKEML HKYSSFIVNY AIRNDIGNII IGDNSSTHDS PNMRGKTNQK ISQNPEQKLK  300
NYIKYKFESI SGRVDIVPEP YTSRKCPHCK NIKKSSPKGR TYKCKKCGFI FDRDGVGAIN  360
IYNENVSFGQ IISPGRIRSL TEPIGMKFHN EIYFKSYVAA                      400

SEQ ID NO: 99           moltype = AA  length = 743
FEATURE                 Location/Qualifiers
source                  1..743
                        mol_type = protein
                        organism = synthetic construct
                        note = Description of Artificial Sequence: Synthetic
                         polypeptide
SEQUENCE: 99
MSVRSFQARV ECDKQTMEHL WRTHKVFNER LPEIIKILFK MKRGECGQND KQKSLYKSIS  60
QSILEANAQN ADYLLNSVSI KGWKPGTAKK YRNASFTWAD DAAKLSSQGI HVYDKKQVLG  120
DLPGMMSQMV CRQSVEAISG HIELTKKWEK EHNEWLKEKE KWESEDEHKK YLDLREKFEQ  180
FEQSIGGKIT KRRGRWHLYL KWLSDNPDFA AWRGNKAVIN PLSEKAQIRI NKAKPNKKNS  240
VERDEFFKAN PEMKALDNLH GYYERNFVRR RKTKKNPDGF DHKPTFTLPH PTIHPRWFVF  300
NKPKTNPEGY RKLILPKKAG DLGSLEMRLL TGEKNKGNYP DDWISVKFKA DPRLSLIRPV  360
KGRRVVRKGK EQGQTKETDS YEFFDKHLKK WRPAKLSGVK LIFPDKTPKA AYLYFTCDIP  420
DEPLTETAKK IQWLETGDVT KKGKKRKKKV LPHGLVSCAV DLSMRRGTTG FATLCRYENG  480
KIHILRSRNL WVGYKEGKGC HPYRWTEGPD LGHIAKHKRE IRILRSKRGK PVKGEESHID  540
LQKHIDYMGE DRFKKAARTI VNFALNTENA ASKNGFYPRA DVLLLENLEG LIPDAEKERG  600
INRALAGWNR RHLVERVIEM AKDAGFKRRV FEIPPYGTSQ VCSKCGALGR RYSIIRENNR  660
REIRFGYVEK LFACPNCGYC ANADHNASVN LNRRFLIEDS FKSYYDWKRL SEKKQKEEIE  720
TIESKLMDKL CAMHKISRGS ISK                                        743

SEQ ID NO: 100          moltype = AA  length = 769
FEATURE                 Location/Qualifiers
source                  1..769
                        mol_type = protein
                        organism = synthetic construct
                        note = Description of Artificial Sequence: Synthetic
                         polypeptide
SEQUENCE: 100
MHLWRTHCVF NQRLPALLKR LFAMRRGEVG GNEAQRQVYQ RVAQFVLARD AKDSVDLLNA  60
VSLRKRSANS AFKKKATISC NGQAREVTGE EVFAEAVALA SKGVFAYDKD DMRAGLPDSL  120
FQPLTRDAVA CMRSHEELVA TWKKEYREWR DRKSEWEAEP EHALYLNLRP KFEEGEAARG  180
GRFRKRAERD HAYLDWLEAN PQLAAWRRKA PPAVVPIDEA GKRRIARAKA WKQASVRAEE  240
FWKRNPELHA LHKIHVQYLR EFVRPRRTRR NKRREGFKQR PTFTMPDPVR HPRWCLFNAP  300
QTSPQGYRLL RLPQSRRTVG SVELRLLTGP SDGAGFPDAW VNVRFKADPR LAQLRPVKVP  360
RTVTRGKNKG AKVEADGFRY YDDQLLIERD AQVSGVKLLF RDIRMAPFAD KPIEDRLLSA  420
TPYLVFAVEI KDEARTERAK AIRFDETSEL TKSGKKRKTL PAGLVSVAVD LDTRGVGFLT  480
RAVIGVPEIQ QTHHGVRLLQ SRYVAVGQVE ARASGEAEWS PGPDLAHIAR HKREIRRLRQ  540
LRGKPVKGER SHVRLQAHID RMGEDRFKKA ARKIVNEALR GSNPAAGDPY TRADVLLYES  600
LETLLPDAER ERGINRALLR WNRAKLIEHL KRMCDDAGIR HFPVSPFGTS QVCSKCGALG  660
RRYSLARENG RAVIRFGWVE RLFACPNPEC PGRRPDRPDR PFTCNSDHNA SVNLHRVFAL  720
GDQAVAAFRA LAPRDSPART LAVKRVEDTL RPQLMRVHKL ADAGVDSPF            769

SEQ ID NO: 101          moltype = AA  length = 666
FEATURE                 Location/Qualifiers
source                  1..666
                        mol_type = protein
```

```
                         organism = synthetic construct
                         note = Description of Artificial Sequence: Synthetic
                          polypeptide
SEQUENCE: 101
MATLVYRYGV RAHGSARQQD AVVSDPAMLE QLRLGHELRN ALVGVQHRYE DGKRAVWSGF  60
ASVAAADHRV TTGETAVAEL EKQARAEHSA DRTAATRQGT AESLKAARAA VKQARADRKA  120
AMAAVAEQAK PKIQALGDDR DAEIKDLYRR FCQDGVLLPR CGRCAGDLRS DGDCTDCGAA  180
HEPRKLYWAT YNAIREDHQT AVKLVEAKRK AGQPARLRFR RWTGDGTLTV QLQRMHGPAC  240
RCVTCAEKLT RRARKTDPQA PAVAADPAYP PTDPPRDPAL LASGQGKWRN VLQLGTWIPP  300
GEWSAMSRAE RRRVGRSHIG WQLGGGRQLT LPVQLHRQMP ADADVAMAQL TRVRVGGRHR  360
MSVALTAKLP DPPQVQGLPP VALHLGWRQR PDGSLRVATW ACPQPLDLPP AVADVVVSHG  420
GRWGEVIMPA RWLADAEVPP RLLGRRDKAM EPVLEALADW LEAHTEACTA RMTPALVRRW  480
RSQGRLAGLT NRWRGQPPTG SAEILTYLEA WRIQDKLLWE RESHLRRRLA ARRDDAWRRV  540
ASWLARHAGV LVVDDADIAE LRRRDDPADT DPTMPASAAQ AARARAALAA PGRLRHLATI  600
TATRDGLGVH TVASAGLTRL HRKCGHQAQP DPRYAASAVV TCPGCGNGYD QDYNAAMLML  660
DRQQQP                                                             666

SEQ ID NO: 102           moltype = AA  length = 564
FEATURE                  Location/Qualifiers
source                   1..564
                         mol_type = protein
                         organism = synthetic construct
                         note = Description of Artificial Sequence: Synthetic
                          polypeptide
SEQUENCE: 102
MSRVELHRAY KFRLYPTPAQ VAELAEWERQ LRRLYNLAHS QRLAAMQRHV RPKSPGVLKS  60
ECLSCGAVAV AEIGTDGKAK KTVKHAVGCS VLECRSCGGS PDAEGRTAHT AACSFVDYYR  120
QGREMTQLLE EDDQLARVVC SARQETLRDL EKAWQRWHKM PGFGKPHFKK RIDSCRIYFS  180
TPKSWAVDLG YLSFTGVASS VGRIKIRQDR VWPGDAKFSS CHVVRDVDEW YAVFPLTFTK  240
EIEKPKGGAV GINRGAVHAI ADSTGRVVDS PKFYARSLGV IRHRARLLDR KVPFGRAVKP  300
SPTKYHGLPK ADIDAAAARV NASPGRLVYE ARARGSIAAA EAHLAALVLP APRQTSQLPS  360
EGRNRERARR FLALAHQRVR RQREWFLHNE SAHYAQSYTK IAIEDWSTKE MTSSEPRDAE  420
EMKRVTRARN RSILDVGWYE LGRQIAYKSE ATGAEFAKVD PGLRETETHV PEAIVRERDV  480
DVSGMLRGEA GISGTCSRCG GLLRASASGH ADAECEVCLH VEVGDVNAAV NVLKRAMFPG  540
AAPPSKEKAK VTIGIKGRKK KRAA                                         564

SEQ ID NO: 103           moltype = AA  length = 565
FEATURE                  Location/Qualifiers
source                   1..565
                         mol_type = protein
                         organism = synthetic construct
                         note = Description of Artificial Sequence: Synthetic
                          polypeptide
SEQUENCE: 103
MSRVELHRAY KFRLYPTPVQ VAELSEWERQ LRRLYNLGHE QRLLTLTRHL RPKSPGVLKG  60
ECLSCDSTQV QEVGADGRPK TTVRHAEQCP TLACRSCGAL RDAEGRTAHT VACAFVDYYR  120
QGREMTELLA ADDQLARVVC SARQEVLRDL DKAWQRWRKM PGFGKPRFKR RTDSCRIYFS  180
TPKAWKLEGG HLSFTGAATT VGAIKMRQDR NWPASVQFSS CHVVRDVDEW YAVFPLTFVA  240
EVARPKGGAV GINRGAVHAI ADSTGRVVDS PRYYARALGV IRHRARLFDR KVPSGHAVKP  300
SPTKYRGLSA IEVDRVARAT GFTPGRVVTE ALNRGGVAYA ECALAAIAVL GHGPERPLTS  360
DGRNREKARK FLALAHQRVR RQREWFLHNE SAHYARTYSK IAIEDWSTKE MTASEPQGEE  420
TRRVTRSRNR SILDVGWYEL GRQLAYKTEA TGAEFAQVDP GLKETETNVP KAIADARDVD  480
VSGMLRGEAG ISGTCSKCGG LLRAPASGHA DAECEICLNV EVGDVNAAVN VLKRAMFPGD  540
APPASGEKPK VSIGIKGRQK KKKAA                                        565

SEQ ID NO: 104           moltype = AA  length = 499
FEATURE                  Location/Qualifiers
source                   1..499
                         mol_type = protein
                         organism = synthetic construct
                         note = Description of Artificial Sequence: Synthetic
                          polypeptide
SEQUENCE: 104
MEAIATGMSP ERRVELGILP GSVELKRAYK FRLYPMKVQQ AELSEWERQL RRLYNLAHEQ  60
RLAALLRYRD WDFQKGACPS CRVAVPGVHT AACDHVDYFR QAREMTQLLE VDAQLSRVIC  120
CARQEVLRDL DKAWQRWRKK LGGRPRFKRR TDSCRIYLST PKHWEIAGRY LRLSGLASSV  180
GEIRIEQDRA FPEGALLSSC SIVRDVDEWY ACLPLTFTQP IERAPHRSVG LNRGVVHALA  240
DSDGRVVDSP KFFERALATV QKRSRDLARK VSGSRNAHKA RIKLAKAHQR VRRQRAAFLH  300
QESAYYSKGF DLVALEDMSV RKMTATAGEA PEMGRGAQRD LNRGILDVGW YELARQIDYK  360
RLAHGGELLR VDPGQTTPLA CVTEEQPARG ISSACAVCGI PLARPASGNA RMRCTACGSS  420
QVGDVNAAEN VLTRALSSAP SGPKSPKASI KIKGRQKRLG TPANRAGEAS GGDPPVRGPV  480
EGGTLAYVVE PVSESQSDT                                               499

SEQ ID NO: 105           moltype = AA  length = 560
FEATURE                  Location/Qualifiers
source                   1..560
                         mol_type = protein
                         organism = synthetic construct
                         note = Description of Artificial Sequence: Synthetic
```

```
                         polypeptide
SEQUENCE: 105
MTVRTYKYRA YPTPEQAEAL TSWLRFASQL YNAALEHRKN AWGRHDAHGR GFRFWDGDAA  60
PRKKSDPPGR WVYRGGGGAH ISKNDQGKLL TEFRREHAEL LPPGMPALVQ HEVLARLERS  120
MAAFFQRATK GQKAGYPRWR SEHRYDSLTF GLTSPSKERF DPETGESLGR GKTVGAGTYH  180
NGDLRLTGLG ELRILEHRRI PMGAIPKSVI VRRSGKRWFV SIAMEMPSVE PAASGRPAVG  240
LDMGVVTWGT AFTADTSAAA ALVADLRRMA TDPSDCRRLE ELEREAAQLS EVLAHCRARG  300
LDPARPRRCP KELTKLYRRS LHRLGELDRA CARIRRRLQA AHDIAEPVPD EAGSAVLIEG  360
SNAGMRHARR VARTQRRVAR RTRAGHAHSN RRKKAVQAYA RAKERERSAR GDHRHKVSRA  420
LVRQFEEISV EALDIKQLTV APEHNPDPQP DLPAHVQRRR NRGELDAAWG AFFAALDYKA  480
ADAGGRVARK PAPHTTQECA RCGTLVPKPI SLRVHRCPAC GYTAPRTVNS ARNVLQRPLE  540
EPGRAGPSGA NGRGVPHAVA                                            560

SEQ ID NO: 106          moltype = AA  length = 404
FEATURE                 Location/Qualifiers
source                  1..404
                        mol_type = protein
                        organism = synthetic construct
                        note = Description of Artificial Sequence: Synthetic
                         polypeptide
SEQUENCE: 106
MNCRYRYRIY PTPGQRQSLA RLFGCVRVVW NDALFLCRQS EKLPKNSELQ KLCITQAKKT  60
EARGWLGQVS AIPLQQSVAD LGVAFKNFFQ SRSGKRKGKK VNPPRVKRRN NRQGARFTRG  120
GFKVKTSKVY LARIGDIKIK WSRPLPSEPS SVTVIKDCAG QYFLSFVVEV KPEIKPPKNP  180
SIGIDLGLKT FASCSNGEKI DSPDYSRLYR KLKRCQRRLA KRQRGSKRRE RMRVKVAKLN  240
AQIRDKRKDF LHKLSTKVVN ENQVIALEDL NVGGMLKNRK LSRAISQAGW YEFRSLCEGK  300
AEKHNRDFRV ISRWEPTSQV CSECGYRWGK IDLSVRSIVC INCGVEHDRD DNASVNIEQA  360
GLKVGVGHTH DSKRTGSACK TSNGAVCVEP STHREYVQLT LFDW                  404

SEQ ID NO: 107          moltype = AA  length = 392
FEATURE                 Location/Qualifiers
source                  1..392
                        mol_type = protein
                        organism = synthetic construct
                        note = Description of Artificial Sequence: Synthetic
                         polypeptide
SEQUENCE: 107
MKSRWTFRCY PTPEQEQHLA RTFGCVRFVW NWALRARTDA FRAGERIGYP ATDKALTLLK  60
QQPETVWLNE VSSVCLQQAL RDLQVAFSNF FDKRAAHPSF KRKEARQSAN YTERGFSFDH  120
ERRILKLAKI GAIKVKWSRK AIPHPSSIRL IRTASGKYFV SLVVETQPAP MPETGESVGV  180
DFGVARLATL SNGERISNPK HGAKWQRRLA FYQKRLARAT KGSKRRMRIK RHVARIHEKI  240
GNSRSDTLHK LSTDLVTRFD LICVEDLNLR GMVKNHSLAR SLHDASIGSA IRMIEEKAER  300
YGKNVVKIDR WFPSSKTCSD CGHIVEQLPL NVREWTCPEC GTTHDRDANA AANILAVGQT  360
VSAHGGTVRR SRAKASERKS QRSANRQGVN RA                              392

SEQ ID NO: 108          moltype = AA  length = 500
FEATURE                 Location/Qualifiers
source                  1..500
                        mol_type = protein
                        organism = synthetic construct
                        note = Description of Artificial Sequence: Synthetic
                         polypeptide
SEQUENCE: 108
KEPLNIGKTA KAVFKEIDPT SLNRAANYDA SIELNCKECK FKPFKNVKRY EFNFYNNWYR  60
CNPNSCLQST YKAQVRKVEI GYEKLKNEIL TQMQYYPWFG RLYQNFFHDE RDKMTSLDEI  120
QVIGVQNKVF FNTVEKAWRE IIKKRFKDNK ETMETIPELK HAAGHGKRKL SNKSLLRRRF  180
AFVQKSFKFV DNSDVSYRSF SNNIACVLPS RIGVDLGGVI SRNPKREYIP QEISFNAFWK  240
QHEGLKKGRN IEIQSVQYKG ETVKRIEADT GEDKAWGKNR QRRFTSLILK LVPKQGGKKV  300
WKYPEKRNEG NYEYFPIPIE FILDSGETSI RFGGDEGEAG KQKHLVIPFN DSKATPLASQ  360
QTLLENSRFN AEVKSCIGLA IYANYFYGYA RNYVISSIYH KNSKNGQAIT AIYLESIAHN  420
YVKAIERQLQ NLLLNLRDFS FMESHKKELK KYFGGDLEGT GGAQKRREKE EKIEKEIEQS  480
YLPRLIRLSL TKMVTKQVEM                                            500

SEQ ID NO: 109          moltype = AA  length = 507
FEATURE                 Location/Qualifiers
source                  1..507
                        mol_type = protein
                        organism = synthetic construct
                        note = Description of Artificial Sequence: Synthetic
                         polypeptide
SEQUENCE: 109
ELIVNENKDP LNIGKTAKAV FKEIDPTSIN RAANYDASIE LACKECKFKP FNNTKRHDFS  60
FYSNWHRCSP NSCLQSTYRA KIRKTEIGYE KLKNEILNQM QYYPWFGRLY QNFFNDQRDK  120
MTSLDEIQVT GVQNKIFFNT VEKAWREIIK KRFRDNKETM RTIPDLKNKS GHGSRKLSNK  180
SLLRRRFAFA QKSFKLVDNS DVSYRAFSNN VACVLPSKIG VDIGGIINKD LKREYIPQEI  240
TFNVFWKQHD GLKKGRNIEI HSVQYKGEIV KRIEADTGED KAWGKNRQRR FTSLILKITP  300
KQGGKKIWKF PEKKNASDYE YFPIPIEFIL DNGDASIKFG GEEGEVGKQK HLLIPFNDSK  360
ATPLSSKQML LETSRFNAEV KSTIGLALYA NYFVSYARNY VIKSTYHKNS KKGQIVTEIY  420
LESISQNFVR AIQRQLQSLM LNLKDWGFMQ THKKELKKYF GSDLEGSKGG QKRREKEEKI  480
```

```
EKEIEASYLP RLIRLSLTKS VTKAEEM                                     507

SEQ ID NO: 110          moltype = AA  length = 529
FEATURE                 Location/Qualifiers
source                  1..529
                        mol_type = protein
                        organism = synthetic construct
                        note = Description of Artificial Sequence: Synthetic
                         polypeptide
SEQUENCE: 110
PEEKTSKLKP NSINLAANYD ANEKFNCKEC KFHPFKNKKR YEFNFYNNLH GCKSCTKSTN  60
NPAVKRIEIG YQKLKFEIKN QMEAYPWFGR LRINFYSDEK RKMSELNEMQ VTGVKNKIFF  120
DAIECAWREI LKKRFRESKE TLITIPKLKN KAGHGARKHR NKKLLIRRRA FMKKNFHFLD  180
NDSISYRSFA NNIACVLPSK VGVDIGGIIS PDVGKDIKPV DISLNLMWAS KEGIKSGRKV  240
EIYSTQYDGN MVKKIEAETG EDKSWGKNRK RRQTSLLLSI PKPSKQVQEF DFKEWPRYKD  300
IEKKVQWRGF PIKIIFDSNH NSIEFGTYQG GKQKVLPIPF NDSKTTPLGS KMNKLEKLRF  360
NSKIKSRLGS AIAANKFLEA ARTYCVDSLY HEVSSANAIG KGKIFIEYYL EILSQNYIEA  420
AQKQLQRFIE SIEQWFVADP FQGRLKQYFK DDLKRAKCFL CANREVQTTC YAAVKLHKSC  480
AEKVKDKNKE LAIKERNNKE DAVIKEVEAS NYPRVIRLKL TKTITNKAM             529

SEQ ID NO: 111          moltype = AA  length = 726
FEATURE                 Location/Qualifiers
source                  1..726
                        mol_type = protein
                        organism = synthetic construct
                        note = Description of Artificial Sequence: Synthetic
                         polypeptide
SEQUENCE: 111
SESENKIIEQ YYAFLYSFRD KYEKPEFKNR GDIKRKLQNK WEDFLKEQNL KNDKKLSNYI  60
FSNRNFRRSY DREEENEEGI DEKKSKPKRI NCFEKEKNLK DQYDKDAINA SANKDGAQKW  120
GCFECIFFPM YKIESGDPNK RIIINKTRFK LFDFYLNLKG CKSCLRSTYH PYRSNVYIES  180
NYDKLKREIG NFLQQKNIFQ RMRKAKVSEG KYLTNLDEYR LSCVAMHFKN RWLFFDSIQK  240
VLRETIKQRL KQMRESYDEQ AKTKRSKGHG RAKYEDQVRM IRRRAYSAQA HKLLDNGYIT  300
LFDYDDKEIN KVCLTAINQE GFDIGGYLNS DIDNVMPPIE ISFHLKWKYN EPILNIESPF  360
SKAKISDYLR KIREDLNLER GKEGKARSKK NVRRKVLASK GEDGYKKIFT DFFSKWKEEL  420
EGNAMERVLS QSSGDIQWSK KKRIHYTTLV LNINLLDKKG VGNLKYYEIA EKTKILSFDK  480
NENKFWPITI QVLLDGYEIG TEYDEIKQLN EKTSKQFTIY DPNTKIIKIP FTDSKAVPLG  540
MLGINIATLK TVKKTERDIK VSKIFKGGLN SKIVSKIGKG IYAGYFPTVD KEILEEVEED  600
TLDNEFSSKS QRNIFLKSII KNYDKMLKEQ LFDFYSFLVR NDLGVRFLTD RELQNIEDES  660
FNLEKRFFET DRDRIARWFD NTNTDDGKEK FKKLANEIVD SYKPRLIRLP VVRVIKRIQP  720
VKQREM                                                            726

SEQ ID NO: 112          moltype = AA  length = 517
FEATURE                 Location/Qualifiers
source                  1..517
                        mol_type = protein
                        organism = synthetic construct
                        note = Description of Artificial Sequence: Synthetic
                         polypeptide
SEQUENCE: 112
KYSTRDFSEL NEIQVTACKQ DEFFKVIQNA WREIIKKRFL ENRENFIEKK IFKNKKGRGK  60
RQESDKTIQR NRASVMKNFQ LIENEKIILR APSGHVACVF PVKVGLDIGG FKTDDLEKNI  120
FPPRTITINV FWKNRDRQRK GRKLEVWGIK ARTKLIEKVH KWDKLEEVKK KRLKSLEQKQ  180
EKSLDNWSEV NNDSFYKVQI DELQEKIDKS LKGRTMNKIL DNKAKESKEA EGLYIEWEKD  240
FEGEMLRRIE ASTGGEEKWG KRRQRRHTSL LLDIKNNSRG SKEIINFYSY AKQGKKEKKI  300
EFFPFPLTIT LDAEEESPLN IKSIPIEDKN ATSKYFSIPF TETRATPLSI LGDRVQKFKT  360
KNISGAIKRN LGSSISSCKI VQNAETSAKS ILSLPNVKED NNMEIFINTM SKNYFRAMMK  420
QMESFIFEME PKTLIDPYKE KAIKWFEVAA SSRAKRKLKK LSKADIKKSE LLLSNTEEFE  480
KEKQEKLEAL EKEIEEFYLP RIVRLQLTKT ILETPVM                          517

SEQ ID NO: 113          moltype = AA  length = 481
FEATURE                 Location/Qualifiers
source                  1..481
                        mol_type = protein
                        organism = synthetic construct
                        note = Description of Artificial Sequence: Synthetic
                         polypeptide
SEQUENCE: 113
KKLQLLGHKI LLKEYDPNAV NAAANFETST AELCGQCKMK PFKNKRRFQY TFGKNYHGCL  60
SCIQNVYYAK KRIVQIAKEE LKHQLTDSIA SIPYKYTSLF SNTNSIDELY ILKQERAAFF  120
SNTNSIDELY ITGIENNIAF KVISAIWDEI IKKRRQRYAE SLTDTGTVKA NRGHGGTAYK  180
SNTRQEKIRA LQKQTLHMVT NPYISLARYK NNYIVATLPR TIGMHIGAIK DRDPQKKLSD  240
YAINFNVFWS DDRQLIELST VQYTGDMVRK IEAETGENNK WGENMKRTKT SLLLEILTKK  300
TTDELTFKDW AFSTKKEIDS VTKKTYQGFP IGIIFEGNES SVKFGSQNYF PLPFDAKITP  360
PTAEGFRLDW LRKGSFSSQM KTSYGLAIYS NKVTNAIPAY VIKNMFYKIA RAENGKQIKA  420
KFLKKYLDIA GNNYVPFIIM QHYRVLDTFE EMPISQPKVI RLSLTKTQHI IIKKDKTDSK  480
M                                                                 481

SEQ ID NO: 114          moltype = AA  length = 534
```

```
FEATURE               Location/Qualifiers
source                1..534
                      mol_type = protein
                      organism = synthetic construct
                      note = Description of Artificial Sequence: Synthetic
                       polypeptide
SEQUENCE: 114
NTSNLINLGK KAINISANYD ANLEVGCKNC KFLSSNGNFP RQTNVKEGCH SCEKSTYEPS  60
IYLVKIGERK AKYDVLDSLK KFTFQSLKYQ SKKSMKSRNK KPKELKEFVI FANKNKAFDV  120
IQKSYNHLIL QIKKEINRMN SKKRKKNHKR RLFRDREKQL NKLRLIESSN LFLPRENKGN  180
NHVFTYVAIH SVGRDIGVIG SYDEKLNFET ELTYQLYFND DKRLLYAYKP KQNKIIKIKE  240
KLWNLRKEKE PLDLEYEKPL NKSITFSIKN DNLFKVSKDL MLRRAKFNIQ GKEKLSKEER  300
KINRDLIKIK GLVNSMSYGR FDELKKEKNI WSPHIYREVR QKEIKPCLIK NGDRIEIFEQ  360
LKKKMERLRR FREKRQKKIS KDLIFAERIA YNFHTKSIKN TSNKINIDQE AKRGKASYMR  420
KRIGYETFKN KYCEQCLSKG NVYRNVQKGC SCFENPFDWI KKGDENLLPK KNEDLRVKGA  480
FRDEALEKQI VKIAFNIAKG YEDFYDNLGE STEKDLKLKF KVGTTINEQE SLKL        534

SEQ ID NO: 115        moltype = AA  length = 537
FEATURE               Location/Qualifiers
source                1..537
                      mol_type = protein
                      organism = synthetic construct
                      note = Description of Artificial Sequence: Synthetic
                       polypeptide
SEQUENCE: 115
TSNPIKLGKK AINISANYDS NLQIGCKNCK FLSYNGNFPR QTNVKEGCHS CEKSTYEPPV  60
YTVRIGERRS KYDVLDSLKK FIFLSLKYRQ SKKMKTRSKG IRGLEEFVIS ANLKKAMDVI  120
QKSYRHLILN IKNEIVRMNG KKRNKNHKRL LFRDREKQLN KLRLIEGSSF FKPPTVKGDN  180
SIFTCVAIHN IGRDIGIAGD YFDKLEPKIE LTYQLYYEYN PKKESEINKR LLYAYKPKQN  240
KIIEIKEKLW NLRKEKSPLD LEYEKPLTKS ITFLVKRDGV FRISKDLMLR KAKFIIQGKE  300
KLSKEERKIN RDLIKIKSNI ISLTYGRFDE LKKDKTIWSP HIFRDVKQGK ITPCIERKGD  360
RMDIFQQLRK KSERLRENRK KRQKKISKDL IFAERIAYNF HTKSIKNTSN LINIKHEAKR  420
GKASYMRKRI GNETFRIKYC EQCFPKNNVY KNVQKGCSCF EDPFEYIKKG NEDLIPNKNQ  480
DLKAKGAFRD DALEKQIIKV AFNIAKGYED FYENLKKTTE KDIRLKFKVG TIISEEM     537

SEQ ID NO: 116        moltype = AA  length = 541
FEATURE               Location/Qualifiers
source                1..541
                      mol_type = protein
                      organism = synthetic construct
                      note = Description of Artificial Sequence: Synthetic
                       polypeptide
SEQUENCE: 116
NNSINLSKKA INISANYDAN LQVRCKNCKF LSSNGNFPRQ TDVKEGCHSC EKSTYEPPVY  60
DVKIGEIKAK YEVLDSLKKF TFQSLKYQLS KSMKFRSKKI KELKEFVIFA KESKALNVIN  120
RSYKHLILNI KNDINRMNSK KRIKNHKGRL FLDRQKQLSK LKLIEGSSFF VPAKNVGNKS  180
VFTCVAIHSI GRDIGIAGLY DSFTKPVNEI TYQIFFSGER RLLYAYKPKQ LKILSIKENL  240
WSLKNEKKPL DLLYEKPLGK NLNFNVKGGD LFRVSKDLMI RNAKFNVHGR QRLSDEERLI  300
NRNFIKIKGE VVSLSYGRFE ELKKDRKLWS PHIFKDVRQN KIKPCLVMQG QRIDIFEQLK  360
RKLELLKKIR KSRQKKLSKD LIFGERIAYN FHTKSIKNTS NKINIDSDAK RGRASYMRKR  420
IGNETFKLKY CDVCFPKANV YRRVQNGCSC SENPYNYIKK GDKDLLPKKD EGLAIKGAFR  480
DEKLNKQIIK VAFNIAKGYE DFYDDLKKRT EKDVDLKFKI GTTVLDQKPM EIFDGIVITW  540
L                                                                 541

SEQ ID NO: 117        moltype = AA  length = 542
FEATURE               Location/Qualifiers
source                1..542
                      mol_type = protein
                      organism = synthetic construct
                      note = Description of Artificial Sequence: Synthetic
                       polypeptide
SEQUENCE: 117
LLTTVVETNN LAKKAINVAA NFDANIDRQY YRCTPNLCRF IAQSPRETKE KDAGCSSCTQ  60
STYDPKVYVI KIGKLLAKYE ILKSLKRFLF MNRYFKQKKT ERAQQKQKIG TELNEMSIFA  120
KATNAMEVIK RATKHCTYDI IPETKSLQML KRRRHRVKVR SLLKILKERR MKIKKIPNTF  180
IEIPKQAKKN KSDYYVAAAL KSCGIDVGLC GAYEKNAEVE AEYTYQLYYE YKGNSSTKRI  240
LYCYNNPQKN IREFWEAFYI QGSKSHVNTP GTIRLKMEKF LSPITIESEA LDFRVWNSDL  300
KIRNGQYGFI KKRSLGKEAR EIKKGMGDIK RKIGNLTYGK SPSELKSIHV YRTERENPKK  360
PRAARKKEDN FMEIFEMQRK KDYEVNKKRR KEATDAAKIM DFAEEPIRHY HTNNLKAVRR  420
IDMNEQVERK KTSVFLKRIM QNGYRGNYCR KCIKAPEGSN RDENVLEKNE GCLDCIGSEF  480
IWKKSSKEKK GLWHTNRLLR RIRLQCFTTA KAYENFYNDL FEKKESSLDI IKLKVSITTK  540
SM                                                                542

SEQ ID NO: 118        moltype = AA  length = 564
FEATURE               Location/Qualifiers
source                1..564
                      mol_type = protein
                      organism = synthetic construct
                      note = Description of Artificial Sequence: Synthetic
```

```
                         polypeptide
SEQUENCE: 118
ASTMNLAKQA INFAANYDSN LEIGCKGCKF MSTWSKKSNP KFYPRQNNQA NKCHSCTYST  60
GEPEVPIIEI GERAAKYKIF TALKKFVFMS VAYKERRRQR FKSKKPKELK ELAICSNREK  120
AMEVIQKSVV HCYGDVKQEI PRIRKIKVLK NHKGRLFYKQ KRSKIKIAKL EKGSFFKTFI  180
PKVHNNGCHS CHEASLNKPI LVTTALNTIG ADIGLINDYS TIAPTETDIS WQVYYEFIPN  240
GDSEAVKKRL LYFYKPKGAL IKSIRDKYFK KGHENAVNTG FFKYQGKIVK GPIKFVNNEL  300
DFARKPDLKS MKIKRAGFAI PSAKRLSKED REINRESIKI KNKIYSLSYG RKKTLSDKDI  360
IKHLYRPVRQ KGVKPLEYRK APDGFLEFFY SLKRKERRLR KQKEKRQKDM SEIIDAADEF  420
AWHRHTGSIK KTTNHINFKS EVKRGKVPIM KKRIANDSFN TRHCGKCVKQ GNAINKYYIE  480
KQKNCFDCNS IEFKWEKAAL EKKGAFKLNK RLQYIVKACF NVAKAYESFY EDFRKGEEES  540
LDLKFKIGTT TTLKQYPQNK ARAM                                      564

SEQ ID NO: 119          moltype = AA  length = 610
FEATURE                 Location/Qualifiers
source                  1..610
                        mol_type = protein
                        organism = synthetic construct
                        note = Description of Artificial Sequence: Synthetic
                         polypeptide
SEQUENCE: 119
HSHNLMLTKL GKQAINFAAN YDANLEIGCK NCKFLSYSPK QANPKKYPRQ TDVHEDGNIA  60
CHSCMQSTKE PPVYIVPIGE RKSKYEILTS LNKFTFLALK YKEKKRQAFR AKKPKELQEL  120
AIAFNKEKAI KVIDKSIQHL ILNIKPEIAR IQRQKRLKNR KGKLLYLHKR YAIKMGLIKN  180
GKYFKVGSPK KDGKKLLVLC ALNTIGRDIG IIGNIEENNR SETEITYQLY FDCLDANPNE  240
LRIKEIEYNR LKSYERKIKR LVYAYKPKQT KILEIRSKFF SKGHENKVNT GSFNFENPLN  300
KSISIKVKNS AFDFKIGAPF IMLRNGKFHI PTKKRLSKEE REINRTLSKI KGRVFRLTYG  360
RNISEQGSKS LHIYRKERQH PKLSLEIRKQ PDSFIDEFEK LRLKQNFISK LKKQRQKKLA  420
DLLQFADRIA YNYHTSSLEK TSNFINYKPE VKRGRTSYIK KRIGNEGFEK LYCETCIKSN  480
DKENAYAVEK EELCFVCKAK PFTWKKTNKD KLGIFKYPSR IKDFIRAAFT VAKSYNDFYE  540
NLKKKDLKNE IFLKFKIGLI LSHEKKNHIS IAKSVAEDER ISGKSIKNIL NKSIKLEKNC  600
YSCFFHKEDM                                                      610

SEQ ID NO: 120          moltype = AA  length = 552
FEATURE                 Location/Qualifiers
source                  1..552
                        mol_type = protein
                        organism = synthetic construct
                        note = Description of Artificial Sequence: Synthetic
                         polypeptide
SEQUENCE: 120
SLERVIDKRN LAKKAINIAA NFDANINKGF YRCETNQCMF IAQKPRKTNN TGCSSCLQST  60
YDPVIYVVKV GEMLAKYEIL KSLKRFVFMN RSFKQKKTEK AKQKERIGGE LNEMSIFANA  120
ALAMGVIKRA IRHCHVDIRP EINRLSELKK TKHRVAAKSL VKIVKQRKTK WKGIPNSFIQ  180
IPQKARNKDA DFYVASALKS GGIDIGLCGT YDKKPHADPR WTYQLYFDTE DESEKRLLYC  240
YNDPQAKIRD FWKTFYERGN PSMVNSPGTI EFRMEGFFEK MTPISIESKD FDFRVWNKDL  300
LIRRGLYEIK KRKNLNRKAR EIKKAMGSVK RVLANMTYGK SPTDKKSIPV YRVEREKPKK  360
PRAVRKEENE LADKLENYRR EDFLIRNRRK REATEIAKII DAAEPPIRHY HTNHLRAVKR  420
IDLSKPVARK NTSVFLKRIM QNGYRGNYCK KCIKGNIDPN KDECRLEDIK KCICCEGTQN  480
IWAKKEKLYT GRINVLNKRI KQMKLECFNV AKAYENFYDN LAALKEGDLK VLKLKVSIPA  540
LNPEASDPEE DM                                                   552

SEQ ID NO: 121          moltype = AA  length = 534
FEATURE                 Location/Qualifiers
source                  1..534
                        mol_type = protein
                        organism = synthetic construct
                        note = Description of Artificial Sequence: Synthetic
                         polypeptide
SEQUENCE: 121
NASINLGKRA INLSANYDSN LVIGCKNCKF LSFNGNFPRQ TNVREGCHSC DKSTYAPEVY  60
IVKIGERKAK YDVLDSLKKF TFQSLKYQIK KSMRERSKKP KELLEFVIFA NKDKAFNVIQ  120
KSYEHLILNI KQEINRMNGK KRIKNHKKRL FKDREKQLNK LRLIGSSSLF FPRENKGDKD  180
LFTYVAIHSV GRDIGVAGSY ESHIEPISDL TYQLFINNEK RLLYAYKPKQ NKIIELKENL  240
WNLKKEKKPL DLEFTKPLEK SITFSVKNDK LFKVSKDLML RQAKFNIQGK EKLSKEERQI  300
NRDFSKIKSN VISLSYGRFE ELKKEKNIWS PHIYREVKQK EIKPCIVRKG DRIELFEQLK  360
RKMDKLKKFR KERQKKISKD LNFAERIAYN FHTKSIKNTS NKINIDQEAK RGKASYMRKR  420
IGNESFRKKY CEQCFSVGNV YHNVQNGCSC FDNPIELIKK GDEGLIPKGK EDRKYKGALR  480
DDNLQMQIIR VAFNIAKGYE DFYNNLKEKT EKDLKLKFKI GTTISTQESN NKEM       534

SEQ ID NO: 122          moltype = AA  length = 577
FEATURE                 Location/Qualifiers
source                  1..577
                        mol_type = protein
                        organism = synthetic construct
                        note = Description of Artificial Sequence: Synthetic
                         polypeptide
SEQUENCE: 122
SNLIKLGKQA INFAANYDAN LEVGCKNCKF LSSTNKYPRQ TNVHLDNKMA CRSCNQSTME  60
```

```
PAIYIVRIGE KKAKYDIYNS LTKFNFQSLK YKAKRSQRFK PKQPKELQEL SIAVRKEKAL  120
DIIQKSIDHL IQDIRPEIPR IKQQKRYKNH VGKLFYLQKR RKNKLNLIGK GSFFKVFSPK  180
EKKNELLVIC ALTNIGRDIG LIGNYNTIIN PLFEVTYQLY YDYIPKKNNK NVQRRLLYAY  240
KSKNEKILKL KEAFFKRGHE NAVNLGSFSY EKPLEKSLTL KIKNDKDDFQ VSPSLRIRTG  300
RFFVPSKRNL SRQEREINRR LVKIKSKIKN MTYGKFETAR DKQSVHIFRL ERQKEKLPLQ  360
FRKDEKEFME EFQKLKRRTN SLKKLRKSRQ KKLADLLQLS EKVVYNNHTG TLKKTSNFLN  420
FSSSVKRGKT AYIKELLGQE GFETLYCSNC INKGQKTRYN IETKEKCFSC KDVPFVWKKK  480
STDKDRKGAF LFPAKLKDVI KATFTVAKAY EDFYDNLKSI DEKKPYIKFK IGLILAHVRH  540
EHKARAKEEA GQKNIYNKPI KIDKNCKECF FFKEEAM                          577

SEQ ID NO: 123         moltype = AA  length = 613
FEATURE                Location/Qualifiers
source                 1..613
                       mol_type = protein
                       organism = synthetic construct
                       note = Description of Artificial Sequence: Synthetic
                        polypeptide
SEQUENCE: 123
NTTRKKFRKR TGFPQSDNIK LAYCSAIVRA ANLDADIQKK HNQCNPNLCV GIKSNEQSRK  60
YEHSDRQALL CYACNQSTGA PKVDYIQIGE IGAKYKILQM VNAYDFLSLA YNLTKLRNGK  120
SRGHQRMSQL DEVVIVADYE KATEVIKRSI NHLLDDIRGQ LSKLKKRTQN EHITEHKQSK  180
IRRKLRKLSR LLKRRRWKWG TIPNPYLKNW VFTKKDPELV TVALLHKLGR DIGLVNRSKR  240
RSKQKLLPKV GFQLYYKWES PSLNNIKKSK AKKLPKRLLI PYKNVKLFDN KQKLENAIKS  300
LLESYQKTIK VEFDQFFQNR TEEIIAEEQQ TLERGLLKQL EKKKNEFASQ KKALKEEKKK  360
IKEPRKAKLL MEESRSLGFL MANVSYALFN TTIEDLYKKS NVVSGCIPQE PVVVFPADIQ  420
NKGSLAKILF APKDGFRIKF SGQHLTIRTA KFKIRGKEIK ILTKTKREIL KNIEKLRRVW  480
YREQHYKLKL FGKEVSAKPR FLDKRKTSIE RRDPNKLADQ TDDRQAELRN KEYELRHKQH  540
KMAERLDNID TNAQNLQTLS FWVGEADKPP KLDEKDARGF GVRTCISAWK WFMEDLLKKQ  600
EEDPLLKLKL SIM                                                    613

SEQ ID NO: 124         moltype = AA  length = 615
FEATURE                Location/Qualifiers
source                 1..615
                       mol_type = protein
                       organism = synthetic construct
                       note = Description of Artificial Sequence: Synthetic
                        polypeptide
SEQUENCE: 124
PKKPKFQKRT GFPQPDNLRK EYCLAIVRAA NLDADFEKKC TKCEGIKTNK KGNIVKGRTY  60
NSADKDNLLC YACNISTGAP AVDYVFVGAL EAKYKILQMV KAYDFHSLAY NLAKLWKGRG  120
RGHQRMGGLN EVVIVSNNEK ALDVIEKSLN HFHDEIRGEL SRLKAKFQNE HLHVHKESKL  180
RRKLRKISRL LKRRRWKWDV IPNSYLRNFT FTKTRPDFIS VALLHRVGRD IGLVTKTKIP  240
KPTDLLPQFG FQIYYTWDEP KLNKLKKSRL RSEPKRLLVP YKKIELYKNK SVLEEAIRHL  300
AEVYTEDLTI CFKDFFETQK RKFVSKEKES LKRELLKELT KLKKDFSERK TALKRDRKEI  360
KEPKKAKLLM EESRSLGFLA ANTSYALFNL IAADLYTKSK KACSTKLPRQ LSTILPLEIK  420
EHKSTTSLAI KPEEGFKIRF SNTHLSIRTP KFKMKGADIK ALTKRKREIL KNATKLEKSW  480
YGLKHYKLKL YGKEVAAKPR FLDKRNPSID RRDPKELMEQ IENRRNEVKD LEYEIRKGQH  540
QMAKRLDNVD TNAQNLQTKS FWVGEADKPP ELDSMEAKKL GLRTCISAWK WFMKDLVLLQ  600
EKSPNLKLKL SLTEM                                                  615

SEQ ID NO: 125         moltype = AA  length = 775
FEATURE                Location/Qualifiers
source                 1..775
                       mol_type = protein
                       organism = synthetic construct
                       note = Description of Artificial Sequence: Synthetic
                        polypeptide
SEQUENCE: 125
KFSKRQEGFL IPDNIDLYKC LAIVRSANLD ADVQGHKSCY GVKKNGTYRV KQNGKKGVKE  60
KGRKYVFDLI AFKGNIEKIP HEAIEEKDQG RVIVLGKFNY KLILNIEKNH NDRASLEIKN  120
KIKKLVQISS LETGEFLSDL LSGKIGIDEV YGIIEPDVFS GKELVCKACQ QSTYAPLVEY  180
MPVGELDAKY KILSAIKGYD FLSLAYNLSR NRANKKRGHQ KLGGGELSEV VISANYDKAL  240
NVIKRSINHY HVEIKPEISK LKKKMQNEPL KVMKQARIRR ELHQLSRKVK RLKWKWGMIP  300
NPELQNIIFE KKEKDFVSYA LLHTLGRDIG LFKDTSMLQV PNISDYGFQI YYSWEDPKLN  360
SIKKIKDLPK RLLIPYKRLD FYIDTILVAK VIKNLIELYR KSYVYETFGE EYGYAKKAED  420
ILFDWDSINL SEGIEQKIQK IKDEFSDLLY EARESKRQNF VESFENILGL YDKNFASDRN  480
SYQEKIQSMI IKKQQENIEQ KLKREFKEVI ERGFEGMDQN KKYYKVLSPN IKGGLLYTDT  540
NNLGFFRSHL AFMLLSKISD DLYRKNNLVS KGGNKGILDQ TPETMLTLEF GKSNLPNISI  600
KRKFFNIKYN SSWIGIRKPK FSIKGAVIRE ITKKVRDEQR LIKSLEGVWH KSTHFKRWGK  660
PRFNLPRHPD REKNNDDNLM ESITSRREQI QLLLREKQKQ QEKMAGRLDK IDKEIQNLQT  720
ANFQIKQIDK KPALTEKSEG KQSVRNALSA WKWFMEDLIK YQKRTPILQL KLAKM       775

SEQ ID NO: 126         moltype = AA  length = 777
FEATURE                Location/Qualifiers
source                 1..777
                       mol_type = protein
                       organism = synthetic construct
                       note = Description of Artificial Sequence: Synthetic
                        polypeptide
```

```
SEQUENCE: 126
KFSKRQEGFV IPENIGLYKC LAIVRSANLD ADVQGHVSCY GVKKNGTYVL KQNGKKSIRE  60
KGRKYASDLV AFKGDIEKIP FEVIEEKKKE QSIVLGKFNY KLVLDVMKGE KDRASLTMKN  120
KSKKLVQVSS LGTDEFLLTL LNEKFGIEEI YGIIEPEVFS GKKLVCKACQ QSTYAPLVEY  180
MPVGELDSKY KILSAIKGYD FLSLAYNLAR HRSNKKRGHQ KLGGGELSEV VISANNAKAL  240
NVIKRSLNHY YSEIKPEISK LRKKMQNEPL KVGKQARMRR ELHQLSRKVK RLKWKWGKIP  300
NLELQNITFK ESDRDFISYA LLHTLGRDIG MFNKTEIKMP SNILGYGFQI YYDWEEPKLN  360
TIKKSKNTPK RILIPYKKLD FYNDSILVAR AIKELVGLFQ ESYEWEIFGN EYNYAKEAEV  420
ELIKLDEESI NGNVEKKLQR IKENFSNLLE KAREKKRQNF IESFESIARL YDESFTADRN  480
EYQREIQSFI IEKQKQSIEK KLKNEFKKIV EKKFNEQEQG KKHYRVLNPT IINEFLPKDK  540
NNLGFLRSKI AFILLSKISD DLYKKSNAVS KGGEKGIIKQ QPETILDLEF SKSKLPSINI  600
KKKLFNIKYT SSWLGIRKPK FNIKGAKIRE ITRRVRDVQR TLKSAESSWY ASTHFRRWGF  660
PRFNQPRHPD KEKKSDDRLI ESITLLREQI QILLREKQKG QKEMAGRLDD VDKKIQNLQT  720
ANFQIKQTGD KPALTEKSAG KQSFRNALSA WKWFMENLLK YQNKTPDLKL KIARTVM     777

SEQ ID NO: 127         moltype = AA  length = 610
FEATURE                Location/Qualifiers
source                 1..610
                       mol_type = protein
                       organism = synthetic construct
                       note = Description of Artificial Sequence: Synthetic
                        polypeptide
SEQUENCE: 127
KWIEPNNIDF NKCLAITRSA NLDADVQGHK MCYGIKTNGT YKAIGKINKK HNTGIIEKRR  60
TYVYDLIVTK EKNEKIVKKT DFMAIDEEIE FDEKKEKLLK KYIKAEVLGT GELIRKDLND  120
GEKFDDLCSI EEPQAFRRSE LVCKACNQST YASDIRYIPI GEIEAKYKIL KAIKGYDFLS  180
LKYNLGRLRD SKKRGHQKMG QGELKEFVIC ANKEKALDVI KRSLNHYLNE VKDEISRLNK  240
KMQNEPLKVN DQARWRRELN QISRRLKRLK WKWGEIPNPE LKNLIFKSSR PEFVSYALIH  300
TLGRDIGLIN ETELKPNNIQ EYGFQIYYKW EDPELNHIKK VKNIPKRFII PYKNLDLFGK  360
YTILSRAIEG ILKLYSSSFQ YKSFKDPNLF AKEGEKKITN EDFELGYDEK IKKIKDDFKS  420
YKKALLEKKK NTLEDSLNSI LSVYEQSLLT EQINNVKKWK EGLLKSKESI HKQKKIENIE  480
DIISRIEELK NVEGWIRTKE RDIVNKEETN LKREIKKELK DSYYEEVRKD FSDLKKGEES  540
EKKPFREEPK PIVIKDYIKF DVLPGENSAL GFFLSHLSFN LFDSIQYELF EKSRLSSSKH  600
PQIPETILDL                                                        610

SEQ ID NO: 128         moltype = AA  length = 632
FEATURE                Location/Qualifiers
source                 1..632
                       mol_type = protein
                       organism = synthetic construct
                       note = Description of Artificial Sequence: Synthetic
                        polypeptide
SEQUENCE: 128
FRKFVKRSGA PQPDNLNKYK CIAIVRAANL DADIMSNESS NCVMCKGIKM NKRKTAKGAA  60
KTTELGRVYA GQSGNLLCTA CTKSTMGPLV DYVPIGRIRA KYTILRAVKE YDFLSLAYNL  120
ARTRVSKKGG RQKMHSLSEL VIAAEYEIAW NIIKSSVIHY HQETKEEISG LRKKLQAEHI  180
HKNKEARIRR EMHQISRRIK RLKWKWHMIP NSELHNFLFK QQDPSFVAVA LLHTLGRDIG  240
MINKPKGSAK REFIPEYGFQ IYYKWMNPKL NDINKQKYRK MPKRSLIPYK NLNVFGDREL  300
IENAMHKLLK LYDENLEVKG SKFFKTRVVA ISSKESEKLK RDLLWKGELA KIKKDFNADK  360
NKMQELFKEV KEPKKANALM KQSRNMGFLL QNISYGALGL LANRMYEASA KQSKGDATKQ  420
PSIVIPLEME FGNAFPKLLL RSGKFAMNVS SPWLTIRKPK FVIKGNKIKN ITKLMKDEKA  480
KLKRLETSYH RATHFRPTLR GSIDWDSPYF SSPKQPNTHR RSPDRLSADI TEYRGRLKSV  540
EAELREGQRA MAKKLDSVDM TASNLQTSNF QLEKGEDPRL TEIDEKGRSI RNCISSWKKF  600
MEDLMKAQEA NPVIKIKIAL KDESSVLSED SM                               632

SEQ ID NO: 129         moltype = AA  length = 625
FEATURE                Location/Qualifiers
source                 1..625
                       mol_type = protein
                       organism = synthetic construct
                       note = Description of Artificial Sequence: Synthetic
                        polypeptide
SEQUENCE: 129
KFHPENLNKS YCLAIVRAAN LDADIQGHIN CIGIKSNKSD RNYENKLESL QNVELLCKAC  60
TKSTYKPNIN SVPVGEKKAK YSILSEIKKY DFNSLVYNLK KYRKGKSRGH QKLNELRELV  120
ITSEYKKALD VINKSVNHYL VNIKNKMSKL KKILQNEHIH VGTLARIRRE RNRISRKLDH  180
YRKKWKFVPN KILKNYVFKN QSPDFVSVAL LHKLGRDIGL ITKTAILQKS FPEYSLQLYY  240
KYDTPKLNYL KKSKFKSLPK RILISYKYPK FDINSNYIEE SIDKLLKLYE ESPIYKNNSK  300
IIEFFKKSED NLIKSENDSL KRGIMKEFEK VTKNFSSKKK KLKEELKLKN EDKNSKMLAK  360
VSRPIGFLKA YLSYMLFNII SNRIFEFSRK SSGRIPQLPS CIINLGNQFE NFKNELQDSN  420
IGSKKNYKYF CNLLLKSSGF NISYEEEHLS IKTPNFFING RKLKEITSEK KKIRKENEQL  480
IKQWKKLTFF KPSNLNGKKT SDKIRFKSPN NPDIERKSED NIVENIAKVK YKLEDLLSEQ  540
RKEFNKLAKK HDGVDVEAQC LQTKSFWIDS NSPIKKSLEK KNEKVSVKKK MKAIRSCISA  600
WKWFMADLIE AQKETPMIKL KLALM                                       625

SEQ ID NO: 130         moltype = AA  length = 517
FEATURE                Location/Qualifiers
source                 1..517
                       mol_type = protein
```

```
                        organism = synthetic construct
                        note = Description of Artificial Sequence: Synthetic
                         polypeptide
SEQUENCE: 130
TTLVPSHLAG IEVMDETTSR NEDMIQKETS RSNEDENYLG VKNKCGINVH KSGRGSSKHE  60
PNMPPEKSGE GQMPKQDSTE MQQRFDESVT GETQVSAGAT ASIKTDARAN SGPRVGTARA  120
LIVKASNLDR DIKLGCKPCE YIRSELPMGK KNGCNHCEKS SDIASVPKVE SGFRKAKYEL  180
VRRFESFAAD SISRHLGKEQ ARTRGKRGKK DKKEQMGKVN LDEIAILKNE SLIEYTENQI  240
LDARSNRIKE WLRSLRLRLR TRNKGLKKSK SIRRQLITLR RDYRKWIKPN PYRPDEDPNE  300
NSLRLHTKLG VDIGVQGGDN KRMNSDDYET SFSITWRDTA TRKICFTKPK GLLPRHMKFK  360
LRGYPELILY NEELRIQDSQ KFPLVDWERI PIFKLRGVSL GKKKVKALNR ITEAPRLVVA  420
KRIQVNIESK KKKVLTRYVY NDKSINGRLV KAEDSNKDPL LEFKKQAEEI NSDAKYYENQ  480
EIAKNYLWGC EGLHKNLLEE QTKNPYLAFK YGFLNIV                          517

SEQ ID NO: 131          moltype = AA  length = 410
FEATURE                 Location/Qualifiers
source                  1..410
                        mol_type = protein
                        organism = synthetic construct
                        note = Description of Artificial Sequence: Synthetic
                         polypeptide
SEQUENCE: 131
LDFKRTCSQE LVLLPEIEGL KLSGTQGVTS LAKKLINKAA NVDRDESYGC HHCIHTRTSL  60
SKPVKKDCNS CNQSTNHPAV PITLKGYKIA FYELWHRFTS WAVDSISKAL HRNKVMGKVN  120
LDEYAVVDNS HIVCYAVRKC YEKRQRSVRL HKKRAYRCRAK HYNKSQPKVG RIYKKSKRRN  180
ARNLKKEAKR YFQPNEITNG SSDALFYKIG VDLGIAKGTP ETEVKVDVSI CFQVYYGDAR  240
RVLRVRKMDE LQSFHLDYTG KLKLKGIGNK DTFTIAKRNE SLKWGSTKYE VSRAHKKFKP  300
FGKKGSVKRK CNDYFRSIAS WSCEAASQRA QSNLKNAFPY QKALVKCYKN LDYKGVKKND  360
MWYRLCSNRI FRYSRIAEDI AQYQSDKGKA KFEFVILAQS VAEYDISAIM             410

SEQ ID NO: 132          moltype = AA  length = 602
FEATURE                 Location/Qualifiers
source                  1..602
                        mol_type = protein
                        organism = synthetic construct
                        note = Description of Artificial Sequence: Synthetic
                         polypeptide
SEQUENCE: 132
VFLTDDKRKT ALRKIRSAFR KTAEIALVRA QEADSLDRQA KKLTIETVSF GAPGAKNAFI  60
GSLQGYNWNS HRANVPSSGS AKDVFRITEL GLGIPQSAHE ASIGKSFELV GNVVRYTANL  120
LSKGYKKGAV NKGAKQQREI KGKEQLSFDL ISNGPISGDK LINGQKDALA WWLIDKMGFH  180
IGLAMEPLSS PNTYGITLQA FWKRHTAPRR YSRGVIRQWQ LPFGRQLAPL IHNFFRKKGA  240
SIPIVLTNAS KKLAGKGVLL EQTALVDPKK WWQVKEQVTG PLSNIWERSV PLVLYTATFT  300
HKHGAAHKRP LTLKVIRISS GSVFLLPLSK VTPGKLVRAW MPDINILRDG RPDEAAYKGP  360
DLIRARERSF PLAYTCVTQI ADEWQKRALE SNRDSITPLE AKLVTGSDLL QIHSTVQQAV  420
EQGIGGRISS PIQELLAKDA LQLVLQQLFM TVDLLRIQWQ LKQEVADGNT SEKAVGWAIR  480
ISNIHKDAYK TAIEPCTSAL KQAWNPLSGF EERTFQLDAS IVRKRSTAKT PDDELVIVLR  540
QQAAEMTVAV TQSVSKELME LAVRHSATLH LLVGEVASKQ LSRSADKDRG AMDHWKLLSQ  600
SM                                                                602

SEQ ID NO: 133          moltype = AA  length = 494
FEATURE                 Location/Qualifiers
source                  1..494
                        mol_type = protein
                        organism = synthetic construct
                        note = Description of Artificial Sequence: Synthetic
                         polypeptide
SEQUENCE: 133
EDLLQKALNT ATNVAAIERH SCISCLFTES EIDVKYKTPD KIGQNTAGCQ SCTFRVGYSG  60
NSHTLPMGNR IALDKLRETI QRYAWHSLLF NVPPAPTSKR VRAISELRVA AGRERLFTVI  120
TFVQTNILSK LQKRYAANWT PKSQERLSRL REEGQHILSL LESGSWQQKE VVREDQDLIV  180
CSALTKPGLS IGAFCRPKYL KPAKHALVLR LIFVEQWPGQ IWGQSKRTRR MRRRKDVERV  240
YDISVQAWAL KGKETRISEC IDTMRRHQQA YIGVLPFLIL SGSTVRGKGD CPILKEITRM  300
RYCPNNEGLI PLGIFYRGSA NKLLRVVKGS SFTLPMWQNI ETLPHPEPFS PEGWTATGAL  360
YEKNLAYWSA LNEAVDWYTG QILSSGLQYP NQNEFLARLQ NVIDSIPRKW FRPQGLKNLK  420
PNGQEDIVPN EFVIPQNAIR AHHVIEWYHK TNDLVAKTLL GWGSQTTLNQ TRPQGDLRFT  480
YTRYYFREKE VPEV                                                   494

SEQ ID NO: 134          moltype = AA  length = 649
FEATURE                 Location/Qualifiers
source                  1..649
                        mol_type = protein
                        organism = synthetic construct
                        note = Description of Artificial Sequence: Synthetic
                         polypeptide
SEQUENCE: 134
VPKKKLMREL AKKAVFEAIF NDPIPGSFGC KRCTLIDGAR VTDAIEKKQG AKRCAGCEPC  60
TFHTLYDSVK HALPAATGCD RTAIDTGLWE ILTALRSYNW MSFRRNAVSD ASQKQVWSIE  120
ELAIWADKER ALRVILSALT HTIGKLKNGF SRDGVWKGGK QLYENLAQKD LAKGLFANGE  180
```

```
IFGKELVEAD HDMLAWTIVP NHQFHIGLIR GNWKPAAVEA STAFDARWLT NGAPLRDTRT  240
HGHRGRRFNR TEKLTVLCIK RDGGVSEEFR QERDYELSVM LLQPKNKLKP EPKGELNSFE  300
DLHDHWWFLK GDEATALVGL TSDPTVGDFI QLGLYIRNPI KAHGETKRRL LICFEPPIKL  360
PLRRAFPSEA FKTWEPTINV FRNGRRDTEA YYDIDRARVF EFPETRVSLE HLSKQWEVLR  420
LEPDRENTDP YEAQQNEGAE LQVYSLLQEA AQKMAPKVVI DPFGQFPLEL FSTFVAQLFN  480
APLSDTKAKI GKPLDSGFVV ESHLHLLEED FAYRDFVRVT FMGTEPTFRV IHYSNGEGYW  540
KKTVLKGKNN IRTALIPEGA KAAVDAYKNK RCPLTLEAAI LNEEKDRRLV LGNKALSLLA  600
QTARGNLTIL EALAAEVLRP LSGTEGVVHL HACVTRHSTL TESTETDNM             649

SEQ ID NO: 135          moltype = AA  length = 414
FEATURE                 Location/Qualifiers
source                  1..414
                        mol_type = protein
                        organism = synthetic construct
                        note = Description of Artificial Sequence: Synthetic
                         polypeptide
SEQUENCE: 135
VEKLFSERLK RAMWLKNEAG RAPPAETLTL KHKRVSGGHE KVKEELQRVL RSLSGTNQAA  60
WNLGLSGGRE PKSSDALKGE KSRVVLETVV FHSGHNRVLY DVIEREDQVH QRSSIMHMRR  120
KGSNLLRLWG RSGKVRRKMR EEVAEIKPVW HKDSRWLAIV EEGRQSVVGI SSAGLAVFAV  180
QESQCTTAEP KPLEYVVSIW FRGSKALNPQ DRYLEFKKLK TTEALRGQQY DPIPFSLKRG  240
AGCSLAIRGE GIKFGSRGPI KQFFGSDRSR PSHADYDGKR RLSLFSKYAG DLADLTEEQW  300
NRTVSAFAED EVRRATLANI QDFLSISHEK YAERLKKRIE SIEEPVSASK LEAYLSAIFE  360
TFVQQREALA SNFLMRLVES VALLISLEEK SPRVEFRVAR YLAESKEGFN RKAM        414

SEQ ID NO: 136          moltype = AA  length = 413
FEATURE                 Location/Qualifiers
source                  1..413
                        mol_type = protein
                        organism = synthetic construct
                        note = Description of Artificial Sequence: Synthetic
                         polypeptide
SEQUENCE: 136
VVITQSELYK ERLLRVMEIK NDRGRKEPRE SQGLVLRFTQ VTGGQEKVKQ KLWLIFEGFS  60
GTNQASWNFG QPAGGRKPNS GDALKGPKSR VTYETVVFHF GLRLLSAVIE RHNLKQQRQT  120
MAYMKRRAAA RKKWARSGKK CSRMRNEVEK IKPKWHKDPR WFDIVKEGEP SIVGISSAGF  180
AIYIVEEPNF PRQDPLEIEY AISIWFRRDR SQYLTFKKIQ KAEKLKELQY NPIPFRLKQE  240
KTSLVFESGD IKFGSRGSIE HFRDEARGKP PKADMDNNRR LTMFSVFSGN LTNLTEEQYA  300
RPVSGLLAPD EKRMPTLLKK LQDFFTPIHE KYGERIKQRL ANSEASKRPF KKLEEYLPAI  360
YLEFRARREG LASNWVLVLI NSVRTLVRIK SEDPYIEFKV SQYLLEKEDN KAL         413

SEQ ID NO: 137          moltype = AA  length = 449
FEATURE                 Location/Qualifiers
source                  1..449
                        mol_type = protein
                        organism = synthetic construct
                        note = Description of Artificial Sequence: Synthetic
                         polypeptide
SEQUENCE: 137
KQDALFEERL KKAIFIKRQA DPLQREELSL LPPNRKIVTG GHESAKDTLK QILRAINGTN  60
QASWNPGTPS GKRDSKSADA LAGPKSRVKL ETVVFHVGHR LLKKVVEYQG HQKQQHGLKA  120
FMRTCAAMRK KWKRSGKVVG ELREQLANIQ PKWHYDSRPL NLCFEGKPSV VGLRSAGIAL  180
YTIQKSVVPV KEPKPIEYAV SIWFRGPKAM DREDRCLEFK KLKIATELRK LQFEPIVSTL  240
TQGIKGFSLY IQGNSVKFGS RGPIKYFSNE SVRQRPPKAD PDGNKRLALF SKFSGDLSDL  300
TEEQWNRPIL AFEGIIRRAT LGNIQDYLTV GHEQFAISLE QLLSEKESVL QMSIEQQRLK  360
KNLGKKAENE WVESFGAEQA RKKAQGIREY ISGFFQEYCS QREQWAENWV QQLNKSVRLF  420
LTIQDSTPFI EFRVARYLPK GEKKKGKAM                                    449

SEQ ID NO: 138          moltype = AA  length = 711
FEATURE                 Location/Qualifiers
source                  1..711
                        mol_type = protein
                        organism = synthetic construct
                        note = Description of Artificial Sequence: Synthetic
                         polypeptide
SEQUENCE: 138
ANHAERHKRL RKEANRAANR NRPLVADCDT GDPLVGICRL LRRGDKMQPN KTGCRSCEQV  60
EPELRDAILV SGPGRLDNYK YELFQRGRAM AVHRLLKRVP KLNRPKKAAG NDEKKAENKK  120
SEIQKEKQKQ RRMMPAVSMK QVSVADFKHV IENTVRHLFG DRRDREIAEC AALRAASKYF  180
LKSRRVRPRK LPKLANPDHG KELKGLRLRE KRAKLKKEKE KQAELARSNQ KGAVLHVATL  240
KKDAPPMPYE KTQGRNDYTT FVISAAIKVG ATRGTKPLLT PQPREWQCSL YWRDGQRWIR  300
GGLLGLQAGI VLGPKLNREL LEAVLQRPIE CRMSGCGNPL QVRGAAVDFF MTTNPFYVSG  360
AAYAQKKFKP FGTKRASEDG AAAKAREKLM TQLAKVLDKV VTQAAHSPLD GIWETRPEAK  420
LRAMIMALEH EWIFLRPGPC HNAAEEVIKC DCTGGHAILW ALIDEARGAL EHKEFYAVTR  480
AHTHDCEKQK LGGRLAGFLD LLIAQDVPLD DAPAARKIKT LLEATPPAPC YKAATSIATC  540
DCEGKFDKLW AIIDATRAGH GTEDLWARTL AYPQNVNCKC KAGKDLTHRL ADFLGLLIKR  600
DGPFRERPPH KVTGDRKLVF SGDKKCKGHQ YVILAKAHNE EVVRAWISRW GLKSRTNKAG  660
YAATELNLLL NWLSICRRRW MDMLTVQRDT PYIRMKTGRL VVDDKKERKA M           711
```

```
SEQ ID NO: 139          moltype = AA  length = 574
FEATURE                 Location/Qualifiers
source                  1..574
                        mol_type = protein
                        organism = synthetic construct
                        note = Description of Artificial Sequence: Synthetic
                         polypeptide
SEQUENCE: 139
AKQREALRVA LERGIVRASN RTYTLVTNCT KGGPLPEQCR MIERGKARAM KWEPKLVGCG  60
SCAAATVDLP AIEEYAQPGR LDVAKYKLTT QILAMATRRM MVRAAKLSRR KGQWPAKVQE  120
EKEEPPEPKK MLKAVEMRPV AIVDFNRVIQ TTIEHLWAER ANADEAELKA LKAAAAYFGP  180
SLKIRARGPP KAAIGRELKK AHRKKAYAER KKARRKRAEL ARSQARGAAA HAAIRERDIP  240
PMAYERTQGR NDVTTIPIAA AIKIAATRGA RPLPAPKPMK WQCSLYWNEG QRWIRGGMLT  300
AQAYAHAANI HRPMRCEMWG VGNPLKVRAF EGRVADPDGA KGRKAEFRLQ TNAFYVSGAA  360
YRNKKFKPFG TDRGGIGSAR KKRERLMAQL AKILDKVVSQ AAHSPLDDIW HTRPAQKLRA  420
MIKQLEHEWM FLRPQAPTVE GTKPDVDVAG NMQRQIKALM APDLPPIEKG SPAKRFTGDK  480
RKKGERAVRV AEAHSDEVVT AWISRWGIQT RRNEGSYAAQ ELELLLNWLQ ICRRRWLDMT  540
AAQRVSPYIR MKSGRMITDA ADEGVAPIPL VENM                              574

SEQ ID NO: 140          moltype = AA  length = 743
FEATURE                 Location/Qualifiers
source                  1..743
                        mol_type = protein
                        organism = synthetic construct
                        note = Description of Artificial Sequence: Synthetic
                         polypeptide
SEQUENCE: 140
KSISGRSIKH MACLKDMLKS EITEIEEKQK KESLRKWDYY SKFSDEILFR RNLNVSANHD  60
ANACYGCNPC AFLKEVYGFR IERRNNERII SYRRGLAGCK SCVQSTGYPP IEFVRRKFGA  120
DKAMEIVREV LHRRNWGALA RNIGREKEAD PILGELNELL LVDARPYFGN KSAANETNLA  180
FNVITRAAKK FRDEGMYDIH KQLDIHSEEG KVPKGRKSRL IRIERKHKAI HGLDPGETWR  240
YPHCGKGEKY GVWLNRSRLI HIKGNEYRCL TAFGTTGRRM SLDVACSVLG HPLVKKKRKK  300
GKKTVDGTEL WQIKKATETL PEDPIDCTFY LYAAKPTKDP FILKVGSLKA PRWKKLHKDF  360
FEYSDTEKTQ GQEKGKRVVR RGKVPRILSL RPDAKFKVSI WDDPYNGKNK EGTLLRMELS  420
GLDGAKKPLI LKRYGEPNTK PKNFVFWRPH ITPHPLTFTP KHDFGDPNKK TKRRRVFNRE  480
YYGHLNDLAK MEPNAKFFED REVSNKKNPK AKNIRIQAKE SLPNIVAKNG RWAAFDPNDS  540
LWKLYLHWRG RRKTIKGGIS QEFQEFKERL DLYKKHEDES EWKEKEKLWE NHEKEWKKTL  600
EIHGSIAEVS QRCVMQSMMG PLDGLVQKKD YVHIGQSSLK AADDAWTFSA NRYKKATGPK  660
WGKISVSNLL YDANQANAEL ISQSISKYLS KQKDNQGCEG RKMKFLIKII EPLRENFVKH  720
TRWLHEMTQK DCEVRAQFSR VSM                                          743

SEQ ID NO: 141          moltype = AA  length = 769
FEATURE                 Location/Qualifiers
source                  1..769
                        mol_type = protein
                        organism = synthetic construct
                        note = Description of Artificial Sequence: Synthetic
                         polypeptide
SEQUENCE: 141
FPSDVGADAL KHVRMLQPRL TDEVRKVALT RAPSDRPALA RFAAVAQDGL AFVRHLNVSA  60
NHDSNCTFPR DPRDPRRGPC EPNPCAFLRE VWGFRIVARG NERALSYRRG LAGCKSCVQS  120
TGFPSVPFHR IGADDCMRKL HEILKARNWR LLARNIGRER EADPLLTELS EYLLVDARTY  180
PDGAAPNSGR LAENVIKRAA KKFRDEGMRD IHAQLRVHSR EGKVPKGRLQ RLRRIERKHR  240
AIHALDPGPS WEAEGSARAE VQGVAVYRSQ LLRVGHHTQQ IEPVGIVART LFGVGRTDLD  300
VAVSVLGAPL TKRKKGSKTL ESTEDFRIAK ARETRAEDKI EVAFVLYPTA SLLRDEIPKD  360
AFPAMRIDRF LLKVGSVQAD REILLQDDYY RFGDAEVKAG KNKGRTVTRP VKVPRLQALR  420
PDAKFRVNVW ADPFGAGDSP GTLLRLEVSG VTRRSQPLRL LRYGQPSTQP ANFLCWRPHR  480
VPDPMTFTPR QKFGERRKNR RTRRPRVFER LYQVHIKHLA HLEPNRKWFE EARVSAQKWA  540
KARAIRRKGA EDIPVVAPPA KRRWAALQPN AELWDLYAHD REARKRFRGG RAAEGEEFKP  600
RLNLYLAHEP EAEWESKRDR WERYEKKWTA VLEEHSRMCA VADRTLPQFL SDPLGARMDD  660
KDYAFVGKSA LAVAEAFVEE GTVERAQGNC SITAKKKFAS NASRKRLSVA NLLDVSDKAD  720
RALVFQAVRQ YVQRQAENGG VEGRRMAFLR KLLAPLRQNF VCHTRWLHM               769

SEQ ID NO: 142          moltype = AA  length = 564
FEATURE                 Location/Qualifiers
source                  1..564
                        mol_type = protein
                        organism = synthetic construct
                        note = Description of Artificial Sequence: Synthetic
                         polypeptide
SEQUENCE: 142
AARKKKRGKI GITVKAKEKS PPAAGPFMAR KLVNVAANVD GVEVHLCVEC EADAHGSASA  60
RLLGGCRSCT GSIGAEGRLM GSVDVDRERV IAEPVHTETE RLGPDVKAFE AGTAESKYAI  120
QRGLEYWGVD LISRNRARTV RKMEEADRPE SSTMEKTSWD EIAIKTYSQA YHASENHLFW  180
ERQRRVRQHA LALFRRARER NRGESPLQST QRPAPLVLAA LHAEAAAISG RARAEYVLRG  240
PSANVRAAAA DIDAKPLGHY KTPSPKVARG FPVKRDLLRA RHRIVGLSRA YFKPSDVVRG  300
TSDAIAHVAG RNIGVAGGKP KEIEKTFTLP FVAYWEDVDR VVHCSSFKAD GPWVRDQRIK  360
IRGVSSAVGT FSLYGLDVAW SKPTSFYIRC SDIRKKFHPK GFGPMKHWRQ WAKELDRLTE  420
QRASCVVRAL QDDEELLQTM ERGQRYYDVF SCAATHATRG EADPSGGCSR CELVSCGVAH  480
```

```
KVTKKAKGDT GIEAVAVAGC SLCESKLVGP SKPRVHRQMA ALRQSHALNY LRRLQREWEA  540
LEAVQAPTPY LRFKYARHLE VRSM                                         564

SEQ ID NO: 143         moltype = AA  length = 565
FEATURE                Location/Qualifiers
source                 1..565
                       mol_type = protein
                       organism = synthetic construct
                       note = Description of Artificial Sequence: Synthetic
                        polypeptide
SEQUENCE: 143
AAKKKKQRGK IGISVKPKEG SAPPADGPFM ARKLVNVAAN VDGVEVNLCI ECEADAHGSA  60
PARLLGGCKS CTGSIGAEGR LMGSVDVDRA DAIAKPVNTE TEKLGPDVQA FEAGTAETKY  120
ALQRGLEYWG VDLISRNRSR TVRRTEEGQP ESATMEKTSW DEIAIKSYTR AYHASENHLF  180
WERQRRVRQH ALALFKRAKE RNRGDSTLPR EPGHGLVAIA ALACEAYAVG GRNLAETVVR  240
GPTFGTARAV RDVEIASLGR YKTPSPKVAH GSPVKRDFLR ARHRIVGLAR AYYRPSDVVR  300
GTSDAIAHVA GRNIGVAGGK PRAVEAVFTL PFVAYWEDVD RVVHCSSFQV SAPWNRDQRM  360
KIAGVTTAAG TFSLHGGELK WAKPTSFYIR CSDTRRKFRP KGFGPMKRWR QWAKDLDRLV  420
EQRASCVVRA LQDDAALLET MERGQRYYDV FACAVTHATR GEADRLAGCS RCALTPCQEA  480
HRVTTKPRGD AGVEQVQTSD CSLCEGKLVG PSKPRLHRTL TLLRQEHGLN YLRRLQREWE  540
SLEAVQVPTP YLRFKYARHL EVRSM                                        565

SEQ ID NO: 144         moltype = AA  length = 499
FEATURE                Location/Qualifiers
source                 1..499
                       mol_type = protein
                       organism = synthetic construct
                       note = Description of Artificial Sequence: Synthetic
                        polypeptide
SEQUENCE: 144
TDSQSESVPE VVYALTGGEV PGRVPPDGGS AEGARNAPTG LRKQRGKIKI SAKPSKPGSP  60
ASSLARTLVN EAANVDGVQS SGCATCRMRA NGSAPRALPI GCVACASSIG RAPQEETVCA  120
LPTTQGPDVR LLEGGHALRK YDIQRALEYW GVDLIGRNLD RQAGRGMEPA EGATATMKRV  180
SMDELAVLDF GKSYYASEQH LFAARQRRVR QHAKALKIRA KHANRSGSVK RALDRSRKQV  240
TALAREFFKP SDVVRGDSDA LAHVVGRNLG VSRHPAREIP QTFTLPLCAY WEDVDRVISC  300
SSLLAGEPFA RDQEIRIEGV SSALGSLRLY RGAIEWHKPT SLYIRCSDTR RKFRPRGGLK  360
KRWRQWAKDL DRLVEQRACC IVRSLQADVE LLQTMERAQR FYDVHDCAAT HVGPVAVRCS  420
PCAGKQFDWD RYRLLAALRQ EHALNYLRRL QREWESLEAQ QVKMPYLRFK YARKLEVSGP  480
LIGLEVRREP SMGTAIAEM                                               499

SEQ ID NO: 145         moltype = AA  length = 358
FEATURE                Location/Qualifiers
source                 1..358
                       mol_type = protein
                       organism = synthetic construct
                       note = Description of Artificial Sequence: Synthetic
                        polypeptide
SEQUENCE: 145
AGTAGRRHGS LGARRSINIA GVTDRHGRWG CESCVYTRDQ AGNRARCAPC DQSTYAPDVQ  60
EVTIGQRQAK YTIFLTLQSF SWTNTMRNNK RAAAGRSKRT TGKRIGQLAE IKITGVGLAH  120
AHNVIQRSLQ HNITKMWRAE KGKSKRVARL KKAKQLTKRR AYFRRRMSRQ SRGNGFFRTG  180
KGGIHAVAPV KIGLDVGMIA SGSSEPADEQ TVTLDAIWKG RKKKIRLIGA KGELAVAACR  240
FREQQTKGDK CIPLILQDGE VRWNQNNWQC HPKKLVPLCG LEVSRKFVSQ ADRLAQNKVA  300
SPLAARFDKT SVKGTLVESD FAAVLVNVTS IYQQCHAMLL RSQEPTPSLR VQRTITSM    358

SEQ ID NO: 146         moltype = AA  length = 369
FEATURE                Location/Qualifiers
source                 1..369
                       mol_type = protein
                       organism = synthetic construct
                       note = Description of Artificial Sequence: Synthetic
                        polypeptide
SEQUENCE: 146
GVRFSPAQSQ VFFRTVIPQS VEARFAINMA AIHDAAGAFG CSVCRFEDRT PRNAKAVHGC  60
SPCTRSTNRP DVFVLPVGAI KAKYDVFMRL LGFNWTHLNR RQAKRVTVRD RIGQLDELAI  120
SMLTGKAKAV LKKSICHNVD KSFKAMRGSL KKLHRKASKT GKSQLRAKLS DLRERTNTTQ  180
EGSHVEGDSD VALNKIGLDV GLVGKPDYPS EESVEVVVCL YFVGKVLILD AQGRIRDMRA  240
KQYDGFKIPI IQRGQLTVLS VKDLGKWSLV RQDYVLAGDL RFEPKISKDR KYAECVKRIA  300
LITLQASLGF KERIPYYVTK QVEIKNASHI AFVTEAIQNC AENFREMTEY LMKYQEKSPD  360
LKVLLTQLM                                                          369

SEQ ID NO: 147         moltype = AA  length = 486
FEATURE                Location/Qualifiers
source                 1..486
                       mol_type = protein
                       organism = synthetic construct
                       note = Description of Artificial Sequence: Synthetic
                        polypeptide
SEQUENCE: 147
```

```
RAVVGKVFLE QARRALNLAT NFGTNHRTGC NGCYVTPGKL SIPQDGEKNA AGCTSCLMKA  60
TASYVSYPKP LGEKVAKYST LDALKGFPWY SLRLNLRPNY RGKPINGVQE VAPVSKFRLA  120
EEVIQAVQRY HFTELEQSFP GGRRRLRELR AFYTKEYRRA PEQRQHVVNG DRNIVVVTVL  180
HELGFSVGMF NEVELLPKTP IECAVNVFIR GNRVLLEVRK PQFDKERLLV ESLWKKDSRR  240
HTAKWTPPNN EGRIFTAEGW KDFQLPLLLG STSRSLRAIE KEGFVQLAPG RDPDYNNTID  300
EQHSGRPFLP LYLYLQGTIS QEYCVFAGTW VIPFQDGISP YSTKDTFQPD LKRKAYSLLL  360
DAVKHRLGNK VASGLQYGRF PAIEELKRLV RMHGATRKIP RGEKDLLKKG DPDTPEWWLL  420
EQYPEFWRLC DAAAKRVSQN VGLLLSLKKQ PLWQRRWLES RTRNEPLDNL PLSMALTLHL  480
TNEEAL                                                            486

SEQ ID NO: 148         moltype = AA  length = 400
FEATURE                Location/Qualifiers
source                 1..400
                       mol_type = protein
                       organism = synthetic construct
                       note = Description of Artificial Sequence: Synthetic
                        polypeptide
SEQUENCE: 148
AAVYSKFYIE NHFKMGIPET LSRIRGPSII QGFSVNENYI NIAGVGDRDF IFGCKKCKYT  60
RGKPSSKKIN KCHPCKRSTY PEPVIDVRGS ISEFKYKIYN KLKQEPNQSI KQNTKGRMNP  120
SDHTSSNDGI IINGIDNRIA YNVIFSSYKH LMEKQINLLR DTTKRKARQI KKYNNSGKKK  180
HSLRSQTKGN LKNRYHMLGM FKKGSLTITN EGDFITAVRK VGLDISLYKN ESLNKQEVET  240
ELCLNIKWGR TKSYTVSGYI PLPINIDWKL YLFEKETGLT LRLFGNKYKI QSKKFLIAQL  300
FKPKRPPCAD PVVKKAQKWS ALNAHVQQMA GLFSDSHLLK RELKNRMHKQ LDFKSLWVGT  360
EDYIKWFEEL SRSYVEGAEK SLEFFRQDYF CFNYTKQTTM                        400

SEQ ID NO: 149         moltype = AA  length = 666
FEATURE                Location/Qualifiers
source                 1..666
                       mol_type = protein
                       organism = synthetic construct
                       note = Description of Artificial Sequence: Synthetic
                        polypeptide
SEQUENCE: 149
PQQQRDLMLM AANYDQDYGN GCGPCTVVAS AAYRPDPQAQ HGCKRHLRTL GASAVTHVGL  60
GDRTATITAL HRLRGPAALA ARARAAQAAS APMTPDTDAP DDRRRLEAID ADDVVLVGAH  120
RALWSAVRRW ADDRRAALRR RLHSEREWLL KDQIRWAELY TLIEASGTPP QGRWRNTLGA  180
LRGQSRWRRV LAPTMRATCA ETHAELWDAL AELVPEMAKD RRGLLRPPVE ADALWRAPMI  240
VEGWRGGHSV VVDAVAPPLD LPQPCAWTAV RLSGDPRQRW GLHLAVPPLG QVQPPDPLKA  300
TLAVSMRHRG GVRVRTLQAM AVDADAPMQR HLQVPLTLQR GGGLQWGIHS RGVRRREARS  360
MASWEGPPIW TGLQLVNRWK GQGSALLAPD RPPDTPPYAP DAAVAPAQPD TKRARRTLKE  420
ACTVCRCAPG HMRQLQVTLT GDGTWRRFRL RAPQGAKRKA EVLKVATQHD ERIANYTAWY  480
LKRPEHAAGC DTCDGDSRLD GACRGCRPLL VGDQCFRRYL DKIEADRDDG LAQIKPKAQE  540
AVAAMAAKRD ARAQKVAARA AKLSEATGQR TAATRDASHE ARAQKELEAV ATEGTTVRHD  600
AAAVSAFGSW VARKGDEYRH QVGVLANRLE HGLRLQELMA PDSVVADQQR ASGHARVGYR  660
YVLTAM                                                            666

SEQ ID NO: 150         moltype = AA  length = 560
FEATURE                Location/Qualifiers
source                 1..560
                       mol_type = protein
                       organism = synthetic construct
                       note = Description of Artificial Sequence: Synthetic
                        polypeptide
SEQUENCE: 150
AVAHPVGRGN AGSPGARGPE ELPRQLVNRA SNVTRPATYG CAPCRHVRLS IPKPVLTGCR  60
ACEQTTHPAP KRAVRGGADA AKYDLAAFFA GWAADLEGRN RRRQVHAPLD PQPDPNHEPA  120
VTLQKIDLAE VSIEEFQRVL ARSVKHRHDG RASREREKAR AYAQVAKKRR NSHAHGARTR  180
RAVRRQTRAV RRAHRMGANS GEILVASGAE DPVPEAIDHA AQLRRRIRAC ARDLEGLRHL  240
SRRYLKTLEK PCRRPRAPDL GRARCHALVE SLQAAERELE ELRRCDSPDT AMRRLDAVLA  300
AAASTDATFA TGWTVVGMDL GVAPRGSAAP EVSPMEMAIS VFWRKGSRRV IVSKPIAGMP  360
IRRHELIRLE GLGTLRLDGN HYTGAGVTKG RGLSEGTEPD FREKSPSTLG FTLSDYRHES  420
RWRPYGAKQG KTARQFFAAM SRELRALVEH QVLAPMGPPL LEAHERRFET LLKGQDNKSI  480
HAGGGGRYVW RGPPDSKKRP AADGDWFRFG RGHADHRGWA NKRHELAANY LQSAFRLWST  540
LAEAQEPTPY ARYKYTRVTM                                             560

SEQ ID NO: 151         moltype = AA  length = 404
FEATURE                Location/Qualifiers
source                 1..404
                       mol_type = protein
                       organism = synthetic construct
                       note = Description of Artificial Sequence: Synthetic
                        polypeptide
SEQUENCE: 151
WDFLTLQVYE RHTSPEVCVA GNSTKCASGT RKSDHTHGVG VKLGAQEINV SANDDRDHEV  60
GCNICVISRV SLDIKGWRYG CESCVQSTPE WRSIVRFDRN HKEAKGECLS RFEYWGAQSI  120
ARSLKRNKLM GGVNLDELAI VQNENVVKTS LKHLFDKRKD RIQANLKAVK VRMRERRKSG  180
RQRKALRRQC RKLKRYLRSY DPSDIKEGNS CSAFTKLGLD IGISPNKPPK IEPKVEVVFS  240
LFYQGACDKI VTVSSPESPL PRSWKIKIDG IRALYVKSTK VKFGGRTFRA GQRNNRRKVR  300
```

```
PPNVKKGKRK GSRSQFFNKF AVGLDAVSQQ LPIASVQGLW GRAETKKAQT ICLKQLESNK  360
PLKESQRCLF LADNWVVRVC GFLRALSQRQ GPTPYIRYRY RCNM                  404

SEQ ID NO: 152          moltype = AA  length = 392
FEATURE                 Location/Qualifiers
source                  1..392
                        mol_type = protein
                        organism = synthetic construct
                        note = Description of Artificial Sequence: Synthetic
                         polypeptide
SEQUENCE: 152
ARNVGQRNAS RQSKRESAKA RSRRVTGGHA SVTQGVALIN AAANADRDHT TGCEPCTWER  60
VNLPLQEVIH GCDSCTKSSP FWRDIKVVNK GYREAKEEIM RIASGISADH LSRALSHNKV  120
MGRLNLDEVC ILDFRTVLDT SLKHLTDSRS NGIKEHIRAV HRKIRMRRKS GKTARALRKQ  180
YFALRRQWKA GHKPNSIREG NSLTALRAVG FDVGVSEGTE PMPAPQTEVV LSVFYKGSAT  240
RILRISSPHP IAKRSWKVKI AGIKALKLIR REHDFSFGRE TYNASQRAEK RKFSPHAARK  300
DFFNSFAVQL DRLAQQLCVS SVENLWVTEP QQKLLTLAKD TAPYGIREGA RFADTRARLA  360
WNWVFRVCGF TRALHQEQEP TPYCRFTWRS KM                               392

SEQ ID NO: 153          moltype = AA  length = 1120
FEATURE                 Location/Qualifiers
source                  1..1120
                        mol_type = protein
                        organism = Listeria seeligeri
SEQUENCE: 153
MWISIKTLIH HLGVLFFCDY MYNRREKKII EVKTMRITKV EVDRKKVLIS RDKNGGKLVY  60
ENEMQDNTEQ IMHHKKSSFY KSVVNKTICR PEQKQMKKLV HGLLQENSQE KIKVSDVTKL  120
NISNFLNHRF KKSLYYFPEN SPDKSEEYRI EINLSQLLED SLKKQQGTFI CWESFSKDME  180
LYINWAENYI SSKTKLIKKS IRNNRIQSTE SRSGQLMDRY MKDILNKNKP FDIQSVSEKY  240
QLEKLTSALK ATFKEAKKND KEINYKLKST LQNHERQIIE ELKENSELNQ FNIEIRKHLE  300
TYFPIKKTNR KVGDIRNLEI GEIQKIVNHR LKNKIVQRIL QEGKLASYEI ESTVNSNSLQ  360
KIKIEEAFAL KFINACLFAS NNLRNMVYPV CKKDILMIGE FKNSFKEIKH KKFIRQWSQF  420
FSQEITVDDI ELASWGLRGA IAPIRNEIIH LKKHSWKKFF NNPTFKVKKS KIINGKTKDV  480
TSEFLYKETL FKDYFYSELD SVPELIINKM ESSKILDYYS SDQLNQVFTI PNFELSLLTS  540
AVPFAPSFKR VYLKGFDYQN QDEAQPDYNL KLNIYNEKAF NSEAFQAQYS LFKMVYYQVF  600
LPQFTTNNDL FKSSVDFILT LNKERKGYAK AFQDIRKMNK DEKPSEYMSY IQSQLMLYQK  660
KQEEKEKINH FEKFINQVFI KGFNSFIEKN RLTYICHPTK NTVPENDNIE IPFHTDMDDS  720
NIAFWLMCKL LDAKQLSELR NEMIKFSCSL QSTEEISTFT KAREVIGLAL LNGEKGCNDW  780
KELFDDKEAW KKNMSLYVSE ELLQSLPYTQ EDGQTPVINR SIDLVKKYGT ETILEKLFSS  840
SDDYKVSAKD IAKLHEYDVT EKIAQQESLH KQWIEKPGLA RDSAWTKKYQ NVINDISNYQ  900
WAKTKVELTQ VRHLHQLTID LLSRLAGYMS IADRDFQFSS NYILERENSE YRVTSWILLS  960
ENKNKNKYND YELYNLKNAS IKVSSKNDPQ LKVDLKQLRL TLEYLELFDN RLKEKRNNIS  1020
HFNYLNGQLG NSILELFDDA RDVLSYDRKL KNAVSKSLKE ILSSHGMEVT FKPLYQTNHH  1080
LKIDKLQPKK IHHLGEKSTV SSNQVSNEYC QLVRTLLTMK                       1120

SEQ ID NO: 154          moltype = AA  length = 1159
FEATURE                 Location/Qualifiers
source                  1..1159
                        mol_type = protein
                        organism = Leptotrichia buccalis
SEQUENCE: 154
MKVTKVGGIS HKKYTSEGRL VKSESEENRT DERLSALLNM RLDMYIKNPS STETKENQKR  60
IGKLKKFFSN KMVYLKDNTL SLKNGKKENI DREYSETDIL ESDVRDKKNF AVLKKIYLNE  120
NVNSEELEVF RNDIKKKLNK INSLKYSFEK NKANYQKINE NNIEKVEGKS KRNIIYDYYR  180
ESAKRDAYVS NVKEAFDKLY KEEDIAKLVL EIENLTKLEK YKIREFYHEI IGRKNDKENF  240
AKIIYEEIQN VNNMKELIEK VPDMSELKKS QVFYKYYLDK EELNDKNIKY AFCHFVEIEM  300
SQLLKNYVYK RLSNISNDKI KRIFEYQNLK KLIENKLLNK LDTYVRNCGK YNYYLQDGEI  360
ATSDFIARNR QNEAFLRNII GVSSVAYFSL RNILETENEN DITGRMRGKT VKNNKGEEKY  420
VSGEVDKIYN ENKKNEVKEN LKMFYSYDFN MDNKNEIEDF FANIDEAISS IRHGIVHFNL  480
ELEGKDIFAF KNIAPSEISK KMFQNEINEK KLKLKIFRQL NSANVFRYLE KYKILNYLKR  540
TRFEFVNKNI PFVPSFTKLY SRIDDLKNSL GIYWKTPKTN DDNKTKEIID AQIYLLKNIY  600
YGEFLNYFMS NNGNFFEISK EIIELNKNDK RNLKTGFYKL QKFEDIQEKI PKEYLANIQS  660
LYMINAGNQD EEEKDTYIDF IQKIFLKGFM TYLANNGRLS LIYIGSDEET NTSLAEKKQE  720
FDKFLKKYEQ NNNIKIPYEI NEFLREIKLG NILKYTERLN MFYLILKLLN HKELTNLKGS  780
LEKYQSANKE EAFSDQLELI NLLNLDNNRV TEDFELEADE IGKFLDFNGN KVKDNKELKK  840
FDTNKIYFDG ENIIKHRAFY NIKKYGMLNL LEKIADKAGY KISIEELKKY SNKKNEIEKN  900
HKMQENLHRK YARPRKDEKF TDEDYESYKQ AIENIEEYTH LKNKVEFNEL NLLQGLLLRI  960
LHRLVGYTSI WERDLRFRLK GEFPENQYIE EIFNFENKKN VKYKGGQIVE KYIKFYKELH  1020
QNDEVKINKY SSANIKVLKQ EKKDLYIRNY IAHFNYIPHA EISLLEVLEN LRKLLSYDRK  1080
LKNAVMKSVV DILKEYGFVA TFKIGADKKI GIQTLESEKI VHLKNLKKKK LMTDRNSEEL  1140
CKLVKIMFEY KMEEKKSEN                                              1159

SEQ ID NO: 155          moltype = AA  length = 1389
FEATURE                 Location/Qualifiers
source                  1..1389
                        mol_type = protein
                        organism = Leptotrichia shahii
SEQUENCE: 155
MGNLFGHKRW YEVRDKKDFK IKRKVKVKRN YDGNKYILNI NENNNKEKID NNKFIRKYIN  60
```

```
YKKNDNILKE FTRKFHAGNI LFKLKGKEGI IRIENNDDFL ETEEVVLYIE AYGKSEKLKA  120
LGITKKKIID EAIRQGITKD DKKIEIKRQE NEEEIEIDIR DEYTNKTLND CSIILRIIEN  180
DELETKKSIY EIFKNINMSL YKIIEKIIEN ETEKVFENRY YEEHLREKLL KDDKIDVILT  240
NFMEIREKIK SNLEILGFVK FYLNVGGDKK KSKNKKMLVE KILNINVDLT VEDIADFVIK  300
ELEFWNITKR IEKVKKVNNE FLEKRRNRTY IKSYVLLDKH EKFKIERENK KDKIVKFFVE  360
NIKNNSIKEK IEKILAEFKI DELIKKLEKE LKKGNCDTEI FGIFKKHYKV NFDSKKFSKK  420
SDEEKELYKI IYRYLKGRIE KILVNEQKVR LKKMEKIEIE KILNESILSE KILKRVKQYT  480
LEHIMYLGKL RHNDIDMTTV NTDDFSRLHA KEELDLELIT FFASTNMELN KIFSRENINN  540
DENIDFFGGD REKNYVLDKK ILNSKIKIIR DLDFIDNKNN ITNNFIRKFT KIGTNERNRI  600
LHAISKERDL QGTQDDYNKV INIIQNLKIS DEEVSKALNL DVVFKDKKNI ITKINDIKIS  660
EENNNDIKYL PSFSKVLPEI LNLYRNNPKN EPFDTIETEK IVLNALIYVN KELYKKLILE  720
DDLEENESKN IFLQELKKTL GNIDEIDENI IENYYKNAQI SASKGNNKAI KKYQKKVIEC  780
YIGYLRKNYE ELFDFSDFKM NIQEIKKQIK DINDNKTYER ITVKTSDKTI VINDDFEYII  840
SIFALLNSNA VINKIRNRFF ATSVWLNTSE YQNIIDILDE IMQLNTLRNE CITENWNLNL  900
EEFIQKMKEI EKDFDDFKIQ TKKEIFNNYY EDIKNNILTE FKDDINGCDV LEKKLEKIVI  960
FDDETKFEID KKSNILQDEQ RKLSNINKKD LKKKVDQYIK DKDQEIKSKI LCRIIFNSDF  1020
LKKYKKEIDN LIEDMESENE NKFQEIYYPK ERKNELYIYK KNLFLNIGNP NFDKIYGLIS  1080
NDIKMADAKF LFNIDGKNIR KNKISEIDAI LKNLNDKLNG YSKEYKEKYI KKLKENDDFF  1140
AKNIQNKNYK SFEKDYNRVS EYKKIRDLVE FNYLNKIESY LIDINWKLAI QMARFERDMH  1200
YIVNGLRELG IIKLSGYNTG ISRAYPKRNG SDGFYTTTAY YKFFDEESYK KFEKICYGFG  1260
IDLSENSEIN KPENESIRNY ISHFYIVRNP FADYSIAEQI DRVSNLLSYS TRYNNSTYAS  1320
VFEVFKKDVN LDYDELKKKF KLIGNNDILE RLMKPKKVSV LELESYNSDY IKNLIIELLT  1380
KIENTNDTL                                                          1389

SEQ ID NO: 156          moltype = AA  length = 1285
FEATURE                 Location/Qualifiers
source                  1..1285
                        mol_type = protein
                        organism = Rhodobacter capsulatus
SEQUENCE: 156
MQIGKVQGRT ISEFGDPAGG LKRKISTDGK NRKELPAHLS SDPKALIGQW ISGIDKIYRK  60
PDSRKSDGKA IHSPTPSKMQ FDARDDLGEA FWKLVSEAGL AQDSDYDQFK RRLHPYGDKF  120
QPADSGAKLK FEADPPEPQA FHGRWYGAMS KRGNDAKELA AALYEHLHVD EKRIDGQPKR  180
NPKTDKFAPG LVVARALGIE SSVLPRGMAR LARNWGEEEI QTYFVVDVAA SVKEVAKAAV  240
SAAQAFDPPR QVSGRSLSPK VGFALAEHLE RVTGSKRCSF DPAAGPSVLA LHDEVKKTYK  300
RLCARGKNAA RAFPADKTEL LALMRHTHEN RVRNQMVRMG RVSEYRGQQA GDLAQSHYWT  360
SAGQTEIKES EIFVRLWVGA FALAGRSMKA WIDPMGKIVN TEKNDRDLTA AVNIRQVISN  420
KEMVAEAMAR RGIYFGETPE LDRLGAEGNE GFVFALLRYL RGCRNQTFHL GARAGFLKEI  480
RKELEKTRWG KAKEAEHVVL TDKTVAAIRA IIDNDAKALG ARLLADLSGA FVAHYASKEH  540
FSTLYSEIVK AVKDAPEVSS GLPRLKLLLK RADGVRGYVH GLRDTRKHAF ATKLPPPPAP  600
RELDDPATKA RYIALLRLYD GPFRAYASGI TGTALAGPAA RAKEAATALA QSVNVTKAYS  660
DVMEGRSSRL RPPNDGETLR EYLSALTGET ATEFRVQIGY ESDSENARKQ AEFIENYRRD  720
MLAFMFEDYI RAKGFDWILK IEPGATAMTR APVLPEPIDT RGQYEHWQAA LYLVMHFVPA  780
SDVSNLLHQL RKWEALQGKY ELVQDGDATD QADARREALD LVKRFRDVLV LFLKTGEARF  840
EGRAAPFDLK PFRALFANPA TFDRLFMATP TTARPAEDDP EGDGASEPEL RVARTLRGLR  900
QIARYNHMAV LSDLFAKHKV RDEEVARLAE IEDETQEKSQ IVAAQELRTD LHDKVMKCHP  960
KTISPEERQS YAAAIKTIEE HRFLVGRVYL GDHLRLHRLM MDVIGRLIDY AGAYERDTGT  1020
FLINASKQLG AGADWAVTIA GAANTDARTQ TRKDLAHFNV LDRADGTPDL TALVNRAREM  1080
MAYDRKRKNA VPRSILDMLA RLGLTLKWQM KDHLLQDATI TQAAIKHLDK VRLTVGGPAA  1140
VTEARFSQDY LQMVAAVFNG SVQNPKPRRR DDGDAWHKPP KPATAQSQPD QKPPNKAPSA  1200
GSRLPPPQVG EVYEGVVVKV IDTGSLGFLA VEGVAGNIGL HISRLRRIRE DAIIVGRRYR  1260
FRVEIYVPPK SNTSKLNAAD LVRID                                        1285

SEQ ID NO: 157          moltype = AA  length = 1175
FEATURE                 Location/Qualifiers
source                  1..1175
                        mol_type = protein
                        organism = Carnobacterium gallinarum
SEQUENCE: 157
MRITKVKIKL DNKLYQVTMQ KEEKYGTLKL NEESRKSTAE ILRLKKASFN KSFHSKTINS  60
QKENKNATIK KNGDYISQIF EKLVGVDTNK NIRKPKMSLT DLKDLPKKDL ALFIKRKFKN  120
DDIVEIKNLD LISLFYNALQ KVPGEHFTDE SWADFCQEMM PYREYKNKFI ERKIILLANS  180
IEQNKGFSIN PETFSKRKRV LHQWAIEVQE RGDFSILDEK LSKLAEIYNF KKMCKRVQDE  240
LNDLEKSMKK GKNPEKEKEA YKKQKNFKIK TIWKDYPYKT HIGLIEKIKE NEELNQFNIE  300
IGKYFEHYFP IKKERCTEDE PYYLNSETIA TTVNYQLKNA LISYLMQIGK YKQFGLENQV  360
LDSKKLQEIG IYEGFQTKFM DACVFATSSL KNIIEPMRSG DILGKREFKE AIATSSFVNY  420
HHFFPYFPFE LKGMKDRESE LIPFGEQTEA KQMQNIWALR GSVQQIRNEI FHSFDKNQKF  480
NLPQLDKSNF EFDASENSTG KSQSYIETDY KFLFEAEKNQ LEQFFIERIK SSGALEYYPL  540
KSLEKLFAKK EMKFSLGSQV VAFAPSYKKL VKKGHSYQTA TEGTANYLGL SYYNRYELKE  600
ESFQAQYYLL KLIYQYVFLP NFSQGNSPAF RETVKAILRI NKDEARKKMK KNKKFLRKYA  660
FEQVREMEFK ETPDQYMSYL QSEMREEKVR KAEKNDKGFE KNITMNFEKL LMQIFVKGFD  720
VFLTTFAGKE LLLSSEEKVI KETEISLSKK INEREKTLKA SIQVEHQLVA TNSAISYWLF  780
CKLLDSRHLN ELRNEMIKFK QSRIKFNHTQ HAELIQNLLP IVELTILSND YDEKNDSQNV  840
DVSAYFEDKS LYETAPYVQT DDRTRVSFRP ILKLEKYHTK SLIEALLKDN PQFRVAATDI  900
QEWMHKREEI GELVEKRKNL HTEWAEGQQT LGAEKREEYR DYCKKIDRFN WKANKVTLTY  960
LSQLHYLITD LLGRMVGFSA LFERDLVYFS RSFSELGGET YHISDYKNLS GVLRLNAEVK  1020
PIKIKNIKVI DNEENPYKGN EPEVKPFLDR LHAYLENVIG IKAVHGKIRN QTAHLSVLQL  1080
ELSMIESMNN LRDLMAYDRK LKNAVTKSMI KILDKHGMIL KLKIDENHKN FEIESLIPKE  1140
IIHLKDKAIK TNQVSEEYCQ LVLALLTTNP GNQLN                              1175
```

```
SEQ ID NO: 158          moltype = AA  length = 1285
FEATURE                 Location/Qualifiers
source                  1..1285
                        mol_type = protein
                        organism = unidentified
                        note = Description of Unknown: Herbinix hemicellulosilytica
                         sequence
SEQUENCE: 158
MKLTRRRISG NSVDQKITAA FYRDMSQGLL YYDSEDNDCT DKVIESMDFE RSWRGRILKN  60
GEDDKNPFYM FVKGLVGSND KIVCEPIDVD SDPDNLDILI NKNLTGFGRN LKAPDSNDTL  120
ENLIRKIQAG IPEEEVLPEL KKIKEMIQKD IVNRKEQLLK SIKNNRIPFS LEGSKLVPST  180
KKMKWLFKLI DVPNKTFNEK MLEKYWEIYD YDKLKANITN RLDKTDKKAR SISRAVSEEL  240
REYHKNLRTN YNRFVSGDRP AAGLDNGGSA KYNPDKEEFL LFLKEVEQYF KKYFPVKSKH  300
SNKSKDKSLV DKYKNYCSYK VVKKEVNRSI INQLVAGLIQ QGKLLYYFYY NDTWQEDFLN  360
SYGLSYIQVE EAFKKSVMTS LSWGINRLTS FFIDDSNTVK FDDITTKKAK EAIESNYFNK  420
LRTCSRMQDH FKEKLAFFYP VYVKDKKDRP DDDIENLIVL VKNAIESVSY LRNRTFHFKE  480
SSLLELLKEL DDKNSGQNKI DYSVAAEFIK RDIENLYDVF REQIRSLGIA EYYKADMISD  540
CFKTCGLEFA LYSPKNSLMP AFKNVYKRGA NLNKAYIRDK GPKETGDQGQ NSYKALEEYR  600
ELTWYIEVKN NDQSYNAYKN LLQLIYYHAF LPEVRENEAL ITDFINRTKE WNRKETEERL  660
NTKNNKKHKN FDENDDITVN TYRYESIPDY QGESLDDYLK VLQRKQMARA KEVNEKEEGN  720
NNYIQFIRDV VVWAFGAYLE NKLKNYKNEL QPPLSKENIG LNDTLKELFP EEKVKSPFNI  780
KCRFSISTFI DNKGKSTDNT SAEAVKTDGK EDEKDKKNIK RKDLLCFYLF LRLLDENEIC  840
KLQHQFIKYR CSLKERRFPG NRTKLEKETE LLAELEELME LVRFTMPSIP EISAKAESGY  900
DTMIKKYFKD FIEKKVFKNP KTSNLYYHSD SKTPVTRKYM ALLMRSAPLH LYKDIFKGYY  960
LITKKECLEY IKLSNIIKDY QNSLNELHEQ LERIKLKSEK QNGKDSLYLD KKDFYKVKEY  1020
VENLEQVARY KHLQHKINFE SLYRIFRIHV DIAARMVGYT QDWERDMHFL FKALVYNGVL  1080
EERRFEAIFN NNDDNNDGRI VKKIQNNLNN KNRELVSMLC WNKKLNKNEF GAIIWKRNPI  1140
AHLNHFTQTE QNSKSSLESL INSLRILLAY DRKRQNAVTK TINDLLLNDY HIRIKWEGRV  1200
DEGQIYFNIK EKEDIENEPI IHLKHLHKKD CYIYKNSYMF DKQKEWICNG IKEEVYDKSI  1260
LKCIGNLFKF DYEDKNKSSA NPKHT                                       1285

SEQ ID NO: 159          moltype = AA  length = 1154
FEATURE                 Location/Qualifiers
source                  1..1154
                        mol_type = protein
                        organism = Paludibacter propionicigenes
SEQUENCE: 159
MRVSKVKVKD GGKDKMVLVH RKTTGAQLVY SGQPVSNETS NILPEKKRQS FDLSTLNKTI  60
IKFDTAKKQK LNVDQYKIVE KIFKYPKQEL PKQIKAEEIL PFLNHKFQEP VKYWKNGKEE  120
SFNLTLLIVE AVQAQDKRKL QPYYDWKTWY IQTKSDLLKK SIENNRIDLT ENLSKRKKAL  180
LAWETEFTAS GSIDLTHYHK VYMTDVLCKM LQDVKPLTDD KGKINTNAYH RGLKKALQNH  240
QPAIFGTREV PNEANRADNQ LSIYHLEVVK YLEHYFPIKT SKRRNTADDI AHYLKAQTLK  300
TTIEKQLVNA IRANIIQQGK TNHHELKADT TSNDLIRIKT NEAFVLNLTG TCAFAANNIR  360
NMVDNEQTND ILGKGDFIKS LLKDNTNSQL YSFFFGEGLS TNKAEKETQL WGIRGAVQQI  420
RNNVNHYKKD ALKTVFNISN FENPTITDPK QQTNYADTIY KARFINELEK IPEAFAQQLK  480
TGGAVSYYTI ENLKSLLTTF QFSLCRSTIP FAPGFKKVFN GGINYQNAKQ DESFYELMLE  540
QYLRKENFAE ESYNARYFML KLIYNNLFLP GFTTDRKAFA DSVGFVQMQN KKQAEKVNPR  600
KKEAYAFEAV RPMTAADSIA DYMAYVQSEL MQEQNKKEEK VAEETRINFE KFVLQVFIKG  660
FDSFLRAKEF DFVQMPQPQL TATASNQQKA DKLNQLEASI TADCKLTPQY AKADDATHIA  720
FYVFCKLLDA AHLSNLRNEL IKFRESVNEF KFHHLLEIIE ICLLSADVVP TDYRDLYSSE  780
ADCLARLRPF IEQGADITNW SDLFVQSDKH SPVIHANIEL SVKYGTTKLL EQIINKDTQF  840
KTTEANFTAW NTAQKSIEQL IKQREDHHEQ WVKAKNADDK EKQERKREKS NFAQKFIEKH  900
GDDYLDICDY INTYNWLDNK MHFVHLNRLH GLTIELLGRM AGFVALFDRD FQFFDEQQIA  960
DEFKLHGFVN LHSIDKKLNE VPTKKIKEIY DIRNKIIQIN GNKINESVRA NLIQFISSKR  1020
NYYNNAFLHV SNDEIKEKQM YDIRNHIAHF NYLTKDAADF SLIDLINELR ELLHYDRKLK  1080
NAVSKAFIDL FDKHGMILKL KLNADHKLKV ESLEPKKIYH LGSSAKDKPE YQYCTNQVMM  1140
AYCNMCRSLL EMKK                                                   1154

SEQ ID NO: 160          moltype = AA  length = 1182
FEATURE                 Location/Qualifiers
source                  1..1182
                        mol_type = protein
                        organism = Leptotrichia wadei
SEQUENCE: 160
MYMKITKIDG VSHYKKQDKG ILKKKWKDLD ERKQREKIEA RYNKQIESKI YKEFFRLKNK  60
KRIEKEEDQN IKSLYFFIKE LYLNEKNEEW ELKNINLEIL DDKERVIKGY KFKEDVYFFK  120
EGYKEYYLRI LFNNLIEKVQ NENREKVRKN KEFLDLKEIF KKYKNRKIDL LLKSINNNKI  180
NLEYKKENVN EEIYGINPTN DREMTFYELL KEIIEKKDEQ KSILEEKLDN FDITNFLENI  240
EKIFNEETEI NIIKGKVLNE LREYIKEKEE NNSDNKLKQI YNLELKKYIE NNFSYKKQKS  300
KSKNGKNDYL YLNFLKKIMF IEEVDEKKEI NKEKFKNKIN SNFKNLFVQH ILDYGKLLYY  360
KENDEYIKNT GQLETKDLEY IKTKETLIRK MAVLVSFAAN SYYNLFGRVS GDILGTEVVK  420
SSKTNVIKVG SHIFKEKMLN YFFDFEIFDA NKIVEILESI SYSIYNVRNG VGHFNKLILG  480
KYKKKDINTN KRIEEDLNNN EEIKGYFIKK RGEIERKVKE KFLSNNLQYY YSKEKIENYF  540
EVYEFEILKR KIPFAPNFKR IIKKGEDLFN NKNNKKYEYF KNFDKNSAEE KKEFLKTRNF  600
LLKELYYNNF YKEFLSKKEE FEKIVLEVKE EKKSRGNINN KKSGVSFQSI DDYDTKINIS  660
DYIASIHKKE MERVEKYNEE KQKDTAKYIR DFVEEIFLTG FINYLEKDKR LHFLKEEFSI  720
LCNNNNNVVD FNININEEKI KEFLKENDSK TLNLYLFFNM IDSKRISEFR NELVKYKQFT  780
KKRLDEEKEF LGIKIELYET LIEFVILTRE KLDTKKSEEI DAWLVDKLYV KDSNEYKEYE  840
```

```
EILKLFVDEK ILSSKEAPYY ATDNKTPILL SNFEKTRKYG TQSFLSEIQS NYKYSKVEKE  900
NIEDYNKKEE IEQKKKSNIE KLQDLKVELH KKWEQNKITE KEIEKYNNTT RKINEYNYLK  960
NKEELQNVYL LHEMLSDLLA RNVAFFNKWE RDFKFIVIAI KQFLRENDKE KVNEFLNPPD  1020
NSKGKKVYFS VSKYKNTVEN IDGIHKNFMN LIFLNNKFMN RKIDKMNCAI WVYFRNYIAH  1080
FLHLHTKNEK ISLISQMNLL IKLFSYDKKV QNHILKSTKT LLEKYNIQIN FEISNDKNEV  1140
FKYKIKNRLY SKKGKMLGKN NKFEILENEF LENVKAMLEY SE                    1182

SEQ ID NO: 161         moltype = AA  length = 1224
FEATURE                Location/Qualifiers
source                 1..1224
                       mol_type = protein
                       organism = Bergeyella zoohelcum
SEQUENCE: 161
MENKTSLGNN IYYNPFKPQD KSYFAGYFNA AMENTDSVFR ELGKRLKGKE YTSENFFDAI  60
FKENISLVEY ERYVKLLSDY FPMARLLDKK EVPIKERKEN FKKNFKGIIK AVRDLRNFYT  120
HKEHGEVEIT DEIFGVLDEM LKSTVLTVKK KKVKTDKTKE ILKKSIEKQL DILCQKKLEY  180
LRDTARKIEE KRRNQRERGE KELVAPFKYS DKRDDLIAAI YNDAFDVYID KKKDSLKESS  240
KAKYNTKSDP QQEEGDLKIP ISKNGVVFLL SLFLTKQEIH AFKSKIAGFK ATVIDEATVS  300
EATVSHGKNS ICFMATHEIF SHLAYKKLKR KVRTAEINYG EAENAEQLSV YAKETLMMQM  360
LDELSKVPDV VYQNLSEDVQ KTFIEDWNEY LKENNGDVGT MEEEQVIHPV IRKRYEDKFN  420
YFAIRFLDEF AQFPTLRFQV HLGNYLHDSR PKENLISDRR IKEKITVFGR LSELEHKKAL  480
FIKNTETNED REHYWEIFPN PNYDFPKENI SVNDKDFPIA GSILDREKQP VAGKIGIKVK  540
LLNQQYVSEV DKAVKAHQLK QRKASKPSIQ NIIEEIVPIN ESNPKEAIVF GGQPTAYLSM  600
NDIHSILYEF FDKWEKKKEK LEKKGEKELR KEIGKELEKK IVGKIQAQIQ QIIDKDTNAK  660
ILKPYQDGNS TAIDKEKLIK DLKQEQNILQ KLKDEQTVRE KEYNDFIAYQ DKNREINKVR  720
DRNHKQYLKD NLKRKYPEAP ARKEVLYYRE KGKVAVWLAN DIKRFMPTDF KNEWKGEQHS  780
LLQKSLAYYE QCKEELKNLL PEKVFQHLPF KLGGYFQQKY LYQFYTCYLD KRLEYISGLV  840
QQAENFKSEN KVFKKVENEC FKFLKKQNYT HKELDARVQS ILGYPIFLER GFMDEKPTII  900
KGKTFKGNEA LFADWFRYYK EYQNFQTFYD TENYPLVELE KKQADRKRKT KIYQQKKNDV  960
FTLLMAKHIF KSVFKQDSID QFSLEDLYQS REERLGNQER ARQTGERNTN YIWNKTVDLK  1020
LCDGKITVEN VKLKNVGDFI KYEYDQRVQA FLKYEENIEW QAFLIKESKE EENYPYVVER  1080
EIEQYEKVRR EELLKEVHLI EEYILEKVKD KEILKKGDNQ NFKYYILNGL LKQLKNEDVE  1140
SYKVFNLNTE PEDVNINQLK QEATDLEQKA FVLTYIRNKF AHNQLPKKEF WDYCQEKYGK  1200
IEKEKTYAEY FAEVFKKEKE ALIK                                        1224

SEQ ID NO: 162         moltype = AA  length = 1126
FEATURE                Location/Qualifiers
source                 1..1126
                       mol_type = protein
                       organism = Prevotella intermedia
SEQUENCE: 162
MEDDKKTTDS IRYELKDKHF WAAFLNLARH NVYITVNHIN KILEEGEINR DGYETTLKNT  60
WNEIKDINKK DRLSKLIIKH FPFLEAATYR LNPTDTTKQK EEKQAEAQSL ESLRKSFFVF  120
IYKLRDLRNH YSHYKHSKSL ERPKFEEGLL EKMYNIFNAS IRLVKEDYQY NKDINPDEDF  180
KHLDRTEEEF NYYFTKDNEG NITESGLLFF VSLFLEKKDA IWMQQKLRGF KDNRENKKKM  240
TNEVFCRSRM LLPKLRLQST QTQDWILLDM LNELIRCPKS LYERLREEDR EKFRVPIEIA  300
DEDYDAEQEP FKNTLVRHQD RFPYFALRYF DYNEIFTNLR FQIDLGTYHF SIYKKQIGDY  360
KESHHLTHKL YGFERIQEFT KQNRPDEWRK FVKTFNSFET SKEPYIPETT PHYHLENQKI  420
GIRFRNDNDK IWPSLKTNSE KNEKSKYKLD KSFQAEAFLS VHELLPMMFY YLLLKTENTD  480
NDNEIETKKK ENKNDKQEKH KIEEIIENKI TEIYALYDTF ANGEIKSIDE LEEYCKGKDI  540
EIGHLPKQMI AILKDEHKVM ATEAERKQEE MLVDVQKSLE SLDNQINEEI ENVERKNSSL  600
KSGKIASWLV NDMMRFQPVQ KDNEGKPLNN SKANSTEYQL LQRTLAFFGS EHERLAPYFK  660
QTKLIESSNP HPFLKDTEWE KCNNILSFYR SYLEAKKNFL ESLKPEDWEK NQYFLKLKEP  720
KTKPKTLVQG WKNGFNLPRG IFTEPIRKWF MKHRENITVA ELKRVGLVAK VIPLFFSEEY  780
KDSVQPFYNY HFNVGNINKP DEKNFLNCEE RRELLRKKKD EFKKMTDKEK EENPSYLEFK  840
SWNKFERELR LVRNQDIVTW LLCMELFNKK KIKELNVEKI YLKNINTNTT KKEKNTEEKN  900
GEEKNIKEKN NILNRIMPMR LPIKVYGREN FSKNKKKKIR RNTFFTVYIE EKGTKLLKQG  960
NFKALERDRR LGGLFSFVKT PSKAESKSNT ISKLRVEYEL GEYQKARIEI IKDMLALEKT  1020
LIDKYNSLDT DNFNKMLTDW LELKGEPDKA SFQNDVDLLI AVRNAFSHNQ YPMRNRIAFA  1080
NINPFSLSSA NTSEEKGLGI ANQLKDKTHK TIEKIIEIEK PIETKE                1126

SEQ ID NO: 163         moltype = AA  length = 1127
FEATURE                Location/Qualifiers
source                 1..1127
                       mol_type = protein
                       organism = Prevotella buccae
SEQUENCE: 163
MQKQDKLFVD RKKNAIFAFP KYITIMENKE KPEPIYYELT DKHFWAAFLN LARHNVYTTI  60
NHINRRLEIA ELKDDGYMMG IKGSWNEQAK KLDKKVRLRD LIMKHFPFLE AAYEMTNSK  120
SPNNKEQREK EQSEALSLNN LKNVLFIFLE KLQVLRNYYS HYKYSEESPK PIFETSLLKN  180
MYKVFDANVR LVKRDYMHHE NIDMQRDFTH LNRKKQVGRT KNIIDSPNFH YHFADKEGNM  240
TIAGLLFFVS LFLDKKDAIW MQKKLKGFKD GRNLREQMTN EVFCRSRISL PKLKLENVQT  300
KDWMQLDMLN ELVRCPKSLY ERLREKDRES FKVPFDIFSD DYNAEEEPFK NTLVRHQDRF  360
PYFVLRYFDL NEIFEQLRFQ IDLGTYHFSI YNKRIGDEDE VRHLTHHLYG FARIQDFAPQ  420
NQPEEWRKLV KDLDHFETSQ EPYISKTAPH YHLENEKIGI KFCSAHNNLF PSLQTDKTCN  480
GRSKFNLGTQ FTAEAFLSVH ELLPMMFYYL LLTKDYSRKE SADKVEGIIR KEISNIYAIY  540
DAFANNEINS IADLTRRLQN TNILQGHLPK QMISILKGRQ KDMGKEAERK IGEMIDDTQR  600
RLDLLCKQTN QKIRIGKRNA GLLKSGKIAD WLVNDMMRFQ PVQKDQNNIP INNSKANSTE  660
YRMLQRALAL FGSENFRLKA YFNQMNLVGN DNPHPFLAET QWEHQTNILS FYRNYLEARK  720
```

```
KYLKGLKPQN WKQYQHFLIL KVQKTNRNTL VTGWKNSFNL PRGIFTQPIR EWFEKHNNSK  780
RIYDQILSFD RVGFVAKAIP LYFAEEYKDN VQPFYDYPFN IGNRLKPKKR QFLDKKERVE  840
LWQKNKELFK NYPSEKKKTD LAYLDFLSWK KFERELRLIK NQDIVTWLMF KELFNMATVE  900
GLKIGEIHLR DIDTNTANEE SNNILNRIMP MKLPVKTYET DNKGNILKER PLATFYIEET  960
ETKVLKQGNF KALVKDRRLN GLFSFAETTD LNLEEHPISK LSVDLELIKY QTTRISIFEM  1020
TLGLEKKLID KYSTLPTDSF RNMLERWLQC KANRPELKNY VNSLIAVRNA FSHNQYPMYD  1080
ATLFAEVKKF TLFPSVDTKK IELNIAPQLL EIVGKAIKEI EKSENKN                1127

SEQ ID NO: 164          moltype = AA  length = 1135
FEATURE                 Location/Qualifiers
source                  1..1135
                        mol_type = protein
                        organism = Porphyromonas gingivalis
SEQUENCE: 164
MNTVPASENK GQSRTVEDDP QYFGLYLNLA RENLIEVESH VRIKFGKKKL NEESLKQSLL  60
CDHLLSVDRW TKVYGHSRRY LPFLHYFDPD SQIEKDHDSK TGVDPDSAQR LIRELYSLLD  120
FLRNDFSHNR LDGTTFEHLE VSPDISSFIT GTYSLACGRA QSRFAVFFKP DDFVLAKNRK  180
EQLISVADGK ECLTVSGFAF FICLFLDREQ ASGMLSRIRG FKRTDENWAR AVHETFCDLC  240
IRHPHDRLES SNTKEALLLD MLNELNRCPR ILYDMLPEEE RAQFLPALDE NSMNNLSENS  300
LDEESRLLWD GSSDWAEALT KRIRHQDRFP YLMLRFIEEM DLLKGIRFRV DLGEIELDSY  360
SKKVGRNGEY DRTITDHALA FGKLSDFQNE EEVSRMISGE ASYPVRFSLF APRYAIYDNK  420
IGYCHTSDPV YPKSKTGEKR ALSNPQSMGF ISVHDLRKLL LMELLCEGSF SRMQSDFLRK  480
ANRILDETAE GKLQFSALFP EMRHRFIPPQ NPKSKDRREK AETTLEKYKQ EIKGRKDKLN  540
SQLLSAFDMD QRQLPSRLLD EWMNIRPASH SVKLRTYVKQ LNEDCRLRLR KFRKDGDGKA  600
RAIPLVGEMA TFLSQDIVRM IISEETKKLI TSAYYNEMQR SLAQYAGEEN RRQFRAIVAE  660
LRLLDPSSGH PFLSATMETA HRYTEGFYKC YLEKKREWLA KIFYRPEQDE NTKRRISVFF  720
VPDGEARKLL PLLIRRRMKE QNDLQDWIRN KQAHPIDLPS HLFDSKVMEL LKVKDGKKKW  780
NEAFKDWWST KYPDGMQPFY GLRRELNIHG KSVSYIPSDG KKFADCYTHL MEKTVRDKKR  840
ELRTAGKPVP PDLAADIKRS FHRAVNEREF MLRLVQEDDR LMLMAINKMM TDREEDILPG  900
LKNIDSILDE ENQFSLAVHA KVLEKEGEGG DNSLSLVPAT IEIKSKRKDW SKYIRYRYDR  960
RVPGLMSHFP EHKATLDEVK TLLGEYDRCR IKIFDWAFAL EGAIMSDRDL KPYLHESSSR  1020
EGKSGEHSTL VKMLVEKKGC LTPDESQYLI LIRNKAAHNQ FPCAAEMPLI YRDVSAKVGS  1080
IEGSSAKDLP EGSSLVDSLW KKYEMIIRKI LPILDPENRF FGKLLNNMSQ PINDL       1135

SEQ ID NO: 165          moltype = AA  length = 1115
FEATURE                 Location/Qualifiers
source                  1..1115
                        mol_type = protein
                        organism = Bacteroides pyogenes
SEQUENCE: 165
MESIKNSQKS TGKTLQKDPP YFGLYLNMAL LNVRKVENHI RKWLGDVALL PEKSGFHSLL  60
TTDNLSSAKW TRFYYKSRKF LPFLEMFDSD KKSYENRRET AECLDTIDRQ KISSLLKEVY  120
GKLQDIRNAF SHYHIDDQSV KHTALIISSE MHRFIENAYS FALQKTRARF TGVFVETDFL  180
QAEEKGDNKK FFAIGGNEGI KLKDNALIFL ICLFLDREEA FKFLSRATGF KSTKEKGFLA  240
VRETFCALCC RQPHERLLSV NPREALLMDM LNELNRCPDI LFEMLDEKDQ KSFLPLLGEE  300
EQAHILENSL NDELCEAIDD PFEMIASLSK RVRYKNRFPY LMLRYIEEKN LLPFIRFRID  360
LGCLELASYP KKMGEENNYE RSVTDHAMAF GRLTDFHNED AVLQQITKGI TDEVRFSLYA  420
PRYAIYNNKI GFVRTSGSDK ISFPTLKKKG GEGHCVAYTL QNTKSFGFIS IYDLRKILLL  480
SFLDKDKAKN IVSGLLEQCE KHWKDLSENL FDAIRTELQK EFPVPLIRYT LPRSKGGKLV  540
SSKLADKQEK YESEFERRKE KLTEILSEKD FDLSQIPRRM IDEWLNVLPT SREKKLKGYV  600
ETLKLDCRER LRVFEKREKG EHPLPPRIGE MATDLAKDII RMVIDQGVKQ RITSAYYSEI  660
QRCLAQYAGD DNRRHLDSII RELRLKDTKN GHPFLGKVLR PGLGHTEKLY QRYFEEKKEW  720
LEATFYPAAS PKRVPRFVNP PTGKQKELPL IIRNLMKERP EWRDWKQRKN SHPIDLPSQL  780
FENEICRLLK DKIGKEPSGK LKWNEMFKLY WDKEFPNGMQ RFYRCKRRVE VFDKVVEYEY  840
SEEGGNYKKY YEALIDEVVR QKISSSKEKS KLQVEDLTLS VRRVFKRAIN EKEYQLRLLC  900
EDDRLLFMAV RDLYDWKEAQ LDLDKIDNML GEPVSVSQVI QLEGGQPDAV IKAECKLKDV  960
SKLMRYCYDG RVKGLMPYFA NHEATQEQVE MELRHYEDHR RRVFNWVFAL EKSVLKNEKL  1020
RRFYEESQGG CEHRRCIDAL RKASLVSEEE YEFLVHIRNK SAHNQFPDLE IGKLPPNVTS  1080
GFCECIWSKY KAIICRIIPF IDPERRFFGK LLEQK                             1115

SEQ ID NO: 166          moltype = AA  length = 668
FEATURE                 Location/Qualifiers
source                  1..668
                        mol_type = protein
                        organism = unidentified
                        note = Description of Unknown: Cas13c sequence
SEQUENCE: 166
MTEKKSIIFK NKSSVEIVKK DIFSQTPDNM IRNYKITLKI SEKNPRVVEA EIEDLMNSTI  60
LKDGRRSARR EKSMTERKLI EEKVAENYSL LANCPMEEVD SIKIYKIKRF LTYRSNMLLY  120
FASINSFLCE GIKGKDNETE EIWHLKDNDV RKEKVKENFK NKLIQSTENY NSSLKNQIEE  180
KEKLLRKESK KGAFYRTIIK KLQQERIKEL SEKSLTEDCE KIIKLYSELR HPLMHYDYQY  240
FENLFENKEN SELTKNLNLD IFKSLPLVRK MKLNNKVNYL EDNDTLFVLQ KTKKAKTLYQ  300
IYDALCEQKN GFNKFINDFF VSDGEENTVF KQIINEKFQS EMEFLEKRIS ESEKKNEKLK  360
KKFDSMKAHF HNINSEDTKE AYFWDIHSSS NYKTKYNERK NLVNEYTELL GSSKEKKLLR  420
EEITQINRKL LKLKQEMEEI TKKNSLFRLE YKMKIAFGFL FCEFDGNISK FKDEFDASNQ  480
EKIIQYHKNG EKYLTYFLKE EEKEKFNLEK MQKIIQKTEE EDWLLPETKN NLFKFYLLTY  540
LLLPYELKGD FLGFVKKHYY DIKNVDFMDE NQNNIQVSQT VEKQEDYFYH KIRLFEKNTK  600
KYEIVKYSIV PNEKLKQYFE DLGIDIKYLT GSVESGEKWL GENLGIDIKY LTVEQKSEVS  660
EEKIKKFL                                                           668
```

```
SEQ ID NO: 167          moltype = AA  length = 796
FEATURE                 Location/Qualifiers
source                  1..796
                        mol_type = protein
                        organism = unidentified
                        note = Description of Unknown: Cas13c sequence
SEQUENCE: 167
MEKDKKGEKI DISQEMIEED LRKILILFSR LRHSMVHYDY EFYQALYSGK DFVISDKNNL  60
ENRMISQLLD LNIFKELSKV KLIKDKAISN YLDKNTTIHV LGQDIKAIRL LDIYRDICGS  120
KNGFNKFINT MITISGEEDR EYKEKVIEHF NKKMENLSTY LEKLEKQDNA KRNNKRVYNL  180
LKQKLIEQQK LKEWFGGPYV YDIHSSKRYK ELYIERKKLV DRHSKLFEEG LDEKNKKELT  240
KINDELSKLN SEMKEMTKLN SKYRLQYKLQ LAFGFILEEF DLNIDTFINN FDKDKDLIIS  300
NFMKKRDIYL NRVLDRGDNR LKNIIKEYKF RDTEDIFCND RDNNLVKLYI LMYILLPVEI  360
RGDFLGFVKK NYYDMKHVDF IDKKDKEDKD TFFHDLRLFE KNIRKLEITD YSLSSGFLSK  420
EHKVDIEKKI NDFINRNGAM KLPEDITIEE FNKSLILPIM KNYQINFKLL NDIEISALFK  480
IAKDRSITFK QAIDEIKNED IKKNSKKNDK NNHKDKNINF TQLMKRALHE KIPYKAGMYQ  540
IRNNISHIDM EQLYIDPLNS YMNSNKNNIT ISEQIEKIID VCVTGGVTGK ELNNNIINDY  600
YMKKEKLVFN LKLRKQNDIV SIESQEKNKR EEFVFKKYGL DYKDGEINII EVIQKVNSLQ  660
EELRNIKETS KEKLKNKETL FRDISLINGT IRKNINFKIK EMVLDIVRMD EIRHINIHIY  720
YKGENYTRSN IIKFKYAIDG ENKKYYLKQH EINDINLELK DKFVTLICNM DKHPNKNKQT  780
INLESNYIQN VKFIIP                                                 796

SEQ ID NO: 168          moltype = AA  length = 897
FEATURE                 Location/Qualifiers
source                  1..897
                        mol_type = protein
                        organism = unidentified
                        note = Description of Unknown: Cas13c sequence
SEQUENCE: 168
MENKGNNKKI DFDENYNILV AQIKEYFTKE IENYNNRIDN IIDKKELLKY SEKKEESEKN  60
KKLEELNKLK SQKLKILTDE EIKADVIKII KIFSDLRHSL MHYEYKYFEN LFENKKNEEL  120
AELLNLNLFK NLTLLRQMKI ENKTNYLEGR EEFNIIGKNI KAKEVLGHYN LLAEQKNGFN  180
NFINSFFVQD GTENLEFKKL IDEHFVNAKK RLERNIKKSK KLEKELEKME QHYQRLNCAY  240
VWDIHTSTTY KKLYNKRKSL IEEYNKQINE IKDKEVITAI NVELLRIKKE MEEITKSNSL  300
FRLKYKMQIA YAFLEIEFGG NIAKFKDEFD CSKMEEVQKY LKKGVKYLKY YKDKEAQKNY  360
EFPFEEIFEN KDTHNEEWLE NTSENNLFKF YILTYLLLPM EFKGDFLGVV KKHYYDIKNV  420
DFTDESEKEL SQVQLDKMIG DSFFHKIRLF EKNTKRYEII KYSILTSDEI KRYFRLLELD  480
VPYFEYEKGT DEIGIFNKNI ILTIFKYYQI IFRLYNDLEI HGLFNISSDL DKILRDLKSY  540
GNKNINFREF LYVIKQNNNS STEEYRKIW ENLEAKYLRL HLLTPEKEEI KTKTKEELEK  600
LNEISNLRNG ICHLNYKEII EEILKTEISE KNKEATLNEK IRKVINFIKE NELDKVELGF  660
NFINDFFMKK EQFMFGQIKQ VKEGNSDSIT TERERKEKNN KKLKETYELN CDNLSEFYET  720
SNNLRERANS SSLLEDSAFL KKIGLYKVKN NKVNSKVKDE EKRIENIKRK LLKDSSDIMG  780
MYKAEVVKKL KEKLILIFKH DEEKRIYVTV YDTSKAVPEN ISKEILVKRN NSKEEYFFED  840
NNKKYVTEYY TLEITETNEL KVIPAKKLEG KEFKTEKNKE NKLMLNNHYC FNVKIIY     897

SEQ ID NO: 169          moltype = AA  length = 919
FEATURE                 Location/Qualifiers
source                  1..919
                        mol_type = protein
                        organism = unidentified
                        note = Description of Unknown: Cas13c sequence
SEQUENCE: 169
MEEIKHKKNK SSIIRVIVSN YDMTGIKEIK VLYQKQGGVD TFNLKTIINL ESGNLEIISC  60
KPKEREKYRY EFNCKTEINT ISITKKDKVL KKEIRKYSLE LYFKNEKKDT VVAKVTDLLK  120
APDKIEGERN HLRKLSSSTE RKLLSKTLCK NYSEISKTPI EEIDSIKIYK IKRFLNYRSN  180
FLIYFALIND FLCAGVKEDD INEVWLIQDK EHTAFLENRI EKITDYIFDK LSKDIENKKN  240
QFEKRIKKYK TSLEELKTET LEKNKTFYID SIKTKITNLE NKITELSLYN SKESLKEDLI  300
KIISIFTNLR HSLMHYDYKS FENLFENIEN EELKNLLDLN LFKSIRMSDE FKTKNRTNYL  360
DGTESFTIVK KHQNLKKLYT YYNNLCDKKN GFNTFINSFF VTDGIENTDF KNLIILHFEK  420
EMEEYKKSIE YYKIKISNEK NKSKKEKLKE KIDLLQSELI NMREHKNLLK QIYFFDIHNS  480
IKYKELYSER KNLIEQYNLQ INGVKDVTAI NHINTKLLSL KNKMDKITKQ NSLYRLKYKL  540
KIAYSFLMIE FDGDVSKFKN NFDPTNLEKR VEYLDKKEEY LNYTAPKNKF NFAKLEEELQ  600
KIQSTSEMGA DYLNVSPENN LFKFYILTYI MLPVEFKGDF LGFVKNHYYN IKNVDFMDES  660
LLDENEVDSN KLNEKIENLK DSSFFNKIRL FEKNIKKYEI VKYSVSTQEN MKEYFKQLNL  720
DIPYLDYKST DEIGIFNKNM ILPIFKYYQN VFKLCNDIEI HALLALANKK QQNLEYAIYC  780
CSKKNSLNYN ELLKTFNRKT YQNLSFIRNK IAHLNYKELF SDLFNNELDL NTKVRCLIEF  840
SQNNKFDQID LGMNFINDYY MKKTRFIFNQ RRLRDLNVPS KEKIIDGKRK QQNDSNNELL  900
KKYGLSRTNI KDIFNKAWY                                              919

SEQ ID NO: 170          moltype = AA  length = 1110
FEATURE                 Location/Qualifiers
source                  1..1110
                        mol_type = protein
                        organism = unidentified
                        note = Description of Unknown: Cas13c sequence
SEQUENCE: 170
MKVRYRKQAQ LDTFIIKTEI VNNDIFIKSI IEKAREKYRY SFLFDGEEKY HFKNKSSVEI  60
VKNDIFSQTP DNMIRNYKIT LKISEKNPRV VEAEIEDLMN STILKDGRRS ARREKSMTER  120
```

```
KLIEEKVAEN YSLLANCPIE EVDSIKIYKI KRFLTYRSNM LLYFASINSF LCEGIKGKDN  180
ETEEIWHLKD NDVRKEKVKE NFKNKLIQST ENYNSSLKNQ IEEKEKLSSK EFKKGAFYRT  240
IIKKLQQERI KELSEKSLTE DCEKIIKLYS ELRHPLMHYD YQYFENLFEN KENSELTKNL  300
NLDIFKSLPL VRKMKLNNKV NYLEDNDTLF VLQKTKKAKT LYQIYDALCE QKNGFNKFIN  360
DFFVSDGEEN TVFKQIINEK FQSEMEFLEK RISESEKKNE KLKKKLDSMK AHFRNINSED  420
TKEAYFWDIH SSRNYKTKYN ERKNLVNEYT KLLGSSKEKK LLREEITKIN RQLLKLKQEM  480
EEITKKNSLF RLEYKMKIAF GFLFCEFDGN ISKFKDEFDA SNQEKIIQYH KNGEKYLTSF  540
LKEEEKEKFN LEKMQKIIQK TEEEDWLLPE TKNNLFKFYL LTYLLLPYEL KGDFLGFVKK  600
HYYDIKNVDF MDENQNNIQV SQTVEKQEDY FYHKIRLFEK NTKKYEIVKY SIVPNEKLKQ  660
YFEDLGIDIK YLTGSVESGE KWLGENLGID IKYLTVEQKS EVSEEKNKKV SLKNNGMFNK  720
TILLFVFKYY QIAFKLFNDI ELYSLFFLRE KSEKPFEVFL EELKDKMIGK QLNFGQLLYV  780
VYEVLVKNKD LDKILSKKID YRKDKSFSPE IAYLRNFLSH LNYSKFLDNF MKINTNKSDE  840
NKEVLIPSIK IQKMIQFIEK CNLQNQIDFD FNFVNDFYMR KEKMFFIQLK QIFPDINSTE  900
KQKKSEKEEI LRKRYHLINK KNEQIKDEHE AQSQLYEKIL SLQKIFSCDK NNFYRRLKEE  960
KLLFLEKQGK KKISMKEIKD KIASDISDLL GILKKEITRD IKDKLTEKFR YCEEKLLNIS  1020
FYNHQDKKKE EGIRVFLIRD KNSDNFKFES ILDDGSNKIF ISKNGKEITI QCCDKVLETL  1080
MIEKNTLKIS SNGKIISLIP HYSYSIDVKY                                  1110

SEQ ID NO: 171         moltype = RNA  length = 41
FEATURE                Location/Qualifiers
source                 1..41
                       mol_type = other RNA
                       organism = synthetic construct
                       note = Description of Artificial Sequence: Synthetic
                        oligonucleotide
SEQUENCE: 171
taatttctac taagtgtaga tccagaacac atagcgacat g                     41

SEQ ID NO: 172         moltype = RNA  length = 41
FEATURE                Location/Qualifiers
source                 1..41
                       mol_type = other RNA
                       organism = synthetic construct
                       note = Description of Artificial Sequence: Synthetic
                        oligonucleotide
SEQUENCE: 172
taatttctac taagtgtaga ttattggtct ccttaaacct g                     41

SEQ ID NO: 173         moltype = DNA  length = 132
FEATURE                Location/Qualifiers
source                 1..132
                       mol_type = unassigned DNA
                       organism = Homo sapiens
SEQUENCE: 173
cgtggcccca ctgatgagct tccctccgcc ctatgggaaa aagtggtctc atacagaact  60
tataagattc ccaaatccaa agacatttca cgtttatggt gatttcccag aacacatagc  120
gacatgcaaa ta                                                      132

SEQ ID NO: 174         moltype = DNA  length = 126
FEATURE                Location/Qualifiers
source                 1..126
                       mol_type = unassigned DNA
                       organism = Homo sapiens
SEQUENCE: 174
cctatcagaa acccaagagt cttctctgtc tccacatgcc cagtttctat tggtctcctt  60
aaacctgtct tgtaaccttg ataccaacct gcccagggcc tcaccaccaa cttcatccac  120
gttcac                                                             126

SEQ ID NO: 175         moltype = RNA  length = 41
FEATURE                Location/Qualifiers
source                 1..41
                       mol_type = other RNA
                       organism = synthetic construct
                       note = Description of Artificial Sequence: Synthetic
                        oligonucleotide
SEQUENCE: 175
taatttctac taagtgtaga taagcttcgc ttgtagatga g                     41

SEQ ID NO: 176         moltype = RNA  length = 41
FEATURE                Location/Qualifiers
source                 1..41
                       mol_type = other RNA
                       organism = synthetic construct
                       note = Description of Artificial Sequence: Synthetic
                        oligonucleotide
SEQUENCE: 176
taatttctac taagtgtaga tacttgcatg cttaagacgc a                     41

SEQ ID NO: 177         moltype = RNA  length = 41
```

```
FEATURE                Location/Qualifiers
source                 1..41
                       mol_type = other RNA
                       organism = synthetic construct
                       note = Description of Artificial Sequence: Synthetic
                        oligonucleotide
SEQUENCE: 177
taatttctac taagtgtaga tatcctggct tagaactaac g                      41

SEQ ID NO: 178         moltype = RNA  length = 41
FEATURE                Location/Qualifiers
source                 1..41
                       mol_type = other RNA
                       organism = synthetic construct
                       note = Description of Artificial Sequence: Synthetic
                        oligonucleotide
SEQUENCE: 178
taatttctac taagtgtaga tattcgatga tacgcgagga a                      41

SEQ ID NO: 179         moltype = RNA  length = 41
FEATURE                Location/Qualifiers
source                 1..41
                       mol_type = other RNA
                       organism = synthetic construct
                       note = Description of Artificial Sequence: Synthetic
                        oligonucleotide
SEQUENCE: 179
taatttctac taagtgtaga tcaacatagg tccacagttg a                      41

SEQ ID NO: 180         moltype = RNA  length = 41
FEATURE                Location/Qualifiers
source                 1..41
                       mol_type = other RNA
                       organism = synthetic construct
                       note = Description of Artificial Sequence: Synthetic
                        oligonucleotide
SEQUENCE: 180
taatttctac taagtgtaga tcaacatagt tccacagttg a                      41

SEQ ID NO: 181         moltype = RNA  length = 41
FEATURE                Location/Qualifiers
source                 1..41
                       mol_type = other RNA
                       organism = synthetic construct
                       note = Description of Artificial Sequence: Synthetic
                        oligonucleotide
SEQUENCE: 181
taatttctac taagtgtaga tcagcatagt tccacagttg a                      41

SEQ ID NO: 182         moltype = RNA  length = 41
FEATURE                Location/Qualifiers
source                 1..41
                       mol_type = other RNA
                       organism = synthetic construct
                       note = Description of Artificial Sequence: Synthetic
                        oligonucleotide
SEQUENCE: 182
taatttctac taagtgtaga tcagcgtaca ctaccagggt a                      41

SEQ ID NO: 183         moltype = RNA  length = 41
FEATURE                Location/Qualifiers
source                 1..41
                       mol_type = other RNA
                       organism = synthetic construct
                       note = Description of Artificial Sequence: Synthetic
                        oligonucleotide
SEQUENCE: 183
taatttctac taagtgtaga tccctaccaa ctagctaata a                      41

SEQ ID NO: 184         moltype = RNA  length = 41
FEATURE                Location/Qualifiers
source                 1..41
                       mol_type = other RNA
                       organism = synthetic construct
                       note = Description of Artificial Sequence: Synthetic
                        oligonucleotide
SEQUENCE: 184
taatttctac taagtgtaga tctacaaagc ttattcctca t                      41
```

```
SEQ ID NO: 185          moltype = RNA  length = 41
FEATURE                 Location/Qualifiers
source                  1..41
                        mol_type = other RNA
                        organism = synthetic construct
                        note = Description of Artificial Sequence: Synthetic
                         oligonucleotide
SEQUENCE: 185
taatttctac taagtgtaga tgggtctata tacaggtgct g                      41

SEQ ID NO: 186          moltype = RNA  length = 41
FEATURE                 Location/Qualifiers
source                  1..41
                        mol_type = other RNA
                        organism = synthetic construct
                        note = Description of Artificial Sequence: Synthetic
                         oligonucleotide
SEQUENCE: 186
taatttctac taagtgtaga tgggtctgta tacaggtgct g                      41

SEQ ID NO: 187          moltype = RNA  length = 41
FEATURE                 Location/Qualifiers
source                  1..41
                        mol_type = other RNA
                        organism = synthetic construct
                        note = Description of Artificial Sequence: Synthetic
                         oligonucleotide
SEQUENCE: 187
taatttctac taagtgtaga tgtgactcag cgtcagtctt g                      41

SEQ ID NO: 188          moltype = RNA  length = 41
FEATURE                 Location/Qualifiers
source                  1..41
                        mol_type = other RNA
                        organism = synthetic construct
                        note = Description of Artificial Sequence: Synthetic
                         oligonucleotide
SEQUENCE: 188
taatttctac taagtgtaga tgttaacacc aagtgtgcat c                      41

SEQ ID NO: 189          moltype = RNA  length = 41
FEATURE                 Location/Qualifiers
source                  1..41
                        mol_type = other RNA
                        organism = synthetic construct
                        note = Description of Artificial Sequence: Synthetic
                         oligonucleotide
SEQUENCE: 189
taatttctac taagtgtaga ttaggaaatg acaaagcgat g                      41

SEQ ID NO: 190          moltype = RNA  length = 41
FEATURE                 Location/Qualifiers
source                  1..41
                        mol_type = other RNA
                        organism = synthetic construct
                        note = Description of Artificial Sequence: Synthetic
                         oligonucleotide
SEQUENCE: 190
taatttctac taagtgtaga ttcatttcct acaaagctta t                      41

SEQ ID NO: 191          moltype = RNA  length = 41
FEATURE                 Location/Qualifiers
source                  1..41
                        mol_type = other RNA
                        organism = synthetic construct
                        note = Description of Artificial Sequence: Synthetic
                         oligonucleotide
SEQUENCE: 191
taatttctac taagtgtaga ttgcatagac ttatatatcc g                      41

SEQ ID NO: 192          moltype = RNA  length = 41
FEATURE                 Location/Qualifiers
source                  1..41
                        mol_type = other RNA
                        organism = synthetic construct
                        note = Description of Artificial Sequence: Synthetic
                         oligonucleotide
SEQUENCE: 192
taatttctac taagtgtaga taggtatgtt tagtgagggg g                      41
```

```
SEQ ID NO: 193          moltype = RNA  length = 41
FEATURE                 Location/Qualifiers
source                  1..41
                        mol_type = other RNA
                        organism = synthetic construct
                        note = Description of Artificial Sequence: Synthetic
                         oligonucleotide
SEQUENCE: 193
taatttctac taagtgtaga tgtgaggggg gtgaagtcgt a                      41

SEQ ID NO: 194          moltype = RNA  length = 41
FEATURE                 Location/Qualifiers
source                  1..41
                        mol_type = other RNA
                        organism = synthetic construct
                        note = Description of Artificial Sequence: Synthetic
                         oligonucleotide
SEQUENCE: 194
taatttctac taagtgtaga tgatttggga atcttataag t                      41

SEQ ID NO: 195          moltype = DNA  length = 131
FEATURE                 Location/Qualifiers
source                  1..131
                        mol_type = unassigned DNA
                        organism = Homo sapiens
SEQUENCE: 195
atgggaaaaa gtggtctcat acagaactta taagattccc aaatccaaag acatttcacg  60
tttatggtga tttcccagaa cacatagcga catgcaaata ttgcagggcg ccactcccct  120
gtccctcaca g                                                       131
```